(12) United States Patent
Graham et al.

(10) Patent No.: US 12,331,199 B2
(45) Date of Patent: *Jun. 17, 2025

(54) SILICON CONTAINING DETECTABLE COMPOUNDS

(71) Applicant: Singular Genomics Systems, Inc., San Diego, CA (US)

(72) Inventors: Ronald Graham, Carlsbad, CA (US); Rodrigo Rodriguez, San Diego, CA (US)

(73) Assignee: Singular Genomics Systems, Inc., San Diego, CA (US)

( * ) Notice: Subject to any disclaimer, the term of this patent is extended or adjusted under 35 U.S.C. 154(b) by 4 days.

This patent is subject to a terminal disclaimer.

(21) Appl. No.: 18/130,212

(22) Filed: Apr. 3, 2023

(65) Prior Publication Data

US 2023/0295437 A1  Sep. 21, 2023

Related U.S. Application Data

(63) Continuation of application No. 16/415,700, filed on May 17, 2019, now Pat. No. 11,697,736.

(60) Provisional application No. 62/673,579, filed on May 18, 2018.

(51) Int. Cl.
| C09B 11/24 | (2006.01) |
| C07F 7/08 | (2006.01) |
| C07H 21/02 | (2006.01) |
| C07H 21/04 | (2006.01) |
| C07H 23/00 | (2006.01) |
| C09B 69/00 | (2006.01) |

(52) U.S. Cl.
CPC ............ *C09B 11/24* (2013.01); *C07F 7/0803* (2013.01); *C07F 7/0825* (2013.01); *C07F 7/083* (2013.01); *C07H 21/02* (2013.01); *C07H 21/04* (2013.01); *C09B 69/008* (2013.01); *C07F 7/0816* (2013.01); *C07H 23/00* (2013.01)

(58) Field of Classification Search
CPC .................................................... C07F 7/0816
See application file for complete search history.

(56) References Cited

U.S. PATENT DOCUMENTS

| 5,268,486 | A | 12/1993 | Waggoner et al. |
| 6,130,101 | A | 10/2000 | Mao et al. |
| 6,664,079 | B2 | 12/2003 | Ju et al. |
| 9,139,868 | B2 | 9/2015 | Zhou et al. |
| 9,649,389 | B2 | 5/2017 | Groves et al. |
| 9,714,260 | B2 | 7/2017 | Nagano et al. |
| 9,933,417 | B2 | 4/2018 | Lavis et al. |
| 10,087,199 | B2 | 10/2018 | Erdmann et al. |
| 10,564,164 | B2 | 2/2020 | Majima et al. |
| 10,738,072 | B1 * | 8/2020 | Graham ............. C07H 19/20 |
| 11,180,657 | B2 | 11/2021 | Kemnitzer et al. |
| 11,535,754 | B2 | 12/2022 | Cila et al. |
| 11,697,736 | B2 * | 7/2023 | Graham ............. C07F 7/0803 536/28.5 |
| 2004/0096825 | A1 * | 5/2004 | Chenna ............... C07H 19/06 435/6.12 |
| 2010/0009353 | A1 * | 1/2010 | Barnes .................. C09B 11/24 435/6.12 |
| 2014/0272990 | A1 | 9/2014 | Zhou et al. |
| 2014/0342384 | A1 * | 11/2014 | Nagano .................. C07F 7/10 556/406 |
| 2015/0353585 | A1 | 12/2015 | Nagano et al. |
| 2016/0115180 | A1 | 4/2016 | Erdmann et al. |
| 2017/0363636 | A1 | 12/2017 | Majima et al. |
| 2018/0274024 | A1 * | 9/2018 | Ju ........................ C07H 19/14 |
| 2019/0100653 | A1 | 4/2019 | Kemnitzer et al. |
| 2019/0352508 | A1 | 11/2019 | Graham et al. |
| 2022/0332752 | A2 | 10/2022 | Graham et al. |

FOREIGN PATENT DOCUMENTS

| EP | 3461815 A1 | 4/2019 | |
| WO | WO-2019164977 A1 * | 8/2019 | ............ C07H 21/04 |
| WO | WO-2019/222653 A1 | 11/2019 | |
| WO | WO-2020/005172 A2 | 1/2020 | |
| WO | WO-2021/092035 A1 | 5/2021 | |

OTHER PUBLICATIONS

U.S. Appl. No. 18/598,995, filed Mar. 7, 2024, Graham; Ronald.*
Brauch et al., "Fast and Efficient MCR-based synthesis of clickable rhodamine tags for protein profiling" Organic and Biomolecular Chemistry vol. 10 pp. 958-965, DOI:10/1039/c1ob06581e (Year: 2012).*
Koide et al., "Development of NIR Fluorescent Dyes Based on Si-rhodamine for in vivo Imaging" J Am Chem Soc vol. 134 pp. 5029-5031 DOI: 10.1021/ja210375e (Year: 2012).*
Xu et al., "Cellular thermal shift and clickable chemical probe assays for the determination of drug-target engagement in live cells" Org Biomol Chem vol. 14 pp. 6179-6183 DOI:10.1039/c6ob01078d (Year: 2016).*
Mathews et al., "Photo-cleavable nucleotides for primer free enzyme mediated DNA synthesis" Organic and Biomolecular Chemistry vol. 14 pp. 8278-8288 DOI:10.1039/c6ob01371f (Year: 2016).*
Shen et al., "Near-infrared probes based on fluorinated Si-rhodamine for live cell imaging" RSC Adv vol. 7 pp. 10922-10927 DOI:10.1039/c6ra28455h (Year: 2017).*
Ju et al., "Four-color DNA sequencing by synthesis using cleavable fluorescent nucleotide reversible terminators" PNAS vol. 103 No. 52 pp. 19635-19640 DOI:10.1073/pnas.0609513103 (Year: 2006).*
Berlier, J.E. et al. (Dec. 2003). "Quantitative comparison of long-wavelength Alexa Fluor dyes to Cy dyes: fluorescence of the dyes and their bioconjugates," *Journal of Histochemistry & Cytochemistry* 51 (12):1699-1712.
Extended European Search Report mailed on Jan. 31, 2022, for EP Patent Application No. 19803002.5, 10 pages.

(Continued)

*Primary Examiner* — Eric Olson
(74) *Attorney, Agent, or Firm* — Mintz, Levin, Cohn, Ferris, Glovsky and Popeo, P.C.

(57) ABSTRACT

Disclosed herein, inter alia, are silicon containing detectable compounds and methods of use thereof.

17 Claims, 6 Drawing Sheets

(56) References Cited

OTHER PUBLICATIONS

Goldstein, S.W. et al. (2017). "Nucleophilic aromatic substitution-addition and identification of an amine," *J Chem Educ* 94(9):1388-1390.
Hutter, D. et al. (Nov. 2010). "Labeled nucleoside triphosphates with reversibly terminating aminoalkoxyl groups," *Nucleosides Nucleotides Nucleic Acids* 29(11):879-895.
International Search report mailed on Oct. 24, 2019, for PCT application PCT/US2019/032907, filed May 17, 2019, 4 pages.
Needleman, S.B .et al. ( Mar. 1970). "A general method applicable to the search for similarities in the amino acid sequence of two proteins," *J Mol Biol* 48(3):443-453.
Pearson, W.R. et al. (Apr. 1988). "Improved tools for biological sequence comparison," *PNAS USA* 85(8):2444-2448.
Randolph, J.B. et al. (Jul. 15, 1997). "Stability, specificity and fluorescence brightness of multiply-labeled fluorescent DNA probes," *Nucleic Acids Res* 25(14):2923-2929.
Rosenblum, B.B. et al. (Nov. 15, 1997). "New dye-labeled terminators for improved DNA sequencing patterns," *Nucleic Acids Res* 25(22):4500-4504.
Smith T.F. et al. (Dec. 1981). "Comparison of biosequences," *Adv Appl Math* 2(4):482-489.
Written Opinion mailed on Oct. 24, 2019, for PCT application PCT/US2019/032907, filed May 17, 2019, 5 pages.
Bentley, D. R. et al. (Nov. 6, 2008). "Accurate whole human genome sequencing using reversible terminator chemistry," *Nature* 456(7218): 53-59.
Berlier, J. E. et al. (Dec. 2003). "Quantitative comparison of long-wavelength Alexa Fluor dyes to Cy dyes: fluorescence of the dyes and their bioconjugates," *J Histochem Cytochem* 51 (12): 1699-1712.
Birtalan, E. et al. (Mar. 1, 2011). "Investigating rhodamine B-labeled peptoids: Scopes and limitations of its applications," *Peptide Science* 96(5): 694-701.
Brauch, S. et al. (Oct. 25, 2011). "Fast and efficient MCR-based synthesis of clickable rhodamine tags for protein profiling," *Organic & biomolecular chemistry* 10(5): 958-965.
Buckley, M. et al. (Jan. 2016, e-published Dec. 10, 2015). "Enhancer scanning to locate regulatory regions in genomic loci," *Nature protocols* 11(1): 46-60.
Choi, A. et al. (Aug. 3, 2018, e-published Jul. 17, 2018). "Silicon substitution in oxazine dyes yields near-infrared azasiline fluorophores that absorb and emit beyond 700 nm," *Organic letters* 20(15): 4482-4485.
Extended European Search Report mailed on Jan. 31, 2022, for EP Patent Application No. EP 19803002.5, 9 pages.
Extended European Search Report mailed on Dec. 4, 2023, for EP Patent Application No. EP 20883841.7, 14 pages.
Goldstein, S. W. et al. (Sep. 12, 2017, e-published Jul. 28, 2017). "Nucleophilic aromatic substitution-addition and identification of an amine," *J Chem Educ* 94(9): 1388-1390.
Grimm, J. B. et al. (Sep. 27, 2017, e-published Aug. 9, 2017). "General Synthetic Method for Si-Fluoresceins and Si-Rhodamines," *ACS Cent Sci* 3(9): 975-985.
Guo, J. et al. (Jul. 8, 2008, e-published Jun. 30, 2008). "Four-color DNA sequencing with 3'- O-modified nucleotide reversible terminators and chemically cleavable fluorescent dideoxynucleotides," *PNAS USA* 105(27): 9145-9150.

Hutter, D. et al. (Nov. 2010, e-published Dec. 1, 2010). "Labeled nucleoside triphosphates with reversibly terminating aminoalkoxyl groups," *Nucleosides Nucleotides Nucleic Acids* 29(11): 879-895.
International Search Report and Written Opinion mailed on Feb. 8, 2021, for PCT application PCT/US2020/058916, filed Nov. 4, 2020, 7 pages.
International Search Report and Written Opinion mailed on Oct. 24, 2019, for PCT Application No. PCT/US2019/032907, filed May 17, 2019, 9 pages.
Ju, J. et al. (Dec. 26, 2006, e-published Dec. 14, 2006). "Four-color DNA sequencing by synthesis using cleavable fluorescent nucleotide reversible terminators," *PNAS USA* 103(52): 19635-19640.
Koide, Y. et al. (Mar. 21, 2012, e-published Mar. 7, 2012). "Development of NIR fluorescent dyes based on Si-rhodamine for in vivo imaging," *Journal of the American Chemical Society* 134(11): 5029-5031.
Kolmakov, K. et al. (Sep. 14, 2015, e-published Aug. 13, 2015) "Far-Red Emitting Fluorescent Dyes for Optical Nanoscopy: Fluorinated Silicon-Rhodamines (SiRF Dyes) and Phosphorylated Oxazines" *Chemistry—A European Journal* 21(38): 13344-13356.
Lee, M. H. et al. (Jul. 10, 2013, e-published Apr. 12, 2013). "Disulfide-cleavage-triggered chemosensors and their biological applications," *Chemical reviews* 113(7): 5071-5109.
Leicher, T. et al. (Dec. 25, 1998). "Coexpression of the KCNA3B gene product with Kv1.5 leads to a novel A-type potassium channel," *J Biol Chem* 273(52): 35095-35101.
Marcaccini, S. et al. (Mar. 2007, e-published Mar. 22, 2007). "The use of the Ugi four-component condensation," *Nature Protocols* 2(3): 632-639.
Mathews, A. S. et al. (Aug. 9, 2016). "Photo-cleavable nucleotides for primer free enzyme mediated DNA synthesis," *Organic & Biomolecular Chemistry* 14(35): 8278-8288.
Needleman, S. B. et al. (Mar. 28, 1970, e-published Oct. 28, 2004). "A general method applicable to the search for similarities in the amino acid sequence of two proteins," *J Mol Biol* 48(3): 443-453.
Pearson, W. R. et al. (Apr. 1, 1988). "Improved tools for biological sequence comparison," *PNAS USA* 85(8): 2444-2448.
Randolph, J. B. et al. (Jul. 1, 1997). "Stability, specificity and fluorescence brightness of multiply-labeled fluorescent DNA probes," *Nucleic Acids Res* 25(14): 2923-2929.
Rosenblum, B.B. et al. (Nov. 1, 1997). "New dye-labeled terminators for improved DNA sequencing patterns," *Nucleic Acids Res* 25(22): 4500-4504.
Ruparel, H. et al. (Apr. 26, 2005, e-published Apr. 13, 2005). "Design and synthesis of a 3'-0-allyl photocleavable fluorescent nucleotide as a reversible terminator for DNA sequencing by synthesis," *PNAS USA* 102(17): 5932-5937.
Shen, S. et al. (Feb. 9, 2017). "Near-infrared probes based on fluorinated Si-rhodamine for live cell imaging," *RSC advances* 7(18): 10922-10927.
Smith T. F. et al. (Dec. 1981, e-published Sep. 3, 2004). "Comparison of biosequences," *Adv Appl Math* 2(4): 482-489.
Wu, J. et al. (Oct. 16, 2007, e-published Oct. 8, 2007). "3'-O-modified nucleotides as reversible terminators for pyrosequencing," *PNAS USA* 104(42): 16462-16467.
Xu, H. et al. (May 19, 2016). "Cellular thermal shift and clickable chemical probe assays for the determination of drug-target engagement in live cells," *Organic & Biomolecular Chemistry* 14(26): 6179-6183.
Zhu, Z. et al. (Aug. 25, 1994). "Directly labeled DNA probes using fluorescent nucleotides with different length linkers," *Nucleic Acids Res* 22(16): 3418-3422.

* cited by examiner siTMR
ring opened
colored form siTMR
spirolactone
colorless form

SILICON CONTAINING DETECTABLE COMPOUNDS

CROSS-REFERENCES TO RELATED APPLICATIONS

This application is a continuation of U.S. patent application Ser. No. 16/415,700, filed May 17, 2019, which claims the benefit of U.S. Provisional Application No. 62/673,579, filed May 18, 2018, which are incorporated herein by reference in their entirety and for all purposes.

BACKGROUND

Rhodamine and rhodol dyes are photostable with large absorption coefficients. The synthesis of red shifted rhodamine dyes is challenging because it requires building up the carbocyclic framework. The brightness, photostability and aqueous solubility of red rhodamines can suffer when the carbocyclic framework is extended. Importantly, the efficiency of certain dyes is hampered by the formation of non-fluorescent species. Disclosed herein, inter alia, are solutions to these and other problems in the art.

BRIEF SUMMARY

In an aspect is provided a compound, or salt thereof, having the formula:

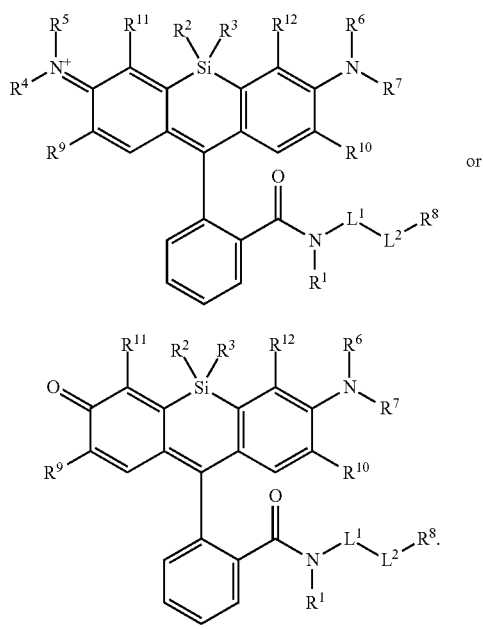

$R^1$, $R^4$, $R^5$, $R^6$, and $R^7$ are each independently hydrogen, halogen, —$CF_3$, —$CCl_3$, —$CI_3$, —$CBr_3$, —$CHF_2$, —$CHCl_2$, —$CHI_2$, —$CHBr_2$, —$CH_2F$, —$CH_2Cl$, —$CH_2I$, —$CH_2Br$, —$OCH_2F$, —$OCH_2Cl$, —$OCH_2I$, —$OCH_2Br$, —$OCHF_2$, —$OCHCl_2$, —$OCHI_2$, —$OCHBr_2$, —$OCF_3$, —$OCCl_3$, —$OCI_3$, —$OCBr_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)NHNH_2, —NHC=(O)NH_2, —$NHSO_2H$, —NHC=(O)H, —NHC(O)OH, —NHOH, —$N_3$, substituted or unsubstituted alkyl, substituted or unsubstituted cycloalkyl, substituted or unsubstituted heterocycloalkyl, substituted or unsubstituted aryl, or substituted or unsubstituted heteroaryl. $R^2$ and $R^3$ are each independently substituted or unsubstituted alkyl, or substituted or unsubstituted heteroalkyl. $R^8$ is hydrogen, a bioconjugate reactive moiety, a nucleotide, a nucleoside, or a nucleic acid. $R^9$, $R^{10}$, $R^{11}$, and $R^{12}$ are each independently hydrogen, substituted or unsubstituted alkyl, or substituted or unsubstituted heteroalkyl. $L^1$ and $L^2$ are each independently a bond or a covalent linker. $R^4$ and $R^5$ substituents bonded to the same nitrogen atom may optionally be joined to form a substituted or unsubstituted heterocycloalkyl, or substituted or unsubstituted heteroaryl. $R^6$ and $R^7$ substituents bonded to the same nitrogen atom may optionally be joined to form a substituted or unsubstituted heterocycloalkyl, or substituted or unsubstituted heteroaryl. $R^4$ and $R^9$ substituents may optionally be joined to form a substituted or unsubstituted heterocycloalkyl, or substituted or unsubstituted heteroaryl. $R^7$ and $R^{10}$ substituents may optionally be joined to form a substituted or unsubstituted heterocycloalkyl, or substituted or unsubstituted heteroaryl. $R^5$ and $R^{11}$ substituents may optionally be joined to form a substituted or unsubstituted heterocycloalkyl, or substituted or unsubstituted heteroaryl. $R^6$ and $R^{12}$ substituents may optionally be joined to form a substituted or unsubstituted heterocycloalkyl, or substituted or unsubstituted heteroaryl.

In an aspect is provided a method of detecting the presence of an agent, wherein the agent is covalently bound to a monovalent compound as described herein (e.g., wherein $R^8$ reacts to form part of the covalent linker), wherein the agent is an oligonucleotide, protein, or a compound.

In another aspect is provided a method of making a compound, or salt thereof, having the formula:

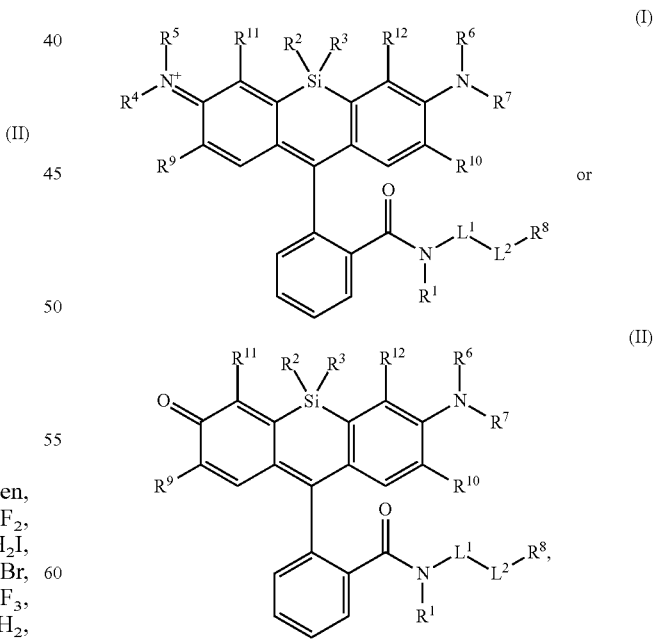

the method including mixing compound A, compound B, and compound C in a reaction vessel. Compound A has the formula:

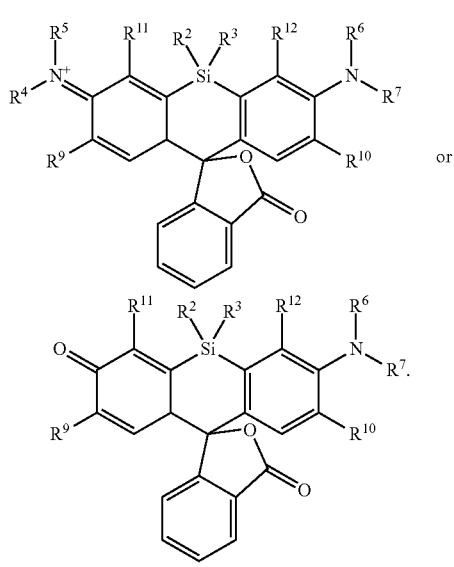

Compound B is a coupling reagent. Compound C has the formula:

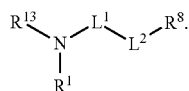

$R^1$, $R^4$, $R^5$, $R^6$, and $R^7$ are each independently hydrogen, halogen, —$CF_3$, —$CCl_3$, —$CI_3$, —$CBr_3$, —$CHF_2$, —$CHCl_2$, —$CHI_2$, —$CHBr_2$, —$CH_2F$, —$CH_2Cl$, —$CH_2I$, —$CH_2Br$, —$OCH_2F$, —$OCH_2Cl$, —$OCH_2I$, —$OCH_2Br$, —$OCHF_2$, —$OCHCl_2$, —$OCHI_2$, —$OCHBr_2$, —$OCF_3$, —$OCCl_3$, —$OCI_3$, —$OCBr_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ and $R^3$ are each independently substituted or unsubstituted alkyl, or substituted or unsubstituted heteroalkyl. $R^8$ is hydrogen, a bioconjugate reactive moiety, a nucleotide, a nucleoside, or a nucleic acid. $R^9$, $R^{10}$, $R^{11}$, and $R^{12}$, are each independently hydrogen, substituted or unsubstituted alkyl, or substituted or unsubstituted heteroalkyl. $R^{13}$ is a leaving group (e.g., hydrogen). $L^1$ and $L^2$ are each independently a bond or a covalent linker. $R^4$ and $R^5$ substituents bonded to the same nitrogen atom may optionally be joined to form a substituted or unsubstituted heterocycloalkyl, or substituted or unsubstituted heteroaryl. $R^6$ and $R^7$ substituents bonded to the same nitrogen atom may optionally be joined to form a substituted or unsubstituted heterocycloalkyl, or substituted or unsubstituted heteroaryl. $R^4$ and $R^9$ substituents may optionally be joined to form a substituted or unsubstituted heterocycloalkyl, or substituted or unsubstituted heteroaryl. $R^7$ and $R^{10}$ substituents may optionally be joined to form a substituted or unsubstituted heterocycloalkyl, or substituted or unsubstituted heteroaryl. $R^5$ and $R^{11}$ substituents may optionally be joined to form a substituted or unsubstituted heterocycloalkyl, or substituted or unsubstituted heteroaryl. $R^6$ and $R^{12}$ substituents may optionally be joined to form a substituted or unsubstituted heterocycloalkyl, or substituted or unsubstituted heteroaryl.

DETAILED DESCRIPTION

I. Definitions

Figure 1A:
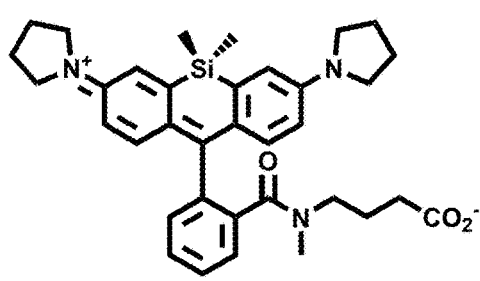
FIGS. 1A-1E. Non-limiting examples of Si-rhodamine dyes synthesized according to the methods described herein.
Figure 1A:
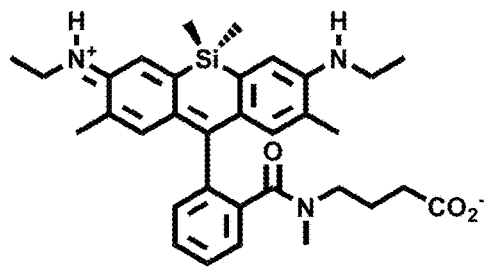
Figure 1A:
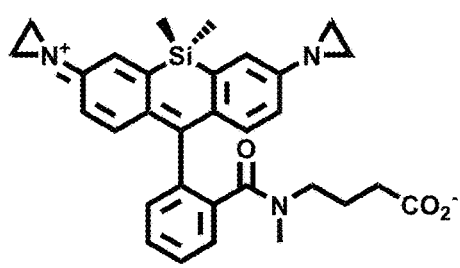
Figure 1A:
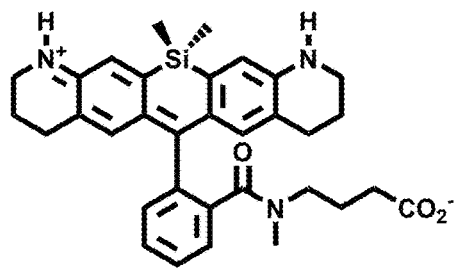
Figure 1A:
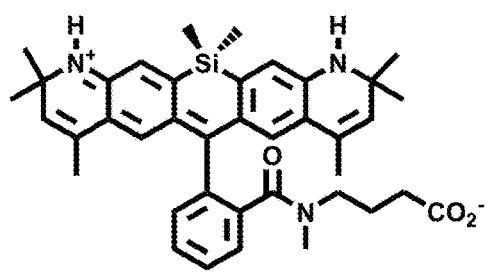
Figure 1A:
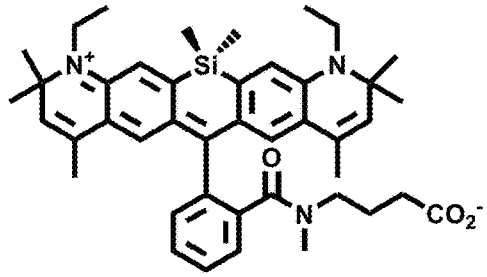
Figure 1A:
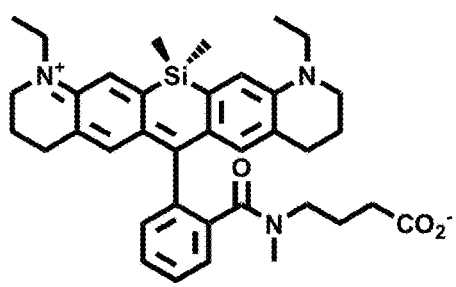
Figure 1A:
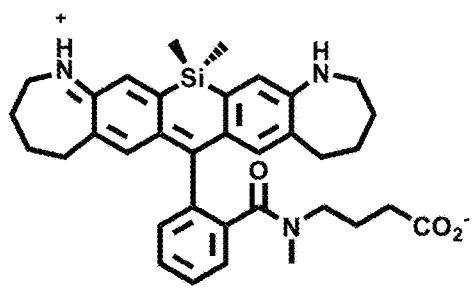

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di-, and multivalent radicals. The alkyl may include a designated number of carbons (e.g., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., O, N, S, Si, or P) may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—S—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form (CH$_2$)$_w$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. In embodiments, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkyl is attached to the parent molecular moiety through any carbon atom contained within the monocyclic cycloalkyl ring. In embodiments, cycloalkyl groups are optionally substituted with one or two groups which are independently oxo or thia. In embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkyl is attached to the parent molecular moiety through any carbon atom contained within the base ring. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic cycloalkenyls include, but are not limited to, norbornenyl and bicyclo[2.2.2]oct 2 enyl. In embodiments, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkenyl is attached to the parent molecular moiety through any carbon atom contained within the monocyclic cycloalkenyl ring. In embodiments, cycloalkenyl groups are optionally substituted with one or two groups which are independently oxo or thia. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkenyl is attached to the parent molecular moiety through any carbon atom contained within the base ring. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. In embodiments, heterocyclyl groups are optionally substituted with one or two groups which are independently oxo or thia. In certain embodiments, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g., substituents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g., all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "⁓" denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

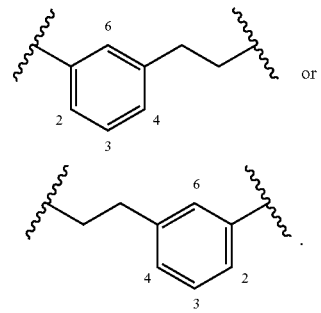

An alkylarylene moiety may be substituted (e.g., with a substituent group) on the alkylene moiety or the arylene linker (e.g., at carbons 2, 3, 4, or 6) with halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$CH$_3$— SO$_3$H, —OSO$_3$H, —SO$_2$NH$_2$, —NHNH$_2$, —ONH$_2$, —NHC(O)NHNH$_2$, substituted or unsubstituted C$_1$-C$_5$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g., cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g., a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —PO$_3$H, —PO$_4$H, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl (e.g., C$_1$-C$_8$ alkyl, C$_1$-C$_6$ alkyl, or C$_1$-C$_4$ alkyl), heteroalkyl (e.g., 2 to 8 membered heteroalkyl, 2 to 6 membered heteroalkyl, or 2 to 4 membered heteroalkyl), cycloalkyl (e.g., C$_3$-C$_8$ cycloalkyl, C$_3$-C$_6$ cycloalkyl, or C$_5$-C$_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., C$_6$-C$_{10}$ aryl, C$_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:

(i) oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —PO$_3$H, —PO$_4$H, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl (e.g., C$_1$-C$_8$ alkyl, C$_1$-C$_6$ alkyl, or C$_1$-C$_4$ alkyl), heteroalkyl (e.g., 2 to 8 membered heteroalkyl, 2 to 6 membered heteroalkyl, or 2 to 4 membered heteroalkyl), cycloalkyl (e.g., C$_3$-C$_8$ cycloalkyl, C$_3$-C$_6$ cycloalkyl, or C$_5$-C$_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., C$_6$-C$_{10}$ aryl, C$_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:

(a) oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —PO$_3$H, —PO$_4$H, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl (e.g., C$_1$-C$_8$ alkyl, C$_1$-C$_6$ alkyl, or C$_1$-C$_4$ alkyl), heteroalkyl (e.g., 2 to 8 membered heteroalkyl, 2 to 6 membered heteroalkyl, or 2 to 4 membered heteroalkyl), cycloalkyl (e.g., C$_3$-C$_8$ cycloalkyl, C$_3$-C$_6$ cycloalkyl, or C$_5$-C$_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., C$_6$-C$_{10}$ aryl, C$_{10}$ aryl, or phenyl), heteroaryl (e.g., 5 to 10 membered heteroaryl, 5 to 9 membered heteroaryl, or 5 to 6 membered heteroaryl), substituted with at least one substituent selected from: oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —PO$_3$H, —PO$_4$H, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound (e.g., nucleotide analogue) is a chemical species set forth in the Examples section, claims, embodiments, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Where a moiety is substituted (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene), the moiety is substituted with at least one substituent (e.g., a substituent group, a size-limited substituent group, or lower substituent group) and each substituent is optionally different. Additionally, where multiple substituents are present on a moiety, each substituent may be optionally different.

In a recited claim or chemical formula description herein, each R substituent or L linker that is described as being "substituted" without reference as to the identity of any chemical moiety that composes the "substituted" group (also referred to herein as an "open substitution" on a R substituent or L linker or an "openly substituted" R substituent or L linker), the recited R substituent or L linker may, in embodiments, be substituted with one or more "first substituent group(s)" as defined below.

The first substituent group is denoted with a corresponding first decimal point numbering system such that, for example, $R^1$ may be substituted with one or more first substituent groups denoted by $R^{1.1}$, $R^2$ may be substituted with one or more first substituent groups denoted by $R^{2.1}$, $R^3$ may be substituted with one or more first substituent groups denoted by $R^{3.1}$, $R^4$ may be substituted with one or more first substituent groups denoted by $R^{4.1}$, $R^5$ may be substituted with one or more first substituent groups denoted by $R^{5.1}$, and the like up to or exceeding an $R^{100}$ that may be substituted with one or more first substituent groups denoted by $R^{100.1}$. As a further example, $R^{1A}$ may be substituted with one or more first substituent groups denoted by $R^{1A.1}$, $R^{2A}$ may be substituted with one or more first substituent groups denoted by $R^{2A.1}$, $R^{3A}$ may be substituted with one or more first substituent groups denoted by $R^{3A.1}$, $R^{4A}$ may be substituted with one or more first substituent groups denoted by $R^{4A.1}$, $R^{5A}$ may be substituted with one or more first substituent groups denoted by $R^{5A.1}$ and the like up to or exceeding an $R^{100A}$ may be substituted with one or more first substituent groups denoted by $R^{100A.1}$. As a further example, $L^1$ may be substituted with one or more first substituent groups denoted by $R^{L1.1}$, $L^2$ may be substituted with one or more first substituent groups denoted by $R^{L2.1}$, $L^3$ may be substituted with one or more first substituent groups denoted by $R^{L3.1}$ $L^4$ may be substituted with one or more first substituent groups denoted by $R^{L4.1}$, $L^5$ may be substituted with one or more first substituent groups denoted by $R^{L5.1}$ and the like up to or exceeding an $L^{100}$ which may be substituted with one or more first substituent groups denoted by $R^{L100.1}$. Thus, each numbered R group or L group (alternatively referred to herein as $R^{WW}$ or $L^{WW}$ wherein "WW" represents the stated superscript number of the subject R group or L group) described herein may be substituted with one or more first substituent groups referred to herein generally as $R^{WW.1}$ or $R^{LWW.1}$, respectively. In turn, each first substituent group (e.g., $R^{1.1}$, $R^{2.1}$, $R^{3.1}$, $R^{4.1}$, $R^{5.1}$ ... $R^{100.1}$; $R^{1A.1}$, $R^{2A.1}$, $R^{3A.1}$, $R^{4A.1}$, $R^{5A.1}$ ... $R^{100A.1}$; $R^{L1.1}$, $R^{L2.1}$, $R^{L3.1}$, $R^{L4.1}$, $R^{L5.1}$ ... $R^{L100.1}$) may be further substituted with one or more second substituent groups (e.g., $R^{1.2}$, $R^{2.2}$, $R^{3.2}$, $R^{4.2}$, $R^{5.2}$ ... $R^{100.2}$; $R^{1A.2}$, $R^{2A.2}$, $R^{3A.2}$, $R^{4A.2}$, $R^{5A.2}$ ... $R^{100A.2}$; $R^{L1.2}$, $R^{L2.2}$, $R^{L3.2}$, $R^{L4.2}$, $R^{L5.2}$ ... $R^{L100.2}$, respectively). Thus, each first substituent group, which may alternatively be represented herein as $R^{WW.1}$ as described above, may be further substituted with one or more second substituent groups, which may alternatively be represented herein as $R^{WW.2}$.

Finally, each second substituent group (e.g., $R^{1.2}$, $R^{2.2}$, $R^{3.2}$, $R^{4.2}$, $R^{5.2}$, ... $R^{100.2}$; $R^{1A.2}$, $R^{2A.2}$, $R^{3A.2}$, $R^{4A.2}$, $R^{5A.2}$ ... $R^{100A.2}$; $R^{L1.2}$, $R^{L2.2}$, $R^{L3.2}$, $R^{L4.2}$, $R^{L5.2}$ ... $R^{L100.2}$) may be further substituted with one or more third substituent groups (e.g., $R^{1.3}$, $R^{2.3}$, $R^{3.3}$, $R^{4.3}$, $R^{5.3}$ .... $R^{100.3}$; $R^{1A.3}$, $R^{2A.3}$, $R^{3A.3}$, $R^{4A.3}$, $R^{5A.3}$ ... $R^{100A.3}$; $R^{L1.3}$, $R^{L2.3}$, $R^{L3.3}$, $R^{L4.3}$, $R^{L5.3}$ ... $R^{L100.3}$; respectively). Thus, each second substituent group, which may alternatively be represented herein as $R^{WW.2}$ as described above, may be further substituted with one or more third substituent groups, which may alternatively be represented herein as $R^{WW.3}$. Each of the first substituent groups may be optionally different. Each of the second substituent groups may be optionally different. Each of the third substituent groups may be optionally different.

Thus, as used herein, $R^{WW}$ represents a substituent recited in a claim or chemical formula description herein, which is openly substituted. "WW" represents the stated superscript number of the subject R group (e.g., 1, 2, 3, 1A, 2A, 3A, 1B, 2B, 3B, etc.). Likewise, $L^{WW}$ is a linker recited in a claim or chemical formula description herein which is openly substituted. Again, "WW" represents the stated superscript number of the subject L group (e.g., 1, 2, 3, 1A, 2A, 3A, 1B, 2B, 3B, etc.). As stated above, in embodiments, each $R^{WW}$ may be unsubstituted or independently substituted with one or more first substituent groups, referred to herein as $R^{WW.1}$; each first substituent group, $R^{WW.1}$, may be unsubstituted or independently substituted with one or more second substituent groups, referred to herein as $R^{WW.2}$; and each second substituent group may be unsubstituted or independently substituted with one or more third substituent groups, referred to herein as $R^{WW.3}$. Similarly, each $L^{WW}$ linker may be unsubstituted or independently substituted with one or more first substituent groups, referred to herein as $R^{LWW.1}$; each first substituent group, $R^{LWW.1}$, may be unsubstituted or independently substituted with one or more second substituent groups, referred to herein as $R^{LWW.2}$; and each second substituent group may be unsubstituted or independently substituted with one or more third substituent groups, referred to herein as $R^{LWW.3}$. Each first substituent group is optionally different. Each second substituent group is optionally different. Each third substituent group is optionally different.

$R^{WW.1}$ is independently oxo, halogen, $-CX^{WW.1}_3$, $-CHX^{WW.1}_2$, $-CH_2X^{WW.1}$, $-OCX^{WW.1}_3$, $-OCH_2X^{WW.1}$, $-OCHX^{WW.1}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-N_3$, $R^{WW.2}$-substituted or unsubstituted alkyl (e.g., $C_1$-$C_8$, $C_1$-$C_6$, $C_1$-$C_4$, or $C_1$-$C_2$), $R^{WW.2}$-substituted or unsubstituted heteroalkyl (e.g., 2 to 8 membered, 2 to 6 membered, 4 to 6 membered, 2 to 3 membered, or 4 to 5 membered), $R^{WW.2}$-substituted or unsubstituted cycloalkyl (e.g., $C_3$-$C_8$, $C_3$-$C_6$, $C_4$-$C_6$, or $C_5$-$C_6$), $R^{WW.2}$-substituted or unsubstituted heterocycloalkyl (e.g., 3 to 8 membered, 3 to 6 membered, 4 to 6 membered, 4 to 5 membered, or 5 to 6 membered), $R^{WW.2}$-substituted or unsubstituted aryl (e.g., $C_6$-$C_{12}$, $C_6$-$C_{10}$, or phenyl), or $R^{WW.2}$-substituted or unsubstituted heteroaryl (e.g., 5 to 12 membered, 5 to 10 membered, 5 to 9 membered, or 5 to 6 membered). In embodiments, $R^{WW.1}$ is independently oxo, halogen, $-CX^{WW.1}_3$, $-CHX^{WW.1}_2$, $-CH_2X^{WW.1}$, $-OCX^{WW.1}_3$, $-OCH_2X^{WW.1}$, $-OCHX^{WW.1}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{WW.1}$ is independently —F, —Cl, —Br, or —I.

$R^{WW.2}$ is independently oxo, halogen, —$CX^{WW.2}_3$, —$CHX^{WW.2}_2$, —$CH_2X^{WW.2}$, —$OCX^{WW.2}_3$, —$OCH_2X^{WW.2}$, —$OCHX^{WW.2}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$N_3$, $R^{WW.3}$-substituted or unsubstituted alkyl (e.g., $C_1$-$C_8$, $C_1$-$C_6$, $C_1$-$C_4$, or $C_1$-$C_2$), $R^{WW.3}$-substituted or unsubstituted heteroalkyl (e.g., 2 to 8 membered, 2 to 6 membered, 4 to 6 membered, 2 to 3 membered, or 4 to 5 membered), $R^{WW.3}$-substituted or unsubstituted cycloalkyl (e.g., $C_3$-$C_8$, $C_3$-$C_6$, $C_4$-$C_6$, or $C_5$-$C_6$), $R^{WW.3}$-substituted or unsubstituted heterocycloalkyl (e.g., 3 to 8 membered, 3 to 6 membered, 4 to 6 membered, 4 to 5 membered, or 5 to 6 membered), $R^{WW.3}$-substituted or unsubstituted aryl (e.g., $C_6$-$C_{12}$, $C_6$-$C_{10}$, or phenyl), or $R^{WW.3}$-substituted or unsubstituted heteroaryl (e.g., 5 to 12 membered, 5 to 10 membered, 5 to 9 membered, or 5 to 6 membered). In embodiments, $R^{WW.2}$ is independently oxo, halogen, —$CX^{WW.2}_3$, —$CHX^{WW.2}_2$, —$CH_2X^{WW.2}$, —$OCX^{WW.2}_3$, —$OCH_2X^{WW.2}$, —$OCHX^{WW.2}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{WW.2}$ is independently —F, —Cl, —Br, or —I.

$R^{WW.3}$ is independently oxo, halogen, —$CX^{WW.3}_3$, —$CHX^{WW.3}_2$, —$CH_2X^{WW.3}$, —$OCX^{WW.3}_3$, —$OCH_2X^{WW.3}$, —$OCHX^{WW.3}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{WW.3}$ is independently —F, —Cl, —Br, or —I.

Where two different $R^{WW}$ substituents are joined together to form an openly substituted ring (e.g., substituted cycloalkyl, substituted heterocycloalkyl, substituted aryl or substituted heteroaryl), in embodiments, the openly substituted ring may be independently substituted with one or more first substituent groups, referred to herein as $R^{WW.1}$; each first substituent group, $R^{WW.1}$, may be unsubstituted or independently substituted with one or more second substituent groups, referred to herein as $R^{WW.2}$; and each second substituent group, $R^{WW.2}$, may be unsubstituted or independently substituted with one or more third substituent groups, referred to herein as $R^{WW.3}$; and each third substituent group, $R^{WW.3}$, is unsubstituted. Each first ring substituent group is optionally different. Each second ring substituent group is optionally different. Each third ring substituent group is optionally different. In the context of two different $R^{WW}$ substituents joined together to form an openly substituted ring, the "WW" symbol in the $R^{WW.1}$, $R^{WW.2}$, and $R^{WW.3}$ refers to the designated number of one of the two different $R^{WW}$ substituents. For example, in embodiments where $R^{100A}$ and $R^{100B}$ are optionally joined together to form an openly substituted ring, $R^{WW.1}$ is $R^{100A.1}$, $R^{WW.2}$ is $R^{100A.2}$, and $R^{WW.3}$ is $R^{100A.3}$. Alternatively, in embodiments where $R^{100A}$ and $R^{100B}$ are optionally joined together to form an openly substituted ring, $R^{WW.1}$ is $R^{100B.1}$, $R^{WW.2}$ is $R^{100B.2}$, and $R^{WW.3}$ is $R^{100B.3}$. $R^{WW.1}$, $R^{WW.2}$, and $R^{WW.3}$ in this paragraph are as defined in the preceding paragraphs.

$R^{LWW.1}$ is independently oxo, halogen, —$CX^{LWW.1}_3$, —$CHX^{LWW.1}_2$, —$CH_2X^{LWW.1}$, —$OCX^{LWW.1}_3$, —$OCH_2X^{LWW.1}$, —$OCHX^{LWW.1}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$N_3$, $R^{LWW.2}$-substituted or unsubstituted alkyl (e.g., $C_1$-$C_8$, $C_1$-$C_6$, $C_1$-$C_4$, or $C_1$-$C_2$), $R^{LWW.2}$-substituted or unsubstituted heteroalkyl (e.g., 2 to 8 membered, 2 to 6 membered, 4 to 6 membered, 2 to 3 membered, or 4 to 5 membered), $R^{LWW.2}$-substituted or unsubstituted cycloalkyl (e.g., $C_3$-$C_8$, $C_3$-$C_6$, $C_4$-$C_6$, or $C_5$-$C_6$), $R^{LWW.2}$-substituted or unsubstituted heterocycloalkyl (e.g., 3 to 8 membered, 3 to 6 membered, 4 to 6 membered, 4 to 5 membered, or 5 to 6 membered), $R^{LWW.2}$-substituted or unsubstituted aryl (e.g., $C_6$-$C_{12}$, $C_6$-$C_{10}$, or phenyl), or $R^{LWW.2}$-substituted or unsubstituted heteroaryl (e.g., 5 to 12 membered, 5 to 10 membered, 5 to 9 membered, or 5 to 6 membered). In embodiments, $R^{LWW.1}$ is independently oxo, halogen, —$CX^{LWW.1}_3$, —$CHX^{LWW.1}_2$, —$CH_2X^{LWW.1}$, —$OCX^{LWW.1}_3$, —$OCH_2X^{LWW.1}$, —$OCHX^{LWW.1}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{LWW.1}$ is independently —F, —Cl, —Br, or —I.

$R^{LWW.2}$ is independently oxo, halogen, —$CX^{LWW.2}{}_3$, —$CHX^{LWW.2}{}_2$, —$CH_2X^{LWW.2}$, —$OCX^{LWW.2}{}_3$, —$OCH_2X^{LWW.2}$, —$OCHX^{LWW.2}{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$N_3$, $R^{LWW.3}$-substituted or unsubstituted alkyl (e.g., $C_1$-$C_8$, $C_1$-$C_6$, $C_1$-$C_4$, or $C_1$-$C_2$), $R^{LWW.3}$-substituted or unsubstituted heteroalkyl (e.g., 2 to 8 membered, 2 to 6 membered, 4 to 6 membered, 2 to 3 membered, or 4 to 5 membered), $R^{WW.3}$-substituted or unsubstituted cycloalkyl (e.g., $C_3$-$C_8$, $C_3$-$C_6$, $C_4$-$C_6$, or $C_5$-$C_6$), $R^{LWW.3}$-substituted or unsubstituted heterocycloalkyl (e.g., 3 to 8 membered, 3 to 6 membered, 4 to 6 membered, 4 to 5 membered, or 5 to 6 membered), $R^{LWW.3}$-substituted or unsubstituted aryl (e.g., $C_6$-$C_{12}$, $C_6$-$C_{10}$, or phenyl), or $R^{LWW.3}$-substituted or unsubstituted heteroaryl (e.g., 5 to 12 membered, 5 to 10 membered, 5 to 9 membered, or 5 to 6 membered). In embodiments, $R^{LWW.2}$ is independently oxo, halogen, —$CX^{LWW.2}{}_3$, —$CHX^{LWW.2}{}_2$, —$CH_2X^{LWW.2}$, —$OCX^{LWW.2}{}_3$, —$OCH_2X^{LWW.2}$, —$OCHX^{LWW.2}{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{LWW.2}$ is independently —F, —Cl, —Br, or —I.

$R^{LWW.3}$ is independently oxo, halogen, —$CX^{LWW.3}{}_3$, —$CHX^{LWW.3}{}_2$, —$CH_2X^{LWW.3}$, —$OCX^{LWW.3}{}_3$, —$OCH_2X^{LWW.3}$, —$OCHX^{LWW.3}{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{LWW.3}$ is independently —F, —Cl, —Br, or —I.

In the event that any R group recited in a claim or chemical formula description set forth herein ($R^{WW}$ substituent) is not specifically defined in this disclosure, then that R group ($R^{WW}$ group) is hereby defined as independently oxo, halogen, —$CX^{WW}{}_3$, —$CHX^{WW}{}_2$, —$CH_2X^{WW}$, —$OCX^{WW}{}_3$, —$OCH_2X^{WW}$, —$OCHX^{WW}{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$N_3$, $R^{WW.1}$-substituted or unsubstituted alkyl (e.g., $C_1$-$C_8$, $C_1$-$C_6$, $C_1$-$C_4$, or $C_1$-$C_2$), $R^{WW.1}$-substituted or unsubstituted heteroalkyl (e.g., 2 to 8 membered, 2 to 6 membered, 4 to 6 membered, 2 to 3 membered, or 4 to 5 membered), $R^{WW.1}$-substituted or unsubstituted cycloalkyl (e.g., $C_3$-$C_8$, $C_3$-$C_6$, $C_4$-$C_6$, or $C_5$-$C_6$), $R^{WW.1}$-substituted or unsubstituted heterocycloalkyl (e.g., 3 to 8 membered, 3 to 6 membered, 4 to 6 membered, 4 to 5 membered, or 5 to 6 membered), $R^{WW.1}$-substituted or unsubstituted aryl (e.g., $C_6$-$C_{12}$, $C_6$-$C_{10}$, or phenyl), or $R^{WW.1}$-substituted or unsubstituted heteroaryl (e.g., 5 to 12 membered, 5 to 10 membered, 5 to 9 membered, or 5 to 6 membered). Again, "WW" represents the stated superscript number of the subject R group (e.g., 1, 2, 3, 1A, 2A, 3A, 1B, 2B, 3B, etc.). $R^{WW.1}$, as well as $X^{WW}$, $R^{WW.2}$, and $R^{WW.3}$, are as defined above.

In the event that any L linker group recited in a claim or chemical formula description set forth herein (i.e., an $L^{WW}$ substituent) is not explicitly defined, then that L group ($L^{WW}$ group) is herein defined as independently —O—, —NH—, —COO—, —CONH—, —S—, —$SO_2NH$—, $R^{LWW.1}$-substituted or unsubstituted alkylene (e.g., $C_1$-$C_8$, $C_1$-$C_6$, $C_1$-$C_4$, or $C_1$-$C_2$), $R^{LWW.1}$-substituted or unsubstituted heteroalkylene (e.g., 2 to 8 membered, 2 to 6 membered, 4 to 6 membered, 2 to 3 membered, or 4 to 5 membered), $R^{LWW.1}$-substituted or unsubstituted cycloalkylene (e.g., $C_3$-$C_8$, $C_3$-$C_6$, $C_4$-$C_6$, or $C_5$-$C_6$), $R^{LWW.1}$-substituted or unsubstituted heterocycloalkylene (e.g., 3 to 8 membered, 3 to 6 membered, 4 to 6 membered, 4 to 5 membered, or 5 to 6 membered), $R^{LWW.1}$-substituted or unsubstituted arylene (e.g., $C_6$-$C_{12}$, $C_6$-$C_{10}$, or phenyl), or $R^{LWW.1}$-substituted or unsubstituted heteroarylene (e.g., 5 to 12 membered, 5 to 10 membered, 5 to 9 membered, or 5 to 6 membered). Again, "WW" represents the stated superscript number of the subject L group (e.g., 1, 2, 3, 1A, 2A, 3A, 1B, 2B, 3B, etc.). $R^{LWW.1}$ is as defined above.

For example, an $R^{WW}$ substituent may be substituted with a first substituent group $R^{WW}$. When $R^{WW}$ is phenyl, the said phenyl group is optionally substituted by one or more $R^{WW.1}$. When $R^{WW.1}$ is substituted alkyl (e.g., methyl), the said alkyl group is optionally substituted by one or more $R^{WW.2}$. The compound that could be formed may include, but are not limited to, the compounds depicted below wherein $R^{WW.2}$ is optionally substituted cyclopentyl, optionally substituted pyridyl, —$NH_2$, or optionally substituted benzoxazolyl, wherein each such optionally substituted $R^{WW.2}$ substituent group is optionally substituted with one or more $R^{WW.3}$. By way of non-limiting examples, such $R^{WW.3}$ substituents could be independently unsubstituted alkyl (e.g., ethyl), halogen (e.g., fluoro), or OH, as shown below.

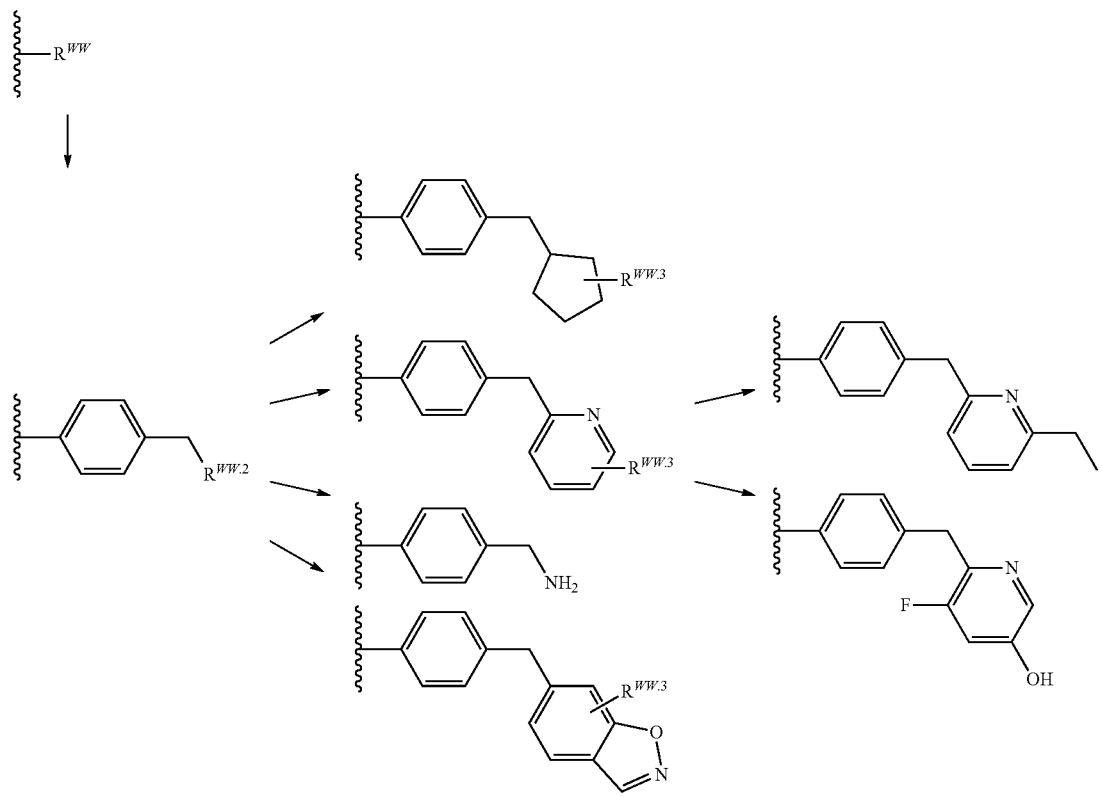

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

Descriptions of the compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g., methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Prodrugs of the compounds described herein may be converted in vivo after administration. Additionally, prodrugs can be converted to the compounds of the present invention by chemical or biochemical methods in an ex vivo environment, such as, for example, when contacted with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

The terms "polypeptide," "peptide," and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A polypeptide, or a cell is "recombinant" when it is artificial or engineered, or derived from or contains an artificial or engineered protein or nucleic acid (e.g., non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

"Contacting" is used in accordance with its plain ordinary meaning and refers to the process of allowing at least two distinct species (e.g., chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture. The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

As defined herein, the term "activation", "activate", "activating", "activator", and the like in reference to a protein-inhibitor interaction means positively affecting (e.g., increasing) the activity or function of the protein relative to the activity or function of the protein in the absence of the activator. In embodiments activation means positively affecting (e.g., increasing) the concentration or levels of the protein relative to the concentration or level of the protein in the absence of the activator. The terms may reference activation, or activating, sensitizing, or up-regulating signal transduction or enzymatic activity or the amount of a protein decreased in a disease. Thus, activation may include, at least in part, partially or totally increasing stimulation, increasing or enabling activation, or activating, sensitizing, or up-regulating signal transduction or enzymatic activity or the amount of a protein associated with a disease (e.g., a protein which is decreased in a disease relative to a non-diseased control). Activation may include, at least in part, partially or totally increasing stimulation, increasing or enabling activation, or activating, sensitizing, or up-regulating signal transduction or enzymatic activity or the amount of a protein.

As defined herein, the term "inhibition", "inhibit", "inhibiting" and the like in reference to a protein-inhibitor interaction means negatively affecting (e.g., decreasing) the activity or function of the protein relative to the activity or function of the protein in the absence of the inhibitor. In embodiments inhibition means negatively affecting (e.g., decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g., an inhibitor binds to the target protein). In embodiments, inhibition refers to a reduction of activity of a target protein from an indirect interaction (e.g., an inhibitor binds to a protein that activates the target protein, thereby preventing target protein activation).

The terms "inhibitor" or "repressor" or "antagonist" or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist.

The term "streptavidin" refers to a tetrameric protein (including homologs, isoforms, and functional fragments thereof) capable of binding biotin. The term includes any recombinant or naturally-occurring form of streptavidin variants thereof that maintain streptavidin activity (e.g., within at least 30%, 40%, 50%, 60%, 70%, 80%, 90%, 95%, or 100% activity compared to wildtype streptavidin).

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

An "effective amount" is an amount sufficient for a compound to accomplish a stated purpose relative to the absence of the compound (e.g., achieve the effect for which it is administered, treat a disease, reduce enzyme activity, increase enzyme activity, reduce a signaling pathway, or reduce one or more symptoms of a disease or condition). An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

The term "aberrant" as used herein refers to different from normal. When used to describe enzymatic activity or protein function, aberrant refers to activity or function that is greater or less than a normal control or the average of normal non-diseased control samples.

"Nucleic acid" or "oligonucleotide" or "polynucleotide" or grammatical equivalents used herein means at least two nucleotides covalently linked together. The term "nucleic acid" includes single-, double-, or multiple-stranded DNA, RNA and analogs (derivatives) thereof. Oligonucleotides are typically from about 5, 6, 7, 8, 9, 10, 12, 15, 25, 30, 40, 50 or more nucleotides in length, up to about 100 nucleotides in length. Nucleic acids and polynucleotides are a polymers of any length, including longer lengths, e.g., 200, 300, 500, 1000, 2000, 3000, 5000, 7000, 10,000, etc. In certain embodiments the nucleic acids herein contain phosphodiester bonds. In other embodiments, nucleic acid analogs are included that may have alternate backbones, comprising, e.g., phosphoramidate, phosphorothioate, phosphorodithioate, or O-methylphosphoroamidite linkages (see, Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. A residue of a nucleic acid, as referred to herein, is a monomer of the nucleic acid (e.g., a nucleotide).

A particular nucleic acid sequence also encompasses "splice variants." Similarly, a particular protein encoded by a nucleic acid encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher, et al., *J. Biol. Chem.* 273(52):35095-35101 (1998).

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Nucleotide," as used herein, refers to a nucleoside-5'-polyphosphate compound, or a structural analog thereof, which can be incorporated (e.g., partially incorporated as a nucleoside-5'-monophosphate or derivative thereof) by a nucleic acid polymerase to extend a growing nucleic acid chain (such as a primer). Nucleotides may include bases such as guanine (G), adenine (A), thymine, (T), uracil (U), cytosine (C), or analogues thereof, and may comprise 2, 3, 4, 5, 6, 7, 8, or more phosphates in the phosphate group. Nucleotides may be modified at one or more of the base, sugar, or phosphate group. A nucleotide may have a label or tag attached (a "labeled nucleotide" or "tagged nucleotide"). In embodiments, the nucleotide is a modified nucleotide which terminates primer extension reversibly. In embodiments, nucleotides may further include a polymerase-compatible cleavable moiety covalently bound to the 3' oxygen.

A "nucleoside" is structurally similar to a nucleotide but lacks the phosphate moieties. An example of a nucleoside analog would be one in which the label is linked to the base and there is no phosphate group attached to the sugar molecule.

The terms also encompass nucleic acids containing known nucleotide analogs or modified backbone residues or linkages, which are synthetic, naturally occurring, or non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see, Eckstein, Oligonucleotides and Analogues: A Practical Approach, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g., phosphorodiamidate morpholino oligos or locked nucleic acids (LNA) as known in the art), including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

In embodiments, "nucleotide analogue," "nucleotide analog," or "nucleotide derivative" shall mean an analogue of A, G, C, T or U (that is, an analogue or derivative of a nucleotide comprising the base A, G, C, T or U), including a phosphate group, which may be recognized by DNA or RNA polymerase (whichever is applicable) and may be incorporated into a strand of DNA or RNA (whichever is appropriate). Examples of nucleotide analogues include, without limitation, 7-deaza-adenine, 7-deaza-guanine, the analogues of deoxynucleotides shown herein, analogues in which a label is attached through a cleavable linker to the 5-position of cytosine or thymine or to the 7-position of deaza-adenine or deaza-guanine, and analogues in which a small chemical moiety is used to cap the —OH group at the 3-position of deoxyribose. Nucleotide analogues and DNA polymerase-based DNA sequencing are also described in U.S. Pat. No. 6,664,079, which is incorporated herein by reference in its entirety for all purposes.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2, or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 10 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., *Current Protocols in Molecular Biology* (Ausubel et al., eds. 1995 supplement)).

The term "bioconjugate group" or "bioconjugate reactive moiety" or "bioconjugate reactive group" refers to a chemical moiety which participates in a reaction to form bioconjugate linker (e.g., covalent linker). Non-limiting examples of bioconjugate groups include —NH$_2$, —COOH, —COOCH$_3$, —N-hydroxysuccinimide, -maleimide,

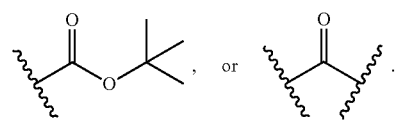

In embodiments, the bioconjugate reactive group may be protected (e.g., with a protecting group). In embodiments, the bioconjugate reactive moiety is

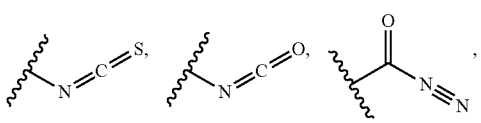

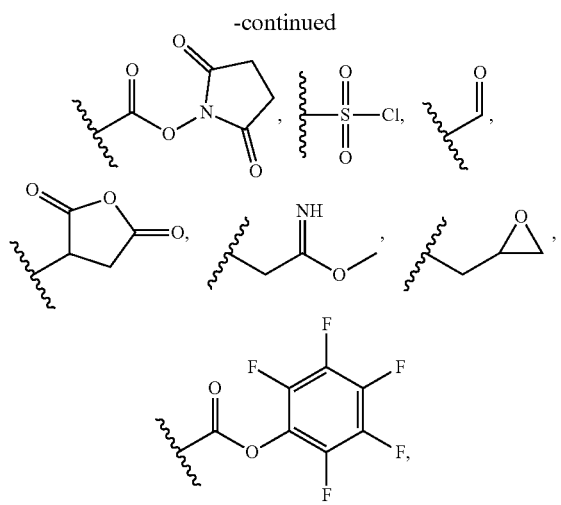

or —NH₂.

As used herein, the term "bioconjugate" or "bioconjugate linker" refers to the resulting association between atoms or molecules of bioconjugate reactive groups. The association can be direct or indirect. For example, a conjugate between a first bioconjugate reactive group (e.g., —NH₂, —COOH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g., a first linker of second linker), or indirect, e.g., by non-covalent bond (e.g., electrostatic interactions (e.g., ionic bond, hydrogen bond, halogen bond), van der Waals interactions (e.g., dipole-dipole, dipole-induced dipole, London dispersion), ring stacking (pi effects), hydrophobic interactions and the like). In embodiments, bioconjugates or bioconjugate linkers are formed using bioconjugate chemistry (i.e., the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g., a sulfhydryl). In embodiments, the first bioconjugate reactive group (e.g., haloacetyl moiety) is covalently attached to the second bioconjugate reactive group (e.g., a sulfhydryl). In embodiments, the first bioconjugate reactive group (e.g., pyridyl moiety) is covalently attached to the second bioconjugate reactive group (e.g., a sulfhydryl). In embodiments, the first bioconjugate reactive group (e.g., —N-hydroxysuccinimide moiety) is covalently attached to the second bioconjugate reactive group (e.g., an amine). In embodiments, the first bioconjugate reactive group (e.g., maleimide moiety) is covalently attached to the second bioconjugate reactive group (e.g., a sulfhydryl). In embodiments, the first bioconjugate reactive group (e.g., -sulfo-N-hydroxysuccin-imide moiety) is covalently attached to the second bioconjugate reactive group (e.g., an amine). In embodiments, the first bioconjugate reactive group (e.g., —COOH) is covalently attached to the second bioconjugate reactive group (e.g., 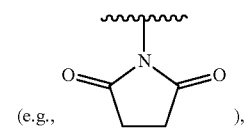 [SMILES: *N1C(=O)CCC1=O]), thereby forming a bioconjugate

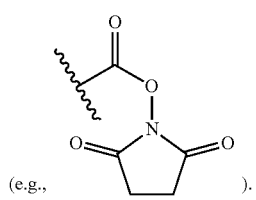 [SMILES: *C(=O)ON1C(=O)CCC1=O]

(e.g., ).

In embodiments, the first bioconjugate reactive group (e.g., —NH₂) is covalently attached to the second bioconjugate reactive group (e.g., ), thereby forming a bioconjugate (e.g., 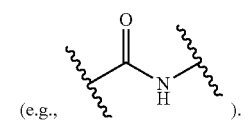).

In embodiments, the first bioconjugate reactive group (e.g., a coupling reagent) is covalently attached to the second bioconjugate reactive group (e.g., ), thereby forming a bioconjugate (e.g., 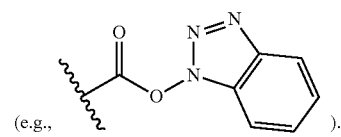 [SMILES: *C(=O)On1nnc2ccccc21]).

Useful bioconjugate reactive moieties used for bioconjugate chemistries herein include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;
(b) hydroxyl groups which can be converted to esters, ethers, aldehydes, etc.
(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;
(d) dienophile groups which are capable of participating in Diels-Alder reactions such as, for example, maleimido or maleimide groups;
(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;
(f) sulfonyl halide groups for subsequent reaction with amines, for example, to form sulfonamides;
(g) thiol groups, which can be converted to disulfides, reacted with acyl halides, or bonded to metals such as gold, or react with maleimides;
(h) amine or sulfhydryl groups (e.g., present in cysteine), which can be, for example, acylated, alkylated or oxidized;
(i) alkenes, which can undergo, for example, cycloadditions, acylation, Michael addition, etc;
(j) epoxides, which can react with, for example, amines and hydroxyl compounds;
(k) phosphoramidites and other standard functional groups useful in nucleic acid synthesis;
(l) metal silicon oxide bonding;
(m) metal bonding to reactive phosphorus groups (e.g., phosphines) to form, for example, phosphate diester bonds;
(n) azides coupled to alkynes using copper catalyzed cycloaddition click chemistry; and
(o) biotin conjugate can react with avidin or strepavidin to form a avidin-biotin complex or streptavidin-biotin complex.

The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

The term "monophosphate" is used in accordance with its ordinary meaning in the arts and refers to a moiety having the formula:

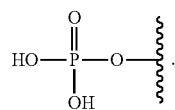

The term "polyphosphate" refers to at least two phosphate groups, having the formula:

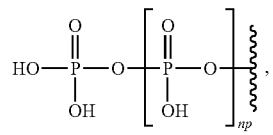

wherein np is an integer of 1 or greater. In embodiments, np is an integer from 0 to 5. In embodiments, np is an integer from 0 to 2. In embodiments, np is 2.

The term "base" as used herein refers to a divalent purine or pyrimidine compound or a derivative thereof, that may be a constituent of nucleic acid (i.e., DNA or RNA, or a derivative thereof). In embodiments, the base is a derivative of a naturally occurring DNA or RNA base (e.g., a base analogue). In embodiments, the base is a hybridizing base. In embodiments, the base hybridizes to a complementary base. In embodiments, the base is capable of forming at least one hydrogen bond with a complementary base (e.g., adenine hydrogen bonds with thymine, adenine hydrogen bonds with uracil, guanine pairs with cytosine). Non-limiting examples of a base include divalent forms of cytosine or a derivative thereof (e.g., cytosine analogue), guanine or a derivative thereof (e.g., guanine analogue), adenine or a derivative thereof (e.g., adenine analogue), thymine or a derivative thereof (e.g., thymine analogue), uracil or a derivative thereof (e.g., uracil analogue), hypoxanthine or a derivative thereof (e.g., hypoxanthine analogue), xanthine or a derivative thereof (e.g., xanthine analogue), 7-methylguanine or a derivative thereof (e.g., 7-methylguanine analogue), deaza-adenine or a derivative thereof (e.g., deaza-adenine analogue), deaza-guanine or a derivative thereof (e.g., deaza-guanine), deaza-hypoxanthine or a derivative thereof, 5,6-dihydrouracil or a derivative thereof (e.g., 5,6-dihydrouracil analogue), 5-methylcytosine or a derivative thereof (e.g., 5-methylcytosine analogue), or 5-hydroxymethylcytosine or a derivative thereof (e.g., 5-hydroxymethylcytosine analogue). In embodiments, the base is a divalent form of adenine, guanine, hypoxanthine, xanthine, theobromine, caffeine, uric acid, or isoguanine. In embodiments, the base is

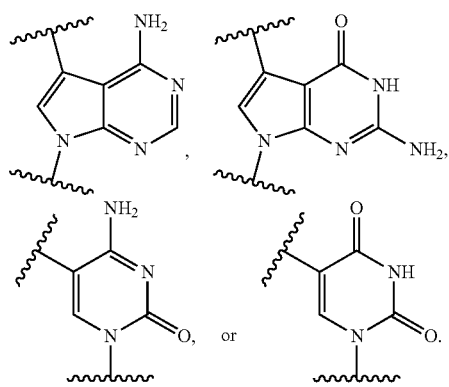

The term "non-covalent linker" is used in accordance with its ordinary meaning and refers to a divalent moiety which includes at least two molecules that are not covalently linked to each other but are capable of interacting with each other via a non-covalent bond (e.g., electrostatic interactions (e.g., ionic bond, hydrogen bond, halogen bond) or van der Waals interactions (e.g., dipole-dipole, dipole-induced dipole, London dispersion). In embodiments, the non-covalent linker is the result of two molecules that are not covalently linked to each other that interact with each other via a non-covalent bond.

The term "cleavable linker" or "cleavable moiety" as used herein refers to a divalent or monovalent, respectively, moiety which is capable of being separated (e.g., detached, split, disconnected, hydrolyzed, a stable bond within the moiety is broken) into distinct entities. A cleavable linker is cleavable (e.g., specifically cleavable) in response to external stimuli (e.g., enzymes, nucleophilic/basic reagents, reducing agents, photo-irradiation, electrophilic/acidic reagents, organometallic and metal reagents, or oxidizing reagents). A chemically cleavable linker refers to a linker which is capable of being split in response to the presence of a chemical (e.g., acid, base, oxidizing agent, reducing agent, Pd(0), tris-(2-carboxyethyl)phosphine, dilute nitrous acid, fluoride, tris(3-hydroxypropyl)phosphine), sodium dithionite ($Na_2S_2O_4$), or hydrazine ($N_2H_4$)). A chemically cleavable linker is non-enzymatically cleavable. In embodiments, the cleavable linker is cleaved by contacting the cleavable linker with a cleaving agent. In embodiments, the cleaving agent is a phosphine containing reagent (e.g., TCEP or THPP), sodium dithionite ($Na_2S_2O_4$), weak acid, hydrazine ($N_2H_4$), Pd(0), or light-irradiation (e.g., ultraviolet radiation).

A photocleavable linker (e.g., including or consisting of an o-nitrobenzyl group) refers to a linker which is capable of being split in response to photo-irradiation (e.g., ultraviolet radiation). An acid-cleavable linker refers to a linker which is capable of being split in response to a change in the pH (e.g., increased acidity). A base-cleavable linker refers to a linker which is capable of being split in response to a change in the pH (e.g., decreased acidity). An oxidant-cleavable linker refers to a linker which is capable of being split in response to the presence of an oxidizing agent. A reductant-cleavable linker refers to a linker which is capable of being split in response to the presence of an reducing agent (e.g., Tris(3-hydroxypropyl)phosphine). In embodiments, the cleavable linker is a dialkylketal linker, an azo linker, an allyl linker, a cyanoethyl linker, a 1-(4,4-dimethyl-2,6-dioxocyclohex-1-ylidene)ethyl linker, or a nitrobenzyl linker.

The term "orthogonally cleavable linker" or "orthogonal cleavable linker" as used herein refer to a cleavable linker that is cleaved by a first cleaving agent (e.g., enzyme, nucleophilic/basic reagent, reducing agent, photo-irradiation, electrophilic/acidic reagent, organometallic and metal reagent, oxidizing reagent) in a mixture of two or more different cleaving agents and is not cleaved by any other different cleaving agent in the mixture of two or more cleaving agents. For example, two different cleavable linkers are both orthogonal cleavable linkers when a mixture of the two different cleavable linkers are reacted with two different cleaving agents and each cleavable linker is cleaved by only one of the cleaving agents and not the other cleaving agent. In embodiments, an orthogonally cleavable linker is a cleavable linker that, following cleavage (e.g., following exposure to a cleaving agent), the two separated entities (e.g., fluorescent dye, bioconjugate reactive group) do not further react and form a new orthogonally cleavable linker.

The term "polymer" refers to a molecule including repeating subunits (e.g., polymerized monomers). For example, polymeric molecules may be based upon polyethylene glycol (PEG), tetraethylene glycol (TEG), polyvinylpyrrolidone (PVP), poly(xylene), or poly(p-xylylene). The term "polymerizable monomer" is used in accordance with its meaning in the art of polymer chemistry and refers to a compound that may covalently bind chemically to other monomer molecules (such as other polymerizable monomers that are the same or different) to form a polymer. In embodiments, polymer refers to PEG, having the formula:

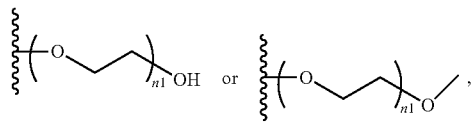

wherein n1 is an integer from 1 to 30.

The term "coupling reagent" is used in accordance with its plain ordinary meaning in the arts and refers to a substance (e.g., a compound or solution) which participates in chemical reaction and results in the formation of a covalent bond (e.g., between bioconjugate reactive moieties, between a bioconjugate reactive moiety and the coupling reagent). In embodiments, the level of reagent is depleted in the course of a chemical reaction. This is in contrast to a solvent, which typically does not get consumed over the course of the chemical reaction. In embodiments, the coupling reagent is a phosphonium reagent. Non-limiting examples of coupling reagents include dicyclohexylcarbodiimide (DCC), diisopropylcarbodiimide (DIC), (N-(3-Dimethylaminopropyl)-N'-ethylcarbodiimide (EDAC), (1-Hydroxybenzotriazole) (HOBt), (Hydroxy-3,4-dihydro-4-oxo-1,2,3-benzotriazine) (HOOBt), (4-(N,N-Dimethylamino)pyridine) (DMAP), (Benzotriazol-1-yloxy-tris (dimethylamino)-phosphonium hexafluorophosphate) (BOP), (Bromo-tripyrrolidino-phosphonium hexafluorophosphate) (PyBrOP), (Ethyl cyano(hydroxyimino)acetato-O2)-tri-(1-pyrrolidinyl)-phosphonium hexafluorophosphate) (PyOxim), (3-(Diethoxy-phosphoryloxy)-1,2,3-benzo[d] triazin-4(3H)-one) (DEPBT), (2-(1H-Benzotriazol-1-yl)-N,N,N',N'-tetramethylaminium tetrafluoroborate/hexafluorophosphate) (TBTU), (2-(6-Chloro-1H-benzotriazol-1-yl)-N,N,N',N'-tetramethylaminium hexafluorophosphate) (HCTU), (N-[(5-Chloro-1H-benzotriazol-1-yl)-dimethylamino-morpholino]-uronium hexafluorophosphate N-oxide) (HDMC), (2-(7-Aza-1H-benzotriazol-1-yl)-N,N,N',N'-tetramethylaminium tetrafluoroborate/hexafluorophosphate) (TATU), (2-(1-Oxy-pyridin-2-yl)-1,1,3,3-tetramethylisothiouronium tetrafluoroborate) (TOTT), (Tetramethylfluoroformamidinium hexafluorophosphate) (TFFH), benzotriazol-1-yl-oxytripyrrolidino-phosphonium hexafluorophosphate (PyBOP), 7-Azabenzotriazol-1-yloxy)tripyrrolidinophosphonium hexafluorophosphate (PyAOP), 6-Chloro-benzotriazole-1-yloxy-tris-pyrrolidinophosphonium hexafluorophosphate (PyClock), 1-[Bis(dimethylamino)methylene]-1H-1,2,3-triazolo[4,5-b] pyridinium 3-oxid hexafluorophosphate (HATU), or 2-(1H-benzotriazol-1-yl)-1,1,3,3-tetramethyluronium hexafluorophosphate (HBTU).

The term "solution" is used in accordance with its plain ordinary meaning in the arts and refers to a liquid mixture in which the minor component (e.g., a solute or compound) is distributed (e.g., uniformly distributed) within the major component (e.g., a solvent).

The term "organic solvent" as used herein is used in accordance with its ordinary meaning in chemistry and refers to a solvent which includes carbon. Non-limiting examples of organic solvents include acetic acid, acetone, acetonitrile, benzene, 1-butanol, 2-butanol, 2-butanone, t-butyl alcohol, carbon tetrachloride, chlorobenzene, chloroform, cyclohexane, 1,2-dichloroethane, diethylene glycol, diethyl ether, diglyme (diethylene glycol, dimethyl ether), 1,2-dimethoxyethane (glyme, DME), dimethylformamide (DMF), dimethyl sulfoxide (DMSO), 1,4-dioxane, ethanol, ethyl acetate, ethylene glycol, glycerin, heptane, hexamethylphosphoramide (HMPA), hexamethylphosphorous, triamide (HMPT), hexane, methanol, methyl t-butyl ether (MTBE), methylene chloride, N-methyl-2-pyrrolidinone (NMP), nitromethane, pentane, petroleum ether (ligroine), 1-propanol, 2-propanol, pyridine, tetrahydrofuran (THF), toluene, triethyl amine, o-xylene, m-xylene, or p-xylene. In embodiments, the organic solvent is or includes chloroform, dichloromethane, methanol, ethanol, tetrahydrofuran, or dioxane.

As used herein, the term "salt" refers to acid or base salts of the compounds described herein. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. In embodiments, compounds may be presented with a positive charge, for example

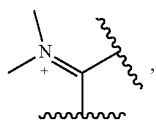

and it is understood an appropriate counter-ion (e.g., chloride ion, fluoride ion, or acetate ion) may also be present, though not explicitly shown. Likewise, for compounds having a negative charge

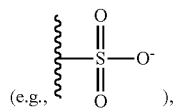

it is understood an appropriate counter-ion (e.g., a proton, sodium ion, potassium ion, or ammonium ion) may also be present, though not explicitly shown. The protonation state of the compound (e.g., a compound described herein) depends on the local environment (i.e., the pH of the environment), therefore, in embodiments, the compound may be described as having a moiety in a protonated state

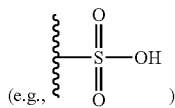 [SMILES: *S(=O)(=O)O]

or an ionic state

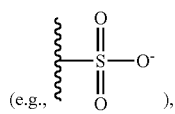

and it is understood these are interchangeable. In embodiments, the counter-ion is represented by the symbol M (e.g., $M^+$ or $M^-$).

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value.

The term "protecting group" is used in accordance with its ordinary meaning in organic chemistry and refers to a moiety covalently bound to a heteroatom, heterocycloalkyl, or heteroaryl to prevent reactivity of the heteroatom, heterocycloalkyl, or heteroaryl during one or more chemical reactions performed prior to removal of the protecting group. Typically a protecting group is bound to a heteroatom (e.g., O) during a part of a multipart synthesis wherein it is not desired to have the heteroatom react (e.g., a chemical reduction) with the reagent. Following protection the protecting group may be removed (e.g., by modulating the pH). In embodiments the protecting group is an alcohol protecting group. Non-limiting examples of alcohol protecting groups include acetyl, benzoyl, benzyl, methoxymethyl ether (MOM), tetrahydropyranyl (THP), and silyl ether (e.g., trimethylsilyl (TMS)). In embodiments the protecting group is an amine protecting group. Non-limiting examples of amine protecting groups include carbobenzyloxy (Cbz), tert-butyloxycarbonyl (BOC), 9-Fluorenylmethyloxycarbonyl (FMOC), acetyl, benzoyl, benzyl, carbamate, p-methoxybenzyl ether (PMB), and tosyl (Ts).

The term "polymerase-compatible cleavable moiety" or a "reversible terminator moiety" as used herein refers to a cleavable moiety which does not interfere with the function of a polymerase (e.g., DNA polymerase, modified DNA polymerase). Methods for determining the function of a polymerase contemplated herein are described in B. Rosenblum et al. (Nucleic Acids Res. 1997 Nov. 15; 25(22): 4500-4504); and Z. Zhu et al. (Nucleic Acids Res. 1994 Aug. 25; 22(16): 3418-3422), which are incorporated by reference herein in their entirety for all purposes. In embodiments, the polymerase-compatible cleavable moiety does not decrease the function of a polymerase relative to the absence of the polymerase-compatible cleavable moiety. In embodiments, the polymerase-compatible cleavable moiety does not negatively affect DNA polymerase recognition. In embodiments, the polymerase-compatible cleavable moiety does not negatively affect (e.g., limit) the read length of the DNA polymerase. Additional examples of a polymerase-compatible cleavable moiety may be found in U.S. Pat. No. 6,664,079, Ju J. et al. (2006) Proc Natl Acad Sci USA 103(52):19635-19640; Ruparel H. et al. (2005) Proc Natl Acad Sci USA 102(17):5932-5937; Wu J. et al. (2007) Proc Natl Acad Sci USA 104(104):16462-16467; Guo J. et al. (2008) Proc Natl Acad Sci USA 105(27): 9145-9150 Bentley D. R. et al. (2008) Nature 456(7218):53-59; or Hutter D. et al. (2010) Nucleosides Nucleotides & Nucleic Acids 29:879-895, which are incorporated herein by reference in their entirety for all purposes. In embodiments, a polymerase-compatible cleavable moiety includes an azido moiety or a dithiol linking moiety. In embodiments, the polymerase-compatible cleavable moiety is independently —$NH_2$, —CN, —$CH_3$, $C_2$-$C_6$ allyl (e.g., —$CH_2$—CH=$CH_2$), methoxyalkyl (e.g., —$CH_2$—O—$CH_3$), or —$CH_2N_3$. In embodiments, the polymerase-compatible cleavable moiety comprises a disulfide moiety. In embodiments, a polymerase-compatible cleavable moiety is a cleavable moiety on a nucleotide, nucleobase, nucleoside, or nucleic acid that does not interfere with the function of a polymerase (e.g., DNA polymerase, modified DNA polymerase). In embodiments, the reversible terminator moiety is

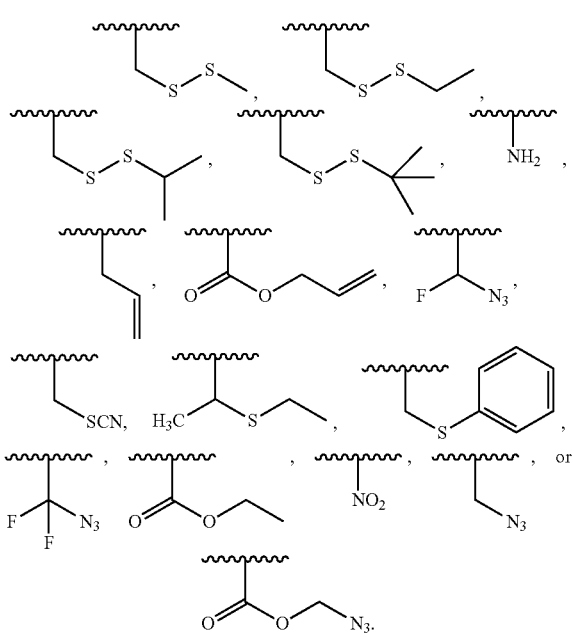

The term "allyl" as described herein refers to an unsubstituted methylene attached to a vinyl group (i.e., —CH=CH$_2$), having the formula

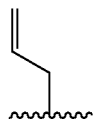

An "allyl linker" refers to a divalent unsubstituted methylene attached to a vinyl group, having the formula

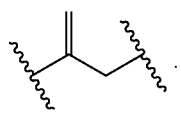 [SMILES: *CC(*)=C]

The terms "DNA polymerase" and "nucleic acid polymerase" are used in accordance with their plain ordinary meaning and refer to enzymes capable of synthesizing nucleic acid molecules from nucleotides (e.g., deoxyribonucleotides). Typically, a DNA polymerase adds nucleotides to the 3'-end of a DNA strand, one nucleotide at a time. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol μ DNA polymerase, Pol λ DNA polymerase, Pol σ DNA polymerase, Pol α DNA polymerase, Pol δ DNA polymerase, Pol ε DNA polymerase, Pol η DNA polymerase, Pol ι DNA polymerase, Pol κ DNA polymerase, Pol ζ DNA polymerase, Pol γ DNA polymerase, Pol θ DNA polymerase, Pol υ DNA polymerase, or a thermophilic nucleic acid polymerase (e.g., Taq polymerase, Therminator γ, 9°N polymerase (exo-), Therminator II, Therminator III, or Therminator IX).

A person of ordinary skill in the art will understand when a variable (e.g., moiety or linker) of a compound or of a compound genus (e.g., a genus described herein) is described by a name or formula of a standalone compound with all valencies filled, the unfilled valence(s) of the variable will be dictated by the context in which the variable is used. For example, when a variable of a compound as described herein is connected (e.g., bonded) to the remainder of the compound through a single bond, that variable is understood to represent a monovalent form (i.e., capable of forming a single bond due to an unfilled valence) of a standalone compound (e.g., if the variable is named "methane" in an embodiment but the variable is known to be attached by a single bond to the remainder of the compound, a person of ordinary skill in the art would understand that the variable is actually a monovalent form of methane, i.e., methyl or —CH$_3$). Likewise, for a linker variable (e.g., L$^1$, L$^2$, L$^3$, or L$^4$ as described herein), a person of ordinary skill in the art will understand that the variable is the divalent form of a standalone compound (e.g., if the variable is assigned to "PEG" or "polyethylene glycol" in an embodiment but the variable is connected by two separate bonds to the remainder of the compound, a person of ordinary skill in the art would understand that the variable is a divalent (i.e., capable of forming two bonds through two unfilled valences) form of PEG instead of the standalone compound PEG).

The term "leaving group" is used in accordance with its ordinary meaning in chemistry and refers to a moiety (e.g., atom, functional group, or molecule) that separates from the molecule following a chemical reaction (e.g., bond formation, reductive elimination, condensation, or cross-coupling reaction) involving an atom or chemical moiety to which the leaving group is attached, also referred to herein as the "leaving group reactive moiety", and a complementary reactive moiety (i.e., a chemical moiety that reacts with the leaving group reactive moiety) to form a new bond between the remnants of the leaving groups reactive moiety and the complementary reactive moiety. Thus, the leaving group reactive moiety and the complementary reactive moiety form a complementary reactive group pair. Non limiting examples of leaving groups include hydrogen, hydroxide, halogen (e.g., Br), perfluoroalkylsulfonates (e.g., triflate), tosylates, mesylates, water, alcohols, nitrate, phosphate, thioether, amines, ammonia, fluoride, carboxylate, phenoxides, boronic acid, boronate esters, substituted or unsubstituted piperazinyl, and alkoxides. In embodiments, two molecules are allowed to contact, wherein at least one of the molecules has a leaving group, and upon a reaction and/or bond formation (e.g., acyloin condensation, aldol condensation, Claisen condensation, or Stille reaction) the leaving group(s) separate from the respective molecule. In embodiments, a leaving group is a bioconjugate reactive moiety. In embodiments, the leaving groups is designed to facilitate the reaction. In embodiments, the leaving group is a substituent group.

The terms "detect" and "detecting" as used herein refer to the act of viewing (e.g., imaging, indicating the presence of, quantifying, or measuring (e.g., spectroscopic measurement), an agent based on an identifiable characteristic of the agent, for example, the light emitted from the present compounds. For example, the compound described herein can be bound to an agent, and, upon being exposed to an absorption light, will emit an emission light. The presence of an emission light can indicate the presence of the agent. Likewise, the quantification of the emitted light intensity can be used to measure the concentration of the agent.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay, etc.) from one location to another. For example, kits include one or more enclosures (e.g., boxes) containing the relevant reaction reagents and/or supporting materials. As used herein, the term "fragmented kit" refers to a delivery system comprising two or more separate containers that each contain a subportion of the total kit components. The containers may be delivered to the intended recipient together or separately. For example, a first container may contain an enzyme for use in an assay, while a second container contains oligonucleotides. In contrast, a "combined kit" refers to a delivery system containing all of the components of a reaction assay in a single container (e.g., in a single box housing each of the desired components). The term "kit" includes both fragmented and combined kits.

The terms "fluorophore" or "fluorescent agent" are used interchangeably and refer to a substance, compound, agent, or composition (e.g., compound) that can absorb light at one or more wavelengths and re-emit light at one or more longer wavelengths, relative to the one or more wavelengths of absorbed light. Examples of fluorophores that may be included in the compounds and compositions described herein include fluorescent proteins, xanthene derivatives (e.g., fluorescein, rhodamine, Oregon green, eosin, or Texas red), cyanine and derivatives (e.g., cyanine, indocarbocyanine, oxacarbocyanine, thiacarbocyanine, or merocyanine), napththalene derivatives (e.g., dansyl or prodan derivatives), coumarin and derivatives, oxadiazole derivatives (e.g., pyridyloxazole, nitrobenzoxadiazole or benzoxadiazole), anthracene derivatives (e.g., anthraquinones, DRAQ5, DRAQ7, or CyTRAK Orange), pyrene derivatives (e.g., cascade blue and derivatives), oxazine derivatives (e.g., Nile red, Nile blue, cresyl violet, or oxazine 170), acridine derivatives (e.g., proflavin, acridine orange, acridine yellow), arylmethine derivatives (e.g., auramine, crystal violet, or malachite green), tetrapyrrole derivatives (e.g., porphin, phthalocyanine, bilirubin), CF Dye™, DRAQ™, CyTRAK™, BODIPY™, Alexa Fluor™ DyLight Fluor™, Atto™, Tracy™, FluoProbes™, Abberior Dyes™, DY™ dyes, MegaStokes Dyes™, Sulfo Cy™, Seta™ dyes, SeTau™ dyes, Square Dyes™, Quasar™ dyes, Cal Fluor™ dyes, SureLight Dyes™, PerCP™, Phycobilisomes™, APC™, APCXL™, RPE™ and/or BPE™. A fluorescent moiety is a radical of a fluorescent agent. The emission from the fluorophores can be detected by any number of methods, including but not limited to, fluorescence spectroscopy, fluorescence microscopy, fluorimeters, fluorescent plate readers, infrared scanner analysis, laser scanning confocal microscopy, automated confocal nanoscanning, laser spectrophotometers, fluorescent-activated cell sorters (FACS), image-based analyzers and fluorescent scanners (e.g., gel/membrane scanners).

II. Compounds and Kits

In an aspect is provided a compound, or salt thereof, having the formula:

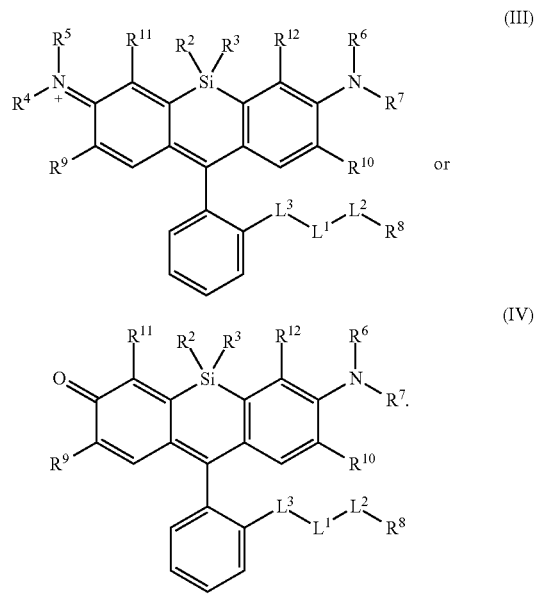

$L^3$ is a bond, —S(O)$_2$—, —NH—, —O—, —S—, —C(O)—, —C(O)NR$^1$—, —NR$^1$C(O)—, —NR$^1$C(O)NR$^{1A}$—, —S(O)$_2$NR$^1$—, —NR$^1$S(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^3$ does not include a —C(O)O— moiety. In embodiments, $L^3$ is not —C(O)O—. In embodiments, $L^3$ does not include an —OC(O)— moiety. In embodiments, $L^3$ is not —OC(O)—. In embodiments, $L^3$ is not —C(O)NH—.

$L^1$ and $L^2$ are each independently a bond or a covalent linker. In embodiments, at least one of $L^1$, $L^2$, and $L^3$ is not a bond. In embodiments, $L^3$ is not a bond. In embodiments, $L^2$ is not a bond. In embodiments, $L^1$ is not a bond.

$R^1$, $R^{1A}$, $R^4$, $R^5$, $R^6$, and $R^7$ are each independently hydrogen, halogen, —CF$_3$, —CCl$_3$, —CI$_3$, —CBr$_3$, —CHF$_2$, —CHCl$_2$, —CHI$_2$, —CHBr$_2$, —CH$_2$F, —CH$_2$Cl, —CH$_2$I, —CH$_2$Br, —OCH$_2$F, —OCH$_2$Cl, —OCH$_2$I, —OCH$_2$Br, —OCHF$_2$, —OCHCl$_2$, —OCHI$_2$, —OCHBr$_2$, —OCF$_3$, —OCCl$_3$, —OCI$_3$, —OCBr$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O) NHNH$_2$, —NHC=(O)NH$_2$, —NHSO$_2$H, —NHC=(O)H, —NHC(O)OH, —NHOH, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$ and $R^3$ are each independently substituted or unsubstituted alkyl, or substituted or unsubstituted heteroalkyl.

$R^8$ is hydrogen, a bioconjugate reactive moiety, a nucleotide, a nucleoside, or a nucleic acid.

$R^9$, $R^{10}$, $R^{11}$, and $R^{12}$ are each independently hydrogen, substituted or unsubstituted alkyl, or substituted or unsubstituted heteroalkyl.

$R^4$ and $R^5$ substituents bonded to the same nitrogen atom may optionally be joined to form a substituted or unsubstituted heterocycloalkyl, or substituted or unsubstituted heteroaryl.

$R^6$ and $R^7$ substituents bonded to the same nitrogen atom may optionally be joined to form a substituted or unsubstituted heterocycloalkyl, or substituted or unsubstituted heteroaryl.

$R^4$ and $R^9$ substituents may optionally be joined to form a substituted or unsubstituted heterocycloalkyl, or substituted or unsubstituted heteroaryl.

$R^7$ and $R^{10}$ substituents may optionally be joined to form a substituted or unsubstituted heterocycloalkyl, or substituted or unsubstituted heteroaryl.

$R^5$ and $R^{11}$ substituents may optionally be joined to form a substituted or unsubstituted heterocycloalkyl, or substituted or unsubstituted heteroaryl.

$R^6$ and $R^{12}$ substituents may optionally be joined to form a substituted or unsubstituted heterocycloalkyl, or substituted or unsubstituted heteroaryl.

In embodiments, $R^1$, $R^{14}$, $R^4$, $R^5$, $R^6$, and $R^7$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —OH, —$NH_2$, —COOH, —$CONH_2$, —SH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^1$ is independently halogen, —$CF_3$, —$CCl_3$, —$CI_3$, —$CBr_3$, —$CHF_2$, —$CHCl_2$, —$CHI_2$, —$CHBr_2$, —$CH_2F$, —$CH_2Cl$, —$CH_2I$, —$CH_2Br$, —$OCH_2F$, —$OCH_2Cl$, —$OCH_2I$, —$OCH_2Br$, —$OCHF_2$, —$OCHCl_2$, —$OCHI_2$, —$OCHBr_2$, —$OCF_3$, —$OCCl_3$, —$OCI_3$, —$OCBr_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^1$ is not hydrogen.

In embodiments, $R^1$ is independently halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —OH, —$NH_2$, —COOH, —$CONH_2$, —SH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{14}$ is independently halogen, —$CF_3$, —$CCl_3$, —$CI_3$, —$CBr_3$, —$CHF_2$, —$CHCl_2$, —$CHI_2$, —$CHBr_2$, —$CH_2F$, —$CH_2Cl$, —$CH_2I$, —$CH_2Br$, —$OCH_2F$, —$OCH_2Cl$, —$OCH_2I$, —$OCH_2Br$, —$OCHF_2$, —$OCHCl_2$, —$OCHI_2$, —$OCHBr_2$, —$OCF_3$, —$OCCl_3$, —$OCI_3$, —$OCBr_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{14}$ is not hydrogen.

In embodiments, $R^{14}$ is independently halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —OH, —$NH_2$, —COOH, —$CONH_2$, —SH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^8$ is hydrogen, a bioconjugate reactive moiety, or a nucleic acid. In embodiments, $R^8$ is hydrogen or a bioconjugate reactive moiety. In embodiments, $R^8$ is a nucleotide or nucleoside. In embodiments, $R^8$ is a nucleotide. In embodiments, $R^8$ is a nucleoside. In embodiments, $R^8$ is a nucleic acid.

In embodiments, the compound, or salt thereof, has the formula:

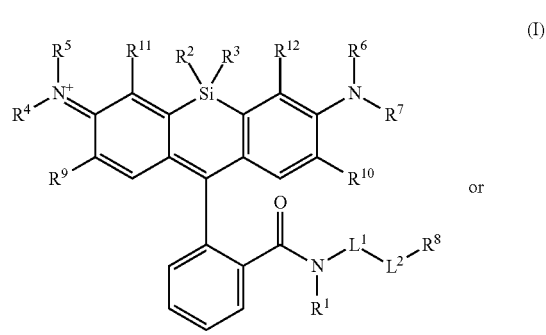

(I)

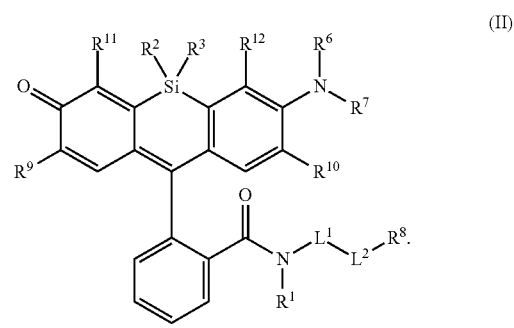

(II)

$L^1$, $L^2$, $R^1$, $R^2$, $R^3$, $R^4$, $R^5$, $R^6$, $R^7$, $R^8$, $R^9$, $R^{10}$, $R^{11}$, and $R^{12}$ are as described herein.

In an aspect is provided a compound, or salt thereof, having the formula:

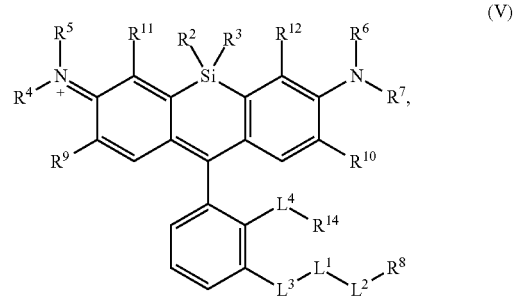

(V)

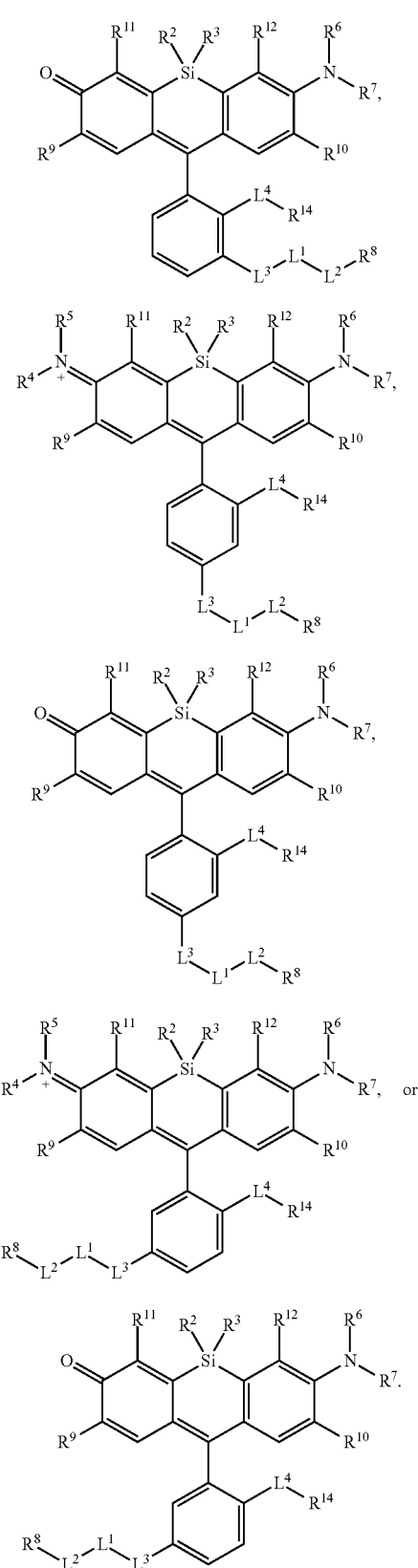

$L^1$, $L^2$, $L^3$, $R^2$, $R^3$, $R^4$, $R^5$, $R^6$, $R^7$, $R^8$, $R^9$, $R^{10}$, $R^{11}$, and $R^{12}$ are as described herein. $L^4$ is a bond, —S(O)$_2$—, —NH—, —O—, —S—, —C(O)—, —C(O)NR$^{54}$—, —NR$^{54}$C(O)—, —NR$^{54}$C(O)NR$^{54A}$—, —S(O)$_2$NR$^{54}$—, —NR$^{54}$S(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^{54}$ and $R^{54A}$ are each independently hydrogen, halogen, —CF$_3$, —CCl$_3$, —CI$_3$, —CBr$_3$, —CHF$_2$, —CHCl$_2$, —CHI$_2$, —CHBr$_2$, —CH$_2$F, —CH$_2$Cl, —CH$_2$I, —CH$_2$Br, —OCH$_2$F, —OCH$_2$Cl, —OCH$_2$I, —OCH$_2$Br, —OCHF$_2$, —OCHCl$_2$, —OCHI$_2$, —OCHBr$_2$, —OCF$_3$, —OCCl$_3$, —OCI$_3$, —OCBr$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC═(O) NHNH$_2$, —NHC═(O)NH$_2$, —NHSO$_2$H, —NHC═(O)H, —NHC(O)OH, —NHOH, —PO$_4$H, —PO$_3$H, —N$_3$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{10}$ or phenyl), or substituted or unsubstituted heteroaryl (e.g., 5 to 10 membered, 5 to 9 membered, or 5 to 6 membered). $R^{14}$ is independently hydrogen, halogen, —CF$_3$, —CCl$_3$, —CI$_3$, —CBr$_3$, —CHF$_2$, —CHCl$_2$, —CHI$_2$, —CHBr$_2$, —CH$_2$F, —CH$_2$Cl, —CH$_2$I, —CH$_2$Br, —OCH$_2$F, —OCH$_2$Cl, —OCH$_2$I, —OCH$_2$Br, —OCHF$_2$, —OCHCl$_2$, —OCHI$_2$, —OCHBr$_2$, —OCF$_3$, —OCCl$_3$, —OCI$_3$, —OCBr$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)OH, —NHOH, —PO$_4$H, —PO$_3$H, —N$_3$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{10}$ or phenyl), substituted or unsubstituted heteroaryl (e.g., 5 to 10 membered, 5 to 9 membered, or 5 to 6 membered), or a polymer (e.g., a monovalent polymer). In embodiments, $L^4$ does not include a —C(O)O— moiety. In embodiments, $L^4$ is not —C(O) O—. In embodiments, $L^4$ does not include an —OC(O)— moiety. In embodiments, $L^4$ is not —OC(O)—.

In embodiments, the compound has the formula:

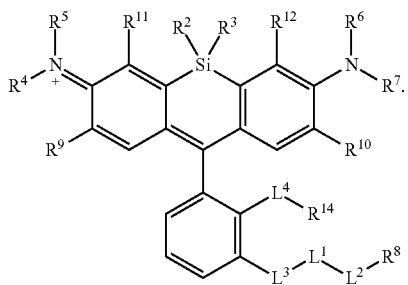

$L^1$, $L^2$, $L^3$, $L^4$, $R^2$, $R^3$, $R^4$, $R^5$, $R^6$, $R^7$, $R^8$, $R^9$, $R^{10}$, $R^{11}$, $R^{12}$, and $R^{14}$ are as described herein. In embodiments, the compound has the formula:

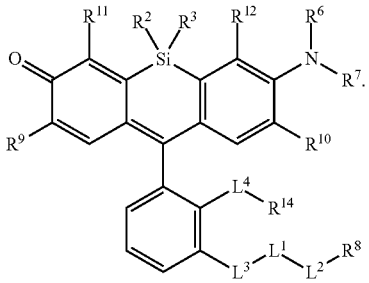
(VI)

$L^1$, $L^2$, $L^3$, $L^4$, $R^2$, $R^3$, $R^6$, $R^7$, $R^8$, $R^9$, $R^{10}$, $R^{11}$, $R^{12}$, and $R^{14}$ are as described herein. In embodiments, the compound has the formula:

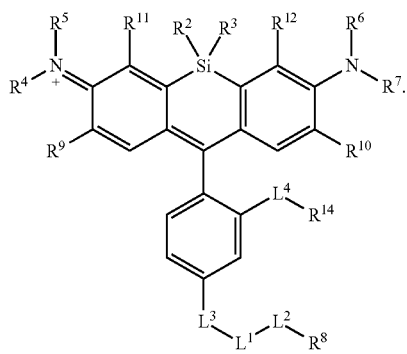
(VII)

$L^1$, $L^2$, $L^3$, $L^4$, $R^2$, $R^3$, $R^4$, $R^5$, $R^6$, $R^7$, $R^8$, $R^9$, $R^{10}$, $R^{11}$, $R^{12}$, and $R^{14}$ are as described herein. In embodiments, the compound has the formula:

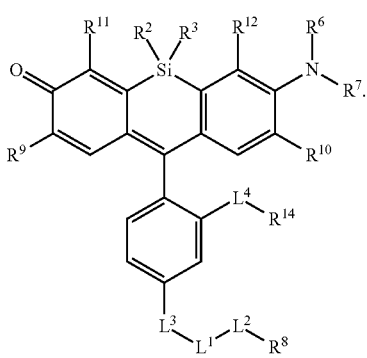
(VIII)

$L^1$, $L^2$, $L^3$, $L^4$, $R^2$, $R^3$, $R^6$, $R^7$, $R^8$, $R^9$, $R^{10}$, $R^{11}$, $R^{12}$, and $R^{14}$ are as described herein. In embodiments, the compound has the formula:

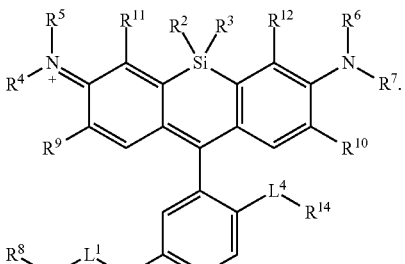
(IX)

$L^1$, $L^2$, $L^3$, $L^4$, $R^2$, $R^3$, $R^4$, $R^5$, $R^6$, $R^7$, $R^8$, $R^9$, $R^{10}$, $R^{11}$, $R^{12}$ and $R^{14}$ are as described herein. In embodiments, the compound has the formula:

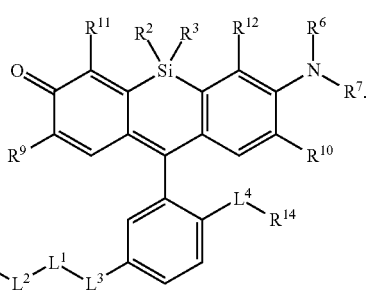
(X)

$L^1$, $L^2$, $L^3$, $L^4$, $R^2$, $R^3$, $R^6$, $R^7$, $R^8$, $R^9$, $R^{10}$, $R^{11}$, $R^{12}$, and $R^{14}$ are as described herein.

In embodiments, $R^{14}$ is independently hydrogen, halogen, —$CF_3$, —$CCl_3$, —$CI_3$, —$CBr_3$, —$CHF_2$, —$CHCl_2$, —$CHI_2$, —$CHBr_2$, —$CH_2F$, —$CH_2Cl$, —$CH_2I$, —$CH_2Br$, —$OCH_2F$, —$OCH_2Cl$, —$OCH_2I$, —$OCH_2Br$, —$OCHF_2$, —$OCHCl_2$, —$OCHI_2$, —$OCHBr_2$, —$OCF_3$, —$OCCl_3$, —$OCI_3$, —$OCBr_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$PO_4H$, —$PO_3H$, —$N_3$, $R^{44}$-substituted or unsubstituted alkyl, $R^{44}$-substituted or unsubstituted heteroalkyl, $R^{44}$-substituted or unsubstituted cycloalkyl, $R^{44}$-substituted or unsubstituted heterocycloalkyl, $R^{44}$-substituted or unsubstituted aryl, $R^{44}$-substituted or unsubstituted heteroaryl, or a polymer. In embodiments, $R^{14}$ is a polymer (e.g., a monovalent polymer). In embodiments, $R^{14}$ is independently —$PO_3H$, —$PO_4H$, —$SO_2NH_2$, —$SO_3H$, or —$SO_4H$. In embodiments, $R^{14}$ is independently —$SO_3H$. In embodiments, $R^{14}$ is independently —$PO_3H$. In embodiments, $R^{14}$ is independently —$SO_2NH_2$. In embodiments, $R^{14}$ is independently —$SO_4H$. In embodiments, $R^{14}$ is independently —$PO_4H$. In embodiments, when $L^{14}$ is a bond, $R^{14}$ is not —COOH. In embodiments, when $L^{14}$ is a bond, $R^{14}$ is not —C(O)NH.

$R^{44}$ is independently oxo, halogen, —$CF_3$, —$CCl_3$, —$CI_3$, —$CBr_3$, —$CHF_2$, —$CHCl_2$, —$CHI_2$, —$CHBr_2$, —$CH_2F$, —$CH_2Cl$, —$CH_2I$, —$CH_2Br$, —$OCH_2F$, —$OCH_2Cl$, —$OCH_2I$, —$OCH_2Br$, —$OCHF_2$, —$OCHCl_2$, —$OCHI_2$, —$OCHBr_2$, —$OCF_3$, —$OCCl_3$, —$OCI_3$, —$OCBr_3$, —CN, —OH, —$NH_2$, —COOH, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —PO$_4$H, —PO$_3$H, —N$_3$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered). In embodiments, R$^{44}$ is independently —PO$_3$H, —PO$_4$H, —SO$_2$NH$_2$, —SO$_3$H, or —SO$_4$H. In embodiments, R$^{44}$ is independently —SO$_3$H. In embodiments, R$^{44}$ is independently —PO$_3$H. In embodiments, R$^{44}$ is independently —SO$_2$NH$_2$. In embodiments, R$^{44}$ is independently —SO$_4$H. In embodiments, R$^{44}$ is independently —PO$_4$H.

In embodiments, L$^4$ is independently a bond, —S(O)$_2$—, —NH—, —O—, —S—, —C(O)—, —C(O)NR$^{54}$—, —NR$^{54}$C(O)—, —NR$^{54}$C(O)NR$^{54A}$—, —S(O)$_2$NR$^{54}$—, —NR$^{54}$S(O)$_2$—, R$^{54}$-substituted or unsubstituted alkylene, R$^{54}$-substituted or unsubstituted heteroalkylene, R$^{54}$-substituted or unsubstituted cycloalkylene, R$^{54}$-substituted or unsubstituted heterocycloalkylene, R$^{54}$-substituted or unsubstituted arylene, or R$^{54}$-substituted or unsubstituted heteroarylene.

In embodiments, L$^4$ is independently

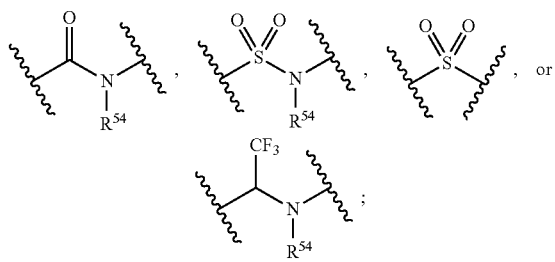

, or and R$^{54}$ is as described herein, including in embodiments. In embodiments, L$^4$ is independently

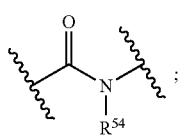

and R$^{54}$ is as described herein, including in embodiments. In embodiments, L$^4$ is independently

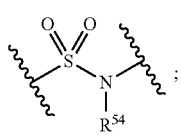

and R$^{54}$ is as described herein, including in embodiments. In embodiments, L$^4$ is independently

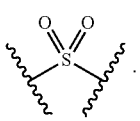

In embodiments, L$^4$ is independently

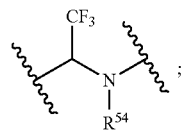

and R$^{54}$ is as described herein, including in embodiments.

In embodiments, R$^{54}$ is independently halogen, —CF$_3$, —CCl$_3$, —CI$_3$, —CBr$_3$, —CHF$_2$, —CHCl$_2$, —CHI$_2$, —CHBr$_2$, —CH$_2$F, —CH$_2$Cl, —CH$_2$I, —CH$_2$Br, —OCH$_2$F, —OCH$_2$Cl, —OCH$_2$I, —OCH$_2$Br, —OCHF$_2$, —OCHCl$_2$, —OCHI$_2$, —OCHBr$_2$, —OCF$_3$, —OCCl$_3$, —OCI$_3$, —OCBr$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —PO$_4$H, —PO$_3$H, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, R$^{54}$ is independently substituted or unsubstituted C$_1$ alkyl. In embodiments, R$^{54}$ is independently substituted or unsubstituted C$_2$ alkyl. In embodiments, R$^{54}$ is independently substituted or unsubstituted C$_3$ alkyl. In embodiments, R$^{54}$ is independently substituted or unsubstituted C$_4$ alkyl. In embodiments, R$^{54}$ is independently substituted or unsubstituted C$_5$ alkyl. In embodiments, R$^{54}$ is independently substituted or unsubstituted C$_6$ alkyl. In embodiments, R$^{54}$ is independently substituted C$_1$ alkyl. In embodiments, R$^{54}$ is independently substituted C$_2$ alkyl. In embodiments, R$^{54}$ is independently substituted C$_3$ alkyl. In embodiments, R$^{54}$ is independently substituted C$_4$ alkyl. In embodiments, R$^{54}$ is independently substituted C$_5$ alkyl. In embodiments, R$^{54}$ is independently substituted C$_6$ alkyl. In embodiments, R$^{54}$ is independently unsubstituted C$_1$ alkyl. In embodiments, R$^{54}$ is independently unsubstituted C$_2$ alkyl. In embodiments, R$^{54}$ is independently unsubstituted C$_3$ alkyl. In embodiments, R$^{54}$ is independently unsubstituted C$_4$ alkyl. In embodiments, R$^{54}$ is independently unsubstituted C$_5$ alkyl. In embodiments, R$^{54}$ is independently unsubstituted C$_6$ alkyl. In embodiments, R$^{54}$ is not hydrogen.

In embodiments, R$^{54A}$ is independently halogen, —CF$_3$, —CCl$_3$, —CI$_3$, —CBr$_3$, —CHF$_2$, —CHCl$_2$, —CHI$_2$, —CHBr$_2$, —CH$_2$F, —CH$_2$Cl, —CH$_2$I, —CH$_2$Br, —OCH$_2$F, —OCH$_2$Cl, —OCH$_2$I, —OCH$_2$Br, —OCHF$_2$, —OCHCl$_2$, —OCHI$_2$, —OCHBr$_2$, —OCF$_3$, —OCCl$_3$, —OCI$_3$, —OCBr$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, R$^{54A}$ is independently substituted or unsubstituted C$_1$ alkyl. In embodiments, R$^{54A}$ is independently substituted or unsubstituted C$_2$ alkyl. In embodiments, R$^{54A}$ is independently substituted or unsubstituted C$_3$ alkyl. In embodiments, R$^{54A}$ is independently substituted or unsubstituted C$_4$ alkyl. In embodiments, R$^{54A}$ is independently substituted or unsubstituted C$_5$ alkyl. In embodiments, R$^{54A}$ is independently substituted or unsubstituted $C_6$ alkyl. In embodiments, $R^{54A}$ is independently substituted $C_1$ alkyl. In embodiments, $R^{54A}$ is independently substituted $C_2$ alkyl. In embodiments, $R^{54A}$ is independently substituted $C_3$ alkyl. In embodiments, $R^{54A}$ is independently substituted $C_4$ alkyl. In embodiments, $R^{54A}$ is independently substituted $C_5$ alkyl. In embodiments, $R^{54A}$ is independently substituted $C_6$ alkyl. In embodiments, $R^{54A}$ is independently unsubstituted $C_1$ alkyl. In embodiments, $R^{54A}$ is independently unsubstituted $C_2$ alkyl. In embodiments, $R^{54A}$ is independently unsubstituted $C_3$ alkyl. In embodiments, $R^{54A}$ is independently unsubstituted $C_4$ alkyl. In embodiments, $R^{54A}$ is independently unsubstituted $C_5$ alkyl. In embodiments, $R^{54A}$ is independently unsubstituted $C_6$ alkyl. In embodiments, $R^{54A}$ is not hydrogen.

In embodiments, $R^{54}$ is independently halogen, $-CF_3$, $-CCl_3$, $-CI_3$, $-CBr_3$, $-CHF_2$, $-CHCl_2$, $-CHI_2$, $-CHBr_2$, $-CH_2F$, $-CH_2Cl$, $-CH_2I$, $-CH_2Br$, $-OCH_2F$, $-OCH_2Cl$, $-OCH_2I$, $-OCH_2Br$, $-OCHF_2$, $-OCHCl_2$, $-OCHI_2$, $-OCHBr_2$, $-OCF_3$, $-OCCl_3$, $-OCI_3$, $-OCBr_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-PO_4H$, $-PO_3H$, $-N_3$, $R^{55}$-substituted or unsubstituted alkyl, $R^{55}$-substituted or unsubstituted heteroalkyl, $R^{55}$-substituted or unsubstituted cycloalkyl, $R^{55}$-substituted or unsubstituted heterocycloalkyl, $R^{55}$-substituted or unsubstituted aryl, or $R^{55}$-substituted or unsubstituted heteroaryl.

In embodiments, $R^{54A}$ is independently halogen, $-CF_3$, $-CCl_3$, $-CI_3$, $-CBr_3$, $-CHF_2$, $-CHCl_2$, $-CHI_2$, $-CHBr_2$, $-CH_2F$, $-CH_2Cl$, $-CH_2I$, $-CH_2Br$, $-OCH_2F$, $-OCH_2Cl$, $-OCH_2I$, $-OCH_2Br$, $-OCHF_2$, $-OCHCl_2$, $-OCHI_2$, $-OCHBr_2$, $-OCF_3$, $-OCCl_3$, $-OCI_3$, $-OCBr_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-PO_4H$, $-PO_3H$, $-N_3$, $R^{55A}$-substituted or unsubstituted alkyl, $R^{55A}$-substituted or unsubstituted heteroalkyl, $R^{55A}$-substituted or unsubstituted cycloalkyl, $R^{55A}$-substituted or unsubstituted heterocycloalkyl, $R^{55A}$-substituted or unsubstituted aryl, or $R^{55A}$-substituted or unsubstituted heteroaryl.

$R^{55}$ and $R^{55A}$ are each independently oxo, halogen, $-CF_3$, $-CCl_3$, $-CI_3$, $-CBr_3$, $-CHF_2$, $-CHCl_2$, $-CHI_2$, $-CHBr_2$, $-CH_2F$, $-CH_2Cl$, $-CH_2I$, $-CH_2Br$, $-OCH_2F$, $-OCH_2Cl$, $-OCH_2I$, $-OCH_2Br$, $-OCHF_2$, $-OCHCl_2$, $-OCHI_2$, $-OCHBr_2$, $-OCF_3$, $-OCCl_3$, $-OCI_3$, $-OCBr_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-PO_4H$, $-PO_3H$, $-N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). In embodiments, $R^{55}$ is independently $-PO_3H$, $-PO_4H$, $-SO_2NH_2$, $-SO_3H$, or $-SO_4H$. In embodiments, $R^{55}$ is independently $-SO_3H$. In embodiments, $R^{55}$ is independently $-PO_3H$. In embodiments, $R^{55}$ is independently $-SO_2NH_2$. In embodiments, $R^{55}$ is independently $-SO_4H$. In embodiments, $R^{55A}$ is independently $-PO_3H$, $-SO_2NH_2$, $-SO_3H$, or $-SO_4H$. In embodiments, $R^{55A}$ is independently $-SO_3H$. In embodiments, $R^{55A}$ is independently $-PO_3H$. In embodiments, $R^{55A}$ is independently $-SO_2NH_2$. In embodiments, $R^{55A}$ is independently $-SO_4H$.

In embodiments, $R^{14}$ is independently a polymer. In embodiments, $R^{14}$ is independently a monovalent PEG polymer. In embodiments, $R^{14}$ is

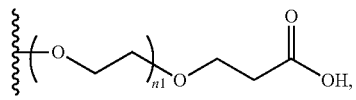

wherein n1 is an integer from 1 to 30. In embodiments, n1 is independently 1. In embodiments, n1 is independently 2. In embodiments, n1 is independently 3. In embodiments, n1 is independently 4. In embodiments, n1 is independently 5. In embodiments, n1 is independently 6. In embodiments, n1 is independently 7. In embodiments, n1 is independently 8. In embodiments, n1 is independently 9. In embodiments, n1 is independently 10. In embodiments, n1 is independently 11. In embodiments, n1 is independently 12. In embodiments, n1 is independently 13. In embodiments, n1 is independently 14. In embodiments, n1 is independently 15. In embodiments, n1 is independently 16. In embodiments, n1 is independently 17. In embodiments, n1 is independently 18. In embodiments, n1 is independently 19. In embodiments, n1 is independently 20. In embodiments, n1 is independently 21. In embodiments, n1 is independently 22. In embodiments, n1 is independently 23. In embodiments, n1 is independently 24. In embodiments, n1 is independently 25. In embodiments, n1 is independently 26. In embodiments, n1 is independently 27. In embodiments, n1 is independently 28. In embodiments, n1 is independently 29. In embodiments, n1 is independently 30. In embodiments, n1 is independently an integer from 1 to 6. In embodiments, n1 is independently an integer from 10 to 20. In embodiments, n1 is independently an integer from 5 to 15. In embodiments, $R^{14}$ is independently

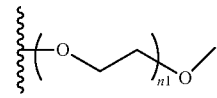

In embodiments, $R^{14}$ is independently

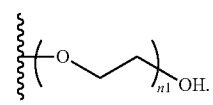

In embodiments, -$L^4$-$R^{14}$ is independently

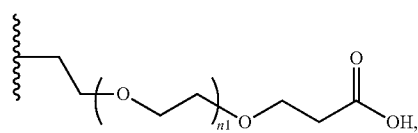

-continued

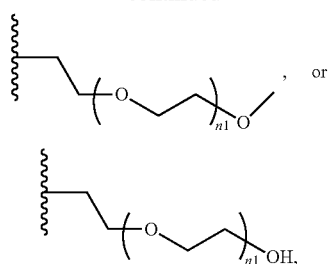, or

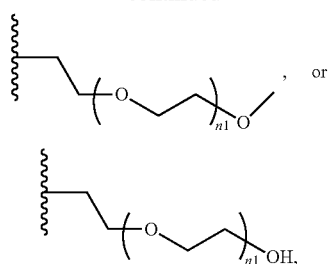, wherein n1 is as described herein (e.g., an integer from 5 to 15).

In embodiments, -L$^4$-R$^{14}$ is

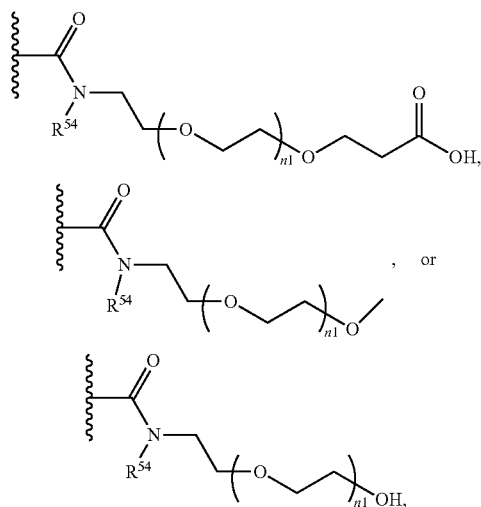

wherein R$^{54}$ and n1 are as described herein (e.g., an integer from 5 to 15). In embodiments, -L$^4$-R$^{14}$ is

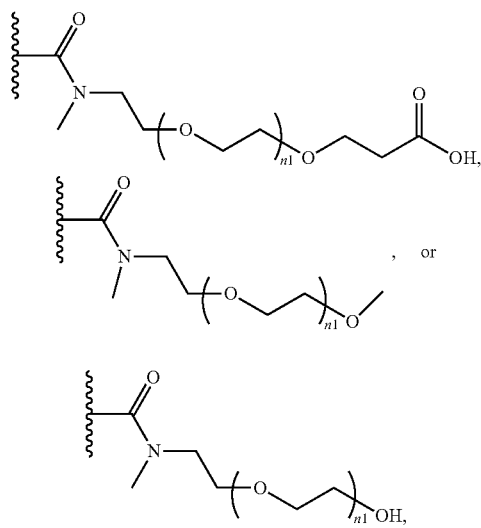

wherein n1 is as described herein (e.g., an integer from 5 to 15).

In embodiments, -L$^4$-R$^{14}$ is

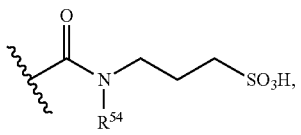

wherein R$^{54}$ is as described herein. In embodiments, -L$^4$-R$^{14}$ is

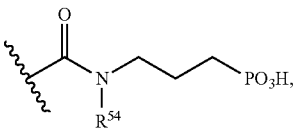

wherein R$^{54}$ is as described herein. In embodiments, -L$^4$-R$^{14}$ is

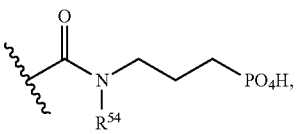

wherein R$^{54}$ is as described herein. In embodiments, -L$^4$-R$^{14}$ is

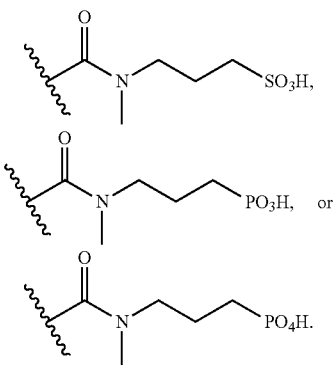

In embodiments, -L$^4$-R$^{14}$ is not —COOH. In embodiments, -L$^4$-R$^{14}$ is not —CH$_3$.

In embodiments, L$^3$ is independently a bond, —S(O)$_2$—, —NH—, —O—, —S—, —C(O)—, —C(O)NR$^1$—, —NR$^1$C(O)—, —NR$^1$C(O)NR$^{1A}$—, —S(O)$_2$NR$^1$—, —NR$^1$S(O)$_2$—, R$^1$-substituted or unsubstituted alkylene, R$^1$-substituted or unsubstituted heteroalkylene, R$^1$-substituted or unsubstituted cycloalkylene, R$^1$-substituted or unsubstituted heterocycloalkylene, R$^1$-substituted or unsubstituted arylene, or R$^1$-substituted or unsubstituted heteroarylene.

In embodiments, L$^3$ is independently

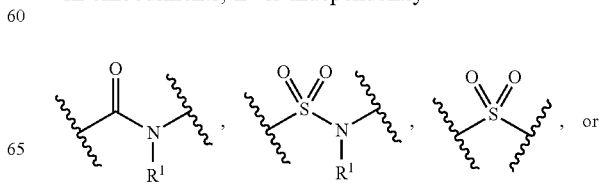, or

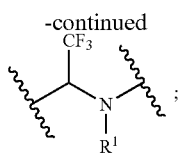

and $R^1$ is as described herein, including in embodiments. In embodiments, $L^3$ is independently

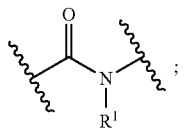

and $R^1$ is as described herein, including in embodiments. In embodiments, $L^3$ is independently

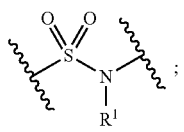

and $R^1$ is as described herein, including in embodiments. In embodiments, $L^3$ is independently

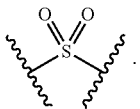

In embodiments, $L^3$ is independently

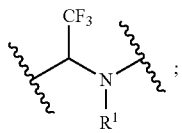

and $R^1$ is as described herein, including in embodiments. In embodiments, $L^3$ is independently

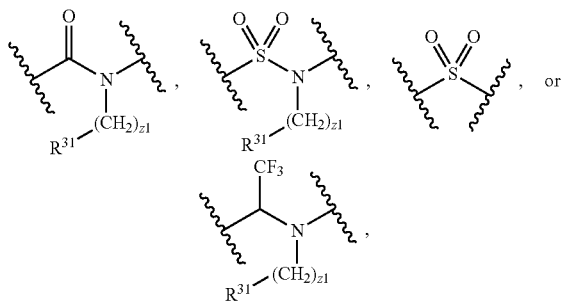

wherein z1 is independently an integer from 1 to 6, and $R^{31}$ is as described herein, including embodiments. In embodiments, z1 is independently an integer from 1 to 3. In embodiments, z1 is independently 1. In embodiments, z1 is independently 2. In embodiments, z1 is independently 3. In embodiments, z1 is independently 4. In embodiments, z1 is independently 5. In embodiments, z1 is independently 6. In embodiments, $R^{31}$ is independently —$PO_3H$, —$PO_4H$, —$SO_2NH_2$, —$SO_3H$, or —$SO_4H$. In embodiments, $R^{31}$ is independently —$SO_3H$. In embodiments, $R^{31}$ is independently —$PO_3H$. In embodiments, $R^{31}$ is independently —$SO_2NH_2$. In embodiments, $R^{31}$ is independently —$PO_4H$. In embodiments, $R^{31}$ is independently —$SO_4H$.

In embodiments, $L^1$ and $L^2$ are each independently a bond, —$S(O)_2$—, —$S(O)_2NH$—, —$NHS(O)_2$—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or a divalent polymer. In embodiments, $L^1$ and $L^2$ are each independently a divalent polymer. In embodiments, $L^1$ and $L^2$ are each independently divalent polyethylene glycol (PEG).

In embodiments, $L^1$ and $L^2$ are each independently a bond, —$S(O)_2$—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or a divalent polymer. In embodiments, when $L^3$ is a bond, $L^1$ is not —C(O)O— or —OC(O)—. In embodiments, when $L^3$ is a bond, $L^2$ is not —C(O)O— or —OC(O)—.

In embodiments, $L^1$ is independently a bond, —$S(O)_2$—, —$S(O)_2NH$—, —$NHS(O)_2$—, —NH—, —O—, —S—, —C(O)—, —C(O)NH—, —NHC(O)—, —NHC(O)NH—, —C(O)O—, —OC(O)—, $R^{51}$-substituted or unsubstituted alkylene, $R^{51}$-substituted or unsubstituted heteroalkylene, $R^{51}$-substituted or unsubstituted cycloalkylene, $R^{51}$-substituted or unsubstituted heterocycloalkylene, $R^{51}$-substituted or unsubstituted arylene, $R^{51}$-substituted or unsubstituted heteroarylene, or a divalent polymer. In embodiments, $L^1$ is independently a divalent polymer. In embodiments, $L^1$ is independently divalent polyethylene glycol (PEG).

In embodiments, $L^1$ is independently a bond, —$S(O)_2$—, —NH—, —O—, —S—, —C(O)—, —C(O)NH—, —NHC(O)—, —NHC(O)NH—, —C(O)O—, —OC(O)—, $R^{51}$-substituted or unsubstituted alkylene, $R^{51}$-substituted or unsubstituted heteroalkylene, $R^{51}$-substituted or unsubstituted cycloalkylene, $R^{51}$-substituted or unsubstituted heterocycloalkylene, $R^{51}$-substituted or unsubstituted arylene, $R^{51}$-substituted or unsubstituted heteroarylene, or a divalent polymer.

$R^{51}$ is independently oxo, halogen, —$CF_3$, —$CCl_3$, —$CI_3$, —$CBr_3$, —$CHF_2$, —$CHCl_2$, —$CHI_2$, —$CHBr_2$, —$CH_2F$, —$CH_2Cl$, —$CH_2I$, —$CH_2Br$, —$OCH_2F$, —$OCH_2Cl$, —$OCH_2I$, —$OCH_2Br$, —$OCHF_2$, —$OCHCl_2$, —$OCHI_2$, —$OCHBr_2$, —$OCF_3$, —$OCCl_3$, —$OCI_3$, —$OCBr_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $L^2$ is independently a bond, —S(O)$_2$—, —S(O)$_2$NH—, —NHS(O)$_2$—, —NH—, —O—, —S—, —C(O)—, —C(O)NH—, —NHC(O)—, —NHC(O)NH—, —C(O)O—, —OC(O)—, $R^{52}$-substituted or unsubstituted alkylene, $R^{52}$-substituted or unsubstituted heteroalkylene, $R^{52}$-substituted or unsubstituted cycloalkylene, $R^{52}$-substituted or unsubstituted heterocycloalkylene, $R^{52}$-substituted or unsubstituted arylene, $R^{52}$-substituted or unsubstituted heteroarylene, or a divalent polymer. In embodiments, $L^2$ is independently a divalent polymer. In embodiments, $L^2$ is independently divalent polyethylene glycol (PEG).

In embodiments, $L^2$ is independently a bond, —S(O)$_2$—, —NH—, —O—, —S—, —C(O)—, —C(O)NH—, —NHC(O)—, —NHC(O)NH—, —C(O)O—, —OC(O)—, $R^{52}$-substituted or unsubstituted alkylene, $R^{52}$-substituted or unsubstituted heteroalkylene, $R^{52}$-substituted or unsubstituted cycloalkylene, $R^{52}$-substituted or unsubstituted heterocycloalkylene, $R^{52}$-substituted or unsubstituted arylene, $R^{52}$-substituted or unsubstituted heteroarylene, or a divalent polymer.

$R^{52}$ is independently oxo, halogen, —CF$_3$, —CCl$_3$, —CI$_3$, —CBr$_3$, —CHF$_2$, —CHCl$_2$, —CHI$_2$, —CHBr$_2$, —CH$_2$F, —CH$_2$Cl, —CH$_2$I, —CH$_2$Br, —OCH$_2$F, —OCH$_2$Cl, —OCH$_2$I, —OCH$_2$Br, —OCHF$_2$, —OCHCl$_2$, —OCHI$_2$, —OCHBr$_2$, —OCF$_3$, —OCCl$_3$, —OCI$_3$, —OCBr$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —N$_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $L^1$ and $L^2$ are each independently substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), or substituted or unsubstituted heteroarylene (e.g., 5 to 10 membered, 5 to 9 membered, or 5 to 6 membered).

In embodiments, $L^1$ and $L^2$ are each independently substituted (e.g., substituted with a substituent group, a size-limited substituent group, or lower substituent group) or unsubstituted alkylene, substituted (e.g., substituted with a substituent group, a size-limited substituent group, or lower substituent group) or unsubstituted heteroalkylene, substituted (e.g., substituted with a substituent group, a size-limited substituent group, or lower substituent group) or unsubstituted cycloalkylene, substituted (e.g., substituted with a substituent group, a size-limited substituent group, or lower substituent group) or unsubstituted heterocycloalkylene, substituted (e.g., substituted with a substituent group, a size-limited substituent group, or lower substituent group) or unsubstituted arylene, or substituted (e.g., substituted with a substituent group, a size-limited substituent group, or lower substituent group) or unsubstituted heteroarylene.

In embodiments, $L^1$ and $L^2$ are each independently unsubstituted alkylene, unsubstituted heteroalkylene, unsubstituted cycloalkylene, unsubstituted heterocycloalkylene, unsubstituted arylene, or unsubstituted heteroarylene.

In embodiments, $L^1$ is independently a bond, —C(O)—, —C(O)NH—, —NHC(O)—, —NHC(O)NH—, —C(O)O—, —OC(O)—, substituted or unsubstituted $C_1$-$C_6$ alkylene. In embodiments, $L^1$ is independently substituted or unsubstituted $C_1$-$C_6$ alkylene.

In embodiments, $L^2$ is independently a bond, —C(O)—, —C(O)NH—, —NHC(O)—, —NHC(O)NH—, —C(O)O—, —OC(O)—, substituted or unsubstituted $C_1$-$C_6$ alkylene. In embodiments, $L^2$ is independently substituted or unsubstituted $C_1$-$C_6$ alkylene. In embodiments, $L^2$ is independently a bond, —C(O)—, —C(O)O—, or —OC(O)—. In embodiments, $L^2$ is independently a bond. In embodiments, $L^2$ is independently —C(O)—. In embodiments, $L^2$ is independently —C(O)O—. In embodiments, $L^2$ is independently —OC(O)—.

In embodiments, $L^1$ includes an orthogonally cleavable linker, photocleavable linker, or cleavable linker. In embodiments, $L^1$ is an orthogonally cleavable linker, photocleavable linker, or cleavable linker. In embodiments, $L^2$ includes an orthogonally cleavable linker, photocleavable linker, or cleavable linker. In embodiments, $L^2$ is an orthogonally cleavable linker, photocleavable linker, or cleavable linker.

In embodiments, $L^1$ is independently a polymer. In embodiments, $L^1$ includes a polymer. In embodiments, $L^1$ includes PEG. In embodiments, $L^1$ includes the divalent moiety having the formula:

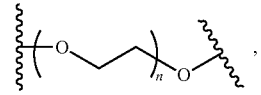

wherein n is an integer from 1 to 30. In embodiments, $L^2$ is independently a polymer. In embodiments, $L^2$ includes a polymer. In embodiments, $L^2$ includes PEG. In embodiments, $L^2$ includes the divalent moiety

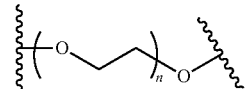

wherein n is as described herein. In embodiments, n is independently 1. In embodiments, n is independently 2. In embodiments, n is independently 3. In embodiments, n is independently an integer from 1 to 6.

In embodiments, -$L^1$-$L^2$-$R^8$ is

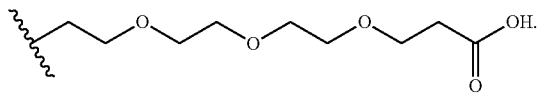 [SMILES: *CCOCCOCCOCCC(=O)O]

In embodiments, L¹ is —C(CH₃)₂CH₂NHC(O)—,
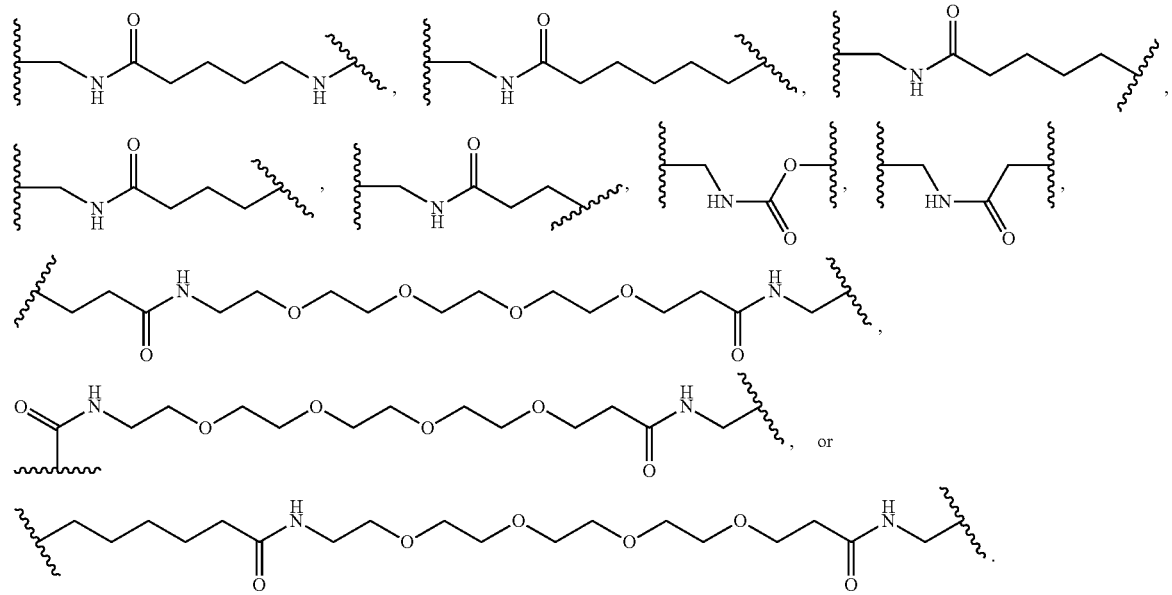
In embodiments, L¹ is
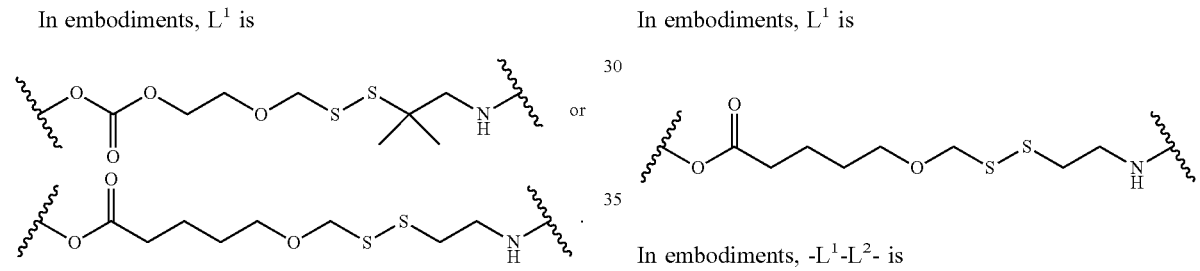
In embodiments, L¹ is
In embodiments, L¹ is
In embodiments, -L¹-L²- is
In embodiments, -L¹-L²- is
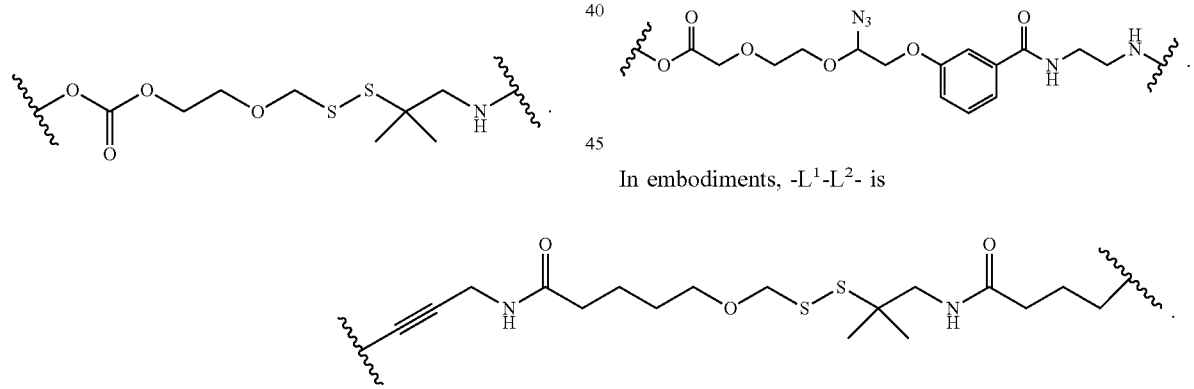
In embodiments, -L¹-L²- is
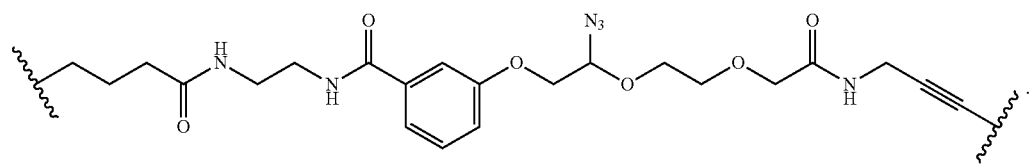 [SMILES: *C#CCNC(=O)COCCOC(COc1cccc(C(=O)NCCNC(=O)CCC*)c1)N=[N+]=[N-]]

In embodiments, L² is —C(CH₃)₂CH₂NHC(O)—,
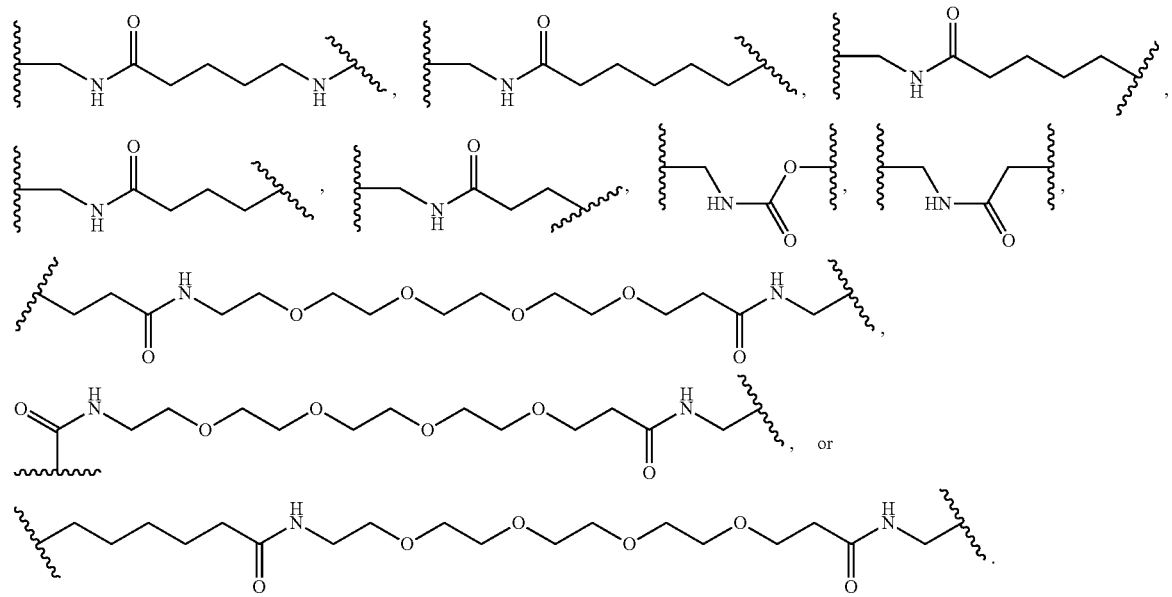
In embodiments, L² is
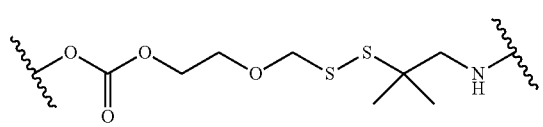
or
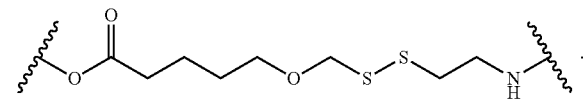 [SMILES: *NCCSSCOCCCCC(=O)O*]
In embodiments, L² is
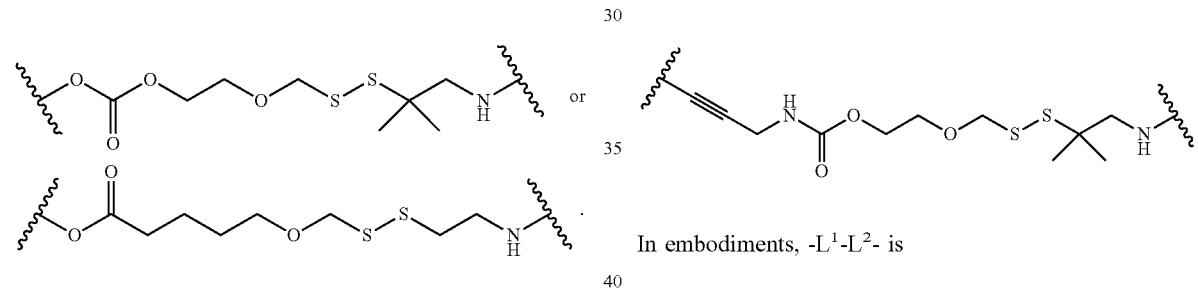
In embodiments, -L¹-L²- is
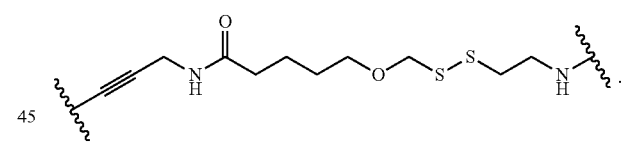
In embodiments, -L¹-L²- is
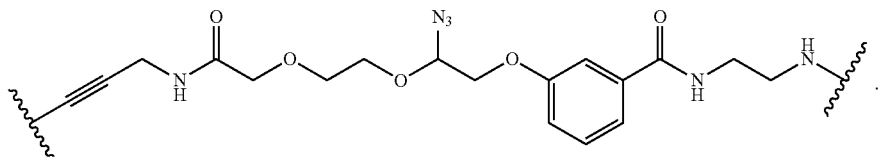 [SMILES: *C#CCNC(=O)COCCOC(COc1cccc(C(=O)NCCN*)c1)N=[N+]=[N-]]
In embodiments, -L¹-L²- is
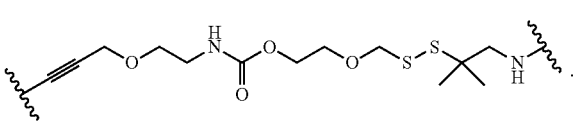 [SMILES: *C#CCOCCNC(=O)OCCOCSSC(C)(C)CN*]

In embodiments, -L¹-L²- is

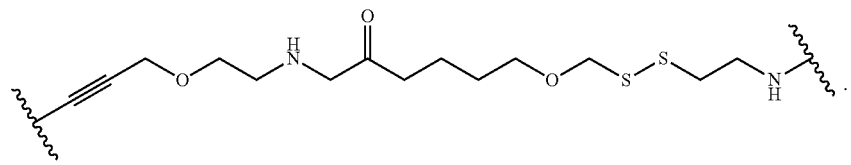 [SMILES: *C#CCOCCNCC(=O)CCCCOCSSCCN*]

In embodiments, -L¹-L²- is

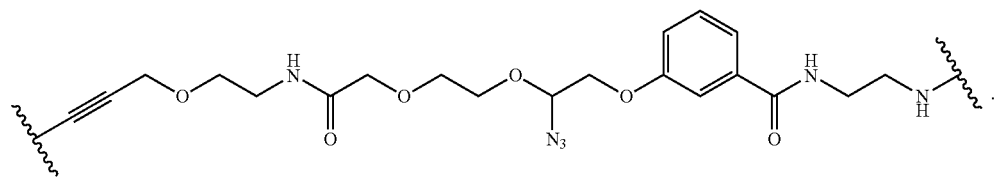 [SMILES: *C#CCOCCNC(=O)COCCOC(COc1cccc(C(=O)NCCN*)c1)N=[N+]=[N-]]

In embodiments, -L¹-L²- is

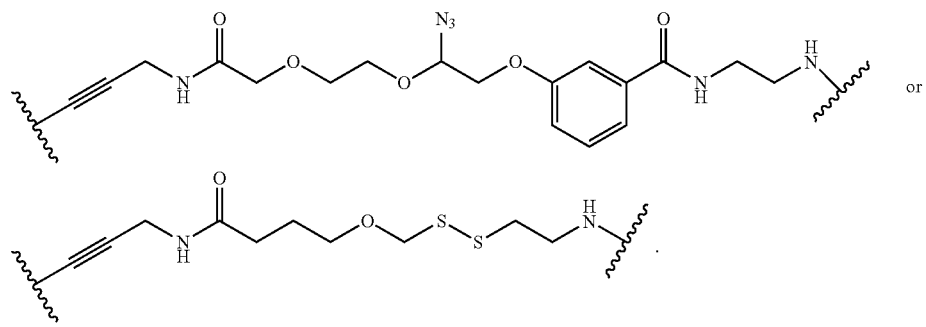

In embodiments, -L¹-L²- is

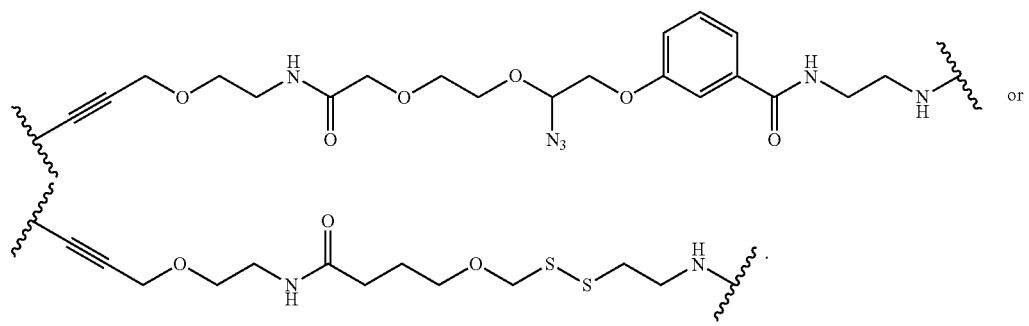

In embodiments, L¹ is L$^{1A}$-L$^{1B}$-L$^{1C}$-L$^{1D}$-L$^{1E}$. L$^{1A}$, L$^{1B}$, L$^{1C}$, L$^{1D}$, or L$^{1E}$ are independently a bond, —SS—, —NN—, —NHC(O)—, —C(O)NH—, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene; wherein at least one of L$^{1A}$, L$^{1B}$, L$^{1C}$, L$^{1D}$, and L$^{1E}$ is not a bond.

In embodiments, $L^{1A}$, $L^{1B}$, $L^{1C}$, $L^{1D}$, or $L^{1E}$ are independently a bond, —NN—, —NHC(O)—, —C(O)NH—, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene; wherein at least one of $L^{1A}$, $L^{1B}$, $L^{1C}$, $L^{1D}$, and $L^{1E}$ is not a bond.

In embodiments, $L^{1A}$ is independently a bond, —SS—, —NN—, —NHC(O)—, —C(O)NH—, $R^{51A}$-substituted or unsubstituted alkylene, $R^{51A}$-substituted or unsubstituted heteroalkylene, $R^{51A}$-substituted or unsubstituted cycloalkylene, $R^{51A}$-substituted or unsubstituted heterocycloalkylene, $R^{51A}$-substituted or unsubstituted arylene, or $R^{51A}$-substituted or unsubstituted heteroarylene.

In embodiments, $L^{1B}$ is independently a bond, —SS—, —NN—, —NHC(O)—, —C(O)NH—, $R^{51B}$-substituted or unsubstituted alkylene, $R^{51B}$-substituted or unsubstituted heteroalkylene, $R^{51B}$-substituted or unsubstituted cycloalkylene, $R^{51B}$-substituted or unsubstituted heterocycloalkylene, $R^{51B}$-substituted or unsubstituted arylene, or $R^{51B}$-substituted or unsubstituted heteroarylene.

In embodiments, $L^{1C}$ is independently a bond, —SS—, —NN—, —NHC(O)—, —C(O)NH—, $R^{51C}$-substituted or unsubstituted alkylene, $R^{51C}$-substituted or unsubstituted heteroalkylene, $R^{51C}$-substituted or unsubstituted cycloalkylene, $R^{51C}$-substituted or unsubstituted heterocycloalkylene, $R^{51C}$-substituted or unsubstituted arylene, or $R^{51C}$-substituted or unsubstituted heteroarylene.

In embodiments, $L^{1D}$ is independently a bond, —SS—, —NN—, —NHC(O)—, —C(O)NH—, $R^{51D}$-substituted or unsubstituted alkylene, $R^{51D}$-substituted or unsubstituted heteroalkylene, $R^{51D}$-substituted or unsubstituted cycloalkylene, $R^{51D}$-substituted or unsubstituted heterocycloalkylene, $R^{51D}$-substituted or unsubstituted arylene, or $R^{51D}$-substituted or unsubstituted heteroarylene.

In embodiments, $L^{1E}$ is independently a bond, —SS—, —NN—, —NHC(O)—, —C(O)NH—, $R^{51E}$-substituted or unsubstituted alkylene, $R^{51E}$-substituted or unsubstituted heteroalkylene, $R^{51E}$-substituted or unsubstituted cycloalkylene, $R^{51E}$-substituted or unsubstituted heterocycloalkylene, $R^{51E}$-substituted or unsubstituted arylene, or $R^{51E}$-substituted or unsubstituted heteroarylene.

$R^{51A}$, $R^{51B}$, $R^{51C}$, $R^{51D}$, and $R^{51E}$ are each independently oxo, halogen, —CF$_3$, —CCl$_3$, —CI$_3$, —CBr$_3$, —CHF$_2$, —CHCl$_2$, —CHI$_2$, —CHBr$_2$, —CH$_2$F, —CH$_2$Cl, —CH$_2$I, —CH$_2$Br, —OCH$_2$F, —OCH$_2$Cl, —OCH$_2$I, —OCH$_2$Br, —OCHF$_2$, —OCHCl$_2$, —OCHI$_2$, —OCHBr$_2$, —OCF$_3$, —OCCl$_3$, —OCI$_3$, —OCBr$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —N$_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $L^1$ is $L^{1A}$-$L^{1B}$-$L^{1C}$-$L^{1D}$-$L^{1E}$; and $L^{1A}$, $L^{1B}$, $L^{1C}$, $L^{1D}$, or $L^{1E}$ are independently a bond, —NN—, —NHC(O)—, —C(O)NH—, substituted (e.g., substituted with a substituent group, size-limited substituent group, or lower substituent group) or unsubstituted $C_1$-$C_{20}$ alkylene (e.g., alkylene, alkenylene, or alkynylene), substituted (e.g., substituted with a substituent group, size-limited substituent group, or lower substituent group) or unsubstituted 2 to 20 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_{20}$ cycloalkylene, substituted (e.g., substituted with a substituent group, size-limited substituent group, or lower substituent group) or unsubstituted 3 to 20 membered heterocycloalkylene, substituted (e.g., substituted with a substituent group, size-limited substituent group, or lower substituent group) or unsubstituted $C_6$-$C_{20}$ arylene, or substituted (e.g., substituted with a substituent group, size-limited substituent group, or lower substituent group) or unsubstituted 5 to 20 membered heteroarylene; wherein at least one of $L^{1A}$, $L^{1B}$, $L^{1C}$, $L^{1D}$, and $L^{1E}$ is not a bond.

In embodiments, $L^1$ is $L^{1A}$-$L^{1B}$-$L^{1C}$-$L^{1D}$-$L^{1E}$; and $L^{1A}$, $L^{1B}$, $L^{1C}$, $L^{1D}$, or $L^{1E}$ are independently a bond, —NN—, —NHC(O)—, —C(O)NH—, substituted (e.g., substituted with a substituent group, size-limited substituent group, or lower substituent group) or unsubstituted $C_1$-$C_{10}$ alkylene (e.g., alkylene, alkenylene, or alkynylene), substituted (e.g., substituted with a substituent group, size-limited substituent group, or lower substituent group) or unsubstituted 2 to 10 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_8$ cycloalkylene, substituted (e.g., substituted with a substituent group, size-limited substituent group, or lower substituent group) or unsubstituted 3 to 8 membered heterocycloalkylene, substituted (e.g., substituted with a substituent group, size-limited substituent group, or lower substituent group) or unsubstituted $C_6$-$C_{10}$ arylene, or substituted (e.g., substituted with a substituent group, size-limited substituent group, or lower substituent group) or unsubstituted 5 to 10 membered heteroarylene; wherein at least one of $L^{1A}$, $L^{1B}$, $L^{1C}$, $L^{1D}$, and $L^{1E}$ is not a bond.

In embodiments, $L^1$ is $L^{1A}$-$L^{1B}$-$L^{1C}$-$L^{1D}$-$L^{1E}$; and $L^{1A}$, $L^{1B}$, $L^{1C}$, $L^{1D}$, or $L^{1E}$ are independently a bond, —NN—, —NHC(O)—, —C(O)NH—, substituted (e.g., substituted with a substituent group, size-limited substituent group, or lower substituent group) or unsubstituted $C_1$-$C_6$ alkylene (e.g., alkylene, alkenylene, or alkynylene), substituted (e.g., substituted with a substituent group, size-limited substituent group, or lower substituent group) or unsubstituted 2 to 6 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_6$ cycloalkylene, substituted (e.g., substituted with a substituent group, size-limited substituent group, or lower substituent group) or unsubstituted 3 to 6 membered heterocycloalkylene, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroarylene; wherein at least one of $L^{1A}$, $L^{1B}$, $L^{1C}$, $L^{1D}$, and $L^{1E}$ is not a bond.

In embodiments, $L^1$ is $L^{1A}$-$L^{1B}$-$L^{1C}$-$L^{1D}$-$L^{1E}$; wherein $L^{1A}$ is a bond, —NN—, —NHC(O)—, —C(O)NH—, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene); $L^{1B}$ is a bond, —NN—, —NHC(O)—, —C(O)NH—, substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, substituted (e.g., substituted with a substituent group, size-limited substituent group, or lower substituent group) or unsubstituted heteroarylene; $L^{1C}$ is a bond, —NN—, —NHC(O)—, —C(O)NH—, substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, substituted (e.g., substituted with a substituent group, size-limited substituent group, or lower substituent group) or unsubstituted heteroarylene; $L^{1D}$ is a bond, —NN—, —NHC(O)—, —C(O)NH—, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene); and $L^{1E}$ is a bond, —NN—, —NHC(O)—, —C(O)NH—, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene; wherein at least one of $L^{1A}$, $L^{1B}$, $L^{1C}$, $L^{1D}$, and $L^{1E}$ is not a bond.

In embodiments, $L^1$ is a bond, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene.

In embodiments, $L^1$ is a bond, substituted (e.g., substituted with a substituent group, size-limited substituent group, or lower substituent group) or unsubstituted $C_1$-$C_{20}$ alkylene (e.g., alkylene, alkenylene, or alkynylene), substituted (e.g., substituted with a substituent group, size-limited substituent group, or lower substituent group) or unsubstituted 2 to 20 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_{20}$ cycloalkylene, substituted (e.g., substituted with a substituent group, size-limited substituent group, or lower substituent group) or unsubstituted 3 to 20 membered heterocycloalkylene, substituted (e.g., substituted with a substituent group, size-limited substituent group, or lower substituent group) or unsubstituted $C_6$-$C_{20}$ arylene, or substituted (e.g., substituted with a substituent group, size-limited substituent group, or lower substituent group) or unsubstituted 5 to 20 membered heteroarylene.

In embodiments, $L^1$ is a bond, substituted (e.g., substituted with a substituent group, size-limited substituent group, or lower substituent group) or unsubstituted $C_1$-$C_8$ alkylene (e.g., alkylene, alkenylene, or alkynylene), substituted (e.g., substituted with a substituent group, size-limited substituent group, or lower substituent group) or unsubstituted 2 to 8 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_8$ cycloalkylene, substituted (e.g., substituted with a substituent group, size-limited substituent group, or lower substituent group) or unsubstituted 3 to 8 membered heterocycloalkylene, substituted (e.g., substituted with a substituent group, size-limited substituent group, or lower substituent group) or unsubstituted $C_6$-$C_{10}$ arylene, or substituted (e.g., substituted with a substituent group, size-limited substituent group, or lower substituent group) or unsubstituted 5 to 10 membered heteroarylene.

In embodiments, $L^1$ is a bond, substituted (e.g., substituted with a substituent group, size-limited substituent group, or lower substituent group) or unsubstituted $C_1$-$C_6$ alkylene (e.g., alkylene, alkenylene, or alkynylene), substituted (e.g., substituted with a substituent group, size-limited substituent group, or lower substituent group) or unsubstituted 2 to 6 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_6$ cycloalkylene, substituted (e.g., substituted with a substituent group, size-limited substituent group, or lower substituent group) or unsubstituted 3 to 6 membered heterocycloalkylene, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroarylene.

In embodiments, $L^1$ is a substituted (e.g., substituted with a substituent group, size-limited substituent group, or lower substituent group) or unsubstituted 3 to 10 membered heteroalkylene (e.g., heteroalkylene, heteroalkenylene, or heteroalkynylene). In embodiments, $L^1$ is a substituted (e.g., substituted with a substituent group, size-limited substituent group, or lower substituent group) or unsubstituted 3 to 8 membered heteroalkylene (e.g., heteroalkylene, heteroalkenylene, or heteroalkynylene). In embodiments, $L^1$ is a substituted (e.g., substituted with a substituent group, size-limited substituent group, or lower substituent group) or unsubstituted 3 to 6 membered heteroalkylene (e.g., heteroalkylene, heteroalkenylene, or heteroalkynylene).

In embodiments, $L^1$ is substituted or unsubstituted methylene. In embodiments, $L^1$ is substituted or unsubstituted $C_2$ alkylene. In embodiments, $L^1$ is substituted or unsubstituted $C_3$ alkylene. In embodiments, $L^1$ is substituted or unsubstituted $C_4$ alkylene. In embodiments, $L^1$ is substituted or unsubstituted $C_5$ alkylene. In embodiments, $L^1$ is substituted or unsubstituted $C_6$ alkylene. In embodiments, $L^1$ is substituted or unsubstituted $C_7$ alkylene. In embodiments, $L^1$ is substituted or unsubstituted $C_8$ alkylene. In embodiments, $L^1$ is substituted methylene. In embodiments, $L^1$ is substituted $C_2$ alkylene. In embodiments, $L^1$ is substituted $C_3$ alkylene. In embodiments, $L^1$ is substituted $C_4$ alkylene. In embodiments, $L^1$ is substituted $C_5$ alkylene. In embodiments, $L^1$ is substituted $C_6$ alkylene. In embodiments, $L^1$ is substituted $C_7$ alkylene. In embodiments, $L^1$ is substituted $C_8$ alkylene. In embodiments, $L^1$ is an unsubstituted methylene. In embodiments, $L^1$ is an unsubstituted $C_2$ alkylene. In embodiments, $L^1$ is an unsubstituted $C_3$ alkylene. In embodiments, $L^1$ is an unsubstituted $C_4$ alkylene. In embodiments, $L^1$ is an unsubstituted $C_5$ alkylene. In embodiments, $L^1$ is an unsubstituted $C_6$ alkylene. In embodiments, $L^1$ is an unsubstituted $C_7$ alkylene. In embodiments, $L^1$ is an unsubstituted $C_8$ alkylene.

In embodiments, $L^1$ is substituted or unsubstituted $C_1$-$C_6$ alkylene. In embodiments, $L^1$ is substituted $C_1$-$C_6$ alkylene. In embodiments, $L^1$ is unsubstituted $C_1$-$C_6$ alkylene. In embodiments, $L^1$ is substituted or unsubstituted $C_2$-$C_6$ alkylene. In embodiments, $L^1$ is substituted $C_2$-$C_6$ alkylene. In embodiments, $L^1$ is unsubstituted $C_2$-$C_6$ alkylene. In embodiments, $L^1$ is substituted or unsubstituted $C_1$ alkylene. In embodiments, $L^1$ is substituted $C_1$ alkylene. In embodiments, $L^1$ is unsubstituted $C_1$ alkylene. In embodiments, $L^1$ is substituted or unsubstituted $C_2$ alkylene. In embodiments, $L^1$ is substituted $C_2$ alkylene. In embodiments, $L^1$ is unsubstituted $C_2$ alkylene. In embodiments, $L^1$ is substituted or unsubstituted $C_3$ alkylene. In embodiments, $L^1$ is substituted $C_3$ alkylene. In embodiments, $L^1$ is unsubstituted $C_3$ alkylene. In embodiments, $L^1$ is substituted or unsubstituted $C_4$ alkylene. In embodiments, $L^1$ is substituted $C_4$ alkylene. In embodiments, $L^1$ is unsubstituted $C_4$ alkylene. In embodiments, $L^1$ is substituted or unsubstituted $C_5$ alkylene. In embodiments, $L^1$ is substituted $C_5$ alkylene. In embodiments, $L^1$ is unsubstituted $C_5$ alkylene. In embodiments, $L^1$ is substituted or unsubstituted $C_6$ alkylene. In embodiments, $L^1$ is substituted $C_6$ alkylene. In embodiments, $L^1$ is unsubstituted $C_6$ alkylene.

In embodiments, $L^1$ is substituted or unsubstituted $C_9$ alkylene. In embodiments, $L^1$ is substituted or unsubstituted $C_{10}$ alkylene. In embodiments, $L^1$ is substituted or unsubstituted $C_{11}$ alkylene. In embodiments, $L^1$ is substituted or unsubstituted $C_{12}$ alkylene. In embodiments, $L^1$ is substituted or unsubstituted $C_{13}$ alkylene. In embodiments, $L^1$ is substituted or unsubstituted $C_{14}$ alkylene. In embodiments, $L^1$ is substituted or unsubstituted $C_{15}$ alkylene. In embodiments, $L^1$ is substituted or unsubstituted $C_{16}$ alkylene. In embodiments, $L^1$ is substituted or unsubstituted $C_{17}$ alkylene. In embodiments, $L^1$ is substituted or unsubstituted $C_{18}$ alkylene. In embodiments, $L^1$ is substituted or unsubstituted $C_{19}$ alkylene. In embodiments, $L^1$ is substituted or unsubstituted $C_{20}$ alkylene.

In embodiments, $L^1$ is substituted or unsubstituted 2 to 8 membered heteroalkylene. In embodiments, $L^1$ is substituted 2 to 8 membered heteroalkylene. In embodiments, $L^1$ is unsubstituted 2 to 8 membered heteroalkylene. In embodiments, $L^1$ is substituted or unsubstituted 2 membered heteroalkylene. In embodiments, $L^1$ is substituted 2 membered heteroalkylene. In embodiments, $L^1$ is unsubstituted 2 membered heteroalkylene. In embodiments, $L^1$ is substituted or unsubstituted 3 membered heteroalkylene. In embodiments, $L^1$ is substituted 3 membered heteroalkylene. In embodiments, $L^1$ is unsubstituted 3 membered heteroalkylene. In embodiments, $L^1$ is substituted or unsubstituted 4 membered heteroalkylene. In embodiments, $L^1$ is substituted 4 membered heteroalkylene. In embodiments, $L^1$ is unsubstituted 4 membered heteroalkylene. In embodiments, $L^1$ is substituted or unsubstituted 5 membered heteroalkylene. In embodiments, $L^1$ is substituted 5 membered heteroalkylene. In embodiments, $L^1$ is unsubstituted 5 membered heteroalkylene. In embodiments, $L^1$ is substituted or unsubstituted 6 membered heteroalkylene. In embodiments, $L^1$ is substituted 6 membered heteroalkylene. In embodiments, $L^1$ is unsubstituted 6 membered heteroalkylene. In embodiments, $L^1$ is substituted or unsubstituted 7 membered heteroalkylene. In embodiments, $L^1$ is substituted 7 membered heteroalkylene. In embodiments, $L^1$ is unsubstituted 7 membered heteroalkylene. In embodiments, $L^1$ is substituted or unsubstituted 8 membered heteroalkylene. In embodiments, $L^1$ is substituted 8 membered heteroalkylene. In embodiments, $L^1$ is unsubstituted 8 membered heteroalkylene.

In embodiments, $L^1$ is substituted or unsubstituted 9 membered heteroalkylene. In embodiments, $L^1$ is substituted 9 membered heteroalkylene. In embodiments, $L^1$ is unsubstituted 9 membered heteroalkylene. In embodiments, $L^1$ is substituted or unsubstituted 10 membered heteroalkylene. In embodiments, $L^1$ is substituted 10 membered heteroalkylene. In embodiments, $L^1$ is unsubstituted 10 membered heteroalkylene. In embodiments, $L^1$ is substituted or unsubstituted 11 membered heteroalkylene. In embodiments, $L^1$ is substituted 11 membered heteroalkylene. In embodiments, $L^1$ is unsubstituted 11 membered heteroalkylene. In embodiments, $L^1$ is substituted or unsubstituted 12 membered heteroalkylene. In embodiments, $L^1$ is substituted 12 membered heteroalkylene. In embodiments, $L^1$ is unsubstituted 12 membered heteroalkylene. In embodiments, $L^1$ is substituted or unsubstituted 13 membered heteroalkylene. In embodiments, $L^1$ is substituted 13 membered heteroalkylene. In embodiments, $L^1$ is unsubstituted 13 membered heteroalkylene. In embodiments, $L^1$ is substituted or unsubstituted 14 membered heteroalkylene. In embodiments, $L^1$ is substituted 14 membered heteroalkylene. In embodiments, $L^1$ is unsubstituted 14 membered heteroalkylene. In embodiments, $L^1$ is substituted or unsubstituted 15 membered heteroalkylene. In embodiments, $L^1$ is substituted 15 membered heteroalkylene. In embodiments, $L^1$ is unsubstituted 15 membered heteroalkylene. In embodiments, $L^1$ is substituted or unsubstituted 16 membered heteroalkylene. In embodiments, $L^1$ is substituted 16 membered heteroalkylene. In embodiments, $L^1$ is unsubstituted 16 membered heteroalkylene. In embodiments, $L^1$ is substituted or unsubstituted 17 membered heteroalkylene. In embodiments, $L^1$ is substituted 17 membered heteroalkylene. In embodiments, $L^1$ is unsubstituted 17 membered heteroalkylene. In embodiments, $L^1$ is substituted or unsubstituted 18 membered heteroalkylene. In embodiments, $L^1$ is substituted 18 membered heteroalkylene. In embodiments, $L^1$ is unsubstituted 18 membered heteroalkylene. In embodiments, $L^1$ is substituted or unsubstituted 19 membered heteroalkylene. In embodiments, $L^1$ is substituted 19 membered heteroalkylene. In embodiments, $L^1$ is unsubstituted 19 membered heteroalkylene. In embodiments, $L^1$ is substituted or unsubstituted 20 membered heteroalkylene. In embodiments, $L^1$ is substituted 20 membered heteroalkylene. In embodiments, $L^1$ is unsubstituted 20 membered heteroalkylene.

In embodiments, $L^1$ is substituted or unsubstituted $C_4$-$C_6$ cycloalkylene. In embodiments, $L^1$ is substituted $C_4$-$C_6$ cycloalkylene. In embodiments, $L^1$ is substituted $C_4$-$C_6$ cycloalkylene. In embodiments, $L^1$ is substituted or unsubstituted $C_4$ cycloalkylene. In embodiments, $L^1$ is substituted $C_4$ cycloalkylene. In embodiments, $L^1$ is substituted $C_4$ cycloalkylene. In embodiments, $L^1$ is substituted or unsubstituted $C_5$ cycloalkylene. In embodiments, $L^1$ is substituted $C_5$ cycloalkylene. In embodiments, $L^1$ is substituted $C_5$ cycloalkylene.

In embodiments, $L^1$ is substituted or unsubstituted 5 to 6 membered heterocycloalkylene. In embodiments, $L^1$ is substituted 5 to 6 membered heterocycloalkylene. In embodiments, $L^1$ is unsubstituted 5 to 6 membered heterocycloalkylene. In embodiments, $L^1$ is substituted or unsubstituted 5 membered heterocycloalkylene. In embodiments, $L^1$ is substituted 5 membered heterocycloalkylene. In embodiments, $L^1$ is unsubstituted 5 membered heterocycloalkylene. In embodiments, $L^1$ is substituted or unsubstituted 6 membered heterocycloalkylene. In embodiments, $L^1$ is substituted 6 membered heterocycloalkylene. In embodiments, $L^1$ is unsubstituted 6 membered heterocycloalkylene.

In embodiments, $L^1$ is substituted or unsubstituted phenylene. In embodiments, $L^1$ is substituted phenylene. In embodiments, $L^1$ is unsubstituted phenylene.

In embodiments, $L^1$ is substituted or unsubstituted 5 to 6 membered heteroarylene. In embodiments, $L^1$ is substituted 5 to 6 membered heteroarylene. In embodiments, $L^1$ is unsubstituted 5 to 6 membered heteroarylene. In embodiments, $L^1$ is substituted or unsubstituted 5 membered heteroarylene. In embodiments, $L^1$ is substituted 5 membered heteroarylene. In embodiments, $L^1$ is unsubstituted 5 membered heteroarylene. In embodiments, $L^1$ is substituted or unsubstituted 6 membered heteroarylene. In embodiments, $L^1$ is substituted 6 membered heteroarylene. In embodiments, $L^1$ is unsubstituted 6 membered heteroarylene.

In embodiments, $L^1$ is a polymer.

In embodiments, $L^{1.4}$ is substituted or unsubstituted methylene. In embodiments, $L^{1.4}$ is substituted or unsubstituted $C_2$ alkylene. In embodiments, $L^{1.4}$ is substituted or unsubstituted $C_3$ alkylene. In embodiments, $L^{1.4}$ is substituted or unsubstituted $C_4$ alkylene. In embodiments, $L^{1.4}$ is substituted or unsubstituted $C_5$ alkylene. In embodiments, $L^{1.4}$ is substituted or unsubstituted $C_6$ alkylene. In embodiments, $L^{1.4}$ is substituted or unsubstituted $C_7$ alkylene. In embodiments, $L^{1.4}$ is substituted or unsubstituted $C_8$ alkylene. In embodiments, $L^{1.4}$ is substituted methylene. In embodiments, $L^{1.4}$ is substituted $C_2$ alkylene. In embodiments, $L^{1.4}$ is substituted $C_3$ alkylene. In embodiments, $L^{1.4}$ is substituted $C_4$ alkylene. In embodiments, $L^{1.4}$ is substituted $C_5$ alkylene. In embodiments, $L^{1.4}$ is substituted $C_6$ alkylene. In embodiments, $L^{1.4}$ is substituted $C_7$ alkylene. In embodiments, $L^{1.4}$ is substituted $C_8$ alkylene. In embodiments, $L^{1.4}$ is an unsubstituted methylene. In embodiments, $L^{1.4}$ is an unsubstituted $C_2$ alkylene. In embodiments, $L^{1.4}$ is an unsubstituted $C_3$ alkylene. In embodiments, $L^{1.4}$ is an unsubstituted $C_4$ alkylene. In embodiments, $L^{1.4}$ is an unsubstituted $C_5$ alkylene. In embodiments, $L^{1.4}$ is an unsubstituted $C_6$ alkylene. In embodiments, $L^{1.4}$ is an unsubstituted $C_7$ alkylene. In embodiments, $L^{1.4}$ is an unsubstituted $C_8$ alkylene.

In embodiments, $L^{1.4}$ is substituted or unsubstituted $C_1$-$C_6$ alkylene. In embodiments, $L^{1.4}$ is substituted $C_1$-$C_6$ alkylene. In embodiments, $L^{1.4}$ is unsubstituted $C_1$-$C_6$ alkylene. In embodiments, $L^{1.4}$ is substituted or unsubstituted $C_2$-$C_6$ alkylene. In embodiments, $L^{1.4}$ is substituted $C_2$-$C_6$ alkylene. In embodiments, $L^{1.4}$ is unsubstituted $C_2$-$C_6$ alkylene. In embodiments, $L^{1.4}$ is substituted or unsubstituted $C_1$ alkylene. In embodiments, $L^{1.4}$ is substituted $C_1$ alkylene. In embodiments, $L^{1.4}$ is unsubstituted $C_1$ alkylene. In embodiments, $L^{1.4}$ is substituted or unsubstituted $C_2$ alkylene. In embodiments, $L^{1.4}$ is substituted $C_2$ alkylene. In embodiments, $L^{1.4}$ is unsubstituted $C_2$ alkylene. In embodiments, $L^{1.4}$ is substituted or unsubstituted $C_3$ alkylene. In embodiments, $L^{1.4}$ is substituted $C_3$ alkylene. In embodiments, $L^{1.4}$ is unsubstituted $C_3$ alkylene. In embodiments, $L^{1.4}$ is substituted or unsubstituted $C_4$ alkylene. In embodiments, $L^{1.4}$ is substituted $C_4$ alkylene. In embodiments, $L^{1.4}$ is unsubstituted $C_4$ alkylene. In embodiments, $L^{1.4}$ is substituted or unsubstituted $C_5$ alkylene. In embodiments, $L^{1.4}$ is substituted $C_5$ alkylene. In embodiments, $L^{1.4}$ is unsubstituted $C_5$ alkylene. In embodiments, $L^{1.4}$ is substituted or unsubstituted $C_6$ alkylene. In embodiments, $L^{1.4}$ is substituted $C_6$ alkylene. In embodiments, $L^{1.4}$ is unsubstituted $C_6$ alkylene.

In embodiments, $L^{1.4}$ is substituted or unsubstituted 2 to 8 membered heteroalkylene. In embodiments, $L^{1.4}$ is substituted 2 to 8 membered heteroalkylene. In embodiments, $L^{1.4}$ is unsubstituted 2 to 8 membered heteroalkylene. In embodiments, $L^{1.4}$ is substituted or unsubstituted 2 membered heteroalkylene. In embodiments, $L^{1.4}$ is substituted 2 membered heteroalkylene. In embodiments, $L^{1.4}$ is unsubstituted 2 membered heteroalkylene. In embodiments, $L^{1.4}$ is substituted or unsubstituted 3 membered heteroalkylene. In embodiments, $L^{1.4}$ is substituted 3 membered heteroalkylene. In embodiments, $L^{1.4}$ is unsubstituted 3 membered heteroalkylene. In embodiments, $L^{1.4}$ is substituted or unsubstituted 4 membered heteroalkylene. In embodiments, $L^{1.4}$ is substituted 4 membered heteroalkylene. In embodiments, $L^{1.4}$ is unsubstituted 4 membered heteroalkylene. In embodiments, $L^{1.4}$ is substituted or unsubstituted 5 membered heteroalkylene. In embodiments, $L^{1.4}$ is substituted 5 membered heteroalkylene. In embodiments, $L^{1.4}$ is unsubstituted 5 membered heteroalkylene. In embodiments, $L^{1.4}$ is substituted or unsubstituted 6 membered heteroalkylene. In embodiments, $L^{1.4}$ is substituted 6 membered heteroalkylene. In embodiments, $L^{1.4}$ is unsubstituted 6 membered heteroalkylene.

In embodiments, $L^{1.4}$ is substituted or unsubstituted $C_4$-$C_6$ cycloalkylene. In embodiments, $L^{1.4}$ is substituted $C_4$-$C_6$ cycloalkylene. In embodiments, $L^{1.4}$ is substituted $C_4$-$C_6$ cycloalkylene. In embodiments, $L^{1.4}$ is substituted or unsubstituted $C_4$ cycloalkylene. In embodiments, $L^{1.4}$ is substituted $C_4$ cycloalkylene. In embodiments, $L^{1.4}$ is substituted $C_4$ cycloalkylene. In embodiments, $L^{1.4}$ is substituted or unsubstituted $C_5$ cycloalkylene. In embodiments, $L^{1.4}$ is substituted $C_5$ cycloalkylene. In embodiments, $L^{1.4}$ is substituted $C_5$ cycloalkylene.

In embodiments, $L^{1A}$ is substituted or unsubstituted 5 to 6 membered heterocycloalkylene. In embodiments, $L^{1A}$ is substituted 5 to 6 membered heterocycloalkylene. In embodiments, $L^{1A}$ is unsubstituted 5 to 6 membered heterocycloalkylene. In embodiments, $L^{1A}$ is substituted or unsubstituted 5 membered heterocycloalkylene. In embodiments, $L^{1A}$ is substituted 5 membered heterocycloalkylene. In embodiments, $L^{1A}$ is unsubstituted 5 membered heterocycloalkylene. In embodiments, $L^{1A}$ is substituted or unsubstituted 6 membered heterocycloalkylene. In embodiments, $L^{1A}$ is substituted 6 membered heterocycloalkylene. In embodiments, $L^{1A}$ is unsubstituted 6 membered heterocycloalkylene.

In embodiments, $L^{1A}$ is substituted or unsubstituted phenylene. In embodiments, $L^{1A}$ is substituted phenylene. In embodiments, $L^{1A}$ is unsubstituted phenylene.

In embodiments, $L^{1A}$ is substituted or unsubstituted 5 to 6 membered heteroarylene. In embodiments, $L^{1A}$ is substituted 5 to 6 membered heteroarylene. In embodiments, $L^{1A}$ is unsubstituted 5 to 6 membered heteroarylene. In embodiments, $L^{1A}$ is substituted or unsubstituted 5 membered heteroarylene. In embodiments, $L^{1A}$ is substituted 5 membered heteroarylene. In embodiments, $L^{1A}$ is unsubstituted 5 membered heteroarylene. In embodiments, $L^{1A}$ is substituted or unsubstituted 6 membered heteroarylene. In embodiments, $L^{1A}$ is substituted 6 membered heteroarylene. In embodiments, $L^{1A}$ is unsubstituted 6 membered heteroarylene.

In embodiments, $L^{1A}$ is a polymer.

In embodiments, $L^{1B}$ is substituted or unsubstituted methylene. In embodiments, $L^{1B}$ is substituted or unsubstituted $C_2$ alkylene. In embodiments, $L^{1B}$ is substituted or unsubstituted $C_3$ alkylene. In embodiments, $L^{1B}$ is substituted or unsubstituted $C_4$ alkylene. In embodiments, $L^{1B}$ is substituted or unsubstituted $C_5$ alkylene. In embodiments, $L^{1B}$ is substituted or unsubstituted $C_6$ alkylene. In embodiments, $L^{1B}$ is substituted or unsubstituted $C_7$ alkylene. In embodiments, $L^{1B}$ is substituted or unsubstituted $C_8$ alkylene. In embodiments, $L^{1B}$ is substituted methylene. In embodiments, $L^{1B}$ is substituted $C_2$ alkylene. In embodiments, $L^{1B}$ is substituted $C_3$ alkylene. In embodiments, $L^{1B}$ is substituted $C_4$ alkylene. In embodiments, $L^{1B}$ is substituted $C_5$ alkylene. In embodiments, $L^{1B}$ is substituted $C_6$ alkylene. In embodiments, $L^{1B}$ is substituted $C_7$ alkylene. In embodiments, $L^{1B}$ is substituted $C_8$ alkylene. In embodiments, $L^{1B}$ is an unsubstituted methylene. In embodiments, $L^{1B}$ is an unsubstituted $C_2$ alkylene. In embodiments, $L^{1B}$ is an unsubstituted $C_3$ alkylene. In embodiments, $L^{1B}$ is an unsubstituted $C_4$ alkylene. In embodiments, $L^{1B}$ is an unsubstituted $C_5$ alkylene. In embodiments, $L^{1B}$ is an unsubstituted $C_6$ alkylene. In embodiments, $L^{1B}$ is an unsubstituted $C_7$ alkylene. In embodiments, $L^{1B}$ is an unsubstituted $C_8$ alkylene.

In embodiments, $L^{1B}$ is substituted or unsubstituted $C_1$-$C_6$ alkylene. In embodiments, $L^{1B}$ is substituted $C_1$-$C_6$ alkylene. In embodiments, $L^{1B}$ is unsubstituted $C_1$-$C_6$ alkylene. In embodiments, $L^{1B}$ is substituted or unsubstituted $C_2$-$C_6$ alkylene. In embodiments, $L^{1B}$ is substituted $C_2$-$C_6$ alkylene. In embodiments, $L^{1B}$ is unsubstituted $C_2$-$C_6$ alkylene. In embodiments, $L^{1B}$ is substituted or unsubstituted $C_1$ alkylene. In embodiments, $L^{1B}$ is substituted $C_1$ alkylene. In embodiments, $L^{1B}$ is unsubstituted $C_1$ alkylene. In embodiments, $L^{1B}$ is substituted or unsubstituted $C_2$ alkylene. In embodiments, $L^{1B}$ is substituted $C_2$ alkylene. In embodiments, $L^{1B}$ is unsubstituted $C_2$ alkylene. In embodiments, $L^{1B}$ is substituted or unsubstituted $C_3$ alkylene. In embodiments, $L^{1B}$ is substituted $C_3$ alkylene. In embodiments, $L^{1B}$ is unsubstituted $C_3$ alkylene. In embodiments, $L^{1B}$ is substituted or unsubstituted $C_4$ alkylene. In embodiments, $L^{1B}$ is substituted $C_4$ alkylene. In embodiments, $L^{1B}$ is unsubstituted $C_4$ alkylene. In embodiments, $L^{1B}$ is substituted or unsubstituted $C_5$ alkylene. In embodiments, $L^{1B}$ is substituted $C_5$ alkylene. In embodiments, $L^{1B}$ is unsubstituted $C_5$ alkylene. In embodiments, $L^{1B}$ is substituted or unsubstituted $C_6$ alkylene. In embodiments, $L^{1B}$ is substituted $C_6$ alkylene. In embodiments, $L^{1B}$ is unsubstituted $C_6$ alkylene.

In embodiments, $L^{1B}$ is substituted or unsubstituted 2 to 8 membered heteroalkylene. In embodiments, $L^{1B}$ is substituted 2 to 8 membered heteroalkylene. In embodiments, $L^{1B}$ is unsubstituted 2 to 8 membered heteroalkylene. In embodiments, $L^{1B}$ is substituted or unsubstituted 2 membered heteroalkylene. In embodiments, $L^{1B}$ is substituted 2 membered heteroalkylene. In embodiments, $L^{1B}$ is unsubstituted 2 membered heteroalkylene. In embodiments, $L^{1B}$ is substituted or unsubstituted 3 membered heteroalkylene. In embodiments, $L^{1B}$ is substituted 3 membered heteroalkylene. In embodiments, $L^{1B}$ is unsubstituted 3 membered heteroalkylene. In embodiments, $L^{1B}$ is substituted or unsubstituted 4 membered heteroalkylene. In embodiments, $L^{1B}$ is substituted 4 membered heteroalkylene. In embodiments, $L^{1B}$ is unsubstituted 4 membered heteroalkylene. In embodiments, $L^{1B}$ is substituted or unsubstituted 5 membered heteroalkylene. In embodiments, $L^{1B}$ is substituted 5 membered heteroalkylene. In embodiments, $L^{1B}$ is unsubstituted 5 membered heteroalkylene. In embodiments, $L^{1B}$ is substituted or unsubstituted 6 membered heteroalkylene. In embodiments, $L^{1B}$ is substituted 6 membered heteroalkylene. In embodiments, $L^{1B}$ is unsubstituted 6 membered heteroalkylene.

In embodiments, $L^{1B}$ is substituted or unsubstituted $C_4$-$C_6$ cycloalkylene. In embodiments, $L^{1B}$ is substituted $C_4$-$C_6$ cycloalkylene. In embodiments, $L^{1B}$ is substituted $C_4$-$C_6$ cycloalkylene. In embodiments, $L^{1B}$ is substituted or unsubstituted $C_4$ cycloalkylene. In embodiments, $L^{1B}$ is substituted $C_4$ cycloalkylene. In embodiments, $L^{1B}$ is substituted $C_4$ cycloalkylene. In embodiments, $L^{1B}$ is substituted or unsubstituted $C_5$ cycloalkylene. In embodiments, $L^{1B}$ is substituted $C_5$ cycloalkylene. In embodiments, $L^{1B}$ is substituted $C_5$ cycloalkylene.

In embodiments, $L^{1B}$ is substituted or unsubstituted 5 to 6 membered heterocycloalkylene. In embodiments, $L^{1B}$ is substituted 5 to 6 membered heterocycloalkylene. In embodiments, $L^{1B}$ is unsubstituted 5 to 6 membered heterocycloalkylene. In embodiments, $L^{1B}$ is substituted or unsubstituted 5 membered heterocycloalkylene. In embodiments, $L^{1B}$ is substituted 5 membered heterocycloalkylene. In embodiments, $L^{1B}$ is unsubstituted 5 membered heterocycloalkylene. In embodiments, $L^{1B}$ is substituted or unsubstituted 6 membered heterocycloalkylene. In embodiments, $L^{1B}$ is substituted 6 membered heterocycloalkylene. In embodiments, $L^{1B}$ is unsubstituted 6 membered heterocycloalkylene.

In embodiments, $L^{1B}$ is substituted or unsubstituted phenylene. In embodiments, $L^{1B}$ is substituted phenylene. In embodiments, $L^{1B}$ is unsubstituted phenylene.

In embodiments, $L^{1B}$ is substituted or unsubstituted 5 to 6 membered heteroarylene. In embodiments, $L^{1B}$ is substituted 5 to 6 membered heteroarylene. In embodiments, $L^{1B}$ is unsubstituted 5 to 6 membered heteroarylene. In embodiments, $L^{1B}$ is substituted or unsubstituted 5 membered heteroarylene. In embodiments, $L^{1B}$ is substituted 5 membered heteroarylene. In embodiments, $L^{1B}$ is unsubstituted 5 membered heteroarylene. In embodiments, $L^{1B}$ is substituted or unsubstituted 6 membered heteroarylene. In embodiments, $L^{1B}$ is substituted 6 membered heteroarylene. In embodiments, $L^{1B}$ is unsubstituted 6 membered heteroarylene.

In embodiments, $L^{1C}$ is substituted or unsubstituted methylene. In embodiments, $L^{1C}$ is substituted or unsubstituted $C_2$ alkylene. In embodiments, $L^{1C}$ is substituted or unsubstituted $C_3$ alkylene. In embodiments, $L^{1C}$ is substituted or unsubstituted $C_4$ alkylene. In embodiments, $L^{1C}$ is substituted or unsubstituted $C_5$ alkylene. In embodiments, $L^{1C}$ is substituted or unsubstituted $C_6$ alkylene. In embodiments, $L^{1C}$ is substituted or unsubstituted $C_7$ alkylene. In embodiments, $L^{1C}$ is substituted or unsubstituted $C_8$ alkylene. In embodiments, $L^{1C}$ is substituted methylene. In embodiments, $L^{1C}$ is substituted $C_2$ alkylene. In embodiments, $L^{1C}$ is substituted $C_3$ alkylene. In embodiments, $L^{1C}$ is substituted $C_4$ alkylene. In embodiments, $L^{1C}$ is substituted $C_5$ alkylene. In embodiments, $L^{1C}$ is substituted $C_6$ alkylene. In embodiments, $L^{1C}$ is substituted $C_7$ alkylene. In embodiments, $L^{1C}$ is substituted $C_8$ alkylene. In embodiments, $L^{1C}$ is an unsubstituted methylene. In embodiments, $L^{1C}$ is an unsubstituted $C_2$ alkylene. In embodiments, $L^{1C}$ is an unsubstituted $C_3$ alkylene. In embodiments, $L^{1C}$ is an unsubstituted $C_4$ alkylene. In embodiments, $L^{1C}$ is an unsubstituted $C_5$ alkylene. In embodiments, $L^{1C}$ is an unsubstituted $C_6$ alkylene. In embodiments, $L^{1C}$ is an unsubstituted $C_7$ alkylene. In embodiments, $L^{1C}$ is an unsubstituted $C_8$ alkylene.

In embodiments, $L^{1C}$ is substituted or unsubstituted $C_1$-$C_6$ alkylene. In embodiments, $L^{1C}$ is substituted $C_1$-$C_6$ alkylene. In embodiments, $L^{1C}$ is unsubstituted $C_1$-$C_6$ alkylene. In embodiments, $L^{1C}$ is substituted or unsubstituted $C_2$-$C_6$ alkylene. In embodiments, $L^{1C}$ is substituted $C_2$-$C_6$ alkylene. In embodiments, $L^{1C}$ is unsubstituted $C_2$-$C_6$ alkylene. In embodiments, $L^{1C}$ is substituted or unsubstituted $C_1$ alkylene. In embodiments, $L^{1C}$ is substituted $C_1$ alkylene. In embodiments, $L^{1C}$ is unsubstituted $C_1$ alkylene. In embodiments, $L^{1C}$ is substituted or unsubstituted $C_2$ alkylene. In embodiments, $L^{1C}$ is substituted $C_2$ alkylene. In embodiments, $L^{1C}$ is unsubstituted $C_2$ alkylene. In embodiments, $L^{1C}$ is substituted or unsubstituted $C_3$ alkylene. In embodiments, $L^{1C}$ is substituted $C_3$ alkylene. In embodiments, $L^{1C}$ is unsubstituted $C_3$ alkylene. In embodiments, $L^{1C}$ is substituted or unsubstituted $C_4$ alkylene. In embodiments, $L^{1C}$ is substituted $C_4$ alkylene. In embodiments, $L^{1C}$ is unsubstituted $C_4$ alkylene. In embodiments, $L^{1C}$ is substituted or unsubstituted $C_5$ alkylene. In embodiments, $L^{1C}$ is substituted $C_5$ alkylene. In embodiments, $L^{1C}$ is unsubstituted $C_5$ alkylene. In embodiments, $L^{1C}$ is substituted or unsubstituted $C_6$ alkylene. In embodiments, $L^{1C}$ is substituted $C_6$ alkylene. In embodiments, $L^{1C}$ is unsubstituted $C_6$ alkylene.

In embodiments, $L^{1C}$ is substituted or unsubstituted 2 to 8 membered heteroalkylene. In embodiments, $L^{1C}$ is substituted 2 to 8 membered heteroalkylene. In embodiments, $L^{1C}$ is unsubstituted 2 to 8 membered heteroalkylene. In embodiments, $L^{1C}$ is substituted or unsubstituted 2 membered heteroalkylene. In embodiments, $L^{1C}$ is substituted 2 membered heteroalkylene. In embodiments, $L^{1C}$ is unsubstituted 2 membered heteroalkylene. In embodiments, $L^{1C}$ is substituted or unsubstituted 3 membered heteroalkylene. In embodiments, $L^{1C}$ is substituted 3 membered heteroalkylene. In embodiments, $L^{1C}$ is unsubstituted 3 membered heteroalkylene. In embodiments, $L^{1C}$ is substituted or unsubstituted 4 membered heteroalkylene. In embodiments, $L^{1C}$ is substituted 4 membered heteroalkylene. In embodiments, $L^{1C}$ is unsubstituted 4 membered heteroalkylene. In embodiments, $L^{1C}$ is substituted or unsubstituted 5 membered heteroalkylene. In embodiments, $L^{1C}$ is substituted 5 membered heteroalkylene. In embodiments, $L^{1C}$ is unsubstituted 5 membered heteroalkylene. In embodiments, $L^{1C}$ is substituted or unsubstituted 6 membered heteroalkylene. In embodiments, $L^{1C}$ is substituted 6 membered heteroalkylene. In embodiments, $L^{1C}$ is unsubstituted 6 membered heteroalkylene.

In embodiments, $L^{1C}$ is substituted or unsubstituted $C_4$-$C_6$ cycloalkylene. In embodiments, $L^{1C}$ is substituted $C_4$-$C_6$ cycloalkylene. In embodiments, $L^{1C}$ is substituted $C_4$-$C_6$ cycloalkylene. In embodiments, $L^{1C}$ is substituted or unsubstituted $C_4$ cycloalkylene. In embodiments, $L^{1C}$ is substituted $C_4$ cycloalkylene. In embodiments, $L^{1C}$ is substituted $C_4$ cycloalkylene. In embodiments, $L^{1C}$ is substituted or unsubstituted $C_5$ cycloalkylene. In embodiments, $L^{1C}$ is substituted $C_5$ cycloalkylene. In embodiments, $L^{1C}$ is substituted $C_5$ cycloalkylene.

In embodiments, $L^{1C}$ is substituted or unsubstituted 5 to 6 membered heterocycloalkylene. In embodiments, $L^{1C}$ is substituted 5 to 6 membered heterocycloalkylene. In embodiments, $L^{1C}$ is unsubstituted 5 to 6 membered heterocycloalkylene. In embodiments, $L^{1C}$ is substituted or unsubstituted 5 membered heterocycloalkylene. In embodiments, $L^{1C}$ is substituted 5 membered heterocycloalkylene. In embodiments, $L^{1C}$ is unsubstituted 5 membered heterocycloalkylene. In embodiments, $L^{1C}$ is substituted or unsubstituted 6 membered heterocycloalkylene. In embodiments, $L^{1C}$ is substituted 6 membered heterocycloalkylene. In embodiments, $L^{1C}$ is unsubstituted 6 membered heterocycloalkylene.

In embodiments, $L^{1C}$ is substituted or unsubstituted phenylene. In embodiments, $L^{1C}$ is substituted phenylene. In embodiments, $L^{1C}$ is unsubstituted phenylene.

In embodiments, $L^{1C}$ is substituted or unsubstituted 5 to 6 membered heteroarylene. In embodiments, $L^{1C}$ is substituted 5 to 6 membered heteroarylene. In embodiments, $L^{1C}$ is unsubstituted 5 to 6 membered heteroarylene. In embodiments, $L^{1C}$ is substituted or unsubstituted 5 membered heteroarylene. In embodiments, $L^{1C}$ is substituted 5 membered heteroarylene. In embodiments, $L^{1C}$ is unsubstituted 5 membered heteroarylene. In embodiments, $L^{1C}$ is substituted or unsubstituted 6 membered heteroarylene. In embodiments, $L^{1C}$ is substituted 6 membered heteroarylene. In embodiments, $L^{1C}$ is unsubstituted 6 membered heteroarylene.

In embodiments, $L^{1D}$ is substituted or unsubstituted methylene. In embodiments, $L^{1D}$ is substituted or unsubstituted $C_2$ alkylene. In embodiments, $L^{1D}$ is substituted or unsubstituted $C_3$ alkylene. In embodiments, $L^{1D}$ is substituted or unsubstituted $C_4$ alkylene. In embodiments, $L^{1D}$ is substituted or unsubstituted $C_5$ alkylene. In embodiments, $L^{1D}$ is substituted or unsubstituted $C_6$ alkylene. In embodiments, $L^{1D}$ is substituted or unsubstituted $C_7$ alkylene. In embodiments, $L^{1D}$ is substituted or unsubstituted $C_8$ alkylene. In embodiments, $L^{1D}$ is substituted methylene. In embodiments, $L^{1D}$ is substituted $C_2$ alkylene. In embodiments, $L^{1D}$ is substituted $C_3$ alkylene. In embodiments, $L^{1D}$ is substituted $C_4$ alkylene. In embodiments, $L^{1D}$ is substituted $C_5$ alkylene. In embodiments, $L^{1D}$ is substituted $C_6$ alkylene. In embodiments, $L^{1D}$ is substituted $C_7$ alkylene. In embodiments, $L^{1D}$ is substituted $C_8$ alkylene. In embodiments, $L^{1D}$ is an unsubstituted methylene. In embodiments, $L^{1D}$ is an unsubstituted $C_2$ alkylene. In embodiments, $L^{1D}$ is an unsubstituted $C_3$ alkylene. In embodiments, $L^{1D}$ is an unsubstituted $C_4$ alkylene. In embodiments, $L^{1D}$ is an unsubstituted $C_5$ alkylene. In embodiments, $L^{1D}$ is an unsubstituted $C_6$ alkylene. In embodiments, $L^{1D}$ is an unsubstituted $C_7$ alkylene. In embodiments, $L^{1D}$ is an unsubstituted $C_8$ alkylene.

In embodiments, $L^{1D}$ is substituted or unsubstituted $C_1$-$C_6$ alkylene. In embodiments, $L^{1D}$ is substituted $C_1$-$C_6$ alkylene. In embodiments, $L^{1D}$ is unsubstituted $C_1$-$C_6$ alkylene. In embodiments, $L^{1D}$ is substituted or unsubstituted $C_2$-$C_6$ alkylene. In embodiments, $L^{1D}$ is substituted $C_2$-$C_6$ alkylene. In embodiments, $L^{1D}$ is unsubstituted $C_2$-$C_6$ alkylene. In embodiments, $L^{1D}$ is substituted or unsubstituted $C_1$ alkylene. In embodiments, $L^{1D}$ is substituted $C_1$ alkylene. In embodiments, $L^{1D}$ is unsubstituted $C_1$ alkylene. In embodiments, $L^{1D}$ is substituted or unsubstituted $C_2$ alkylene. In embodiments, $L^{1D}$ is substituted $C_2$ alkylene. In embodiments, $L^{1D}$ is unsubstituted $C_2$ alkylene. In embodiments, $L^{1D}$ is substituted or unsubstituted $C_3$ alkylene. In embodiments, $L^{1D}$ is substituted $C_3$ alkylene. In embodiments, $L^{1D}$ is unsubstituted $C_3$ alkylene. In embodiments, $L^{1D}$ is substituted or unsubstituted $C_4$ alkylene. In embodiments, $L^{1D}$ is substituted $C_4$ alkylene. In embodiments, $L^{1D}$ is unsubstituted $C_4$ alkylene. In embodiments, $L^{1D}$ is substituted or unsubstituted $C_5$ alkylene. In embodiments, $L^{1D}$ is substituted $C_5$ alkylene. In embodiments, $L^{1D}$ is unsubstituted $C_5$ alkylene. In embodiments, $L^{1D}$ is substituted or unsubstituted $C_6$ alkylene. In embodiments, $L^{1D}$ is substituted $C_6$ alkylene. In embodiments, $L^{1D}$ is unsubstituted $C_6$ alkylene.

In embodiments, $L^{1D}$ is substituted or unsubstituted 2 to 8 membered heteroalkylene. In embodiments, $L^{1D}$ is substituted 2 to 8 membered heteroalkylene. In embodiments, $L^{1D}$ is unsubstituted 2 to 8 membered heteroalkylene. In embodiments, $L^{1D}$ is substituted or unsubstituted 2 membered heteroalkylene. In embodiments, $L^{1D}$ is substituted 2 membered heteroalkylene. In embodiments, $L^{1D}$ is unsubstituted 2 membered heteroalkylene. In embodiments, $L^{1D}$ is substituted or unsubstituted 3 membered heteroalkylene. In embodiments, $L^{1D}$ is substituted 3 membered heteroalkylene. In embodiments, $L^{1D}$ is unsubstituted 3 membered heteroalkylene. In embodiments, $L^{1D}$ is substituted or unsubstituted 4 membered heteroalkylene. In embodiments, $L^{1D}$ is substituted 4 membered heteroalkylene. In embodiments, $L^{1D}$ is unsubstituted 4 membered heteroalkylene. In embodiments, $L^{1D}$ is substituted or unsubstituted 5 membered heteroalkylene. In embodiments, $L^{1D}$ is substituted 5 membered heteroalkylene. In embodiments, $L^{1D}$ is unsubstituted 5 membered heteroalkylene. In embodiments, $L^{1D}$ is substituted or unsubstituted 6 membered heteroalkylene. In embodiments, $L^{1D}$ is substituted 6 membered heteroalkylene. In embodiments, $L^{1D}$ is unsubstituted 6 membered heteroalkylene.

In embodiments, $L^{1D}$ is substituted or unsubstituted $C_4$-$C_6$ cycloalkylene. In embodiments, $L^{1D}$ is substituted $C_4$-$C_6$ cycloalkylene. In embodiments, $L^{1D}$ is substituted $C_4$-$C_6$ cycloalkylene. In embodiments, $L^{1D}$ is substituted or unsubstituted $C_4$ cycloalkylene. In embodiments, $L^{1D}$ is substituted $C_4$ cycloalkylene. In embodiments, $L^{1D}$ is substituted $C_4$ cycloalkylene. In embodiments, $L^{1D}$ is substituted or unsubstituted $C_5$ cycloalkylene. In embodiments, $L^{1D}$ is substituted $C_5$ cycloalkylene. In embodiments, $L^{1D}$ is substituted $C_5$ cycloalkylene.

In embodiments, $L^{1D}$ is substituted or unsubstituted 5 to 6 membered heterocycloalkylene. In embodiments, $L^{1D}$ is substituted 5 to 6 membered heterocycloalkylene. In embodiments, $L^{1D}$ is unsubstituted 5 to 6 membered heterocycloalkylene. In embodiments, $L^{1D}$ is substituted or unsubstituted 5 membered heterocycloalkylene. In embodiments, $L^{1D}$ is substituted 5 membered heterocycloalkylene. In embodiments, $L^{1D}$ is unsubstituted 5 membered heterocycloalkylene. In embodiments, $L^{1D}$ is substituted or unsubstituted 6 membered heterocycloalkylene. In embodiments, $L^{1D}$ is substituted 6 membered heterocycloalkylene. In embodiments, $L^{1D}$ is unsubstituted 6 membered heterocycloalkylene.

In embodiments, $L^{1D}$ is substituted or unsubstituted phenylene. In embodiments, $L^{1D}$ is substituted phenylene. In embodiments, $L^{1D}$ is unsubstituted phenylene.

In embodiments, $L^{1D}$ is substituted or unsubstituted 5 to 6 membered heteroarylene. In embodiments, $L^{1D}$ is substituted 5 to 6 membered heteroarylene. In embodiments, $L^{1D}$ is unsubstituted 5 to 6 membered heteroarylene. In embodiments, $L^{1D}$ is substituted or unsubstituted 5 membered heteroarylene. In embodiments, $L^{1D}$ is substituted 5 membered heteroarylene. In embodiments, $L^{1D}$ is unsubstituted 5 membered heteroarylene. In embodiments, $L^{1D}$ is substituted or unsubstituted 6 membered heteroarylene. In embodiments, $L^{1D}$ is substituted 6 membered heteroarylene. In embodiments, $L^{1D}$ is unsubstituted 6 membered heteroarylene.

In embodiments, $L^{1E}$ is substituted or unsubstituted methylene. In embodiments, $L^{1E}$ is substituted or unsubstituted $C_2$ alkylene. In embodiments, $L^{1E}$ is substituted or unsubstituted $C_3$ alkylene. In embodiments, $L^{1E}$ is substituted or unsubstituted $C_4$ alkylene. In embodiments, $L^{1E}$ is substituted or unsubstituted $C_5$ alkylene. In embodiments, $L^{1E}$ is substituted or unsubstituted $C_6$ alkylene. In embodiments, $L^{1E}$ is substituted or unsubstituted $C_7$ alkylene. In embodiments, $L^{1E}$ is substituted or unsubstituted $C_8$ alkylene. In embodiments, $L^{1E}$ is substituted methylene. In embodiments, $L^{1E}$ is substituted $C_2$ alkylene. In embodiments, $L^{1E}$ is substituted $C_3$ alkylene. In embodiments, $L^{1E}$ is substituted $C_4$ alkylene. In embodiments, $L^{1E}$ is substituted $C_5$ alkylene. In embodiments, $L^{1E}$ is substituted $C_6$ alkylene. In embodiments, $L^{1E}$ is substituted $C_7$ alkylene. In embodiments, $L^{1E}$ is substituted $C_8$ alkylene. In embodiments, $L^{1E}$ is an unsubstituted methylene. In embodiments, $L^{1E}$ is an unsubstituted $C_2$ alkylene. In embodiments, $L^{1E}$ is an unsubstituted $C_3$ alkylene. In embodiments, $L^{1E}$ is an unsubstituted $C_4$ alkylene. In embodiments, $L^{1E}$ is an unsubstituted $C_5$ alkylene. In embodiments, $L^{1E}$ is an unsubstituted $C_6$ alkylene. In embodiments, $L^{1E}$ is an unsubstituted $C_7$ alkylene. In embodiments, $L^{1E}$ is an unsubstituted $C_8$ alkylene.

In embodiments, $L^{1E}$ is substituted or unsubstituted $C_1$-$C_6$ alkylene. In embodiments, $L^{1E}$ is substituted $C_1$-$C_6$ alkylene. In embodiments, $L^{1E}$ is unsubstituted $C_1$-$C_6$ alkylene. In embodiments, $L^{1E}$ is substituted or unsubstituted $C_2$-$C_6$ alkylene. In embodiments, $L^{1E}$ is substituted $C_2$-$C_6$ alkylene. In embodiments, $L^{1E}$ is unsubstituted $C_2$-$C_6$ alkylene. In embodiments, $L^{1E}$ is substituted or unsubstituted $C_1$ alkylene. In embodiments, $L^{1E}$ is substituted $C_1$ alkylene. In embodiments, $L^{1E}$ is unsubstituted $C_1$ alkylene. In embodiments, $L^{1E}$ is substituted or unsubstituted $C_2$ alkylene. In embodiments, $L^{1E}$ is substituted $C_2$ alkylene. In embodiments, $L^{1E}$ is unsubstituted $C_2$ alkylene. In embodiments, $L^{1E}$ is substituted or unsubstituted $C_3$ alkylene. In embodiments, $L^{1E}$ is substituted $C_3$ alkylene. In embodiments, $L^{1E}$ is unsubstituted $C_3$ alkylene. In embodiments, $L^{1E}$ is substituted or unsubstituted $C_4$ alkylene. In embodiments, $L^{1E}$ is substituted $C_4$ alkylene. In embodiments, $L^{1E}$ is unsubstituted $C_4$ alkylene. In embodiments, $L^{1E}$ is substituted or unsubstituted $C_5$ alkylene. In embodiments, $L^{1E}$ is substituted $C_5$ alkylene. In embodiments, $L^{1E}$ is unsubstituted $C_5$ alkylene. In embodiments, $L^{1E}$ is substituted or unsubstituted $C_6$ alkylene. In embodiments, $L^{1E}$ is substituted $C_6$ alkylene. In embodiments, $L^{1E}$ is unsubstituted $C_6$ alkylene.

In embodiments, $L^{1E}$ is substituted or unsubstituted 2 to 8 membered heteroalkylene. In embodiments, $L^{1E}$ is substituted 2 to 8 membered heteroalkylene. In embodiments, $L^{1E}$ is unsubstituted 2 to 8 membered heteroalkylene. In embodiments, $L^{1E}$ is substituted or unsubstituted 2 membered heteroalkylene. In embodiments, $L^{1E}$ is substituted 2 membered heteroalkylene. In embodiments, $L^{1E}$ is unsubstituted 2 membered heteroalkylene. In embodiments, $L^{1E}$ is substituted or unsubstituted 3 membered heteroalkylene. In embodiments, $L^{1E}$ is substituted 3 membered heteroalkylene. In embodiments, $L^{1E}$ is unsubstituted 3 membered heteroalkylene. In embodiments, $L^{1E}$ is substituted or unsubstituted 4 membered heteroalkylene. In embodiments, $L^{1E}$ is substituted 4 membered heteroalkylene. In embodiments, $L^{1E}$ is unsubstituted 4 membered heteroalkylene. In embodiments, $L^{1E}$ is substituted or unsubstituted 5 membered heteroalkylene. In embodiments, $L^{1E}$ is substituted 5 membered heteroalkylene. In embodiments, $L^{1E}$ is unsubstituted 5 membered heteroalkylene. In embodiments, $L^{1E}$ is substituted or unsubstituted 6 membered heteroalkylene. In embodiments, $L^{1E}$ is substituted 6 membered heteroalkylene. In embodiments, $L^{1E}$ is unsubstituted 6 membered heteroalkylene.

In embodiments, $L^{1E}$ is substituted or unsubstituted $C_4$-$C_6$ cycloalkylene. In embodiments, $L^{1E}$ is substituted $C_4$-$C_6$ cycloalkylene. In embodiments, $L^{1E}$ is substituted $C_4$-$C_6$ cycloalkylene. In embodiments, $L^{1E}$ is substituted or unsubstituted $C_4$ cycloalkylene. In embodiments, $L^{1E}$ is substituted $C_4$ cycloalkylene. In embodiments, $L^{1E}$ is substituted $C_4$ cycloalkylene. In embodiments, $L^{1E}$ is substituted or unsubstituted $C_5$ cycloalkylene. In embodiments, $L^{1E}$ is substituted $C_5$ cycloalkylene. In embodiments, $L^{1E}$ is substituted $C_5$ cycloalkylene.

In embodiments, $L^{1E}$ is substituted or unsubstituted 5 to 6 membered heterocycloalkylene. In embodiments, $L^{1E}$ is substituted 5 to 6 membered heterocycloalkylene. In embodiments, $L^{1E}$ is unsubstituted 5 to 6 membered heterocycloalkylene. In embodiments, $L^{1E}$ is substituted or unsubstituted 5 membered heterocycloalkylene. In embodiments, $L^{1E}$ is substituted 5 membered heterocycloalkylene. In embodiments, $L^{1E}$ is unsubstituted 5 membered heterocycloalkylene. In embodiments, $L^{1E}$ is substituted or unsubstituted 6 membered heterocycloalkylene. In embodiments, $L^{1E}$ is substituted 6 membered heterocycloalkylene. In embodiments, $L^{1E}$ is unsubstituted 6 membered heterocycloalkylene.

In embodiments, $L^{1E}$ is substituted or unsubstituted phenylene. In embodiments, $L^{1E}$ is substituted phenylene. In embodiments, $L^{1E}$ is unsubstituted phenylene.

In embodiments, $L^{1E}$ is substituted or unsubstituted 5 to 6 membered heteroarylene. In embodiments, $L^{1E}$ is substituted 5 to 6 membered heteroarylene. In embodiments, $L^{1E}$ is unsubstituted 5 to 6 membered heteroarylene. In embodiments, $L^{1E}$ is substituted or unsubstituted 5 membered heteroarylene. In embodiments, $L^{1E}$ is substituted 5 membered heteroarylene. In embodiments, $L^{1E}$ is unsubstituted 5 membered heteroarylene. In embodiments, $L^{1E}$ is substituted or unsubstituted 6 membered heteroarylene. In embodiments, $L^{1E}$ is substituted 6 membered heteroarylene. In embodiments, $L^{1E}$ is unsubstituted 6 membered heteroarylene.

In embodiments, $L^{1A}$ is a bond. In embodiments, $L^{1B}$ is a bond. In embodiments, $L^{1C}$ is a bond. In embodiments, $L^{1D}$ is a bond. In embodiments, $L^{1E}$ is a bond.

In embodiments, $L^2$ is $L^{2A}$-$L^{2B}$-$L^{2C}$-$L^{2D}$-$L^{2E}$. $L^{2A}$, $L^{2B}$, $L^{2C}$, $L^{2D}$, or $L^{2E}$ are independently a bond, —SS—, —NN—, —NHC(O)—, —C(O)NH—, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene; wherein at least one of $L^{2A}$, $L^{2B}$, $L^{2C}$, $L^{2D}$, and $L^{2E}$ is not a bond.

In embodiments, $L^{2A}$, $L^{2B}$, $L^{2C}$, $L^{2D}$, or $L^{2E}$ are independently a bond, —NN—, —NHC(O)—, —C(O)NH—, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene; wherein at least one of $L^{2A}$, $L^{2B}$, $L^{2C}$, $L^{2D}$, and $L^{2E}$ is not a bond.

In embodiments, $L^{2A}$ is independently a bond, —SS—, —NN—, —NHC(O)—, —C(O)NH—, $R^{52A}$-substituted or unsubstituted alkylene, $R^{52A}$-substituted or unsubstituted heteroalkylene, $R^{52A}$-substituted or unsubstituted cycloalkylene, $R^{52A}$-substituted or unsubstituted heterocycloalkylene, $R^{52A}$-substituted or unsubstituted arylene, or $R^{52A}$-substituted or unsubstituted heteroarylene.

In embodiments, $L^{2B}$ is independently a bond, —SS—, —NN—, —NHC(O)—, —C(O)NH—, $R^{52B}$-substituted or unsubstituted alkylene, $R^{52B}$-substituted or unsubstituted heteroalkylene, $R^{52B}$-substituted or unsubstituted cycloalkylene, $R^{52B}$-substituted or unsubstituted heterocycloalkylene, $R^{52B}$-substituted or unsubstituted arylene, or $R^{52B}$-substituted or unsubstituted heteroarylene.

In embodiments, $L^{2C}$ is independently a bond, —SS—, —NN—, —NHC(O)—, —C(O)NH—, $R^{52C}$-substituted or unsubstituted alkylene, $R^{52C}$-substituted or unsubstituted heteroalkylene, $R^{52C}$-substituted or unsubstituted cycloalkylene, $R^{52C}$-substituted or unsubstituted heterocycloalkylene, $R^{52C}$-substituted or unsubstituted arylene, or $R^{52C}$-substituted or unsubstituted heteroarylene.

In embodiments, $L^{2D}$ is independently a bond, —SS—, —NN—, —NHC(O)—, —C(O)NH—, $R^{52D}$-substituted or unsubstituted alkylene, $R^{52D}$-substituted or unsubstituted heteroalkylene, $R^{52D}$-substituted or unsubstituted cycloal-
kylene, $R^{52D}$-substituted or unsubstituted heterocycloalkylene, $R^{52D}$-substituted or unsubstituted arylene, or $R^{52D}$-substituted or unsubstituted heteroarylene.

In embodiments, $L^{2E}$ is independently a bond, —SS—, —NN—, —NHC(O)—, —C(O)NH—, $R^{52E}$-substituted or unsubstituted alkylene, $R^{52E}$-substituted or unsubstituted heteroalkylene, $R^{52E}$-substituted or unsubstituted cycloalkylene, $R^{52E}$-substituted or unsubstituted heterocycloalkylene, $R^{52E}$-substituted or unsubstituted arylene, or $R^{52E}$-substituted or unsubstituted heteroarylene.

$R^{52A}$, $R^{52B}$, $R^{52C}$, $R^{52D}$, and $R^{52E}$ are each independently halogen, —CF$_3$, —CCl$_3$, —CI$_3$, —CBr$_3$, —CHF$_2$, —CHCl$_2$, —CHI$_2$, —CHBr$_2$, —CH$_2$F, —CH$_2$Cl, —CH$_2$I, —CH$_2$Br, —OCH$_2$F, —OCH$_2$Cl, —OCH$_2$I, —OCH$_2$Br, —OCHF$_2$, —OCHCl$_2$, —OCHI$_2$, —OCHBr$_2$, —OCF$_3$, —OCCl$_3$, —OCI$_3$, —OCBr$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —N$_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $L^2$ is $L^{2A}$-$L^B$-$L^{2C}$-$L^{2D}$-$L^{2E}$; and $L^{2A}$, $L^{2B}$, $L^{2C}$, $L^{2D}$, or $L^{2E}$ are independently a bond, —NN—, —NHC(O)—, —C(O)NH—, substituted (e.g., substituted with a substituent group, size-limited substituent group, or lower substituent group) or unsubstituted $C_1$-$C_{20}$ alkylene (e.g., alkylene, alkenylene, or alkynylene), substituted (e.g., substituted with a substituent group, size-limited substituent group, or lower substituent group) or unsubstituted 2 to 20 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_{20}$ cycloalkylene, substituted (e.g., substituted with a substituent group, size-limited substituent group, or lower substituent group) or unsubstituted 3 to 20 membered heterocycloalkylene, substituted (e.g., substituted with a substituent group, size-limited substituent group, or lower substituent group) or unsubstituted $C_6$-$C_{20}$ arylene, or substituted (e.g., substituted with a substituent group, size-limited substituent group, or lower substituent group) or unsubstituted 5 to 20 membered heteroarylene; wherein at least one of $L^{2A}$, $L^{2B}$, $L^{2C}$, $L^{2D}$, and $L^{2E}$ is not a bond.

In embodiments, $L^2$ is $L^{2A}$-$L^{2B}$-$L^{2C}$-$L^{2D}$-$L^{2E}$; and $L^{2A}$, $L^{2B}$, $L^{2C}$, $L^{2D}$, or $L^{2E}$ are independently a bond, —NN—, —NHC(O)—, —C(O)NH—, substituted (e.g., substituted with a substituent group, size-limited substituent group, or lower substituent group) or unsubstituted $C_1$-$C_{10}$ alkylene (e.g., alkylene, alkenylene, or alkynylene), substituted (e.g., substituted with a substituent group, size-limited substituent group, or lower substituent group) or unsubstituted 2 to 10 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_8$ cycloalkylene, substituted (e.g., substituted with a substituent group, size-limited substituent group, or lower substituent group) or unsubstituted 3 to 8 membered heterocycloalkylene, substituted (e.g., substituted with a substituent group, size-limited substituent group, or lower substituent group) or unsubstituted $C_6$-$C_{10}$ arylene, or substituted (e.g., substituted with a substituent group, size-limited substituent group, or lower substituent group) or unsubstituted 5 to 10 membered heteroarylene; wherein at least one of $L^{2A}$, $L^{2B}$, $L^{2C}$, $L^{2D}$, and $L^{2E}$ is not a bond.

In embodiments, $L^2$ is $L^{2A}$-$L^{2B}$-$L^{2C}$-$L^{2D}$-$L^{2E}$; and $L^{2A}$, $L^{2B}$, $L^{2C}$, $L^{2D}$, or $L^{2E}$ are independently a bond, —NN—, —NHC(O)—, —C(O)NH—, substituted (e.g., substituted with a substituent group, size-limited substituent group, or lower substituent group) or unsubstituted $C_1$-$C_6$ alkylene (e.g., alkylene, alkenylene, or alkynylene), substituted (e.g., substituted with a substituent group, size-limited substituent group, or lower substituent group) or unsubstituted 2 to 6 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_6$ cycloalkylene, substituted (e.g., substituted with a substituent group, size-limited substituent group, or lower substituent group) or unsubstituted 3 to 6 membered heterocycloalkylene, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroarylene; wherein at least one of $L^{2A}$, $L^{2B}$, $L^{2C}$, $L^{2D}$, and $L^{2E}$ is not a bond.

In embodiments, $L^2$ is $L^{2A}$-$L^{2B}$-$L^{2C}$-$L^{2D}$-$L^{2E}$; wherein $L^{2A}$ is a bond, —NN—, —NHC(O)—, —C(O)NH—, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene); $L^{2B}$ is a bond, —NN—, —NHC(O)—, —C(O)NH—, substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, substituted (e.g., substituted with a substituent group, size-limited substituent group, or lower substituent group) or unsubstituted heteroarylene; $L^{2C}$ is a bond, —NN—, —NHC(O)—, —C(O)NH—, substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, substituted (e.g., substituted with a substituent group, size-limited substituent group, or lower substituent group) or unsubstituted heteroarylene; $L^{2D}$ is a bond, —NN—, —NHC(O)—, —C(O)NH—, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene); and $L^{2E}$ is a bond, —NN—, —NHC(O)—, —C(O)NH—, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene; wherein at least one of $L^{2A}$, $L^{2B}$, $L^{2C}$, $L^{2D}$, and $L^{2E}$ is not a bond.

In embodiments, $L^2$ is a bond, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene.

In embodiments, $L^2$ is a bond, substituted (e.g., substituted with a substituent group, size-limited substituent group, or lower substituent group) or unsubstituted $C_1$-$C_{20}$ alkylene (e.g., alkylene, alkenylene, or alkynylene), substituted (e.g., substituted with a substituent group, size-limited substituent group, or lower substituent group) or unsubstituted 2 to 20 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_{20}$ cycloalkylene, substituted (e.g., substituted with a substituent group, size-limited substituent group, or lower substituent group) or unsubstituted 3 to 20 membered heterocycloalkylene, substituted (e.g., substituted with a substituent group, size-limited substituent group, or lower substituent group) or unsubstituted $C_6$-$C_{20}$ arylene, or substituted (e.g., substituted with a substituent group, size-limited substituent group, or lower substituent group) or unsubstituted 5 to 20 membered heteroarylene.

In embodiments, $L^2$ is a bond, substituted (e.g., substituted with a substituent group, size-limited substituent group, or lower substituent group) or unsubstituted $C_1$-$C_8$ alkylene (e.g., alkylene, alkenylene, or alkynylene), substituted (e.g., substituted with a substituent group, size-limited substituent group, or lower substituent group) or unsubstituted 2 to 8 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_8$ cycloalkylene, substituted (e.g., substituted with a substituent group, size-limited substituent group, or lower substituent group) or unsubstituted 3 to 8 membered heterocycloalkylene, substituted (e.g., substituted with a substituent group, size-limited substituent group, or lower substituent group) or unsubstituted $C_6$-$C_{10}$ arylene, or substituted (e.g., substituted with a substituent group, size-limited substituent group, or lower substituent group) or unsubstituted 5 to 10 membered heteroarylene.

In embodiments, $L^2$ is a bond, substituted (e.g., substituted with a substituent group, size-limited substituent group, or lower substituent group) or unsubstituted $C_1$-$C_6$ alkylene (e.g., alkylene, alkenylene, or alkynylene), substituted (e.g., substituted with a substituent group, size-limited substituent group, or lower substituent group) or unsubstituted 2 to 6 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_6$ cycloalkylene, substituted (e.g., substituted with a substituent group, size-limited substituent group, or lower substituent group) or unsubstituted 3 to 6 membered heterocycloalkylene, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroarylene.

In embodiments, $L^2$ is a substituted (e.g., substituted with a substituent group, size-limited substituent group, or lower substituent group) or unsubstituted 3 to 10 membered heteroalkylene (e.g., heteroalkylene, heteroalkenylene, or heteroalkynylene). In embodiments, $L^2$ is a substituted (e.g., substituted with a substituent group, size-limited substituent group, or lower substituent group) or unsubstituted 3 to 8 membered heteroalkylene (e.g., heteroalkylene, heteroalkenylene, or heteroalkynylene). In embodiments, $L^2$ is a substituted (e.g., substituted with a substituent group, size-limited substituent group, or lower substituent group) or unsubstituted 3 to 6 membered heteroalkylene (e.g., heteroalkylene, heteroalkenylene, or heteroalkynylene).

In embodiments, $L^2$ is substituted or unsubstituted methylene. In embodiments, $L^2$ is substituted or unsubstituted $C_2$ alkylene. In embodiments, $L^2$ is substituted or unsubstituted $C_3$ alkylene. In embodiments, $L^2$ is substituted or unsubstituted $C_4$ alkylene. In embodiments, $L^2$ is substituted or unsubstituted $C_5$ alkylene. In embodiments, $L^2$ is substituted or unsubstituted $C_6$ alkylene. In embodiments, $L^2$ is substituted or unsubstituted $C_7$ alkylene. In embodiments, $L^2$ is substituted or unsubstituted $C_5$ alkylene. In embodiments, $L^2$ is substituted methylene. In embodiments, $L^2$ is substituted $C_2$ alkylene. In embodiments, $L^2$ is substituted $C_3$ alkylene. In embodiments, $L^2$ is substituted $C_4$ alkylene. In embodiments, $L^2$ is substituted $C_5$ alkylene. In embodiments, $L^2$ is substituted $C_6$ alkylene. In embodiments, $L^2$ is substituted $C_7$ alkylene. In embodiments, $L^2$ is substituted $C_5$ alkylene. In embodiments, $L^2$ is an unsubstituted methylene. In embodiments, $L^2$ is an unsubstituted $C_2$ alkylene. In embodiments, $L^2$ is an unsubstituted $C_3$ alkylene. In embodiments, $L^2$ is an unsubstituted $C_4$ alkylene. In embodiments, $L^2$ is an unsubstituted $C_5$ alkylene. In embodiments, $L^2$ is an unsubstituted $C_6$ alkylene. In embodiments, $L^2$ is an unsubstituted $C_7$ alkylene. In embodiments, $L^2$ is an unsubstituted $C_5$ alkylene.

In embodiments, $L^2$ is substituted or unsubstituted $C_1$-$C_6$ alkylene. In embodiments, $L^2$ is substituted $C_1$-$C_6$ alkylene. In embodiments, $L^2$ is unsubstituted $C_1$-$C_6$ alkylene. In embodiments, $L^2$ is substituted or unsubstituted $C_2$-$C_6$ alkylene. In embodiments, $L^2$ is substituted $C_2$-$C_6$ alkylene.

In embodiments, $L^2$ is unsubstituted $C_2$-$C_6$ alkylene. In embodiments, $L^2$ is substituted or unsubstituted $C_1$ alkylene. In embodiments, $L^2$ is substituted $C_1$ alkylene. In embodiments, $L^2$ is unsubstituted $C_1$ alkylene. In embodiments, $L^2$ is substituted or unsubstituted $C_2$ alkylene. In embodiments, $L^2$ is substituted $C_2$ alkylene. In embodiments, $L^2$ is unsubstituted $C_2$ alkylene. In embodiments, $L^2$ is substituted or unsubstituted $C_3$ alkylene. In embodiments, $L^2$ is substituted $C_3$ alkylene. In embodiments, $L^2$ is unsubstituted $C_3$ alkylene. In embodiments, $L^2$ is substituted or unsubstituted $C_4$ alkylene. In embodiments, $L^2$ is substituted $C_4$ alkylene. In embodiments, $L^2$ is unsubstituted $C_4$ alkylene. In embodiments, $L^2$ is substituted or unsubstituted $C_5$ alkylene. In embodiments, $L^2$ is substituted $C_5$ alkylene. In embodiments, $L^2$ is unsubstituted $C_5$ alkylene. In embodiments, $L^2$ is substituted or unsubstituted $C_6$ alkylene. In embodiments, $L^2$ is substituted $C_6$ alkylene. In embodiments, $L^2$ is unsubstituted $C_6$ alkylene.

In embodiments, $L^2$ is substituted or unsubstituted $C_9$ alkylene. In embodiments, $L^2$ is substituted or unsubstituted $C_{10}$ alkylene. In embodiments, $L^2$ is substituted or unsubstituted $C_{11}$ alkylene. In embodiments, $L^2$ is substituted or unsubstituted $C_{12}$ alkylene. In embodiments, $L^2$ is substituted or unsubstituted $C_{13}$ alkylene. In embodiments, $L^2$ is substituted or unsubstituted $C_{14}$ alkylene. In embodiments, $L^2$ is substituted or unsubstituted $C_{15}$ alkylene. In embodiments, $L^2$ is substituted or unsubstituted $C_{16}$ alkylene. In embodiments, $L^2$ is substituted or unsubstituted $C_{17}$ alkylene. In embodiments, $L^2$ is substituted or unsubstituted $C_{18}$ alkylene. In embodiments, $L^2$ is substituted or unsubstituted $C_{19}$ alkylene. In embodiments, $L^2$ is substituted or unsubstituted $C_{20}$ alkylene.

In embodiments, $L^2$ is substituted or unsubstituted 2 to 8 membered heteroalkylene. In embodiments, $L^2$ is substituted 2 to 8 membered heteroalkylene. In embodiments, $L^2$ is unsubstituted 2 to 8 membered heteroalkylene. In embodiments, $L^2$ is substituted or unsubstituted 2 membered heteroalkylene. In embodiments, $L^2$ is substituted 2 membered heteroalkylene. In embodiments, $L^2$ is unsubstituted 2 membered heteroalkylene. In embodiments, $L^2$ is substituted or unsubstituted 3 membered heteroalkylene. In embodiments, $L^2$ is substituted 3 membered heteroalkylene. In embodiments, $L^2$ is unsubstituted 3 membered heteroalkylene. In embodiments, $L^2$ is substituted or unsubstituted 4 membered heteroalkylene. In embodiments, $L^2$ is substituted 4 membered heteroalkylene. In embodiments, $L^2$ is unsubstituted 4 membered heteroalkylene. In embodiments, $L^2$ is substituted or unsubstituted 5 membered heteroalkylene. In embodiments, $L^2$ is substituted 5 membered heteroalkylene. In embodiments, $L^2$ is unsubstituted 5 membered heteroalkylene. In embodiments, $L^2$ is substituted or unsubstituted 6 membered heteroalkylene. In embodiments, $L^2$ is substituted 6 membered heteroalkylene. In embodiments, $L^2$ is unsubstituted 6 membered heteroalkylene. In embodiments, $L^2$ is substituted or unsubstituted 7 membered heteroalkylene. In embodiments, $L^2$ is substituted 7 membered heteroalkylene. In embodiments, $L^2$ is unsubstituted 7 membered heteroalkylene. In embodiments, $L^2$ is substituted or unsubstituted 8 membered heteroalkylene. In embodiments, $L^2$ is substituted 8 membered heteroalkylene. In embodiments, $L^2$ is unsubstituted 8 membered heteroalkylene.

In embodiments, $L^2$ is substituted or unsubstituted 9 membered heteroalkylene. In embodiments, $L^2$ is substituted 9 membered heteroalkylene. In embodiments, $L^2$ is unsubstituted 9 membered heteroalkylene. In embodiments, $L^2$ is substituted or unsubstituted 10 membered heteroalkylene. In embodiments, $L^2$ is substituted 10 membered heteroalkylene. In embodiments, $L^2$ is unsubstituted 10 membered heteroalkylene. In embodiments, $L^2$ is substituted or unsubstituted 11 membered heteroalkylene. In embodiments, $L^2$ is substituted 11 membered heteroalkylene. In embodiments, $L^2$ is unsubstituted 11 membered heteroalkylene. In embodiments, $L^2$ is substituted or unsubstituted 12 membered heteroalkylene. In embodiments, $L^2$ is substituted 12 membered heteroalkylene. In embodiments, $L^2$ is unsubstituted 12 membered heteroalkylene. In embodiments, $L^2$ is substituted or unsubstituted 13 membered heteroalkylene. In embodiments, $L^2$ is substituted 13 membered heteroalkylene. In embodiments, $L^2$ is unsubstituted 13 membered heteroalkylene. In embodiments, $L^2$ is substituted or unsubstituted 14 membered heteroalkylene. In embodiments, $L^2$ is substituted 14 membered heteroalkylene. In embodiments, $L^2$ is unsubstituted 14 membered heteroalkylene. In embodiments, $L^2$ is substituted or unsubstituted 15 membered heteroalkylene. In embodiments, $L^2$ is substituted 15 membered heteroalkylene. In embodiments, $L^2$ is unsubstituted 15 membered heteroalkylene. In embodiments, $L^2$ is substituted or unsubstituted 16 membered heteroalkylene. In embodiments, $L^2$ is substituted 16 membered heteroalkylene. In embodiments, $L^2$ is unsubstituted 16 membered heteroalkylene. In embodiments, $L^2$ is substituted or unsubstituted 17 membered heteroalkylene. In embodiments, $L^2$ is substituted 17 membered heteroalkylene. In embodiments, $L^2$ is unsubstituted 17 membered heteroalkylene. In embodiments, $L^2$ is substituted or unsubstituted 18 membered heteroalkylene. In embodiments, $L^2$ is substituted 18 membered heteroalkylene. In embodiments, $L^2$ is unsubstituted 18 membered heteroalkylene. In embodiments, $L^2$ is substituted or unsubstituted 19 membered heteroalkylene. In embodiments, $L^2$ is substituted 19 membered heteroalkylene. In embodiments, $L^2$ is unsubstituted 19 membered heteroalkylene. In embodiments, $L^2$ is substituted or unsubstituted 20 membered heteroalkylene. In embodiments, $L^2$ is substituted 20 membered heteroalkylene. In embodiments, $L^2$ is unsubstituted 20 membered heteroalkylene.

In embodiments, $L^2$ is substituted or unsubstituted $C_4$-$C_6$ cycloalkylene. In embodiments, $L^2$ is substituted $C_4$-$C_6$ cycloalkylene. In embodiments, $L^2$ is substituted $C_4$-$C_6$ cycloalkylene. In embodiments, $L^2$ is substituted or unsubstituted $C_4$ cycloalkylene. In embodiments, $L^2$ is substituted $C_4$ cycloalkylene. In embodiments, $L^2$ is substituted $C_4$ cycloalkylene. In embodiments, $L^2$ is substituted or unsubstituted $C_5$ cycloalkylene. In embodiments, $L^2$ is substituted $C_5$ cycloalkylene. In embodiments, $L^2$ is substituted $C_5$ cycloalkylene.

In embodiments, $L^2$ is substituted or unsubstituted 5 to 6 membered heterocycloalkylene. In embodiments, $L^2$ is substituted 5 to 6 membered heterocycloalkylene. In embodiments, $L^2$ is unsubstituted 5 to 6 membered heterocycloalkylene. In embodiments, $L^2$ is substituted or unsubstituted 5 membered heterocycloalkylene. In embodiments, $L^2$ is substituted 5 membered heterocycloalkylene. In embodiments, $L^2$ is unsubstituted 5 membered heterocycloalkylene. In embodiments, $L^2$ is substituted or unsubstituted 6 membered heterocycloalkylene. In embodiments, $L^2$ is substituted 6 membered heterocycloalkylene. In embodiments, $L^2$ is unsubstituted 6 membered heterocycloalkylene.

In embodiments, $L^2$ is substituted or unsubstituted phenylene. In embodiments, $L^2$ is substituted phenylene. In embodiments, $L^2$ is unsubstituted phenylene.

In embodiments, $L^2$ is substituted or unsubstituted 5 to 6 membered heteroarylene. In embodiments, $L^2$ is substituted 5 to 6 membered heteroarylene. In embodiments, $L^2$ is unsubstituted 5 to 6 membered heteroarylene. In embodiments, $L^2$ is substituted or unsubstituted 5 membered heteroarylene. In embodiments, $L^2$ is substituted 5 membered heteroarylene. In embodiments, $L^2$ is unsubstituted 5 membered heteroarylene. In embodiments, $L^2$ is substituted or unsubstituted 6 membered heteroarylene. In embodiments, $L^2$ is substituted 6 membered heteroarylene. In embodiments, $L^2$ is unsubstituted 6 membered heteroarylene.

In embodiments, $L^2$ is a polymer.

In embodiments, $L^{2A}$ is substituted or unsubstituted methylene. In embodiments, $L^{2A}$ is substituted or unsubstituted $C_2$ alkylene. In embodiments, $L^{2A}$ is substituted or unsubstituted $C_3$ alkylene. In embodiments, $L^{2A}$ is substituted or unsubstituted $C_4$ alkylene. In embodiments, $L^{2A}$ is substituted or unsubstituted $C_5$ alkylene. In embodiments, $L^{2A}$ is substituted or unsubstituted $C_6$ alkylene. In embodiments, $L^{2A}$ is substituted or unsubstituted $C_7$ alkylene. In embodiments, $L^{2A}$ is substituted or unsubstituted $C_8$ alkylene. In embodiments, $L^{2A}$ is substituted methylene. In embodiments, $L^{2A}$ is substituted $C_2$ alkylene. In embodiments, $L^{2A}$ is substituted $C_3$ alkylene. In embodiments, $L^{2A}$ is substituted $C_4$ alkylene. In embodiments, $L^{2A}$ is substituted $C_5$ alkylene. In embodiments, $L^{2A}$ is substituted $C_6$ alkylene. In embodiments, $L^{2A}$ is substituted $C_7$ alkylene. In embodiments, $L^{2A}$ is substituted $C_8$ alkylene. In embodiments, $L^{2A}$ is an unsubstituted methylene. In embodiments, $L^{2A}$ is an unsubstituted $C_2$ alkylene. In embodiments, $L^{2A}$ is an unsubstituted $C_3$ alkylene. In embodiments, $L^{2A}$ is an unsubstituted $C_4$ alkylene. In embodiments, $L^{2A}$ is an unsubstituted $C_5$ alkylene. In embodiments, $L^{2A}$ is an unsubstituted $C_6$ alkylene. In embodiments, $L^{2A}$ is an unsubstituted $C_7$ alkylene. In embodiments, $L^{2A}$ is an unsubstituted $C_8$ alkylene.

In embodiments, $L^{2A}$ is substituted or unsubstituted $C_1$-$C_6$ alkylene. In embodiments, $L^{2A}$ is substituted $C_1$-$C_6$ alkylene. In embodiments, $L^{2A}$ is unsubstituted $C_1$-$C_6$ alkylene. In embodiments, $L^{2A}$ is substituted or unsubstituted $C_{2-6}$ alkylene. In embodiments, $L^{2A}$ is substituted $C_2$-$C_6$ alkylene. In embodiments, $L^{2A}$ is unsubstituted $C_2$-$C_6$ alkylene. In embodiments, $L^{2A}$ is substituted or unsubstituted $C_1$ alkylene. In embodiments, $L^{2A}$ is substituted $C_1$ alkylene. In embodiments, $L^{2A}$ is unsubstituted $C_1$ alkylene. In embodiments, $L^{2A}$ is substituted or unsubstituted $C_2$ alkylene. In embodiments, $L^{2A}$ is substituted $C_2$ alkylene. In embodiments, $L^{2A}$ is unsubstituted $C_2$ alkylene. In embodiments, $L^{2A}$ is substituted or unsubstituted $C_3$ alkylene. In embodiments, $L^{2A}$ is substituted $C_3$ alkylene. In embodiments, $L^{2A}$ is unsubstituted $C_3$ alkylene. In embodiments, $L^{2A}$ is substituted or unsubstituted $C_4$ alkylene. In embodiments, $L^{2A}$ is substituted $C_4$ alkylene. In embodiments, $L^{2A}$ is unsubstituted $C_4$ alkylene. In embodiments, $L^{2A}$ is substituted or unsubstituted $C_5$ alkylene. In embodiments, $L^{2A}$ is substituted $C_5$ alkylene. In embodiments, $L^{2A}$ is unsubstituted $C_5$ alkylene. In embodiments, $L^{2A}$ is substituted or unsubstituted $C_6$ alkylene. In embodiments, $L^{2A}$ is substituted $C_6$ alkylene. In embodiments, $L^{2A}$ is unsubstituted $C_6$ alkylene.

In embodiments, $L^{2A}$ is substituted or unsubstituted 2 to 8 membered heteroalkylene. In embodiments, $L^{2A}$ is substituted 2 to 8 membered heteroalkylene. In embodiments, $L^{2A}$ is unsubstituted 2 to 8 membered heteroalkylene. In embodiments, $L^{2A}$ is substituted or unsubstituted 2 membered heteroalkylene. In embodiments, $L^{2A}$ is substituted 2 membered heteroalkylene. In embodiments, $L^{2A}$ is unsubstituted 2 membered heteroalkylene. In embodiments, $L^{2A}$ is substituted or unsubstituted 3 membered heteroalkylene. In embodiments, $L^{2A}$ is substituted 3 membered heteroalkylene. In embodiments, $L^{2A}$ is unsubstituted 3 membered heteroalkylene. In embodiments, $L^{2A}$ is substituted or unsubstituted 4 membered heteroalkylene. In embodiments, $L^{2A}$ is substituted 4 membered heteroalkylene. In embodiments, $L^{2A}$ is unsubstituted 4 membered heteroalkylene. In embodiments, $L^{2A}$ is substituted or unsubstituted 5 membered heteroalkylene. In embodiments, $L^{2A}$ is substituted 5 membered heteroalkylene. In embodiments, $L^{2A}$ is unsubstituted 5 membered heteroalkylene. In embodiments, $L^{2A}$ is substituted or unsubstituted 6 membered heteroalkylene. In embodiments, $L^{2A}$ is substituted 6 membered heteroalkylene. In embodiments, $L^{2A}$ is unsubstituted 6 membered heteroalkylene.

In embodiments, $L^{2A}$ is substituted or unsubstituted $C_4$-$C_6$ cycloalkylene. In embodiments, $L^{2A}$ is substituted $C_4$-$C_6$ cycloalkylene. In embodiments, $L^{2A}$ is substituted $C_4$-$C_6$ cycloalkylene. In embodiments, $L^{2A}$ is substituted or unsubstituted $C_4$ cycloalkylene. In embodiments, $L^{2A}$ is substituted $C_4$ cycloalkylene. In embodiments, $L^{2A}$ is substituted $C_4$ cycloalkylene. In embodiments, $L^{2A}$ is substituted or unsubstituted $C_5$ cycloalkylene. In embodiments, $L^{2A}$ is substituted $C_5$ cycloalkylene. In embodiments, $L^{2A}$ is substituted $C_5$ cycloalkylene.

In embodiments, $L^{2A}$ is substituted or unsubstituted 5 to 6 membered heterocycloalkylene. In embodiments, $L^{2A}$ is substituted 5 to 6 membered heterocycloalkylene. In embodiments, $L^{2A}$ is unsubstituted 5 to 6 membered heterocycloalkylene. In embodiments, $L^{2A}$ is substituted or unsubstituted 5 membered heterocycloalkylene. In embodiments, $L^{2A}$ is substituted 5 membered heterocycloalkylene. In embodiments, $L^{2A}$ is unsubstituted 5 membered heterocycloalkylene. In embodiments, $L^{2A}$ is substituted or unsubstituted 6 membered heterocycloalkylene. In embodiments, $L^{2A}$ is substituted 6 membered heterocycloalkylene. In embodiments, $L^{2A}$ is unsubstituted 6 membered heterocycloalkylene.

In embodiments, $L^{2A}$ is substituted or unsubstituted phenylene. In embodiments, $L^{2A}$ is substituted phenylene. In embodiments, $L^{2A}$ is unsubstituted phenylene.

In embodiments, $L^{2A}$ is substituted or unsubstituted 5 to 6 membered heteroarylene. In embodiments, $L^{2A}$ is substituted 5 to 6 membered heteroarylene. In embodiments, $L^{2A}$ is unsubstituted 5 to 6 membered heteroarylene. In embodiments, $L^{2A}$ is substituted or unsubstituted 5 membered heteroarylene. In embodiments, $L^{2A}$ is substituted 5 membered heteroarylene. In embodiments, $L^{2A}$ is unsubstituted 5 membered heteroarylene. In embodiments, $L^{2A}$ is substituted or unsubstituted 6 membered heteroarylene. In embodiments, $L^{2A}$ is substituted 6 membered heteroarylene. In embodiments, $L^{2A}$ is unsubstituted 6 membered heteroarylene.

In embodiments, $L^{2A}$ is a polymer.

In embodiments, $L^{2B}$ is substituted or unsubstituted methylene. In embodiments, $L^{2B}$ is substituted or unsubstituted $C_2$ alkylene. In embodiments, $L^{2B}$ is substituted or unsubstituted $C_3$ alkylene. In embodiments, $L^{2B}$ is substituted or unsubstituted $C_4$ alkylene. In embodiments, $L^{2B}$ is substituted or unsubstituted $C_5$ alkylene. In embodiments, $L^{2B}$ is substituted or unsubstituted $C_6$ alkylene. In embodiments, $L^{2B}$ is substituted or unsubstituted $C_7$ alkylene. In embodiments, $L^{2B}$ is substituted or unsubstituted $C_8$ alkylene. In embodiments, $L^{2B}$ is substituted methylene. In embodiments, $L^{2B}$ is substituted $C_2$ alkylene. In embodiments, $L^{2B}$ is substituted $C_3$ alkylene. In embodiments, $L^{2B}$ is substituted $C_4$ alkylene. In embodiments, $L^{2B}$ is substituted $C_5$ alkylene. In embodiments, $L^{2B}$ is substituted $C_6$ alkylene. In embodiments, $L^{2B}$ is substituted $C_7$ alkylene. In embodiments, $L^{2B}$ is substituted $C_8$ alkylene. In embodiments, $L^{2B}$ is an unsubstituted methylene. In embodiments, $L^{2B}$ is an unsubstituted $C_2$ alkylene. In embodiments $L^{2B}$ is an unsubstituted $C_3$ alkylene. In embodiments, $L^{2B}$ is an unsubstituted $C_4$ alkylene. In embodiments, $L^{2B}$ is an unsubstituted $C_5$ alkylene. In embodiments, $L^{2B}$ is an unsubstituted $C_6$ alkylene. In embodiments, $L^{2B}$ is an unsubstituted $C_7$ alkylene. In embodiments, $L^{2B}$ is an unsubstituted $C_8$ alkylene.

In embodiments, $L^{2B}$ is substituted or unsubstituted $C_1$-$C_6$ alkylene. In embodiments, $L^{2B}$ is substituted $C_1$-$C_6$ alkylene. In embodiments, $L^{2B}$ is unsubstituted $C_1$-$C_6$ alkylene. In embodiments, $L^{2B}$ is substituted or unsubstituted $C_2$-$C_6$ alkylene. In embodiments, $L^{2B}$ is substituted $C_2$-$C_6$ alkylene. In embodiments, $L^{2B}$ is unsubstituted $C_2$-$C_6$ alkylene. In embodiments, $L^{2B}$ is substituted or unsubstituted $C_1$ alkylene. In embodiments, $L^{2B}$ is substituted $C_1$ alkylene. In embodiments, $L^{2B}$ is unsubstituted $C_1$ alkylene. In embodiments, $L^{2B}$ is substituted or unsubstituted $C_2$ alkylene. In embodiments, $L^{2B}$ is substituted $C_2$ alkylene. In embodiments, $L^{2B}$ is unsubstituted $C_2$ alkylene. In embodiments, $L^{2B}$ is substituted or unsubstituted $C_3$ alkylene. In embodiments, $L^{2B}$ is substituted $C_3$ alkylene. In embodiments, $L^{2B}$ is unsubstituted $C_3$ alkylene. In embodiments, $L^{2B}$ is substituted or unsubstituted $C_4$ alkylene. In embodiments, $L^{2B}$ is substituted $C_4$ alkylene. In embodiments, $L^{2B}$ is unsubstituted $C_4$ alkylene. In embodiments, $L^{2B}$ is substituted or unsubstituted $C_5$ alkylene. In embodiments, $L^{2B}$ is substituted $C_5$ alkylene. In embodiments, $L^{2B}$ is unsubstituted $C_5$ alkylene. In embodiments, $L^{2B}$ is substituted or unsubstituted $C_6$ alkylene. In embodiments, $L^{2B}$ is substituted $C_6$ alkylene. In embodiments, $L^{2B}$ is unsubstituted $C_6$ alkylene.

In embodiments, $L^{2B}$ is substituted or unsubstituted 2 to 8 membered heteroalkylene. In embodiments, $L^{2B}$ is substituted 2 to 8 membered heteroalkylene. In embodiments, $L^{2B}$ is unsubstituted 2 to 8 membered heteroalkylene. In embodiments, $L^{2B}$ is substituted or unsubstituted 2 membered heteroalkylene. In embodiments, $L^{2B}$ is substituted 2 membered heteroalkylene. In embodiments, $L^{2B}$ is unsubstituted 2 membered heteroalkylene. In embodiments, $L^{2B}$ is substituted or unsubstituted 3 membered heteroalkylene. In embodiments, $L^{2B}$ is substituted 3 membered heteroalkylene. In embodiments, $L^{2B}$ is unsubstituted 3 membered heteroalkylene. In embodiments, $L^{2B}$ is substituted or unsubstituted 4 membered heteroalkylene. In embodiments, $L^{2B}$ is substituted 4 membered heteroalkylene. In embodiments, $L^{2B}$ is unsubstituted 4 membered heteroalkylene. In embodiments, $L^{2B}$ is substituted or unsubstituted 5 membered heteroalkylene. In embodiments, $L^{2B}$ is substituted 5 membered heteroalkylene. In embodiments, $L^{2B}$ is unsubstituted 5 membered heteroalkylene. In embodiments, $L^{2B}$ is substituted or unsubstituted 6 membered heteroalkylene. In embodiments, $L^{2B}$ is substituted 6 membered heteroalkylene. In embodiments, $L^{2B}$ is unsubstituted 6 membered heteroalkylene.

In embodiments, $L^{2B}$ is substituted or unsubstituted $C_4$-$C_6$ cycloalkylene. In embodiments, $L^{2B}$ is substituted $C_4$-$C_6$ cycloalkylene. In embodiments, $L^{2B}$ is substituted $C_4$-$C_6$ cycloalkylene. In embodiments, $L^{2B}$ is substituted or unsubstituted $C_4$ cycloalkylene. In embodiments, $L^{2B}$ is substituted $C_4$ cycloalkylene. In embodiments, $L^{2B}$ is substituted $C_4$ cycloalkylene. In embodiments, $L^{2B}$ is substituted or unsubstituted $C_5$ cycloalkylene. In embodiments, $L^{2B}$ is substituted $C_5$ cycloalkylene. In embodiments, $L^{2B}$ is substituted $C_5$ cycloalkylene.

In embodiments, $L^{2B}$ is substituted or unsubstituted 5 to 6 membered heterocycloalkylene. In embodiments, $L^{2B}$ is substituted 5 to 6 membered heterocycloalkylene. In embodiments, $L^{2B}$ is unsubstituted 5 to 6 membered heterocycloalkylene. In embodiments, $L^{2B}$ is substituted or unsubstituted 5 membered heterocycloalkylene. In embodiments, $L^{2B}$ is substituted 5 membered heterocycloalkylene. In embodiments, $L^{2B}$ is unsubstituted 5 membered heterocycloalkylene. In embodiments, $L^{2B}$ is substituted or unsubstituted 6 membered heterocycloalkylene. In embodiments, $L^{2B}$ is substituted 6 membered heterocycloalkylene. In embodiments, $L^{2B}$ is unsubstituted 6 membered heterocycloalkylene.

In embodiments, $L^{2B}$ is substituted or unsubstituted phenylene. In embodiments, $L^{2B}$ is substituted phenylene. In embodiments, $L^{2B}$ is unsubstituted phenylene.

In embodiments, $L^{2B}$ is substituted or unsubstituted 5 to 6 membered heteroarylene. In embodiments, $L^{2B}$ is substituted 5 to 6 membered heteroarylene. In embodiments, $L^{2B}$ is unsubstituted 5 to 6 membered heteroarylene. In embodiments, $L^{2B}$ is substituted or unsubstituted 5 membered heteroarylene. In embodiments, $L^{2B}$ is substituted 5 membered heteroarylene. In embodiments, $L^{2B}$ is unsubstituted 5 membered heteroarylene. In embodiments, $L^{2B}$ is substituted or unsubstituted 6 membered heteroarylene. In embodiments, $L^{2B}$ is substituted 6 membered heteroarylene. In embodiments, $L^{2B}$ is unsubstituted 6 membered heteroarylene.

In embodiments, $L^{2C}$ is substituted or unsubstituted methylene. In embodiments, $L^{2C}$ is substituted or unsubstituted $C_2$ alkylene. In embodiments, $L^{2C}$ is substituted or unsubstituted $C_3$ alkylene. In embodiments, $L^{2C}$ is substituted or unsubstituted $C_4$ alkylene. In embodiments, $L^{2C}$ is substituted or unsubstituted $C_5$ alkylene. In embodiments, $L^{2C}$ is substituted or unsubstituted $C_6$ alkylene. In embodiments, $L^{2C}$ is substituted or unsubstituted $C_7$ alkylene. In embodiments, LC is substituted or unsubstituted $C_8$ alkylene. In embodiments, $L^{2C}$ is substituted methylene. In embodiments, $L^{2C}$ is substituted $C_2$ alkylene. In embodiments, $L^{2C}$ is substituted $C_3$ alkylene. In embodiments, $L^{2C}$ is substituted $C_4$ alkylene. In embodiments, $L^{2C}$ is substituted $C_5$ alkylene. In embodiments, $L^{2C}$ is substituted $C_6$ alkylene. In embodiments, $L^{2C}$ is substituted $C_7$ alkylene. In embodiments, $L^{2C}$ is substituted $C_8$ alkylene. In embodiments, $L^{2C}$ is an unsubstituted methylene. In embodiments, $L^{2C}$ is an unsubstituted $C_2$ alkylene. In embodiments, $L^{2C}$ is an unsubstituted $C_3$ alkylene. In embodiments, $L^{2C}$ is an unsubstituted $C_4$ alkylene. In embodiments, $L^{2C}$ is an unsubstituted $C_5$ alkylene. In embodiments, $L^{2C}$ is an unsubstituted $C_6$ alkylene. In embodiments, $L^{2C}$ is an unsubstituted $C_7$ alkylene. In embodiments, $L^{2C}$ is an unsubstituted $C_8$ alkylene.

In embodiments, $L^{2C}$ is substituted or unsubstituted $C_1$-$C_6$ alkylene. In embodiments, $L^{2C}$ is substituted $C_1$-$C_6$ alkylene. In embodiments, $L^{2C}$ is unsubstituted $C_1$-$C_6$ alkylene. In embodiments, $L^{2C}$ is substituted or unsubstituted $C_2$-$C_6$ alkylene. In embodiments, $L^{2C}$ is substituted $C_2$-$C_6$ alkylene. In embodiments, $L^{2C}$ is unsubstituted $C_2$-$C_6$ alkylene. In embodiments, $L^{2C}$ is substituted or unsubstituted $C_1$ alkylene. In embodiments, $L^{2C}$ is substituted $C_1$ alkylene. In embodiments, $L^{2C}$ is unsubstituted $C_1$ alkylene. In embodiments, $L^{2C}$ is substituted or unsubstituted $C_2$ alkylene. In embodiments, $L^{2C}$ is substituted $C_2$ alkylene. In embodiments, $L^{2C}$ is unsubstituted $C_2$ alkylene. In embodiments, $L^{2C}$ is substituted or unsubstituted $C_3$ alkylene. In embodiments, $L^{2C}$ is substituted $C_3$ alkylene. In embodiments, $L^{2C}$ is unsubstituted $C_3$ alkylene. In embodiments, $L^{2C}$ is substituted or unsubstituted $C_4$ alkylene. In embodiments, $L^{2C}$ is substituted $C_4$ alkylene. In embodiments, $L^{2C}$ is unsubstituted $C_4$ alkylene. In embodiments, $L^{2C}$ is substituted or unsubstituted $C_5$ alkylene. In embodiments, $L^{2C}$ is substituted $C_5$ alkylene. In embodiments, $L^{2C}$ is unsubstituted $C_5$ alkylene. In embodiments, $L^{2C}$ is substituted or unsubstituted $C_6$ alkylene. In embodiments, $L^{2C}$ is substituted $C_6$ alkylene. In embodiments, $L^{2C}$ is unsubstituted $C_6$ alkylene.

In embodiments, $L^{2C}$ is substituted or unsubstituted 2 to 8 membered heteroalkylene. In embodiments, $L^{2C}$ is substituted 2 to 8 membered heteroalkylene. In embodiments, $L^{2C}$ is unsubstituted 2 to 8 membered heteroalkylene. In embodiments, $L^{2C}$ is substituted or unsubstituted 2 membered heteroalkylene. In embodiments, $L^{2C}$ is substituted 2 membered heteroalkylene. In embodiments, $L^{2C}$ is unsubstituted 2 membered heteroalkylene. In embodiments, $L^{2C}$ is substituted or unsubstituted 3 membered heteroalkylene. In embodiments, $L^{2C}$ is substituted 3 membered heteroalkylene. In embodiments, $L^{2C}$ is unsubstituted 3 membered heteroalkylene. In embodiments, $L^{2C}$ is substituted or unsubstituted 4 membered heteroalkylene. In embodiments, $L^{2C}$ is substituted 4 membered heteroalkylene. In embodiments, $L^{2C}$ is unsubstituted 4 membered heteroalkylene. In embodiments, $L^{2C}$ is substituted or unsubstituted 5 membered heteroalkylene. In embodiments, $L^{2C}$ is substituted 5 membered heteroalkylene. In embodiments, $L^{2C}$ is unsubstituted 5 membered heteroalkylene. In embodiments, $L^{2C}$ is substituted or unsubstituted 6 membered heteroalkylene. In embodiments, $L^{2C}$ is substituted 6 membered heteroalkylene. In embodiments, $L^{2C}$ is unsubstituted 6 membered heteroalkylene.

In embodiments, $L^{2C}$ is substituted or unsubstituted $C_4$-$C_6$ cycloalkylene. In embodiments, $L^{2C}$ is substituted $C_4$-$C_6$ cycloalkylene. In embodiments, $L^{2C}$ is substituted $C_4$-$C_6$ cycloalkylene. In embodiments, $L^{2C}$ is substituted or unsubstituted $C_4$ cycloalkylene. In embodiments, $L^{2C}$ is substituted $C_4$ cycloalkylene. In embodiments, $L^{2C}$ is substituted $C_4$ cycloalkylene. In embodiments, $L^{2C}$ is substituted or unsubstituted $C_5$ cycloalkylene. In embodiments, $L^{2C}$ is substituted $C_5$ cycloalkylene. In embodiments, $L^{2C}$ is substituted $C_5$ cycloalkylene.

In embodiments, $L^{2C}$ is substituted or unsubstituted 5 to 6 membered heterocycloalkylene. In embodiments, $L^{2C}$ is substituted 5 to 6 membered heterocycloalkylene. In embodiments, $L^{2C}$ is unsubstituted 5 to 6 membered heterocycloalkylene. In embodiments, $L^{2C}$ is substituted or unsubstituted 5 membered heterocycloalkylene. In embodiments, $L^{2C}$ is substituted 5 membered heterocycloalkylene. In embodiments, $L^{2C}$ is unsubstituted 5 membered heterocycloalkylene. In embodiments, $L^{2C}$ is substituted or unsubstituted 6 membered heterocycloalkylene. In embodiments, $L^{2C}$ is substituted 6 membered heterocycloalkylene. In embodiments, $L^{2C}$ is unsubstituted 6 membered heterocycloalkylene.

In embodiments, $L^{2C}$ is substituted or unsubstituted phenylene. In embodiments, $L^{2C}$ is substituted phenylene. In embodiments, $L^{2C}$ is unsubstituted phenylene.

In embodiments, $L^{2C}$ is substituted or unsubstituted 5 to 6 membered heteroarylene. In embodiments, $L^{2C}$ is substituted 5 to 6 membered heteroarylene. In embodiments, $L^{2C}$ is unsubstituted 5 to 6 membered heteroarylene. In embodiments, $L^{2C}$ is substituted or unsubstituted 5 membered heteroarylene. In embodiments, $L^{2C}$ is substituted 5 membered heteroarylene. In embodiments, $L^{2C}$ is unsubstituted 5 membered heteroarylene. In embodiments, $L^{2C}$ is substituted or unsubstituted 6 membered heteroarylene. In embodiments, $L^{2C}$ is substituted 6 membered heteroarylene. In embodiments, $L^{2C}$ is unsubstituted 6 membered heteroarylene.

In embodiments, $L^{2D}$ is substituted or unsubstituted methylene. In embodiments, $L^{2D}$ is substituted or unsubstituted $C_2$ alkylene. In embodiments, $L^{2D}$ is substituted or unsubstituted $C_3$ alkylene. In embodiments, $L^{2D}$ is substituted or unsubstituted $C_4$ alkylene. In embodiments, $L^{2D}$ is substituted or unsubstituted $C_5$ alkylene. In embodiments, $L^{2D}$ is substituted or unsubstituted $C_6$ alkylene. In embodiments, $L^{2D}$ is substituted or unsubstituted $C_7$ alkylene. In embodiments, $L^{2D}$ is substituted or unsubstituted $C_8$ alkylene. In embodiments, $L^{2D}$ is substituted methylene. In embodiments, $L^{2D}$ is substituted $C_2$ alkylene. In embodiments, $L^{2D}$ is substituted $C_3$ alkylene. In embodiments, $L^{2D}$ is substituted $C_4$ alkylene. In embodiments, $L^{2D}$ is substituted $C_5$ alkylene. In embodiments, $L^{2D}$ is substituted $C_6$ alkylene. In embodiments, $L^{2D}$ is substituted $C_7$ alkylene. In embodiments, $L^{2D}$ is substituted $C_8$ alkylene. In embodiments, $L^{2D}$ is an unsubstituted methylene. In embodiments, $L^{2D}$ is an unsubstituted $C_2$ alkylene. In embodiments $L^{2D}$ is an unsubstituted $C_3$ alkylene. In embodiments, $L^{2D}$ is an unsubstituted $C_4$ alkylene. In embodiments, $L^{2D}$ is an unsubstituted $C_5$ alkylene. In embodiments, $L^{2D}$ is an unsubstituted $C_6$ alkylene. In embodiments, $L^{2D}$ is an unsubstituted $C_7$ alkylene. In embodiments, $L^{2D}$ is an unsubstituted $C_8$ alkylene.

In embodiments, $L^{2D}$ is substituted or unsubstituted $C_1$-$C_6$ alkylene. In embodiments, $L^{2D}$ is substituted $C_1$-$C_6$ alkylene. In embodiments, $L^{2D}$ is unsubstituted $C_1$-$C_6$ alkylene. In embodiments, $L^{2D}$ is substituted or unsubstituted $C_2$-$C_6$ alkylene. In embodiments, $L^{2D}$ is substituted $C_2$-$C_6$ alkylene. In embodiments, $L^{2D}$ is unsubstituted $C_2$-$C_6$ alkylene. In embodiments, $L^{2D}$ is substituted or unsubstituted $C_1$ alkylene. In embodiments, $L^{2D}$ is substituted $C_1$ alkylene. In embodiments, $L^{2D}$ is unsubstituted $C_1$ alkylene. In embodiments, $L^{2D}$ is substituted or unsubstituted $C_2$ alkylene. In embodiments, $L^{2D}$ is substituted $C_2$ alkylene. In embodiments, $L^{2D}$ is unsubstituted $C_2$ alkylene. In embodiments, $L^{2D}$ is substituted or unsubstituted $C_3$ alkylene. In embodiments, $L^{2D}$ is substituted $C_3$ alkylene. In embodiments, $L^{2D}$ is unsubstituted $C_3$ alkylene. In embodiments, $L^{2D}$ is substituted or unsubstituted $C_4$ alkylene. In embodiments, $L^{2D}$ is substituted $C_4$ alkylene. In embodiments, $L^{2D}$ is unsubstituted $C_4$ alkylene. In embodiments, $L^{2D}$ is substituted or unsubstituted $C_5$ alkylene. In embodiments, $L^{2D}$ is substituted $C_5$ alkylene. In embodiments, $L^{2D}$ is unsubstituted $C_5$ alkylene. In embodiments, $L^{2D}$ is substituted or unsubstituted $C_6$ alkylene. In embodiments, $L^{2D}$ is substituted $C_6$ alkylene. In embodiments, $L^{2D}$ is unsubstituted $C_6$ alkylene.

In embodiments, $L^{2D}$ is substituted or unsubstituted 2 to 8 membered heteroalkylene. In embodiments, $L^{2D}$ is substituted 2 to 8 membered heteroalkylene. In embodiments, $L^{2D}$ is unsubstituted 2 to 8 membered heteroalkylene. In embodiments, $L^{2D}$ is substituted or unsubstituted 2 membered heteroalkylene. In embodiments, $L^{2D}$ is substituted 2 membered heteroalkylene. In embodiments, $L^{2D}$ is unsubstituted 2 membered heteroalkylene. In embodiments, $L^{2D}$ is substituted or unsubstituted 3 membered heteroalkylene. In embodiments, $L^{2D}$ is substituted 3 membered heteroalkylene. In embodiments, $L^{2D}$ is unsubstituted 3 membered heteroalkylene. In embodiments, $L^{2D}$ is substituted or unsubstituted 4 membered heteroalkylene. In embodiments, $L^{2D}$ is substituted 4 membered heteroalkylene. In embodiments, $L^{2D}$ is unsubstituted 4 membered heteroalkylene. In embodiments, $L^{2D}$ is substituted or unsubstituted 5 membered heteroalkylene. In embodiments, $L^{2D}$ is substituted 5 membered heteroalkylene. In embodiments, $L^{2D}$ is unsubstituted 5 membered heteroalkylene. In embodiments, $L^{2D}$ is substituted or unsubstituted 6 membered heteroalkylene. In embodiments, $L^{2D}$ is substituted 6 membered heteroalkylene. In embodiments, $L^{2D}$ is unsubstituted 6 membered heteroalkylene.

In embodiments, $L^{2D}$ is substituted or unsubstituted $C_4$-$C_6$ cycloalkylene. In embodiments, $L^{2D}$ is substituted $C_4$-$C_6$ cycloalkylene. In embodiments, $L^{2D}$ is substituted $C_4$-$C_6$ cycloalkylene. In embodiments, $L^{2D}$ is substituted or unsubstituted $C_4$ cycloalkylene. In embodiments, $L^{2D}$ is substituted $C_4$ cycloalkylene. In embodiments, $L^{2D}$ is substituted $C_4$ cycloalkylene. In embodiments, $L^{2D}$ is substituted or unsubstituted $C_5$ cycloalkylene. In embodiments, $L^{2D}$ is substituted $C_5$ cycloalkylene. In embodiments, $L^{2D}$ is substituted $C_5$ cycloalkylene.

In embodiments, $L^{2D}$ is substituted or unsubstituted 5 to 6 membered heterocycloalkylene. In embodiments, $L^{2D}$ is substituted 5 to 6 membered heterocycloalkylene. In embodiments, $L^{2D}$ is unsubstituted 5 to 6 membered heterocycloalkylene. In embodiments, $L^{2D}$ is substituted or unsubstituted 5 membered heterocycloalkylene. In embodiments, $L^{2D}$ is substituted 5 membered heterocycloalkylene. In embodiments, $L^{2D}$ is unsubstituted 5 membered heterocycloalkylene. In embodiments, $L^{2D}$ is substituted or unsubstituted 6 membered heterocycloalkylene. In embodiments, $L^{2D}$ is substituted 6 membered heterocycloalkylene. In embodiments, $L^{2D}$ is unsubstituted 6 membered heterocycloalkylene.

In embodiments, $L^{2D}$ is substituted or unsubstituted phenylene. In embodiments, $L^{2D}$ is substituted phenylene. In embodiments, $L^{2D}$ is unsubstituted phenylene.

In embodiments, $L^{2D}$ is substituted or unsubstituted 5 to 6 membered heteroarylene. In embodiments, $L^{2D}$ is substituted 5 to 6 membered heteroarylene. In embodiments, $L^{2D}$ is unsubstituted 5 to 6 membered heteroarylene. In embodiments, $L^{2D}$ is substituted or unsubstituted 5 membered heteroarylene. In embodiments, $L^{2D}$ is substituted 5 membered heteroarylene. In embodiments, $L^{2D}$ is unsubstituted 5 membered heteroarylene. In embodiments, $L^{2D}$ is substituted or unsubstituted 6 membered heteroarylene. In embodiments, $L^{2D}$ is substituted 6 membered heteroarylene. In embodiments, $L^{2D}$ is unsubstituted 6 membered heteroarylene.

In embodiments, $L^{2E}$ is substituted or unsubstituted methylene. In embodiments, $L^{2E}$ is substituted or unsubstituted $C_2$ alkylene. In embodiments, $L^{2E}$ is substituted or unsubstituted $C_3$ alkylene. In embodiments, $L^{2E}$ is substituted or unsubstituted $C_4$ alkylene. In embodiments, $L^{2E}$ is substituted or unsubstituted $C_5$ alkylene. In embodiments, $L^{2E}$ is substituted or unsubstituted $C_6$ alkylene. In embodiments, $L^{2E}$ is substituted or unsubstituted $C_7$ alkylene. In embodiments, $L^{2E}$ is substituted or unsubstituted $C_8$ alkylene. In embodiments, $L^{2E}$ is substituted methylene. In embodiments, $L^{2E}$ is substituted $C_2$ alkylene. In embodiments, $L^{2E}$ is substituted $C_3$ alkylene. In embodiments, $L^{2E}$ is substituted $C_4$ alkylene. In embodiments, $L^{2E}$ is substituted $C_5$ alkylene. In embodiments, $L^{2E}$ is substituted $C_6$ alkylene. In embodiments, $L^{2E}$ is substituted $C_7$ alkylene. In embodiments, $L^{2E}$ is substituted $C_8$ alkylene. In embodiments, $L^{2E}$ is an unsubstituted methylene. In embodiments, $L^{2E}$ is an unsubstituted $C_2$ alkylene. In embodiments, $L^{2E}$ is an unsubstituted $C_3$ alkylene. In embodiments, $L^{2E}$ is an unsubstituted $C_4$ alkylene. In embodiments, $L^{2E}$ is an unsubstituted $C_5$ alkylene. In embodiments, $L^{2E}$ is an unsubstituted $C_6$ alkylene. In embodiments, $L^{2E}$ is an unsubstituted $C_7$ alkylene. In embodiments, $L^{2E}$ is an unsubstituted $C_8$ alkylene.

In embodiments, $L^{2E}$ is substituted or unsubstituted $C_1$-$C_6$ alkylene. In embodiments, $L^{2E}$ is substituted $C_1$-$C_6$ alkylene. In embodiments, $L^{2E}$ is unsubstituted $C_1$-$C_6$ alkylene. In embodiments, $L^{2E}$ is substituted or unsubstituted $C_2$-$C_6$ alkylene. In embodiments, $L^{2E}$ is substituted $C_2$-$C_6$ alkylene. In embodiments, $L^{2E}$ is unsubstituted $C_2$-$C_6$ alkylene. In embodiments, $L^{2E}$ is substituted or unsubstituted $C_1$ alkylene. In embodiments, $L^{2E}$ is substituted $C_1$ alkylene. In embodiments, $L^{2E}$ is unsubstituted $C_1$ alkylene. In embodiments, $L^{2E}$ is substituted or unsubstituted $C_2$ alkylene. In embodiments, $L^{2E}$ is substituted $C_2$ alkylene. In embodiments, $L^{2E}$ is unsubstituted $C_2$ alkylene. In embodiments, $L^{2E}$ is substituted or unsubstituted $C_3$ alkylene. In embodiments, $L^{2E}$ is substituted $C_3$ alkylene. In embodiments, $L^{2E}$ is unsubstituted $C_3$ alkylene. In embodiments, $L^{2E}$ is substituted or unsubstituted $C_4$ alkylene. In embodiments, $L^{2E}$ is substituted $C_4$ alkylene. In embodiments, $L^{2E}$ is unsubstituted $C_4$ alkylene. In embodiments, $L^{2E}$ is substituted or unsubstituted $C_5$ alkylene. In embodiments, $L^{2E}$ is substituted $C_5$ alkylene. In embodiments, $L^{2E}$ is unsubstituted $C_5$ alkylene. In embodiments, $L^{2E}$ is substituted or unsubstituted $C_6$ alkylene. In embodiments, $L^{2E}$ is substituted $C_6$ alkylene. In embodiments, $L^{2E}$ is unsubstituted $C_6$ alkylene.

In embodiments, $L^{2E}$ is substituted or unsubstituted 2 to 8 membered heteroalkylene. In embodiments, $L^{2E}$ is substituted 2 to 8 membered heteroalkylene. In embodiments, $L^{2E}$ is unsubstituted 2 to 8 membered heteroalkylene. In embodiments, $L^{2E}$ is substituted or unsubstituted 2 membered heteroalkylene. In embodiments, $L^{2E}$ is substituted 2 membered heteroalkylene. In embodiments, $L^{2E}$ is unsubstituted 2 membered heteroalkylene. In embodiments, $L^{2E}$ is substituted or unsubstituted 3 membered heteroalkylene. In embodiments, $L^{2E}$ is substituted 3 membered heteroalkylene. In embodiments, $L^{2E}$ is unsubstituted 3 membered heteroalkylene. In embodiments, $L^{2E}$ is substituted or unsubstituted 4 membered heteroalkylene. In embodiments, $L^{2E}$ is substituted 4 membered heteroalkylene. In embodiments, $L^{2E}$ is unsubstituted 4 membered heteroalkylene. In embodiments, $L^{2E}$ is substituted or unsubstituted 5 membered heteroalkylene. In embodiments, $L^{2E}$ is substituted 5 membered heteroalkylene. In embodiments, $L^{2E}$ is unsubstituted 5 membered heteroalkylene. In embodiments, $L^{2E}$ is substituted or unsubstituted 6 membered heteroalkylene. In embodiments, $L^{2E}$ is substituted 6 membered heteroalkylene. In embodiments, $L^{2E}$ is unsubstituted 6 membered heteroalkylene.

In embodiments, $L^{2E}$ is substituted or unsubstituted $C_4$-$C_6$ cycloalkylene. In embodiments, $L^{2E}$ is substituted $C_4$-$C_6$ cycloalkylene. In embodiments, $L^{2E}$ is substituted $C_4$-$C_6$ cycloalkylene. In embodiments, $L^{2E}$ is substituted or unsubstituted $C_4$ cycloalkylene. In embodiments, $L^{2E}$ is substituted $C_4$ cycloalkylene. In embodiments, $L^{2E}$ is substituted $C_4$ cycloalkylene. In embodiments, $L^{2E}$ is substituted or unsubstituted $C_5$ cycloalkylene. In embodiments, $L^{2E}$ is substituted $C_5$ cycloalkylene. In embodiments, $L^{2E}$ is substituted $C_5$ cycloalkylene.

In embodiments, $L^{2E}$ is substituted or unsubstituted 5 to 6 membered heterocycloalkylene. In embodiments, $L^{2E}$ is substituted 5 to 6 membered heterocycloalkylene. In embodiments, $L^{2E}$ is unsubstituted 5 to 6 membered heterocycloalkylene. In embodiments, $L^{2E}$ is substituted or unsubstituted 5 membered heterocycloalkylene. In embodiments, $L^{2E}$ is substituted 5 membered heterocycloalkylene. In embodiments, $L^{2E}$ is unsubstituted 5 membered heterocycloalkylene. In embodiments, $L^{2E}$ is substituted or unsubstituted 6 membered heterocycloalkylene. In embodiments, $L^{2E}$ is substituted 6 membered heterocycloalkylene. In embodiments, $L^{2E}$ is unsubstituted 6 membered heterocycloalkylene.

In embodiments, $L^{2E}$ is substituted or unsubstituted phenylene. In embodiments, $L^{2E}$ is substituted phenylene. In embodiments, $L^{2E}$ is unsubstituted phenylene.

In embodiments, $L^{2E}$ is substituted or unsubstituted 5 to 6 membered heteroarylene. In embodiments, $L^{2E}$ is substituted 5 to 6 membered heteroarylene. In embodiments, $L^{2E}$ is unsubstituted 5 to 6 membered heteroarylene. In embodiments, $L^{2E}$ is substituted or unsubstituted 5 membered heteroarylene. In embodiments, $L^{2E}$ is substituted 5 membered heteroarylene. In embodiments, $L^{2E}$ is unsubstituted 5 membered heteroarylene. In embodiments, $L^{2E}$ is substituted or unsubstituted 6 membered heteroarylene. In embodiments, $L^{2E}$ is substituted 6 membered heteroarylene. In embodiments, $L^{2E}$ is unsubstituted 6 membered heteroarylene.

In embodiments, $L^{2A}$ is a bond. In embodiments, $L^{2B}$ is a bond. In embodiments, $L^{2C}$ is a bond. In embodiments, $L^{2D}$ is a bond. In embodiments, $L^{2E}$ is a bond.

In embodiments, $L^{1A}$ is

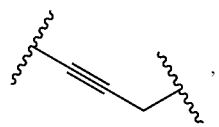 [SMILES: *C#CC*]

$L^{1B}$ is

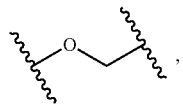 [SMILES: *CO*]

$L^{1C}$ is

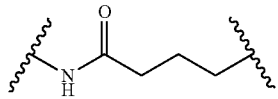

$L^{1D}$ is

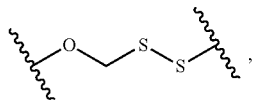 [SMILES: *OCSS*]

and $L^{1E}$ is

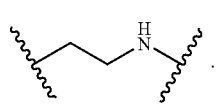

In embodiments, $L^{1A}$ is

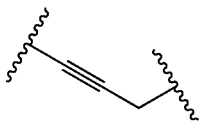

In embodiments, $L^{1B}$ is

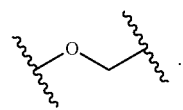

In embodiments, $L^{1C}$ is

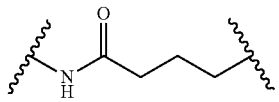

In embodiments, $L^{1D}$ is

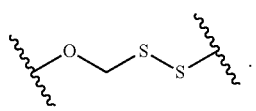 [SMILES: *OCSS*]

In embodiments, $L^{1E}$ is

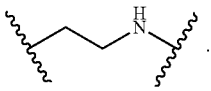

In embodiments, $L^{1A}$ is

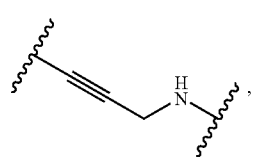 [SMILES: *C#CCN*]

$L^{1B}$ is

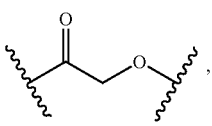

$L^{1C}$ is
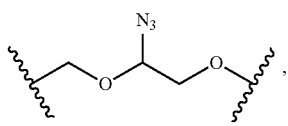 [SMILES: *COC(CO*)N=[N+]=[N-]]
$L^{1D}$ is
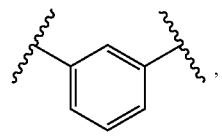
and $L^{1E}$ is
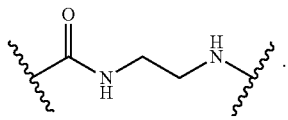 [SMILES: *NCCNC(*)=O]
In embodiments, $L^{1A}$ is
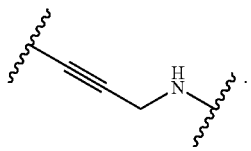
In embodiments, $L^{1B}$ is
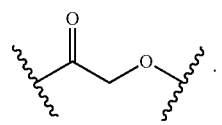 [SMILES: *OCC(*)=O]
In embodiments, $L^{1C}$ is
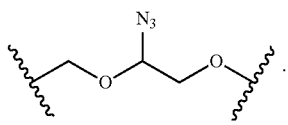 [SMILES: *COC(CO*)N=[N+]=[N-]]
In embodiments, $L^{1D}$ is
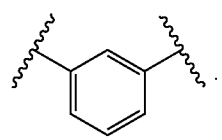 [SMILES: *c1cccc(*)c1]
In embodiments, $L^{1E}$ is
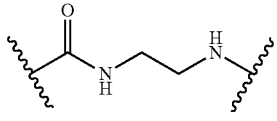
In embodiments, $L^{1A}$ is
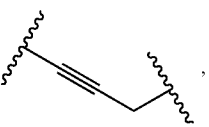
$L^{1B}$ is
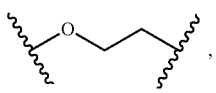
$L^{1C}$ is
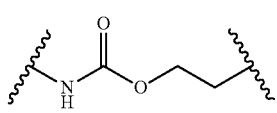
$L^{1D}$ is
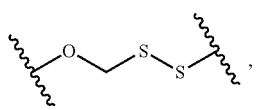
and $L^{1E}$ is
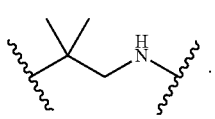 [SMILES: *NCC(*)(C)C]
In embodiments, $L^{1A}$ is
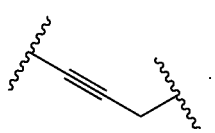 [SMILES: *C#CC*]
In embodiments, $L^{1B}$ is
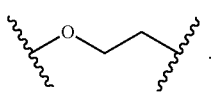

In embodiments, $L^{1C}$ is
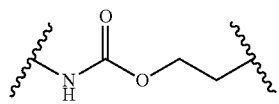
In embodiments, $L^{1D}$ is
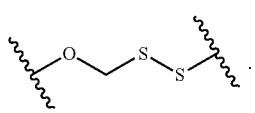 [SMILES: *OCSS*]
In embodiments, $L^{1E}$ is
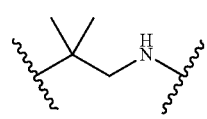
In embodiments, $L^{1A}$ is
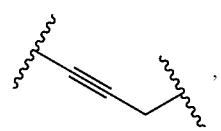 [SMILES: *C#CC*]
$L^{1B}$ is
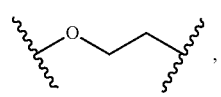
$L^{1C}$ is
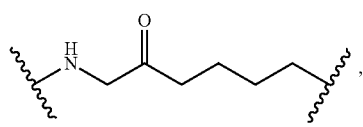 [SMILES: *CCCCC(=O)CN*]
$L^{1D}$ is
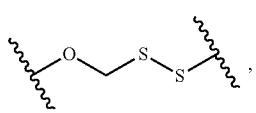
and $L^{1E}$ is
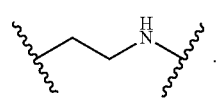
In embodiments, $L^{1A}$ is
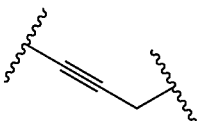
In embodiments, $L^{1B}$ is
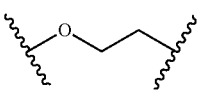
In embodiments, $L^{1C}$ is
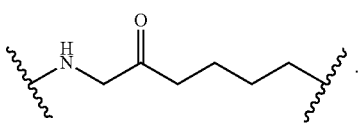 [SMILES: *CCCCC(=O)CN*]
In embodiments, $L^{1D}$ is
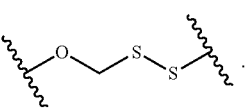 [SMILES: *OCSS*]
In embodiments, $L^{1E}$ is
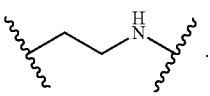
In embodiments, $L^{1A}$ is
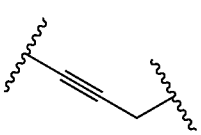
$L^{1B}$ is
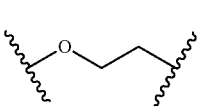
$L^{1C}$ is
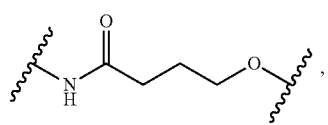 [SMILES: *NC(=O)CCCO*]

$L^{1D}$ is
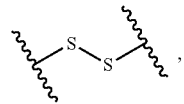 [SMILES: *SS*]
and $L^{1E}$ is
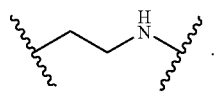
In embodiments, $L^{1A}$ is
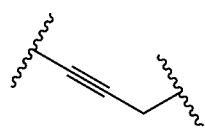
In embodiments $L^{1B}$ is
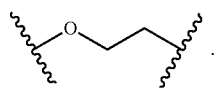 [SMILES: *CCO*]
In embodiments, $L^{1C}$ is
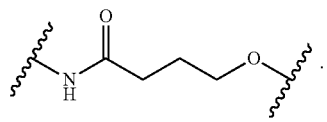 [SMILES: *NC(=O)CCCO*]
In embodiments, $L^{1D}$ is
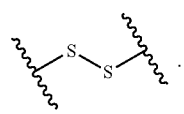
In embodiments, $L^{1E}$ is
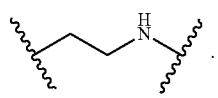
In embodiments, $L^{1A}$ is
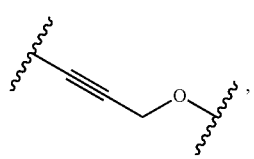 [SMILES: *C#CCO*]
$L^{1B}$ is
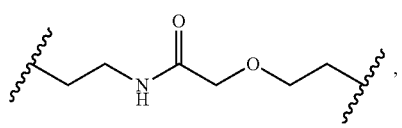 [SMILES: *CCNC(=O)COCC*]
$L^{1C}$ is
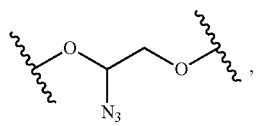
$L^{1D}$ is
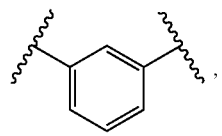 [SMILES: *c1cccc(*)c1]
and $L^{1E}$ is
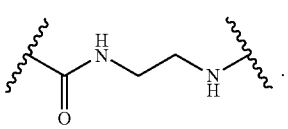 [SMILES: *NCCNC(*)=O]
In embodiments, $L^{1A}$ is
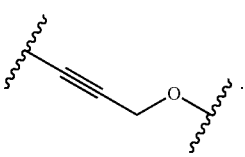 [SMILES: *C#CCO*]
In embodiments, $L^{1B}$ is
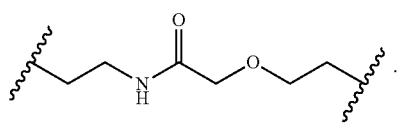 [SMILES: *CCNC(=O)COCC*]
In embodiments, $L^{1C}$ is
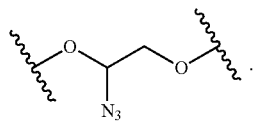

In embodiments, $L^{1D}$ is
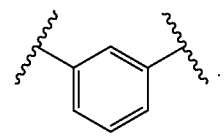 [SMILES: *c1cccc(*)c1]
In embodiments, $L^{1E}$ is
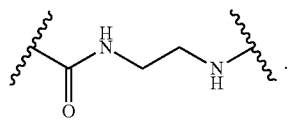 [SMILES: *NCCNC(*)=O]
In embodiments, $L^{1A}$ is
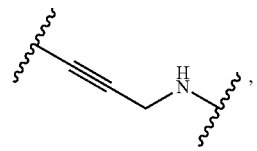 [SMILES: *C#CCN*]
$L^{1B}$ is
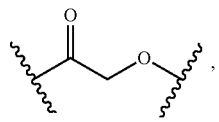 [SMILES: *OCC(*)=O]
$L^{1C}$ is
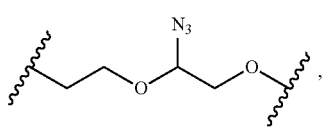 [SMILES: *CCOC(CO*)N=[N+]=[N-]]
$L^{1D}$ is
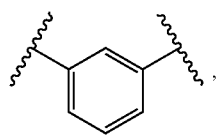
and $L^{1E}$ is
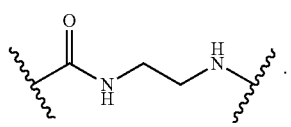 [SMILES: *NCCNC(*)=O]
In embodiments, $L^{1A}$ is
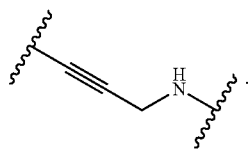 [SMILES: *C#CCN*]
In embodiments, $L^{1B}$ is
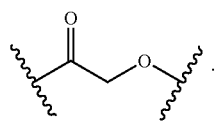
In embodiments, $L^{1C}$ is
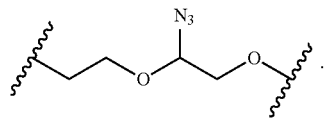
In embodiments, $L^{1D}$ is
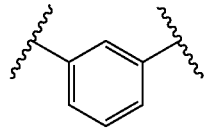
In embodiments, $L^{1E}$ is
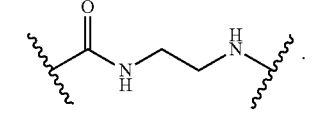 [SMILES: *NCCNC(*)=O]
In embodiments, $L^{1A}$ is
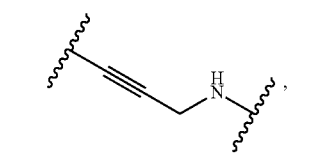
$L^{1B}$ is
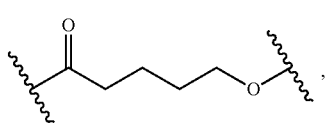 [SMILES: *OCCCCC(*)=O]

$L^{1C}$ is
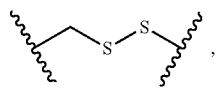,
$L^{1D}$ is
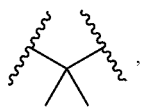,
and $L^{1E}$ is
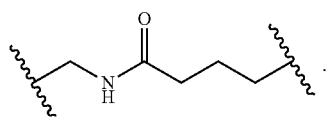 [SMILES: *CCCC(=O)NC*].
In embodiments, $L^{1A}$ is
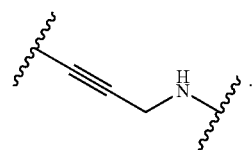.
In embodiments, $L^{1B}$ is
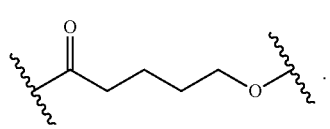 [SMILES: *OCCCCC(*)=O].
In embodiments, $L^{1C}$ is
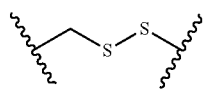.
In embodiments, $L^{1D}$ is
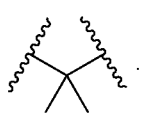.
In embodiments, $L^{1E}$ is
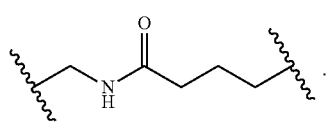 [SMILES: *CCCC(=O)NC*].
In embodiments, $L^{1A}$ is
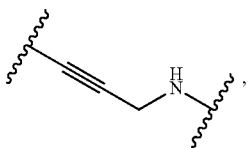 [SMILES: *C#CCN*],
$L^{1B}$ is
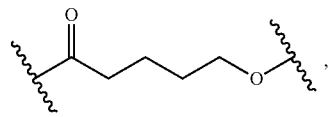 [SMILES: *OCCCCC(*)=O],
$L^{1C}$ is
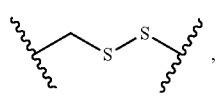,
$L^{1D}$ is
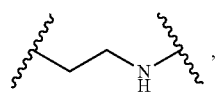 [SMILES: *CCN*],
and $L^{1E}$ is a bond. In embodiments, $L^{1A}$ is
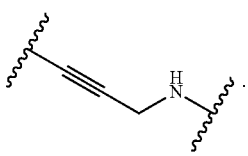 [SMILES: *C#CCN*].
In embodiments, $L^{1B}$ is
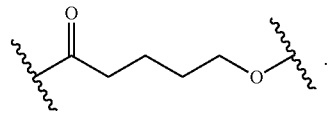 [SMILES: *OCCCCC(*)=O].
In embodiments, $L^{1C}$ is
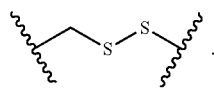.
In embodiments, $L^{1D}$ is
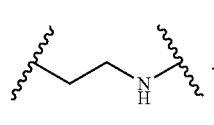.
In embodiments, $L^{1E}$ is a bond.

In embodiments, $L^{1A}$ is
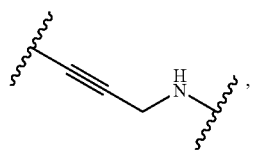 [SMILES: *C#CCN*]
$L^{1B}$ is
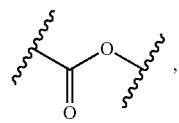
$L^{1C}$ is
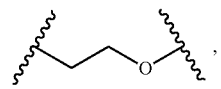 [SMILES: *CCO*]
$L^{1D}$ is
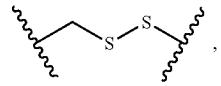 [SMILES: *CSS*]
and $L^{1E}$ is
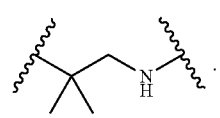 [SMILES: *NCC(*)(C)C]
In embodiments, $L^{1A}$ is
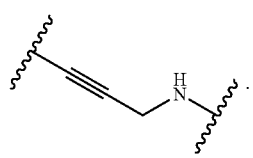 [SMILES: *C#CCN*]
In embodiments, $L^{1B}$ is
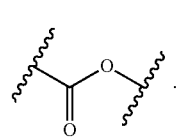 [SMILES: *OC(*)=O]
In embodiments, $L^{1C}$ is
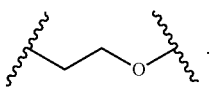 [SMILES: *CCO*]
In embodiments, $L^{1D}$ is
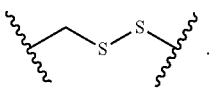 [SMILES: *CSS*]
In embodiments, $L^{1E}$ is
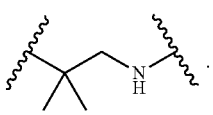 [SMILES: *NCC(*)(C)C]
In embodiments, $L^{1A}$ is
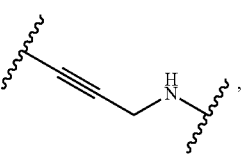
$L^{1B}$ is
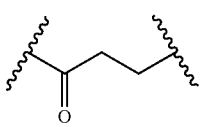
$L^{1C}$ is
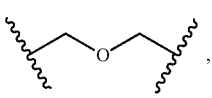 [SMILES: *COC*]
$L^{1D}$ is
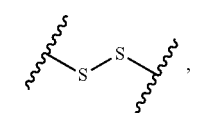
and $L^{1E}$ is
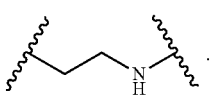 [SMILES: *CCN*]

In embodiments, $L^{1A}$ is
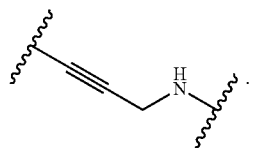 [SMILES: *C#CCN*]
In embodiments, $L^{1B}$ is
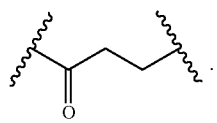
In embodiments, $L^{1C}$ is
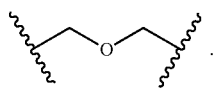
In embodiments, $L^{1D}$ is
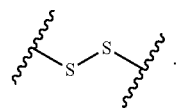
In embodiments, $L^{1E}$ is
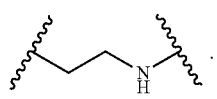 [SMILES: *CCN*]
In embodiments, $L^{1A}$ is
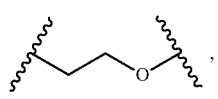
$L^{1B}$ is
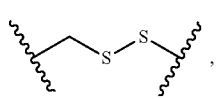 [SMILES: *CSS*]
$L^{1C}$ is
$L^{1D}$ is
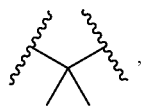
and $L^{1E}$ is
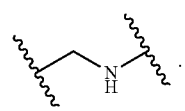
In embodiments, $L^{1A}$ is
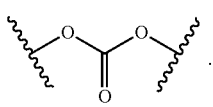 [SMILES: *OC(=O)O*]
In embodiments, $L^{1B}$ is
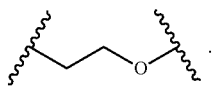
In embodiments, $L^{1C}$ is
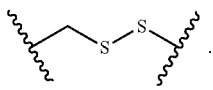 [SMILES: *CSS*]
In embodiments, $L^{1D}$ is
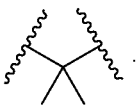 [SMILES: *C(*)(C)C]
In embodiments, $L^{1E}$ is
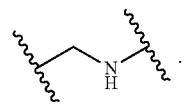
In embodiments, $L^{1A}$ is
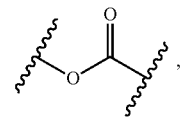

$L^{1B}$ is
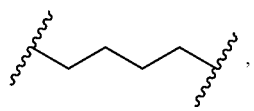
$L^{1C}$ is
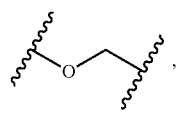
$L^{1D}$ is
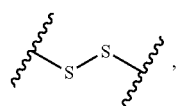
and $L^{1E}$ is
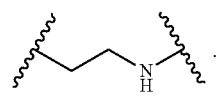
In embodiments, $L^{1A}$ is
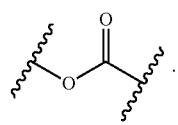
In embodiments, $L^{1B}$ is
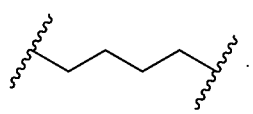 [SMILES: *CCCC*]
In embodiments, $L^{1C}$ is
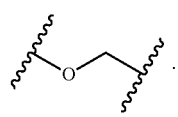 [SMILES: *CO*]
In embodiments, $L^{1D}$ is
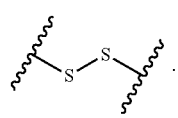 [SMILES: *SS*]
In embodiments, $L^{1E}$ is
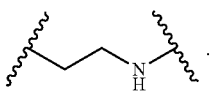
In embodiments, $L^{1A}$ is
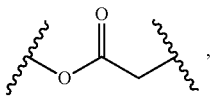
$L^{1B}$ is
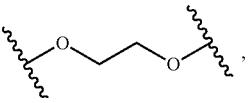 [SMILES: *OCCO*]
$L^{1C}$ is
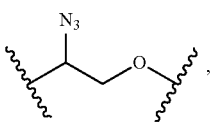 [SMILES: *OCC(*)N=[N+]=[N-]]
$L^{1D}$ is
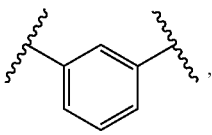 [SMILES: *c1cccc(*)c1]
and $L^{1E}$ is
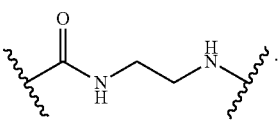 [SMILES: *NCCNC(*)=O]
In embodiments, $L^{1A}$ is
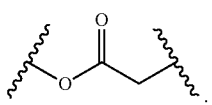 [SMILES: *CC(=O)O*]
In embodiments, $L^{1B}$ is
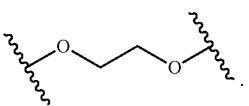 [SMILES: *OCCO*]

In embodiments, $L^{1C}$ is
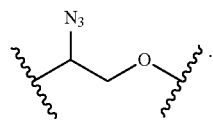 [SMILES: *OCC(*)N=[N+]=[N-]]
In embodiments, $L^{1D}$ is
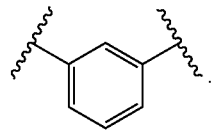 [SMILES: *c1cccc(*)c1]
In embodiments, $L^{1E}$ is
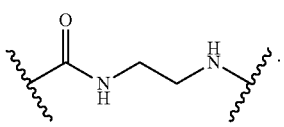 [SMILES: *NCCNC(*)=O]
In embodiments, $L^{1A}$ is
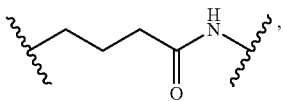 [SMILES: *CCCC(=O)N*]
$L^{1B}$ is
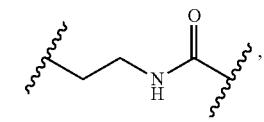 [SMILES: *CCNC(*)=O]
$L^{1C}$ is
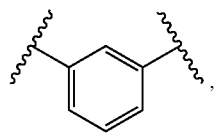 [SMILES: *c1cccc(*)c1]
$L^{1D}$ is
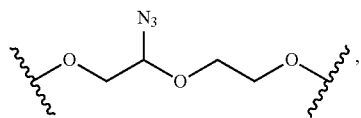 [SMILES: *OCCOC(CO*)N=[N+]=[N-]]
and $L^{1E}$ is
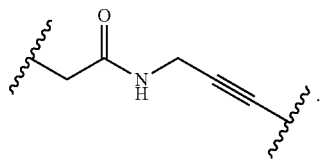 [SMILES: *C#CCNC(=O)C*]
In embodiments, $L^{1A}$ is
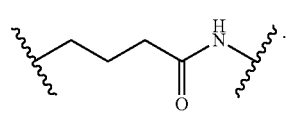 [SMILES: *CCCC(=O)N*]
In embodiments, $L^{1B}$ is
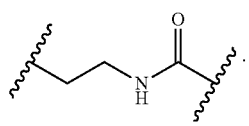 [SMILES: *CCNC(*)=O]
In embodiments, $L^{1C}$ is
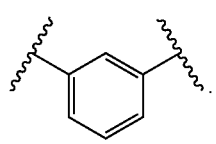 [SMILES: *c1cccc(*)c1]
In embodiments, $L^{1D}$ is
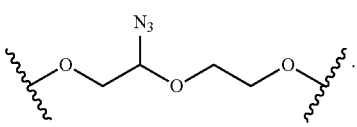 [SMILES: *OCCOC(CO*)N=[N+]=[N-]]
In embodiments, $L^{1E}$ is
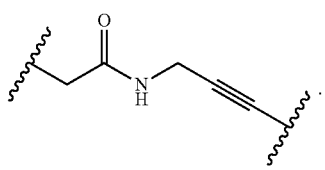 [SMILES: *C#CCNC(=O)C*]
In embodiments, $L^{2A}$ is
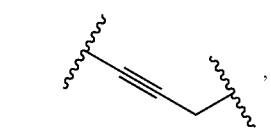 [SMILES: *C#CC*]

$L^{2B}$ is
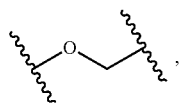 [SMILES: *CO*]
$L^{2C}$ is
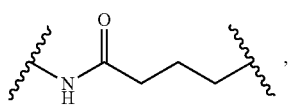 [SMILES: *CCCC(=O)N*]
$L^{2D}$ is
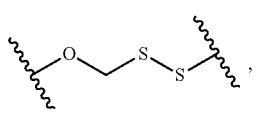
and $L^{2E}$ is
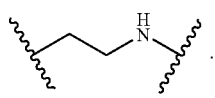
In embodiments, $L^{2A}$ is
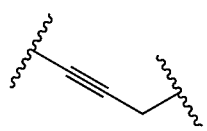
In embodiments, $L^{2B}$ is
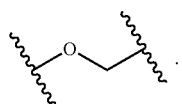 [SMILES: *CO*]
In embodiments, $L^{2C}$ is
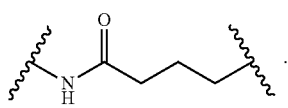 [SMILES: *CCCC(=O)N*]
In embodiments, $L^{2D}$ is
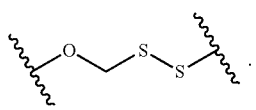 [SMILES: *OCSS*]
In embodiments, $L^{2E}$ is
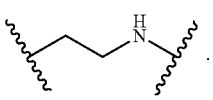 [SMILES: *CCN*]
In embodiments, $L^{2A}$ is
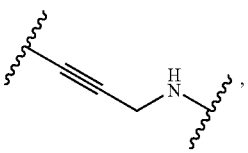
$L^{2B}$ is
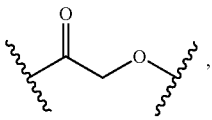
$L^{2C}$ is
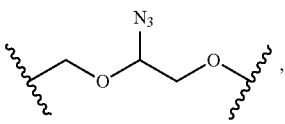 [SMILES: *COC(CO*)N=[N+]=[N-]]
$L^{2D}$ is
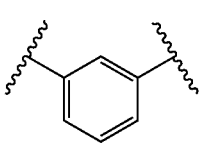
and $L^{2E}$ is
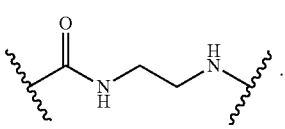
In embodiments, $L^{2A}$ is
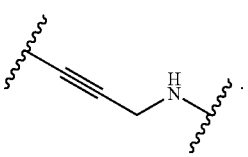

In embodiments, $L^{2B}$ is
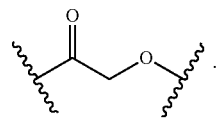 [SMILES: *OCC(*)=O]
In embodiments, $L^{2C}$ is
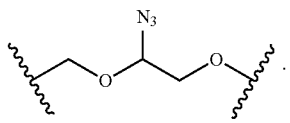 [SMILES: *COC(CO*)N=[N+]=[N-]]
In embodiments, $L^{2D}$ is
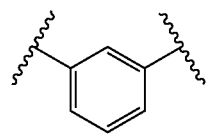
In embodiments, $L^{2E}$ is
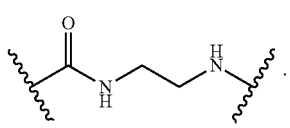 [SMILES: *NCCNC(*)=O]
In embodiments, $L^{2A}$ is
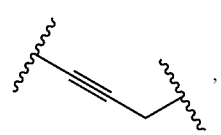 [SMILES: *C#CC*]
$L^{2B}$ is
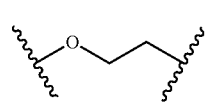
$L^{2C}$ is
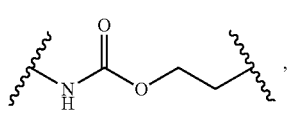
$L^{2D}$ is
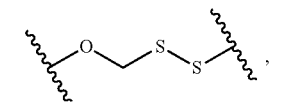
and $L^{2E}$ is
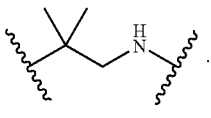 [SMILES: *NCC(*)(C)C]
In embodiments, $L^{2A}$ is
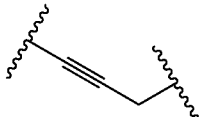
In embodiments, $L^{2B}$ is
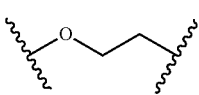
In embodiments, $L^{2C}$ is
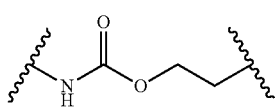
In embodiments, $L^{2D}$ is
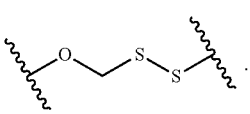
In embodiments, $L^{2E}$ is
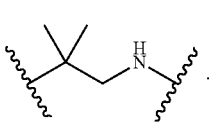 [SMILES: *NCC(*)(C)C]
In embodiments, $L^{2A}$ is
$L^{2B}$ is

$L^{2C}$ is
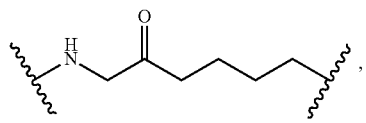 [SMILES: *CCCCC(=O)CN*]
$L^{2D}$ is
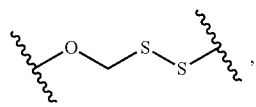
and $L^{2E}$ is
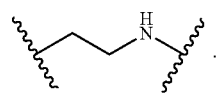
In embodiments, $L^{2A}$ is
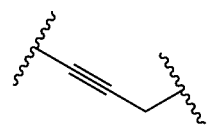
In embodiments, $L^{2B}$ is
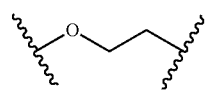
In embodiments, $L^{2C}$ is
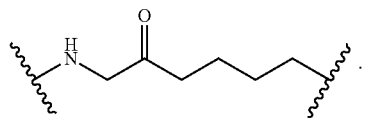 [SMILES: *CCCCC(=O)CN*]
In embodiments, $L^{2D}$ is
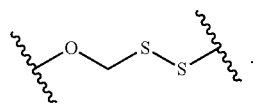 [SMILES: *OCSS*]
In embodiments, $L^{2E}$ is
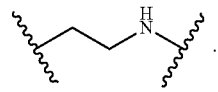
In embodiments, $L^{2A}$ is
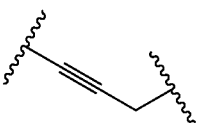
$L^{2B}$ is
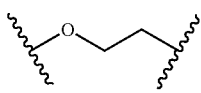
$L^{2C}$ is
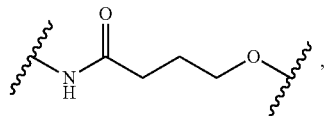 [SMILES: *NC(=O)CCCO*]
$L^{2D}$ is
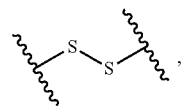
and $L^{2E}$ is
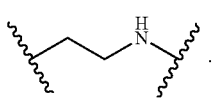 [SMILES: *CCN*]
In embodiments, $L^{2A}$ is
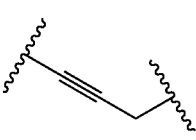
In embodiments, $L^{2B}$ is
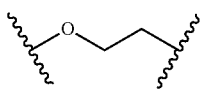

In embodiments, $L^{2C}$ is
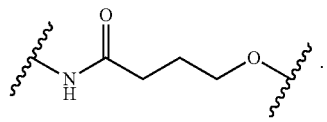 [SMILES: *NC(=O)CCCO*]
In embodiments, $L^{2D}$ is
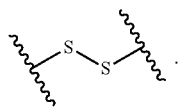
In embodiments, $L^{2E}$ is
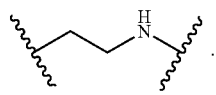
In embodiments, $L^{2A}$ is
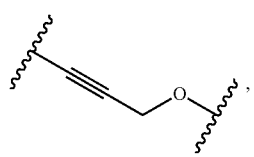 [SMILES: *C#CCO*]
$L^{2B}$ is
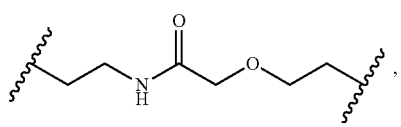 [SMILES: *CCNC(=O)COCC*]
$L^{2C}$ is
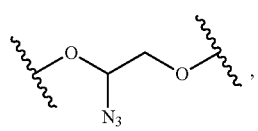
$L^{2D}$ is
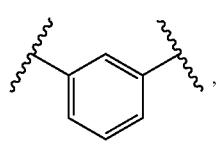
and $L^{2E}$ is
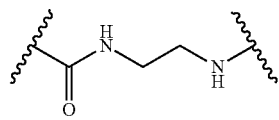
In embodiments, $L^{2A}$ is
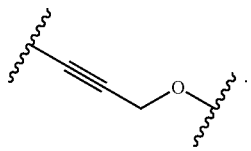 [SMILES: *C#CCO*]
In embodiments, $L^{2B}$ is
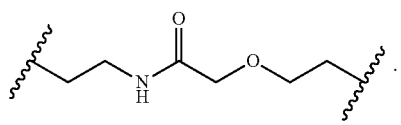 [SMILES: *CCNC(=O)COCC*]
In embodiments, $L^{2C}$ is
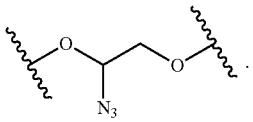 [SMILES: *OCC(N=[N+]=[N-])O*]
In embodiments, $L^{2D}$ is
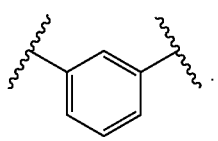 [SMILES: *c1cccc(*)c1]
In embodiments, $L^{2E}$ is
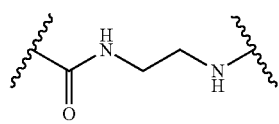
In embodiments, $L^{2A}$ is
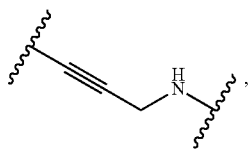 [SMILES: *C#CCN*]

$L^{2B}$ is
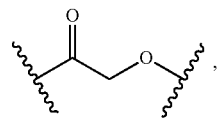
$L^{2C}$ is
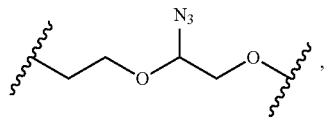 [SMILES: *CCOC(CO*)N=[N+]=[N-]]
$L^{2D}$ is
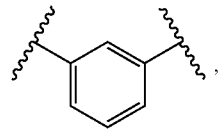
and $L^{2E}$ is
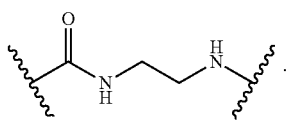 [SMILES: *NCCNC(*)=O]
In embodiments, $L^{2A}$ is
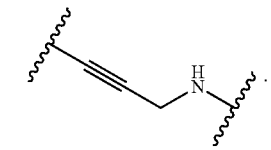 [SMILES: *C#CCN*]
In embodiments, $L^{2B}$ is
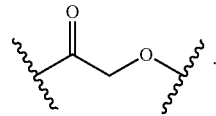 [SMILES: *OCC(*)=O]
In embodiments, $L^{2C}$ is
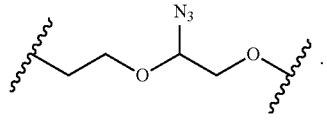 [SMILES: *CCOC(CO*)N=[N+]=[N-]]
In embodiments, $L^{2D}$ is
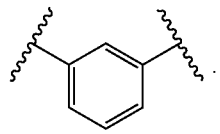 [SMILES: *c1cccc(*)c1]
In embodiments, $L^{2E}$ is
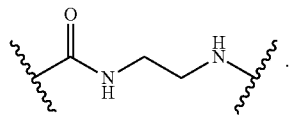 [SMILES: *NCCNC(*)=O]
In embodiments, $L^{2A}$ is
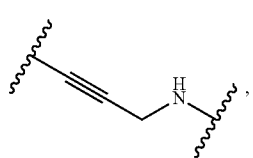 [SMILES: *C#CCN*]
$L^{2B}$ is
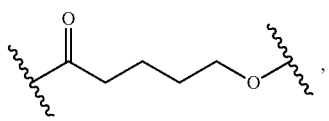 [SMILES: *OCCCCC(*)=O]
$L^{2C}$ is
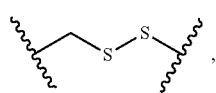
$L^{2D}$ is
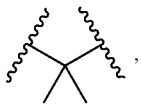 [SMILES: *C(*)(C)C]
and $L^{2E}$ is
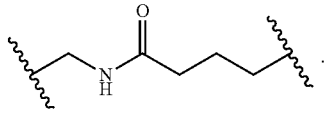 [SMILES: *CCCC(=O)NC*]

In embodiments, $L^{2A}$ is
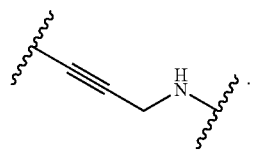
In embodiments, $L^{2B}$ is
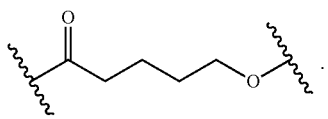 [SMILES: *OCCCCC(*)=O]
In embodiments, $L^{2C}$ is
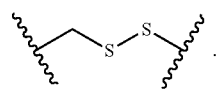
In embodiments, $L^{2D}$ is
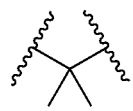
In embodiments, $L^{2E}$ is
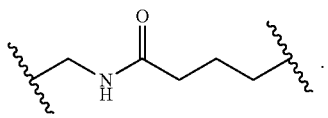 [SMILES: *CCCC(=O)NC*]
In embodiments, $L^{2A}$ is
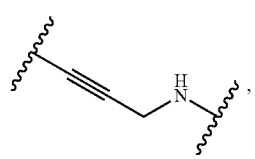 [SMILES: *C#CCN*]
$L^{2B}$ is
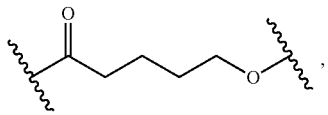 [SMILES: *OCCCCC(*)=O]
$L^{2C}$ is
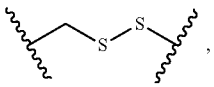
$L^{2D}$ is
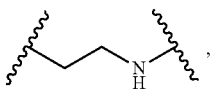 [SMILES: *CCN*]
and $L^{2E}$ is a bond. In embodiments, $L^{2A}$ is
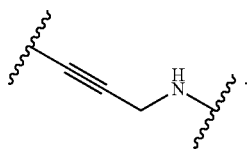 [SMILES: *C#CCN*]
In embodiments, $L^{2B}$ is
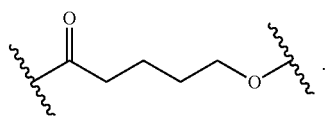 [SMILES: *OCCCCC(*)=O]
In embodiments, $L^{2C}$ is
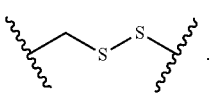
In embodiments, $L^{2D}$ is
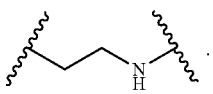 [SMILES: *CCN*]
In embodiments, $L^{2E}$ is a bond.
In embodiments, $L^{2A}$ is
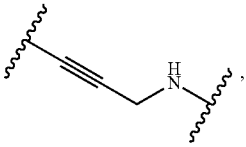 [SMILES: *C#CCN*]

$L^{2B}$ is
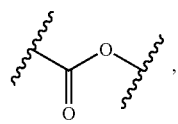,
$L^{2C}$ is
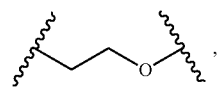 [SMILES: *CCO*],
$L^{2D}$ is
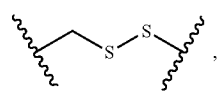,
and $L^{2E}$ is
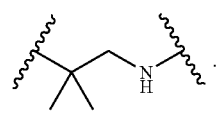 [SMILES: *NCC(*)(C)C].
In embodiments, $L^{2A}$ is
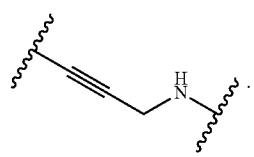.
In embodiments, $L^{2B}$ is
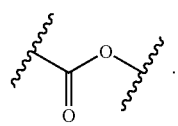 [SMILES: *OC(*)=O].
In embodiments, $L^{2C}$ is
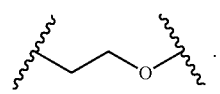 [SMILES: *CCO*].
In embodiments, $L^{2D}$ is
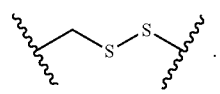.
In embodiments, $L^{2E}$ is
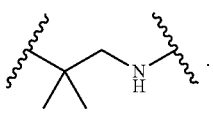 [SMILES: *NCC(*)(C)C].
In embodiments, $L^{2A}$ is
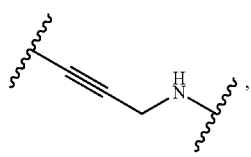,
$L^{2B}$ is
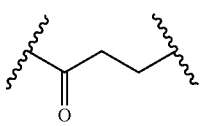,
$L^{2C}$ is
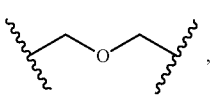,
$L^{2D}$ is
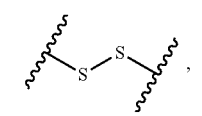,
and $L^{2E}$ is
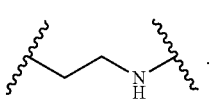.
In embodiments, $L^{2A}$ is
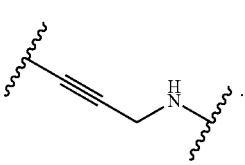 [SMILES: *C#CCN*]

In embodiments, L$^{2B}$ is
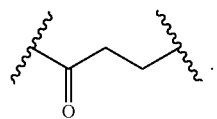 [SMILES: *CCC(*)=O]
In embodiments, L$^{2C}$ is
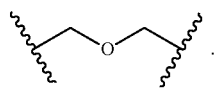
In embodiments, L$^{2D}$ is
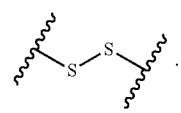
In embodiments, L$^{2E}$ is
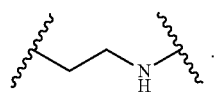 [SMILES: *CCN*]
In embodiments, L$^{2A}$ is
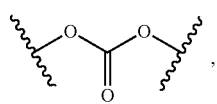 [SMILES: *OC(=O)O*]
L$^{2B}$ is
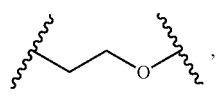 [SMILES: *CCO*]
L$^{2C}$ is
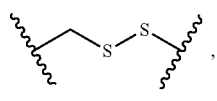 [SMILES: *CSS*]
L$^{2D}$ is
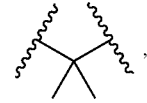
and L$^{2E}$ is
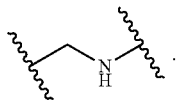
In embodiments, L$^{2A}$ is
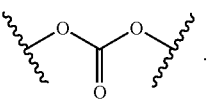 [SMILES: *OC(=O)O*]
In embodiments, L$^{2B}$ is
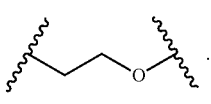 [SMILES: *CCO*]
In embodiments, L$^{2C}$ is
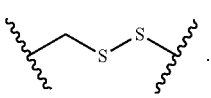 [SMILES: *CSS*]
In embodiments, L$^{2D}$ is
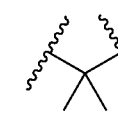
In embodiments, L$^{2E}$ is
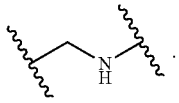
In embodiments, L$^{2A}$ is
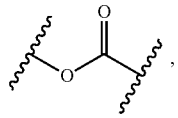
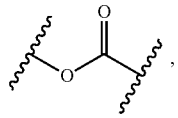
L$^{2B}$ is
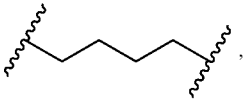 [SMILES: *CCCC*]

$L^{2C}$ is
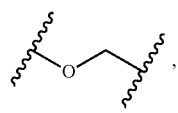
$L^{2D}$ is
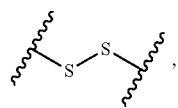
and $L^{2E}$ is
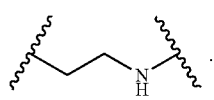
In embodiments, $L^{2A}$ is
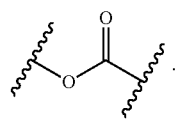
In embodiments, $L^{2B}$ is
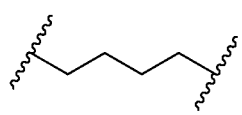
In embodiments, $L^{2C}$ is
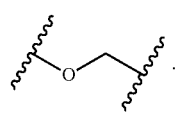
In embodiments, $L^{2D}$ is
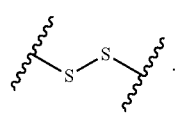 [SMILES: *SS*]
In embodiments, $L^{2E}$ is
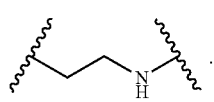 [SMILES: *CCN*]
In embodiments, $L^{2A}$ is
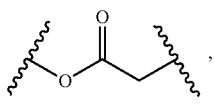
$L^{2B}$ is
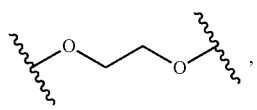 [SMILES: *OCCO*]
$L^{2C}$ is
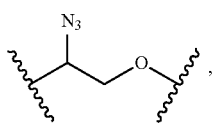
$L^{2D}$ is
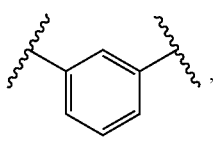 [SMILES: *c1cccc(*)c1]
and $L^{2E}$ is
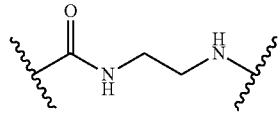
In embodiments, $L^{2A}$ is
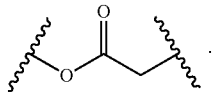 [SMILES: *CC(=O)O*]
In embodiments, $L^{2B}$ is
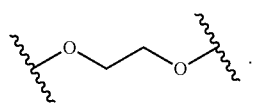 [SMILES: *OCCO*]
In embodiments, $L^{2C}$ is
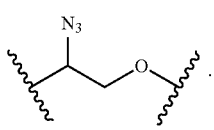

In embodiments, $L^{2D}$ is

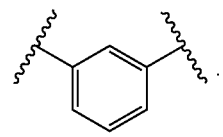 [SMILES: *c1cccc(*)c1]

In embodiments, $L^{2E}$ is

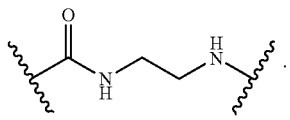 [SMILES: *NCCNC(*)=O]

In embodiments, $L^{2A}$ is

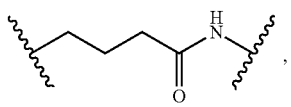

$L^{2B}$ is

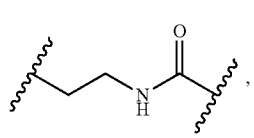 [SMILES: *CCNC(*)=O]

$L^{2C}$ is

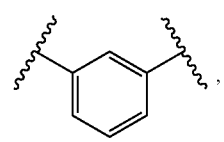 [SMILES: *c1cccc(*)c1]

$L^{2D}$ is

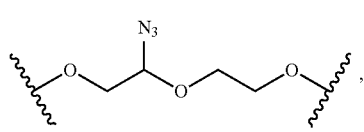 [SMILES: *OCCOC(CO*)N=[N+]=[N-]]

and $L^{2E}$ is

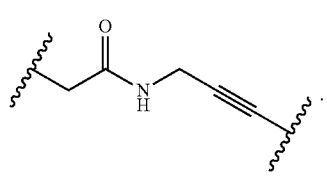 [SMILES: *C#CCNC(=O)C*]

In embodiments, $L^{2A}$ is

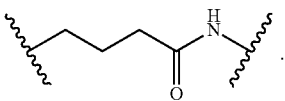 [SMILES: *CCCC(=O)N*]

In embodiments, $L^{2B}$ is

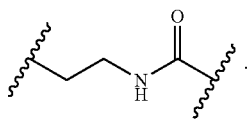

In embodiments, $L^{2C}$ is

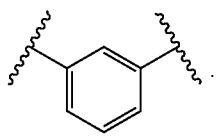 [SMILES: *c1cccc(*)c1]

In embodiments, $L^{2D}$ is

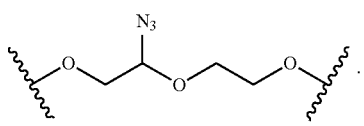 [SMILES: *OCCOC(CO*)N=[N+]=[N-]]

In embodiments, $L^{2E}$ is

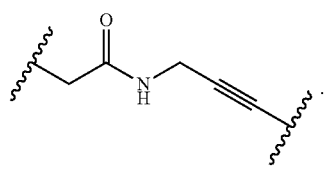 [SMILES: *C#CCNC(=O)C*]

In embodiments, $R^1$ is substituted or unsubstituted $C_1$-$C_6$ alkyl. In embodiments, $R^1$ is substituted or unsubstituted $C_1$-$C_3$ alkyl. In embodiments, $R^1$ is substituted or unsubstituted methyl.

In embodiments, $R^1$ is substituted or unsubstituted $C_1$ alkyl. In embodiments, $R^1$ is substituted or unsubstituted $C_2$ alkyl. In embodiments, $R^1$ is substituted or unsubstituted $C_3$ alkyl. In embodiments, $R^1$ is substituted or unsubstituted $C_4$ alkyl. In embodiments, $R^1$ is substituted or unsubstituted $C_5$ alkyl. In embodiments, $R^1$ is substituted or unsubstituted $C_6$ alkyl. In embodiments, $R^1$ is substituted $C_1$ alkyl. In embodiments, $R^1$ is substituted $C_2$ alkyl. In embodiments, $R^1$ is substituted $C_3$ alkyl. In embodiments, $R^1$ is substituted $C_4$ alkyl. In embodiments, $R^1$ is substituted $C_5$ alkyl. In embodiments, $R^1$ is substituted $C_6$ alkyl. In embodiments, $R^1$ is unsubstituted $C_1$ alkyl. In embodiments, $R^1$ is unsubstituted $C_2$ alkyl. In embodiments, $R^1$ is unsubstituted $C_3$ alkyl. In embodiments, $R^1$ is unsubstituted $C_4$ alkyl. In embodiments, $R^1$ is unsubstituted $C_5$ alkyl. In embodiments, $R^1$ is unsubstituted $C_6$ alkyl.

In embodiments, $R^1$ is $R^{31}$-substituted or unsubstituted alkyl, $R^{31}$-substituted or unsubstituted heteroalkyl, $R^{31}$-substituted or unsubstituted cycloalkyl, $R^{31}$-substituted or unsubstituted heterocycloalkyl, $R^{31}$-substituted or unsubstituted aryl, or $R^{31}$-substituted or unsubstituted heteroaryl. In embodiments, $R^1$ is $R^{31}$-substituted or unsubstituted alkyl (e.g., $C_1$-$C_6$ alkyl), wherein $R^{31}$ is independently —$PO_3H$, —$PO_4H$, —$SO_2NH_2$, —$SO_3H$, or —$SO_4H$.

$R^{31}$ is independently oxo, halogen, —$CF_3$, —$CCl_3$, —$CI_3$, —$CBr_3$, —$CHF_2$, —$CHCl_2$, —$CHI_2$, —$CHBr_2$, —$CH_2F$, —$CH_2Cl$, —$CH_2I$, —$CH_2Br$, —$OCH_2F$, —$OCH_2Cl$, —$OCH_2I$, —$OCH_2Br$, —$OCHF_2$, —$OCHCl_2$, —$OCHI_2$, —$OCHBr_2$, —$OCF_3$, —$OCCl_3$, —$OCI_3$, —$OCBr_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$PO_4H$, —$PO_3H$, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). In embodiments, $R^{31}$ is independently —$PO_3H$, —$PO_4H$, —$SO_2NH_2$, —$SO_3H$, or —$SO_4H$. In embodiments, $R^{31}$ is independently —$SO_3H$. In embodiments, $R^{31}$ is independently —$PO_3H$. In embodiments, $R^{31}$ is independently —$SO_2NH_2$. In embodiments, $R^{31}$ is independently —$SO_4H$.

In embodiments, $R^1$ is substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^1$ is substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^1$ is unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{1A}$ is substituted or unsubstituted $C_1$-$C_6$ alkyl. In embodiments, $R^{1A}$ is substituted or unsubstituted $C_1$-$C_3$ alkyl. In embodiments, $R^{1A}$ is substituted or unsubstituted methyl.

In embodiments, $R^{1A}$ is substituted or unsubstituted $C_1$ alkyl. In embodiments, $R^{1A}$ is substituted or unsubstituted $C_2$ alkyl. In embodiments, $R^{1A}$ is substituted or unsubstituted $C_3$ alkyl. In embodiments, $R^{1A}$ is substituted or unsubstituted $C_4$ alkyl. In embodiments, $R^{1A}$ is substituted or unsubstituted $C_5$ alkyl. In embodiments, $R^{1A}$ is substituted or unsubstituted $C_6$ alkyl. In embodiments, $R^{1A}$ is substituted $C_1$ alkyl. In embodiments, $R^{1A}$ is substituted $C_2$ alkyl. In embodiments, $R^{1A}$ is substituted $C_3$ alkyl. In embodiments, $R^{1A}$ is substituted $C_4$ alkyl. In embodiments, $R^{1A}$ is substituted $C_5$ alkyl. In embodiments, $R^{1A}$ is substituted $C_6$ alkyl. In embodiments, $R^{1A}$ is unsubstituted $C_1$ alkyl. In embodiments, $R^{1A}$ is unsubstituted $C_2$ alkyl. In embodiments, $R^{1A}$ is unsubstituted $C_3$ alkyl. In embodiments, $R^{1A}$ is unsubstituted $C_4$ alkyl. In embodiments, $R^{1A}$ is unsubstituted $C_5$ alkyl. In embodiments, $R^{1A}$ is unsubstituted $C_6$ alkyl.

In embodiments, $R^{1A}$ is $R^{31A}$-substituted or unsubstituted alkyl, $R^{31A}$-substituted or unsubstituted heteroalkyl, $R^{31A}$-substituted or unsubstituted cycloalkyl, $R^{31A}$-substituted or unsubstituted heterocycloalkyl, $R^{31A}$-substituted or unsubstituted aryl, or $R^{31A}$-substituted or unsubstituted heteroaryl.

$R^{31A}$ is independently oxo, halogen, —$CF_3$, —$CCl_3$, —$CI_3$, —$CBr_3$, —$CHF_2$, —$CHCl_2$, —$CHI_2$, —$CHBr_2$, —$CH_2F$, —$CH_2Cl$, —$CH_2I$, —$CH_2Br$, —$OCH_2F$, —$OCH_2Cl$, —$OCH_2I$, —$OCH_2Br$, —$OCHF_2$, —$OCHCl_2$, —$OCHI_2$, —$OCHBr_2$, —$OCF_3$, —$OCCl_3$, —$OCI_3$, —$OCBr_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{1A}$ is substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{1A}$ is substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^{1A}$ is unsubstituted alkyl, unsubstituted heteroalkyl, unsubstituted cycloalkyl, unsubstituted heterocycloalkyl, unsubstituted aryl, or unsubstituted heteroaryl.

In embodiments, $R^1$, $R^4$, $R^5$, $R^6$, and $R^7$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CHF_2$, —$CH_2Br$, —$CH_2Cl$, —$CH_2I$, —OH, —$NH_2$, —COOH, —CONH$_2$, or —SH. In embodiments, R$^1$, R$^4$, R$^5$, R$^6$, and R$^7$ are each independently hydrogen. In embodiments, R$^1$, R$^4$, R$^5$, R$^6$, and R$^7$ are each independently halogen. In embodiments, R$^1$, R$^4$, R$^5$, R$^6$, and R$^7$ are each independently —CF$_3$. In embodiments, R$^1$, R$^4$, R$^5$, R$^6$, and R$^7$ are each independently —CBr$_3$. In embodiments, R$^1$, R$^4$, R$^5$, R$^6$, and R$^7$ are each independently —CCl$_3$. In embodiments, R$^1$, R$^4$, R$^5$, R$^6$, and R$^7$ are each independently —CI$_3$. In embodiments, R$^1$, R$^4$, R$^5$, R$^6$, and R$^7$ are each independently —CHF$_2$. In embodiments, R$^1$, R$^4$, R$^5$, R$^6$, and R$^7$ are each independently —CHBr$_2$. In embodiments, R$^1$, R$^4$, R$^5$, R$^6$, and R$^7$ are each independently —CHCl$_2$. In embodiments, R$^1$, R$^4$, R$^5$, R$^6$, and R$^7$ are each independently —CHI$_2$. In embodiments, R$^1$, R$^4$, R$^5$, R$^6$, and R$^7$ are each independently —CHF$_2$. In embodiments, R$^1$, R$^4$, R$^5$, R$^6$, and R$^7$ are each independently —CH$_2$Br. In embodiments, R$^1$, R$^4$, R$^5$, R$^6$, and R$^7$ are each independently —CH$_2$Cl. In embodiments, R$^1$, R$^4$, R$^5$, R$^6$, and R$^7$ are each independently —CH$_2$I. In embodiments, R$^1$, R$^4$, R$^5$, R$^6$, and R$^7$ are each independently —OH. In embodiments, R$^1$, R$^4$, R$^5$, R$^6$, and R$^7$ are each independently —NH$_2$. In embodiments, R$^1$, R$^4$, R$^5$, R$^6$, and R$^7$ are each independently —COOH. In embodiments, R$^1$, R$^4$, R$^5$, R$^6$, and R$^7$ are each independently —CONH$_2$. In embodiments, R$^1$, R$^4$, R$^5$, R$^6$, and R$^7$ are each independently —SH.

In embodiments, R$^1$ is independently hydrogen, halogen, —CF$_3$, —CCl$_3$, —CI$_3$, —CBr$_3$, —CHF$_2$, —CHCl$_2$, —CHI$_2$, —CHBr$_2$, —CH$_2$F, —CH$_2$Cl, —CH$_2$I, —CH$_2$Br, —OCH$_2$F, —OCH$_2$Cl, —OCH$_2$I, —OCH$_2$Br, —OCHF$_2$, —OCHCl$_2$, —OCHI$_2$, —OCHBr$_2$, —OCF$_3$, —OCCl$_3$, —OCI$_3$, —OCBr$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, or —N$_3$. In embodiments, R$^1$ is independently hydrogen. In embodiments, R$^1$ is independently halogen. In embodiments, R$^1$ is independently —CF$_3$. In embodiments, R$^1$ is independently —CCl$_3$. In embodiments, R$^1$ is independently —CI$_3$. In embodiments, R$^1$ is independently —CBr$_3$. In embodiments, R$^1$ is independently —CHF$_2$. In embodiments, R$^1$ is independently —CHCl$_2$. In embodiments, R$^1$ is independently —CHI$_2$. In embodiments, R$^1$ is independently —CHBr$_2$. In embodiments, R$^1$ is independently —CH$_2$F. In embodiments, R$^1$ is independently —CH$_2$Cl. In embodiments, R$^1$ is independently —CH$_2$I. In embodiments, R$^1$ is independently —CH$_2$Br. In embodiments, R$^1$ is independently —OCH$_2$F. In embodiments, R$^1$ is independently —OCH$_2$Cl. In embodiments, R$^1$ is independently —OCH$_2$I. In embodiments, R$^1$ is independently —OCH$_2$Br. In embodiments, R$^1$ is independently —OCHF$_2$. In embodiments, R$^1$ is independently —OCHCl$_2$. In embodiments, R$^1$ is independently —OCHI$_2$. In embodiments, R$^1$ is independently —OCHBr$_2$. In embodiments, R$^1$ is independently —OCF$_3$. In embodiments, R$^1$ is independently —OCCl$_3$. In embodiments, R$^1$ is independently —OCI$_3$. In embodiments, R$^1$ is independently —OCBr$_3$. In embodiments, R$^1$ is independently —CN. In embodiments, R$^1$ is independently —OH. In embodiments, R$^1$ is independently —NH$_2$. In embodiments, R$^1$ is independently —COOH. In embodiments, R$^1$ is independently —CONH$_2$. In embodiments, R$^1$ is independently —NO$_2$. In embodiments, R$^1$ is independently —SH. In embodiments, R$^1$ is independently —SO$_3$H. In embodiments, R$^1$ is independently —SO$_4$H. In embodiments, R$^1$ is independently —SO$_2$NH$_2$. In embodiments, R$^1$ is independently —NHNH$_2$. In embodiments, R$^1$ is independently —ONH$_2$. In embodiments, R$^1$ is independently —NHC=(O)NHNH$_2$. In embodiments, R$^1$ is independently —NHC=(O)NH$_2$. In embodiments, R$^1$ is independently —NHSO$_2$H. In embodiments, R$^1$ is independently —NHC=(O)H. In embodiments, R$^1$ is independently —NHC(O)OH. In embodiments, R$^1$ is independently —NHOH.

In embodiments, R$^1$ is substituted (e.g., substituted with a substituent group, a size-limited substituent group, or lower substituent group) or unsubstituted alkyl. In embodiments, R$^1$ is substituted (e.g., substituted with a substituent group, a size-limited substituent group, or lower substituent group) alkyl. In embodiments, R$^1$ is unsubstituted alkyl. In embodiments, R$^1$ is substituted or unsubstituted alkyl (e.g., C$_1$-C$_8$, C$_1$-C$_6$, C$_1$-C$_4$, or C$_1$-C$_2$). In embodiments, R$^1$ is substituted alkyl (e.g., C$_1$-C$_8$, C$_1$-C$_6$, C$_1$-C$_4$, or C$_1$-C$_2$). In embodiments, R$^1$ is unsubstituted alkyl (e.g., C$_1$-C$_8$, C$_1$-C$_6$, C$_1$-C$_4$, or C$_1$-C$_2$).

In embodiments, R$^2$ is R$^{32}$-substituted or unsubstituted alkyl, or R$^{32}$-substituted or unsubstituted heteroalkyl. In embodiments, R$^2$ is R$^{32}$-substituted or unsubstituted alkyl (e.g., C$_1$-C$_6$ alkyl), wherein R$^{32}$ is independently —PO$_3$H, —PO$_4$H, —SO$_2$NH$_2$, —SO$_3$H, or —SO$_4$H.

R$^{32}$ is independently oxo, halogen, —CF$_3$, —CCl$_3$, —CI$_3$, —CBr$_3$, —CHF$_2$, —CHCl$_2$, —CHI$_2$, —CHBr$_2$, —CH$_2$F, —CH$_2$Cl, —CH$_2$I, —CH$_2$Br, —OCH$_2$F, —OCH$_2$Cl, —OCH$_2$I, —OCH$_2$Br, —OCHF$_2$, —OCHCl$_2$, —OCHI$_2$, —OCHBr$_2$, —OCF$_3$, —OCCl$_3$, —OCI$_3$, —OCBr$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —PO$_4$H, —PO$_3$H, —N$_3$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered). In embodiments, R$^{32}$ is independently —PO$_3$H, —PO$_4$H, —SO$_2$NH$_2$, —SO$_3$H, or —SO$_4$H. In embodiments, R$^{32}$ is independently —SO$_3$H. In embodiments, R$^{32}$ is independently —PO$_3$H. In embodiments, R$^{32}$ is independently —SO$_2$NH$_2$. In embodiments, R$^{32}$ is independently —SO$_4$H.

In embodiments, R$^2$ is independently substituted or unsubstituted C$_1$-C$_6$ alkyl. In embodiments, R$^2$ is independently substituted or unsubstituted C$_1$-C$_3$ alkyl. In embodiments, R$^2$ is independently substituted or unsubstituted methyl. In embodiments, R$^2$ is independently substituted or unsubstituted ethyl. In embodiments, R$^2$ is independently substituted or unsubstituted C$_3$ alkyl (e.g., n-propyl or iso-propyl).

In embodiments, R$^2$ is independently substituted or unsubstituted C$_1$ alkyl. In embodiments, R$^2$ is independently substituted or unsubstituted C$_2$ alkyl. In embodiments, R$^2$ is independently substituted or unsubstituted C$_3$ alkyl. In embodiments, R$^2$ is independently substituted or unsubstituted C$_4$ alkyl. In embodiments, R$^2$ is independently substituted or unsubstituted C$_5$ alkyl. In embodiments, R$^2$ is independently substituted or unsubstituted C$_6$ alkyl. In embodiments, R$^2$ is independently substituted C$_1$ alkyl. In embodiments, R$^2$ is independently substituted C$_2$ alkyl. In embodiments, R$^2$ is independently substituted C$_3$ alkyl. In embodiments, R$^2$ is independently substituted C$_4$ alkyl. In embodiments, R$^2$ is independently substituted C$_5$ alkyl. In embodiments, $R^2$ is independently substituted $C_6$ alkyl. In embodiments, $R^2$ is independently unsubstituted $C_1$ alkyl. In embodiments, $R^2$ is independently unsubstituted $C_2$ alkyl. In embodiments, $R^2$ is independently unsubstituted $C_3$ alkyl. In embodiments, $R^2$ is independently unsubstituted $C_4$ alkyl. In embodiments, $R^2$ is independently unsubstituted $C_5$ alkyl. In embodiments, $R^2$ is independently unsubstituted $C_6$ alkyl.

In embodiments, $R^2$ is substituted or unsubstituted alkyl (e.g., $C_1$-$C_8$, $C_1$-$C_6$, $C_1$-$C_4$, or $C_1$-$C_2$) or substituted or unsubstituted heteroalkyl (e.g., 2 to 8 membered, 2 to 6 membered, 4 to 6 membered, 2 to 3 membered, or 4 to 5 membered). In embodiments, $R^2$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^2$ is unsubstituted alkyl or unsubstituted heteroalkyl.

In embodiments, $R^2$ is substituted (e.g., substituted with a substituent group, a size-limited substituent group, or lower substituent group) or unsubstituted alkyl. In embodiments, $R^2$ is substituted (e.g., substituted with a substituent group, a size-limited substituent group, or lower substituent group) alkyl. In embodiments, $R^2$ is unsubstituted alkyl. In embodiments, $R^2$ is substituted or unsubstituted alkyl (e.g., $C_1$-$C_8$, $C_1$-$C_6$, $C_1$-$C_4$, or $C_1$-$C_2$). In embodiments, $R^2$ is substituted alkyl (e.g., $C_1$-$C_8$, $C_1$-$C_6$, $C_1$-$C_4$, or $C_1$-$C_2$). In embodiments, $R^2$ is unsubstituted alkyl (e.g., $C_1$-$C_8$, $C_1$-$C_6$, $C_1$-$C_4$, or $C_1$-$C_2$).

In embodiments, $R^3$ is $R^{33}$-substituted or unsubstituted alkyl, or $R^{33}$-substituted or unsubstituted heteroalkyl. In embodiments, $R^3$ is $R^{33}$-substituted or unsubstituted alkyl (e.g., $C_1$-$C_6$ alkyl), wherein $R^{33}$ is independently —$PO_3H$, —$PO_4H$, —$SO_2NH_2$, —$SO_3H$, or —$SO_4H$.

$R^{33}$ is independently oxo, halogen, —$CF_3$, —$CCl_3$, —$CI_3$, —$CBr_3$, —$CHF_2$, —$CHCl_2$, —$CHI_2$, —$CHBr_2$, —$CH_2F$, —$CH_2Cl$, —$CH_2I$, —$CH_2Br$, —$OCH_2F$, —$OCH_2Cl$, —$OCH_2I$, —$OCH_2Br$, —$OCHF_2$, —$OCHCl_2$, —$OCHI_2$, —$OCHBr_2$, —$OCF_3$, —$OCCl_3$, —$OCI_3$, —$OCBr_3$, —$CN$, —$OH$, —$NH_2$, —$COOH$, —$CONH_2$, —$NO_2$, —$SH$, —$SO_3H$, —$SO_4H$, —$SO_2NH_2$, —$NHNH_2$, —$ONH_2$, —$NHC=(O)NHNH_2$, —$NHC=(O)NH_2$, —$NHSO_2H$, —$NHC=(O)H$, —$NHC(O)OH$, —$NHOH$, —$PO_4H$, —$PO_3H$, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). In embodiments, $R^{33}$ is independently —$PO_3H$, —$PO_4H$, —$SO_2NH_2$, —$SO_3H$, or —$SO_4H$. In embodiments, $R^{33}$ is independently —$SO_3H$. In embodiments, $R^{33}$ is independently —$PO_3H$. In embodiments, $R^{33}$ is independently —$SO_2NH_2$. In embodiments, $R^{33}$ is independently —$SO_4H$.

In embodiments, $R^3$ is substituted or unsubstituted $C_1$-$C_6$ alkyl. In embodiments, $R^3$ is substituted or unsubstituted $C_1$-$C_3$ alkyl. In embodiments, $R^3$ is substituted or unsubstituted methyl. In embodiments, $R^3$ is substituted or unsubstituted ethyl. In embodiments, $R^3$ is substituted or unsubstituted $C_3$ alkyl (e.g., n-propyl or isopropyl).

In embodiments, $R^3$ is independently substituted or unsubstituted $C_1$ alkyl. In embodiments, $R^3$ is substituted or unsubstituted $C_2$ alkyl. In embodiments, $R^3$ is independently substituted or unsubstituted $C_3$ alkyl. In embodiments, $R^3$ is independently substituted or unsubstituted $C_4$ alkyl. In embodiments, $R^3$ is independently substituted or unsubstituted $C_5$ alkyl. In embodiments, $R^3$ is independently substituted or unsubstituted $C_6$ alkyl. In embodiments, $R^3$ is independently substituted $C_1$ alkyl. In embodiments, $R^3$ is independently substituted $C_2$ alkyl. In embodiments, $R^3$ is independently substituted $C_3$ alkyl. In embodiments, $R^3$ is independently substituted $C_4$ alkyl. In embodiments, $R^3$ is independently substituted $C_5$ alkyl. In embodiments, $R^3$ is independently substituted $C_6$ alkyl. In embodiments, $R^3$ is independently unsubstituted $C_1$ alkyl. In embodiments, $R^3$ is independently unsubstituted $C_2$ alkyl. In embodiments, $R^3$ is independently unsubstituted $C_3$ alkyl. In embodiments, $R^3$ is independently unsubstituted $C_4$ alkyl. In embodiments, $R^3$ is independently unsubstituted $C_5$ alkyl. In embodiments, $R^3$ is independently unsubstituted $C_6$ alkyl.

In embodiments, $R^3$ is substituted or unsubstituted alkyl (e.g., $C_1$-$C_8$, $C_1$-$C_6$, $C_1$-$C_4$, or $C_1$-$C_2$), or substituted or unsubstituted heteroalkyl (e.g., 2 to 8 membered, 2 to 6 membered, 4 to 6 membered, 2 to 3 membered, or 4 to 5 membered). In embodiments, $R^3$ is substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl. In embodiments, $R^3$ is unsubstituted alkyl, unsubstituted heteroalkyl.

In embodiments, $R^3$ is substituted (e.g., substituted with a substituent group, a size-limited substituent group, or lower substituent group) or unsubstituted alkyl. In embodiments, $R^3$ is substituted (e.g., substituted with a substituent group, a size-limited substituent group, or lower substituent group) alkyl. In embodiments, $R^3$ is unsubstituted alkyl. In embodiments, $R^3$ is substituted or unsubstituted alkyl (e.g., $C_1$-$C_8$, $C_1$-$C_6$, $C_1$-$C_4$, or $C_1$-$C_2$). In embodiments, $R^3$ is substituted alkyl (e.g., $C_1$-$C_8$, $C_1$-$C_6$, $C_1$-$C_4$, or $C_1$-$C_2$). In embodiments, $R^3$ is unsubstituted alkyl (e.g., $C_1$-$C_8$, $C_1$-$C_6$, $C_1$-$C_4$, or $C_1$-$C_2$).

In embodiments, $R^4$ is independently hydrogen, halogen, —$CF_3$, —$CCl_3$, —$CI_3$, —$CBr_3$, —$CHF_2$, —$CHCl_2$, —$CHI_2$, —$CHBr_2$, —$CH_2F$, —$CH_2Cl$, —$CH_2I$, —$CH_2Br$, —$OCH_2F$, —$OCH_2Cl$, —$OCH_2I$, —$OCH_2Br$, —$OCHF_2$, —$OCHCl_2$, —$OCHI_2$, —$OCHBr_2$, —$OCF_3$, —$OCCl_3$, —$OCI_3$, —$OCBr_3$, —$CN$, —$OH$, —$NH_2$, —$COOH$, —$CONH_2$, —$NO_2$, —$SH$, —$SO_3H$, —$SO_4H$, —$SO_2NH_2$, —$NHNH_2$, —$ONH_2$, —$NHC=(O)NHNH_2$, —$NHC=(O)NH_2$, —$NHSO_2H$, —$NHC=(O)H$, —$NHC(O)OH$, —$NHOH$, or —$N_3$. In embodiments, $R^4$ is independently hydrogen. In embodiments, $R^4$ is independently halogen. In embodiments, $R^4$ is independently —$CF_3$. In embodiments, $R^4$ is independently —$CCl_3$. In embodiments, $R^4$ is independently —$CI_3$. In embodiments, $R^4$ is independently —$CBr_3$. In embodiments, $R^4$ is independently —$CHF_2$. In embodiments, $R^4$ is independently —$CHCl_2$. In embodiments, $R^4$ is independently —$CHI_2$. In embodiments, $R^4$ is independently —$CHBr_2$. In embodiments, $R^4$ is independently —$CH_2F$. In embodiments, $R^4$ is independently —$CH_2Cl$. In embodiments, $R^4$ is independently —$CH_2I$. In embodiments, $R^4$ is independently —$CH_2Br$. In embodiments, $R^4$ is independently —$OCH_2F$. In embodiments, $R^4$ is independently —$OCH_2Cl$. In embodiments, $R^4$ is independently —$OCH_2I$. In embodiments, $R^4$ is independently —$OCH_2Br$. In embodiments, $R^4$ is independently —$OCHF_2$. In embodiments, $R^4$ is independently —$OCHCl_2$. In embodiments, $R^4$ is independently —$OCHI_2$. In embodiments, $R^4$ is independently —$OCHBr_2$. In embodiments, $R^4$ is independently —$OCF_3$. In embodiments, $R^4$ is independently —$OCCl_3$. In embodiments, $R^4$ is independently —$OCI_3$. In embodiments, $R^4$ is independently —$OCBr_3$. In embodiments, $R^4$ is independently —CN. In embodiments, $R^4$ is independently —OH. In embodiments, $R^4$ is independently —$NH_2$. In embodiments, $R^4$ is independently —COOH. In embodiments, $R^4$ is independently —$CONH_2$. In embodiments, $R^4$ is independently —$NO_2$. In embodiments, $R^4$ is independently —SH. In embodiments, $R^4$ is independently —$SO_3H$. In embodiments, $R^4$ is independently —$SO_4H$. In embodiments, $R^4$ is independently —$SO_2NH_2$. In embodiments, $R^4$ is independently —$NHNH_2$. In embodiments, $R^4$ is independently —$ONH_2$. In embodiments, $R^4$ is independently —NHC=(O)$NHNH_2$. In embodiments, $R^4$ is independently —NHC=(O)$NH_2$. In embodiments, $R^4$ is independently —$NHSO_2H$. In embodiments, $R^4$ is independently —NHC=(O)H. In embodiments, $R^4$ is independently —NHC(O)OH. In embodiments, $R^4$ is independently —NHOH.

In embodiments, $R^4$ is $R^{34}$-substituted or unsubstituted alkyl, $R^{34}$-substituted or unsubstituted heteroalkyl, $R^{34}$-substituted or unsubstituted cycloalkyl, $R^{34}$-substituted or unsubstituted heterocycloalkyl, $R^{34}$-substituted or unsubstituted aryl, or $R^{34}$-substituted or unsubstituted heteroaryl.

$R^{34}$ is independently oxo, halogen, —$CF_3$, —$CCl_3$, —$CI_3$, —$CBr_3$, —$CHF_2$, —$CHCl_2$, —$CHI_2$, —$CHBr_2$, —$CH_2F$, —$CH_2Cl$, —$CH_2I$, —$CH_2Br$, —$OCH_2F$, —$OCH_2Cl$, —$OCH_2I$, —$OCH_2Br$, —$OCHF_2$, —$OCHCl_2$, —$OCHI_2$, —$OCHBr_2$, —$OCF_3$, —$OCCl_3$, —$OCI_3$, —$OCBr_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$PO_4H$, —$PO_3H$, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). In embodiments, $R^{34}$ is independently —$PO_3H$, —$PO_4H$, —$SO_2NH_2$, —$SO_3H$, or —$SO_4H$. In embodiments, $R^{34}$ is independently —$SO_3H$. In embodiments, $R^{34}$ is independently —$PO_3H$. In embodiments, $R^{34}$ is independently —$SO_2NH_2$. In embodiments, $R^{34}$ is independently —$SO_4H$.

In embodiments, $R^4$ is hydrogen, or substituted or unsubstituted $C_1$-$C_6$ alkyl. In embodiments, $R^4$ is hydrogen. In embodiments, $R^4$ is substituted or unsubstituted $C_1$-$C_6$ alkyl. In embodiments, $R^4$ is substituted or unsubstituted $C_1$ alkyl. In embodiments, $R^4$ is substituted or unsubstituted $C_2$ alkyl. In embodiments, $R^4$ is substituted or unsubstituted $C_3$ alkyl. In embodiments, $R^4$ is substituted or unsubstituted $C_4$ alkyl. In embodiments, $R^4$ is substituted or unsubstituted $C_5$ alkyl. In embodiments, $R^4$ is substituted or unsubstituted $C_6$ alkyl. In embodiments, $R^4$ is substituted $C_1$ alkyl. In embodiments, $R^4$ is substituted $C_2$ alkyl. In embodiments, $R^4$ is substituted $C_3$ alkyl. In embodiments, $R^4$ is substituted $C_4$ alkyl. In embodiments, $R^4$ is substituted $C_5$ alkyl. In embodiments, $R^4$ is substituted $C_6$ alkyl. In embodiments, $R^4$ is unsubstituted $C_1$ alkyl. In embodiments, $R^4$ is unsubstituted $C_2$ alkyl. In embodiments, $R^4$ is unsubstituted $C_3$ alkyl. In embodiments, $R^4$ is unsubstituted $C_4$ alkyl. In embodiments, $R^4$ is unsubstituted $C_5$ alkyl. In embodiments, $R^4$ is unsubstituted $C_6$ alkyl. In embodiments, $R^4$ is $R^{34}$-substituted or unsubstituted alkyl (e.g., $C_1$-$C_6$ alkyl), wherein $R^{34}$ is independently —$PO_3H$, —$PO_4H$, —$SO_2NH_2$, —$SO_3H$, or —$SO_4H$.

In embodiments, $R^4$ is substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^4$ is substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^4$ is unsubstituted alkyl, unsubstituted heteroalkyl, unsubstituted cycloalkyl, unsubstituted heterocycloalkyl, unsubstituted aryl, or unsubstituted heteroaryl.

In embodiments, $R^4$ is substituted (e.g., substituted with a substituent group, a size-limited substituent group, or lower substituent group) or unsubstituted alkyl. In embodiments, $R^4$ is substituted (e.g., substituted with a substituent group, a size-limited substituent group, or lower substituent group) alkyl. In embodiments, $R^4$ is unsubstituted alkyl. In embodiments, $R^4$ is substituted or unsubstituted alkyl (e.g., $C_1$-$C_8$, $C_1$-$C_6$, $C_1$-$C_4$, or $C_1$-$C_2$). In embodiments, $R^4$ is substituted alkyl (e.g., $C_1$-$C_8$, $C_1$-$C_6$, $C_1$-$C_4$, or $C_1$-$C_2$). In embodiments, $R^4$ is unsubstituted alkyl (e.g., $C_1$-$C_8$, $C_1$-$C_6$, $C_1$-$C_4$, or $C_1$-$C_2$).

In embodiments, $R^5$ is independently hydrogen, halogen, —$CF_3$, —$CCl_3$, —$CI_3$, —$CBr_3$, —$CHF_2$, —$CHCl_2$, —$CHI_2$, —$CHBr_2$, —$CH_2F$, —$CH_2Cl$, —$CH_2I$, —$CH_2Br$, —$OCH_2F$, —$OCH_2Cl$, —$OCH_2I$, —$OCH_2Br$, —$OCHF_2$, —$OCHCl_2$, —$OCHI_2$, —$OCHBr_2$, —$OCF_3$, —$OCCl_3$, —$OCI_3$, —$OCBr_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, or —$N_3$. In embodiments, $R^5$ is independently hydrogen. In embodiments, $R^5$ is independently halogen. In embodiments, $R^5$ is independently —$CF_3$. In embodiments, $R^5$ is independently —$CCl_3$. In embodiments, $R^5$ is independently —$CI_3$. In embodiments, $R^5$ is independently —$CBr_3$. In embodiments, $R^5$ is independently —$CHF_2$. In embodiments, $R^5$ is independently —$CHCl_2$. In embodiments, $R^5$ is independently —$CHI_2$. In embodiments, $R^5$ is independently —$CHBr_2$. In embodiments, $R^5$ is independently —$CH_2F$. In embodiments, $R^5$ is independently —$CH_2Cl$. In embodiments, $R^5$ is independently —$CH_2I$. In embodiments, $R^5$ is independently —$CH_2Br$. In embodiments, $R^5$ is independently —$OCH_2F$. In embodiments, $R^5$ is independently —$OCH_2Cl$. In embodiments, $R^5$ is independently —$OCH_2I$. In embodiments, $R^5$ is independently —OCH$_2$Br. In embodiments, R$^5$ is independently —OCHF$_2$. In embodiments, R$^5$ is independently —OCHCl$_2$. In embodiments, R$^5$ is independently —OCHI$_2$. In embodiments, R$^5$ is independently —OCHBr$_2$. In embodiments, R$^5$ is independently —OCF$_3$. In embodiments, R$^5$ is independently —OCCl$_3$. In embodiments, R$^5$ is independently —OCI$_3$. In embodiments, R$^5$ is independently —OCBr$_3$. In embodiments, R$^5$ is independently —CN. In embodiments, R$^5$ is independently —OH. In embodiments, R$^5$ is independently —NH$_2$. In embodiments, R$^5$ is independently —COOH. In embodiments, R$^5$ is independently —CONH$_2$. In embodiments, R$^5$ is independently —NO$_2$. In embodiments, R$^5$ is independently —SH. In embodiments, R$^5$ is independently —SO$_3$H. In embodiments, R$^5$ is independently —SO$_4$H. In embodiments, R$^5$ is independently —SO$_2$NH$_2$. In embodiments, R$^5$ is independently —NHNH$_2$. In embodiments, R$^5$ is independently —ONH$_2$. In embodiments, R$^5$ is independently —NHC=(O)NHNH$_2$. In embodiments, R$^5$ is independently —NHC=(O)NH$_2$. In embodiments, R$^5$ is independently —NHSO$_2$H. In embodiments, R$^5$ is independently —NHC=(O)H. In embodiments, R$^5$ is independently —NHC(O)OH. In embodiments, R$^5$ is independently —NHOH.

In embodiments, R$^5$ is R$^{35}$-substituted or unsubstituted alkyl, R$^{35}$-substituted or unsubstituted heteroalkyl, R$^{35}$-substituted or unsubstituted cycloalkyl, R$^{35}$-substituted or unsubstituted heterocycloalkyl, R$^{35}$-substituted or unsubstituted aryl, or R$^{35}$-substituted or unsubstituted heteroaryl.

R$^{35}$ is independently oxo, halogen, —CF$_3$, —CCl$_3$, —CI$_3$, —CBr$_3$, —CHF$_2$, —CHCl$_2$, —CHI$_2$, —CHBr$_2$, —CH$_2$F, —CH$_2$Cl, —CH$_2$I, —CH$_2$Br, —OCH$_2$F, —OCH$_2$Cl, —OCH$_2$I, —OCH$_2$Br, —OCHF$_2$, —OCHCl$_2$, —OCHI$_2$, —OCHBr$_2$, —OCF$_3$, —OCCl$_3$, —OCI$_3$, —OCBr$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —PO$_4$H, —PO$_3$H, —N$_3$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered). In embodiments, R$^{35}$ is independently —PO$_3$H, —PO$_4$H, —SO$_2$NH$_2$, —SO$_3$H, or —SO$_4$H. In embodiments, R$^{35}$ is independently —SO$_3$H. In embodiments, R$^{35}$ is independently —PO$_3$H. In embodiments, R$^{35}$ is independently —SO$_2$NH$_2$. In embodiments, R$^{35}$ is independently —SO$_4$H.

In embodiments, R$^5$ is hydrogen, or substituted or unsubstituted C$_1$-C$_6$ alkyl. In embodiments, R$^5$ is hydrogen. In embodiments, R$^5$ is substituted or unsubstituted C$_1$-C$_6$ alkyl. In embodiments, R$^5$ is substituted or unsubstituted C$_1$ alkyl. In embodiments, R$^5$ is substituted or unsubstituted C$_2$ alkyl. In embodiments, R$^5$ is substituted or unsubstituted C$_3$ alkyl. In embodiments, R$^5$ is substituted or unsubstituted C$_4$ alkyl. In embodiments, R$^5$ is substituted or unsubstituted C$_5$ alkyl. In embodiments, R$^5$ is substituted or unsubstituted C$_6$ alkyl. In embodiments, R$^5$ is substituted C$_1$ alkyl. In embodiments, R$^5$ is substituted C$_2$ alkyl. In embodiments, R$^5$ is substituted C$_3$ alkyl. In embodiments, R$^5$ is substituted C$_4$ alkyl. In embodiments, R$^5$ is substituted C$_5$ alkyl. In embodiments, R$^5$ is substituted C$_6$ alkyl. In embodiments, R$^5$ is unsubstituted C$_1$ alkyl. In embodiments, R$^5$ is unsubstituted C$_2$ alkyl. In embodiments, R$^5$ is unsubstituted C$_3$ alkyl. In embodiments, R$^5$ is unsubstituted C$_4$ alkyl. In embodiments, R$^5$ is unsubstituted C$_5$ alkyl. In embodiments, R$^5$ is unsubstituted C$_6$ alkyl. In embodiments, R$^5$ is R$^{35}$-substituted or unsubstituted alkyl (e.g., C$_1$-C$_6$ alkyl), wherein R$^{35}$ is independently —PO$_3$H, —PO$_4$H, —SO$_2$NH$_2$, —SO$_3$H, or —SO$_4$H.

In embodiments, R$^5$ is substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{10}$ or phenyl), or substituted or unsubstituted heteroaryl (e.g., 5 to 10 membered, 5 to 9 membered, or 5 to 6 membered). In embodiments, R$^5$ is substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, R$^5$ is unsubstituted alkyl, unsubstituted heteroalkyl, unsubstituted cycloalkyl, unsubstituted heterocycloalkyl, unsubstituted aryl, or unsubstituted heteroaryl.

In embodiments, R$^5$ is substituted (e.g., substituted with a substituent group, a size-limited substituent group, or lower substituent group) or unsubstituted alkyl. In embodiments, R$^5$ is substituted (e.g., substituted with a substituent group, a size-limited substituent group, or lower substituent group) alkyl. In embodiments, R$^5$ is unsubstituted alkyl. In embodiments, R$^5$ is substituted or unsubstituted alkyl (e.g., C$_1$-C$_8$, C$_1$-C$_6$, C$_1$-C$_4$, or C$_1$-C$_2$). In embodiments, R$^5$ is substituted alkyl (e.g., C$_1$-C$_8$, C$_1$-C$_6$, C$_1$-C$_4$, or C$_1$-C$_2$). In embodiments, R$^5$ is unsubstituted alkyl (e.g., C$_1$-C$_8$, C$_1$-C$_6$, C$_1$-C$_4$, or C$_1$-C$_2$).

In embodiments, R$^6$ is independently hydrogen, halogen, —CF$_3$, —CCl$_3$, —CI$_3$, —CBr$_3$, —CHF$_2$, —CHCl$_2$, —CHI$_2$, —CHBr$_2$, —CH$_2$F, —CH$_2$Cl, —CH$_2$I, —CH$_2$Br, —OCH$_2$F, —OCH$_2$Cl, —OCH$_2$I, —OCH$_2$Br, —OCHF$_2$, —OCHCl$_2$, —OCHI$_2$, —OCHBr$_2$, —OCF$_3$, —OCCl$_3$, —OCI$_3$, —OCBr$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, or —N$_3$. In embodiments, R$^6$ is independently hydrogen. In embodiments, R$^6$ is independently halogen. In embodiments, R$^6$ is independently —CF$_3$. In embodiments, R$^6$ is independently —CCl$_3$. In embodiments, R$^6$ is independently —CI$_3$. In embodiments, R$^6$ is independently —CBr$_3$. In embodiments, R$^6$ is independently —CHF$_2$. In embodiments, R$^6$ is independently —CHCl$_2$. In embodiments, R$^6$ is independently —CHI$_2$. In embodiments, R$^6$ is independently —CHBr$_2$. In embodiments, R$^6$ is independently —CH$_2$F. In embodiments, R$^6$ is independently —CH$_2$Cl. In embodiments, R$^6$ is independently —CH$_2$I. In embodiments, $R^6$ is independently —$CH_2Br$. In embodiments, $R^6$ is independently —$OCH_2F$. In embodiments, $R^6$ is independently —$OCH_2Cl$. In embodiments, $R^6$ is independently —$OCH_2I$. In embodiments, $R^6$ is independently —$OCH_2Br$. In embodiments, $R^6$ is independently —$OCHF_2$. In embodiments, $R^6$ is independently —$OCHCl_2$. In embodiments, $R^6$ is independently —$OCHI_2$. In embodiments, $R^6$ is independently —$OCHBr_2$. In embodiments, $R^6$ is independently —$OCF_3$. In embodiments, $R^6$ is independently —$OCCl_3$. In embodiments, $R^6$ is independently —$OCI_3$. In embodiments, $R^6$ is independently —$OCBr_3$. In embodiments, $R^6$ is independently —CN. In embodiments, $R^6$ is independently —OH. In embodiments, $R^6$ is independently —$NH_2$. In embodiments, $R^6$ is independently —COOH. In embodiments, $R^6$ is independently —$CONH_2$. In embodiments, $R^6$ is independently —$NO_2$. In embodiments, $R^6$ is independently —SH. In embodiments, $R^6$ is independently —$SO_3H$. In embodiments, $R^6$ is independently —$SO_4H$. In embodiments, $R^6$ is independently —$SO_2NH_2$. In embodiments, $R^6$ is independently —$NHNH_2$. In embodiments, $R^6$ is independently —$ONH_2$. In embodiments, $R^6$ is independently —NHC=(O)$NHNH_2$. In embodiments, $R^6$ is independently —NHC=(O)$NH_2$. In embodiments, $R^6$ is independently —$NHSO_2H$. In embodiments, $R^6$ is independently —NHC=(O)H. In embodiments, $R^6$ is independently —NHC(O)OH. In embodiments, $R^6$ is independently —NHOH.

In embodiments, $R^6$ is $R^{36}$-substituted or unsubstituted alkyl, $R^{36}$-substituted or unsubstituted heteroalkyl, $R^{36}$-substituted or unsubstituted cycloalkyl, $R^{36}$-substituted or unsubstituted heterocycloalkyl, $R^{36}$-substituted or unsubstituted aryl, or $R^{36}$-substituted or unsubstituted heteroaryl.

$R^{36}$ is independently oxo, halogen, —$CF_3$, —$CCl_3$, —$CI_3$, —$CBr_3$, —$CHF_2$, —$CHCl_2$, —$CHI_2$, —$CHBr_2$, —$CH_2F$, —$CH_2Cl$, —$CH_2I$, —$CH_2Br$, —$OCH_2F$, —$OCH_2Cl$, —$OCH_2I$, —$OCH_2Br$, —$OCHF_2$, —$OCHCl_2$, —$OCHI_2$, —$OCHBr_2$, —$OCF_3$, —$OCCl_3$, —$OCI_3$, —$OCBr_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$PO_4H$, —$PO_3H$, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). In embodiments, $R^{36}$ is independently —$PO_3H$, —$PO_4H$, —$SO_2NH_2$, —$SO_3H$, or —$SO_4H$. In embodiments, $R^{36}$ is independently —$SO_3H$. In embodiments, $R^{36}$ is independently —$PO_3H$. In embodiments, $R^{36}$ is independently —$SO_2NH_2$. In embodiments, $R^{36}$ is independently —$SO_4H$.

In embodiments, $R^6$ is hydrogen, or substituted or unsubstituted $C_1$-$C_6$ alkyl. In embodiments, $R^6$ is hydrogen. In embodiments, $R^6$ is substituted or unsubstituted $C_1$-$C_6$ alkyl. In embodiments, $R^6$ is substituted or unsubstituted $C_1$ alkyl. In embodiments, $R^6$ is substituted or unsubstituted $C_2$ alkyl. In embodiments, $R^6$ is substituted or unsubstituted $C_3$ alkyl. In embodiments, $R^6$ is substituted or unsubstituted $C_4$ alkyl. In embodiments, $R^6$ is substituted or unsubstituted $C_5$ alkyl. In embodiments, $R^6$ is substituted or unsubstituted $C_6$ alkyl. In embodiments, $R^6$ is substituted $C_1$ alkyl. In embodiments, $R^6$ is substituted $C_2$ alkyl. In embodiments, $R^6$ is substituted $C_3$ alkyl. In embodiments, $R^6$ is substituted $C_4$ alkyl. In embodiments, $R^6$ is substituted $C_5$ alkyl. In embodiments, $R^6$ is substituted $C_6$ alkyl. In embodiments, $R^6$ is unsubstituted $C_1$ alkyl. In embodiments, $R^6$ is unsubstituted $C_2$ alkyl. In embodiments, $R^6$ is unsubstituted $C_3$ alkyl. In embodiments, $R^6$ is unsubstituted $C_4$ alkyl. In embodiments, $R^6$ is unsubstituted $C_5$ alkyl. In embodiments, $R^6$ is unsubstituted $C_6$ alkyl. In embodiments, $R^6$ is $R^{36}$-substituted or unsubstituted alkyl (e.g., $C_1$-$C_6$ alkyl), wherein $R^{36}$ is independently —$PO_3H$, —$PO_4H$, —$SO_2NH_2$, —$SO_3H$, or —$SO_4H$.

In embodiments, $R^6$ is substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^6$ is substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^6$ is unsubstituted alkyl, unsubstituted heteroalkyl, unsubstituted cycloalkyl, unsubstituted heterocycloalkyl, unsubstituted aryl, or unsubstituted heteroaryl.

In embodiments, $R^6$ is substituted (e.g., substituted with a substituent group, a size-limited substituent group, or lower substituent group) or unsubstituted alkyl. In embodiments, $R^6$ is substituted (e.g., substituted with a substituent group, a size-limited substituent group, or lower substituent group) alkyl. In embodiments, $R^6$ is unsubstituted alkyl. In embodiments, $R^6$ is substituted or unsubstituted alkyl (e.g., $C_1$-$C_8$, $C_1$-$C_6$, $C_1$-$C_4$, or $C_1$-$C_2$). In embodiments, $R^6$ is substituted alkyl (e.g., $C_1$-$C_8$, $C_1$-$C_6$, $C_1$-$C_4$, or $C_1$-$C_2$). In embodiments, $R^6$ is unsubstituted alkyl (e.g., $C_1$-$C_8$, $C_1$-$C_6$, $C_1$-$C_4$, or $C_1$-$C_2$).

In embodiments, $R^7$ is independently hydrogen, halogen, —$CF_3$, —$CCl_3$, —$CI_3$, —$CBr_3$, —$CHF_2$, —$CHCl_2$, —$CHI_2$, —$CHBr_2$, —$CH_2F$, —$CH_2Cl$, —$CH_2I$, —$CH_2Br$, —$OCH_2F$, —$OCH_2Cl$, —$OCH_2I$, —$OCH_2Br$, —$OCHF_2$, —$OCHCl_2$, —$OCHI_2$, —$OCHBr_2$, —$OCF_3$, —$OCCl_3$, —$OCI_3$, —$OCBr_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, or —$N_3$. In embodiments, $R^7$ is independently hydrogen. In embodiments, $R^7$ is independently halogen. In embodiments, $R^7$ is independently —$CF_3$. In embodiments, $R^7$ is independently —$CCl_3$. In embodiments, $R^7$ is independently —$CI_3$. In embodiments, $R^7$ is independently —$CBr_3$. In embodiments, $R^7$ is independently —$CHF_2$. In embodiments, $R^7$ is independently —$CHCl_2$. In embodiments, $R^7$ is independently —CHI$_2$. In embodiments, $R^7$ is independently —CHBr$_2$. In embodiments, $R^7$ is independently —CH$_2$F. In embodiments, $R^7$ is independently —CH$_2$Cl. In embodiments, $R^7$ is independently —CH$_2$I. In embodiments, $R^7$ is independently —CH$_2$Br. In embodiments, $R^7$ is independently —OCH$_2$F. In embodiments, $R^7$ is independently —OCH$_2$Cl. In embodiments, $R^7$ is independently —OCH$_2$I. In embodiments, $R^7$ is independently —OCH$_2$Br. In embodiments, $R^7$ is independently —OCHF$_2$. In embodiments, $R^7$ is independently —OCHCl$_2$. In embodiments, $R^7$ is independently —OCHI$_2$. In embodiments, $R^7$ is independently —OCHBr$_2$. In embodiments, $R^7$ is independently —OCF$_3$. In embodiments, $R^7$ is independently —OCCl$_3$. In embodiments, $R^7$ is independently —OCI$_3$. In embodiments, $R^7$ is independently —OCBr$_3$. In embodiments, $R^7$ is independently —CN. In embodiments, $R^7$ is independently —OH. In embodiments, $R^7$ is independently —NH$_2$. In embodiments, $R^7$ is independently —COOH. In embodiments, $R^7$ is independently —CONH$_2$. In embodiments, $R^7$ is independently —NO$_2$. In embodiments, $R^7$ is independently —SH. In embodiments, $R^7$ is independently —SO$_3$H. In embodiments, $R^7$ is independently —SO$_4$H. In embodiments, $R^7$ is independently —SO$_2$NH$_2$. In embodiments, $R^7$ is independently —NHNH$_2$. In embodiments, $R^7$ is independently —ONH$_2$. In embodiments, $R^7$ is independently —NHC=(O)NHNH$_2$. In embodiments, $R^7$ is independently —NHC=(O)NH$_2$. In embodiments, $R^7$ is independently —NHSO$_2$H. In embodiments, $R^7$ is independently —NHC=(O)H. In embodiments, $R^7$ is independently —NHC(O)OH. In embodiments, $R^7$ is independently —NHOH.

In embodiments, $R^7$ is $R^{37}$-substituted or unsubstituted alkyl, $R^{37}$-substituted or unsubstituted heteroalkyl, $R^{37}$-substituted or unsubstituted cycloalkyl, $R^{37}$-substituted or unsubstituted heterocycloalkyl, $R^{37}$-substituted or unsubstituted aryl, or $R^{37}$-substituted or unsubstituted heteroaryl.

$R^{37}$ is independently oxo, halogen, —CF$_3$, —CCl$_3$, —CI$_3$, —CBr$_3$, —CHF$_2$, —CHCl$_2$, —CHI$_2$, —CHBr$_2$, —CH$_2$F, —CH$_2$Cl, —CH$_2$I, —CH$_2$Br, —OCH$_2$F, —OCH$_2$Cl, —OCH$_2$I, —OCH$_2$Br, —OCHF$_2$, —OCHCl$_2$, —OCHI$_2$, —OCHBr$_2$, —OCF$_3$, —OCCl$_3$, —OCI$_3$, —OCBr$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —PO$_4$H, —PO$_3$H, —N$_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). In embodiments, $R^{37}$ is independently —PO$_3$H, —PO$_4$H, —SO$_2$NH$_2$, —SO$_3$H, or —SO$_4$H. In embodiments, $R^{37}$ is independently —SO$_3$H. In embodiments, $R^{37}$ is independently —PO$_3$H. In embodiments, $R^{37}$ is independently —SO$_2$NH$_2$. In embodiments, $R^{37}$ is independently —SO$_4$H.

In embodiments, $R^7$ is hydrogen, or substituted or unsubstituted $C_1$-$C_6$ alkyl. In embodiments, $R^7$ is hydrogen. In embodiments, $R^7$ is substituted or unsubstituted $C_1$-$C_6$ alkyl. In embodiments, $R^7$ is substituted or unsubstituted $C_1$ alkyl. In embodiments, $R^7$ is substituted or unsubstituted $C_2$ alkyl. In embodiments, $R^7$ is substituted or unsubstituted $C_3$ alkyl. In embodiments, $R^7$ is substituted or unsubstituted $C_4$ alkyl. In embodiments, $R^7$ is substituted or unsubstituted $C_5$ alkyl. In embodiments, $R^7$ is substituted or unsubstituted $C_6$ alkyl. In embodiments, $R^7$ is substituted $C_1$ alkyl. In embodiments, $R^7$ is substituted $C_2$ alkyl. In embodiments, $R^7$ is substituted $C_3$ alkyl. In embodiments, $R^7$ is substituted $C_4$ alkyl. In embodiments, $R^7$ is substituted $C_5$ alkyl. In embodiments, $R^7$ is substituted $C_6$ alkyl. In embodiments, $R^7$ is unsubstituted $C_1$ alkyl. In embodiments, $R^7$ is unsubstituted $C_2$ alkyl. In embodiments, $R^7$ is unsubstituted $C_3$ alkyl. In embodiments, $R^7$ is unsubstituted $C_4$ alkyl. In embodiments, $R^7$ is unsubstituted $C_5$ alkyl. In embodiments, $R^7$ is unsubstituted $C_6$ alkyl. In embodiments, $R^7$ is $R^{37}$-substituted or unsubstituted alkyl (e.g., $C_1$-$C_6$ alkyl), wherein $R^{37}$ is independently —PO$_3$H, —PO$_4$H, —SO$_2$NH$_2$, —SO$_3$H, or —SO$_4$H.

In embodiments, $R^7$ is substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^7$ is substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^7$ is unsubstituted alkyl, unsubstituted heteroalkyl, unsubstituted cycloalkyl, unsubstituted heterocycloalkyl, unsubstituted aryl, or unsubstituted heteroaryl.

In embodiments, $R^7$ is substituted (e.g., substituted with a substituent group, a size-limited substituent group, or lower substituent group) or unsubstituted alkyl. In embodiments, $R^7$ is substituted (e.g., substituted with a substituent group, a size-limited substituent group, or lower substituent group) alkyl. In embodiments, $R^7$ is unsubstituted alkyl. In embodiments, $R^7$ is substituted or unsubstituted alkyl (e.g., $C_1$-$C_8$, $C_1$-$C_6$, $C_1$-$C_4$, or $C_1$-$C_2$). In embodiments, $R^7$ is substituted alkyl (e.g., $C_1$-$C_8$, $C_1$-$C_6$, $C_1$-$C_4$, or $C_1$-$C_2$). In embodiments, $R^7$ is unsubstituted alkyl (e.g., $C_1$-$C_8$, $C_1$-$C_6$, $C_1$-$C_4$, or $C_1$-$C_2$).

In embodiments, $R^4$ and $R^5$ substituents bonded to the same nitrogen atom may optionally be joined to form a substituted or unsubstituted 3 to 6 membered heterocycloalkyl. In embodiments, $R^4$ and $R^5$ substituents bonded to the same nitrogen atom may optionally be joined to form a substituted or unsubstituted 3 membered heterocycloalkyl. In embodiments, $R^4$ and $R^5$ substituents bonded to the same nitrogen atom may optionally be joined to form a substituted or unsubstituted 4 membered heterocycloalkyl. In embodiments, $R^4$ and $R^5$ substituents bonded to the same nitrogen atom may optionally be joined to form a substituted or unsubstituted 5 membered heterocycloalkyl. In embodiments, $R^4$ and $R^5$ substituents bonded to the same nitrogen atom may optionally be joined to form a substituted or unsubstituted 6 membered heterocycloalkyl. In embodiments, $R^4$ and $R^5$ substituents bonded to the same nitrogen atom may optionally be joined to form an unsubstituted 3 to 6 membered heterocycloalkyl. In embodiments, $R^4$ and $R^5$ substituents bonded to the same nitrogen atom may optionally be joined to form an unsubstituted 3 membered heterocycloalkyl. In embodiments, $R^4$ and $R^5$ substituents bonded to the same nitrogen atom may optionally be joined to form an unsubstituted 4 membered heterocycloalkyl. In embodiments, $R^4$ and $R^5$ substituents bonded to the same nitrogen atom may optionally be joined to form an unsubstituted 5 membered heterocycloalkyl. In embodiments, $R^4$ and $R^5$ substituents bonded to the same nitrogen atom may optionally be joined to form an unsubstituted 6 membered heterocycloalkyl. In embodiments, $R^4$ and $R^5$ substituents bonded to the same nitrogen atom may optionally be joined to form a substituted 3 to 6 membered heterocycloalkyl. In embodiments, $R^4$ and $R^5$ substituents bonded to the same nitrogen atom may optionally be joined to form a substituted 3 membered heterocycloalkyl. In embodiments, $R^4$ and $R^5$ substituents bonded to the same nitrogen atom may optionally be joined to form a substituted 4 membered heterocycloalkyl. In embodiments, $R^4$ and $R^5$ substituents bonded to the same nitrogen atom may optionally be joined to form a substituted 5 membered heterocycloalkyl. In embodiments, $R^4$ and $R^5$ substituents bonded to the same nitrogen atom may optionally be joined to form a substituted 6 membered heterocycloalkyl.

In embodiments, $R^4$ and $R^5$ substituents bonded to the same nitrogen atom may optionally be joined to form an $R^{34}$-substituted or unsubstituted 3 to 6 membered heterocycloalkyl. In embodiments, $R^4$ and $R^5$ substituents bonded to the same nitrogen atom may optionally be joined to form an $R^{34}$-substituted or unsubstituted 3 membered heterocycloalkyl. In embodiments, $R^4$ and $R^5$ substituents bonded to the same nitrogen atom may optionally be joined to form an $R^{34}$-substituted or unsubstituted 4 membered heterocycloalkyl. In embodiments, $R^4$ and $R^5$ substituents bonded to the same nitrogen atom may optionally be joined to form an $R^{34}$-substituted or unsubstituted 5 membered heterocycloalkyl. In embodiments, $R^4$ and $R^5$ substituents bonded to the same nitrogen atom may optionally be joined to form an $R^{34}$-substituted or unsubstituted 6 membered heterocycloalkyl. In embodiments, $R^4$ and $R^5$ substituents bonded to the same nitrogen atom may optionally be joined to form an $R^{34}$-substituted 3 to 6 membered heterocycloalkyl. In embodiments, $R^4$ and $R^5$ substituents bonded to the same nitrogen atom may optionally be joined to form an $R^{34}$-substituted 3 membered heterocycloalkyl. In embodiments, $R^4$ and $R^5$ substituents bonded to the same nitrogen atom may optionally be joined to form an $R^4$-substituted 4 membered heterocycloalkyl. In embodiments, $R^4$ and $R^5$ substituents bonded to the same nitrogen atom may optionally be joined to form an $R^{34}$-substituted 5 membered heterocycloalkyl. In embodiments, $R^4$ and $R^5$ substituents bonded to the same nitrogen atom may optionally be joined to form an $R^{34}$-substituted 6 membered heterocycloalkyl.

In embodiments, $R^4$ and $R^5$ substituents bonded to the same nitrogen atom may optionally be joined to form an $R^{35}$-substituted or unsubstituted 3 to 6 membered heterocycloalkyl. In embodiments, $R^4$ and $R^5$ substituents bonded to the same nitrogen atom may optionally be joined to form an $R^{35}$-substituted or unsubstituted 3 membered heterocycloalkyl. In embodiments, $R^4$ and $R^5$ substituents bonded to the same nitrogen atom may optionally be joined to form an $R^{35}$-substituted or unsubstituted 4 membered heterocycloalkyl. In embodiments, $R^4$ and $R^5$ substituents bonded to the same nitrogen atom may optionally be joined to form an $R^{35}$-substituted or unsubstituted 5 membered heterocycloalkyl. In embodiments, $R^4$ and $R^5$ substituents bonded to the same nitrogen atom may optionally be joined to form an $R^{35}$-substituted or unsubstituted 6 membered heterocycloalkyl. In embodiments, $R^4$ and $R^5$ substituents bonded to the same nitrogen atom may optionally be joined to form an $R^{35}$-substituted 3 to 6 membered heterocycloalkyl. In embodiments, $R^4$ and $R^5$ substituents bonded to the same nitrogen atom may optionally be joined to form an $R^{35}$-substituted 3 membered heterocycloalkyl. In embodiments, $R^4$ and $R^5$ substituents bonded to the same nitrogen atom may optionally be joined to form an $R^{35}$-substituted 4 membered heterocycloalkyl. In embodiments, $R^4$ and $R^5$ substituents bonded to the same nitrogen atom may optionally be joined to form an $R^{35}$-substituted 5 membered heterocycloalkyl. In embodiments, $R^4$ and $R^5$ substituents bonded to the same nitrogen atom may optionally be joined to form an $R^{35}$-substituted 6 membered heterocycloalkyl.

In embodiments, $R^4$ and $R^5$ substituents bonded to the same nitrogen atom may optionally be joined to form a substituted (e.g., substituted with a substituent group, a size-limited substituent group, or lower substituent group) or unsubstituted heterocycloalkyl. In embodiments, $R^4$ and $R^5$ substituents bonded to the same nitrogen atom may optionally be joined to form a substituted (e.g., substituted with a substituent group, a size-limited substituent group, or lower substituent group) heterocycloalkyl. In embodiments, $R^4$ and $R^5$ substituents bonded to the same nitrogen atom may optionally be joined to form an unsubstituted heterocycloalkyl. In embodiments, $R^4$ and $R^5$ substituents bonded to the same nitrogen atom may optionally be joined to form a substituted or unsubstituted heterocycloalkyl (e.g., 3 to 8 membered, 3 to 6 membered, 4 to 6 membered, 4 to 5 membered, or 5 to 6 membered). In embodiments, $R^4$ and $R^5$ substituents bonded to the same nitrogen atom may optionally be joined to form a substituted heterocycloalkyl (e.g., 3 to 8 membered, 3 to 6 membered, 4 to 6 membered, 4 to 5 membered, or 5 to 6 membered). In embodiments, $R^4$ and $R^5$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

In embodiments, $R^6$ and $R^7$ substituents bonded to the same nitrogen atom may optionally be joined to form a substituted or unsubstituted 3 to 6 membered heterocycloalkyl.

In embodiments, $R^6$ and $R^7$ substituents bonded to the same nitrogen atom may optionally be joined to form a substituted or unsubstituted 3 to 6 membered heterocycloalkyl. In embodiments, $R^6$ and $R^7$ substituents bonded to the same nitrogen atom may optionally be joined to form a substituted or unsubstituted 3 membered heterocycloalkyl. In embodiments, $R^6$ and $R^7$ substituents bonded to the same nitrogen atom may optionally be joined to form a substituted or unsubstituted 4 membered heterocycloalkyl. In embodiments, $R^6$ and $R^7$ substituents bonded to the same nitrogen atom may optionally be joined to form a substituted or unsubstituted 5 membered heterocycloalkyl. In embodiments, $R^6$ and $R^7$ substituents bonded to the same nitrogen atom may optionally be joined to form a substituted or unsubstituted 6 membered heterocycloalkyl. In embodiments, $R^6$ and $R^7$ substituents bonded to the same nitrogen atom may optionally be joined to form an unsubstituted 3 to 6 membered heterocycloalkyl. In embodiments, $R^6$ and $R^7$ substituents bonded to the same nitrogen atom may optionally be joined to form an unsubstituted 3 membered heterocycloalkyl. In embodiments, $R^6$ and $R^7$ substituents bonded to the same nitrogen atom may optionally be joined to form an unsubstituted 4 membered heterocycloalkyl. In embodiments, $R^6$ and $R^7$ substituents bonded to the same nitrogen atom may optionally be joined to form an unsubstituted 5 membered heterocycloalkyl. In embodiments, $R^6$ and $R^7$ substituents bonded to the same nitrogen atom may optionally be joined to form an unsubstituted 6 membered heterocycloalkyl. In embodiments, $R^6$ and $R^7$ substituents bonded to the same nitrogen atom may optionally be joined to form a substituted 3 to 6 membered heterocycloalkyl. In embodiments, $R^6$ and $R^7$ substituents bonded to the same nitrogen atom may optionally be joined to form a substituted 3 membered heterocycloalkyl. In embodiments, $R^6$ and $R^7$ substituents bonded to the same nitrogen atom may optionally be joined to form a substituted 4 membered heterocycloalkyl. In embodiments, $R^6$ and $R^7$ substituents bonded to the same nitrogen atom may optionally be joined to form a substituted 5 membered heterocycloalkyl. In embodiments, $R^6$ and $R^7$ substituents bonded to the same nitrogen atom may optionally be joined to form a substituted 6 membered heterocycloalkyl.

In embodiments, $R^6$ and $R^7$ substituents bonded to the same nitrogen atom may optionally be joined to form an $R^{36}$-substituted or unsubstituted 3 to 6 membered heterocycloalkyl. In embodiments, $R^6$ and $R^7$ substituents bonded to the same nitrogen atom may optionally be joined to form an $R^{36}$-substituted or unsubstituted 3 to 6 membered heterocycloalkyl. In embodiments, $R^6$ and $R^7$ substituents bonded to the same nitrogen atom may optionally be joined to form an $R^{36}$-substituted or unsubstituted 3 membered heterocycloalkyl. In embodiments, $R^6$ and $R^7$ substituents bonded to the same nitrogen atom may optionally be joined to form an $R^{36}$-substituted or unsubstituted 4 membered heterocycloalkyl. In embodiments, $R^6$ and $R^7$ substituents bonded to the same nitrogen atom may optionally be joined to form an $R^{36}$-substituted or unsubstituted 5 membered heterocycloalkyl. In embodiments, $R^6$ and $R^7$ substituents bonded to the same nitrogen atom may optionally be joined to form an $R^{36}$-substituted or unsubstituted 6 membered heterocycloalkyl. In embodiments, $R^6$ and $R^7$ substituents bonded to the same nitrogen atom may optionally be joined to form an $R^{36}$-substituted 3 to 6 membered heterocycloalkyl. In embodiments, $R^6$ and $R^7$ substituents bonded to the same nitrogen atom may optionally be joined to form an $R^{36}$-substituted 3 membered heterocycloalkyl. In embodiments, $R^6$ and $R^7$ substituents bonded to the same nitrogen atom may optionally be joined to form an $R^{36}$-substituted 4 membered heterocycloalkyl. In embodiments, $R^6$ and $R^7$ substituents bonded to the same nitrogen atom may optionally be joined to form an $R^{36}$-substituted 5 membered heterocycloalkyl. In embodiments, $R^6$ and $R^7$ substituents bonded to the same nitrogen atom may optionally be joined to form an $R^{36}$-substituted 6 membered heterocycloalkyl.

In embodiments, $R^6$ and $R^7$ substituents bonded to the same nitrogen atom may optionally be joined to form an $R^{37}$-substituted or unsubstituted 3 to 6 membered heterocycloalkyl. In embodiments, $R^6$ and $R^7$ substituents bonded to the same nitrogen atom may optionally be joined to form an $R^{37}$-substituted or unsubstituted 3 to 6 membered heterocycloalkyl. In embodiments, $R^6$ and $R^7$ substituents bonded to the same nitrogen atom may optionally be joined to form an $R^{37}$-substituted or unsubstituted 3 membered heterocycloalkyl. In embodiments, $R^6$ and $R^7$ substituents bonded to the same nitrogen atom may optionally be joined to form an $R^{37}$-substituted or unsubstituted 4 membered heterocycloalkyl. In embodiments, $R^6$ and $R^7$ substituents bonded to the same nitrogen atom may optionally be joined to form an $R^{37}$-substituted or unsubstituted 5 membered heterocycloalkyl. In embodiments, $R^6$ and $R^7$ substituents bonded to the same nitrogen atom may optionally be joined to form an $R^{37}$-substituted or unsubstituted 6 membered heterocycloalkyl. In embodiments, $R^6$ and $R^7$ substituents bonded to the same nitrogen atom may optionally be joined to form an $R^{37}$-substituted 3 to 6 membered heterocycloalkyl. In embodiments, $R^6$ and $R^7$ substituents bonded to the same nitrogen atom may optionally be joined to form an $R^{37}$-substituted 3 membered heterocycloalkyl. In embodiments, $R^6$ and $R^7$ substituents bonded to the same nitrogen atom may optionally be joined to form an $R^{37}$-substituted 4 membered heterocycloalkyl. In embodiments, $R^6$ and $R^7$ substituents bonded to the same nitrogen atom may optionally be joined to form an $R^{37}$-substituted 5 membered heterocycloalkyl. In embodiments, $R^6$ and $R^7$ substituents bonded to the same nitrogen atom may optionally be joined to form an $R^{37}$-substituted 6 membered heterocycloalkyl.

In embodiments, $R^6$ and $R^7$ substituents bonded to the same nitrogen atom may optionally be joined to form a substituted (e.g., substituted with a substituent group, a size-limited substituent group, or lower substituent group) or unsubstituted heterocycloalkyl. In embodiments, $R^6$ and $R^7$ substituents bonded to the same nitrogen atom may optionally be joined to form a substituted (e.g., substituted with a substituent group, a size-limited substituent group, or lower substituent group) heterocycloalkyl. In embodiments, $R^6$ and $R^7$ substituents bonded to the same nitrogen atom may optionally be joined to form an unsubstituted heterocycloalkyl. In embodiments, $R^6$ and $R^7$ substituents bonded to the same nitrogen atom may optionally be joined to form a substituted or unsubstituted heterocycloalkyl (e.g., 3 to 8 membered, 3 to 6 membered, 4 to 6 membered, 4 to 5 membered, or 5 to 6 membered). In embodiments, $R^6$ and $R^7$ substituents bonded to the same nitrogen atom may optionally be joined to form a substituted heterocycloalkyl (e.g., 3 to 8 membered, 3 to 6 membered, 4 to 6 membered, 4 to 5 membered, or 5 to 6 membered). In embodiments, $R^6$ and $R^7$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

In embodiments, $R^4$ and $R^9$ substituents may optionally be joined to form a substituted or unsubstituted 3 to 8 membered heterocycloalkyl, or substituted or unsubstituted 5 to 6 membered heteroaryl.

In embodiments, $R^4$ and $R^9$ substituents may optionally be joined to form a substituted or unsubstituted 3 to 8 membered heterocycloalkyl. In embodiments, $R^4$ and $R^9$ substituents may optionally be joined to form a substituted or unsubstituted 4 to 7 membered heterocycloalkyl. In embodiments, $R^4$ and $R^9$ substituents may optionally be joined to form a substituted or unsubstituted 4 to 6 membered heterocycloalkyl.

In embodiments, $R^4$ and $R^9$ substituents may optionally be joined to form a substituted or unsubstituted 3 membered heterocycloalkyl. In embodiments, $R^4$ and $R^9$ substituents may optionally be joined to form a substituted or unsubstituted 4 membered heterocycloalkyl. In embodiments, $R^4$ and $R^9$ substituents may optionally be joined to form a substituted or unsubstituted 5 membered heterocycloalkyl. In embodiments, $R^4$ and $R^9$ substituents may optionally be joined to form a substituted or unsubstituted 6 membered heterocycloalkyl. In embodiments, $R^4$ and $R^9$ substituents may optionally be joined to form a substituted or unsubstituted 7 membered heterocycloalkyl. In embodiments, $R^4$ and $R^9$ substituents may optionally be joined to form a substituted or unsubstituted 8 membered heterocycloalkyl. In embodiments, $R^4$ and $R^9$ substituents may optionally be joined to form a substituted 3 membered heterocycloalkyl. In embodiments, $R^4$ and $R^9$ substituents may optionally be joined to form a substituted 4 membered heterocycloalkyl. In embodiments, $R^4$ and $R^9$ substituents may optionally be joined to form a substituted 5 membered heterocycloalkyl. In embodiments, $R^4$ and $R^9$ substituents may optionally be joined to form a substituted 6 membered heterocycloalkyl. In embodiments, $R^4$ and $R^9$ substituents may optionally be joined to form a substituted 7 membered heterocycloalkyl. In embodiments, $R^4$ and $R^9$ substituents may optionally be joined to form a substituted 8 membered heterocycloalkyl. In embodiments, $R^4$ and $R^9$ substituents may optionally be joined to form an unsubstituted 3 membered heterocycloalkyl. In embodiments, $R^4$ and $R^9$ substituents may optionally be joined to form an unsubstituted 4 membered heterocycloalkyl. In embodiments, $R^4$ and $R^9$ substituents may optionally be joined to form an unsubstituted 5 membered heterocycloalkyl. In embodiments, $R^4$ and $R^9$ substituents may optionally be joined to form an unsubstituted 6 membered heterocycloalkyl. In embodiments, $R^4$ and $R^9$ substituents may optionally be joined to form an unsubstituted 7 membered heterocycloalkyl. In embodiments, $R^4$ and $R^9$ substituents may optionally be joined to form an unsubstituted 8 membered heterocycloalkyl.

In embodiments, $R^4$ and $R^9$ substituents may optionally be joined to form an $R^{34}$-substituted or unsubstituted 3 to 8 membered heterocycloalkyl, or $R^{34}$-substituted or unsubstituted 5 to 6 membered heteroaryl. In embodiments, $R^4$ and $R^9$ substituents may optionally be joined to form an $R^{34}$-substituted or unsubstituted 3 membered heterocycloalkyl. In embodiments, $R^4$ and $R^9$ substituents may optionally be joined to form an $R^{34}$-substituted or unsubstituted 4 membered heterocycloalkyl. In embodiments, $R^4$ and $R^9$ substituents may optionally be joined to form an $R^{34}$-substituted or unsubstituted 5 membered heterocycloalkyl. In embodiments, $R^4$ and $R^9$ substituents may optionally be joined to form an $R^{34}$-substituted or unsubstituted 6 membered heterocycloalkyl. In embodiments, $R^4$ and $R^9$ substituents may optionally be joined to form an $R^{34}$-substituted or unsubstituted 7 membered heterocycloalkyl. In embodiments, $R^4$ and $R^9$ substituents may optionally be joined to form an $R^{34}$-substituted or unsubstituted 8 membered heterocycloalkyl. In embodiments, $R^4$ and $R^9$ substituents may optionally be joined to form an $R^{34}$-substituted 3 membered heterocycloalkyl. In embodiments, $R^4$ and $R^9$ substituents may optionally be joined to form an $R^{34}$-substituted 4 membered heterocycloalkyl. In embodiments, $R^4$ and $R^9$ substituents may optionally be joined to form an $R^{34}$-substituted 5 membered heterocycloalkyl. In embodiments, $R^4$ and $R^9$ substituents may optionally be joined to form an $R^{34}$-substituted 6 membered heterocycloalkyl. In embodiments, $R^4$ and $R^9$ substituents may optionally be joined to form an $R^{34}$-substituted 7 membered heterocycloalkyl. In embodiments, $R^4$ and $R^9$ substituents may optionally be joined to form an $R^{34}$-substituted 8 membered heterocycloalkyl.

In embodiments, $R^4$ and $R^9$ substituents may optionally be joined to form an $R^{39}$-substituted or unsubstituted 3 to 8 membered heterocycloalkyl, or $R^{39}$-substituted or unsubstituted 5 to 6 membered heteroaryl. In embodiments, $R^4$ and $R^9$ substituents may optionally be joined to form an $R^{39}$-substituted or unsubstituted 3 membered heterocycloalkyl. In embodiments, $R^4$ and $R^9$ substituents may optionally be joined to form an $R^{39}$-substituted or unsubstituted 4 membered heterocycloalkyl. In embodiments, $R^4$ and $R^9$ substituents may optionally be joined to form an $R^{39}$-substituted or unsubstituted 5 membered heterocycloalkyl. In embodiments, $R^4$ and $R^9$ substituents may optionally be joined to form an $R^{39}$-substituted or unsubstituted 6 membered heterocycloalkyl. In embodiments, $R^4$ and $R^9$ substituents may optionally be joined to form an $R^{39}$-substituted or unsubstituted 7 membered heterocycloalkyl. In embodiments, $R^4$ and $R^9$ substituents may optionally be joined to form an $R^{39}$-substituted or unsubstituted 8 membered heterocycloalkyl. In embodiments, $R^4$ and $R^9$ substituents may optionally be joined to form an $R^{39}$-substituted 3 membered heterocycloalkyl. In embodiments, $R^4$ and $R^9$ substituents may optionally be joined to form an $R^{39}$-substituted 4 membered heterocycloalkyl. In embodiments, $R^4$ and $R^9$ substituents may optionally be joined to form an $R^{39}$-substituted 5 membered heterocycloalkyl. In embodiments, $R^4$ and $R^9$ substituents may optionally be joined to form an $R^{39}$-substituted 6 membered heterocycloalkyl. In embodiments, $R^4$ and $R^9$ substituents may optionally be joined to form an $R^{39}$-substituted 7 membered heterocycloalkyl. In embodiments, $R^4$ and $R^9$ substituents may optionally be joined to form an $R^{39}$-substituted 8 membered heterocycloalkyl.

In embodiments, $R^4$ and $R^9$ substituents may optionally be joined to form a substituted or unsubstituted 5 to 6 membered heteroaryl. In embodiments, $R^4$ and $R^9$ substituents may optionally be joined to form a substituted or unsubstituted 5 membered heteroaryl. In embodiments, $R^4$ and $R^9$ substituents may optionally be joined to form a substituted or unsubstituted 6 membered heteroaryl. In embodiments, $R^4$ and $R^9$ substituents may optionally be joined to form a substituted 5 to 6 membered heteroaryl. In embodiments, $R^4$ and $R^9$ substituents may optionally be joined to form a substituted 5 membered heteroaryl. In embodiments, $R^4$ and $R^9$ substituents may optionally be joined to form a substituted 6 membered heteroaryl. In embodiments, $R^4$ and $R^9$ substituents may optionally be joined to form an unsubstituted 5 to 6 membered heteroaryl. In embodiments, $R^4$ and $R^9$ substituents may optionally be joined to form an unsubstituted 5 membered heteroaryl. In embodiments, $R^4$ and $R^9$ substituents may optionally be joined to form an unsubstituted 6 membered heteroaryl.

In embodiments, $R^4$ and $R^9$ substituents may optionally be joined to form an $R^4$-substituted or unsubstituted 5 to 6 membered heteroaryl. In embodiments, $R^4$ and $R^9$ substituents may optionally be joined to form an $R^{34}$-substituted or unsubstituted 5 membered heteroaryl. In embodiments, $R^4$ and $R^9$ substituents may optionally be joined to form an $R^{34}$-substituted or unsubstituted 6 membered heteroaryl. In embodiments, $R^4$ and $R^9$ substituents may optionally be joined to form an $R^{34}$-substituted 5 to 6 membered heteroaryl. In embodiments, $R^4$ and $R^9$ substituents may optionally be joined to form an $R^{34}$-substituted 5 membered heteroaryl. In embodiments, $R^4$ and $R^9$ substituents may optionally be joined to form an $R^{34}$-substituted 6 membered heteroaryl.

In embodiments, $R^4$ and $R^9$ substituents may optionally be joined to form an $R^{39}$-substituted or unsubstituted 5 to 6 membered heteroaryl. In embodiments, $R^4$ and $R^9$ substituents may optionally be joined to form an $R^{39}$-substituted or unsubstituted 5 membered heteroaryl. In embodiments, $R^4$ and $R^9$ substituents may optionally be joined to form an $R^{39}$-substituted or unsubstituted 6 membered heteroaryl. In embodiments, $R^4$ and $R^9$ substituents may optionally be joined to form an $R^{39}$-substituted 5 to 6 membered heteroaryl. In embodiments, $R^4$ and $R^9$ substituents may optionally be joined to form an $R^{39}$-substituted 5 membered heteroaryl. In embodiments, $R^4$ and $R^9$ substituents may optionally be joined to form an $R^{39}$-substituted 6 membered heteroaryl.

In embodiments, $R^4$ and $R^9$ substituents bonded to the same nitrogen atom may optionally be joined to form a substituted (e.g., substituted with a substituent group, a size-limited substituent group, or lower substituent group) or unsubstituted heterocycloalkyl. In embodiments, $R^4$ and $R^9$ substituents bonded to the same nitrogen atom may optionally be joined to form a substituted (e.g., substituted with a substituent group, a size-limited substituent group, or lower substituent group) heterocycloalkyl. In embodiments, $R^4$ and $R^9$ substituents bonded to the same nitrogen atom may optionally be joined to form an unsubstituted heterocycloalkyl. In embodiments, $R^4$ and $R^9$ substituents bonded to the same nitrogen atom may optionally be joined to form a substituted or unsubstituted heterocycloalkyl (e.g., 3 to 8 membered, 3 to 6 membered, 4 to 6 membered, 4 to 5 membered, or 5 to 6 membered). In embodiments, $R^4$ and $R^9$ substituents bonded to the same nitrogen atom may optionally be joined to form a substituted heterocycloalkyl (e.g., 3 to 8 membered, 3 to 6 membered, 4 to 6 membered, 4 to 5 membered, or 5 to 6 membered). In embodiments, $R^4$ and $R^9$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

In embodiments, $R^4$ and $R^9$ substituents may optionally be joined to form substituted (e.g., substituted with a substituent group, a size-limited substituent group, or lower substituent group) or unsubstituted heteroaryl. In embodiments, $R^4$ and $R^9$ substituents may optionally be joined to form substituted (e.g., substituted with a substituent group, a size-limited substituent group, or lower substituent group) heteroaryl. In embodiments, $R^4$ and $R^9$ substituents may optionally be joined to form an unsubstituted heteroaryl. In embodiments, $R^4$ and $R^9$ substituents may optionally be joined to form substituted or unsubstituted heteroaryl (e.g., 5 to 10 membered, 5 to 9 membered, or 5 to 6 membered). In embodiments, $R^4$ and $R^9$ substituents may optionally be joined to form substituted heteroaryl (e.g., 5 to 10 membered, 5 to 9 membered, or 5 to 6 membered). In embodiments, $R^4$ and $R^9$ substituents may optionally be joined to form an unsubstituted heteroaryl (e.g., 5 to 10 membered, 5 to 9 membered, or 5 to 6 membered).

In embodiments, $R^7$ and $R^{10}$ substituents may optionally be joined to form a substituted or unsubstituted 3 to 8 membered heterocycloalkyl, or substituted or unsubstituted 5 to 6 membered heteroaryl.

In embodiments, $R^7$ and $R^{10}$ substituents may optionally be joined to form a substituted or unsubstituted 3 to 8 membered heterocycloalkyl. In embodiments, $R^7$ and $R^{10}$ substituents may optionally be joined to form a substituted or unsubstituted 4 to 7 membered heterocycloalkyl. In embodiments, $R^7$ and $R^{10}$ substituents may optionally be joined to form a substituted or unsubstituted 4 to 6 membered heterocycloalkyl.

In embodiments, $R^7$ and $R^{10}$ substituents may optionally be joined to form a substituted or unsubstituted 3 membered heterocycloalkyl. In embodiments, $R^7$ and $R^{10}$ substituents may optionally be joined to form a substituted or unsubstituted 4 membered heterocycloalkyl. In embodiments, $R^7$ and $R^{10}$ substituents may optionally be joined to form a substituted or unsubstituted 5 membered heterocycloalkyl. In embodiments, $R^7$ and $R^{10}$ substituents may optionally be joined to form a substituted or unsubstituted 6 membered heterocycloalkyl. In embodiments, $R^7$ and $R^{10}$ substituents may optionally be joined to form a substituted or unsubstituted 7 membered heterocycloalkyl. In embodiments, $R^7$ and $R^{10}$ substituents may optionally be joined to form a substituted or unsubstituted 8 membered heterocycloalkyl. In embodiments, $R^7$ and $R^{10}$ substituents may optionally be joined to form a substituted 3 membered heterocycloalkyl. In embodiments, $R^7$ and $R^{10}$ substituents may optionally be joined to form a substituted 4 membered heterocycloalkyl. In embodiments, $R^7$ and $R^{10}$ substituents may optionally be joined to form a substituted 5 membered heterocycloalkyl. In embodiments, $R^7$ and $R^{10}$ substituents may optionally be joined to form a substituted 6 membered heterocycloalkyl. In embodiments, $R^7$ and $R^{10}$ substituents may optionally be joined to form a substituted 7 membered heterocycloalkyl. In embodiments, $R^7$ and $R^{10}$ substituents may optionally be joined to form a substituted 8 membered heterocycloalkyl. In embodiments, $R^7$ and $R^{10}$ substituents may optionally be joined to form an unsubstituted 3 membered heterocycloalkyl. In embodiments, $R^7$ and $R^{10}$ substituents may optionally be joined to form an unsubstituted 4 membered heterocycloalkyl. In embodiments, $R^7$ and $R^{10}$ substituents may optionally be joined to form an unsubstituted 5 membered heterocycloalkyl. In embodiments, $R^7$ and $R^{10}$ substituents may optionally be joined to form an unsubstituted 6 membered heterocycloalkyl. In embodiments, $R^7$ and $R^{10}$ substituents may optionally be joined to form an unsubstituted 7 membered heterocycloalkyl. In embodiments, $R^7$ and $R^{10}$ substituents may optionally be joined to form an unsubstituted 8 membered heterocycloalkyl.

In embodiments, $R^7$ and $R^{10}$ substituents may optionally be joined to form an $R^{37}$-substituted or unsubstituted 3 to 8 membered heterocycloalkyl, or $R^{37}$-substituted or unsubstituted 5 to 6 membered heteroaryl. In embodiments, $R^7$ and $R^{10}$ substituents may optionally be joined to form an $R^{37}$-substituted or unsubstituted 3 membered heterocycloalkyl. In embodiments, $R^7$ and $R^{10}$ substituents may optionally be joined to form an $R^{37}$-substituted or unsubstituted 4 membered heterocycloalkyl. In embodiments, $R^7$ and $R^{10}$ substituents may optionally be joined to form an $R^{37}$-substituted or unsubstituted 5 membered heterocycloalkyl. In embodiments, $R^7$ and $R^{10}$ substituents may optionally be joined to form an $R^{37}$-substituted or unsubstituted 6 membered heterocycloalkyl. In embodiments, $R^7$ and $R^{10}$ substituents may optionally be joined to form an $R^{37}$-substituted or unsubstituted 7 membered heterocycloalkyl. In embodiments, $R^7$ and $R^{10}$ substituents may optionally be joined to form an $R^{37}$-substituted or unsubstituted 8 membered heterocycloalkyl. In embodiments, $R^7$ and $R^{10}$ substituents may optionally be joined to form an $R^{37}$-substituted 3 membered heterocycloalkyl. In embodiments, $R^7$ and $R^{10}$ substituents may optionally be joined to form an $R^{37}$-substituted 4 membered heterocycloalkyl. In embodiments, $R^7$ and $R^{10}$ substituents may optionally be joined to form an $R^{37}$-substituted 5 membered heterocycloalkyl. In embodiments, $R^7$ and $R^{10}$ substituents may optionally be joined to form an $R^{37}$-substituted 6 membered heterocycloalkyl. In embodiments, $R^7$ and $R^{10}$ substituents may optionally be joined to form an $R^{37}$-substituted 7 membered heterocycloalkyl. In embodiments, $R^7$ and $R^{10}$ substituents may optionally be joined to form an $R^{37}$-substituted 8 membered heterocycloalkyl.

In embodiments, $R^7$ and $R^{10}$ substituents may optionally be joined to form an $R^{40}$-substituted or unsubstituted 3 to 8 membered heterocycloalkyl, or $R^{40}$-substituted or unsubstituted 5 to 6 membered heteroaryl. In embodiments, $R^7$ and $R^{10}$ substituents may optionally be joined to form an $R^{40}$-substituted or unsubstituted 3 membered heterocycloalkyl.

In embodiments, $R^7$ and $R^{10}$ substituents may optionally be joined to form an $R^{40}$-substituted or unsubstituted 4 membered heterocycloalkyl. In embodiments, $R^7$ and $R^{10}$ substituents may optionally be joined to form an $R^{40}$-substituted or unsubstituted 5 membered heterocycloalkyl. In embodiments, $R^7$ and $R^{10}$ substituents may optionally be joined to form an $R^{40}$-substituted or unsubstituted 6 membered heterocycloalkyl. In embodiments, $R^7$ and $R^{10}$ substituents may optionally be joined to form an $R^{40}$-substituted or unsubstituted 7 membered heterocycloalkyl. In embodiments, $R^7$ and $R^{10}$ substituents may optionally be joined to form an $R^{40}$-substituted or unsubstituted 8 membered heterocycloalkyl. In embodiments, $R^7$ and $R^{10}$ substituents may optionally be joined to form an $R^{40}$-substituted 3 membered heterocycloalkyl. In embodiments, $R^7$ and $R^{10}$ substituents may optionally be joined to form an $R^{40}$-substituted 4 membered heterocycloalkyl. In embodiments, $R^7$ and $R^{10}$ substituents may optionally be joined to form an $R^{40}$-substituted 5 membered heterocycloalkyl. In embodiments, $R^7$ and $R^{10}$ substituents may optionally be joined to form an $R^{40}$-substituted 6 membered heterocycloalkyl. In embodiments, $R^7$ and $R^{10}$ substituents may optionally be joined to form an $R^{40}$-substituted 7 membered heterocycloalkyl. In embodiments, $R^7$ and $R^{10}$ substituents may optionally be joined to form an $R^{40}$-substituted 8 membered heterocycloalkyl.

In embodiments, $R^7$ and $R^{10}$ substituents may optionally be joined to form a substituted or unsubstituted 5 to 6 membered heteroaryl. In embodiments, $R^7$ and $R^{10}$ substituents may optionally be joined to form a substituted or unsubstituted 5 membered heteroaryl. In embodiments, $R^7$ and $R^{10}$ substituents may optionally be joined to form a substituted or unsubstituted 6 membered heteroaryl. In embodiments, $R^7$ and $R^{10}$ substituents may optionally be joined to form a substituted 5 to 6 membered heteroaryl. In embodiments, $R^7$ and $R^{10}$ substituents may optionally be joined to form a substituted 5 membered heteroaryl. In embodiments, $R^7$ and $R^{10}$ substituents may optionally be joined to form a substituted 6 membered heteroaryl. In embodiments, $R^7$ and $R^{10}$ substituents may optionally be joined to form an unsubstituted 5 to 6 membered heteroaryl. In embodiments, $R^7$ and $R^{10}$ substituents may optionally be joined to form an unsubstituted 5 membered heteroaryl. In embodiments, $R^7$ and $R^{10}$ substituents may optionally be joined to form an unsubstituted 6 membered heteroaryl.

In embodiments, $R^7$ and $R^{10}$ substituents may optionally be joined to form an $R^{37}$-substituted or unsubstituted 5 to 6 membered heteroaryl. In embodiments, $R^7$ and $R^{10}$ substituents may optionally be joined to form an $R^{37}$-substituted or unsubstituted 5 membered heteroaryl. In embodiments, $R^7$ and $R^{10}$ substituents may optionally be joined to form an $R^{37}$-substituted or unsubstituted 6 membered heteroaryl. In embodiments, $R^7$ and $R^{10}$ substituents may optionally be joined to form an $R^{37}$-substituted 5 to 6 membered heteroaryl. In embodiments, $R^7$ and $R^{10}$ substituents may optionally be joined to form an $R^{37}$-substituted 5 membered heteroaryl. In embodiments, $R^7$ and $R^{10}$ substituents may optionally be joined to form an $R^{37}$-substituted 6 membered heteroaryl.

In embodiments, $R^7$ and $R^{10}$ substituents may optionally be joined to form an $R^{40}$-substituted or unsubstituted 5 to 6 membered heteroaryl. In embodiments, $R^7$ and $R^{10}$ substituents may optionally be joined to form an $R^{40}$-substituted or unsubstituted 5 membered heteroaryl. In embodiments, $R^7$ and $R^{10}$ substituents may optionally be joined to form an $R^{40}$-substituted or unsubstituted 6 membered heteroaryl. In embodiments, $R^7$ and $R^{10}$ substituents may optionally be joined to form an $R^{40}$-substituted 5 to 6 membered heteroaryl. In embodiments, $R^7$ and $R^{10}$ substituents may optionally be joined to form an $R^{40}$-substituted 5 membered heteroaryl. In embodiments, $R^7$ and $R^{10}$ substituents may optionally be joined to form an $R^{40}$-substituted 6 membered heteroaryl.

In embodiments, $R^7$ and $R^{10}$ substituents bonded to the same nitrogen atom may optionally be joined to form a substituted (e.g., substituted with a substituent group, a size-limited substituent group, or lower substituent group) or unsubstituted heterocycloalkyl. In embodiments, $R^7$ and $R^{10}$ substituents bonded to the same nitrogen atom may optionally be joined to form a substituted (e.g., substituted with a substituent group, a size-limited substituent group, or lower substituent group) heterocycloalkyl. In embodiments, $R^7$ and $R^{10}$ substituents bonded to the same nitrogen atom may optionally be joined to form an unsubstituted heterocycloalkyl. In embodiments, $R^7$ and $R^{10}$ substituents bonded to the same nitrogen atom may optionally be joined to form a substituted or unsubstituted heterocycloalkyl (e.g., 3 to 8 membered, 3 to 6 membered, 4 to 6 membered, 4 to 5 membered, or 5 to 6 membered). In embodiments, $R^7$ and $R^{10}$ substituents bonded to the same nitrogen atom may optionally be joined to form a substituted heterocycloalkyl (e.g., 3 to 8 membered, 3 to 6 membered, 4 to 6 membered, 4 to 5 membered, or 5 to 6 membered). In embodiments, $R^7$ and $R^{10}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

In embodiments, $R^7$ and $R^{10}$ substituents may optionally be joined to form substituted (e.g., substituted with a substituent group, a size-limited substituent group, or lower substituent group) or unsubstituted heteroaryl. In embodiments, $R^7$ and $R^{10}$ substituents may optionally be joined to form substituted (e.g., substituted with a substituent group, a size-limited substituent group, or lower substituent group) heteroaryl. In embodiments, $R^7$ and $R^{10}$ substituents may optionally be joined to form an unsubstituted heteroaryl. In embodiments, $R^7$ and $R^{10}$ substituents may optionally be joined to form substituted or unsubstituted heteroaryl (e.g., 5 to 10 membered, 5 to 9 membered, or 5 to 6 membered). In embodiments, $R^7$ and $R^{10}$ substituents may optionally be joined to form substituted heteroaryl (e.g., 5 to 10 membered, 5 to 9 membered, or 5 to 6 membered). In embodiments, $R^7$ and $R^{10}$ substituents may optionally be joined to form an unsubstituted heteroaryl (e.g., 5 to 10 membered, 5 to 9 membered, or 5 to 6 membered).

In embodiments, $R^5$ and $R^{11}$ substituents may optionally be joined to form a substituted or unsubstituted 3 to 8 membered heterocycloalkyl, or substituted or unsubstituted 5 to 6 membered heteroaryl.

In embodiments, $R^5$ and $R^{11}$ substituents may optionally be joined to form a substituted or unsubstituted 3 to 8 membered heterocycloalkyl. In embodiments, $R^5$ and $R^{11}$ substituents may optionally be joined to form a substituted or unsubstituted 4 to 7 membered heterocycloalkyl. In embodiments, $R^5$ and $R^{11}$ substituents may optionally be joined to form a substituted or unsubstituted 4 to 6 membered heterocycloalkyl.

In embodiments, $R^5$ and $R^{11}$ substituents may optionally be joined to form a substituted or unsubstituted 3 membered heterocycloalkyl. In embodiments, $R^5$ and $R^{11}$ substituents may optionally be joined to form a substituted or unsubstituted 4 membered heterocycloalkyl. In embodiments, $R^5$ and $R^{11}$ substituents may optionally be joined to form a substituted or unsubstituted 5 membered heterocycloalkyl. In embodiments, $R^5$ and $R^{11}$ substituents may optionally be joined to form a substituted or unsubstituted 6 membered heterocycloalkyl. In embodiments, $R^5$ and $R^{11}$ substituents may optionally be joined to form a substituted or unsubstituted 7 membered heterocycloalkyl. In embodiments, $R^5$ and $R^{11}$ substituents may optionally be joined to form a substituted or unsubstituted 8 membered heterocycloalkyl. In embodiments, $R^5$ and $R^{11}$ substituents may optionally be joined to form a substituted 3 membered heterocycloalkyl. In embodiments, $R^5$ and $R^{11}$ substituents may optionally be joined to form a substituted 4 membered heterocycloalkyl. In embodiments, $R^5$ and $R^{11}$ substituents may optionally be joined to form a substituted 5 membered heterocycloalkyl. In embodiments, $R^5$ and $R^{11}$ substituents may optionally be joined to form a substituted 6 membered heterocycloalkyl. In embodiments, $R^5$ and $R^{11}$ substituents may optionally be joined to form a substituted 7 membered heterocycloalkyl. In embodiments, $R^5$ and $R^{11}$ substituents may optionally be joined to form a substituted 8 membered heterocycloalkyl. In embodiments, $R^5$ and $R^{11}$ substituents may optionally be joined to form an unsubstituted 3 membered heterocycloalkyl. In embodiments, $R^5$ and $R^{11}$ substituents may optionally be joined to form an unsubstituted 4 membered heterocycloalkyl. In embodiments, $R^5$ and $R^{11}$ substituents may optionally be joined to form an unsubstituted 5 membered heterocycloalkyl. In embodiments, $R^5$ and $R^{11}$ substituents may optionally be joined to form an unsubstituted 6 membered heterocycloalkyl. In embodiments, $R^5$ and $R^{11}$ substituents may optionally be joined to form an unsubstituted 7 membered heterocycloalkyl. In embodiments, $R^5$ and $R^{11}$ substituents may optionally be joined to form an unsubstituted 8 membered heterocycloalkyl.

In embodiments, $R^5$ and $R^{11}$ substituents may optionally be joined to form an $R^5$-substituted or unsubstituted 3 to 8 membered heterocycloalkyl, or $R^{35}$-substituted or unsubstituted 5 to 6 membered heteroaryl. In embodiments, $R^5$ and $R^{11}$ substituents may optionally be joined to form an $R^{35}$-substituted or unsubstituted 3 membered heterocycloalkyl. In embodiments, $R^5$ and $R^{11}$ substituents may optionally be joined to form an $R^{35}$-substituted or unsubstituted 4 membered heterocycloalkyl. In embodiments, $R^5$ and $R^{11}$ substituents may optionally be joined to form an $R^{35}$-substituted or unsubstituted 5 membered heterocycloalkyl. In embodiments, $R^5$ and $R^{11}$ substituents may optionally be joined to form an $R^{35}$-substituted or unsubstituted 6 membered heterocycloalkyl. In embodiments, $R^5$ and $R^{11}$ substituents may optionally be joined to form an $R^{35}$-substituted or unsubstituted 7 membered heterocycloalkyl. In embodiments, $R^5$ and $R^{11}$ substituents may optionally be joined to form an $R^{35}$-substituted or unsubstituted 8 membered heterocycloalkyl. In embodiments, $R^5$ and $R^{11}$ substituents may optionally be joined to form an $R^{35}$-substituted 3 membered heterocycloalkyl. In embodiments, $R^5$ and $R^{11}$ substituents may optionally be joined to form an $R^{35}$-substituted 4 membered heterocycloalkyl. In embodiments, $R^5$ and $R^{11}$ substituents may optionally be joined to form an $R^{35}$-substituted 5 membered heterocycloalkyl. In embodiments, $R^5$ and $R^{11}$ substituents may optionally be joined to form an $R^{35}$-substituted 6 membered heterocycloalkyl. In embodiments, $R^5$ and $R^{11}$ substituents may optionally be joined to form an $R^{35}$-substituted 7 membered heterocycloalkyl. In embodiments, $R^5$ and $R^{11}$ substituents may optionally be joined to form an $R^{35}$-substituted 8 membered heterocycloalkyl.

In embodiments, $R^5$ and $R^{11}$ substituents may optionally be joined to form an $R^{41}$-substituted or unsubstituted 3 to 8 membered heterocycloalkyl, or $R^{41}$-substituted or unsubstituted 5 to 6 membered heteroaryl. In embodiments, $R^5$ and $R^{11}$ substituents may optionally be joined to form an $R^{41}$-substituted or unsubstituted 3 membered heterocycloalkyl. In embodiments, $R^5$ and $R^{11}$ substituents may optionally be joined to form an $R^{41}$-substituted or unsubstituted 4 membered heterocycloalkyl. In embodiments, $R^5$ and $R^{11}$ substituents may optionally be joined to form an $R^{41}$-substituted or unsubstituted 5 membered heterocycloalkyl. In embodiments, $R^5$ and $R^{11}$ substituents may optionally be joined to form an $R^{41}$-substituted or unsubstituted 6 membered heterocycloalkyl. In embodiments, $R^5$ and $R^{11}$ substituents may optionally be joined to form an $R^{41}$-substituted or unsubstituted 7 membered heterocycloalkyl. In embodiments, $R^5$ and $R^{11}$ substituents may optionally be joined to form an $R^{41}$-substituted or unsubstituted 8 membered heterocycloalkyl. In embodiments, $R^5$ and $R^{11}$ substituents may optionally be joined to form an $R^{41}$-substituted 3 membered heterocycloalkyl. In embodiments, $R^5$ and $R^{11}$ substituents may optionally be joined to form an $R^{41}$-substituted 4 membered heterocycloalkyl. In embodiments, $R^5$ and $R^{11}$ substituents may optionally be joined to form an $R^{41}$-substituted 5 membered heterocycloalkyl. In embodiments, $R^5$ and $R^{11}$ substituents may optionally be joined to form an $R^{41}$-substituted 6 membered heterocycloalkyl. In embodiments, $R^5$ and $R^{11}$ substituents may optionally be joined to form an $R^{41}$-substituted 7 membered heterocycloalkyl. In embodiments, $R^5$ and $R^{11}$ substituents may optionally be joined to form an $R^{41}$-substituted 8 membered heterocycloalkyl.

In embodiments, $R^5$ and $R^{11}$ substituents may optionally be joined to form a substituted or unsubstituted 5 to 6 membered heteroaryl. In embodiments, $R^5$ and $R^{11}$ substituents may optionally be joined to form a substituted or unsubstituted 5 membered heteroaryl. In embodiments, $R^5$ and $R^{11}$ substituents may optionally be joined to form a substituted or unsubstituted 6 membered heteroaryl. In embodiments, $R^5$ and $R^{11}$ substituents may optionally be joined to form a substituted 5 to 6 membered heteroaryl. In embodiments, $R^5$ and $R^{11}$ substituents may optionally be joined to form a substituted 5 membered heteroaryl. In embodiments, $R^5$ and $R^{11}$ substituents may optionally be joined to form a substituted 6 membered heteroaryl. In embodiments, $R^5$ and $R^{11}$ substituents may optionally be joined to form an unsubstituted 5 to 6 membered heteroaryl. In embodiments, $R^5$ and $R^{11}$ substituents may optionally be joined to form an unsubstituted 5 membered heteroaryl. In embodiments, $R^5$ and $R^{11}$ substituents may optionally be joined to form an unsubstituted 6 membered heteroaryl.

In embodiments, $R^5$ and $R^{11}$ substituents may optionally be joined to form an $R^{35}$-substituted or unsubstituted 5 to 6 membered heteroaryl. In embodiments, $R^5$ and $R^{11}$ substituents may optionally be joined to form an $R^{35}$-substituted or unsubstituted 5 membered heteroaryl. In embodiments, $R^5$ and $R^{11}$ substituents may optionally be joined to form an $R^{35}$-substituted or unsubstituted 6 membered heteroaryl. In embodiments, $R^5$ and $R^{11}$ substituents may optionally be joined to form an $R^{35}$-substituted 5 to 6 membered heteroaryl. In embodiments, $R^5$ and $R^{11}$ substituents may optionally be joined to form an $R^{35}$-substituted 5 membered heteroaryl. In embodiments, $R^5$ and $R^{11}$ substituents may optionally be joined to form an $R^{35}$-substituted 6 membered heteroaryl.

In embodiments, $R^5$ and $R^{11}$ substituents may optionally be joined to form an $R^{41}$-substituted or unsubstituted 5 to 6 membered heteroaryl. In embodiments, $R^5$ and $R^{11}$ substituents may optionally be joined to form an $R^{41}$-substituted or unsubstituted 5 membered heteroaryl. In embodiments, $R^5$ and $R^{11}$ substituents may optionally be joined to form an $R^{41}$-substituted or unsubstituted 6 membered heteroaryl. In embodiments, $R^5$ and $R^{11}$ substituents may optionally be joined to form an $R^{41}$-substituted 5 to 6 membered heteroaryl. In embodiments, $R^5$ and $R^{11}$ substituents may optionally be joined to form an $R^{41}$-substituted 5 membered heteroaryl. In embodiments, $R^5$ and $R^{11}$ substituents may optionally be joined to form an $R^{41}$-substituted 6 membered heteroaryl.

In embodiments, $R^5$ and $R^{11}$ substituents bonded to the same nitrogen atom may optionally be joined to form a substituted (e.g., substituted with a substituent group, a size-limited substituent group, or lower substituent group) or unsubstituted heterocycloalkyl. In embodiments, $R^5$ and $R^{11}$ substituents bonded to the same nitrogen atom may optionally be joined to form a substituted (e.g., substituted with a substituent group, a size-limited substituent group, or lower substituent group) heterocycloalkyl. In embodiments, $R^5$ and $R^{11}$ substituents bonded to the same nitrogen atom may optionally be joined to form an unsubstituted heterocycloalkyl. In embodiments, $R^5$ and $R^{11}$ substituents bonded to the same nitrogen atom may optionally be joined to form a substituted or unsubstituted heterocycloalkyl (e.g., 3 to 8 membered, 3 to 6 membered, 4 to 6 membered, 4 to 5 membered, or 5 to 6 membered). In embodiments, $R^5$ and $R^{11}$ substituents bonded to the same nitrogen atom may optionally be joined to form a substituted heterocycloalkyl (e.g., 3 to 8 membered, 3 to 6 membered, 4 to 6 membered, 4 to 5 membered, or 5 to 6 membered). In embodiments, $R^5$ and $R^{11}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

In embodiments, $R^5$ and $R^{11}$ substituents may optionally be joined to form substituted (e.g., substituted with a substituent group, a size-limited substituent group, or lower substituent group) or unsubstituted heteroaryl. In embodiments, $R^5$ and $R^{11}$ substituents may optionally be joined to form substituted (e.g., substituted with a substituent group, a size-limited substituent group, or lower substituent group) heteroaryl. In embodiments, $R^5$ and $R^{11}$ substituents may optionally be joined to form an unsubstituted heteroaryl. In embodiments, $R^5$ and $R^{11}$ substituents may optionally be joined to form substituted or unsubstituted heteroaryl (e.g., 5 to 10 membered, 5 to 9 membered, or 5 to 6 membered). In embodiments, $R^5$ and $R^{11}$ substituents may optionally be joined to form substituted heteroaryl (e.g., 5 to 10 membered, 5 to 9 membered, or 5 to 6 membered). In embodiments, $R^5$ and $R^{11}$ substituents may optionally be joined to form an unsubstituted heteroaryl (e.g., 5 to 10 membered, 5 to 9 membered, or 5 to 6 membered).

In embodiments, $R^6$ and $R^{12}$ substituents may optionally be joined to form a substituted or unsubstituted 3 to 8 membered heterocycloalkyl, or substituted or unsubstituted 5 to 6 membered heteroaryl.

In embodiments, $R^6$ and $R^{12}$ substituents may optionally be joined to form a substituted or unsubstituted 3 to 8 membered heterocycloalkyl. In embodiments, $R^6$ and $R^{12}$ substituents may optionally be joined to form a substituted or unsubstituted 4 to 7 membered heterocycloalkyl. In embodiments, $R^6$ and $R^{12}$ substituents may optionally be joined to form a substituted or unsubstituted 4 to 6 membered heterocycloalkyl.

In embodiments, $R^6$ and $R^{12}$ substituents may optionally be joined to form a substituted or unsubstituted 3 membered heterocycloalkyl. In embodiments, $R^6$ and $R^{12}$ substituents may optionally be joined to form a substituted or unsubstituted 4 membered heterocycloalkyl. In embodiments, $R^6$ and $R^{12}$ substituents may optionally be joined to form a substituted or unsubstituted 5 membered heterocycloalkyl. In embodiments, $R^6$ and $R^{12}$ substituents may optionally be joined to form a substituted or unsubstituted 6 membered heterocycloalkyl. In embodiments, $R^6$ and $R^{12}$ substituents may optionally be joined to form a substituted or unsubstituted 7 membered heterocycloalkyl. In embodiments, $R^6$ and $R^{12}$ substituents may optionally be joined to form a substituted or unsubstituted 8 membered heterocycloalkyl. In embodiments, $R^6$ and $R^{12}$ substituents may optionally be joined to form a substituted 3 membered heterocycloalkyl. In embodiments, $R^6$ and $R^{12}$ substituents may optionally be joined to form a substituted 4 membered heterocycloalkyl. In embodiments, $R^6$ and $R^{12}$ substituents may optionally be joined to form a substituted 5 membered heterocycloalkyl. In embodiments, $R^6$ and $R^{12}$ substituents may optionally be joined to form a substituted 6 membered heterocycloalkyl. In embodiments, $R^6$ and $R^{12}$ substituents may optionally be joined to form a substituted 7 membered heterocycloalkyl. In embodiments, $R^6$ and $R^{12}$ substituents may optionally be joined to form a substituted 8 membered heterocycloalkyl. In embodiments, $R^6$ and $R^{12}$ substituents may optionally be joined to form an unsubstituted 3 membered heterocycloalkyl. In embodiments, $R^6$ and $R^{12}$ substituents may optionally be joined to form an unsubstituted 4 membered heterocycloalkyl. In embodiments, $R^6$ and $R^{12}$ substituents may optionally be joined to form an unsubstituted 5 membered heterocycloalkyl. In embodiments, $R^6$ and $R^{12}$ substituents may optionally be joined to form an unsubstituted 6 membered heterocycloalkyl. In embodiments, $R^6$ and $R^{12}$ substituents may optionally be joined to form an unsubstituted 7 membered heterocycloalkyl. In embodiments, $R^6$ and $R^{12}$ substituents may optionally be joined to form an unsubstituted 8 membered heterocycloalkyl.

In embodiments, $R^6$ and $R^{12}$ substituents may optionally be joined to form an $R^{36}$-substituted or unsubstituted 3 to 8 membered heterocycloalkyl, or $R^{36}$-substituted or unsubstituted 5 to 6 membered heteroaryl. In embodiments, $R^6$ and $R^{12}$ substituents may optionally be joined to form an $R^{36}$-substituted or unsubstituted 3 membered heterocycloalkyl. In embodiments, $R^6$ and $R^{12}$ substituents may optionally be joined to form an $R^{36}$-substituted or unsubstituted 4 membered heterocycloalkyl. In embodiments, $R^6$ and $R^{12}$ substituents may optionally be joined to form an $R^{36}$-substituted or unsubstituted 5 membered heterocycloalkyl. In embodiments, $R^6$ and $R^{12}$ substituents may optionally be joined to form an $R^{36}$-substituted or unsubstituted 6 membered heterocycloalkyl. In embodiments, $R^6$ and $R^{12}$ substituents may optionally be joined to form an $R^{36}$-substituted or unsubstituted 7 membered heterocycloalkyl. In embodiments, $R^6$ and $R^{12}$ substituents may optionally be joined to form an $R^{36}$-substituted or unsubstituted 8 membered heterocycloalkyl. In embodiments, $R^6$ and $R^{12}$ substituents may optionally be joined to form an $R^{36}$-substituted 3 membered heterocycloalkyl. In embodiments, $R^6$ and $R^{12}$ substituents may optionally be joined to form an $R^{36}$-substituted 4 membered heterocycloalkyl. In embodiments, $R^6$ and $R^{12}$ substituents may optionally be joined to form an $R^{36}$-substituted 5 membered heterocycloalkyl. In embodiments, $R^6$ and $R^{12}$ substituents may optionally be joined to form an $R^{36}$-substituted 6 membered heterocycloalkyl. In embodiments, $R^6$ and $R^{12}$ substituents may optionally be joined to form an $R^{36}$-substituted 7 membered heterocycloalkyl. In embodiments, $R^6$ and $R^{12}$ substituents may optionally be joined to form an $R^{36}$-substituted 8 membered heterocycloalkyl.

In embodiments, $R^6$ and $R^{12}$ substituents may optionally be joined to form an $R^{42}$-substituted or unsubstituted 3 to 8 membered heterocycloalkyl, or $R^{42}$-substituted or unsubstituted 5 to 6 membered heteroaryl. In embodiments, $R^6$ and $R^{12}$ substituents may optionally be joined to form an $R^{42}$-substituted or unsubstituted 3 membered heterocycloalkyl. In embodiments, $R^6$ and $R^{12}$ substituents may optionally be joined to form an $R^{42}$-substituted or unsubstituted 4 membered heterocycloalkyl. In embodiments, $R^6$ and $R^{12}$ substituents may optionally be joined to form an $R^{42}$-substituted or unsubstituted 5 membered heterocycloalkyl. In embodiments, $R^6$ and $R^{12}$ substituents may optionally be joined to form an $R^{42}$-substituted or unsubstituted 6 membered heterocycloalkyl. In embodiments, $R^6$ and $R^{12}$ substituents may optionally be joined to form an $R^{42}$-substituted or unsubstituted 7 membered heterocycloalkyl. In embodiments, $R^6$ and $R^{12}$ substituents may optionally be joined to form an $R^{42}$-substituted or unsubstituted 8 membered heterocycloalkyl. In embodiments, $R^6$ and $R^{12}$ substituents may optionally be joined to form an $R^{42}$-substituted 3 membered heterocycloalkyl. In embodiments, $R^6$ and $R^{12}$ substituents may optionally be joined to form an $R^{42}$-substituted 4 membered heterocycloalkyl. In embodiments, $R^6$ and $R^{12}$ substituents may optionally be joined to form an $R^{42}$-substituted 5 membered heterocycloalkyl. In embodiments, $R^6$ and $R^{12}$ substituents may optionally be joined to form an $R^{42}$-substituted 6 membered heterocycloalkyl. In embodiments, $R^6$ and $R^{12}$ substituents may optionally be joined to form an $R^{42}$-substituted 7 membered heterocycloalkyl. In embodiments, $R^6$ and $R^{12}$ substituents may optionally be joined to form an $R^{42}$-substituted 8 membered heterocycloalkyl.

In embodiments, $R^6$ and $R^{12}$ substituents may optionally be joined to form a substituted or unsubstituted 5 to 6 membered heteroaryl. In embodiments, $R^6$ and $R^{12}$ substituents may optionally be joined to form a substituted or unsubstituted 5 membered heteroaryl. In embodiments, $R^6$ and $R^{12}$ substituents may optionally be joined to form a substituted or unsubstituted 6 membered heteroaryl. In embodiments, $R^6$ and $R^{12}$ substituents may optionally be joined to form a substituted 5 to 6 membered heteroaryl. In embodiments, $R^6$ and $R^{12}$ substituents may optionally be joined to form a substituted 5 membered heteroaryl. In embodiments, $R^6$ and $R^{12}$ substituents may optionally be joined to form a substituted 6 membered heteroaryl. In embodiments, $R^6$ and $R^{12}$ substituents may optionally be joined to form an unsubstituted 5 to 6 membered heteroaryl. In embodiments, $R^6$ and $R^{12}$ substituents may optionally be joined to form an unsubstituted 5 membered heteroaryl. In embodiments, $R^6$ and $R^{12}$ substituents may optionally be joined to form an unsubstituted 6 membered heteroaryl.

In embodiments, $R^6$ and $R^{12}$ substituents may optionally be joined to form an $R^{36}$-substituted or unsubstituted 5 to 6 membered heteroaryl. In embodiments, $R^6$ and $R^{12}$ substituents may optionally be joined to form an $R^{36}$-substituted or unsubstituted 5 membered heteroaryl. In embodiments, $R^6$ and $R^{12}$ substituents may optionally be joined to form an $R^{36}$-substituted or unsubstituted 6 membered heteroaryl. In embodiments, $R^6$ and $R^{12}$ substituents may optionally be joined to form an $R^{36}$-substituted 5 to 6 membered heteroaryl. In embodiments, $R^6$ and $R^{12}$ substituents may optionally be joined to form an $R^{36}$-substituted 5 membered heteroaryl. In embodiments, $R^6$ and $R^{12}$ substituents may optionally be joined to form an $R^{36}$-substituted 6 membered heteroaryl.

In embodiments, $R^6$ and $R^{12}$ substituents may optionally be joined to form an $R^{42}$-substituted or unsubstituted 5 to 6 membered heteroaryl. In embodiments, $R^6$ and $R^{12}$ substituents may optionally be joined to form an $R^{42}$-substituted or unsubstituted 5 membered heteroaryl. In embodiments, $R^6$ and $R^{12}$ substituents may optionally be joined to form an $R^{42}$-substituted or unsubstituted 6 membered heteroaryl. In embodiments, $R^6$ and $R^{12}$ substituents may optionally be joined to form an $R^{42}$-substituted 5 to 6 membered heteroaryl. In embodiments, $R^6$ and $R^{12}$ substituents may optionally be joined to form an $R^{42}$-substituted 5 membered heteroaryl. In embodiments, $R^6$ and $R^{12}$ substituents may optionally be joined to form an $R^{42}$-substituted 6 membered heteroaryl.

In embodiments, $R^6$ and $R^{12}$ substituents bonded to the same nitrogen atom may optionally be joined to form a substituted (e.g., substituted with a substituent group, a size-limited substituent group, or lower substituent group) or unsubstituted heterocycloalkyl. In embodiments, $R^6$ and $R^{12}$ substituents bonded to the same nitrogen atom may optionally be joined to form a substituted (e.g., substituted with a substituent group, a size-limited substituent group, or lower substituent group) heterocycloalkyl. In embodiments, $R^6$ and $R^{12}$ substituents bonded to the same nitrogen atom may optionally be joined to form an unsubstituted heterocycloalkyl. In embodiments, $R^6$ and $R^{12}$ substituents bonded to the same nitrogen atom may optionally be joined to form a substituted or unsubstituted heterocycloalkyl (e.g., 3 to 8 membered, 3 to 6 membered, 4 to 6 membered, 4 to 5 membered, or 5 to 6 membered). In embodiments, $R^6$ and $R^{12}$ substituents bonded to the same nitrogen atom may optionally be joined to form a substituted heterocycloalkyl (e.g., 3 to 8 membered, 3 to 6 membered, 4 to 6 membered, 4 to 5 membered, or 5 to 6 membered). In embodiments, $R^6$ and $R^{12}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

In embodiments, $R^6$ and $R^{12}$ substituents may optionally be joined to form substituted (e.g., substituted with a substituent group, a size-limited substituent group, or lower substituent group) or unsubstituted heteroaryl. In embodiments, $R^6$ and $R^{12}$ substituents may optionally be joined to form substituted (e.g., substituted with a substituent group, a size-limited substituent group, or lower substituent group) heteroaryl. In embodiments, $R^6$ and $R^{12}$ substituents may optionally be joined to form an unsubstituted heteroaryl. In embodiments, $R^6$ and $R^{12}$ substituents may optionally be joined to form substituted or unsubstituted heteroaryl (e.g., 5 to 10 membered, 5 to 9 membered, or 5 to 6 membered). In embodiments, $R^6$ and $R^{12}$ substituents may optionally be joined to form substituted heteroaryl (e.g., 5 to 10 membered, 5 to 9 membered, or 5 to 6 membered). In embodiments, $R^6$ and $R^{12}$ substituents may optionally be joined to form an unsubstituted heteroaryl (e.g., 5 to 10 membered, 5 to 9 membered, or 5 to 6 membered).

In embodiments, $R^8$ is hydrogen or a bioconjugate reactive moiety. In embodiments, $R^8$ is hydrogen. In embodiments, $R^8$ is —NH$_2$, 167
-continued
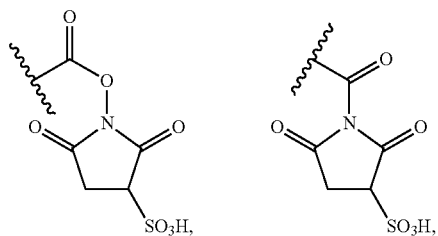
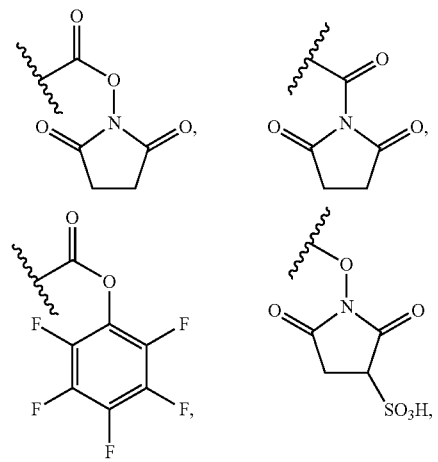
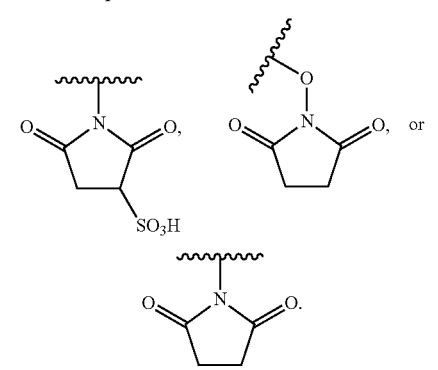
In embodiments, R⁸ is —NH₂,
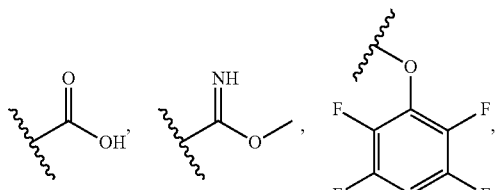
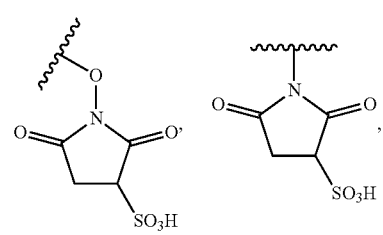
168
-continued
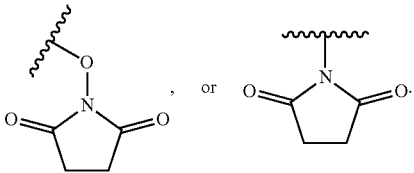
In embodiments, R⁸ is —NH₂,
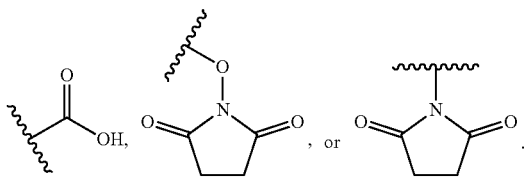
In embodiments, R⁸ is —NH₂. In embodiments, R⁸ is
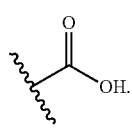 [SMILES: *C(=O)O]
In embodiments, R⁸ is
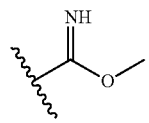
In embodiments, R⁸ is
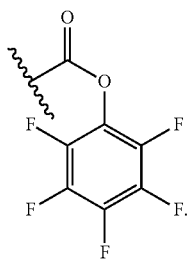 [SMILES: *C(=O)Oc1c(F)c(F)c(F)c(F)c1F]
In embodiments, R⁸ is
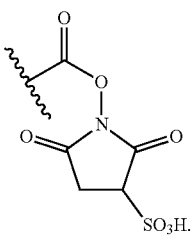 [SMILES: *C(=O)ON1C(=O)CC(S(=O)(=O)O)C1=O]

In embodiments, R⁸ is
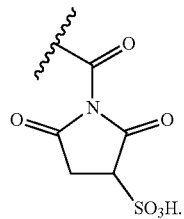
In embodiments, R⁸ is
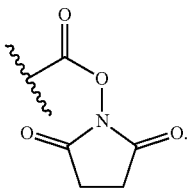 [SMILES: *C(=O)ON1C(=O)CCC1=O]
In embodiments, R⁸ is
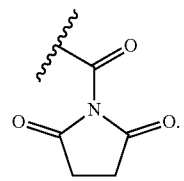 [SMILES: *C(=O)N1C(=O)CCC1=O]
In embodiments, R⁸ is
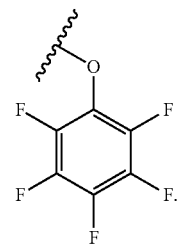
In embodiments, R⁸ is
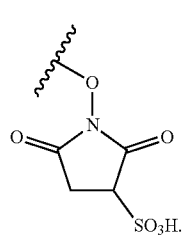
In embodiments, R⁸ is
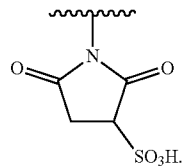 [SMILES: *N1C(=O)CC(S(=O)(=O)O)C1=O]
In embodiments, R⁸ is
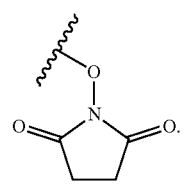 [SMILES: *ON1C(=O)CCC1=O]
In embodiments, R⁸ is
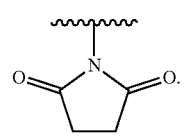
In embodiments, R⁸ is
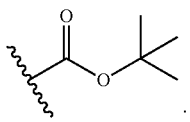 [SMILES: *C(=O)OC(C)(C)C]
In embodiments, R⁸ is
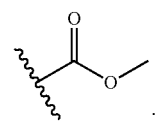 [SMILES: *C(=O)OC]
In embodiments, R⁸ is
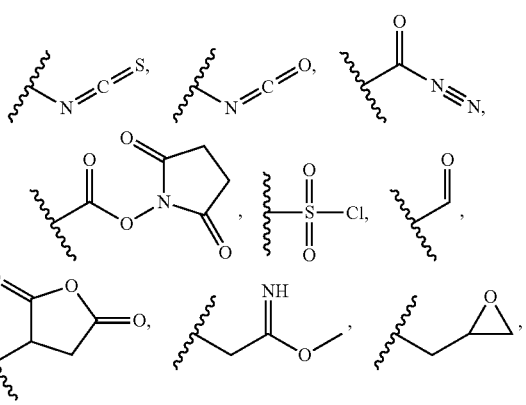

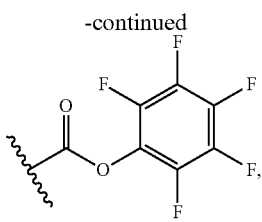

In embodiments, $R^8$ is

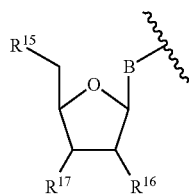

B is a divalent base.

$R^{15}$ is independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{10}$ or phenyl), substituted or unsubstituted heteroaryl (e.g., 5 to 10 membered, 5 to 9 membered, or 5 to 6 membered), a 5'-nucleoside protecting group, monophosphate moiety or derivative thereof (e.g., phosphoramidate moiety, phosphorothioate moiety, phosphorodithioate moiety, or O-methylphosphoroamidite moiety), polyphosphate moiety or derivative thereof (e.g., including a phosphoramidate, phosphorothioate, phosphorodithioate, or O-methylphosphoroamidite), or nucleic acid moiety or derivative thereof (e.g., including a phosphoramidate, phosphorothioate, phosphorodithioate, or O-methylphosphoroamidite).

$R^{16}$ and $R^{17}$ are each independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{10}$ or phenyl), substituted or unsubstituted heteroaryl (e.g., 5 to 10 membered, 5 to 9 membered, or 5 to 6 membered); polyphosphate moiety or derivative thereof (e.g., including a phosphoramidate, phosphorothioate, phosphorodithioate, or O-methylphosphoroamidite), nucleic acid moiety or derivative thereof (e.g., including a phosphoramidate, phosphorothioate, phosphorodithioate, or O-methylphosphoroamidite), a polymerase-compatible cleavable moiety, or an —O-polymerase-compatible cleavable moiety.

In embodiments, B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof.

In embodiments, B is a divalent cytosine or a derivative thereof. In embodiments, B is a divalent guanine or a derivative thereof. In embodiments, B is a divalent adenine or a derivative thereof. In embodiments, B is a divalent thymine or a derivative thereof. In embodiments, B is a divalent uracil or a derivative thereof. In embodiments, B is a divalent hypoxanthine or a derivative thereof. In embodiments, B is a divalent xanthine or a derivative thereof. In embodiments, B is a divalent 7-methylguanine or a derivative thereof. In embodiments, B is a divalent 5,6-dihydrouracil or a derivative thereof. In embodiments, B is a divalent 5-methylcytosine or a derivative thereof. In embodiments, B is a divalent 5-hydroxymethylcytosine or a derivative thereof.

In embodiments, B is a divalent cytosine. In embodiments, B is a divalent guanine. In embodiments, B is a divalent adenine. In embodiments, B is a divalent thymine. In embodiments, B is a divalent uracil. In embodiments, B is a divalent hypoxanthine. In embodiments, B is a divalent xanthine. In embodiments, B is a divalent 7-methylguanine. In embodiments, B is a divalent 5,6-dihydrouracil. In embodiments, B is a divalent 5-methylcytosine. In embodiments, B is a divalent 5-hydroxymethylcytosine.

In embodiments, $R^{15}$ is independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a 5'-nucleoside protecting group, monophosphate moiety, polyphosphate moiety, or nucleic acid moiety. In embodiments, $R^{15}$ is independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —NH$_2$, —COOH, —CONH$_2$, —NO$_2$, —SH, —SO$_3$H, —SO$_2$NH$_2$, —NHNH$_2$, —NHC(O)NHNH$_2$, —NHC(O)NH$_2$, —NHSO$_2$H, —NHC(O)H, —NHC(O)OH, —NHOH, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{15}$ is a 5'-nucleoside protecting group. In embodiments, $R^{15}$ is a monophosphate moiety, polyphosphate moiety, or nucleic acid moiety. In embodiments, $R^{15}$ is a monophosphate moiety. In embodiments, $R^{15}$ is a polyphosphate moiety. In embodiments, $R^{15}$ is a nucleic acid moiety. In embodiments, $R^{15}$ is hydrogen. In embodiments, $R^{15}$ is a triphosphate moiety. In embodiments, $R^{15}$ is —OH.

In embodiments, $R^{15}$ is independently a 5'-nucleoside protecting group; and the 5'-nucleoside protecting group is

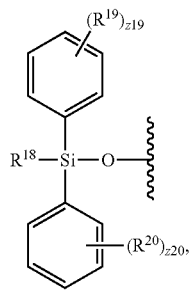

wherein $R^{18}$ is substituted or unsubstituted $C_1$-$C_4$ alkyl. $R^{19}$ and $R^{20}$ are each independently halogen, —$CF_3$, —$CCl_3$, —$CI_3$, —$CBr_3$, —$CHF_2$, —$CHCl_2$, —$CHI_2$, —$CHBr_2$, —$CH_2F$, —$CH_2Cl$, —$CH_2I$, —$CH_2Br$, —$OCH_2F$, —$OCH_2Cl$, —$OCH_2I$, —$OCH_2Br$, —$OCHF_2$, —$OCHCl_2$, —$OCHI_2$, —$OCHBr_2$, —$OCF_3$, —$OCCl_3$, —$OCI_3$, —$OCBr_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). The symbols z19 and z20 are each independently integers from 0 to 5. In embodiments, z19 and z20 are 0.

In embodiments, $R^{18}$ is independently substituted (e.g., substituted with a substituent group, a size-limited substituent group, or lower substituent group) $C_1$-$C_4$ alkyl. In embodiments, $R^{18}$ is an unsubstituted methyl. In embodiments, $R^{18}$ is an unsubstituted $C_2$ alkyl. In embodiments, $R^{18}$ is an unsubstituted $C_3$ alkyl. In embodiments, $R^{18}$ is an unsubstituted $C_4$ alkyl. In embodiments, $R^{18}$ is an unsubstituted tert-butyl.

In embodiments, $R^{18}$ is independently $R^{48}$-substituted or unsubstituted $C_1$-$C_4$ alkyl.

In embodiments, $R^{19}$ and $R^{20}$ are each independently substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^{19}$ and $R^{20}$ are each independently unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{19}$ is independently halogen, —$CF_3$, —$CCl_3$, —$CI_3$, —$CBr_3$, —$CHF_2$, —$CHCl_2$, —$CHI_2$, —$CHBr_2$, —$CH_2F$, —$CH_2Cl$, —$CH_2I$, —$CH_2Br$, —$OCH_2F$, —$OCH_2Cl$, —$OCH_2I$, —$OCH_2Br$, —$OCHF_2$, —$OCHCl_2$, —$OCHI_2$, —$OCHBr_2$, —$OCF_3$, —$OCCl_3$, —$OCI_3$, —$OCBr_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$N_3$, $R^{49}$-substituted or unsubstituted alkyl, $R^{49}$-substituted or unsubstituted heteroalkyl, $R^{49}$-substituted or unsubstituted cycloalkyl, $R^{49}$-substituted or unsubstituted heterocycloalkyl, $R^{49}$-substituted or unsubstituted aryl, or $R^{49}$-substituted or unsubstituted heteroaryl.

In embodiments, $R^{20}$ is independently halogen, —$CF_3$, —$CCl_3$, —$CI_3$, —$CBr_3$, —$CHF_2$, —$CHCl_2$, —$CHI_2$, —$CHBr_2$, —$CH_2F$, —$CH_2Cl$, —$CH_2I$, —$CH_2Br$, —$OCH_2F$, —$OCH_2Cl$, —$OCH_2I$, —$OCH_2Br$, —$OCHF_2$, —$OCHCl_2$, —$OCHI_2$, —$OCHBr_2$, —$OCF_3$, —$OCCl_3$, —$OCI_3$, —$OCBr_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$N_3$, $R^{50}$-substituted or unsubstituted alkyl, $R^{50}$-substituted or unsubstituted heteroalkyl, $R^{50}$-substituted or unsubstituted cycloalkyl, $R^{50}$-substituted or unsubstituted heterocycloalkyl, $R^{50}$-substituted or unsubstituted aryl, or $R^{50}$-substituted or unsubstituted heteroaryl.

$R^{48}$, $R^{49}$, and $R^{50}$ are each independently oxo, halogen, —$CF_3$, —$CCl_3$, —$CI_3$, —$CBr_3$, —$CHF_2$, —$CHCl_2$, —$CHI_2$, —$CHBr_2$, —$CH_2F$, —$CH_2Cl$, —$CH_2I$, —$CH_2Br$, —$OCH_2F$, —$OCH_2Cl$, —$OCH_2I$, —$OCH_2Br$, —$OCHF_2$, —$OCHCl_2$, —$OCHI_2$, —$OCHBr_2$, —$OCF_3$, —$OCCl_3$, —$OCI_3$, —$OCBr_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{16}$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, R$^{16}$ is independently a polymerase-compatible cleavable moiety. In embodiments, R$^{16}$ is independently an —O-polymerase-compatible cleavable moiety.

In embodiments, R$^{16}$ is independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, R$^{46}$-substituted or unsubstituted alkyl, R$^{46}$-substituted or unsubstituted heteroalkyl, R$^{46}$-substituted or unsubstituted cycloalkyl, R$^{46}$-substituted or unsubstituted heterocycloalkyl, R$^{46}$-substituted or unsubstituted aryl, or R$^{46}$-substituted or unsubstituted heteroaryl.

In embodiments, R$^{16}$ is hydrogen. In embodiments, R$^{16}$ is —OH. In embodiments, R$^{16}$ is —O-polymerase-compatible cleavable moiety.

In embodiments, R$^{16}$ is a polymerase-compatible cleavable moiety or an —O-polymerase-compatible cleavable moiety; and the polymerase-compatible cleavable moiety is independently

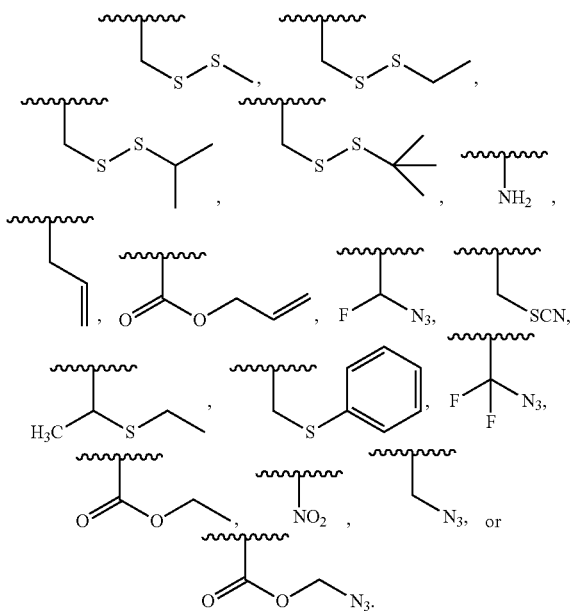

In embodiments, the —O-polymerase cleavable moiety is a moiety described in US 2018/0274024, which is incorporated herein in its entirety for all purposes.

In embodiments, R$^{17}$ is independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, R$^{17}$ is independently a polymerase-compatible cleavable moiety. In embodiments, R$^{17}$ is independently an —O-polymerase-compatible cleavable moiety.

In embodiments, R$^{17}$ is independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, R$^{47}$-substituted or unsubstituted alkyl, R$^{47}$-substituted or unsubstituted heteroalkyl, R$^{47}$-substituted or unsubstituted cycloalkyl, R$^{47}$-substituted or unsubstituted heterocycloalkyl, R$^{47}$-substituted or unsubstituted aryl, or R$^{47}$-substituted or unsubstituted heteroaryl.

R$^{46}$ and R$^{47}$ are each independently oxo, halogen, —CF$_3$, —CCl$_3$, —CI$_3$, —CBr$_3$, —CHF$_2$, —CHCl$_2$, —CHI$_2$, —CHBr$_2$, —CH$_2$F, —CH$_2$Cl, —CH$_2$I, —CH$_2$Br, —OCH$_2$F, —OCH$_2$Cl, —OCH$_2$I, —OCH$_2$Br, —OCHF$_2$, —OCHCl$_2$, —OCHI$_2$, —OCHBr$_2$, —OCF$_3$, —OCCl$_3$, —OCI$_3$, —OCBr$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, R$^{17}$ is hydrogen. In embodiments, R$^{17}$ is —OH. In embodiments, R$^{17}$ is —O-polymerase-compatible cleavable moiety.

In embodiments, R$^{17}$ is a polymerase-compatible cleavable moiety or an —O-polymerase-compatible cleavable moiety; and the polymerase-compatible cleavable moiety is independently

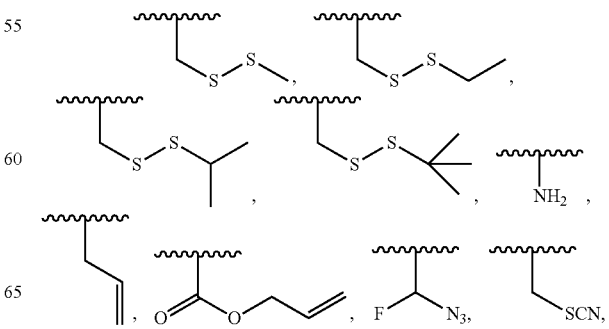

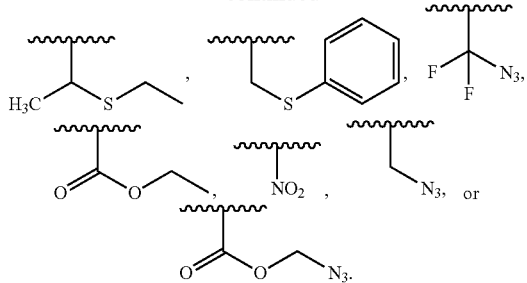

In embodiments, the polymerase-compatible cleavable moiety is independently

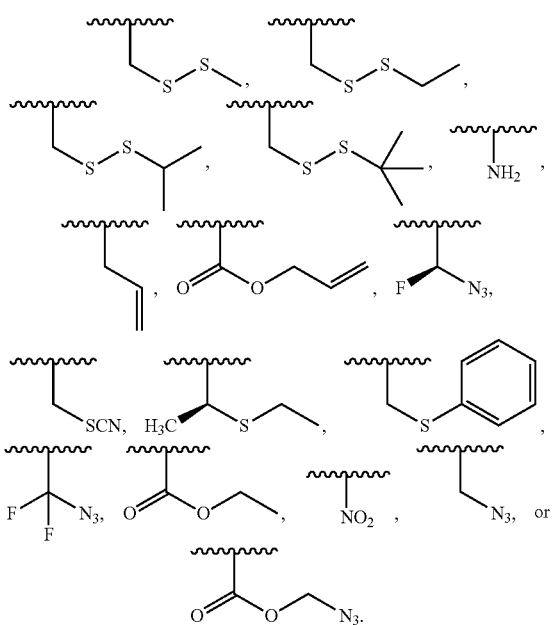

In embodiments, the polymerase-compatible cleavable moiety is independently

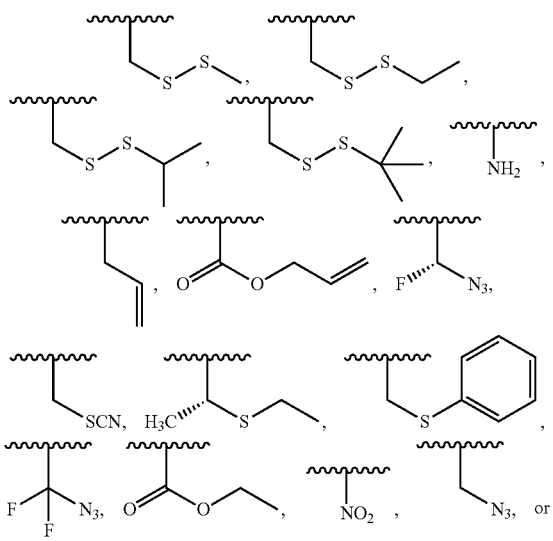

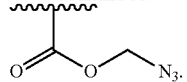

In embodiments, $R^9$ is independently hydrogen, $R^{39}$-substituted or unsubstituted alkyl, or $R^{39}$-substituted or unsubstituted heteroalkyl. In embodiments, $R^9$ is hydrogen. In embodiments, $R^9$ is substituted or unsubstituted $C_1$ alkyl. In embodiments, $R^9$ is substituted or unsubstituted $C_2$ alkyl. In embodiments, $R^9$ is substituted or unsubstituted $C_3$ alkyl. In embodiments, $R^9$ is substituted or unsubstituted $C_4$ alkyl. In embodiments, $R^9$ is substituted or unsubstituted $C_5$ alkyl. In embodiments, $R^9$ is substituted or unsubstituted $C_6$ alkyl. In embodiments, $R^9$ is substituted $C_1$ alkyl. In embodiments, $R^9$ is substituted $C_2$ alkyl. In embodiments, $R^9$ is substituted $C_3$ alkyl. In embodiments, $R^9$ is substituted $C_4$ alkyl. In embodiments, $R^9$ is substituted $C_5$ alkyl. In embodiments, $R^9$ is substituted $C_6$ alkyl. In embodiments, $R^9$ is unsubstituted $C_1$ alkyl. In embodiments, $R^9$ is unsubstituted $C_2$ alkyl. In embodiments, $R^9$ is unsubstituted $C_3$ alkyl. In embodiments, $R^9$ is unsubstituted $C_4$ alkyl. In embodiments, $R^9$ is unsubstituted $C_5$ alkyl. In embodiments, $R^9$ is unsubstituted $C_6$ alkyl. In embodiments, $R^9$ is $R^{39}$-substituted or unsubstituted alkyl (e.g., $C_1$-$C_6$ alkyl), wherein $R^{39}$ is independently —$PO_3H$, —$PO_4H$, —$SO_2NH_2$, —$SO_3H$, or —$SO_4H$.

In embodiments, $R^9$ is independently hydrogen, substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl.

In embodiments, $R^{10}$ is independently hydrogen, $R^{40}$-substituted or unsubstituted alkyl, or $R^{40}$-substituted or unsubstituted heteroalkyl. In embodiments, $R^{10}$ is hydrogen. In embodiments, $R^{10}$ is substituted or unsubstituted $C_1$ alkyl. In embodiments, $R^{10}$ is substituted or unsubstituted $C_2$ alkyl. In embodiments, $R^{10}$ is substituted or unsubstituted $C_3$ alkyl. In embodiments, $R^{10}$ is substituted or unsubstituted $C_4$ alkyl. In embodiments, $R^{10}$ is substituted or unsubstituted $C_5$ alkyl. In embodiments, $R^{10}$ is substituted or unsubstituted $C_6$ alkyl. In embodiments, $R^{10}$ is substituted $C_1$ alkyl. In embodiments, $R^{10}$ is substituted $C_2$ alkyl. In embodiments, $R^{10}$ is substituted $C_3$ alkyl. In embodiments, $R^{10}$ is substituted $C_4$ alkyl. In embodiments, $R^{10}$ is substituted $C_5$ alkyl. In embodiments, $R^{10}$ is substituted $C_6$ alkyl. In embodiments, $R^{10}$ is unsubstituted $C_1$ alkyl. In embodiments, $R^{10}$ is unsubstituted $C_2$ alkyl. In embodiments, $R^{10}$ is unsubstituted $C_3$ alkyl. In embodiments, $R^{10}$ is unsubstituted $C_4$ alkyl. In embodiments, $R^{10}$ is unsubstituted $C_5$ alkyl. In embodiments, $R^{10}$ is unsubstituted $C_6$ alkyl. In embodiments, $R^{10}$ is $R^{40}$-substituted or unsubstituted alkyl (e.g., $C_1$-$C_6$ alkyl), wherein $R^{40}$ is independently —$PO_3H$, —$PO_4H$, —$SO_2NH_2$, —$SO_3H$, or —$SO_4H$.

In embodiments, $R^{10}$ is independently hydrogen, substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl.

In embodiments, $R^{11}$ is independently hydrogen, $R^{41}$-substituted or unsubstituted alkyl, or $R^{41}$-substituted or unsubstituted heteroalkyl. In embodiments, $R^{11}$ is hydrogen. In embodiments, $R^{11}$ is substituted or unsubstituted $C_1$ alkyl. In embodiments, $R^{11}$ is substituted or unsubstituted $C_2$ alkyl. In embodiments, $R^{11}$ is substituted or unsubstituted $C_3$ alkyl.

In embodiments, $R^{11}$ is substituted or unsubstituted $C_4$ alkyl. In embodiments, $R^{11}$ is substituted or unsubstituted $C_5$ alkyl. In embodiments, $R^{11}$ is substituted or unsubstituted $C_6$ alkyl. In embodiments, $R^{11}$ is substituted $C_1$ alkyl. In embodiments, $R^{11}$ is substituted $C_2$ alkyl. In embodiments, $R^{11}$ is substituted $C_3$ alkyl. In embodiments, $R^{11}$ is substituted $C_4$ alkyl. In embodiments, $R^{11}$ is substituted $C_5$ alkyl. In embodiments, $R^{11}$ is substituted $C_6$ alkyl. In embodiments, $R^{11}$ is unsubstituted $C_1$ alkyl. In embodiments, $R^{11}$ is unsubstituted $C_2$ alkyl. In embodiments, $R^{11}$ is unsubstituted $C_3$ alkyl. In embodiments, $R^{11}$ is unsubstituted $C_4$ alkyl. In embodiments, $R^{11}$ is unsubstituted $C_5$ alkyl. In embodiments, $R^{11}$ is unsubstituted $C_6$ alkyl. In embodiments, $R^{11}$ is $R^{41}$-substituted or unsubstituted alkyl (e.g., $C_1$-$C_6$ alkyl), wherein $R^{41}$ is independently —$PO_3H$, —$PO_4H$, —$SO_2NH_2$, —$SO_3H$, or —$SO_4H$.

In embodiments, $R^{11}$ is independently hydrogen, substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl.

In embodiments, $R^{12}$ is independently hydrogen, $R^{42}$-substituted or unsubstituted alkyl, or $R^{42}$-substituted or unsubstituted heteroalkyl. In embodiments, $R^{12}$ is hydrogen. In embodiments, $R^{12}$ is substituted or unsubstituted $C_1$ alkyl. In embodiments, $R^{12}$ is substituted or unsubstituted $C_2$ alkyl. In embodiments, $R^{12}$ is substituted or unsubstituted $C_3$ alkyl. In embodiments, $R^{12}$ is substituted or unsubstituted $C_4$ alkyl. In embodiments, $R^{12}$ is substituted or unsubstituted $C_5$ alkyl. In embodiments, $R^{12}$ is substituted or unsubstituted $C_6$ alkyl. In embodiments, $R^{12}$ is substituted $C_1$ alkyl. In embodiments, $R^{12}$ is substituted $C_2$ alkyl. In embodiments, $R^{12}$ is substituted $C_3$ alkyl. In embodiments, $R^{12}$ is substituted $C_4$ alkyl. In embodiments, $R^{12}$ is substituted $C_5$ alkyl. In embodiments, $R^{12}$ is substituted $C_6$ alkyl. In embodiments, $R^{12}$ is unsubstituted $C_1$ alkyl. In embodiments, $R^{12}$ is unsubstituted $C_2$ alkyl. In embodiments, $R^{12}$ is unsubstituted $C_3$ alkyl. In embodiments, $R^{12}$ is unsubstituted $C_4$ alkyl. In embodiments, $R^{12}$ is unsubstituted $C_5$ alkyl. In embodiments, $R^{12}$ is unsubstituted $C_6$ alkyl. In embodiments, $R^{12}$ is $R^{42}$-substituted or unsubstituted alkyl (e.g., $C_1$-$C_6$ alkyl), wherein $R^{42}$ is independently —$PO_3H$, —$PO_4H$, —$SO_2NH_2$, —$SO_3H$, or —$SO_4H$.

In embodiments, $R^{12}$ is independently hydrogen, substituted (e.g., substituted with a substituent group, a size-limited substituent group, or lower substituent group) or unsubstituted alkyl, or substituted (e.g., substituted with a substituent group, a size-limited substituent group, or lower substituent group) or unsubstituted heteroalkyl.

$R^{39}$, $R^{40}$, $R^{41}$, and $R^{42}$ are each independently halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$PO_4H$, —$PO_3H$, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). In embodiments, $R^{39}$, $R^{40}$, $R^{41}$, and $R^{42}$ are each independently —$PO_3H$, —$PO_4H$, —$SO_2NH_2$, —$SO_3H$, or —$SO_4H$. In embodiments, $R^{39}$, $R^{40}$, $R^{41}$, and $R^{42}$ are each independently —$SO_3H$. In embodiments, $R^{39}$, $R^{40}$, $R^{41}$, and $R^{42}$ are each independently —$PO_3H$. In embodiments, $R^{39}$, $R^{40}$, $R^{41}$, and $R^{42}$ are each independently —$SO_2NH_2$. In embodiments, $R^{39}$, $R^{40}$, $R^{41}$, and $R^{42}$ are each independently —$SO_4H$.

In embodiments, the compound has the formula:

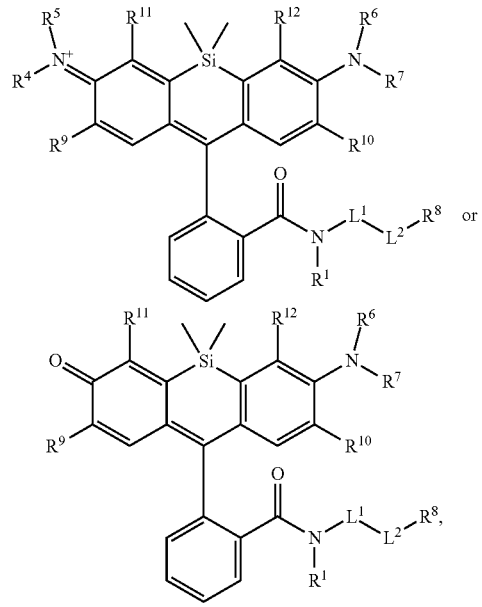

wherein $R^4$, $R^5$, $R^9$, $R^{11}$, $R^{12}$, $R^6$, $R^7$, $R^{10}$, $R^1$, $L^1$, $L^2$, and $R^8$ are as described herein, including embodiments.

In embodiments, the compound has the formula:

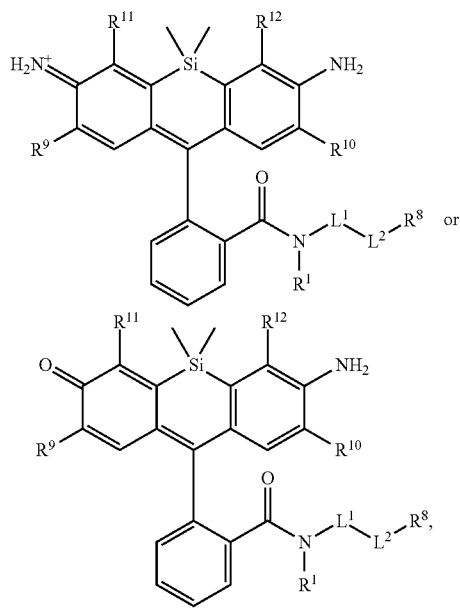

wherein $R^9$, $R^{11}$, $R^{12}$, $R^{10}$, $R^1$, $L^1$, $L^2$, and $R^8$ are as described herein, including embodiments.

In embodiments, the compound has the formula:

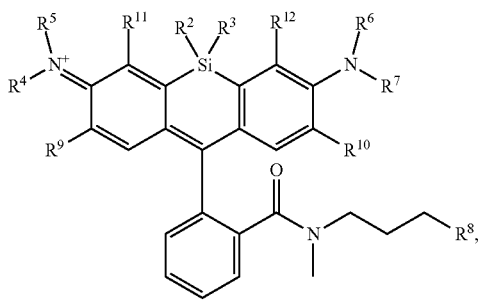

wherein $R^4$, $R^5$, $R^9$, $R^{11}$, $R^2$, $R^3$, $R^{12}$, $R^6$, $R^7$, $R^{10}$, and $R^8$ are as described herein, including embodiments.

In embodiments, the compound has the formula:

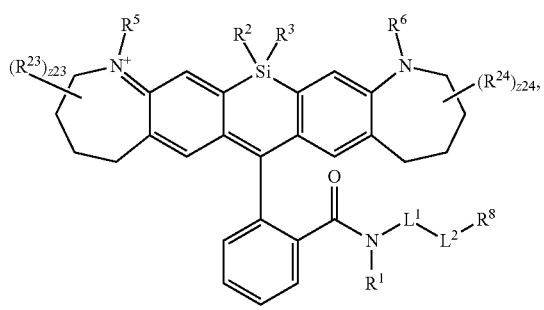

wherein $R^5$, $R^6$, $R^2$, $R^3$, $R^1$, $L^1$, $L^2$, and $R^8$ are as described herein, including embodiments. $R^{23}$ and $R^{24}$ are independently a substituent group, a size-limited substituent group, or lower substituent group. The symbols z23 and z24 are independently integers from 0 to 6.

In embodiments, $R^{23}$ is independently oxo, halogen, —CF$_3$, —CCl$_3$, —CI$_3$, —CBr$_3$, —CHF$_2$, —CHCl$_2$, —CHI$_2$, —CHBr$_2$, —CH$_2$F, —CH$_2$Cl, —CH$_2$I, —CH$_2$Br, —OCH$_2$F, —OCH$_2$Cl, —OCH$_2$I, —OCH$_2$Br, —OCHF$_2$, —OCHCl$_2$, —OCHI$_2$, —OCHBr$_2$, —OCF$_3$, —OCCl$_3$, —OCI$_3$, —OCBr$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —PO$_4$H, —PO$_3$H, —N$_3$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{10}$ or phenyl), or substituted or unsubstituted heteroaryl (e.g., 5 to 10 membered, 5 to 9 membered, or 5 to 6 membered).

In embodiments, $R^{24}$ is independently oxo, halogen, —CF$_3$, —CCl$_3$, —CI$_3$, —CBr$_3$, —CHF$_2$, —CHCl$_2$, —CHI$_2$, —CHBr$_2$, —CH$_2$F, —CH$_2$Cl, —CH$_2$I, —CH$_2$Br, —OCH$_2$F, —OCH$_2$Cl, —OCH$_2$I, —OCH$_2$Br, —OCHF$_2$, —OCHCl$_2$, —OCHI$_2$, —OCHBr$_2$, —OCF$_3$, —OCCl$_3$, —OCI$_3$, —OCBr$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —PO$_4$H, —PO$_3$H, —N$_3$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{10}$ or phenyl), or substituted or unsubstituted heteroaryl (e.g., 5 to 10 membered, 5 to 9 membered, or 5 to 6 membered).

In embodiments, $R^{24}$ is substituted or unsubstituted C$_1$ alkyl. In embodiments, $R^{24}$ is substituted or unsubstituted C$_2$ alkyl. In embodiments, $R^{24}$ is substituted or unsubstituted C$_3$ alkyl. In embodiments, $R^{24}$ is substituted or unsubstituted C$_4$ alkyl. In embodiments, $R^{24}$ is substituted or unsubstituted C$_5$ alkyl. In embodiments, $R^{24}$ is substituted or unsubstituted C$_6$ alkyl. In embodiments, $R^{24}$ is substituted C$_1$ alkyl. In embodiments, $R^{24}$ is substituted C$_2$ alkyl. In embodiments, $R^{24}$ is substituted C$_3$ alkyl. In embodiments, $R^{24}$ is substituted C$_4$ alkyl. In embodiments, $R^{24}$ is substituted C$_5$ alkyl. In embodiments, $R^{24}$ is substituted C$_6$ alkyl. In embodiments, $R^{24}$ is unsubstituted C$_1$ alkyl. In embodiments, $R^{24}$ is unsubstituted C$_2$ alkyl. In embodiments, $R^{24}$ is unsubstituted C$_3$ alkyl. In embodiments, $R^{24}$ is unsubstituted C$_4$ alkyl. In embodiments, $R^{24}$ is unsubstituted C$_5$ alkyl. In embodiments, $R^{24}$ is unsubstituted C$_6$ alkyl. In embodiments, $R^{24}$ is a substituted or unsubstituted alkyl (e.g., C$_1$-C$_6$ alkyl), wherein $R^{24}$ is independently substituted with a substituent group selected from —PO$_3$H, —PO$_4$H, —SO$_2$NH$_2$, —SO$_3$H, or —SO$_4$H. In embodiments, $R^{23}$ is substituted or unsubstituted C$_1$ alkyl. In embodiments, $R^{23}$ is substituted or unsubstituted C$_2$ alkyl. In embodiments, $R^{23}$ is substituted or unsubstituted C$_3$ alkyl. In embodiments, $R^{23}$ is substituted or unsubstituted C$_4$ alkyl. In embodiments, $R^{23}$ is substituted or unsubstituted C$_5$ alkyl. In embodiments, $R^{23}$ is substituted or unsubstituted C$_6$ alkyl. In embodiments, $R^{23}$ is substituted C$_1$ alkyl. In embodiments, $R^{23}$ is substituted C$_2$ alkyl. In embodiments, $R^{23}$ is substituted C$_3$ alkyl. In embodiments, $R^{23}$ is substituted C$_4$ alkyl. In embodiments, $R^{23}$ is substituted C$_5$ alkyl. In embodiments, $R^{23}$ is substituted C$_6$ alkyl. In embodiments, $R^{23}$ is unsubstituted C$_1$ alkyl. In embodiments, $R^{23}$ is unsubstituted C$_2$ alkyl. In embodiments, $R^{23}$ is unsubstituted C$_3$ alkyl. In embodiments, $R^{23}$ is unsubstituted C$_4$ alkyl. In embodiments, $R^{23}$ is unsubstituted C$_5$ alkyl. In embodiments, $R^{23}$ is unsubstituted C$_6$ alkyl. In embodiments, $R^{23}$ is a substituted or unsubstituted alkyl (e.g., C$_1$-C$_6$ alkyl), wherein $R^{23}$ is independently substituted with a substituent group selected from —PO$_3$H, —PO$_4$H, —SO$_2$NH$_2$, —SO$_3$H, or —SO$_4$H.

In embodiments, the compound has the formula:

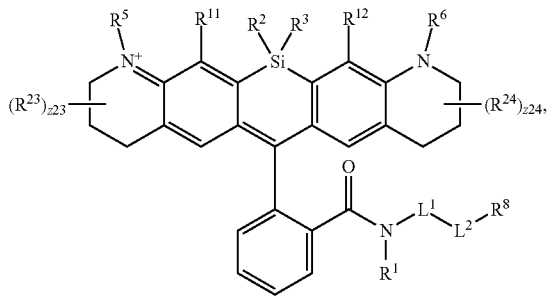

wherein $R^5$, $R^{11}$, $R^{12}$, $R^2$, $R^3$, $R^6$, $R^1$, $L^1$, $L^2$ and $R^8$ are as described herein, including embodiments. $R^{23}$ and $R^{24}$ are independently a substituent group, a size-limited substituent group, or lower substituent group. The symbols z23 and z24 are independently integers from 0 to 6. In embodiments, z23 is 0. In embodiments, z23 is 1. In embodiments, z23 is 2. In embodiments, z23 is 3. In embodiments, z23 is 4. In embodiments, z23 is 5. In embodiments, z23 is 6. In embodiments, z24 is 0. In embodiments, z24 is 1. In embodiments, z24 is 2. In embodiments, z24 is 3. In embodiments, z24 is 4. In embodiments, z24 is 5. In embodiments, z24 is 6.

In embodiments, the compound has the formula:

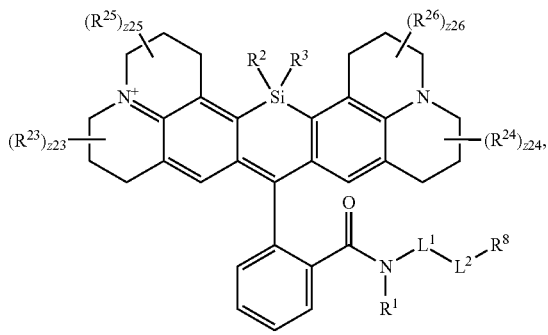

wherein $R^2$, $R^3$, $R^1$, $L^1$, $L^2$, and $R^8$ are as described herein, including embodiments. $R^{23}$, $R^{24}$, $R^{25}$, and $R^{26}$ are independently a substituent group, a size-limited substituent group, or lower substituent group. The symbols z23, z24, z25, and z26 are independently integers from 0 to 6. In embodiments, z25 is 0. In embodiments, z25 is 1. In embodiments, z25 is 2. In embodiments, z25 is 3. In embodiments, z25 is 4. In embodiments, z25 is 5. In embodiments, z25 is 6. In embodiments, z26 is 0. In embodiments, z26 is 1. In embodiments, z26 is 2. In embodiments, z26 is 3. In embodiments, z26 is 4. In embodiments, z26 is 5. In embodiments, z26 is 6.

In embodiments, $R^{25}$ is independently oxo, halogen, —CF$_3$, —CCl$_3$, —CI$_3$, —CBr$_3$, —CHF$_2$, —CHCl$_2$, —CHI$_2$, —CHBr$_2$, —CH$_2$F, —CH$_2$Cl, —CH$_2$I, —CH$_2$Br, —OCH$_2$F, —OCH$_2$Cl, —OCH$_2$I, —OCH$_2$Br, —OCHF$_2$, —OCHCl$_2$, —OCHI$_2$, —OCHBr$_2$, —OCF$_3$, —OCCl$_3$, —OCI$_3$, —OCBr$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —PO$_4$H, —PO$_3$H, —N$_3$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{10}$ or phenyl), or substituted or unsubstituted heteroaryl (e.g., 5 to 10 membered, 5 to 9 membered, or 5 to 6 membered).

In embodiments, $R^{26}$ is independently oxo, halogen, —CF$_3$, —CCl$_3$, —CI$_3$, —CBr$_3$, —CHF$_2$, —CHCl$_2$, —CHI$_2$, —CHBr$_2$, —CH$_2$F, —CH$_2$Cl, —CH$_2$I, —CH$_2$Br, —OCH$_2$F, —OCH$_2$Cl, —OCH$_2$I, —OCH$_2$Br, —OCHF$_2$, —OCHCl$_2$, —OCHI$_2$, —OCHBr$_2$, —OCF$_3$, —OCCl$_3$, —OCI$_3$, —OCBr$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —PO$_4$H, —PO$_3$H, —N$_3$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{10}$ or phenyl), or substituted or unsubstituted heteroaryl (e.g., 5 to 10 membered, 5 to 9 membered, or 5 to 6 membered).

In embodiments, $R^{25}$ is substituted or unsubstituted C$_1$ alkyl. In embodiments, $R^{25}$ is substituted or unsubstituted C$_2$ alkyl. In embodiments, $R^{25}$ is substituted or unsubstituted C$_3$ alkyl. In embodiments, $R^{25}$ is substituted or unsubstituted C$_4$ alkyl. In embodiments, $R^{25}$ is substituted or unsubstituted C$_5$ alkyl. In embodiments, $R^{25}$ is substituted or unsubstituted C$_6$ alkyl. In embodiments, $R^{25}$ is substituted C$_1$ alkyl. In embodiments, $R^{25}$ is substituted C$_2$ alkyl. In embodiments, $R^{25}$ is substituted C$_3$ alkyl. In embodiments, $R^{25}$ is substituted C$_4$ alkyl. In embodiments, $R^{25}$ is substituted C$_5$ alkyl. In embodiments, $R^{25}$ is substituted C$_6$ alkyl. In embodiments, $R^{25}$ is unsubstituted C$_1$ alkyl. In embodiments, $R^{25}$ is unsubstituted C$_2$ alkyl. In embodiments, $R^{25}$ is unsubstituted C$_3$ alkyl. In embodiments, $R^{25}$ is unsubstituted C$_4$ alkyl. In embodiments, $R^{25}$ is unsubstituted C$_5$ alkyl. In embodiments, $R^{25}$ is unsubstituted C$_6$ alkyl. In embodiments, $R^{25}$ is a substituted or unsubstituted alkyl (e.g., C$_1$-C$_6$ alkyl), wherein $R^{25}$ is independently substituted with a substituent group selected from —PO$_3$H, —PO$_4$H, —SO$_2$NH$_2$, —SO$_3$H, or —SO$_4$H. In embodiments, $R^{26}$ is substituted or unsubstituted C$_1$ alkyl. In embodiments, $R^{26}$ is substituted or unsubstituted C$_2$ alkyl. In embodiments, $R^{26}$ is substituted or unsubstituted C$_3$ alkyl. In embodiments, $R^{26}$ is substituted or unsubstituted C$_4$ alkyl. In embodiments, $R^{26}$ is substituted or unsubstituted C$_5$ alkyl. In embodiments, $R^{26}$ is substituted or unsubstituted C$_6$ alkyl. In embodiments, $R^{26}$ is substituted C$_1$ alkyl. In embodiments, $R^{26}$ is substituted C$_2$ alkyl. In embodiments, $R^{26}$ is substituted C$_3$ alkyl. In embodiments, $R^{26}$ is substituted C$_4$ alkyl. In embodiments, $R^{26}$ is substituted C$_5$ alkyl. In embodiments, $R^{26}$ is substituted C$_6$ alkyl. In embodiments, $R^{26}$ is unsubstituted C$_1$ alkyl. In embodiments, $R^{26}$ is unsubstituted C$_2$ alkyl. In embodiments, $R^{26}$ is unsubstituted C$_3$ alkyl. In embodiments, $R^{26}$ is unsubstituted C$_4$ alkyl. In embodiments, $R^{26}$ is unsubstituted C$_5$ alkyl. In embodiments, $R^{26}$ is unsubstituted C$_6$ alkyl. In embodiments, $R^{26}$ is a substituted or unsubstituted alkyl (e.g., C$_1$-C$_6$ alkyl), wherein $R^{26}$ is independently substituted with a substituent group selected from —PO$_3$H, —PO$_4$H, —SO$_2$NH$_2$, —SO$_3$H, or —SO$_4$H.

In embodiments, the compound has the formula:

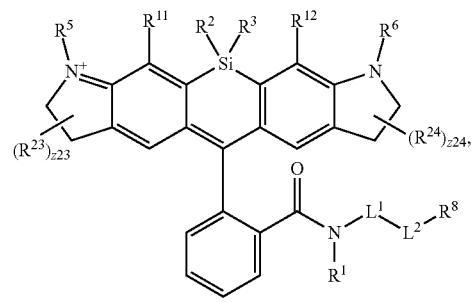

wherein $R^2$, $R^3$, $R^5$, $R^{11}$, $R^{12}$, $R^6$, $R^1$, $L^1$, $L^2$, and $R^8$ are as described herein, including embodiments. $R^{23}$ and $R^{24}$ are independently a substituent group, a size-limited substituent group, or lower substituent group. The symbols z23 and z24 are independently integers from 0 to 6. In embodiments, the compound has the formula:

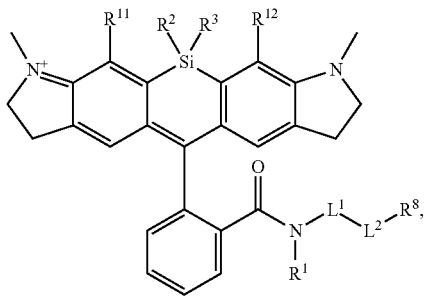

wherein $R^2$, $R^3$, $R^{11}$, $R^{12}$, $R^1$, $L^1$, $L^2$, and $R^8$ are as described herein, including embodiments. In embodiments, the compound has the formula:

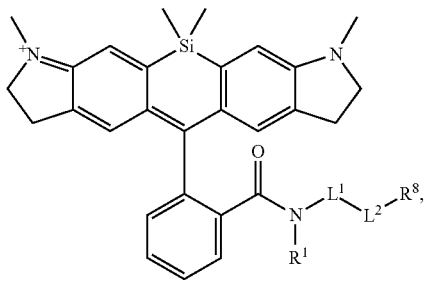

wherein $R^1$, $L^1$, $L^2$, and $R^8$ are as described herein, including embodiments. In embodiments, the compound has the formula:

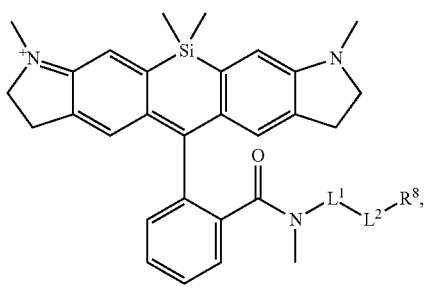

wherein $L^1$, $L^2$ and $R^8$ are as described herein, including embodiments. In embodiments, the compound has the formula:

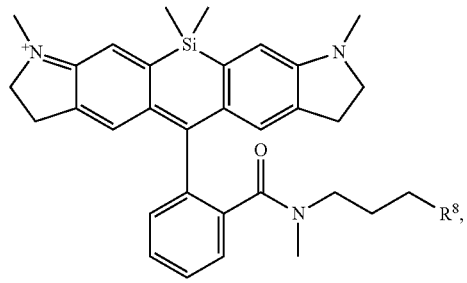

Wherein $R^8$ is as described herein, including embodiments.
In embodiments, the compound has the formula:

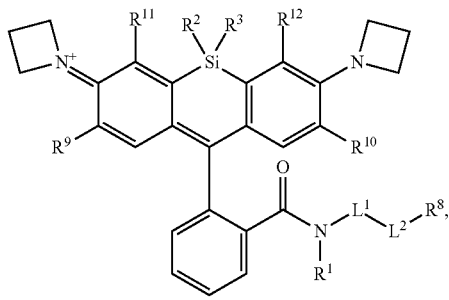

wherein $R^2$, $R^3$, $R^{11}$, $R^{12}$, $R^9$, $R^{10}$, $L^1$, $R^1$, $L^2$, and $R^8$ are as described herein, including embodiments.
In embodiments, the compound has the formula:

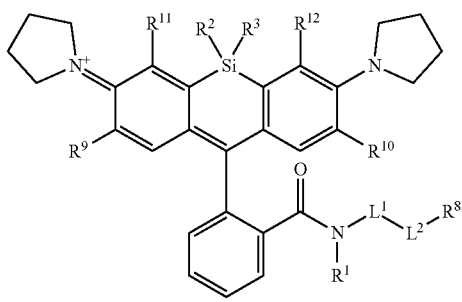

wherein $R^2$, $R^3$, $R^{11}$, $R^{12}$, $R^9$, $R^{10}$, $L^1$, $R^1$, $L^2$, and $R^8$ are as described herein, including embodiments.
In embodiments, the compound has the formula:

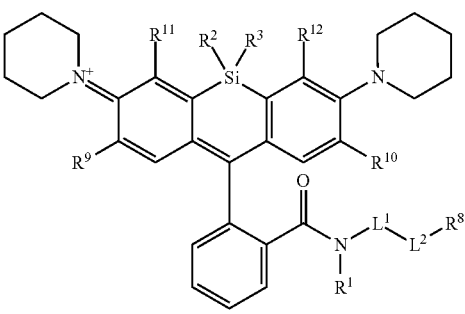

wherein $R^2$, $R^3$, $R^{11}$, $R^{12}$, $R^9$, $R^{10}$, $L^1$, $R^1$, $L^2$, and $R^8$ are as described herein, including embodiments.

In embodiments, the compound has the formula:

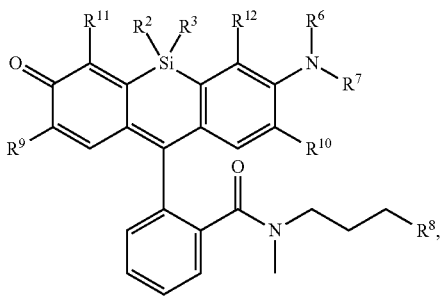

wherein $R^2$, $R^3$, $R^{11}$, $R^{12}$, $R^9$, $R^{10}$, $L^1$, $R^1$, $L^2$, and $R^8$ are as described herein, including embodiments.

In embodiments, the compound has the formula:

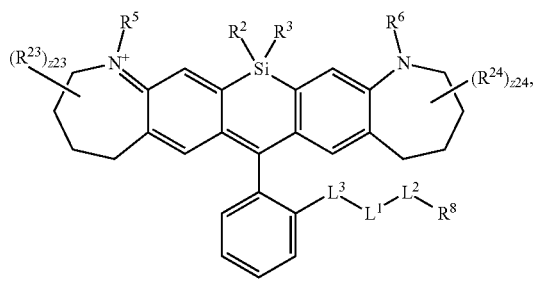

wherein $R^5$, $R^6$, $R^2$, $R^3$, $L^1$, $L^2$, and $R^8$ are as described herein, including embodiments; and $L^3$ is independently

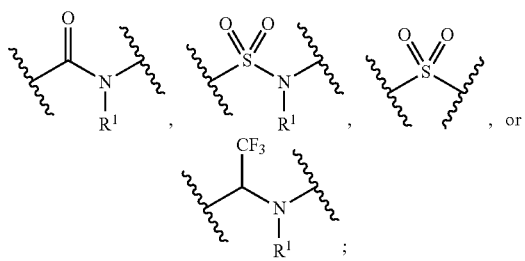

and $R^1$ is as described herein, including in embodiments. $R^{23}$ and $R^{24}$ are independently a substituent group, a size-limited substituent group, or lower substituent group. The symbols z23 and z24 are independently integers from 0 to 6.

In embodiments, the compound has the formula:

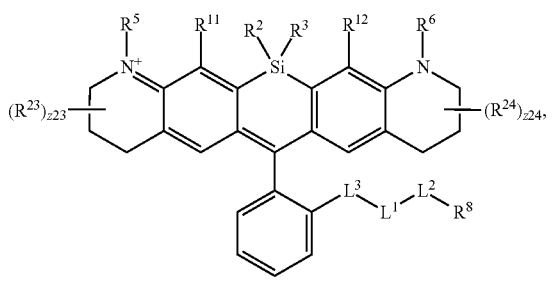

wherein $R^5$, $R^{11}$, $R^{12}$, $R^2$, $R^3$, $R^6$, $L^1$, $L^2$, and $R^8$ are as described herein, including embodiments; and $L^3$ is independently

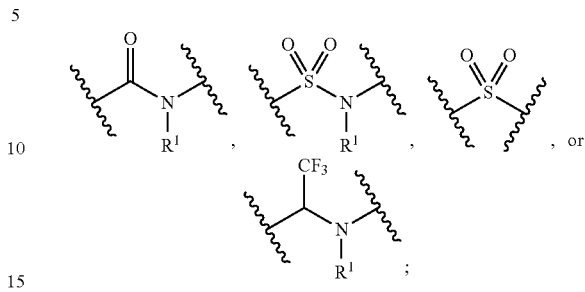

and $R^1$ is as described herein, including in embodiments. $R^{23}$ and $R^{24}$ are independently a substituent group, a size-limited substituent group, or lower substituent group. The symbols z23 and z24 are independently integers from 0 to 6. In embodiments, z23 is 0. In embodiments, z23 is 1. In embodiments, z23 is 2. In embodiments, z23 is 3. In embodiments, z23 is 4. In embodiments, z23 is 5. In embodiments, z23 is 6. In embodiments, z24 is 0. In embodiments, z24 is 1. In embodiments, z24 is 2. In embodiments, z24 is 3. In embodiments, z24 is 4. In embodiments, z24 is 5. In embodiments, z24 is 6.

In embodiments, the compound has the formula:

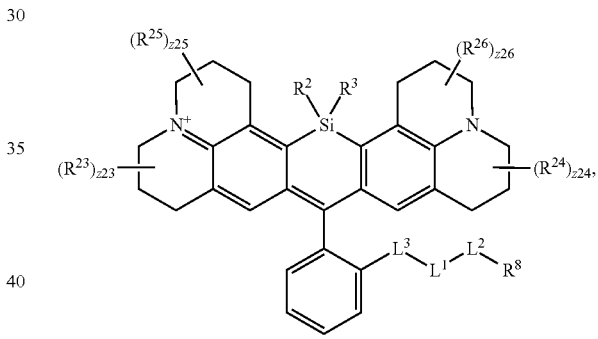

wherein $R^2$, $R^3$, $L^1$, $L^2$, and $R^8$ are as described herein, including embodiments; and $L^3$ is independently

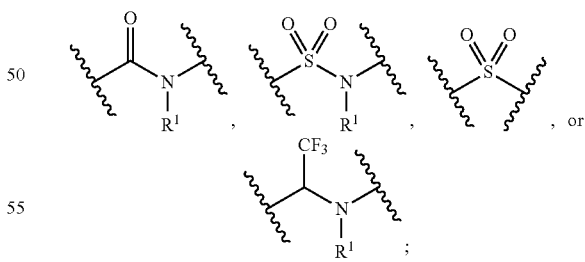

and $R^1$ is as described herein, including in embodiments. $R^{23}$, $R^{24}$, $R^{25}$, and $R^{26}$ are independently a substituent group, a size-limited substituent group, or lower substituent group. The symbols z23, z24, z25, and z26 are independently integers from 0 to 6. In embodiments, z25 is 0. In embodiments, z25 is 1. In embodiments, z25 is 2. In embodiments, z25 is 3. In embodiments, z25 is 4. In embodiments, z25 is 5. In embodiments, z25 is 6. In embodiments, z26 is 0. In embodiments, z26 is 1. In embodiments, z26 is 2. In embodiments, z26 is 3. In embodiments, z26 is 4. In embodiments, z26 is 5. In embodiments, z26 is 6.

In embodiments, the compound has the formula:

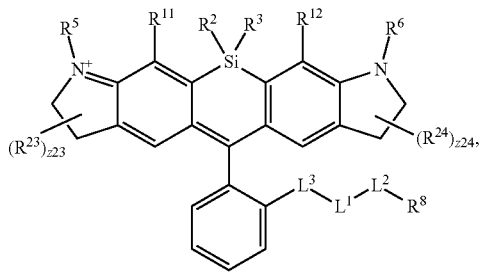

wherein $R^2$, $R^3$, $R^5$, $R^{11}$, $R^{12}$, $L^1$, $L^2$, and $R^8$ are as described herein, including embodiments; and $L^3$ is independently

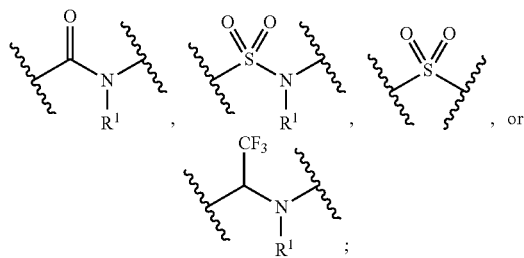

and $R^1$ is as described herein, including in embodiments. $R^{23}$ and $R^{24}$ are independently a substituent group, a size-limited substituent group, or lower substituent group. The symbols z23 and z24 are independently integers from 0 to 6. In embodiments, z23 is 1. In embodiments, z24 is 1. In embodiments, $R^{24}$ is substituted or unsubstituted $C_1$ alkyl. In embodiments, $R^{24}$ is substituted or unsubstituted $C_2$ alkyl. In embodiments, $R^{24}$ is substituted or unsubstituted $C_3$ alkyl. In embodiments, $R^{24}$ is substituted or unsubstituted $C_4$ alkyl. In embodiments, $R^{24}$ is substituted or unsubstituted $C_5$ alkyl. In embodiments, $R^{24}$ is substituted or unsubstituted $C_6$ alkyl. In embodiments, $R^{24}$ is substituted $C_1$ alkyl. In embodiments, $R^{24}$ is substituted $C_2$ alkyl. In embodiments, $R^{24}$ is substituted $C_3$ alkyl. In embodiments, $R^{24}$ is substituted $C_4$ alkyl. In embodiments, $R^{24}$ is substituted $C_5$ alkyl. In embodiments, $R^{24}$ is substituted $C_6$ alkyl. In embodiments, $R^{24}$ is unsubstituted $C_1$ alkyl. In embodiments, $R^{24}$ is unsubstituted $C_2$ alkyl. In embodiments, $R^{24}$ is unsubstituted $C_3$ alkyl. In embodiments, $R^{24}$ is unsubstituted $C_4$ alkyl. In embodiments, $R^{24}$ is unsubstituted $C_5$ alkyl. In embodiments, $R^{24}$ is unsubstituted $C_6$ alkyl. In embodiments, $R^{24}$ is a substituted or unsubstituted alkyl (e.g., $C_1$-$C_6$ alkyl), wherein $R^{24}$ is independently substituted with a substituent group selected from —$PO_3H$, —$PO_4H$, —$SO_2NH_2$, —$SO_3H$, or —$SO_4H$. In embodiments, $R^{23}$ is substituted or unsubstituted $C_1$ alkyl. In embodiments, $R^{23}$ is substituted or unsubstituted $C_2$ alkyl. In embodiments, $R^{23}$ is substituted or unsubstituted $C_3$ alkyl. In embodiments, $R^{23}$ is substituted or unsubstituted $C_4$ alkyl. In embodiments, $R^{23}$ is substituted or unsubstituted $C_5$ alkyl. In embodiments, $R^{23}$ is substituted or unsubstituted $C_6$ alkyl. In embodiments, $R^{23}$ is substituted $C_1$ alkyl. In embodiments, $R^{23}$ is substituted $C_2$ alkyl. In embodiments, $R^{23}$ is substituted $C_3$ alkyl. In embodiments, $R^{23}$ is substituted $C_4$ alkyl. In embodiments, $R^{23}$ is substituted $C_5$ alkyl. In embodiments, $R^{23}$ is substituted $C_6$ alkyl. In embodiments, $R^{23}$ is unsubstituted $C_1$ alkyl. In embodiments, $R^{23}$ is unsubstituted $C_2$ alkyl. In embodiments, $R^{23}$ is unsubstituted $C_3$ alkyl. In embodiments, $R^{23}$ is unsubstituted $C_4$ alkyl. In embodiments, $R^{23}$ is unsubstituted $C_5$ alkyl. In embodiments, $R^{23}$ is unsubstituted $C_6$ alkyl. In embodiments, $R^{23}$ is a substituted or unsubstituted alkyl (e.g., $C_1$-$C_6$ alkyl), wherein $R^{23}$ is independently substituted with a substituent group selected from —$PO_3H$, —$PO_4H$, —$SO_2NH_2$, —$SO_3H$, or —$SO_4H$.

In embodiments, the compound has the formula:

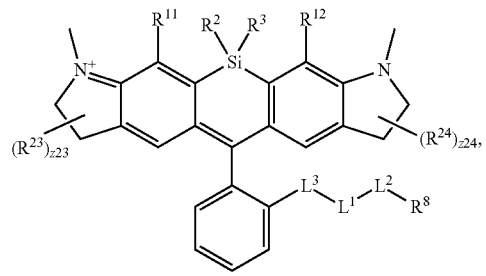

wherein $R^2$, $R^3$, $R^{11}$, $R^{12}$, $L^1$, $L^2$, and $R^8$ are as described herein, including embodiments; and $L^3$ is independently

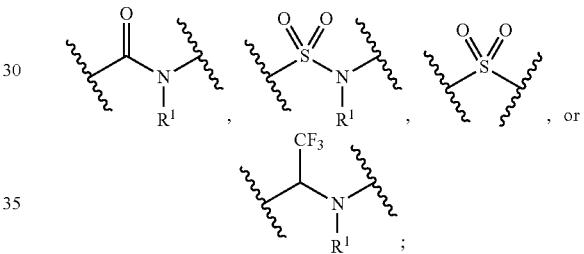

and $R^1$ is as described herein, including in embodiments. $R^{23}$ and $R^{24}$ are independently a substituent group, a size-limited substituent group, or lower substituent group. The symbols z23 and z24 are independently integers from 0 to 6. In embodiments, z23 is 0. In embodiments, z23 is 1. In embodiments, z23 is 2. In embodiments, z23 is 3. In embodiments, z23 is 4. In embodiments, z23 is 5. In embodiments, z23 is 6. In embodiments, z24 is 0. In embodiments, z24 is 1. In embodiments, z24 is 2. In embodiments, z24 is 3. In embodiments, z24 is 4. In embodiments, z24 is 5. In embodiments, z24 is 6.

In embodiments, the compound has the formula:

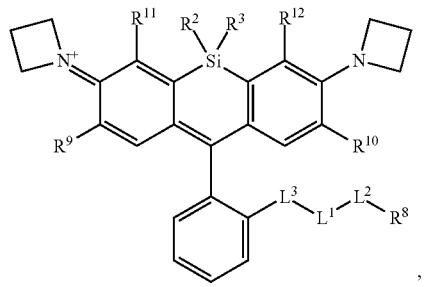

wherein $R^2$, $R^3$, $R^{11}$, $R^{12}$, $R^9$, $R^{10}$, $L^1$, $L^2$, and $R^8$ are as described herein, including embodiments; and $L^3$ is independently

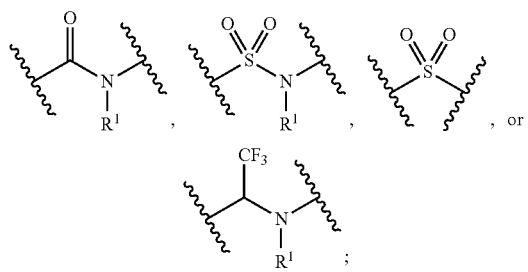

and R[1] is as described herein, including in embodiments.

In embodiments, the compound has the formula:

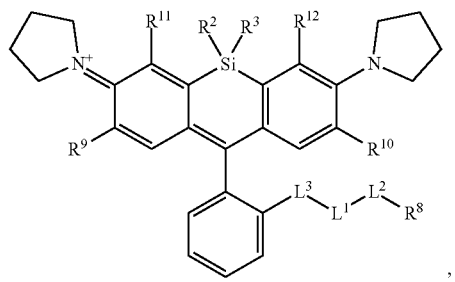

wherein R[2], R[3], R[11], R[12], R[9], R[10], L[1], L[2], and R[8] are as described herein, including embodiments; and L[3] is independently

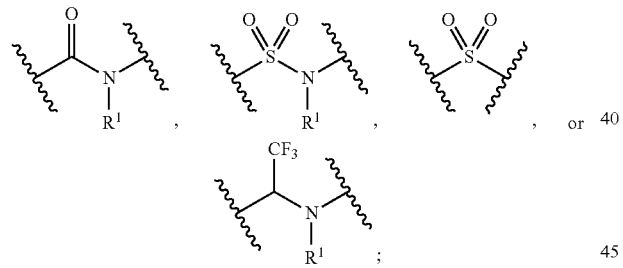

and R[1] is as described herein, including in embodiments.

In embodiments, the compound has the formula:

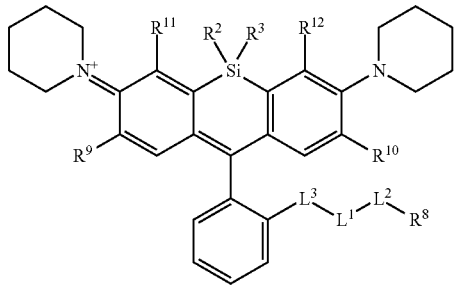

wherein R[2], R[3], R[11], R[12], R[9], R[10], L[1], L[2], and R[8] are as described herein, including embodiments; and L[3] is independently

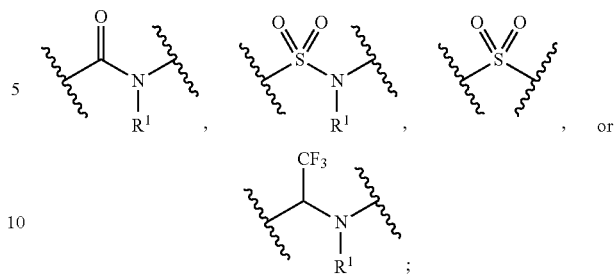

and R[1] is as described herein, including in embodiments.

In embodiments, the compound has the formula:

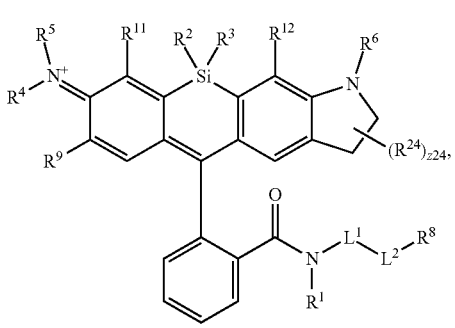

wherein R[1], L[1], L[2], R[2], R[3], R[4], R[5], R[6], R[9], R[11], R[12], R[8], R[24] and z24 are as described herein. In embodiments, the compound has the formula:

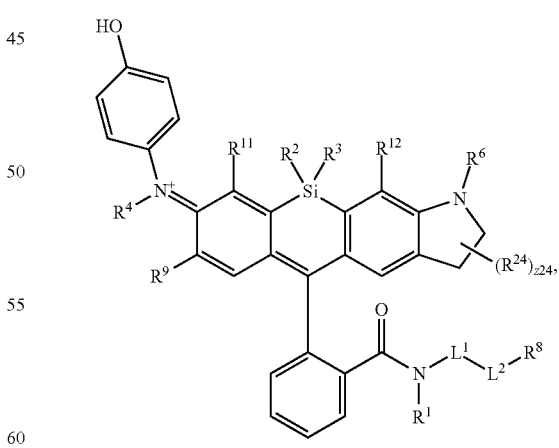

wherein R[1], L[1], L[2], R[2], R[3], R[4], R[6], R[9], R[11], R[12], R[8], R[24] and z24 are as described herein. In embodiments the compound has the formula:

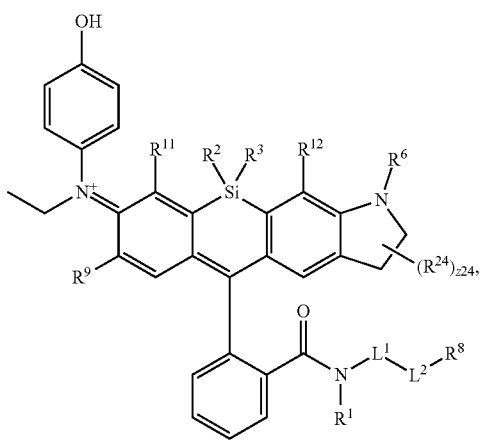

wherein $R^1, L^1, L^2, R^2, R^3, R^6, R^9, R^{11}, R^{12}, R^8, R^{24}$ and z24 are as described herein. In embodiments, the compound has the formula:

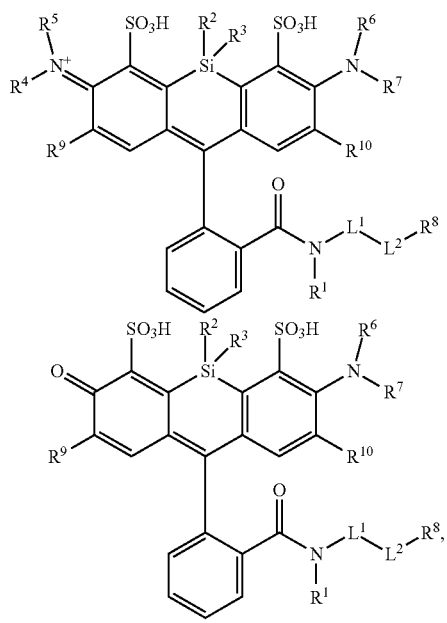

or wherein $R^1, L^1, L^2, R^2, R^3, R^4, R^5, R^6, R^7, R^9$, and $R^8$ are as described herein. In embodiments, the compound has the formula:

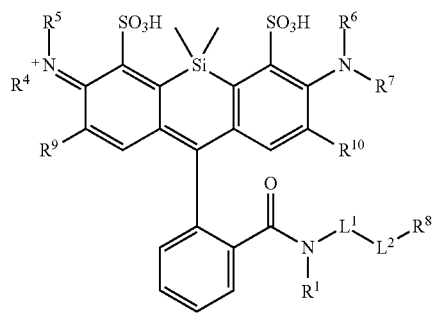

or

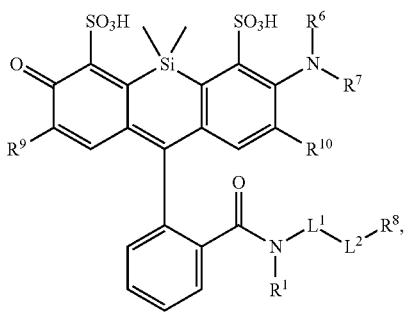

wherein $R^1, L^1, L^2, R^4, R^5, R^6, R^7, R^9$, and $R^8$ are as described herein. In embodiments, the compound has the formula:

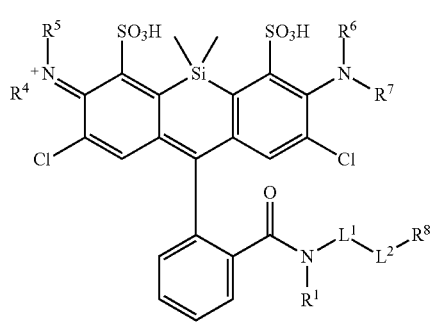

or wherein $R^1, L^1, L^2, R^4, R^5, R^6, R^7$, and $R^8$ are as described herein. In embodiments, the compound has the formula:

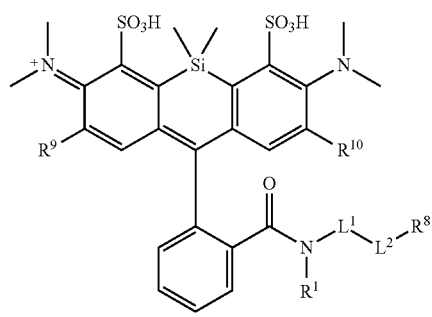

or

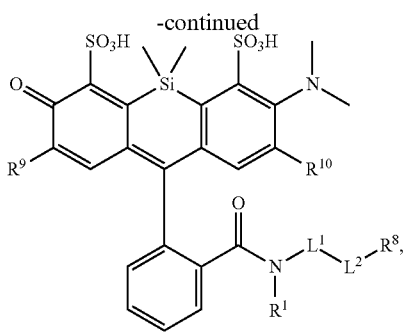

wherein $R^1$, $L^1$, $L^2$, $R^9$, and $R^8$ are as described herein. In embodiments, the compound has the formula:

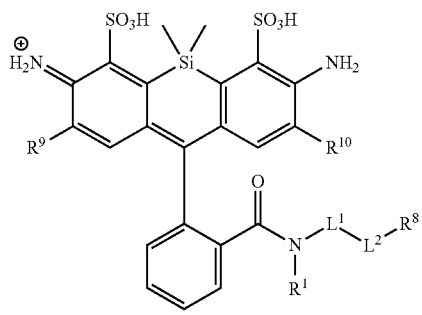

or

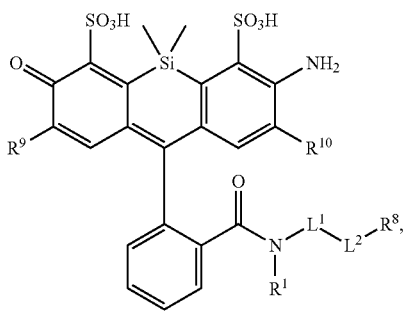

wherein $R^1$, $L^1$, $L^2$, $R^9$, and $R^8$ are as described herein. In embodiments, the compound has the formula:

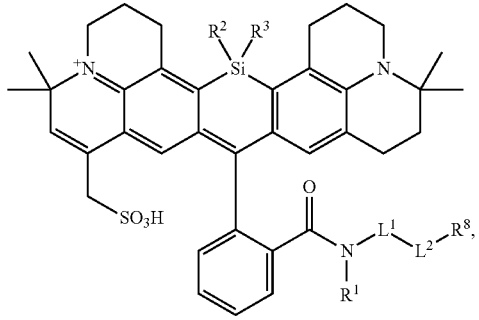

wherein $R^1$, $L^1$, $L^2$, $R^2$, $R^3$, and $R^8$ are as described herein. In embodiments, the compound has the formula:

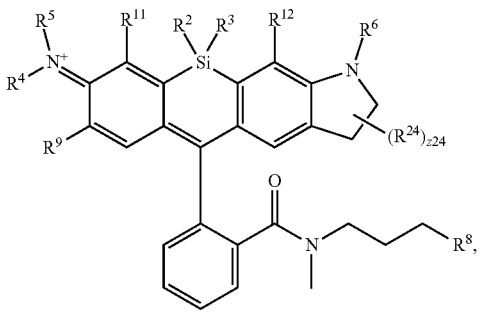

wherein $R^2$, $R^3$, $R^4$, $R^5$, $R^6$, $R^9$, $R^{11}$, $R^{12}$, $R^{24}$, and z24 are as described herein.

In embodiments, the compound has the formula:

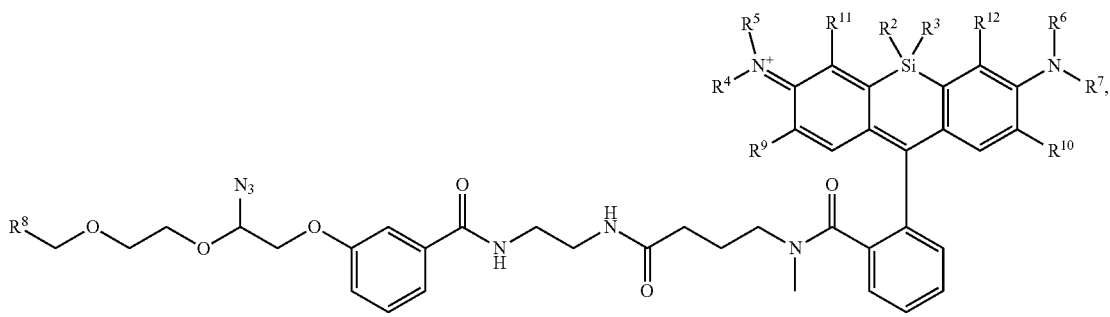

wherein $R^2$, $R^3$, $R^{11}$, $R^{12}$, $R^9$, $R^{10}$, and $R^8$ are as described herein, including embodiments.

In embodiments, the compound has the formula:

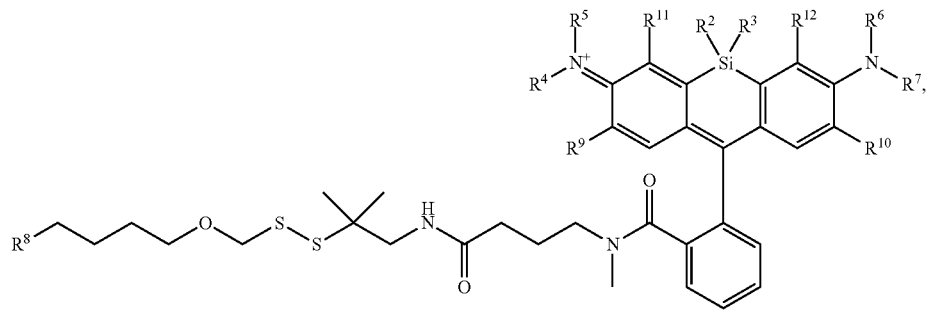

wherein $R^2$, $R^3$, $R^{11}$, $R^{12}$, $R^9$, $R^{10}$, and $R^8$ are as described herein, including embodiments.

In embodiments, the compound has the formula:

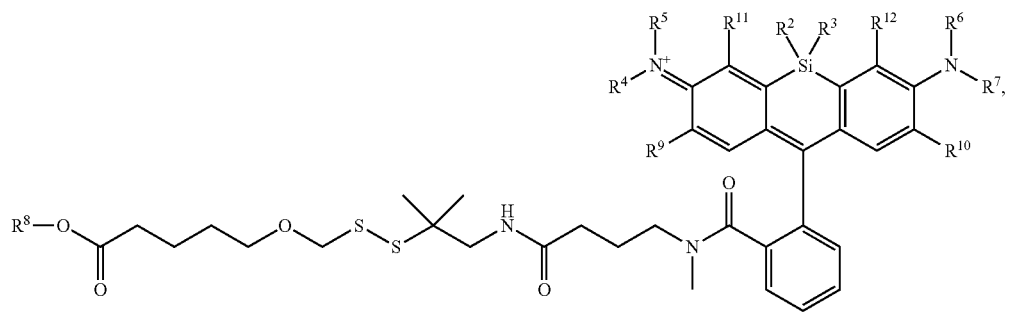

wherein $R^2$, $R^3$, $R^{11}$, $R^{12}$, $R^9$, $R^{10}$, and $R^8$ are as described herein, including embodiments.

In embodiments, the compound has the formula:

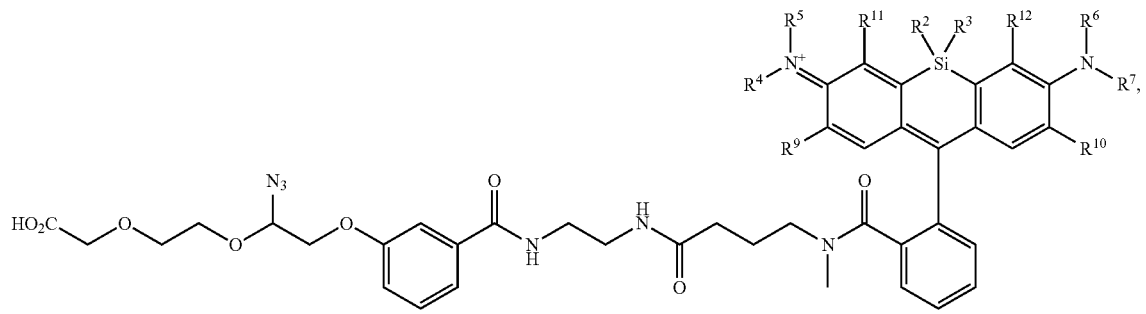

wherein $R^2$, $R^3$, $R^{11}$, $R^{12}$, $R^9$, and $R^{10}$ are as described herein, including embodiments.

In embodiments, the compound has the formula:

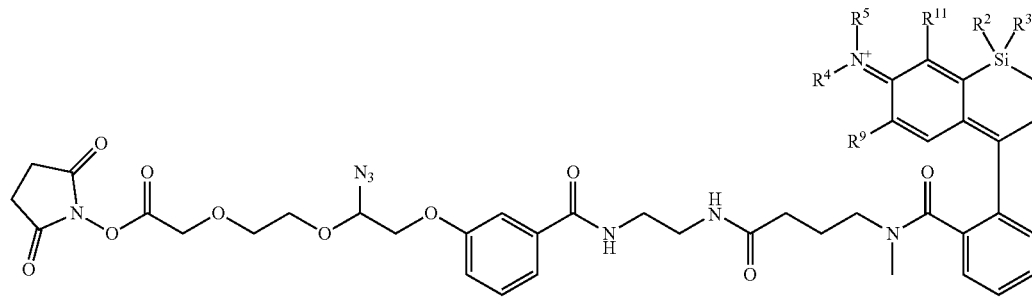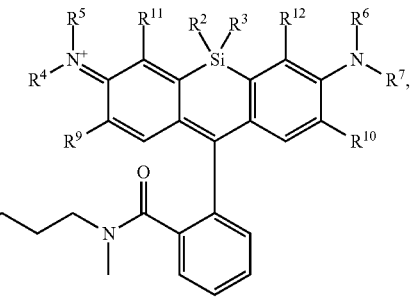

wherein R², R³, R¹¹, R¹², R⁹, and R¹⁰ are as described herein, including embodiments.

In embodiments, the compound has the formula:

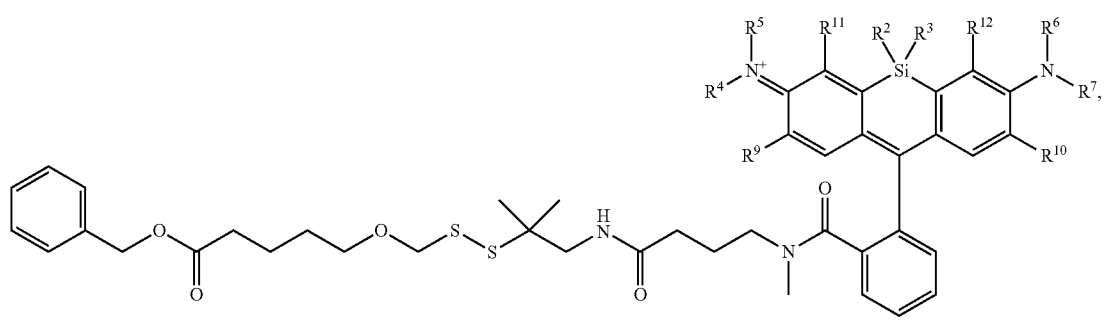

wherein R², R³, R¹¹, R¹², R⁹, and R¹⁰ are as described herein, including embodiments.

In embodiments, the compound has the formula:

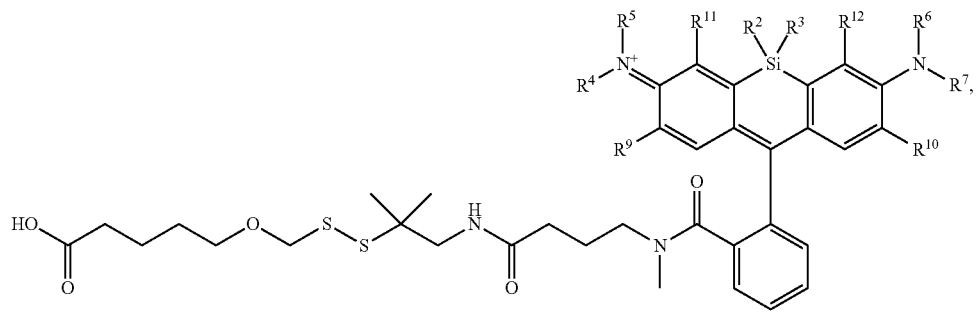

wherein R², R³, R¹¹, R¹², R⁹, and R¹⁰ are as described herein, including embodiments.

In embodiments, the compound has the formula:

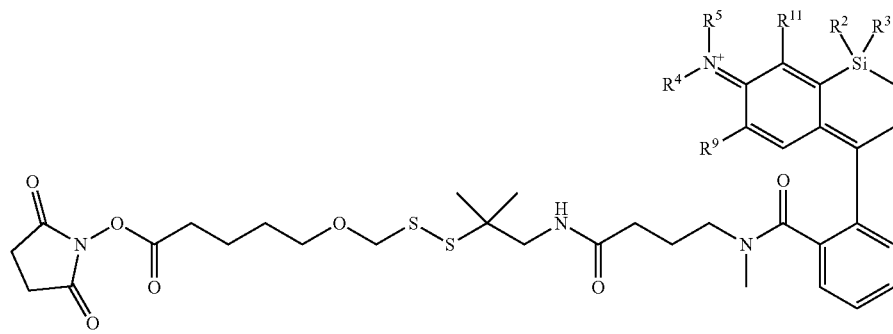

wherein $R^2$, $R^3$, $R^{11}$, $R^{12}$, $R^9$, and $R^{10}$ are as described herein, including embodiments.

In embodiments, the compound has the formula:

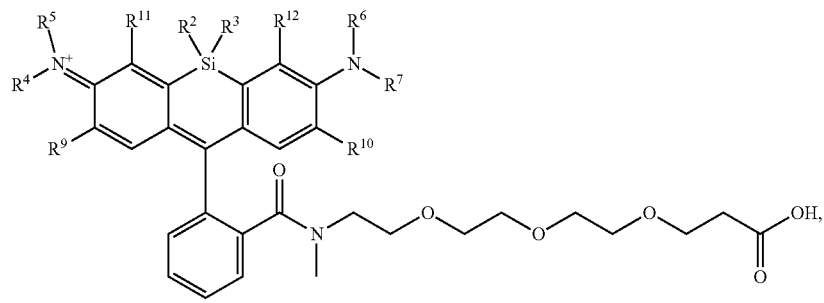

wherein $R^2$, $R^3$, $R^{11}$, $R^{12}$, $R^9$, and $R^{10}$ are as described herein, including embodiments.

In embodiments, the compound has the formula:

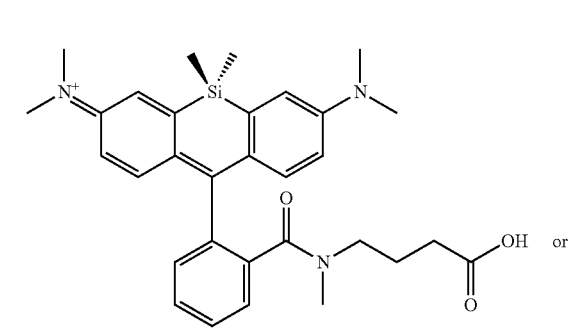 or

In embodiments, the compound has the formula:

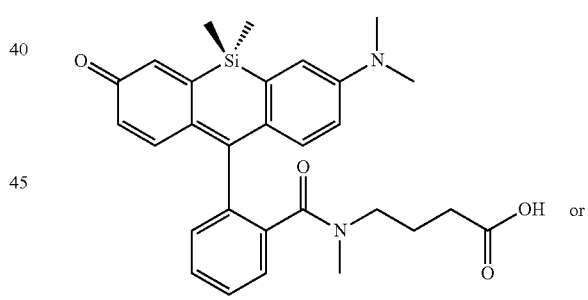 or

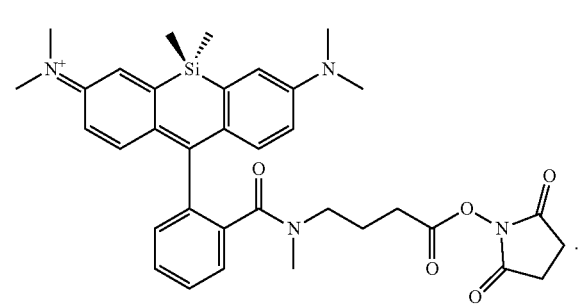

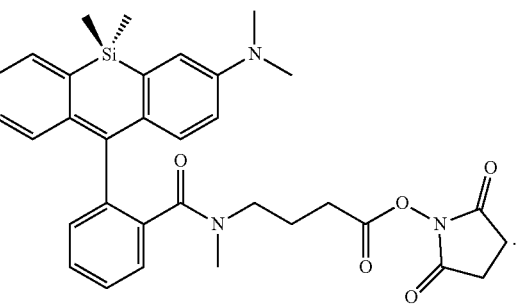

In embodiments, the compound has the formula:
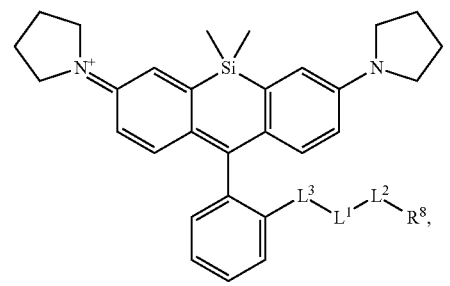
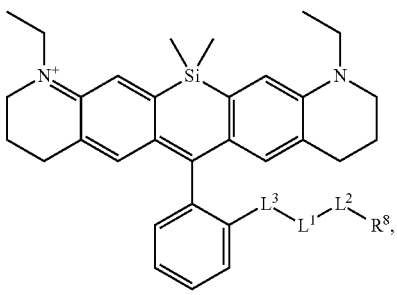
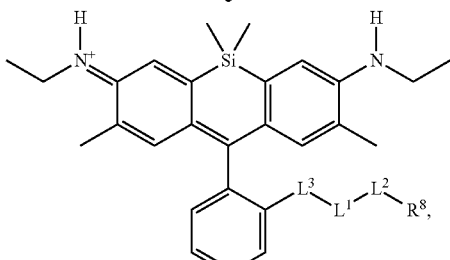
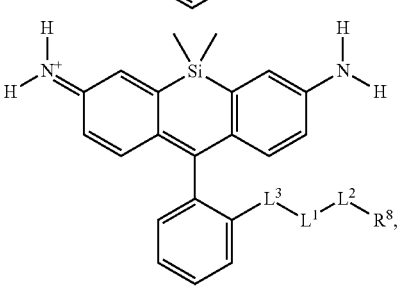
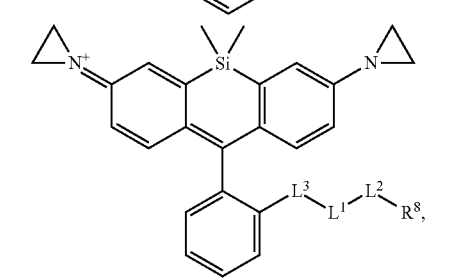
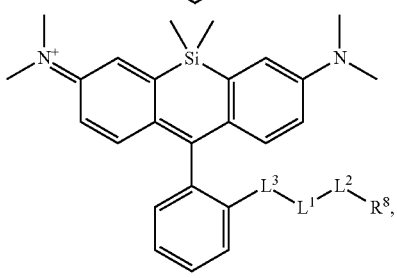
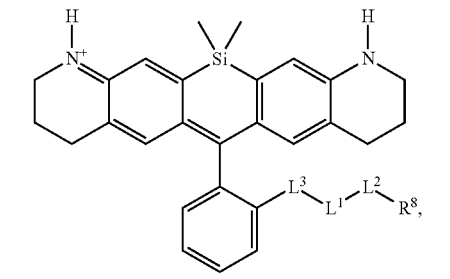
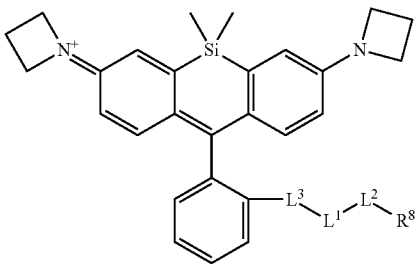
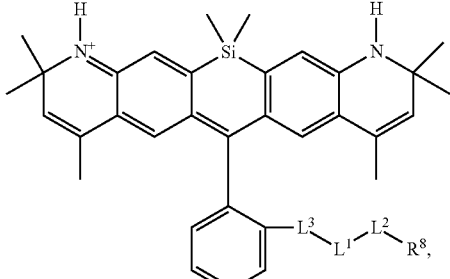
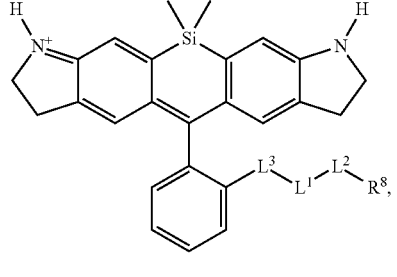
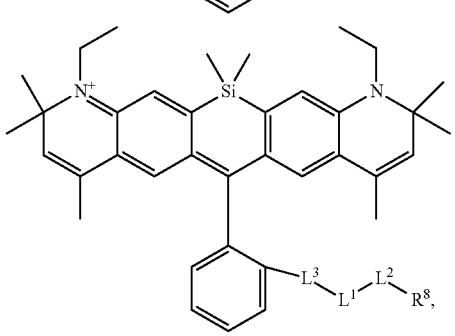
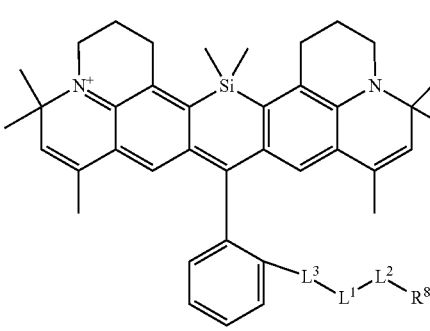

205
-continued
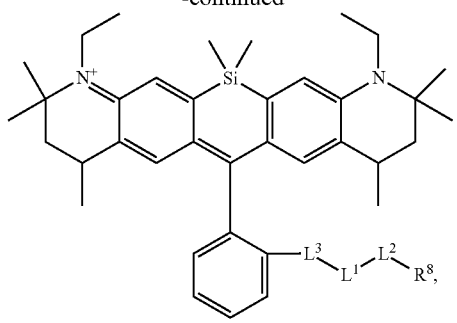
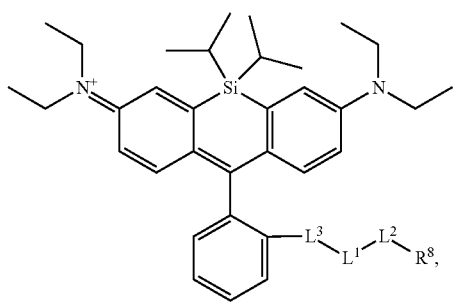
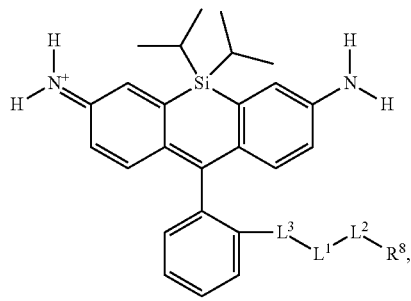
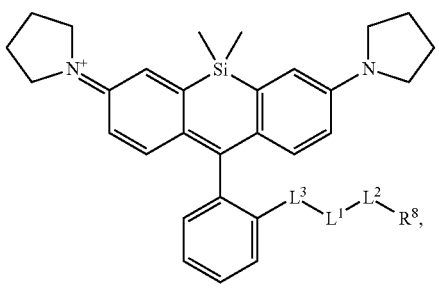
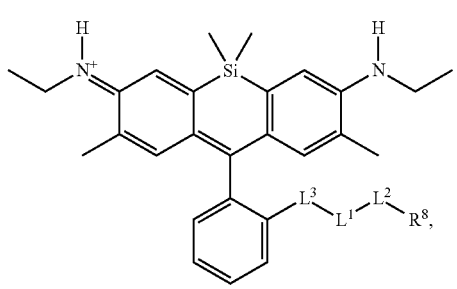
206
-continued
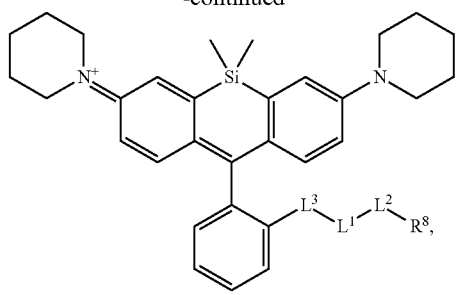
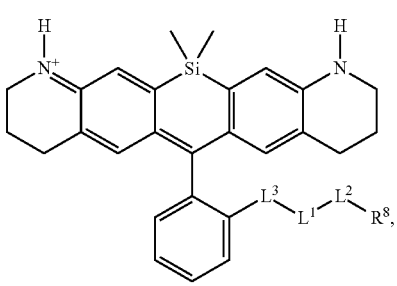
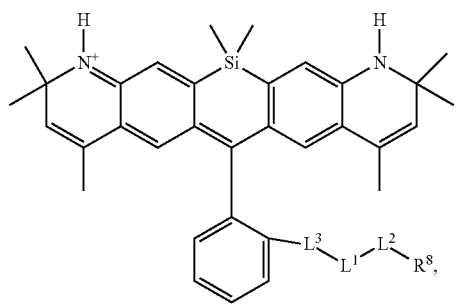
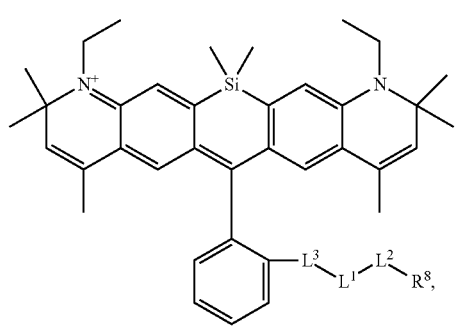
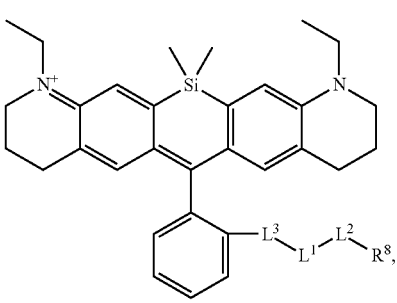

207
-continued
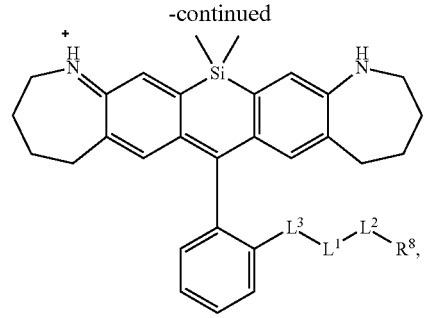
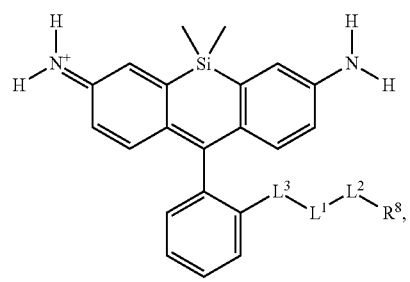
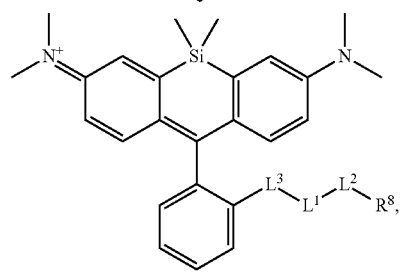
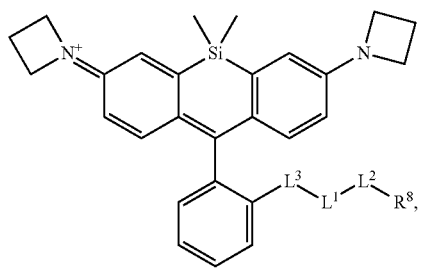
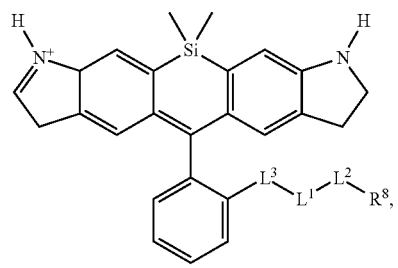
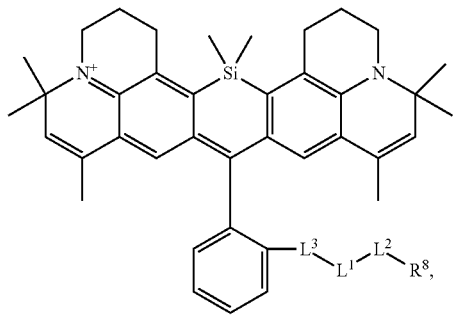
208
-continued
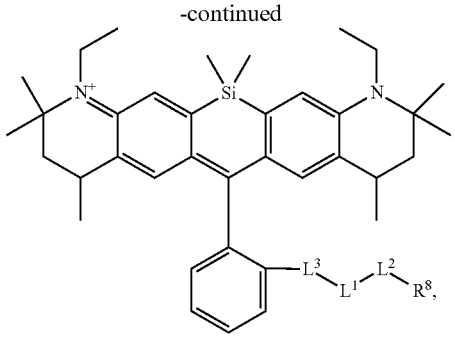
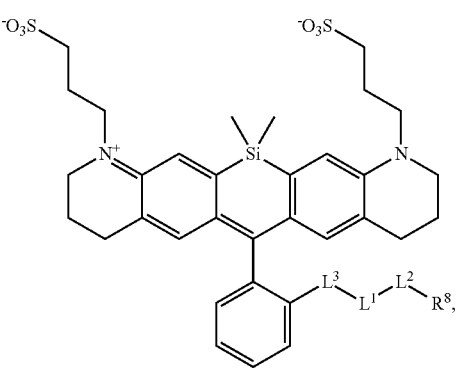
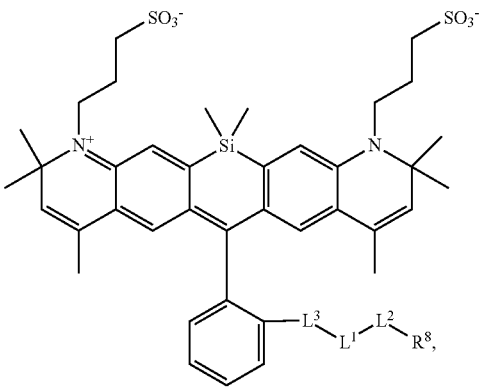
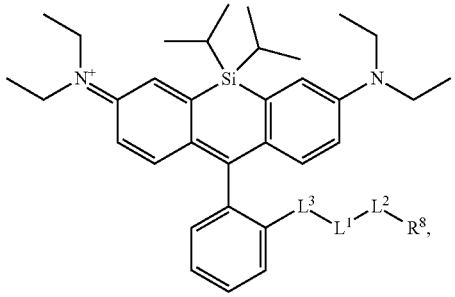
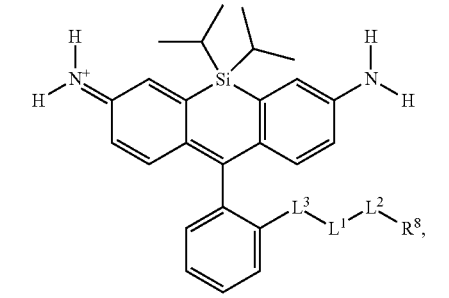

209
-continued
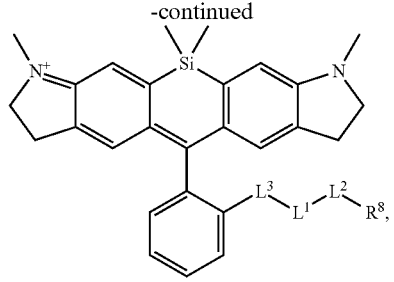
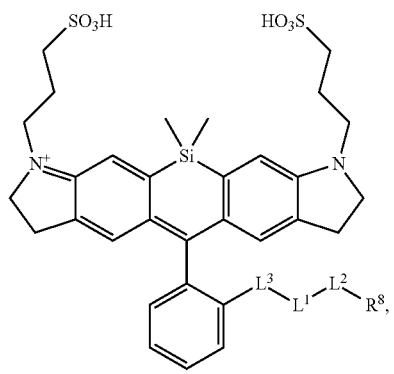
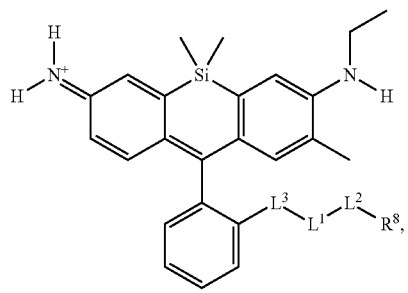
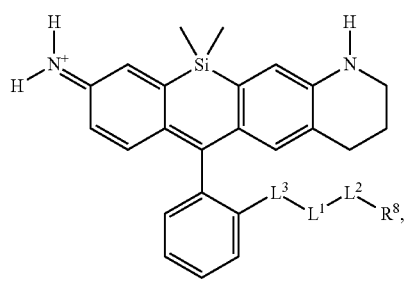
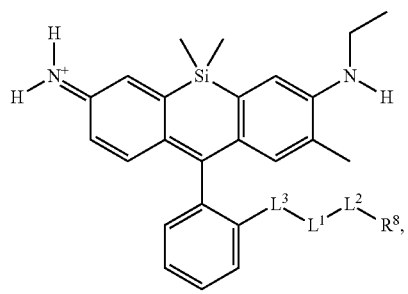
210
-continued
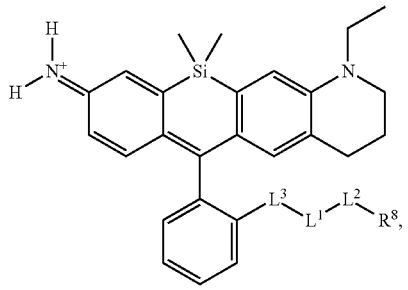
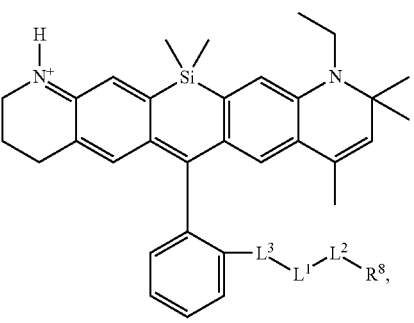
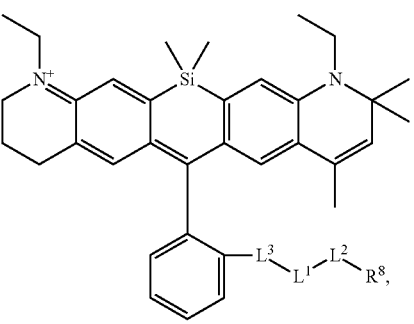
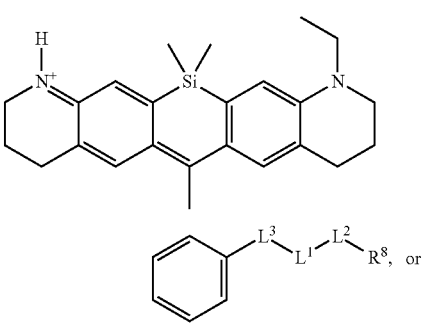, or
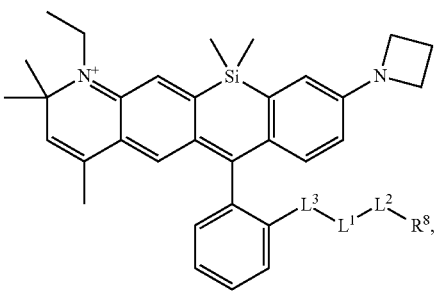
wherein $L^3$, $L^1$, $L^2$, and $R^8$ are as described herein, including embodiments.

In embodiments, the compound has the formula:
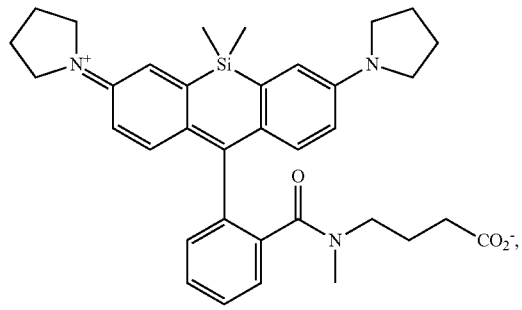
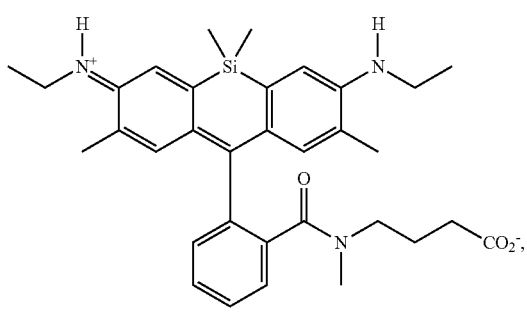
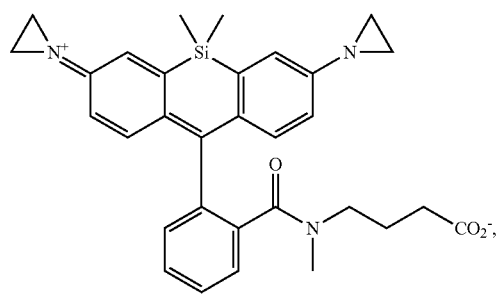
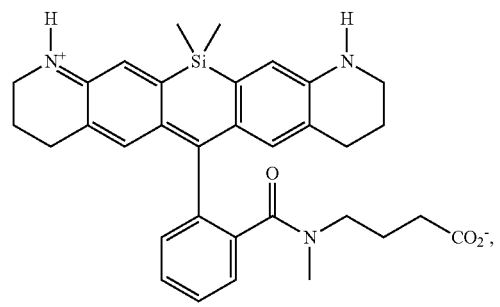
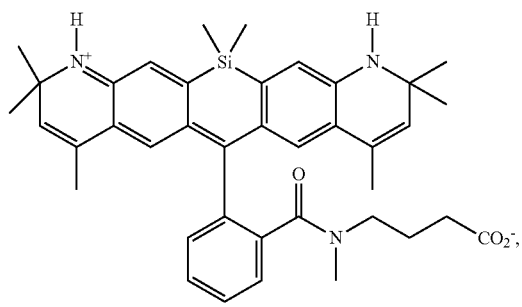
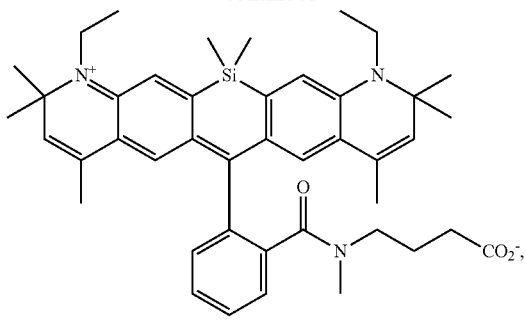
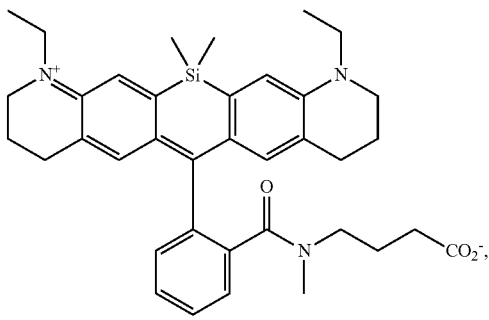
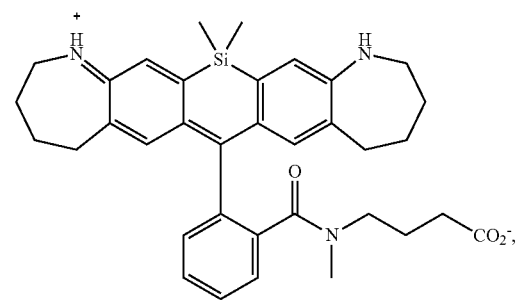
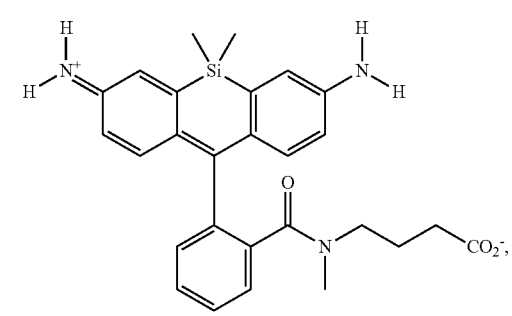
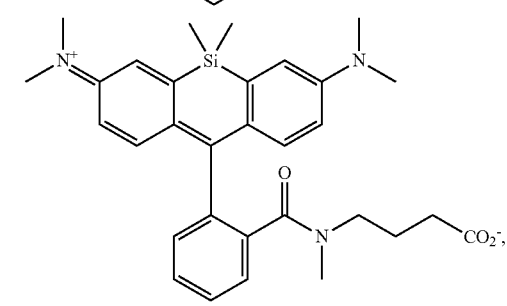

213
-continued
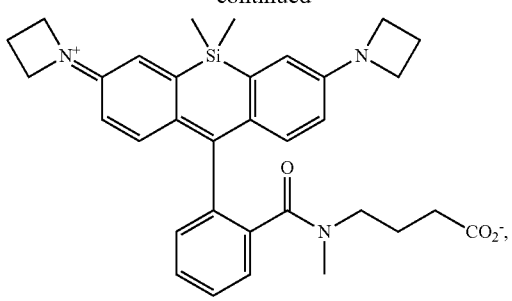
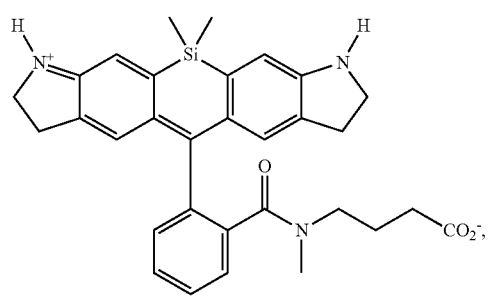
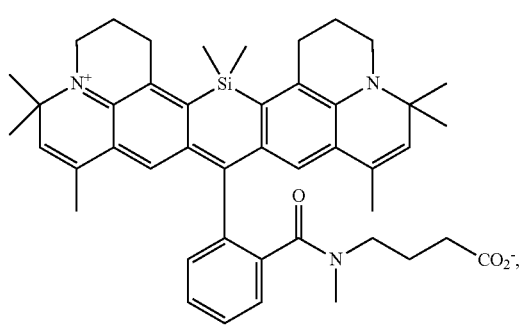
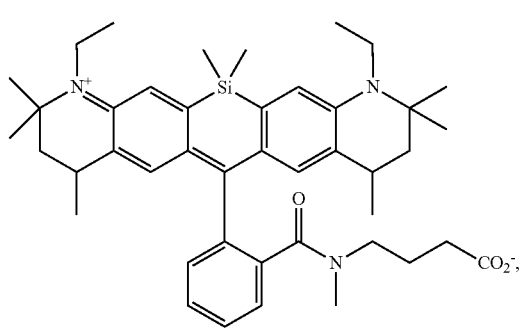
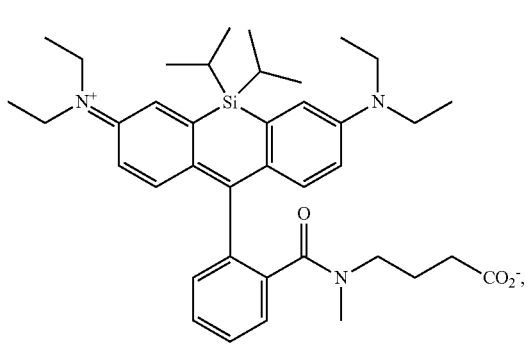
214
-continued
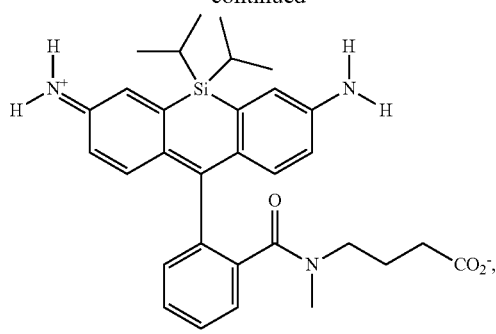
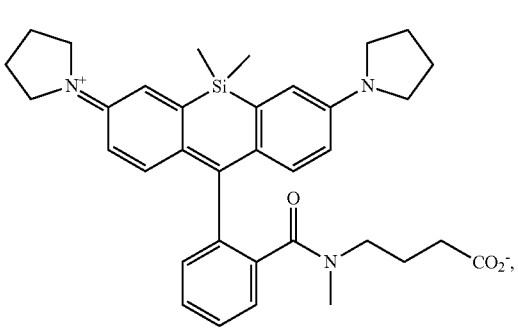
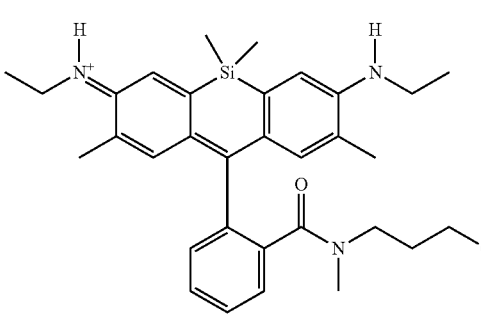
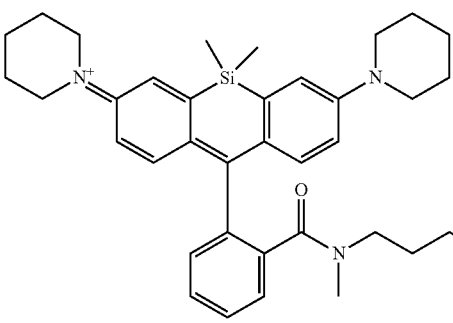
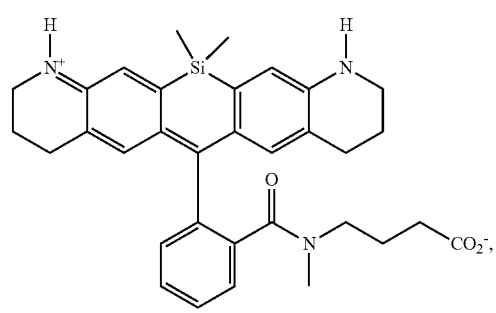

215
-continued
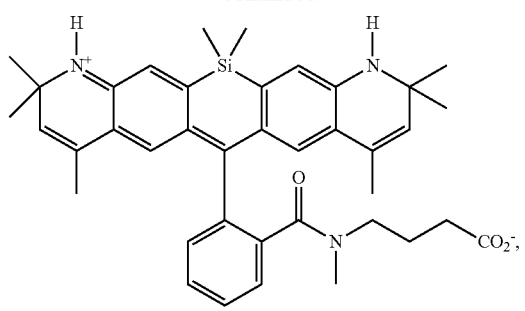
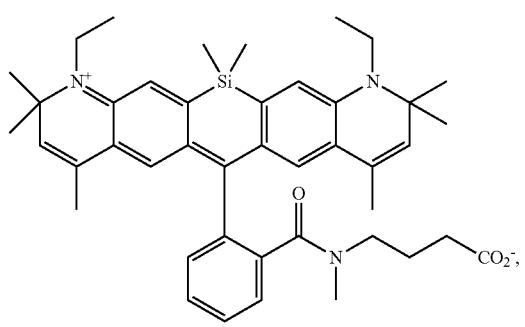
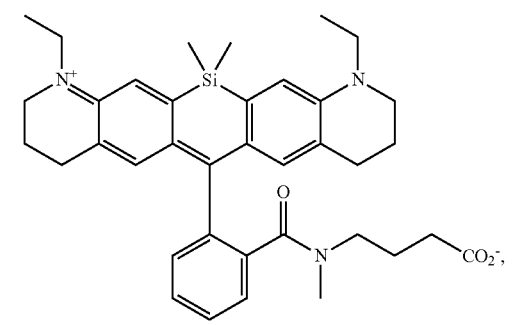
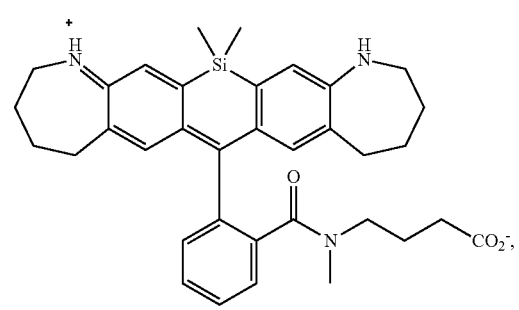
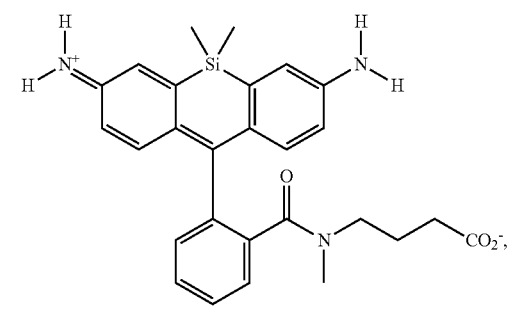
216
-continued
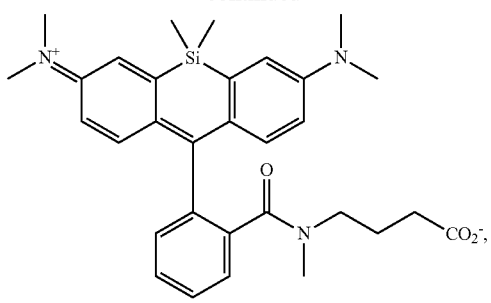
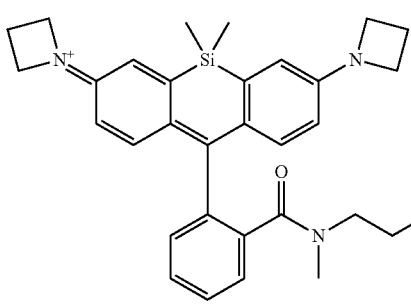
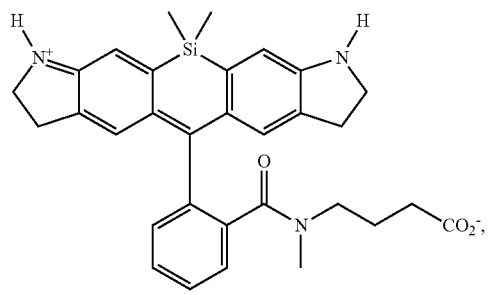
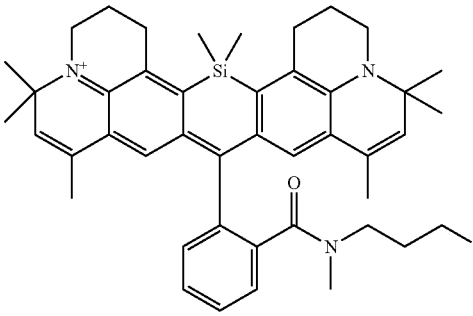
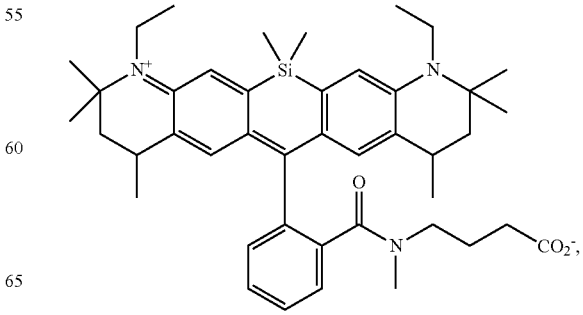

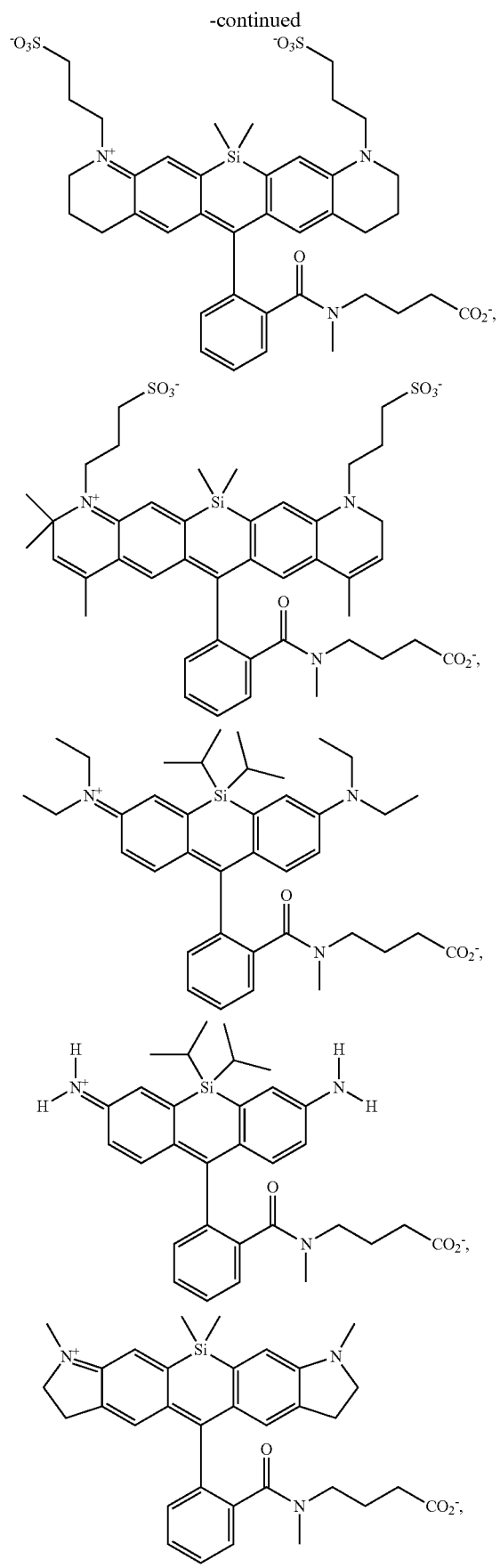

219
-continued
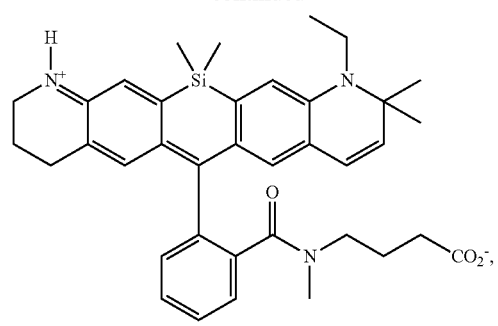
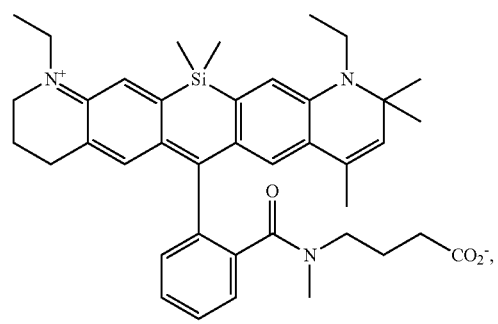
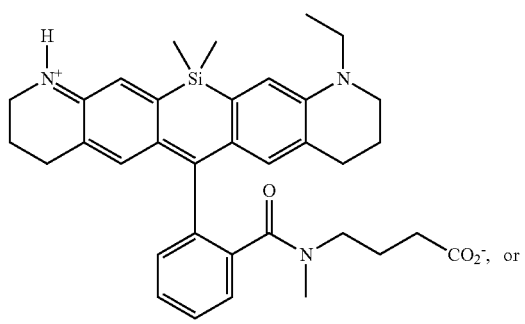, or
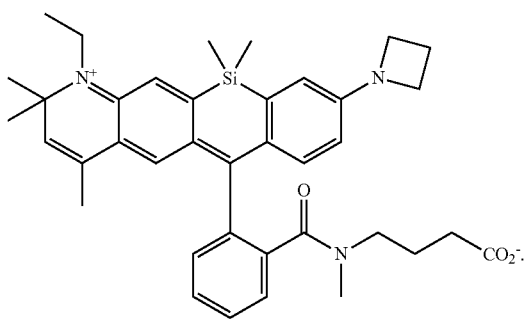
In embodiments, the compound has the formula:
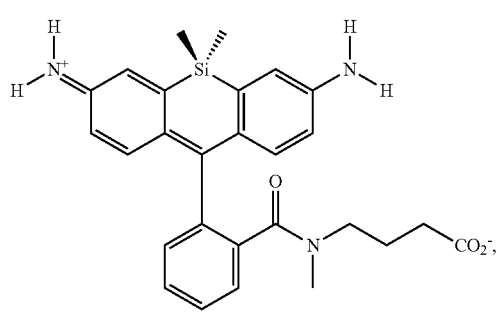
220
-continued
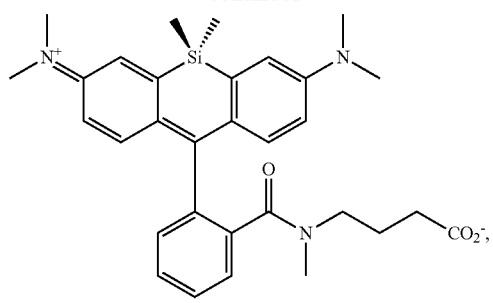
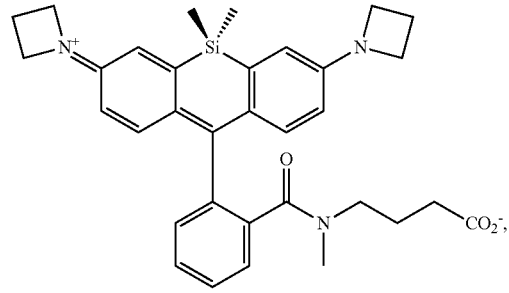
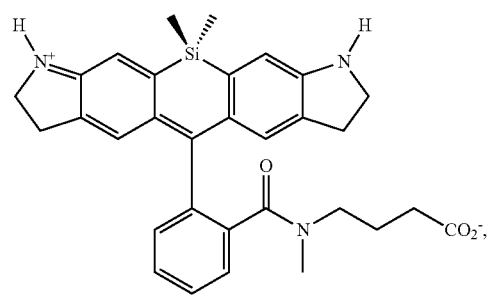
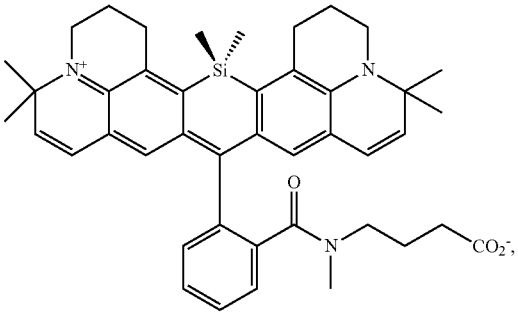
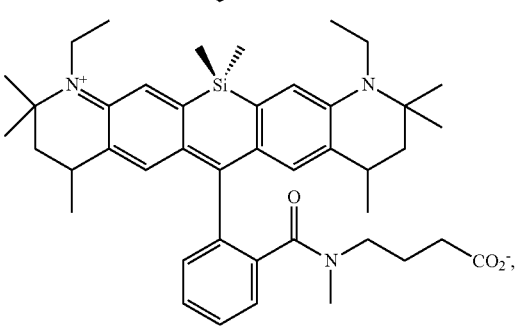

221
-continued
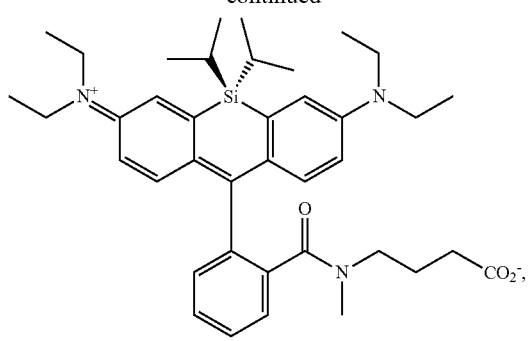
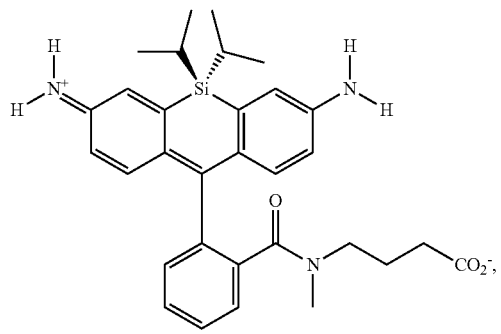
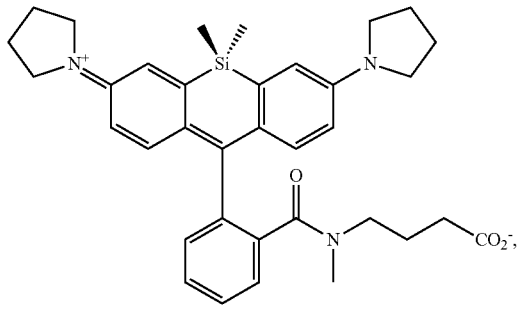
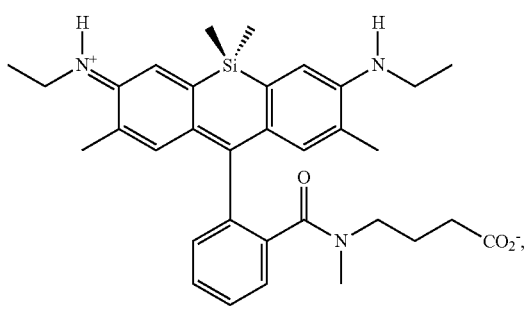
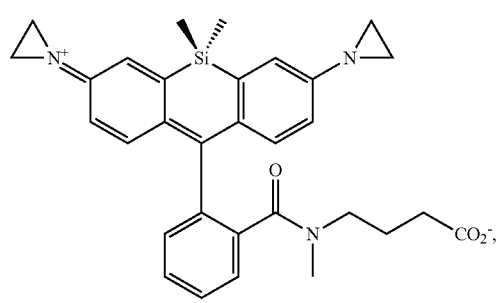
222
-continued
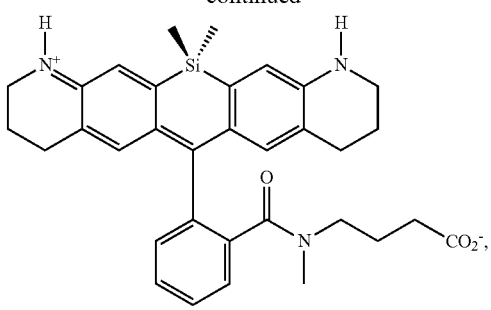
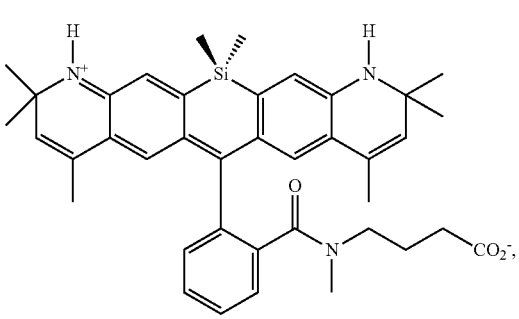
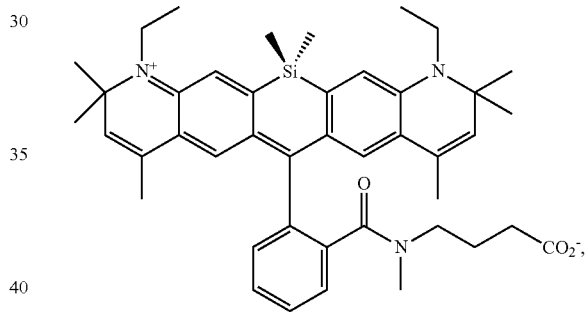
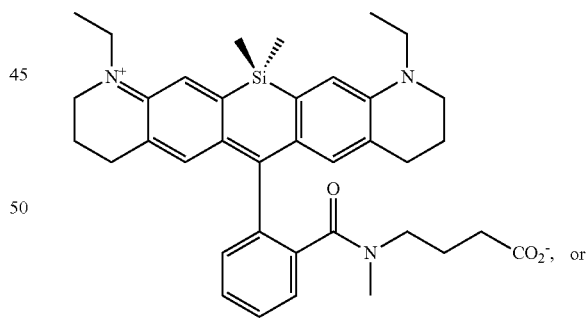
or
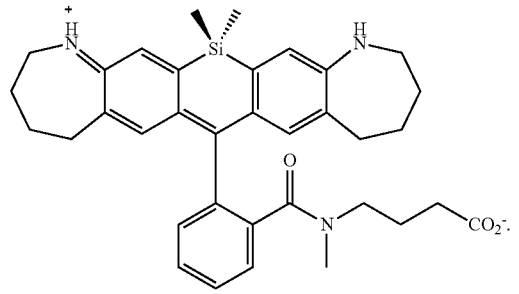

In embodiments, the compound has the formula:
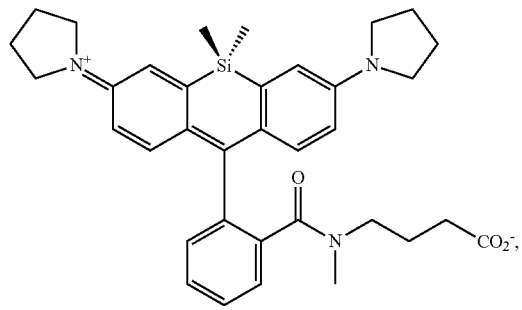
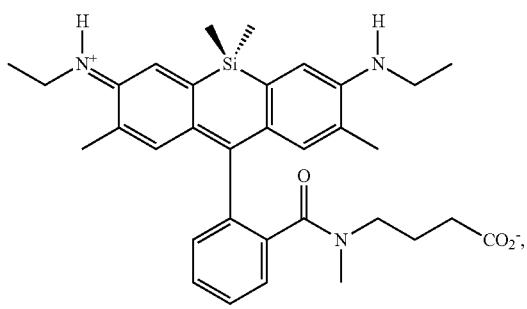
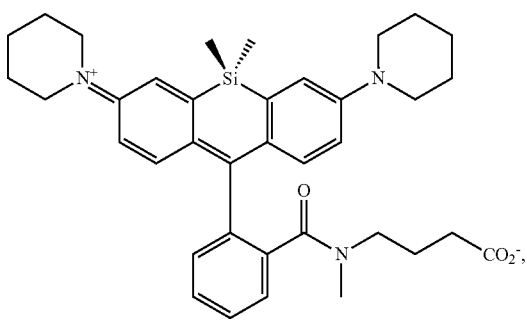
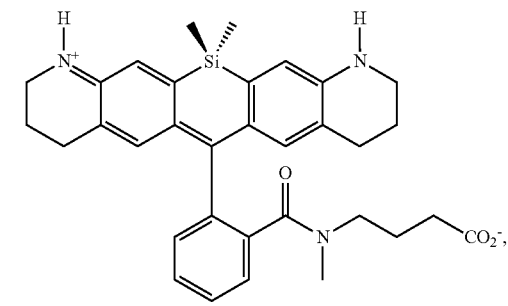
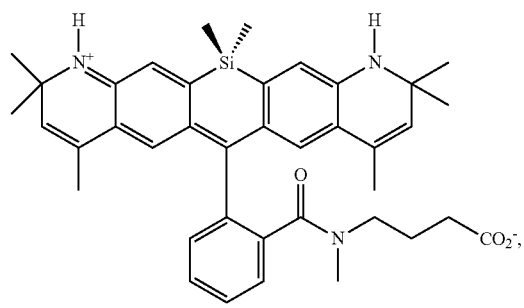
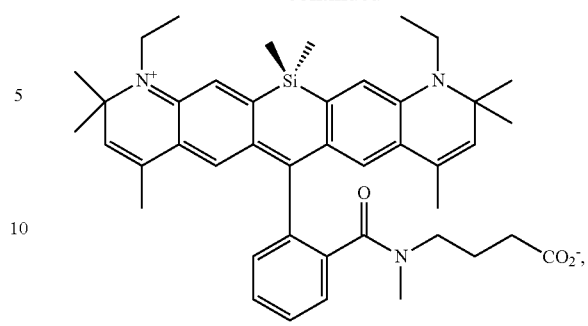
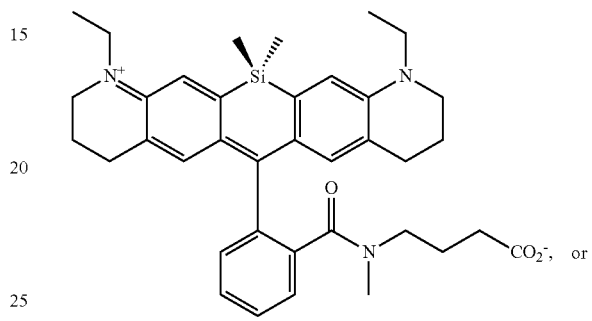
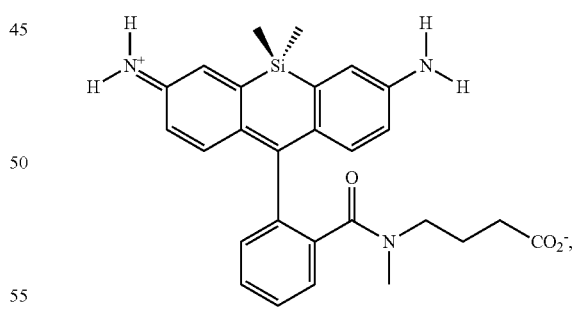 or
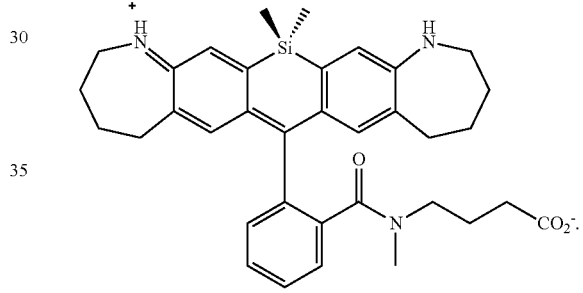
In embodiments, the compound has the formula:
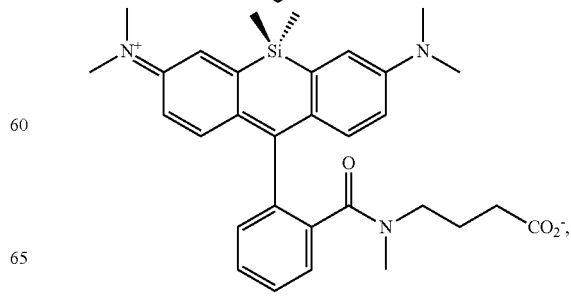

225
-continued
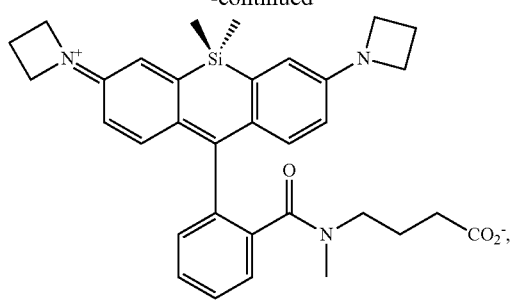
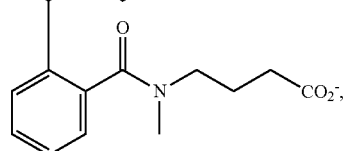
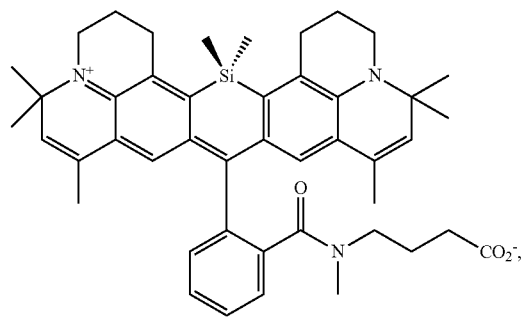
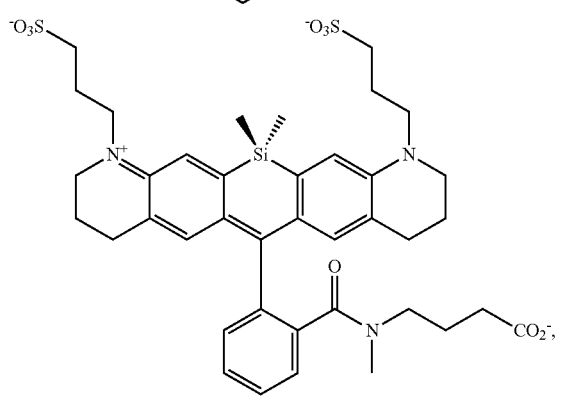
226
-continued
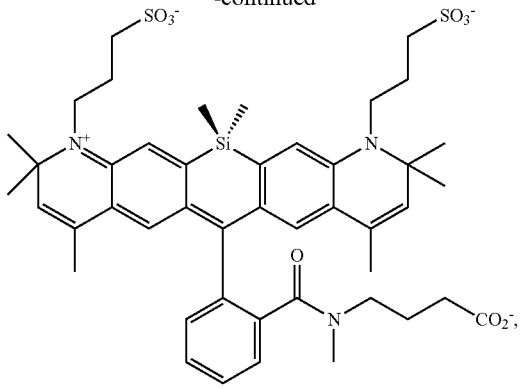
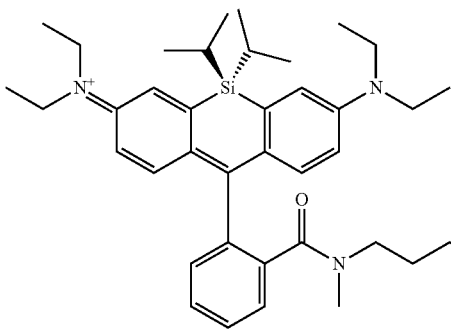
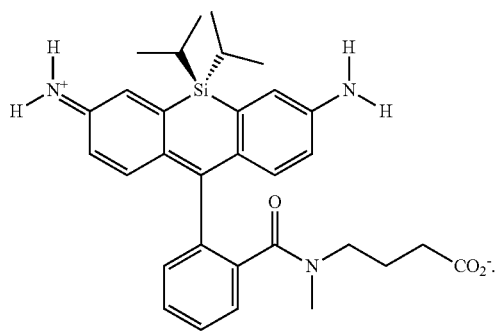, or
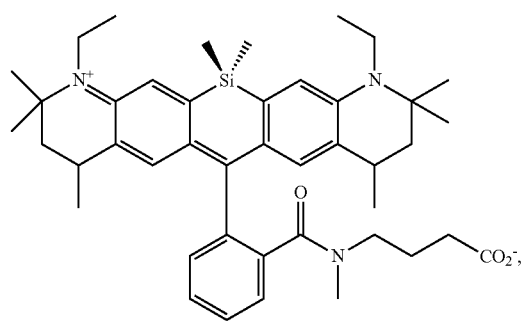
In embodiments, the compound has the formula:
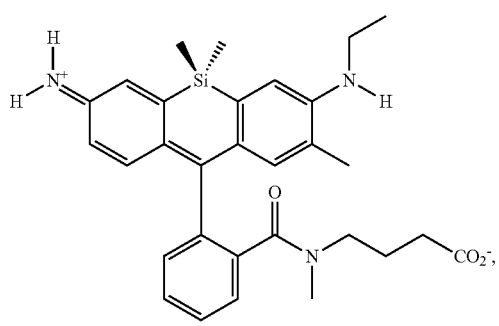

227
-continued
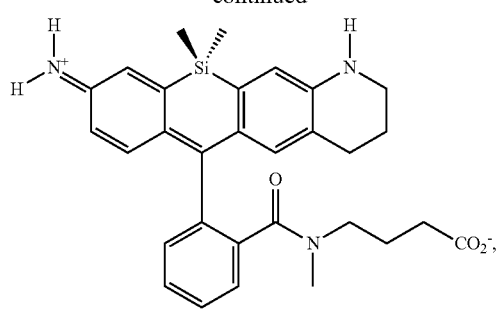
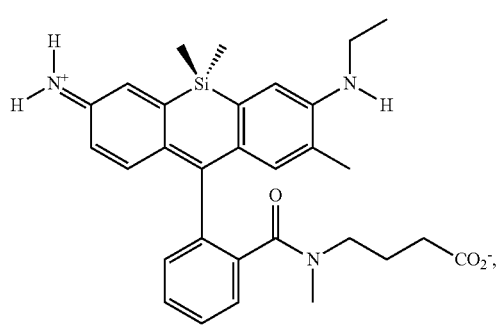
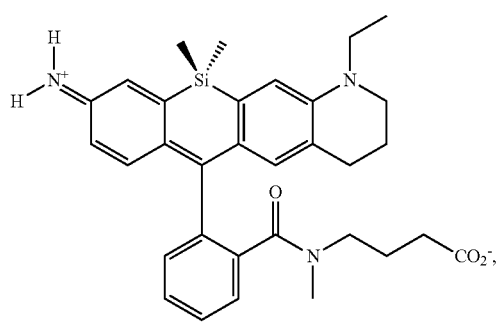
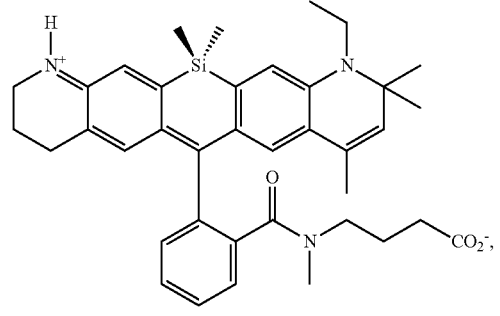
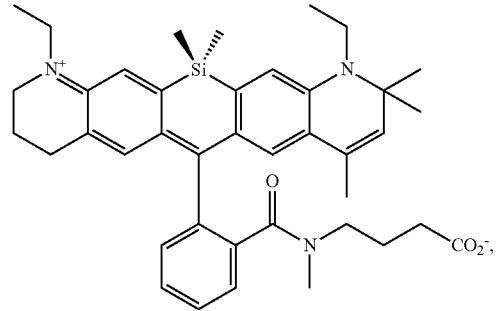
228
-continued
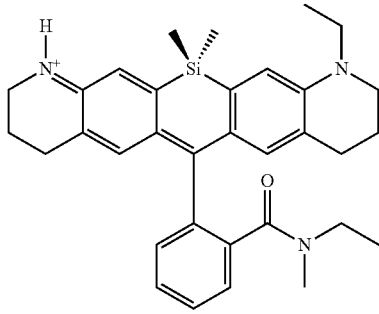, or
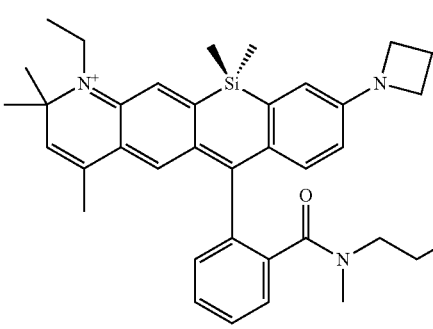
In embodiments, the compound has the formula:
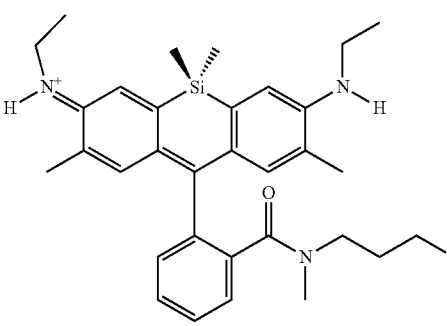 or
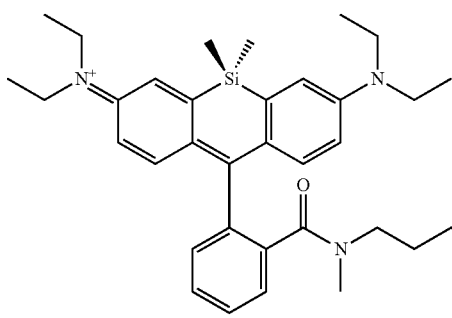

In embodiments, the compound has the formula:
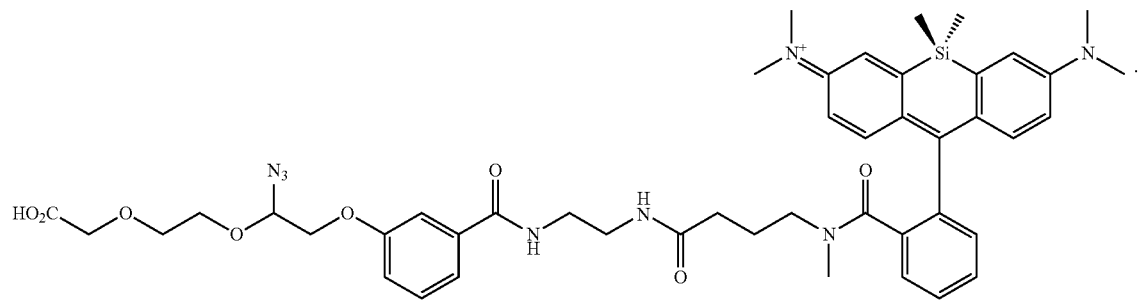
In embodiments, the compound has the formula:
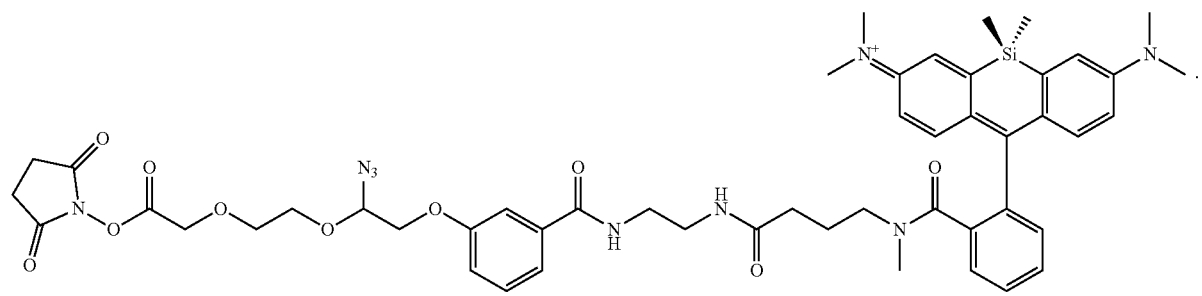
In embodiments, the compound has the formula:
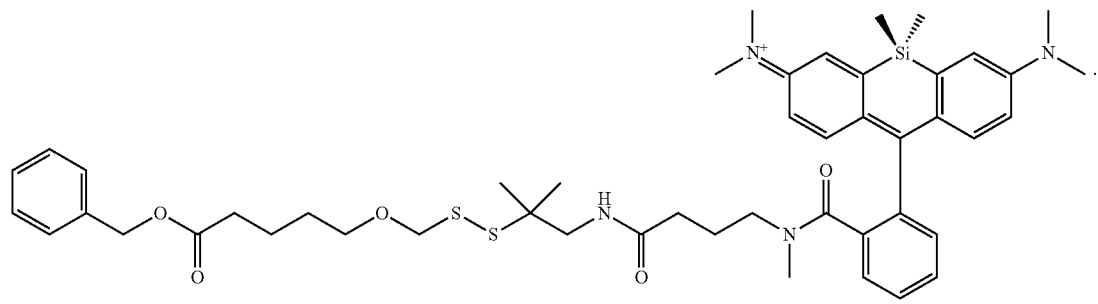
In embodiments, the compound has the formula:
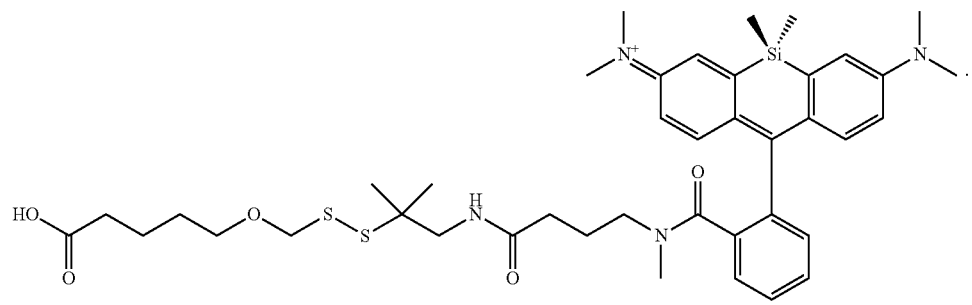

In embodiments, the compound has the formula:

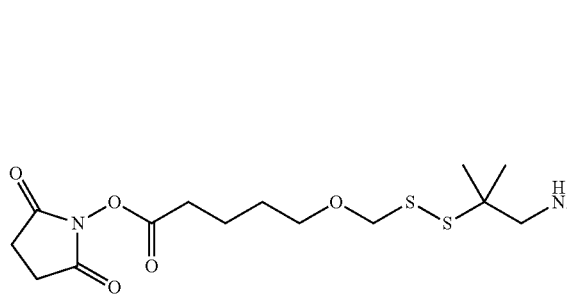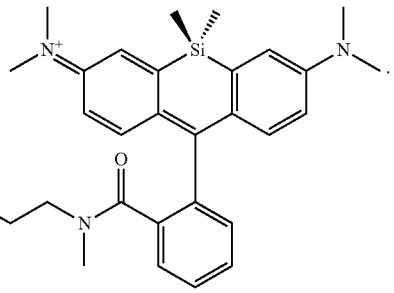

In embodiments, the compound has a maximum excitation of about 500 nm to about 700 nm. In embodiments, the compound has a maximum excitation of about 600 nm to about 700 nm. In embodiments, the compound has a maximum excitation of about 620 nm to about 700 nm. In embodiments, the compound has a maximum excitation of about 630 nm to about 700 nm. In embodiments, the compound has a maximum excitation of about 630 nm to about 670 nm. In embodiments, the compound has a maximum excitation of about 630 nm to about 660 nm. In embodiments, the compound is excited at about 510 nm to about 650 nm. In embodiments, the compound is excited at about 520 nm. In embodiments, the compound is excited at about 637 nm.

In embodiments, the compound has a maximum excitation of about 630 nm, 631 nm, 632 nm, 633 nm, 634 nm, 635 nm, 636 nm, 637 nm, 638 nm, 639 nm, 640 nm, 641 nm, 642 nm, 643 nm, 644 nm, 645 nm, 646 nm, 647 nm, 648 nm, 649 nm, 650 nm, 651 nm, 652 nm, 653 nm, 654 nm, 655 nm, 656 nm, 657 nm, 658 nm, 659 nm, 660 nm, 661 nm, 662 nm, 663 nm, 664 nm, 665 nm, 666 nm, 667 nm, 668 nm, 669 nm, or about 670 nm.

In embodiments, the compound has a maximum emission of about 500 nm to about 800 nm. In embodiments, the compound has a maximum emission of about 500 nm to about 700 nm. In embodiments, the compound has a maximum emission of about 600 nm to about 700 nm. In embodiments, the compound has a maximum emission of about 620 nm to about 700 nm. In embodiments, the compound has a maximum emission of about 630 nm to about 700 nm. In embodiments, the compound has a maximum emission of about 640 nm to about 680 nm. In embodiments, the compound has a maximum emission of about 650 nm to about 680 nm. In embodiments, the compound has a maximum emission of about 700 nm to about 800 nm.

In embodiments, the compound has a maximum emission of about 640 nm, 641 nm, 642 nm, 643 nm, 644 nm, 645 nm, 646 nm, 647 nm, 648 nm, 649 nm, 650 nm, 651 nm, 652 nm, 653 nm, 654 nm, 655 nm, 656 nm, 657 nm, 658 nm, 659 nm, 660 nm, 661 nm, 662 nm, 663 nm, 664 nm, 665 nm, 666 nm, 667 nm, 668 nm, 669 nm, 670 nm, 671 nm, 672 nm, 673 nm, 674 nm, 675 nm, 676 nm, 677 nm, 678 nm, 679 nm, or about 680 nm. In embodiments, the compound has a maximum emission of about 680 nm, 681 nm, 682 nm, 683 nm, 684 nm, 685 nm, 686 nm, 687 nm, 688 nm, 689 nm, 690 nm, 691 nm, 692 nm, 693 nm, 694 nm, 695 nm, 696 nm, 697 nm, 698 nm, 699 nm, 700 nm, 701 nm, 702 nm, 703 nm, 704 nm, 705 nm, 706 nm, 707 nm, 708 nm, 709 nm, 710 nm, 711 nm, 712 nm, 713 nm, 714 nm, 715 nm, 716 nm, 717 nm, 718 nm, 719 nm, 720 nm, 721 nm, 722 nm, 723 nm, 724 nm, 725 nm, 726 nm, 727 nm, 728 nm, 729 nm, 730 nm, 731 nm, 732 nm, 733 nm, 734 nm, 735 nm, 736 nm, 737 nm, 738 nm, 739 nm, 740 nm, 741 nm, 742 nm, 743 nm, 744 nm, 745 nm, 746 nm, 747 nm, 748 nm, 749 nm, 750 nm, 751 nm, 752 nm, 753 nm, 754 nm, 755 nm, 756 nm, 757 nm, 758 nm, 759 nm, 760 nm, 761 nm, 762 nm, 763 nm, 764 nm, 765 nm, 766 nm, 767 nm, 768 nm, 769 nm, 770 nm, 771 nm, 772 nm, 773 nm, 774 nm, 775 nm, 776 nm, 777 nm, 778 nm, 779 nm, 780 nm, 781 nm, 782 nm, 783 nm, 784 nm, 785 nm, 786 nm, 787 nm, 788 nm, 789 nm, 790 nm, 791 nm, 792 nm, 793 nm, 794 nm, 795 nm, 796 nm, 797 nm, 798 nm, 799 nm, or 800 nm.

In an aspect is provided a nucleotide covalently bound to a monovalent compound described herein (e.g., wherein the $R^8$ moiety of a compound described herein has reacted with a bioconjugate reactive group to form a bioconjugate linker thereby covalently bonding the monovalent compound to the monovalent nucleotide).

In an aspect is provided a nucleoside covalently bound to a monovalent compound described herein (e.g., wherein the $R^8$ moiety of a compound described herein has reacted with a bioconjugate reactive group to form a bioconjugate linker thereby covalently bonding the monovalent compound to the monovalent nucleoside).

In embodiments, the monovalent compound is a compound described herein, wherein the $R^8$ moiety has reacted with a bioconjugate reactive group, wherein the monovalent compound has the formula:

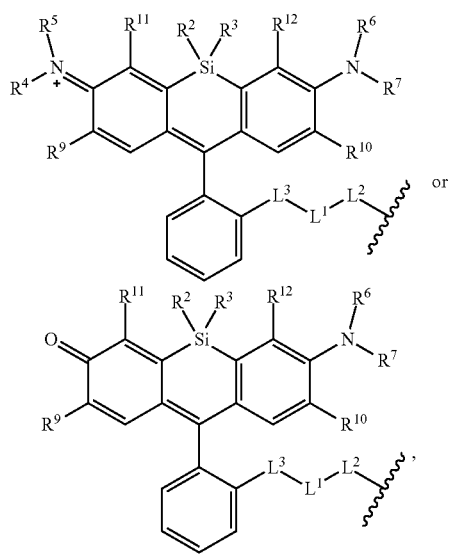

wherein $R^2$, $R^3$, $R^4$, $R^5$, $R^6$, $R^7$, $L^1$, $L^2$, $L^3$, $R^{11}$, $R^{12}$, $R^9$, and $R^{10}$ are as described herein, including embodiments.

In embodiments, the compound has the formula:

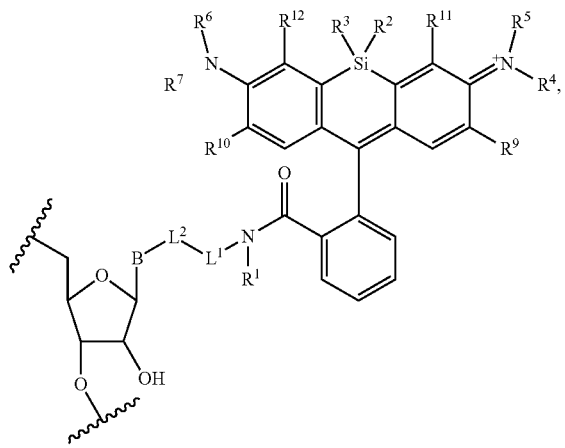

wherein $R^1, R^2, R^3, R^4, R^5, R^6, R^7, L^1, L^2, R^{11}, R^{12}, R^9$, and $R^{10}$ are as described herein, including embodiments. The symbol B is a base or analogue thereof. The symbol ⌇ in the formula above refers to an attachment point to a phosphate (e.g., monophosphate or polyphosphate), a hydrogen, or a reversible terminator moiety (e.g., a substituted or unsubstituted alkyl, or substituted or unsubstituted heteroalkyl moiety).

In embodiments, the compound has the formula:

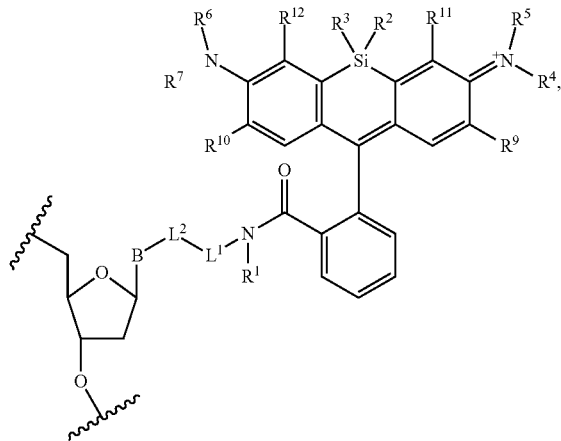

wherein $R^1, R^2, R^3, R^4, R^5, R^6, R^7, L^1, L^2, R^{11}, R^{12}, R^9$, and $R^{10}$ are as described herein, including embodiments. The symbol B is a base or analogue thereof. The symbol ⌇ in the formula above refers to an attachment point to a phosphate (e.g., monophosphate or polyphosphate), a hydrogen, or a reversible terminator moiety (e.g., a substituted or unsubstituted alkyl, or substituted or unsubstituted heteroalkyl moiety).

In embodiments, the compound has the formula:

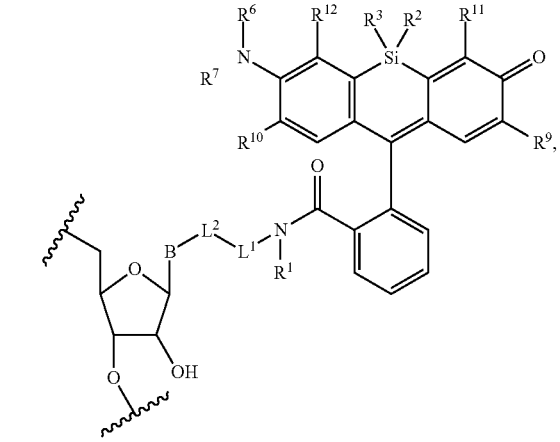

wherein $R^2, R^3, R^4, R^5, R^6, R^7, L^1, L^2, R^{11}, R^{12}, R^9$, and $R^{10}$ are as described herein, including embodiments. The symbol B is a base or analogue thereof. The symbol ⌇ in the formula above refers to an attachment point to a phosphate (e.g., monophosphate or polyphosphate), a hydrogen, or a reversible terminator moiety (e.g., a substituted or unsubstituted alkyl, or substituted or unsubstituted heteroalkyl moiety).

In embodiments, the compound has the formula:

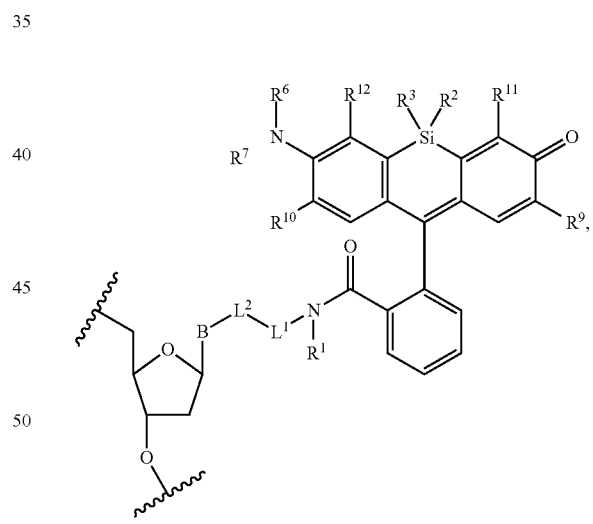

wherein $R^2, R^3, R^4, R^5, R^6, R^7, L^1, L^2, R^{11}, R^{12}, R^9$, and $R^{10}$ are as described herein, including embodiments. The symbol B is a base or analogue thereof. The symbol ⌇ in the formula above refers to an attachment point to a phosphate (e.g., monophosphate or polyphosphate), a hydrogen, or a reversible terminator moiety (e.g., a substituted or unsubstituted alkyl, or substituted or unsubstituted heteroalkyl moiety).

In embodiments, the compound has the formula:

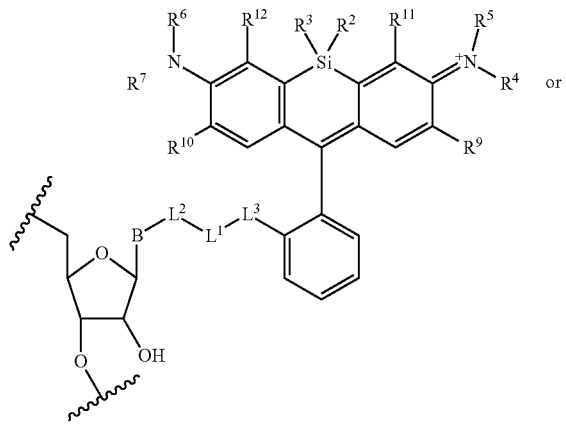

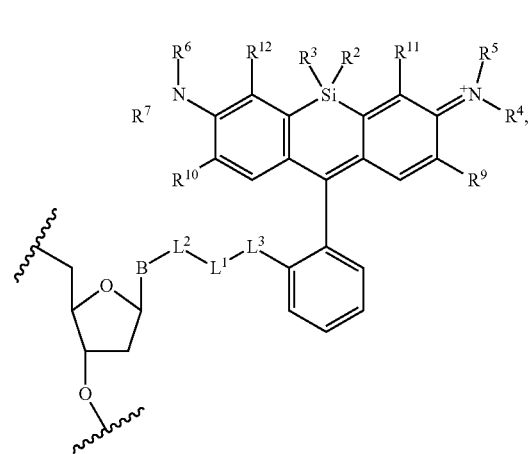

wherein $R^2$, $R^3$, $R^4$, $R^5$, $R^6$, $R^7$, $L^1$, $L^2$, $R^{11}$, $R^{12}$, $R^9$, and $R^{10}$ are as described herein, including embodiments. The symbol ⌇ in the formula above refers to an attachment point to a phosphate (e.g., monophosphate or polyphosphate), a hydrogen, or a reversible terminator moiety (e.g., a substituted or unsubstituted alkyl, or substituted or unsubstituted heteroalkyl moiety). $L^3$ is independently

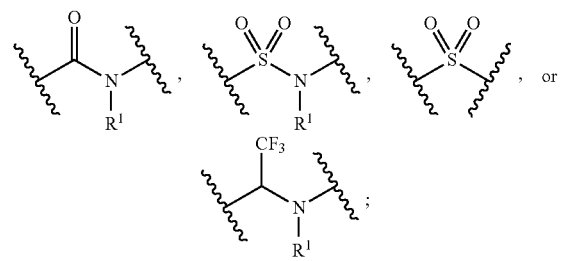

and $R^1$ is as described herein, including in embodiments. The symbol B is a base or analogue thereof.

In embodiments, the compound has the formula:

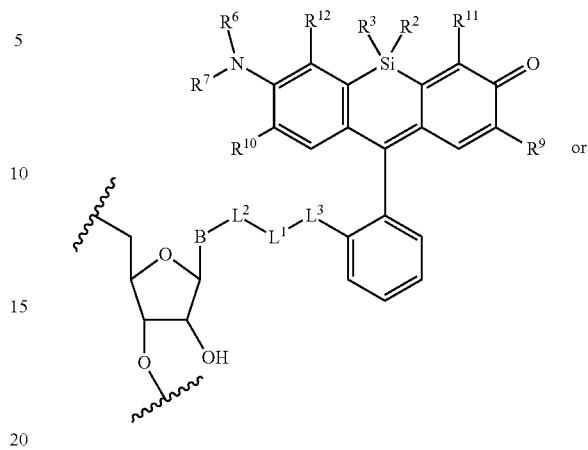

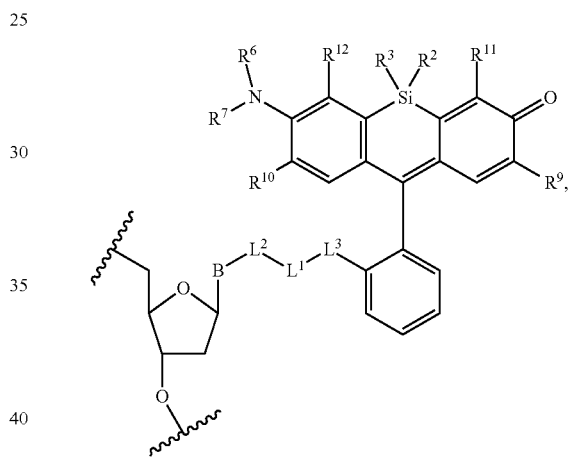

wherein $R^2$, $R^3$, $R^6$, $R^7$, $L^1$, $L^2$, $R^{11}$, $R^{12}$, $R^9$, and $R^{10}$ are as described herein, including embodiments. The symbol ⌇ in the formula above refers to an attachment point to a phosphate (e.g., monophosphate or polyphosphate), a hydrogen, or a reversible terminator moiety (e.g., a substituted or unsubstituted alkyl, or substituted or unsubstituted heteroalkyl moiety). $L^3$ is independently

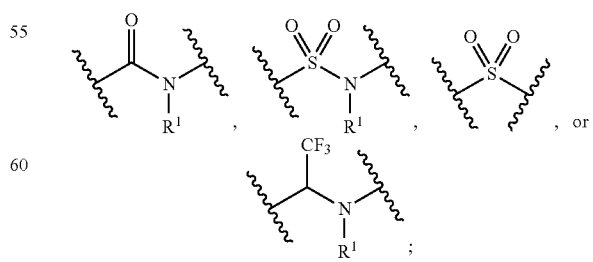

and $R^1$ is as described herein, including in embodiments. The symbol B is a base or analogue thereof.

In embodiments, the compound has the formula:

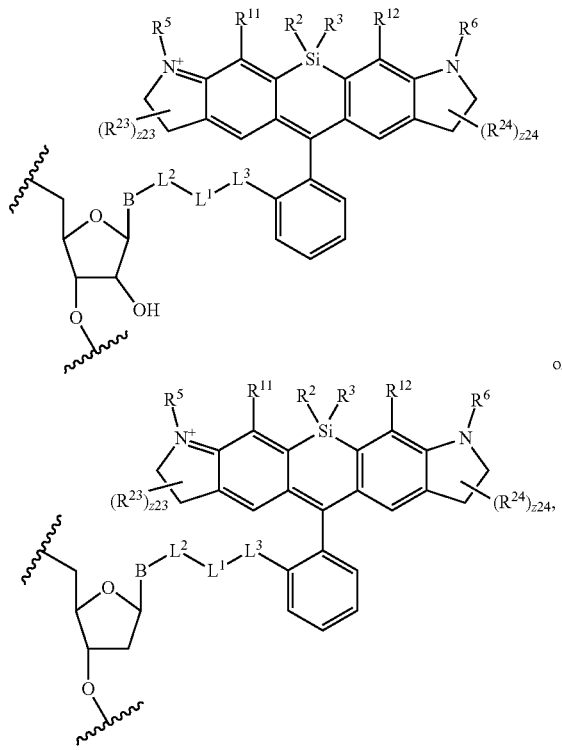

or

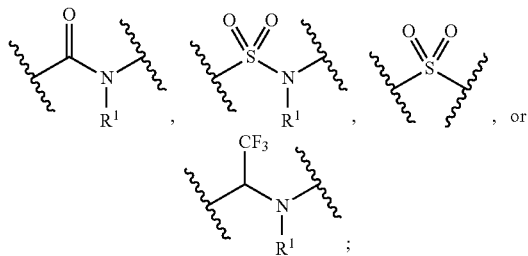

wherein $R^2$, $R^3$, $R^{24}$, $R^5$, $R^6$, $R^{25}$, $L^1$, $L^2$, $R^{11}$, z23, z24, and $R^{12}$ are as described herein, including embodiments. The symbol ⌇ in the formula above refers to an attachment point to a phosphate (e.g., monophosphate or polyphosphate), a hydrogen, or a reversible terminator moiety (e.g., a substituted or unsubstituted alkyl or substituted or unsubstituted heteroalkyl moiety). $L^3$ is independently

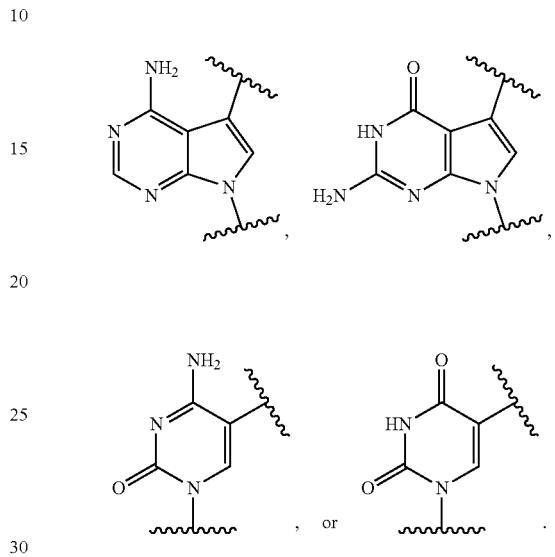

and $R^1$ is as described herein, including in embodiments. The symbol B is a base or analogue thereof.

In embodiments, B is cytosine or a derivative thereof, guanine or a derivative thereof, adenine or a derivative thereof, thymine or a derivative thereof, uracil or a derivative thereof, hypoxanthine or a derivative thereof, xanthine or a derivative thereof, deaza-adenine or a derivative thereof, deaza-guanine or a derivative thereof, deaza-hypoxanthine or a derivative thereof, 7-methylguanine or a derivative thereof, 5,6-dihydrouracil or a derivative thereof, 5-methylcytosine or a derivative thereof, or 5-hydroxymethylcytosine or a derivative thereof.

In embodiments, B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof.

In embodiments, B is

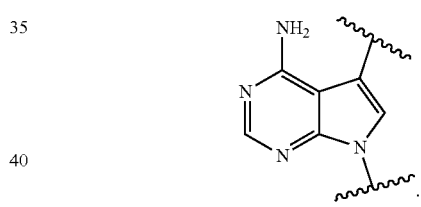

In embodiments, B is

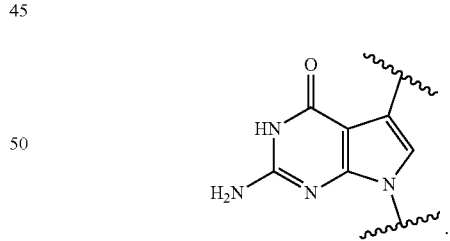

In embodiments, B is

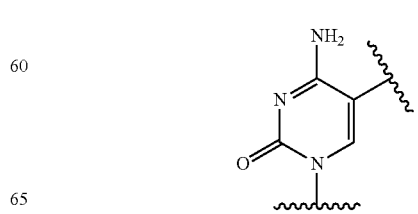

In embodiments, B is

In embodiments, B is

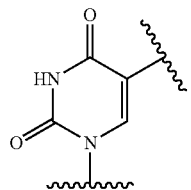

Altering the pH and/or temperature could have a dramatic effect on the fluorescence intensity of some fluorophores. For example, it is widely known that the fluorescent intensity of fluorescein is highly susceptible to changes in pH. In embodiments, the spectral properties (e.g., the emission wavelength and/or the emission intensity) of the compounds described herein do not significantly increase or decrease as a result of a change in the pH. In embodiments, the spectral properties (e.g., the emission wavelength and/or the emission intensity) of the compounds described herein do not significantly decrease as a result of a change in the pH. In embodiments, the emission intensity (i.e., the resulting fluorescence of the compound described herein following excitation) of the compounds described herein does not decrease as a result of a change in the pH. In embodiments, the emission intensity (i.e., the resulting fluorescence of the compound described herein following excitation) of the compounds described herein does not decrease more than 10%, 20%, or 30% as a result of a change in the pH. In embodiments, the fluorescence intensity of the compounds described herein is maintained over a pH range of about 4.0 to about 11.0. In embodiments, the fluorescence intensity of the compounds described herein is maintained over a pH range of about 8.0 to about 11.0. In embodiments, the fluorescence intensity of the compounds described herein is maintained over a pH range of about 9.0 to about 11.0.

In embodiments, the spectral properties (e.g., the emission wavelength and/or the emission intensity) of the compounds described herein do not significantly increase or decrease as a result of a change in the temperature. In embodiments, the spectral properties (e.g., the emission wavelength and/or the emission intensity) of the compounds described herein do not significantly decrease as a result of a change in the temperature. In embodiments, the emission intensity (i.e., the resulting fluorescence of the compound described herein following excitation) of the compounds described herein does not decrease as a result of a change in the temperature. In embodiments, the emission intensity (i.e., the resulting fluorescence of the compound described herein following excitation) of the compounds described herein does not decrease more than 10%, 20%, or 30% as a result of a change in the temperature. In embodiments, the fluorescence intensity of the compounds described herein is maintained at a temperature of about 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., or 80° C.

In embodiments, when $R^1$ is substituted, $R^1$ is substituted with one or more first substituent denoted by $R^{1.1}$ as explained in the definitions section above in the description of "first substituent group(s)". In embodiments, when an $R^{1.1}$ substituent group is substituted, the $R^{1.1}$ substituent group is substituted with one or more second substituent groups denoted by $R^{1.2}$ as explained in the definitions section above in the description of "first substituent group(s)". In embodiments, when an $R^{1.2}$ substituent group is substituted, the $R^{1.2}$ substituent group is substituted with one or more third substituent groups denoted by $R^{1.3}$ as explained in the definitions section above in the description of "first substituent group(s)". In the above embodiments, $R^1$, $R^{1.1}$, $R^{1.2}$, and $R^{1.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^1$, $R^{1.1}$, $R^{1.2}$, and $R^{1.3}$, respectively.

In embodiments, when $R^{1.4}$ is substituted, $R^{1.4}$ is substituted with one or more first substituent groups denoted by $R^{1.4.1}$ as explained in the definitions section above in the description of "first substituent group(s)". In embodiments, when an $R^{1.4.1}$ substituent group is substituted, the $R^{1.4.1}$ substituent group is substituted with one or more second substituent groups denoted by $R^{1.4.2}$ as explained in the definitions section above in the description of "first substituent group(s)". In embodiments, when an $R^{1.4.2}$ substituent group is substituted, the $R^{1.4.2}$ substituent group is substituted with one or more third substituent groups denoted by $R^{1.4.3}$ as explained in the definitions section above in the description of "first substituent group(s)". In the above embodiments, $R^{1.4}$, $R^{1.4.1}$, $R^{1.4.2}$, and $R^{1.4.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{1.4}$, $R^{1.4.1}$, $R^{1.4.2}$, and $R^{1.4.3}$, respectively.

In embodiments, when $R^2$ is substituted, $R^2$ is substituted with one or more first substituent groups denoted by $R^{2.1}$ as explained in the definitions section above in the description of "first substituent group(s)". In embodiments, when an $R^{2.1}$ substituent group is substituted, the $R^{2.1}$ substituent group is substituted with one or more second substituent groups denoted by $R^{2.2}$ as explained in the definitions section above in the description of "first substituent group(s)". In embodiments, when an $R^{2.2}$ substituent group is substituted, the $R^{2.2}$ substituent group is substituted with one or more third substituent groups denoted by $R^{2.3}$ as explained in the definitions section above in the description of "first substituent group(s)". In the above embodiments, $R^2$, $R^{2.1}$, $R^{2.2}$, and $R^{2.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^2$, $R^{2.1}$, $R^{2.2}$, and $R^{2.3}$, respectively.

In embodiments, when $R^3$ is substituted, $R^3$ is substituted with one or more first substituent groups denoted by $R^{3.1}$ as explained in the definitions section above in the description of "first substituent group(s)". In embodiments, when an $R^{3.1}$ substituent group is substituted, the $R^{3.1}$ substituent group is substituted with one or more second substituent groups denoted by $R^{3.2}$ as explained in the definitions section above in the description of "first substituent group(s)". In embodiments, when an $R^{3.2}$ substituent group is substituted, the $R^{3.2}$ substituent group is substituted with one or more third substituent groups denoted by $R^{3.3}$ as explained in the definitions section above in the description of "first substituent group(s)". In the above embodiments, $R^3$, $R^{3.1}$, $R^{3.2}$, and $R^{3.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^3$, $R^{3.1}$, $R^{3.2}$ and $R^{3.3}$, respectively.

In embodiments, when $R^4$ is substituted, $R^4$ is substituted with one or more first substituent groups denoted by $R^{4.1}$ as explained in the definitions section above in the description of "first substituent group(s)". In embodiments, when an $R^{4.1}$ substituent group is substituted, the $R^{4.1}$ substituent group is substituted with one or more second substituent groups denoted by $R^{4.2}$ as explained in the definitions section above in the description of "first substituent group(s)". In embodiments, when an $R^{4.2}$ substituent group is substituted, the $R^{4.2}$ substituent group is substituted with one or more third substituent groups denoted by $R^{4.3}$ as explained in the definitions section above in the description of "first substituent group(s)". In the above embodiments, $R^4$, $R^{4.1}$, $R^{4.2}$, and $R^{4.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^4$, $R^{4.1}$, $R^{4.2}$ and $R^{4.3}$, respectively.

In embodiments, when $R^5$ is substituted, $R^5$ is substituted with one or more first substituent groups denoted by $R^{5.1}$ as explained in the definitions section above in the description of "first substituent group(s)". In embodiments, when an $R^{5.1}$ substituent group is substituted, the $R^{5.1}$ substituent group is substituted with one or more second substituent groups denoted by $R^{5.2}$ as explained in the definitions section above in the description of "first substituent group(s)". In embodiments, when an $R^{5.2}$ substituent group is substituted, the $R^{5.2}$ substituent group is substituted with one or more third substituent groups denoted by $R^{5.3}$ as explained in the definitions section above in the description of "first substituent group(s)". In the above embodiments, $R^5$, $R^{5.1}$, $R^{5.2}$, and $R^{5.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^5$, $R^{5.1}$, $R^{5.2}$ and $R^{5.3}$, respectively.

In embodiments, when $R^6$ is substituted, $R^6$ is substituted with one or more first substituent groups denoted by $R^{6.1}$ as explained in the definitions section above in the description of "first substituent group(s)". In embodiments, when an $R^{6.1}$ substituent group is substituted, the $R^{6.1}$ substituent group is substituted with one or more second substituent groups denoted by $R^6$ as explained in the definitions section above in the description of "first substituent group(s)". In embodiments, when an $R^{6.2}$ substituent group is substituted, the $R^{6.2}$ substituent group is substituted with one or more third substituent groups denoted by $R^{6.3}$ as explained in the definitions section above in the description of "first substituent group(s)". In the above embodiments, $R^6$, $R^{6.1}$, $R^{6.2}$, and $R^{6.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^6$, $R^{6.1}$, $R^{6.2}$ and $R^{6.3}$, respectively.

In embodiments, when $R^7$ is substituted, $R^7$ is substituted with one or more first substituent groups denoted by $R^{7.1}$ as explained in the definitions section above in the description of "first substituent group(s)". In embodiments, when an $R^{7.1}$ substituent group is substituted, the $R^{7.1}$ substituent group is substituted with one or more second substituent groups denoted by $R^{7.2}$ as explained in the definitions section above in the description of "first substituent group(s)". In embodiments, when an $R^{7.2}$ substituent group is substituted, the $R^{7.2}$ substituent group is substituted with one or more third substituent groups denoted by $R^{7.3}$ as explained in the definitions section above in the description of "first substituent group(s)". In the above embodiments, $R^7$, $R^{7.1}$, $R^{7.2}$, and $R^{7.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^7$, $R^{7.1}$, $R^{7.2}$, and $R^{7.3}$, respectively.

In embodiments, when $R^8$ is substituted, $R^8$ is substituted with one or more first substituent groups denoted by $R^{8.1}$ as explained in the definitions section above in the description of "first substituent group(s)". In embodiments, when an $R^{8.1}$ substituent group is substituted, the $R^{8.1}$ substituent group is substituted with one or more second substituent groups denoted by $R^{8.2}$ as explained in the definitions section above in the description of "first substituent group(s)". In embodiments, when an $R^{8.2}$ substituent group is substituted, the $R^{8.2}$ substituent group is substituted with one or more third substituent groups denoted by $R^{8.3}$ as explained in the definitions section above in the description of "first substituent group(s)". In the above embodiments, $R^8$, $R^{8.1}$, $R^{8.2}$, and $R^{8.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^8$, $R^{8.1}$, $R^{8.2}$ and $R^{8.3}$, respectively.

In embodiments, when $R^9$ is substituted, $R^9$ is substituted with one or more first substituent groups denoted by $R^{9.1}$ as explained in the definitions section above in the description of "first substituent group(s)". In embodiments, when an $R^{9.1}$ substituent group is substituted, the $R^{9.1}$ substituent group is substituted with one or more second substituent groups denoted by $R^{9.2}$ as explained in the definitions section above in the description of "first substituent group(s)". In embodiments, when an $R^{9.2}$ substituent group is substituted, the $R^{9.2}$ substituent group is substituted with one or more third substituent groups denoted by $R^{9.3}$ as explained in the definitions section above in the description of "first substituent group(s)". In the above embodiments, $R^9$, $R^{9.1}$, $R^{9.2}$, and $R^{9.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^9$, $R^{9.1}$, $R^{9.2}$, and $R^{9.3}$, respectively.

In embodiments, when $R^{10}$ is substituted, $R^{10}$ is substituted with one or more first substituent groups denoted by $R^{10.1}$ as explained in the definitions section above in the description of "first substituent group(s)". In embodiments, when an $R^{10.1}$ substituent group is substituted, the $R^{10.1}$ substituent group is substituted with one or more second substituent groups denoted by $R^{10.2}$ as explained in the definitions section above in the description of "first substituent group(s)". In embodiments, when an $R^{10.2}$ substituent group is substituted, the $R^{10.2}$ substituent group is substituted with one or more third substituent groups denoted by $R^{10.3}$ as explained in the definitions section above in the description of "first substituent group(s)". In the above embodiments, $R^{10}$, $R^{10.1}$, $R^{10.2}$, and $R^{10.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10}$, $R^{10.1}$, $R^{10.2}$, and $R^{10.3}$, respectively.

In embodiments, when $R^{11}$ is substituted, $R^{11}$ is substituted with one or more first substituent groups denoted by $R^{11.1}$ as explained in the definitions section above in the description of "first substituent group(s)". In embodiments, when an $R^{11.1}$ substituent group is substituted, the $R^{11.1}$ substituent group is substituted with one or more second substituent groups denoted by $R^{11.2}$ as explained in the definitions section above in the description of "first substituent group(s)". In embodiments, when an $R^{11.2}$ substituent group is substituted, the $R^{11.2}$ substituent group is substituted with one or more third substituent groups denoted by $R^{11.3}$ as explained in the definitions section above in the description of "first substituent group(s)". In the above embodiments, $R^{11}$, $R^{11.1}$, $R^{11.2}$, and $R^{11.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{11}$, $R^{11.1}$, $R^{11.2}$, and $R^{11.3}$, respectively.

In embodiments, when $R^{12}$ is substituted, $R^{12}$ is substituted with one or more first substituent groups denoted by $R^{12.1}$ as explained in the definitions section above in the description of "first substituent group(s)". In embodiments, when an $R^{12.1}$ substituent group is substituted, the $R^{12.1}$ substituent group is substituted with one or more second substituent groups denoted by $R^{12.2}$ as explained in the definitions section above in the description of "first substituent group(s)". In embodiments, when an $R^{12.2}$ substituent group is substituted, the $R^{12.2}$ substituent group is substituted with one or more third substituent groups denoted by $R^{12.3}$ as explained in the definitions section above in the description of "first substituent group(s)". In the above embodiments, $R^{12}$, $R^{12.1}$, $R^{12.2}$, and $R^{12.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{12}$, $R^{12.1}$, $R^{12.2}$, and $R^{12.3}$, respectively.

In embodiments, when $R^{14}$ is substituted, $R^{14}$ is substituted with one or more first substituent groups denoted by $R^{14.1}$ as explained in the definitions section above in the description of "first substituent group(s)". In embodiments, when an $R^{14.1}$ substituent group is substituted, the $R^{14.1}$ substituent group is substituted with one or more second substituent groups denoted by $R^{14.2}$ as explained in the definitions section above in the description of "first substituent group(s)". In embodiments, when an $R^{14.2}$ substituent group is substituted, the $R^{14.2}$ substituent group is substituted with one or more third substituent groups denoted by $R^{14.3}$ as explained in the definitions section above in the description of "first substituent group(s)". In the above embodiments, $R^{14}$, $R^{14.1}$, $R^{14.2}$, and $R^{14.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{14}$, $R^{14.1}$, $R^{14.2}$, and $R^{14.3}$, respectively.

In embodiments, when $R^{15}$ is substituted, $R^{15}$ is substituted with one or more first substituent groups denoted by $R^{15.1}$ as explained in the definitions section above in the description of "first substituent group(s)". In embodiments, when an $R^{15.1}$ substituent group is substituted, the $R^{15.1}$ substituent group is substituted with one or more second substituent groups denoted by $R^{15.2}$ as explained in the definitions section above in the description of "first substituent group(s)". In embodiments, when an $R^{15.2}$ substituent group is substituted, the $R^{15.2}$ substituent group is substituted with one or more third substituent groups denoted by $R^{15.3}$ as explained in the definitions section above in the description of "first substituent group(s)". In the above embodiments, $R^{15}$, $R^{15.1}$, $R^{15.2}$, and $R^{15.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{15}$, $R^{15.1}$, $R^{15.2}$ and $R^{15.3}$, respectively.

In embodiments, when $R^{16}$ is substituted, $R^{16}$ is substituted with one or more first substituent groups denoted by $R^{16.1}$ as explained in the definitions section above in the description of "first substituent group(s)". In embodiments, when an $R^{16.1}$ substituent group is substituted, the $R^{16.1}$ substituent group is substituted with one or more second substituent groups denoted by $R^{16.2}$ as explained in the definitions section above in the description of "first substituent group(s)". In embodiments, when an $R^{16.2}$ substituent group is substituted, the $R^{16.2}$ substituent group is substituted with one or more third substituent groups denoted by $R^{16.3}$ as explained in the definitions section above in the description of "first substituent group(s)". In the above embodiments, $R^{16}$, $R^{16.1}$, $R^{16.2}$, and $R^{16.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{16}$, $R^{16.1}$, $R^{16.2}$, and $R^{16.3}$, respectively.

In embodiments, when $R^{17}$ is substituted, $R^{17}$ is substituted with one or more first substituent groups denoted by $R^{17.1}$ as explained in the definitions section above in the description of "first substituent group(s)". In embodiments, when an $R^{17.1}$ substituent group is substituted, the $R^{17.1}$ substituent group is substituted with one or more second substituent groups denoted by $R^{17.2}$ as explained in the definitions section above in the description of "first substituent group(s)". In embodiments, when an $R^{17.2}$ substituent group is substituted, the $R^{17.2}$ substituent group is substituted with one or more third substituent groups denoted by $R^{17.3}$ as explained in the definitions section above in the description of "first substituent group(s)". In the above embodiments, $R^{17}$, $R^{17.1}$, $R^{17.2}$, and $R^{17.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{17}$, $R^{17.1}$, $R^{17.2}$, and $R^{17.3}$, respectively.

In embodiments, when $R^{18}$ is substituted, $R^{18}$ is substituted with one or more first substituent groups denoted by $R^{18.1}$ as explained in the definitions section above in the description of "first substituent group(s)". In embodiments, when an $R^{18.1}$ substituent group is substituted, the $R^{18.1}$ substituent group is substituted with one or more second substituent groups denoted by $R^{18.2}$ as explained in the definitions section above in the description of "first substituent group(s)". In embodiments, when an $R^{18.2}$ substituent group is substituted, the $R^{18.2}$ substituent group is substituted with one or more third substituent groups denoted by $R^{18.3}$ as explained in the definitions section above in the description of "first substituent group(s)". In the above embodiments, $R^{18}$, $R^{18.1}$, $R^{18.2}$, and $R^{18.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{18}$, $R^{18.1}$, $R^{18.2}$, and $R^{18.3}$, respectively.

In embodiments, when $R^{19}$ is substituted, $R^{19}$ is substituted with one or more first substituent groups denoted by $R^{19.1}$ as explained in the definitions section above in the description of "first substituent group(s)". In embodiments, when an $R^{19.1}$ substituent group is substituted, the $R^{19.1}$ substituent group is substituted with one or more second substituent groups denoted by $R^{19.2}$ as explained in the definitions section above in the description of "first substituent group(s)". In embodiments, when an $R^{19.2}$ substituent group is substituted, the $R^{19.2}$ substituent group is substituted with one or more third substituent groups denoted by $R^{19.3}$ as explained in the definitions section above in the description of "first substituent group(s)". In the above embodiments, $R^{19}$, $R^{19.1}$, $R^{19.2}$, and $R^{19.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{19}$, $R^{19.1}$, $R^{19.2}$, and $R^{19.3}$, respectively.

In embodiments, when $R^{20}$ is substituted, $R^{20}$ is substituted with one or more first substituent groups denoted by $R^{20.1}$ as explained in the definitions section above in the description of "first substituent group(s)". In embodiments, when an $R^{20.1}$ substituent group is substituted, the $R^{20.1}$ substituent group is substituted with one or more second substituent groups denoted by $R^{20.2}$ as explained in the definitions section above in the description of "first substituent group(s)". In embodiments, when an $R^{20.2}$ substituent group is substituted, the $R^{20.2}$ substituent group is substituted with one or more third substituent groups denoted by $R^{20.3}$ as explained in the definitions section above in the description of "first substituent group(s)". In the above embodiments, $R^{20}$, $R^{20.1}$, $R^{20.2}$, and $R^{20.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{20}$, $R^{20.1}$, $R^{20.2}$, and $R^{20.3}$, respectively.

In embodiments, when $R^{23}$ is substituted, $R^{23}$ is substituted with one or more first substituent groups denoted by $R^{23.1}$ as explained in the definitions section above in the description of "first substituent group(s)". In embodiments, when an $R^{23.1}$ substituent group is substituted, the $R^{23.1}$ substituent group is substituted with one or more second substituent groups denoted by $R^{23.2}$ as explained in the definitions section above in the description of "first substituent group(s)". In embodiments, when an $R^{23.2}$ substituent group is substituted, the $R^{23.2}$ substituent group is substituted with one or more third substituent groups denoted by $R^{23.3}$ as explained in the definitions section above in the description of "first substituent group(s)". In the above embodiments, $R^{23}$, $R^{23.1}$, $R^{23.2}$, and $R^{23.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{23}$, $R^{23.1}$, $R^{23.2}$, and $R^{23.3}$, respectively.

In embodiments, when $R^{24}$ is substituted, $R^{24}$ is substituted with one or more first substituent groups denoted by $R^{24.1}$ as explained in the definitions section above in the description of "first substituent group(s)". In embodiments, when an $R^{24.1}$ substituent group is substituted, the $R^{24.1}$ substituent group is substituted with one or more second substituent groups denoted by $R^{24.2}$ as explained in the definitions section above in the description of "first substituent group(s)". In embodiments, when an $R^{24.2}$ substituent group is substituted, the $R^{24.2}$ substituent group is substituted with one or more third substituent groups denoted by $R^{24.3}$ as explained in the definitions section above in the description of "first substituent group(s)". In the above embodiments, $R^{24}$, $R^{24.1}$, $R^{24.2}$, and $R^{24.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{24}$, $R^{24.1}$, $R^{24.2}$, and $R^{24.3}$, respectively.

In embodiments, when $R^{25}$ is substituted, $R^{25}$ is substituted with one or more first substituent groups denoted by $R^{25.1}$ as explained in the definitions section above in the description of "first substituent group(s)". In embodiments, when an $R^{25.1}$ substituent group is substituted, the $R^{25.1}$ substituent group is substituted with one or more second substituent groups denoted by $R^{25.2}$ as explained in the definitions section above in the description of "first substituent group(s)". In embodiments, when an $R^{25.2}$ substituent group is substituted, the $R^{25.2}$ substituent group is substituted with one or more third substituent groups denoted by $R^{25.3}$ as explained in the definitions section above in the description of "first substituent group(s)". In the above embodiments, $R^{25}$, $R^{25.1}$, $R^{25.2}$, and $R^{25.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{25}$, $R^{25.1}$, $R^{25.2}$, and $R^{25.3}$, respectively.

In embodiments, when $R^{26}$ is substituted, $R^{26}$ is substituted with one or more first substituent groups denoted by $R^{26.1}$ as explained in the definitions section above in the description of "first substituent group(s)". In embodiments, when an $R^{26.1}$ substituent group is substituted, the $R^{26.1}$ substituent group is substituted with one or more second substituent groups denoted by $R^{26.2}$ as explained in the definitions section above in the description of "first substituent group(s)". In embodiments, when an $R^{26.2}$ substituent group is substituted, the $R^{26.2}$ substituent group is substituted with one or more third substituent groups denoted by $R^{26.3}$ as explained in the definitions section above in the description of "first substituent group(s)". In the above embodiments, $R^{26}$, $R^{26.1}$, $R^{26.2}$, and $R^{26.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{26}$, $R^{26.1}$, $R^{26.2}$, and $R^{26.3}$, respectively.

In embodiments, when $R^{54}$ is substituted, $R^{54}$ is substituted with one or more first substituent groups denoted by $R^{54.1}$ as explained in the definitions section above in the description of "first substituent group(s)". In embodiments, when an $R^{54.1}$ substituent group is substituted, the $R^{54.1}$ substituent group is substituted with one or more second substituent groups denoted by $R^{54.2}$ as explained in the definitions section above in the description of "first substituent group(s)". In embodiments, when an $R^{54.2}$ substituent group is substituted, the $R^{54.2}$ substituent group is substituted with one or more third substituent groups denoted by $R^{54.3}$ as explained in the definitions section above in the description of "first substituent group(s)". In the above embodiments, $R^{54}$, $R^{54.1}$, $R^{54.2}$, and $R^{54.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{54}$, $R^{54.1}$, $R^{54.2}$, and $R^{54.3}$, respectively.

In embodiments, when $R^{54.4}$ is substituted, $R^{54.4}$ is substituted with one or more first substituent groups denoted by $R^{54.4.1}$ as explained in the definitions section above in the description of "first substituent group(s)". In embodiments, when an $R^{54A.1}$ substituent group is substituted, the $R^{54A.1}$ substituent group is substituted with one or more second substituent groups denoted by $R^{54A.2}$ as explained in the definitions section above in the description of "first substituent group(s)". In embodiments, when an $R^{54A.2}$ substituent group is substituted, the $R^{54A.2}$ substituent group is substituted with one or more third substituent groups denoted by $R^{54A.3}$ as explained in the definitions section above in the description of "first substituent group(s)". In the above embodiments, $R^{54A}$, $R^{54A.1}$, $R^{54A.2}$, and $R^{54A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{54A}$, $R^{54A.1}$, $R^{54A.2}$, and $R^{54A.3}$, respectively.

In embodiments, when $L^1$ is substituted, $L^1$ is substituted with one or more first substituent groups denoted by $R^{L1.1}$ as explained in the definitions section above in the description of "first substituent group(s)". In embodiments, when an $R^{L1.1}$ substituent group is substituted, the $R^{L1.1}$ substituent group is substituted with one or more second substituent groups denoted by $R^{L1.2}$ as explained in the definitions section above in the description of "first substituent group(s)". In embodiments, when an $R^{L1.2}$ substituent group is substituted, the $R^{L1.2}$ substituent group is substituted with one or more third substituent groups denoted by $R^{L1.3}$ as explained in the definitions section above in the description of "first substituent group(s)". In the above embodiments, $L^1$, $R^{L1.1}$, $R^{L1.2}$, and $R^{L1.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are L, $R^{LWW.1}$, $R^{LWW.2}$, and $R^{LWW.3}$, respectively.

In embodiments, when $L^{1A}$ is substituted, $L^{1A}$ is substituted with one or more first substituent groups denoted by $R^{L1A.1}$ as explained in the definitions section above in the description of "first substituent group(s)". In embodiments, when an $R^{L1A.1}$ substituent group is substituted, the $R^{L1A.1}$ substituent group is substituted with one or more second substituent groups denoted by $R^{L1A.2}$ as explained in the definitions section above in the description of "first substituent group(s)". In embodiments, when an $R^{L1A.2}$ substituent group is substituted, the $R^{L1A.2}$ substituent group is substituted with one or more third substituent groups denoted by $R^{L1A.3}$ as explained in the definitions section above in the description of "first substituent group(s)". In the above embodiments, $L^{1A}$, $R^{L1A.1}$, $R^{L1A.2}$, and $R^{L1A.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{1A}$, $R^{L1A.1}$, $R^{L1A.2}$, and $R^{L1A.3}$, respectively.

In embodiments, when $L^{1B}$ is substituted, $L^{1B}$ is substituted with one or more first substituent groups denoted by $R^{L1B.1}$ as explained in the definitions section above in the description of "first substituent group(s)". In embodiments, when an $R^{L1B.1}$ substituent group is substituted, the $R^{L1B.1}$ substituent group is substituted with one or more second substituent groups denoted by $R^{L1B.2}$ as explained in the definitions section above in the description of "first substituent group(s)". In embodiments, when an $R^{L1B.2}$ substituent group is substituted, the $R^{L1B.2}$ substituent group is substituted with one or more third substituent groups denoted by $R^{L1B.3}$ as explained in the definitions section above in the description of "first substituent group(s)". In the above embodiments, $L^{1B}$, $R^{L1B.1}$, $R^{L1B.2}$, and $R^{L1B.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{1B}$, $R^{L1B.1}$, $R^{L1B.2}$, and $R^{L1B.3}$, respectively.

In embodiments, when $L^{1C}$ is substituted, $L^{1C}$ is substituted with one or more first substituent groups denoted by $R^{L1C.1}$ as explained in the definitions section above in the description of "first substituent group(s)". In embodiments, when an $R^{L1C.1}$ substituent group is substituted, the $R^{L1C.1}$ substituent group is substituted with one or more second substituent groups denoted by $R^{L1C.2}$ as explained in the definitions section above in the description of "first substituent group(s)". In embodiments, when an $R^{L1C.2}$ substituent group is substituted, the $R^{L1C.2}$ substituent group is substituted with one or more third substituent groups denoted by $R^{L1C.3}$ as explained in the definitions section above in the description of "first substituent group(s)". In the above embodiments, $L^{1C}$, $R^{L1C.1}$, $R^{L1C.2}$, and $R^{L1C.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{1C}$, $R^{L1C.1}$, $R^{L1C.2}$, and $R^{L1C.3}$, respectively.

In embodiments, when $L^{1D}$ is substituted, $L^{1D}$ is substituted with one or more first substituent groups denoted by $R^{L1D.1}$ as explained in the definitions section above in the description of "first substituent group(s)". In embodiments, when an $R^{L1D.1}$ substituent group is substituted, the $R^{L1D.1}$ substituent group is substituted with one or more second substituent groups denoted by $R^{L1D.2}$ as explained in the definitions section above in the description of "first substituent group(s)". In embodiments, when an $R^{L1D.2}$ substituent group is substituted, the $R^{L1D.2}$ substituent group is substituted with one or more third substituent groups denoted by $R^{L1D.3}$ as explained in the definitions section above in the description of "first substituent group(s)". In the above embodiments, $L^{1D}$, $R^{L1D.1}$, $R^{L1D.2}$, and $R^{L1D.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{1D}$, $R^{L1D.1}$, $R^{L1D.2}$, and $R^{L1D.3}$, respectively.

In embodiments, when $L^{1E}$ is substituted, $L^{1E}$ is substituted with one or more first substituent groups denoted by $R^{L1E.1}$ as explained in the definitions section above in the description of "first substituent group(s)". In embodiments, when an $R^{L1E.1}$ substituent group is substituted, the $R^{L1E.1}$ substituent group is substituted with one or more second substituent groups denoted by $R^{L1E.2}$ as explained in the definitions section above in the description of "first substituent group(s)". In embodiments, when an $R^{L1E.2}$ substituent group is substituted, the $R^{L1E.2}$ substituent group is substituted with one or more third substituent groups denoted by $R^{L1E.3}$ as explained in the definitions section above in the description of "first substituent group(s)". In the above embodiments, $L^{1E}$, $R^{L1E.1}$, $R^{L1E.2}$, and $R^{L1E.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{1E}$, $R^{L1E.1}$, $R^{L1E.2}$, and $R^{L1E.3}$, respectively.

In embodiments, when $L^2$ is substituted, $L^2$ is substituted with one or more first substituent groups denoted by $R^{L2.1}$ as explained in the definitions section above in the description of "first substituent group(s)". In embodiments, when an $R^{L2.1}$ substituent group is substituted, the $R^{L2.1}$ substituent group is substituted with one or more second substituent groups denoted by $R^{L2.2}$ as explained in the definitions section above in the description of "first substituent group(s)". In embodiments, when an $R^{L2.2}$ substituent group is substituted, the $R^{L2.2}$ substituent group is substituted with one or more third substituent groups denoted by $R^{L2.3}$ as explained in the definitions section above in the description of "first substituent group(s)". In the above embodiments, $L^2$, $R^{L2.1}$, $R^{L2.2}$, and $R^{L2.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^2$, $R^{L2.1}$, $R^{L2.2}$, and $R^{L2.3}$, respectively.

In embodiments, when $L^{2A}$ is substituted, $L^{2A}$ is substituted with one or more first substituent groups denoted by $R^{L2A.1}$ as explained in the definitions section above in the description of "first substituent group(s)". In embodiments, when an $R^{L2A.1}$ substituent group is substituted, the $R^{L2A.1}$ substituent group is substituted with one or more second substituent groups denoted by $R^{L2A.2}$ as explained in the definitions section above in the description of "first substituent group(s)". In embodiments, when an $R^{L2A.2}$ substituent group is substituted, the $R^{L2A.2}$ substituent group is substituted with one or more third substituent groups denoted by $R^{L2A.3}$ as explained in the definitions section above in the description of "first substituent group(s)". In the above embodiments, $L^{2A}$, $R^{L2A.1}$, $R^{L2A.2}$, and $R^{L2A.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{2A}$, $R^{L2A.1}$, $R^{L2A.2}$, and $R^{L2A.3}$, respectively.

In embodiments, when $L^{2B}$ is substituted, $L^{2B}$ is substituted with one or more first substituent groups denoted by $R^{L2B.1}$ as explained in the definitions section above in the description of "first substituent group(s)". In embodiments, when an $R^{L2B.1}$ substituent group is substituted, the $R^{L2B.1}$ substituent group is substituted with one or more second substituent groups denoted by $R^{L2B.2}$ as explained in the definitions section above in the description of "first substituent group(s)". In embodiments, when an $R^{L2B.2}$ substituent group is substituted, the $R^{L2B.2}$ substituent group is substituted with one or more third substituent groups denoted by $R^{L2B.3}$ as explained in the definitions section above in the description of "first substituent group(s)". In the above embodiments, $L^{2B}$, $R^{L2B.1}$, $R^{L2B.2}$, and $R^{L2B.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{2B}$, $R^{L2B.1}$, $R^{L2B.2}$, and $R^{L2B.3}$, respectively.

In embodiments, when $L^{2C}$ is substituted, $L^{2C}$ is substituted with one or more first substituent groups denoted by $R^{L2C.1}$ as explained in the definitions section above in the description of "first substituent group(s)". In embodiments, when an $R^{L2C.1}$ substituent group is substituted, the $R^{L2C.1}$ substituent group is substituted with one or more second substituent groups denoted by $R^{L2C.2}$ as explained in the definitions section above in the description of "first substituent group(s)". In embodiments, when an $R^{L2C.2}$ substituent group is substituted, the $R^{L2C.2}$ substituent group is substituted with one or more third substituent groups denoted by $R^{L2C.3}$ as explained in the definitions section above in the description of "first substituent group(s)". In the above embodiments, $L^{2C}$, $R^{L2C.1}$, $R^{L2C.2}$, and $R^{L2C.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{2C}$, $R^{L2C.1}$, $R^{L2C.2}$, and $R^{L2C.3}$, respectively.

In embodiments, when $L^{2D}$ is substituted, $L^{2D}$ is substituted with one or more first substituent groups denoted by $R^{L2D.1}$ as explained in the definitions section above in the description of "first substituent group(s)". In embodiments, when an $R^{L2D.1}$ substituent group is substituted, the $R^{L2D.1}$ substituent group is substituted with one or more second substituent groups denoted by $R^{L2D.2}$ as explained in the definitions section above in the description of "first substituent group(s)". In embodiments, when an $R^{L2D.2}$ substituent group is substituted, the $R^{L2D.2}$ substituent group is substituted with one or more third substituent groups denoted by $R^{L2D.3}$ as explained in the definitions section above in the description of "first substituent group(s)". In the above embodiments, $L^{2D}$, $R^{L2D.1}$, $R^{L2D.2}$, and $R^{L2D.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{2D}$, $R^{L2D.1}$, $R^{L2D.2}$, and $R^{L2D.3}$, respectively.

In embodiments, when $L^{2E}$ is substituted, $L^{2E}$ is substituted with one or more first substituent groups denoted by $R^{L2E.1}$ as explained in the definitions section above in the description of "first substituent group(s)". In embodiments, when an $R^{L2E.1}$ substituent group is substituted, the $R^{L2E.1}$ substituent group is substituted with one or more second substituent groups denoted by $R^{L2E.2}$ as explained in the definitions section above in the description of "first substituent group(s)". In embodiments, when an $R^{L2E.2}$ substituent group is substituted, the $R^{L2E.2}$ substituent group is substituted with one or more third substituent groups denoted by $R^{L2E.3}$ as explained in the definitions section above in the description of "first substituent group(s)". In the above embodiments, $L^{2E}$, $R^{L2E.1}$, $R^{L2E.2}$, and $R^{L2E.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{2E}$, $R^{L2E.1}$, $R^{L2E.2}$, and $R^{L2E.3}$, respectively.

In embodiments, when $L^3$ is substituted, $L^3$ is substituted with one or more first substituent groups denoted by $R^{L3.1}$ as explained in the definitions section above in the description of "first substituent group(s)". In embodiments, when an $R^{L3.1}$ substituent group is substituted, the $R^{L3.1}$ substituent group is substituted with one or more second substituent groups denoted by $R^{L3.2}$ as explained in the definitions section above in the description of "first substituent group(s)". In embodiments, when an $R^{L3.2}$ substituent group is substituted, the $R^{L3.2}$ substituent group is substituted with one or more third substituent groups denoted by $R^{L3.3}$ as explained in the definitions section above in the description of "first substituent group(s)". In the above embodiments, $L^3$, $R^{L3.1}$, $R^{L3.2}$, and $R^{L3.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^3$, $R^{L3.1}$, $R^{L3.2}$, and $R^{L3.3}$, respectively.

In embodiments, when $L^4$ is substituted, $L^4$ is substituted with one or more first substituent groups denoted by $R^{L4.1}$ as explained in the definitions section above in the description of "first substituent group(s)". In embodiments, when an $R^{L4.1}$ substituent group is substituted, the $R^{L4.1}$ substituent group is substituted with one or more second substituent groups denoted by $R^{L4.2}$ as explained in the definitions section above in the description of "first substituent group(s)". In embodiments, when an $R^{L4.2}$ substituent group is substituted, the $R^{L4.2}$ substituent group is substituted with one or more third substituent groups denoted by $R^{L4.3}$ as explained in the definitions section above in the description of "first substituent group(s)". In the above embodiments, $L^4$, $R^{L4.1}$, $R^{L4.2}$, and $R^{L4.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^4$, $R^{L4.1}$, $R^{L4.2}$, and $R^{L4.3}$, respectively.

In embodiments, the compounds described herein are not cell-permeable. In embodiments, the compounds described herein do not include a spirolactone moiety. In embodiments, the compounds described herein are not capable (e.g., under standard, equilibrium conditions) of forming a spirolactone moiety, for example:

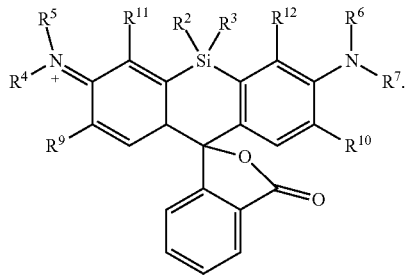

In embodiments, the compound is less than 20% in a spirolactone form. In embodiments, the compound is less than 15% in a spirolactone form. In embodiments, the compound is less than 10% in a spirolactone form. In embodiments, the compound is less than 5% in a spirolactone form. In embodiments, the compound is less than 4% in a spirolactone form. In embodiments, the compound is less than 3% in a spirolactone form. In embodiments, the compound is less than 2% in a spirolactone form. In embodiments, the compound is less than 1% in a spirolactone form.

In embodiments, the compounds described herein do not include a spirolactam moiety. In embodiments, the compounds described herein are not capable (e.g., under standard, equilibrium conditions) of forming a spirolactam moiety, for example:

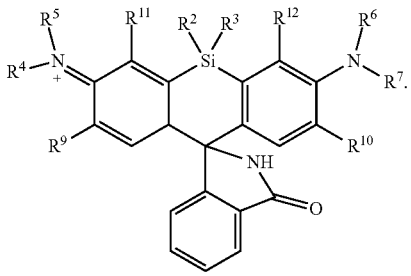

In embodiments, the compound is less than 20% in a spirolactam form. In embodiments, the compound is less than 15% in a spirolactam form. In embodiments, the compound is less than 10% in a spirolactam form. In embodiments, the compound is less than 5% in a spirolactam form. In embodiments, the compound is less than 4% in a spirolactam form. In embodiments, the compound is less than 3% in a spirolactam form. In embodiments, the compound is less than 2% in a spirolactam form. In embodiments, the compound is less than 1% in a spirolactam form.

In embodiments, $-L^3-L^1-L^2-R^8$ is not $-CH_2-COOH$. In embodiments, $-L^3-L^1-L^2-R^8$ is not $-CH_2-CO_2CH_3$. In embodiments, $-L^3-L^1-L^2-R^8$ is not $-CH_3$. In embodiments, $-L^3-L^1-L^2-R^8$ is not $-SO_3$. In embodiments, $-L^3-L^1-L^2-R^8$ is not hydrogen. In embodiments, $-L^3-L^1-L^2-R^8$ is not $-OH$. In embodiments, $-L^3-L^1-L^2-R^8$ is not $-OCH_3$. In embodiments, $-L^3-L^1-L^2-R^8$ is not $-NO_2$. In embodiments, $-L^3-L^1-L^2-R^8$ is not $-CH_2SO_3$.

In embodiments, $-L^4-R^{14}$ is not $-CH_2-COOH$. In embodiments, $-L^4-R^{14}$ is not $-CH_2-CO_2CH_3$. In embodiments, $-L^4-R^{14}$ is not $-CH_3$. In embodiments, $-L^4-R^{14}$ is not $-SO_3$. In embodiments, $-L^4-R^{14}$ is not hydrogen. In embodiments, $-L^4-R^{14}$ is not $-OH$. In embodiments, $-L^4-R^{14}$ is not $-OCH_3$. In embodiments, $-L^4-R^{14}$ is not $-NO_2$. In embodiments, $-L^4-R^{14}$ is not $-CH_2SO_3$.

In embodiments, $R^4$ and $R^5$ substituents bonded to the same nitrogen atom do not form a substituted or unsubstituted heterocycloalkyl. In embodiments, $R^4$ and $R^5$ substituents bonded to the same nitrogen atom do not form a substituted heterocycloalkyl. In embodiments, $R^4$ and $R^5$ substituents bonded to the same nitrogen atom do not form an unsubstituted heterocycloalkyl. In embodiments, $R^4$ and $R^5$ substituents bonded to the same nitrogen atom do not form an unsubstituted 4 membered heterocycloalkyl (e.g., azetidinyl). In embodiments, $R^6$ and $R^7$ substituents bonded to the same nitrogen atom do not form a substituted or unsubstituted heterocycloalkyl. In embodiments, $R^6$ and $R^7$ substituents bonded to the same nitrogen atom do not form a substituted heterocycloalkyl. In embodiments, $R^6$ and $R^7$ substituents bonded to the same nitrogen atom do not form an unsubstituted heterocycloalkyl. In embodiments, $R^6$ and $R^7$ substituents bonded to the same nitrogen atom do not form an unsubstituted 4 membered heterocycloalkyl (e.g., azetidinyl).

In yet another aspect, is provided a kit including a compound described herein. In embodiments, the kit further includes one or more sets of instructions. In embodiments, the kit includes nucleotides or nucleosides. Such kits will generally include at least one modified nucleotide or nucleoside, wherein the modified nucleotide or nucleoside is covalently bound to a compound described herein. In embodiments, the kit may include a modified nucleotide, wherein the modified nucleotide is covalently bound to a compound described herein, and a second modified nucleotide, wherein the second modified nucleotide or nucleoside is covalently bound to a different fluorophore. In embodiments, combinations of nucleotides may be provided as separate individual components or as nucleotide mixtures. In embodiments, the kit may further contain an unlabelled nucleotide. In embodiments, the kit includes a compound described herein. In embodiments, the kit includes a compound described herein covalently bound to a nucleotide (e.g., wherein the $R^8$ moiety of a compound described herein has reacted with a bioconjugate reactive group to form a bioconjugate linker thereby covalently bonding the compound described herein to the nucleotide). In embodiments, the kit includes a compound described herein covalently bound to a nucleoside (e.g., wherein the $R^8$ moiety of a compound described herein has reacted with a bioconjugate reactive group to form a bioconjugate linker thereby covalently bonding the compound described herein to the nucleoside).

In embodiments, the kit includes a plurality (e.g., two, three, or four) of modified nucleotides, wherein each modified nucleotide is covalently bound to a compound described herein. In embodiments, wherein the kit includes a plurality of modified nucleotides, the different nucleotides may be labelled (e.g., covalently bonded) with different compounds (e.g., compounds described herein) that are spectrally distinguishable compounds. As used herein, the term "spectrally distinguishable compounds" refers to compounds as described herein that emit fluorescent energy at wavelengths that can be distinguished by fluorescent detection equipment when two or more such compounds are present in one sample. In embodiments, when two modified nucleotides, each modified nucleotide covalently bound to a compound described herein, are supplied within a kit, the spectrally distinguishable compounds can be excited at the same wavelength, such as, for example by the same laser. In embodiments, when four modified nucleotides, each modified nucleotide covalently bound to a compound described herein, are supplied within a kit, two of the spectrally distinguishable compounds can both be excited at one wavelength and the other two spectrally distinguishable compounds can both be excited at another wavelength.

In embodiments, the kit may include a DNA polymerase enzyme capable of catalyzing incorporation of the modified nucleotides into a polynucleotide. In embodiments, the kit includes a buffer. In embodiments, the modified nucleotides may be provided in the kit in a concentrated form to be diluted prior to use. In such embodiments, a suitable dilution buffer may also be included.

In an aspect is provided a nucleotide or oligonucleotide covalently bound to a compound as described herein. In embodiments, when a nucleotide or oligonucleotide covalently bound to a compound as described herein, it may be referred to as a labelled nucleotide or labelled oligonucleotide. The labelled nucleotide or oligonucleotide may have the label attached via a covalent linker. The labelled nucleotide or oligonucleotide may have the label attached to the $C_5$ position of a pyrimidine base or the $C_7$ position of a 7-deaza purine base through a linker moiety. In embodiments, the labelled nucleotide or oligonucleotide may also have a 3'-O-polymerase compatible cleavable moiety covalently attached to the ribose or deoxyribose sugar of the nucleotide.

In an aspect is provided an oligonucleotide including a compound as described herein.

III. Methods of Use and Making

In an aspect is provided a method of detecting the presence of an agent, wherein the agent is covalently bound to a monovalent compound as described herein (e.g., wherein $R^8$ reacts to form part of the covalent linker), wherein the agent is an oligonucleotide, protein, nucleotide, nucleoside, or compound. In embodiments, the agent is an oligonucleotide, protein, or compound. In embodiments, the agent is an oligonucleotide (e.g., DNA, RNA, or siRNA), protein (e.g., antibody or antibody fragment), or a compound. In embodiments, the method includes a spectroscopic measurement (e.g., measure the emission from the compound described herein bonded to the agent). In embodiments, the spectroscopic measurement is an ultraviolet-visible spectroscopy measurement. In embodiments, the compound is present in an effective amount. In embodiments, the agent is a nucleic acid. In embodiments, the agent is a nucleotide. In embodiments, the agent is a nucleoside. In embodiments, the method includes detecting in vitro. In embodiments, the method includes detecting in a nucleic acid sequencing device. In embodiments, the agent is a protein, a carbohydrate, a polysaccharide, a glycoprotein, a hormone, a receptor, an antigen, an antibody, or a virus.

In embodiments, the monovalent compound has the formula:

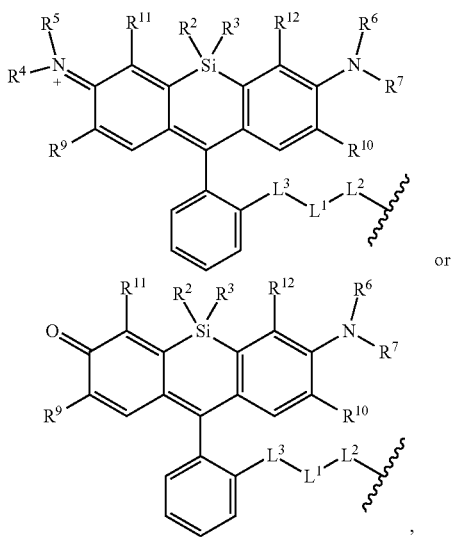

wherein $L^1$, $L^2$, $L^3$, $R^2$, $R^3$, $R^4$, $R^5$, $R^6$, $R^7$, $R^9$, $R^{10}$, $R^{11}$, and $R^{12}$ are as described herein, including in embodiments.

In embodiments, the agent covalently bound to the monovalent compound has the formula:

(XI)

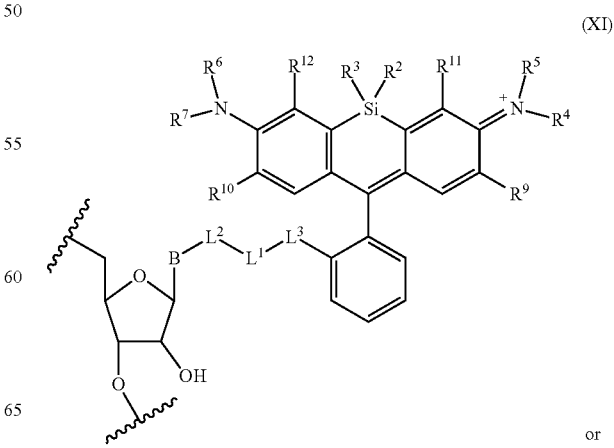

or (XII)

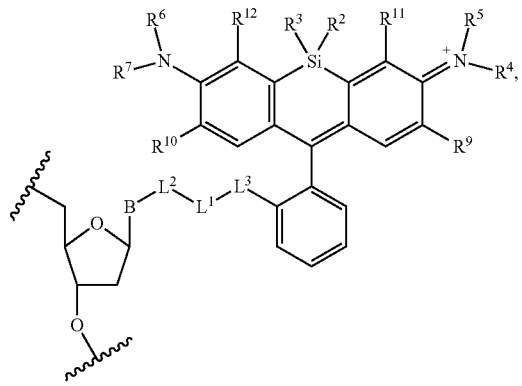

wherein the symbol B is a divalent base or analogue thereof;

and the symbol ⌇ in formula (XI) or (XII) refers to an attachment point to hydrogen, a phosphate moiety, or a reversible terminator moiety. $L^1$, $L^2$, $L^3$, $R^2$, $R^3$, $R^4$, $R^5$, $R^6$, $R^7$, $R^9$, $R^{10}$, $R^{11}$, and $R^{12}$ are as described herein, including in embodiments.

In embodiments, the agent covalently bound to the monovalent compound has the formula:

(XIII)

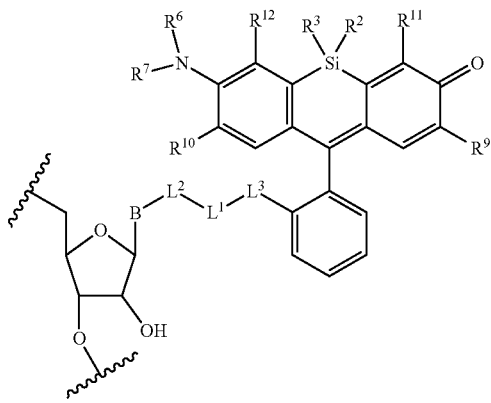

or (XIV)

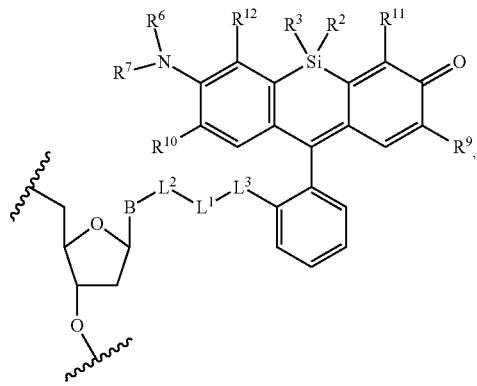

wherein the symbol B is a divalent base or analogue thereof;

and the symbol ⌇ in formula (XIII) or (XIV) refers to an attachment point to hydrogen, a phosphate moiety, or a reversible terminator moiety. $L^1$, $L^2$, $L^3$, $R^2$, $R^3$, $R^6$, $R^7$, $R^9$, $R^{10}$, $R^{11}$, and $R^{12}$ are as described herein, including in embodiments.

In embodiments, the method includes detecting the presence of a nucleotide. In embodiments, the method includes detecting the presence of a polynucleotide. Such polynucleotides may be DNA or RNA comprised respectively of deoxyribonucleotides or ribonucleotides joined in phosphodiester linkage. In embodiments, the polynucleotides include naturally occurring nucleotides and/or non-naturally occurring (or modified) nucleotides, that is modified nucleotides other than the labelled nucleotides, or any combination thereof, provided that at least one modified nucleotide is a nucleotide covalently bound to a compound described herein. Polynucleotides according to the invention may also include non-natural backbone linkages and/or non-nucleotide chemical modifications.

In embodiments, the method includes (i) incorporating one or more modified nucleotides into a polynucleotide, wherein the modified nucleotide is a nucleotide covalently bound to a compound described herein; and (ii) detecting the one or more modified nucleotide(s) incorporated into the polynucleotide by detecting or quantitatively measuring their fluorescence. In embodiments, the modified nucleotide is incorporated into a polynucleotide by a DNA polymerase (e.g., a DNA polymerase described herein). In embodiments, step (i) includes incubating a template polynucleotide strand with a reaction mixture including modified nucleotides and a DNA polymerase under conditions that allow for the formation of a phosphodiester linkage between a free 3' hydroxyl group on a polynucleotide strand annealed to the template polynucleotide strand and a 5' phosphate group on the modified nucleotide. In embodiments, step (ii) may be carried out while the polynucleotide strand is annealed to a template strand, or after a denaturation step in which the two strands are separated.

In embodiments, the method includes exposing the compound described herein, which is bound to the agent, to electromagnetic radiation, wherein the electromagnetic radiation has a wavelength selected from 100 to 1000 nm. In embodiments, the electromagnetic radiation has a wavelength selected from about 500 nm to about 700 nm. In embodiments, the electromagnetic radiation has a wavelength selected from about 600 nm to about 700 nm. In embodiments, the electromagnetic radiation has a wavelength selected from about 620 nm to about 700 nm. In embodiments, the electromagnetic radiation has a wavelength selected from about 630 nm to about 700 nm. In embodiments, the electromagnetic radiation has a wavelength selected from about 630 nm to about 670 nm. In embodiments, the electromagnetic radiation has a wavelength selected from about 630 nm to about 660 nm.

In embodiments, the method includes detecting the emission wavelength of the compound described herein bound to the agent (e.g., detecting the emission wavelength of the compound following exposure to the electromagnetic radiation). In embodiments, the emission wavelength is about 500 nm to about 700 nm. In embodiments, the emission wavelength is about 500 nm to about 800 nm. In embodiments, the emission wavelength is about 600 nm to about 700 nm. In embodiments, the emission wavelength is about 620 nm to about 700 nm. In embodiments, the emission wavelength is about 630 nm to about 700 nm. In embodiments, the emission wavelength is about 640 nm to about 680 nm. In embodiments, the emission wavelength is about 650 nm to about 680 nm. In embodiments, the emission wavelength is about 650 nm to about 800 nm. In embodiments, the emission wavelength is about 675 nm to about 800 nm. In embodiments, the emission wavelength is about 700 nm to about 800 nm. In embodiments, the emission wavelength is about 710 nm to about 800 nm. In embodiments, the emission wavelength is about 720 nm to about 800 nm. In embodiments, the emission wavelength is about 730 nm to about 800 nm. In embodiments, the emission wavelength is about 740 nm to about 800 nm. In embodiments, the emission wavelength is about 750 nm to about 800 nm. In embodiments, the emission wavelength is about 760 nm to about 800 nm. In embodiments, the emission wavelength is about 780 nm to about 800 nm. In embodiments, the emission wavelength is about 790 nm to about 800 nm.

In another aspect is provided a method of making a compound, or salt thereof, having the formula:

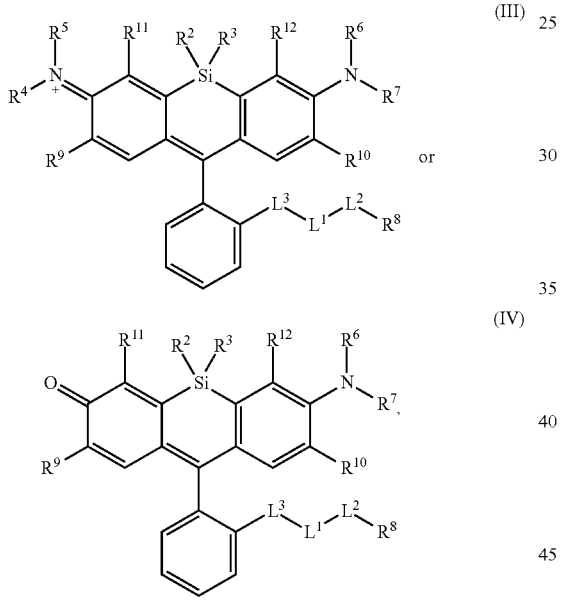

the method including mixing compound A, compound B, and compound C in a reaction vessel. $L^3$, $R^2$, $R^3$, $R^4$, $R^5$, $R^6$, $R^7$, $R^8$, $R^9$, $R^{10}$, $R^{11}$, $R^{12}$, $L^1$, and $L^2$ are as described herein, including in embodiments. Compound A has the formula:

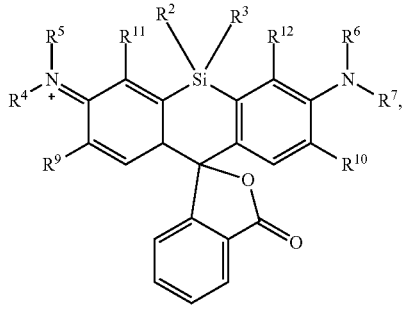

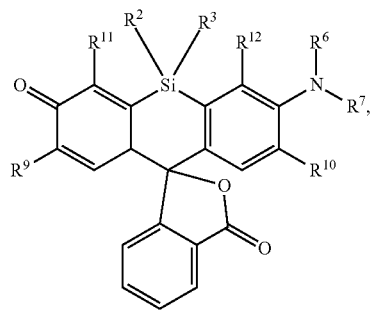

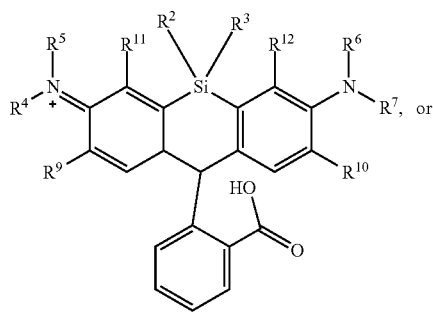

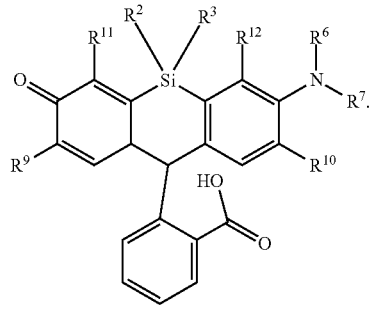

$R^2$, $R^3$, $R^4$, $R^5$, $R^6$, $R^7$, $R^9$, $R^{10}$, $R^{11}$, and $R^{12}$ are as described herein, including in embodiments. Compound B is a coupling reagent. Compound C has the formula:

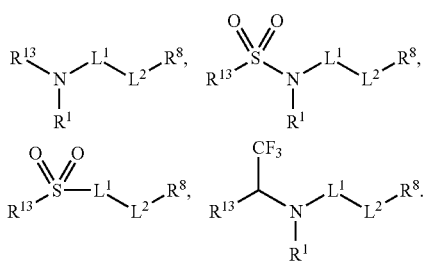

$R^1$, $L^1$, $L^2$, and $R^8$ are as described herein, including embodiments. $R^{13}$ is a leaving group.

In another aspect is provided a method of making a compound, or salt thereof, having the formula:

(I)

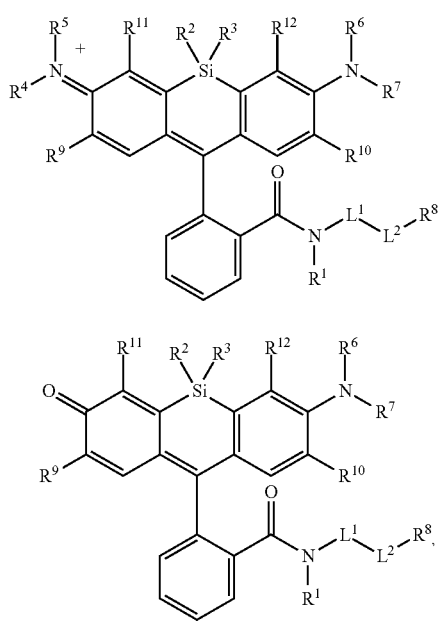

or (II)

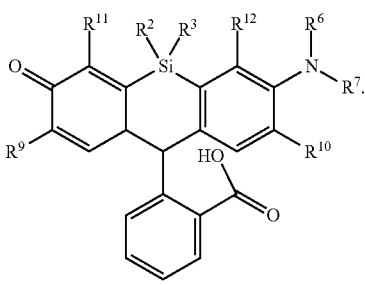

$R^2$, $R^3$, $R^4$, $R^5$, $R^6$, $R^7$, $R^9$, $R^{10}$, $R^{11}$, and $R^{12}$ are as described herein, including in embodiments.

Compound B is a coupling reagent. Compound C has the formula:

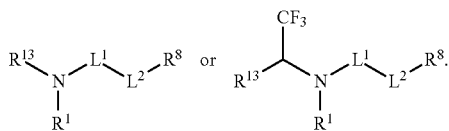

$R^1$, $L^1$, $L^2$, and $R^8$ are as described herein, including embodiments. $R^{13}$ is a leaving group (e.g., hydrogen).

In embodiments, Compound A has the formula:

the method including mixing compound A, compound B, and compound C in a reaction vessel. $R^1$, $R^2$, $R^3$, $R^4$, $R^5$, $R^6$, $R^7$, $R^8$, $R^9$, $R^{10}$, $R^{11}$, $R^{12}$, $L^1$, and $L^2$ are as described herein, including in embodiments. Compound A has the formula:

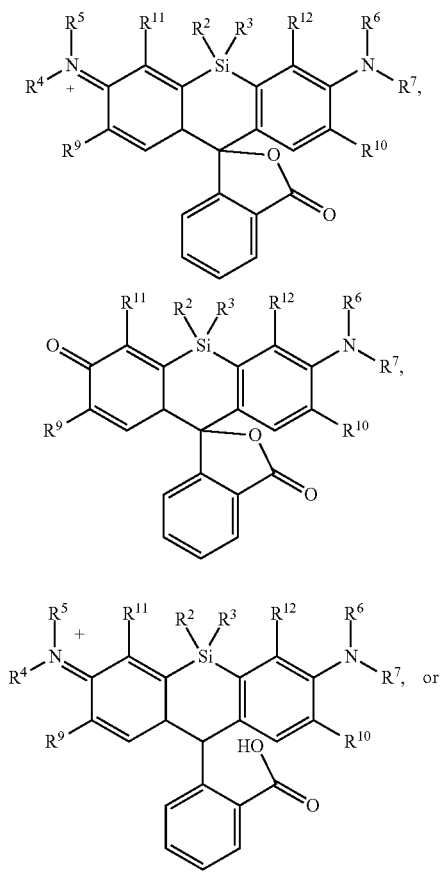

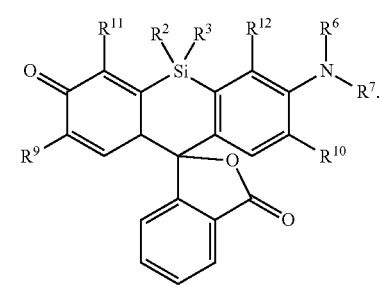

$R^2$, $R^3$, $R^4$, $R^5$, $R^6$, $R^7$, $R^9$, $R^{10}$, $R^{11}$, and $R^{12}$ are as described herein, including in embodiments. In embodiments, Compound A has the formula:

$R^2$, $R^3$, $R^6$, $R^7$, $R^9$, $R^{10}$, $R^{11}$, and $R^{12}$ are as described herein, including in embodiments. In embodiments, Compound A has the formula:

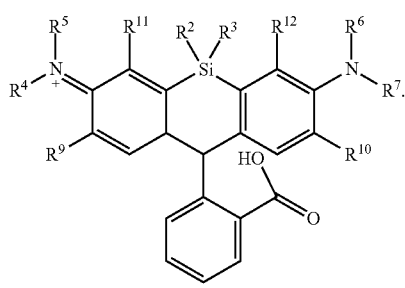

$R^2$, $R^3$, $R^4$, $R^5$, $R^6$, $R^7$, $R^9$, $R^{10}$, $R^{11}$, and $R^{12}$ are as described herein, including in embodiments. In embodiments, Compound A has the formula:

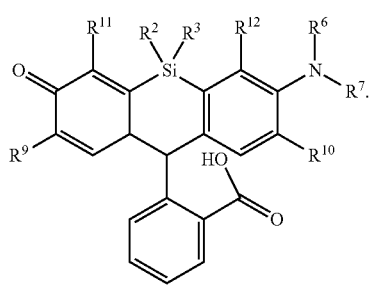

$R^2$, $R^3$, $R^6$, $R^7$, $R^9$, $R^{10}$, $R^{11}$, and $R^{12}$ are as described herein, including in embodiments.

In embodiments, compound B is (PyBOP), (PyAOP), (PyClock), (HATU), or (HBTU).

In embodiments, compound B is

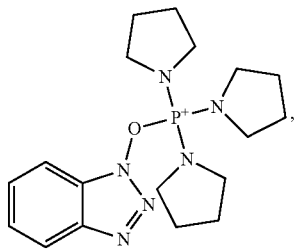 [SMILES: c1ccc2c(c1)nnn2O[P+](N1CCCC1)(N1CCCC1)N1CCCC1]

also referred to herein as PyBOP.

In embodiments, compound C is

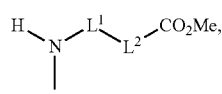

wherein $L^1$ and $L^2$ are as described herein. In embodiments, compound C is

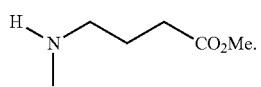

In embodiments, compound C is

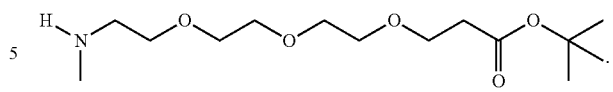

In embodiments, compound C is

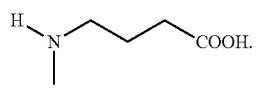

In embodiments, compound C is

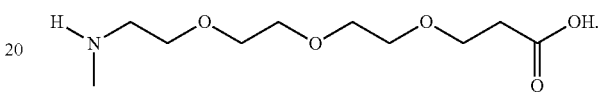

In embodiments, compound C includes a cleavable moiety. In embodiments, compound C includes a cleavable linker. In embodiments, compound C includes a polymer.

In embodiments, the compound is a compound described herein, including embodiments. In embodiments, the compound is a compound described herein (e.g., a compound described above in the section entitled "Compounds and kits").

In embodiments, the compound is

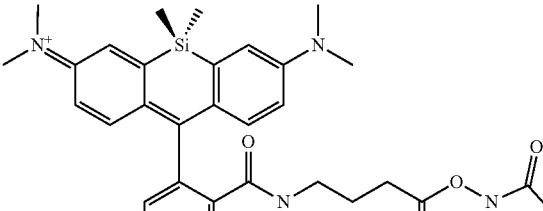

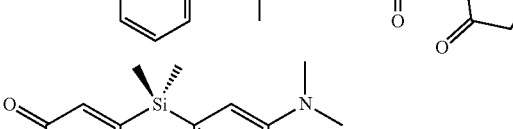

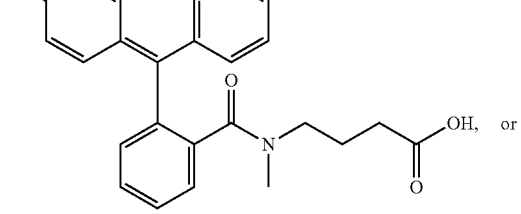

263

-continued

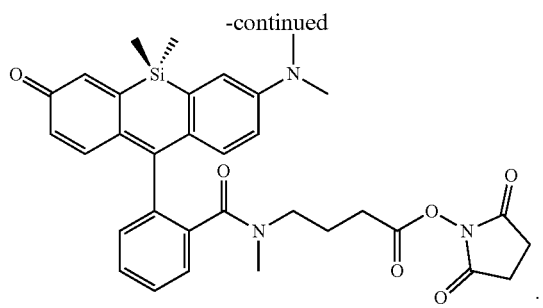

In embodiments, the compound is

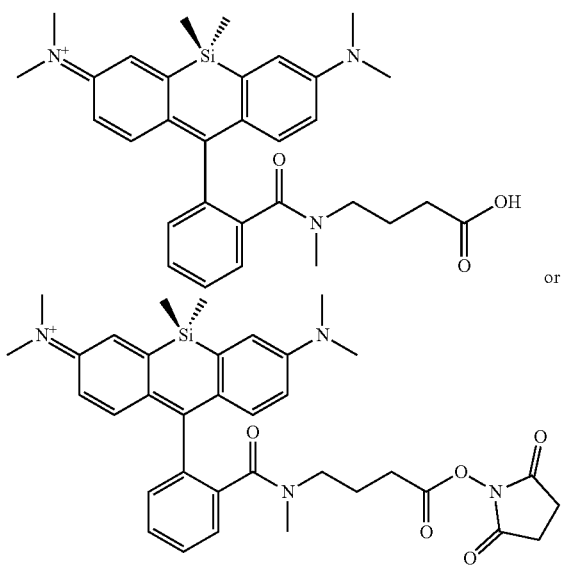

In embodiments, the method further includes adding a solvent to the reaction vessel. In embodiments, the method further includes adding an organic solvent to the reaction vessel. In embodiments, the solvent is tetrahydrofuran (THF), water, dimethylformamide (DMF), methanol, trimethylamine (TEA), or a combination thereof. In embodiments, the temperature of the reaction is maintained below 0° C. In embodiments, the temperature of the reaction is maintained at −78° C. In embodiments, the method is a method described here (e.g., in a scheme).

In embodiments, the method further includes a reagent. In embodiments, the solvent or reagent is N,N,N',N'-Tetramethyl-O—(N-succinimidyl)uronium tetrafluoroborate, O-[N-Succinimidyl)-1,1,3,3-tetramethyluronium tetrafluoroborate (TSTU), N-Hydroxysuccinimide (NHS), dicyclohexylcarbodiimide (DCC), ethyl(dimethylaminopropyl) carbodiimide (EDC), N-Succinimidyl carbonate (DSC), N-Ethyl-N'-(3-dimethylaminopropyl)carbodiimide hydrochloride (EDAC), N-Trifluoroacetoxy Succinimide (TFA-NHS), or 1,1'-Carbonyldiimidazole (CDI). In embodiments, the solvent or reagent is benzotriazol-1-yl-oxytripyrrolidinophosphonium hexafluorophosphate (PyBOP), 7-Azabenzotriazol-1-yloxy)tripyrrolidinophosphonium hexafluorophosphate (PyAOP), 6-Chloro-benzotriazole-1-yloxy-trispyrrolidinophosphonium hexafluorophosphate (PyClock), 1-[Bis(dimethylamino)methylene]-1H-1,2,3-triazolo[4,5-b]pyridinium 3-oxid hexafluorophosphate (HATU), or 2-(1H-benzotriazol-1-yl)-1,1,3,3-tetramethyluronium hexafluorophosphate (HBTU).

264

In another aspect is provided a method for detecting the presence of a nucleotide, wherein the nucleotide is covalently bound to a compound (e.g., a compound described herein) (i.e., detect the presence of the compound and thereby detect the presence of the covalently bound nucleotide).

In embodiments the method includes use of the modified nucleotides or nucleosides labelled with compounds described herein in a method of nucleic acid sequencing, re-sequencing, whole genome sequencing, single nucleotide polymorphism scoring, any other application involving the detection of the modified nucleotide or nucleoside when incorporated into a polynucleotide, or any other application requiring the use of polynucleotides labelled with the modified nucleotides, wherein the modified nucleotide is a nucleotide covalently bound to a compound described herein.

In an aspect is provided a method of nucleic acid sequencing including incorporating a modified nucleotide (e.g., a nucleotide covalently bound to a compound described herein) into a polynucleotide.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

IV. Embodiments

Embodiment P1. A compound, or salt thereof, having the formula:

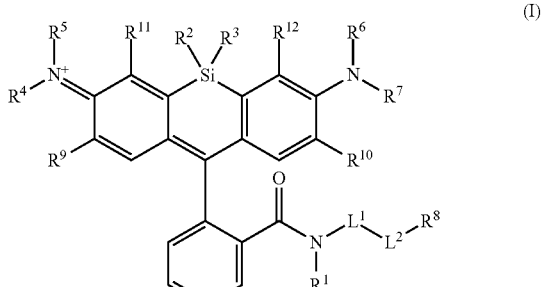

(I)

or

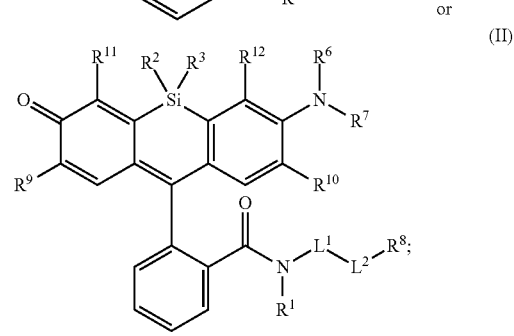

(II)

wherein, $R^1$, $R^4$, $R^5$, $R^6$, and $R^7$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —OH, —$NH_2$, —COOH, —$CONH_2$, —SH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ and $R^3$ are each independently substituted or unsubstituted alkyl, or substituted or unsubstituted heteroalkyl;

$R^8$ is hydrogen or a bioconjugate reactive moiety;

$R^9$, $R^{10}$, $R^{11}$, and $R^{12}$ are each independently hydrogen, substituted or unsubstituted alkyl, or substituted or unsubstituted heteroalkyl;

$L^1$ and $L^2$ are each independently a bond or a covalent linker;

$R^4$ and $R^5$ substituents bonded to the same nitrogen atom may optionally be joined to form a substituted or unsubstituted heterocycloalkyl, or substituted or unsubstituted heteroaryl;

$R^6$ and $R^7$ substituents bonded to the same nitrogen atom may optionally be joined to form a substituted or unsubstituted heterocycloalkyl, or substituted or unsubstituted heteroaryl;

$R^4$ and $R^9$ substituents may optionally be joined to form a substituted or unsubstituted heterocycloalkyl, or substituted or unsubstituted heteroaryl;

$R^7$ and $R^{10}$ substituents may optionally be joined to form a substituted or unsubstituted heterocycloalkyl, or substituted or unsubstituted heteroaryl;

$R^5$ and $R^{11}$ substituents may optionally be joined to form a substituted or unsubstituted heterocycloalkyl, or substituted or unsubstituted heteroaryl; and $R^6$ and $R^{12}$ substituents may optionally be joined to form a substituted or unsubstituted heterocycloalkyl, or substituted or unsubstituted heteroaryl.

Embodiment P2. The compound of embodiment P1, wherein $L^1$ and $L^2$ are each independently a bond, —S(O)$_2$—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or a polymer.

Embodiment P3. The compound of embodiment P1, wherein $L^1$ and $L^2$ are each independently a bond, —C(O)—, —C(O)NH—, —NHC(O)—, —NHC(O)NH—, —C(O)O—, —OC(O)—, substituted or unsubstituted $C_1$-$C_6$ alkylene.

Embodiment P4. The compound of embodiment P1, wherein $L^1$ is substituted or unsubstituted $C_1$-$C_6$ alkylene.

Embodiment P5. The compound of embodiment P1, wherein $L^2$ is a bond, —C(O)—, —C(O)O—, or —OC(O)—.

Embodiment P6. The compound of any one of embodiments P1 to P5, wherein $R^1$, $R^2$, and $R^3$ are each independently substituted or unsubstituted $C_1$-$C_6$ alkyl.

Embodiment P7. The compound of any one of embodiments P1 to P5, wherein $R^1$, $R^2$, and $R^3$ are each independently substituted or unsubstituted $C_1$-$C_3$ alkyl.

Embodiment P8. The compound of embodiment P1, having the formula:

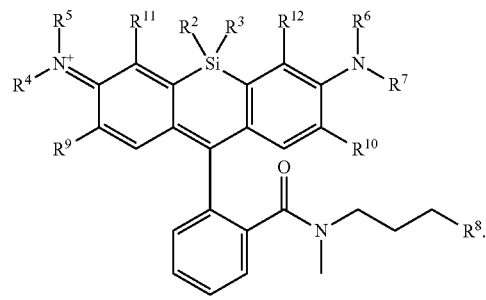

Embodiment P9. The compound of any one of embodiments P1 to P8, wherein $R^4$, $R^5$, $R^6$, and $R^7$ are each independently hydrogen, or substituted or unsubstituted $C_1$-$C_6$ alkyl.

Embodiment P10. The compound of any one of embodiments P1 to P9, wherein $R^4$ and $R^5$ substituents bonded to the same nitrogen atom may optionally be joined to form a substituted or unsubstituted 3 to 6 membered heterocycloalkyl.

Embodiment P11. The compound of any one of embodiments P1 to P10, wherein $R^6$ and $R^7$ substituents bonded to the same nitrogen atom may optionally be joined to form a substituted or unsubstituted 3 to 6 membered heterocycloalkyl.

Embodiment P12. The compound of any one of embodiments P1 to P11, wherein $R^4$ and $R^9$ substituents may optionally be joined to form a substituted or unsubstituted 3 to 8 membered heterocycloalkyl, or substituted or unsubstituted 5 to 6 membered heteroaryl.

Embodiment P13. The compound of any one of embodiments P1 to P12, wherein $R^7$ and $R^{10}$ substituents may optionally be joined to form a substituted or unsubstituted 3 to 8 membered heterocycloalkyl, or substituted or unsubstituted 5 to 6 membered heteroaryl.

Embodiment P14. The compound of any one of embodiments P1 to P8, wherein $R^4$, $R^5$, $R^6$, and $R^7$ are each independently hydrogen.

Embodiment P15. The compound of any one of embodiments P1 to P13, wherein $R^5$ and $R^{11}$ substituents may optionally be joined to form a substituted or unsubstituted 3 to 8 membered heterocycloalkyl, or substituted or unsubstituted 5 to 6 membered heteroaryl.

Embodiment P16. The compound of any one of embodiments P1 to P15, wherein $R^6$ and $R^{12}$ substituents may optionally be joined to form a substituted or unsubstituted 3 to 8 membered heterocycloalkyl, or substituted or unsubstituted 5 to 6 membered heteroaryl.

Embodiment P17. The compound of any one of embodiments P1 to P16, wherein $R^8$ is hydrogen.

Embodiment P18. The compound of any one of embodiments P1 to P16, wherein $R^8$ is —NH$_2$,

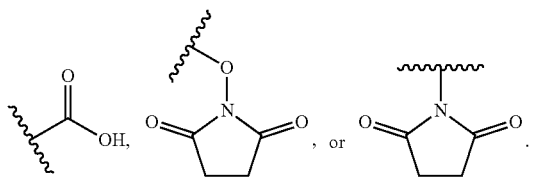

Embodiment P19. The compound of embodiment P1, wherein the compound is

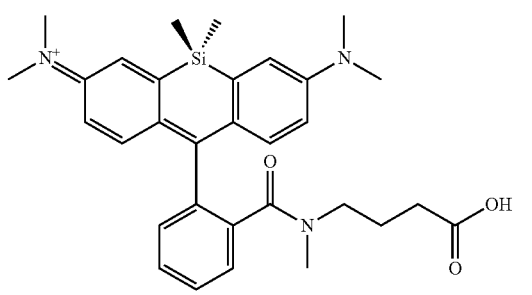

or

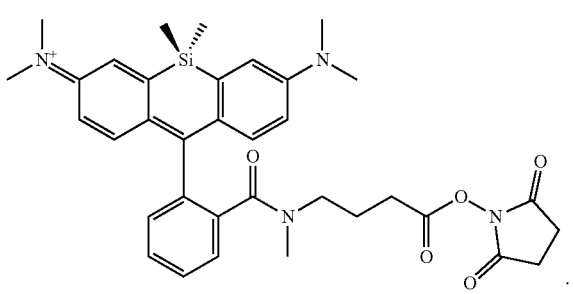

Embodiment P20. A method of detecting the presence of an agent, wherein said agent is covalently bound to a compound of any one of embodiments P1 to P19, and said agent is an oligonucleotide, protein, or compound.

Embodiment P21. A method of making a compound, or salt thereof, having the formula:

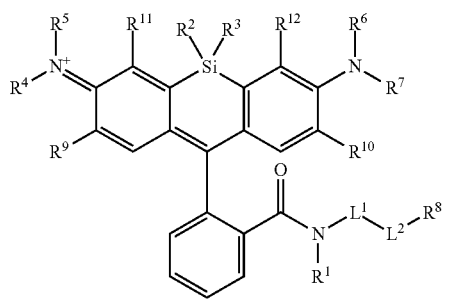

(I)

or

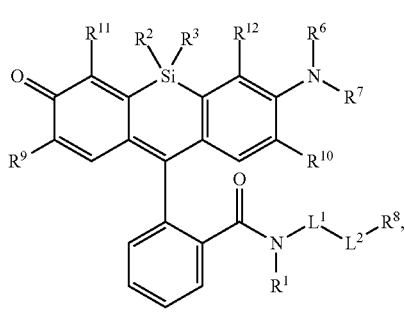

(II)

said method comprising mixing compound A, compound B, and compound C in a reaction vessel, wherein compound A has the formula:

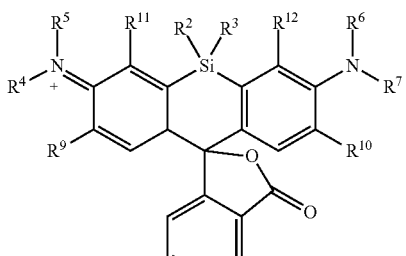

or

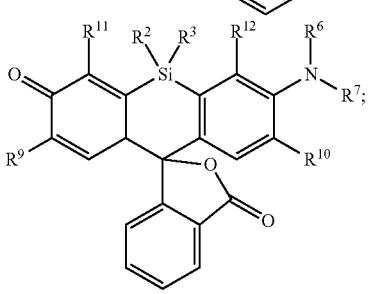

compound B is a coupling reagent;
compound C has the formula:

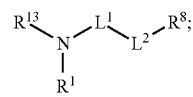

wherein
$R^1$, $R^4$, $R^5$, $R^6$, and $R^7$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —OH, —$NH_2$, —COOH, —$CONH_2$, —SH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ and $R^3$ are each independently substituted or unsubstituted alkyl, or substituted or unsubstituted heteroalkyl;

$R^8$ is hydrogen or a bioconjugate reactive moiety;

$R^9$, $R^{10}$, $R^{11}$, and $R^{12}$, are each independently hydrogen, substituted or unsubstituted alkyl, or substituted or unsubstituted heteroalkyl;

$R^{13}$ is a leaving group;

$L^1$ and $L^2$ are each independently a bond or a covalent linker;

$R^4$ and $R^5$ substituents bonded to the same nitrogen atom may optionally be joined to form a substituted or unsubstituted heterocycloalkyl, or substituted or unsubstituted heteroaryl;

$R^6$ and $R^7$ substituents bonded to the same nitrogen atom may optionally be joined to form a substituted or unsubstituted heterocycloalkyl, or substituted or unsubstituted heteroaryl;

$R^4$ and $R^9$ substituents may optionally be joined to form a substituted or unsubstituted heterocycloalkyl, or substituted or unsubstituted heteroaryl;

$R^7$ and $R^{10}$ substituents may optionally be joined to form a substituted or unsubstituted heterocycloalkyl, or substituted or unsubstituted heteroaryl;

R⁵ and R¹¹ substituents may optionally be joined to form a substituted or unsubstituted heterocycloalkyl, or substituted or unsubstituted heteroaryl; and R⁶ and R¹² substituents may optionally be joined to form a substituted or unsubstituted heterocycloalkyl, or substituted or unsubstituted heteroaryl.

Embodiment P22. The method of embodiment P20, wherein compound B is:

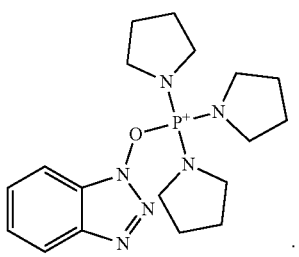 [SMILES: c1ccc2c(c1)nnn2O[P+](N1CCCC1)(N1CCCC1)N1CCCC1]

Embodiment P23. The method of embodiment P20, wherein compound C is

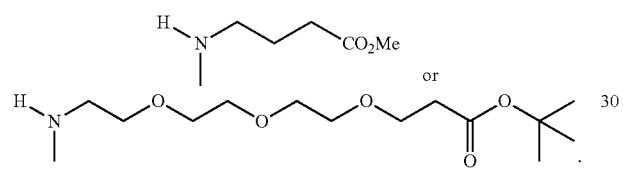

Embodiment P24. The method of embodiment P20, wherein the compound is

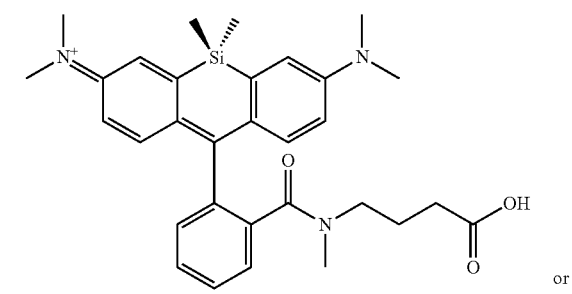

or

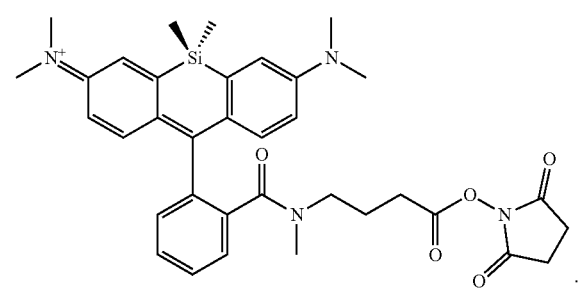

V. Additional Embodiments

Embodiment 1. A compound, or salt thereof, having the formula:

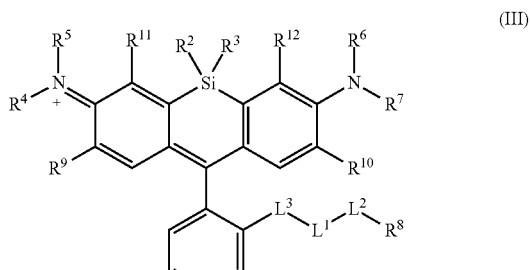
(III)

or

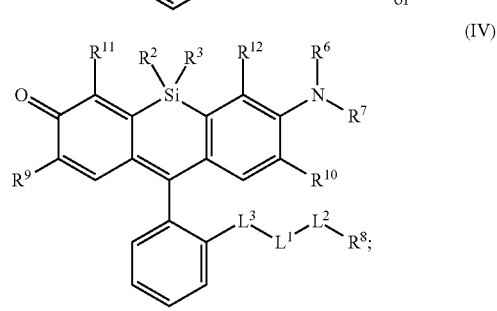
(IV)

wherein, $L^3$ is

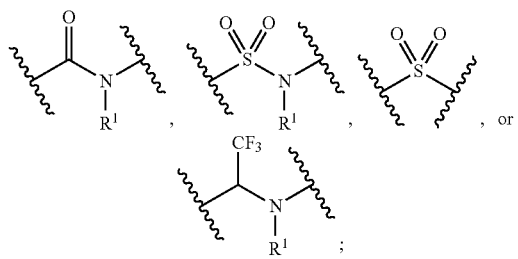
;

$L^1$ and $L^2$ are each independently a bond or a covalent linker;

$R^1$ is independently halogen, —CF₃, —CBr₃, —CCl₃, —CI₃, —CHF₂, —CHBr₂, —CHCl₂, —CHI₂, —CH₂F, —CH₂Br, —CH₂Cl, —CH₂I, —OH, —NH₂, —COOH, —CONH₂, —SH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ and $R^3$ are each independently substituted or unsubstituted alkyl, or substituted or unsubstituted heteroalkyl;

$R^4$, $R^5$, $R^6$, and $R^7$ are each independently hydrogen, halogen, —CF₃, —CBr₃, —CCl₃, —CI₃, —CHF₂, —CHBr₂, —CHCl₂, —CHI₂, —CH₂F, —CH₂Br, —CH₂Cl, —CH₂I, —OH, —NH₂, —COOH, —CONH₂, —SH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^8$ is hydrogen, a bioconjugate reactive moiety, a nucleotide, a nucleoside, or a nucleic acid;

R$^9$, R$^{10}$, R$^{11}$, and R$^{12}$ are each independently hydrogen, substituted or unsubstituted alkyl, or substituted or unsubstituted heteroalkyl;

R$^4$ and R$^5$ substituents bonded to the same nitrogen atom may optionally be joined to form a substituted or unsubstituted heterocycloalkyl, or substituted or unsubstituted heteroaryl;

R$^6$ and R$^7$ substituents bonded to the same nitrogen atom may optionally be joined to form a substituted or unsubstituted heterocycloalkyl, or substituted or unsubstituted heteroaryl;

R$^4$ and R$^9$ substituents may optionally be joined to form a substituted or unsubstituted heterocycloalkyl, or substituted or unsubstituted heteroaryl;

R$^7$ and R$^{10}$ substituents may optionally be joined to form a substituted or unsubstituted heterocycloalkyl, or substituted or unsubstituted heteroaryl;

R$^5$ and R$^{11}$ substituents may optionally be joined to form a substituted or unsubstituted heterocycloalkyl, or substituted or unsubstituted heteroaryl; and R$^6$ and R$^{12}$ substituents may optionally be joined to form a substituted or unsubstituted heterocycloalkyl, or substituted or unsubstituted heteroaryl.

Embodiment 2. The compound of embodiment 1, wherein L$^1$ and L$^2$ are each independently a bond, —S(O)$_2$—, —S(O)$_2$NH—, —NHS(O)$_2$—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or a polymer.

Embodiment 3. The compound of embodiment 1, wherein L$^1$ and L$^2$ are each independently a bond, —C(O)—, —C(O)NH—, —NHC(O)—, —NHC(O)NH—, —C(O)O—, —OC(O)—, or substituted or unsubstituted C$_1$-C$_6$ alkylene.

Embodiment 4. The compound of embodiment 1, wherein L$^1$ is substituted or unsubstituted C$_1$-C$_6$ alkylene.

Embodiment 5. The compound of any one of embodiments 1 to 4, wherein L$^2$ is a bond, —C(O)—, —C(O)O—, or —OC(O)—.

Embodiment 6. The compound of any one of embodiments 1 to 5, wherein R$^1$ is substituted or unsubstituted C$_1$-C$_6$ alkyl.

Embodiment 7. The compound of any one of embodiments 1 to 5, wherein R$^1$ is substituted or unsubstituted C$_1$-C$_3$ alkyl.

Embodiment 8. The compound of any one of embodiments 1 to 7, wherein R$^2$ and R$^3$ are each independently substituted or unsubstituted C$_1$-C$_6$ alkyl, or substituted or unsubstituted 2 to 6 membered heteroalkyl.

Embodiment 9. The compound of any one of embodiments 1 to 7, wherein R$^2$ and R$^3$ are each independently substituted or unsubstituted C$_1$-C$_3$ alkyl, or substituted or unsubstituted 2 to 4 membered heteroalkyl.

Embodiment 10. The compound of embodiment 1, having the formula:

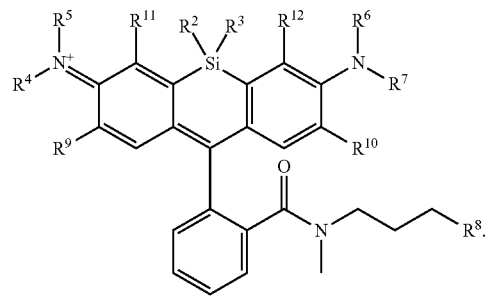

Embodiment 11. The compound of any one of embodiments 1 to 10, wherein R$^4$, R$^5$, R$^6$, and R$^7$ are each independently hydrogen, substituted or unsubstituted C$_1$-C$_6$ alkyl, or substituted or unsubstituted 2 to 6 membered heteroalkyl.

Embodiment 12. The compound of any one of embodiments 1 to 11, wherein R$^4$ and R$^5$ substituents bonded to the same nitrogen atom may optionally be joined to form a substituted or unsubstituted 3 to 6 membered heterocycloalkyl.

Embodiment 13. The compound of any one of embodiments 1 to 12, wherein R$^6$ and R$^7$ substituents bonded to the same nitrogen atom may optionally be joined to form a substituted or unsubstituted 3 to 6 membered heterocycloalkyl.

Embodiment 14. The compound of any one of embodiments 1 to 13, wherein R$^4$ and R$^9$ substituents may optionally be joined to form a substituted or unsubstituted 3 to 8 membered heterocycloalkyl, or substituted or unsubstituted 5 to 6 membered heteroaryl.

Embodiment 15. The compound of any one of embodiments 1 to 14, wherein R$^7$ and R$^{10}$ substituents may optionally be joined to form a substituted or unsubstituted 3 to 8 membered heterocycloalkyl, or substituted or unsubstituted 5 to 6 membered heteroaryl.

Embodiment 16. The compound of any one of embodiments 1 to 10, wherein R$^4$, R$^5$, R$^6$, and R$^7$ are each independently hydrogen.

Embodiment 17. The compound of any one of embodiments 1 to 15, wherein R$^5$ and R$^{11}$ substituents may optionally be joined to form a substituted or unsubstituted 3 to 8 membered heterocycloalkyl, or substituted or unsubstituted 5 to 6 membered heteroaryl.

Embodiment 18. The compound of any one of embodiments 1 to 17, wherein R$^6$ and R$^{12}$ substituents may optionally be joined to form a substituted or unsubstituted 3 to 8 membered heterocycloalkyl, or substituted or unsubstituted 5 to 6 membered heteroaryl.

Embodiment 19. The compound of any one of embodiments 1 to 18, wherein R$^8$ is hydrogen.

Embodiment 20. The compound of any one of embodiments 1 to 18, wherein R$^8$ is —NH$_2$,

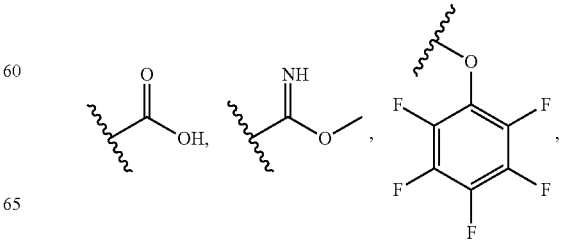

-continued

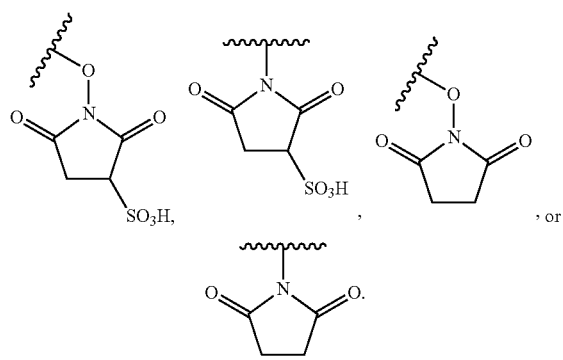

Embodiment 21. The compound of embodiment 1, wherein the compound is

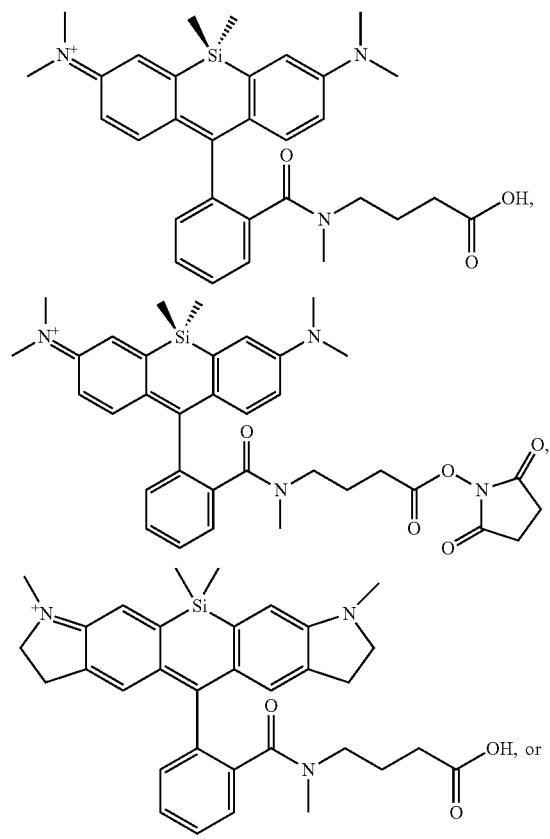

Embodiment 22. The compound of embodiment 1, wherein R⁸ is

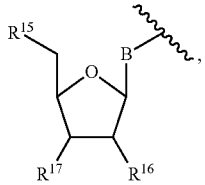

wherein B is a divalent base; $R^{15}$ is independently a 5'-nucleoside protecting group, monophosphate moiety, polyphosphate moiety, or nucleic acid moiety; and $R^{16}$ and $R^{17}$ are each independently hydrogen, a polymerase-compatible cleavable moiety or an —O-polymerase-compatible cleavable moiety.

Embodiment 23. The compound of embodiment 22, wherein $R^7$ is an —O-polymerase-compatible cleavable moiety.

Embodiment 24. The compound of embodiment 23, wherein the polymerase-compatible cleavable moiety is:

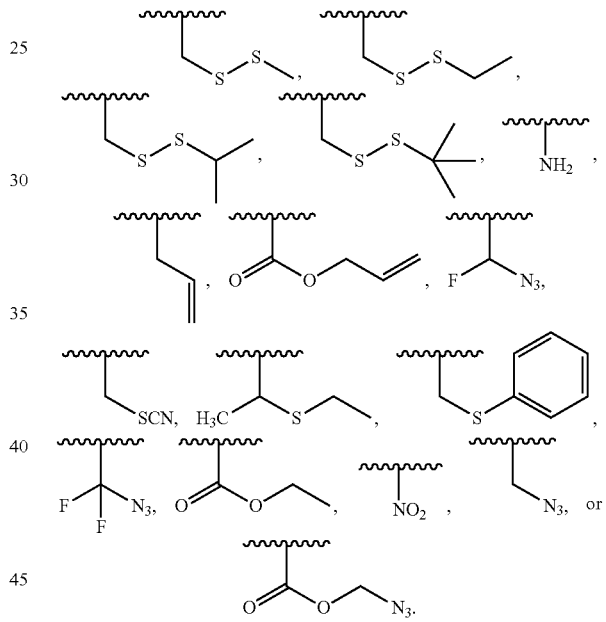

Embodiment 25. The compound of one of embodiments 22 to 24, wherein $R^{16}$ is hydrogen.

Embodiment 26. The compound of one of embodiments 22 to 24, wherein $R^{16}$ is —OH.

Embodiment 27. The compound of one of embodiments 22 to 24, wherein $R^{16}$ is an —O-polymerase-compatible cleavable moiety.

Embodiment 28. The compound of one of embodiments 22 to 27, wherein $R^{15}$ is hydrogen.

Embodiment 29. The compound of one of embodiments 22 to 27, wherein $R^{15}$ is a monophosphate moiety.

Embodiment 30. The compound of one of embodiments 22 to 27, wherein $R^{15}$ is a polyphosphate moiety.

Embodiment 31. The compound of one of embodiments 22 to 27, wherein $R^{15}$ is a triphosphate moiety.

Embodiment 32. The compound of one of embodiments 22 to 27, wherein $R^{15}$ is a nucleic acid moiety.

Embodiment 33. The compound of one of embodiments 22 to 32, wherein B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof.

Embodiment 34. The compound of embodiment 33, wherein B is

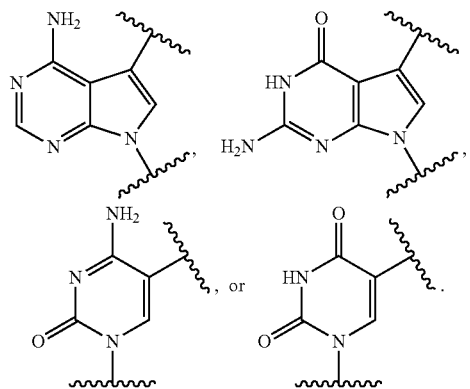

Embodiment 35. A method of detecting the presence of an agent, wherein said agent is covalently bound to a monovalent form of a compound, and said agent is an oligonucleotide, protein, or compound, wherein said monovalent form of the compound has the formula:

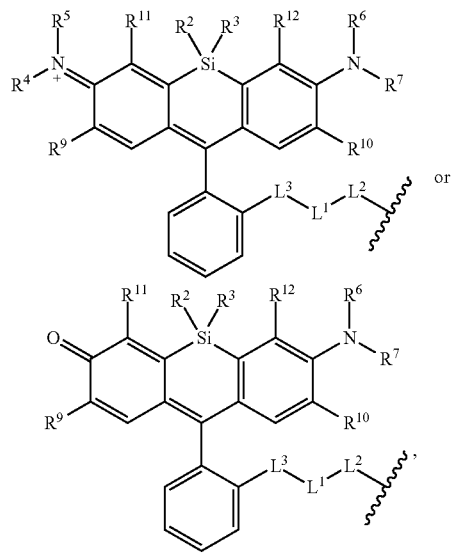

wherein,
$L^3$ is

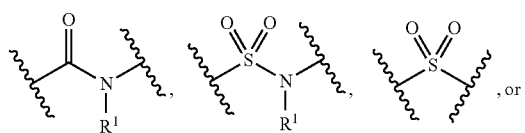

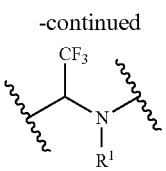

$L^1$ and $L^2$ are each independently a covalent linker or a bond;

$R^1$ is independently substituted or unsubstituted alkyl, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —OH, —$NH_2$, —COOH, —$CONH_2$, —SH, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ and $R^3$ are each independently substituted or unsubstituted alkyl, or substituted or unsubstituted heteroalkyl;

$R^4$, $R^5$, $R^6$, and $R^7$ are each independently hydrogen, substituted or unsubstituted alkyl, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —OH, —$NH_2$, —COOH, —$CONH_2$, —SH, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$, $R^{10}$, $R^{11}$, and $R^{12}$ are each independently hydrogen, substituted or unsubstituted alkyl, or substituted or unsubstituted heteroalkyl;

$R^4$ and $R^5$ substituents bonded to the same nitrogen atom may optionally be joined to form a substituted or unsubstituted heterocycloalkyl, or substituted or unsubstituted heteroaryl;

$R^6$ and $R^7$ substituents bonded to the same nitrogen atom may optionally be joined to form a substituted or unsubstituted heterocycloalkyl, or substituted or unsubstituted heteroaryl;

$R^4$ and $R^9$ substituents may optionally be joined to form a substituted or unsubstituted heterocycloalkyl, or substituted or unsubstituted heteroaryl;

$R^7$ and $R^{10}$ substituents may optionally be joined to form a substituted or unsubstituted heterocycloalkyl, or substituted or unsubstituted heteroaryl;

$R^5$ and $R^{11}$ substituents may optionally be joined to form a substituted or unsubstituted heterocycloalkyl, or substituted or unsubstituted heteroaryl; and $R^6$ and $R^{12}$ substituents may optionally be joined to form a substituted or unsubstituted heterocycloalkyl, or substituted or unsubstituted heteroaryl.

Embodiment 36. The method of embodiment 35, wherein said agent is an oligonucleotide.

Embodiment 37. The method of one of embodiments 35 to 36, wherein the agent covalently bound to the monovalent form of the compound has the formula:

(XI)

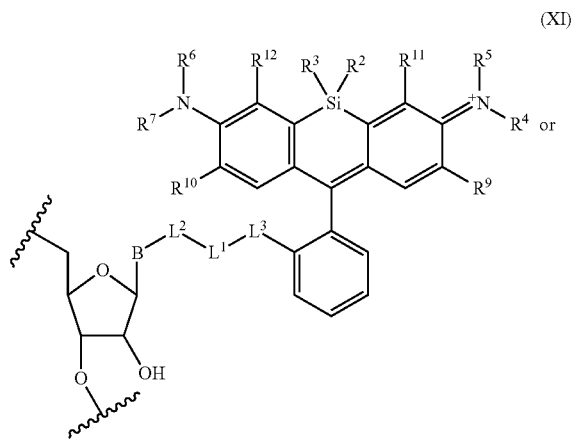

(II)

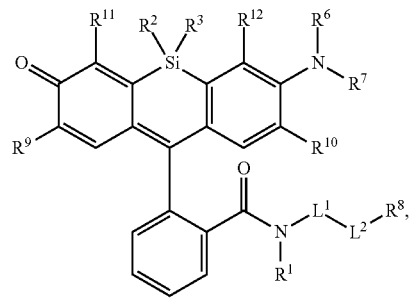

said method comprising mixing compound A, compound B, and compound C in a reaction vessel, wherein compound A has the formula:

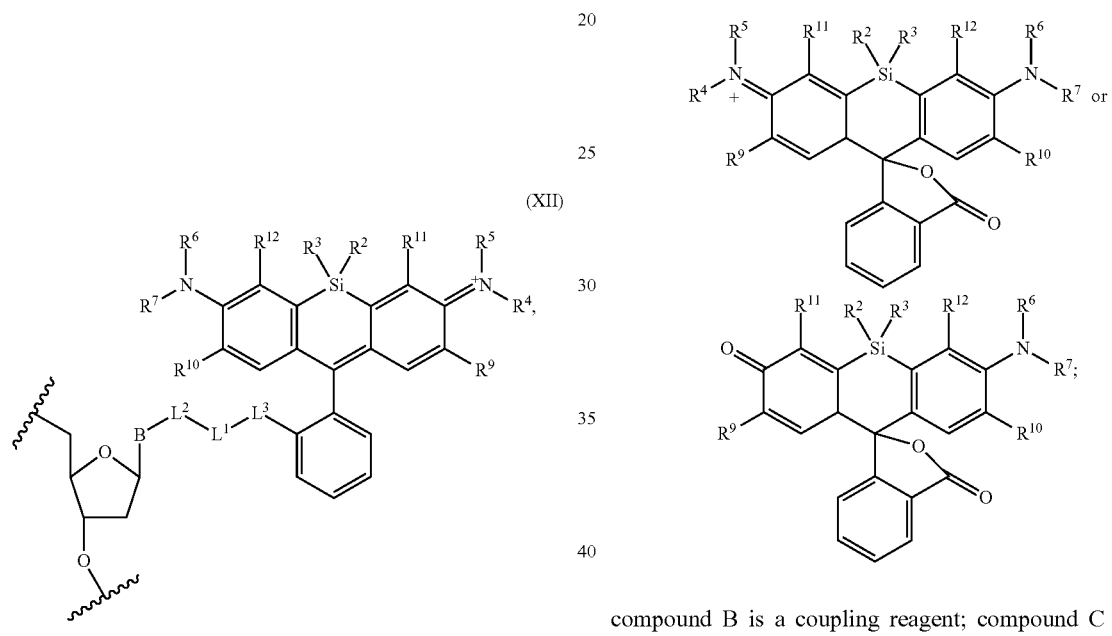

(XII)

compound B is a coupling reagent; compound C has the formula:

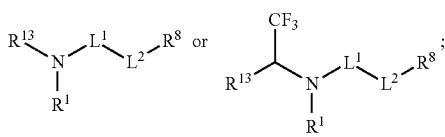

wherein the symbol B is a divalent base or analogue thereof; and the symbol ⌇ in formula (XI) or (XII) refers to an attachment point to hydrogen, a phosphate moiety, or a reversible terminator moiety.

Embodiment 38. A method of making a compound, or salt thereof, having the formula:

(I)

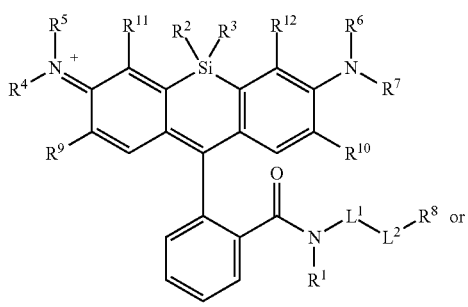

wherein $R^1$, $R^4$, $R^5$, $R^6$, and $R^7$ are each independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —OH, —$NH_2$, —COOH, —$CONH_2$, —SH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ and $R^3$ are each independently substituted or unsubstituted alkyl, or substituted or unsubstituted heteroalkyl; $R^8$ is hydrogen or a bioconjugate reactive moiety; $R^9$, $R^{10}$, $R^{11}$, and $R^{12}$, are each independently hydrogen, substituted or unsubstituted alkyl, or substituted or unsubstituted heteroalkyl; $R^{13}$ is a leaving group; $L^1$ and $L^2$ are each independently a bond or a covalent linker; $R^4$ and $R^5$ substituents bonded to the same nitrogen atom may optionally be joined to form a substituted or unsubstituted heterocycloalkyl, or substituted or unsubstituted heteroaryl; $R^6$ and $R^7$ substituents bonded to the same nitrogen atom may optionally be joined to form a substituted or unsubstituted heterocycloalkyl, or substituted or unsubstituted heteroaryl; $R^4$ and $R^9$ substituents may optionally be joined to form a substituted or unsubstituted heterocycloalkyl, or substituted or unsubstituted heteroaryl; $R^7$ and $R^{10}$ substituents may optionally be joined to form a substituted or unsubstituted heterocycloalkyl, or substituted or unsubstituted heteroaryl; $R^5$ and $R^{11}$ substituents may optionally be joined to form a substituted or unsubstituted heterocycloalkyl, or substituted or unsubstituted heteroaryl; and $R^6$ and $R^{12}$ substituents may optionally be joined to form a substituted or unsubstituted heterocycloalkyl, or substituted or unsubstituted heteroaryl.

Embodiment 39. The method of embodiment 38, wherein compound B is

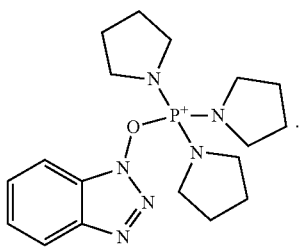 [SMILES: c1ccc2c(c1)nnn2O[P+](N1CCCC1)(N1CCCC1)N1CCCC1]

Embodiment 40. The method of one of embodiments 38 to 39, wherein compound C is

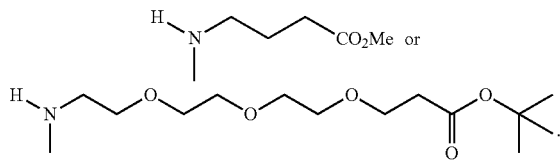

Embodiment 41. The method of one of embodiments 38 to 40, wherein the compound is

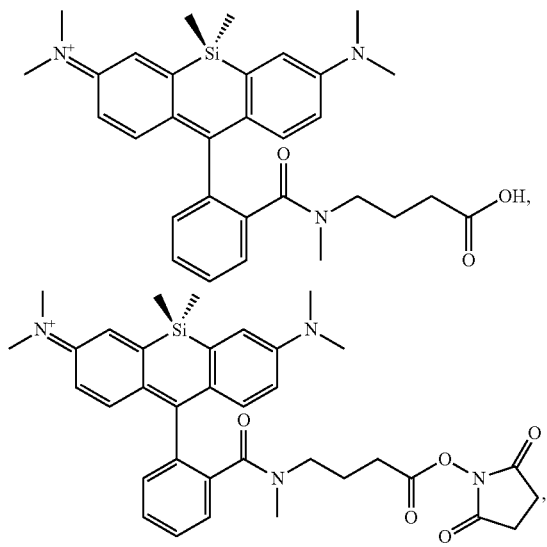

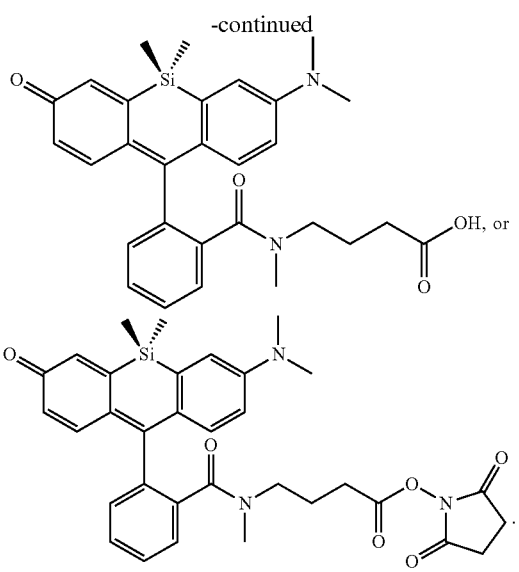

EXAMPLES

Example 1: Ortho Conjugated Silicon Rhodamine Dyes

Currently available red-emitting fluorescent dyes, such as rhodamines and cyanines, suffer from low water-solubility and some derivatives suffer from poor photostability characteristics. For example, due to their hydrophobic nature, most commercially available rhodamine dyes are somewhat insoluble in water. Red-emitting cyanine dyes such as Cy5, although water-soluble, are photo unstable. Thus, available red-emitting rhodamine and cyanine dyes are not well-suited for many aqueous-based biological applications, such as cell staining or nucleic acid sequencing.

Rhodamine dyes such as tetramethyl rhodamine are bright and photostable. Red shifted rhodamine dyes are required for multiplexing. Synthesis of red shifted rhodamine dyes is challenging because it requires building up the carbocyclic framework. The brightness, photostability and aqueous solubility of red rhodamines can suffer when the carbocyclic framework is extended. Research has found that replacement of the oxygen atom at position 10 of the xanthene with a geminal dimethyl group resulted in an approximately 50 nm red shift. Carbopyronine dyes, however, are challenging to synthesize because quaternary carbons in general are difficult to synthesize. Silicon rhodamines are a new class of xanthene dyes in which the oxygen atom at position 10 is replaced with a silicon atom (e.g., a geminal dimethyl silicon). Silicon rhodamines are red shifted by approximately 100 nm relative to traditional rhodamines, with additional fluorescent tunability provided with additional substituents. Importantly, silicon rhodamines are easier to synthesize than carbopyronines because quaternary silicon atoms are easier to synthesize than quaternary carbon atoms.

Fluorescent dye molecules with improved fluorescence properties (such as fluorescence intensity, maximum emission wavelength) can improve the speed and accuracy of nucleic acid sequencing. Fluorescence signal intensity is particularly important when measurements are made in solvents typically used in nucleic acid sequencing technologies (e.g., water based biological buffers) and at elevated temperature (e.g., 60° C. to 80° C.) as fluorescence of most dyes is significantly lower at such conditions. Optimization of the structure of the fluorescent dyes can improve their fluorescent properties and also improve the efficiency of nucleotide incorporation, reduce the level of sequencing errors and decrease the usage of reagents in, and therefore the costs of, nucleic acid sequencing.

Scheme 1. Comparison of tetramethyl rhodamine, tetramethyl carbopyronine and tetramethyl silicon rhodamine dyes. Max ex/em is the maximum excitation and emission values. The fluorescence quantum yield is represented by $\Phi_f$ and the molar extinction coefficient is represented by $\varepsilon$.

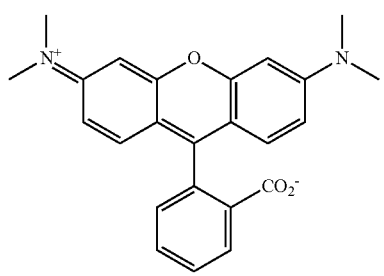

tetramethyl rhodamine
(TMR)
max ex/em 548/577 nm
$\Phi_f$ 45%
$\varepsilon$ 60k cm$^{-1}$M$^{-1}$

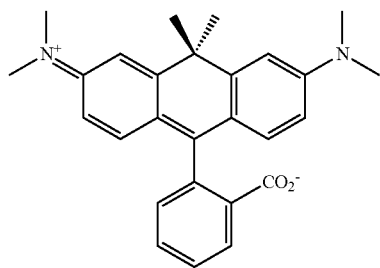

tetramethyl carbopyronine
(TMcP)
max ex/em 606/626 nm
$\Phi_f$ 52%
$\varepsilon$ 121k cm$^{-1}$M$^{-1}$

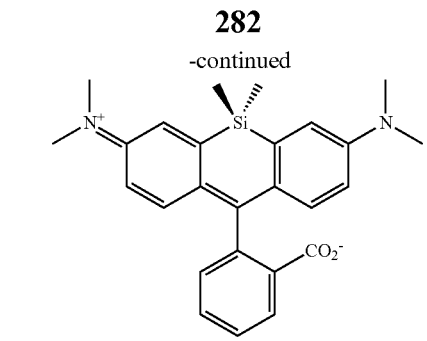

silicon tetramethyl rhodamine
(siTMR)
max ex/em 643-662 nm
$\Phi_f$ 41%
$\varepsilon$ 141k cm$^{-1}$M$^{-1}$ Rhodamine dyes can exist in equilibrium between a fluorescent, ring-opened form and a non-fluorescent, spirolactone form (Scheme 2). Carbopyronine and silicon rhodamine dyes also exist in equilibrium between ring-opened and spirolactone forms. Silicon rhodamine dyes favor the spirolactone, non-fluorescent, form. This spirolactonization is caused by an intramolecular nucleophilic attack and suggested that nucleophilic moieties at the ortho position (e.g., —COOH) should be avoided to prevent the formation of the spirolactone. For nucleic acid analysis however, the equilibrium lowers the fluorescence brightness in DNA sequence dependent manner. Limiting, or eliminating, the formation of spirolactone, non-fluorescent, species is beneficial and improves the overall efficiency and fluorescence brightness in DNA. Additionally, the fluorophore must be stable in the presence of various reactive species, as well as stable during pH and temperature changes, to make it a useful candidate for nucleic acid sequencing.

Scheme 2. Equilibrium between the fluorescent, ring-opened form and non-fluorescent, spirolactone form of TMR, TMcP, and siTMR. Colored form is fluorescent and colorless is non-fluorescent or less fluorescent than the corresponding colored form.

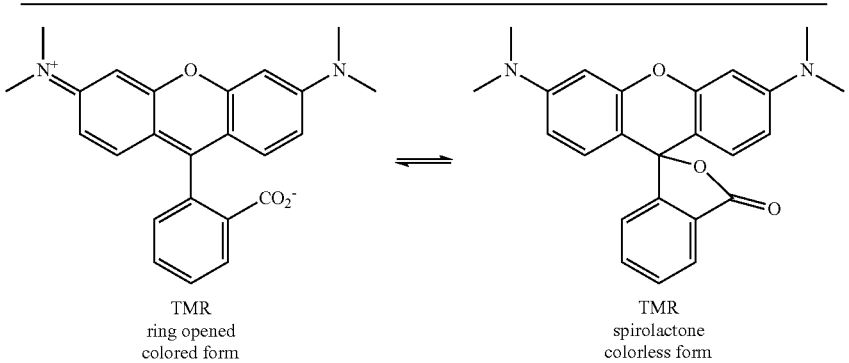

TMR
ring opened
colored form

TMR
spirolactone
colorless form

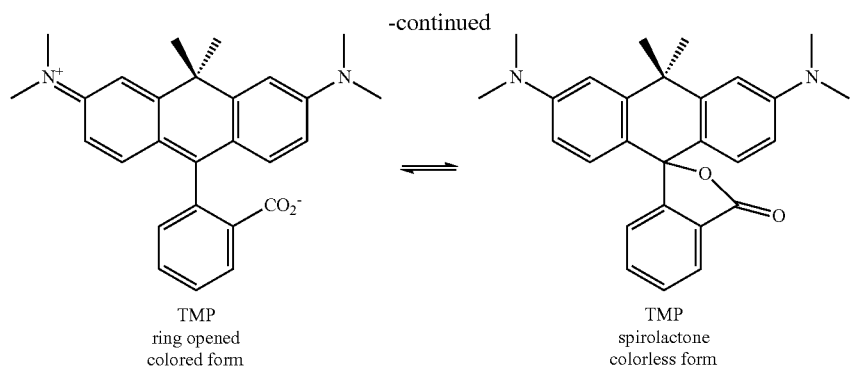

TMP
ring opened
colored form

TMP
spirolactone
colorless form

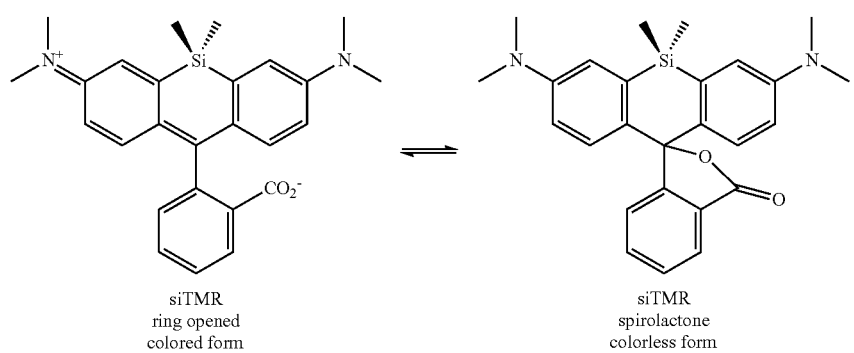

siTMR
ring opened
colored form siTMR
spirolactone
colorless form

The problem of unwanted spirolactone formation was address for rhodamine and carbopyronine dyes by ortho conjugation as exemplified by STAR635P and Atto647N (Scheme 3). In both cases the secondary amide bond prevents spirolactonization to the non-fluorescent form.

Scheme 3. Abberior STAR635P is an ortho conjugated rhodamine. Atto647N is an ortho conjugated carbopyronine.

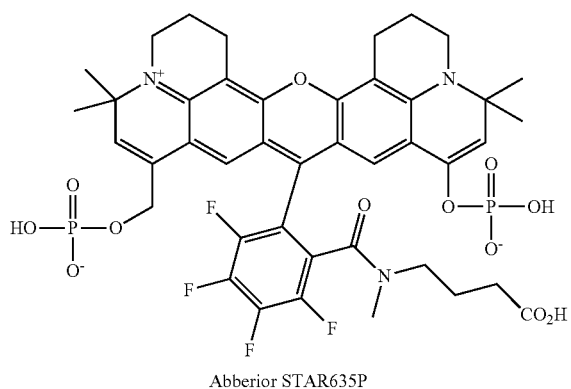

Abberior STAR635P

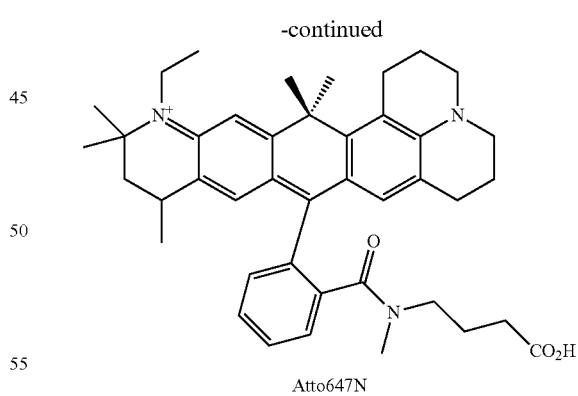

Atto647N

Previous research attempts were unsuccessful in applying ortho conjugation to silicon rhodamines (Scheme 4 and Scheme 4A). When they attempted to saponify the methyl ester, i.e., Scheme 4, they observed concomitant hydrolysis of the amide.

Scheme 4.

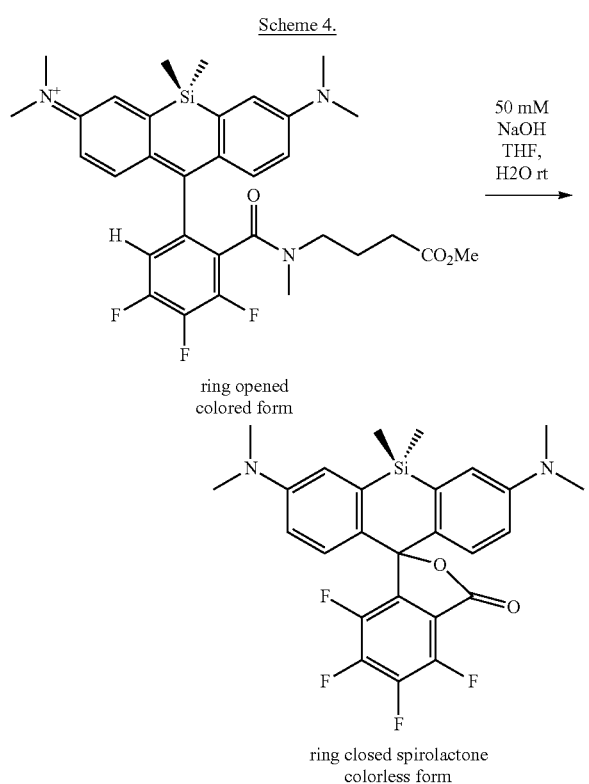

Within the context of nucleic acid sequencing, it is desirable to use a fluorophore that is stable and non-reactive. The presence of additional electrophilic moieties (e.g., a halogen) on the phenyl ring may compromise the stability of the compounds. For example, it is well known that under basic conditions, at least one of the fluorine atoms on the phenyl is vulnerable to a nucleophilic substitution (e.g., wherein the nucleophile is an amine, alkoxide, sulfide, or stabilized carbanion), see (Goldstein et al, *J. Chem. Educ.* 2017, 94, 9, 1388-1390). We hypothesized that the substitutions on the phenyl ring (e.g., 3 electronegative fluorine atoms on the phenyl ring observed in Scheme 4; or the para amide and COOH observed in Scheme 4A) resulted in the unusual hydrolytic instability of the amide bond. We tested this hypothesis by synthesizing a similar silicon rhodamine lacking the 3 fluorine atoms (Scheme 5). Without the fluorine atoms the ortho amide was stable to the conditions used to saponify the methyl ester. Additionally, the saponification step may be avoided completely by utilizing a non-protected compound as depicted in Scheme 5A.

Scheme 4A.

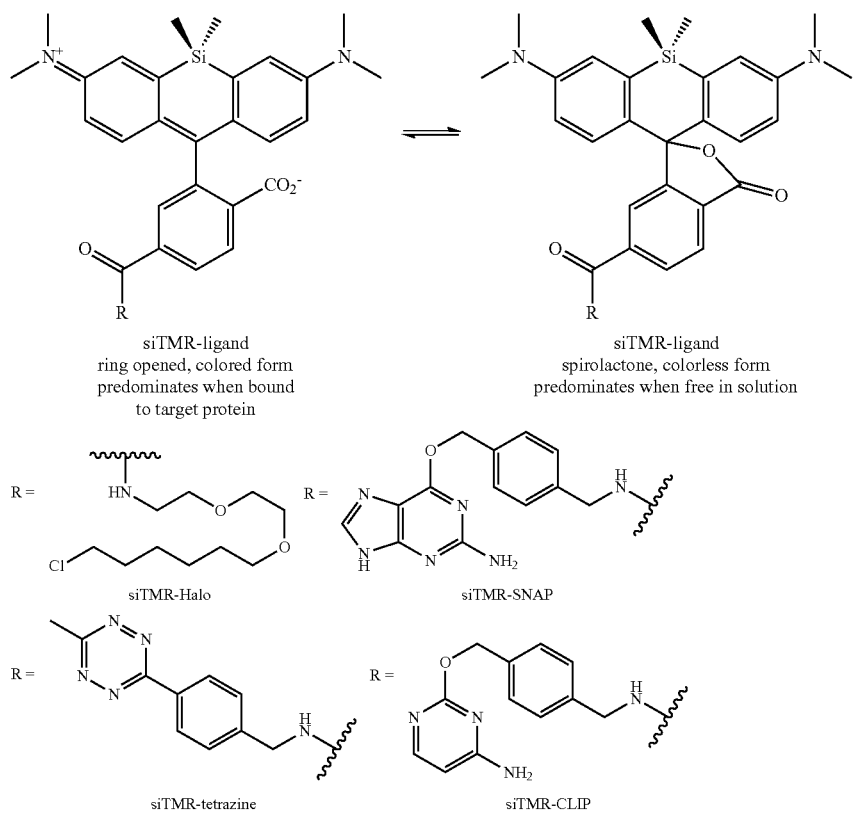

Scheme 5. Synthetic protocol to limit formation of the spirolactone scaffold.
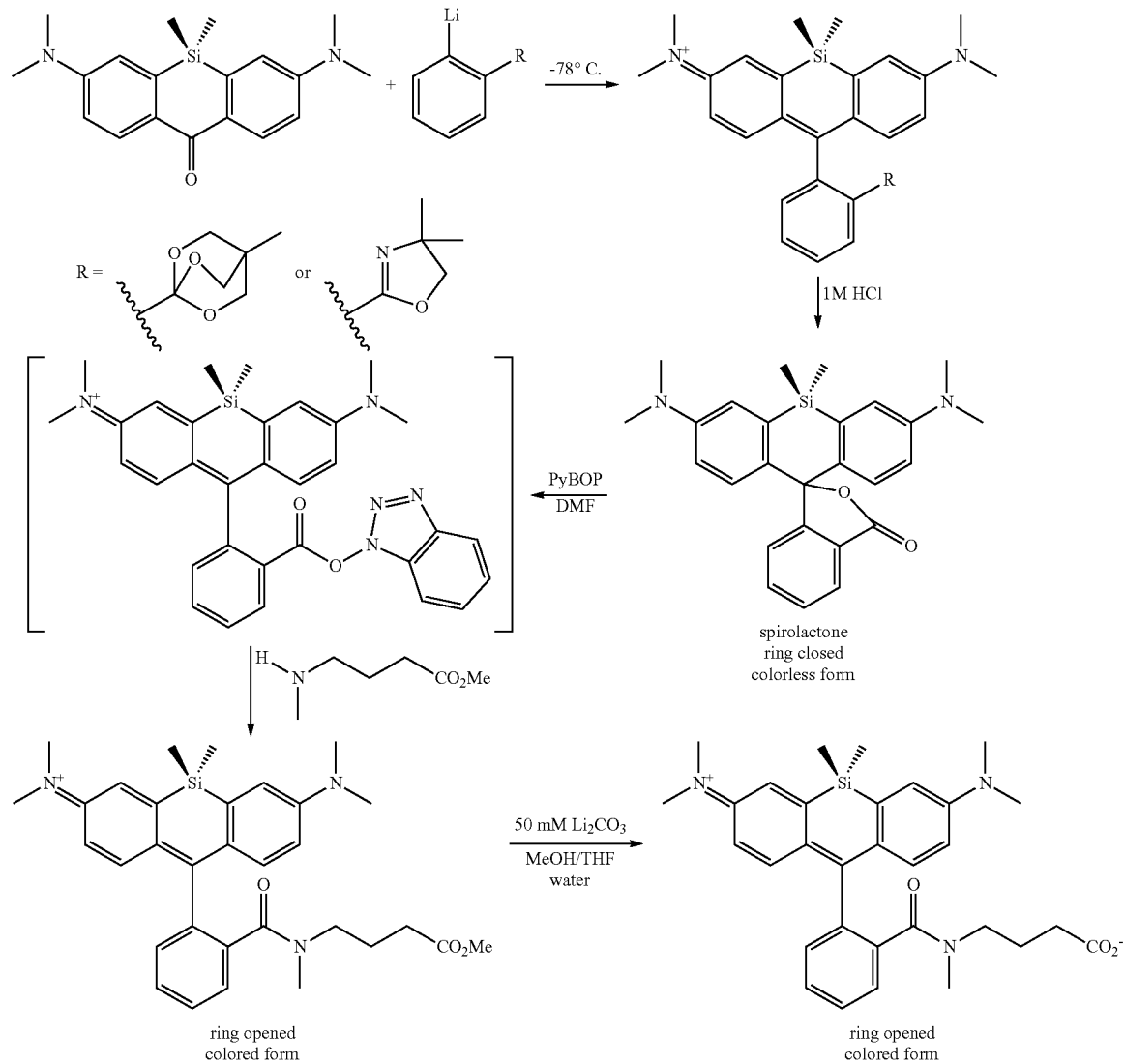
Scheme 5A. Shortened synthetic protocol to limit formation of the spirolactone scaffold.
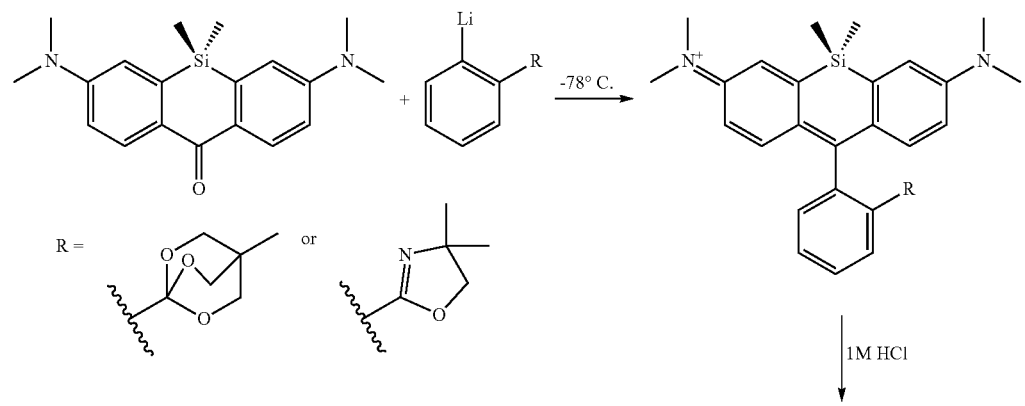

289

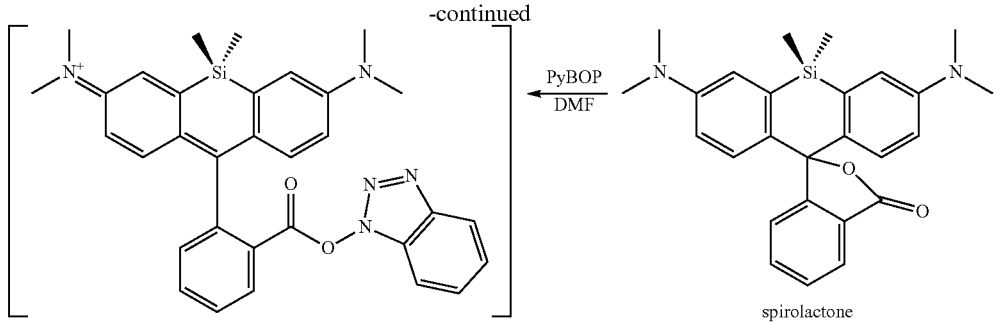

290 spirolactone
ring closed
colorless form

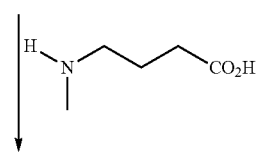

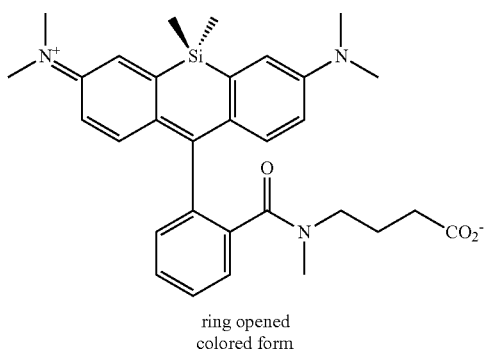

ring opened
colored form

Following synthesis of a silicon rhodamine dye that is not subject to spirolactone formation, we conjugated the ortho amide silicon rhodamine to a reversible terminator (Scheme 6) for use in nucleic acid analysis. Scheme 6 is intended to be a representative of the possible linking chemistry to append the Si-fluorescent dye to a nucleic acid. One having ordinary skill in the art would appreciate the various conjugation strategies to incorporate the Si-fluorescent dye to a variety of agents (e.g., oligonucleotide (e.g., DNA, RNA, or siRNA), protein (e.g., antibody or antibody fragment), or compound (e.g., small molecule). The symbol  in the schemes 6, 7, and 8 refers to an attachment point to a phosphate (e.g., monophosphate or polyphosphate), a hydrogen, or a reversible terminator moiety known in the art (e.g., a substituted or unsubstituted alkyl or substituted or unsubstituted heteroalkyl moiety).

Scheme 6. Synthetic scheme depicting the attachment of a Si-Rhodamine compound to a nucleic acid base via a covalent linker.

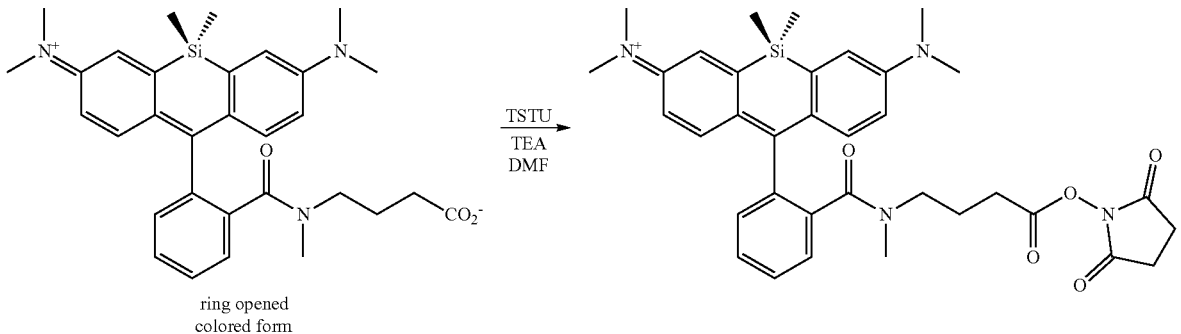

ring opened
colored form

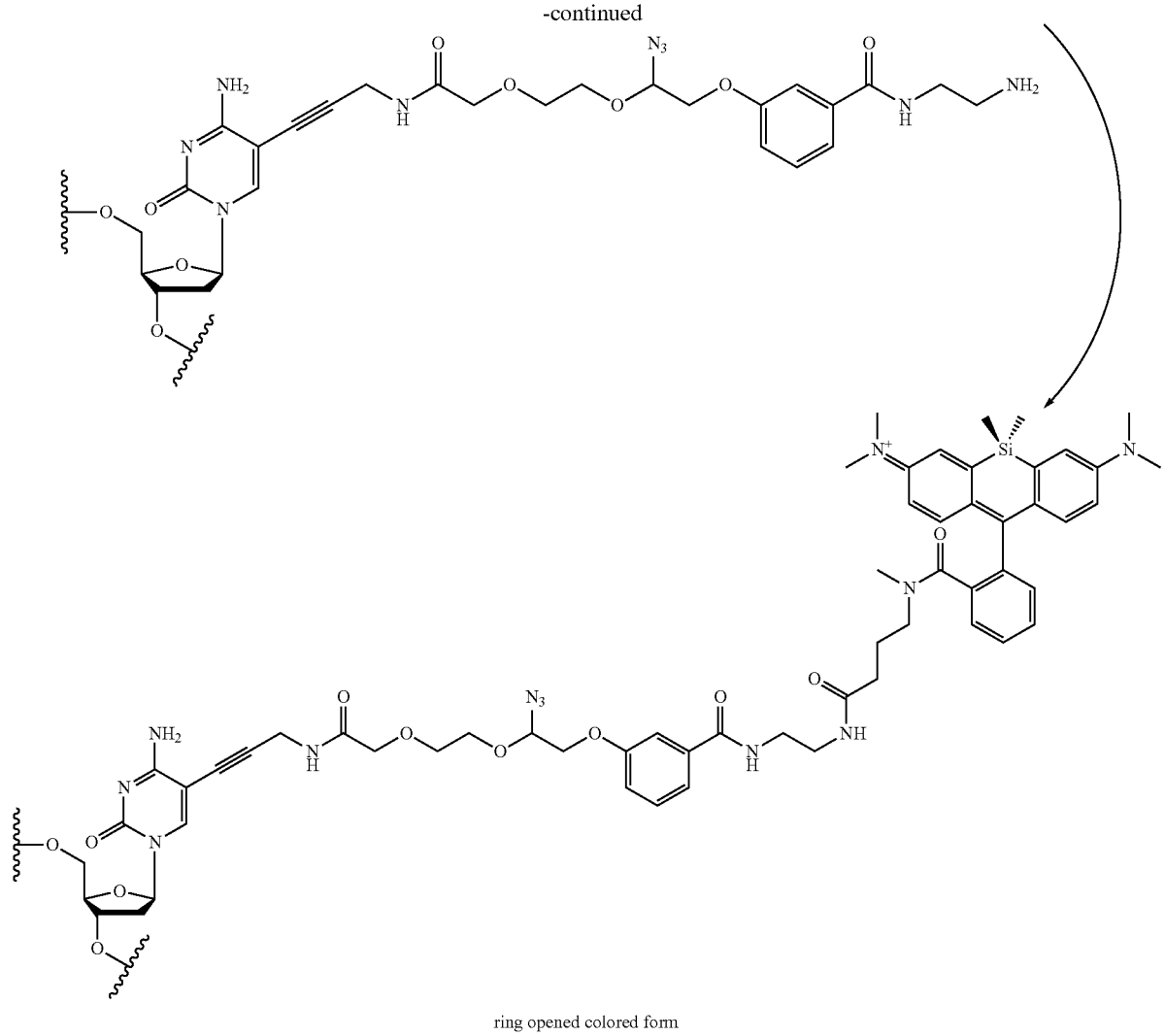

ring opened colored form

Figure 1B:
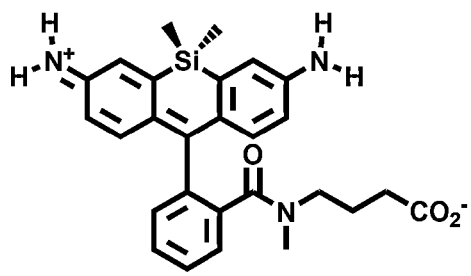
Figure 1B:
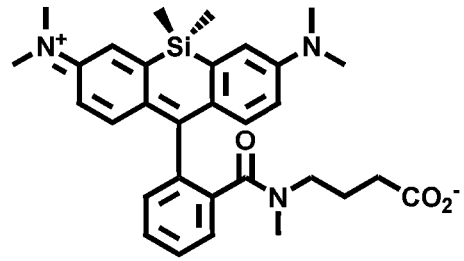
Figure 1B:
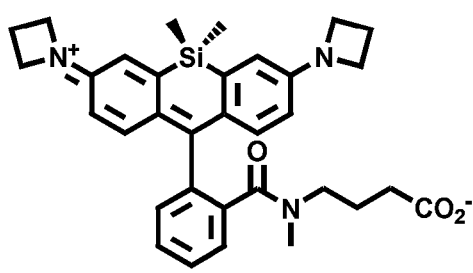
Figure 1B:
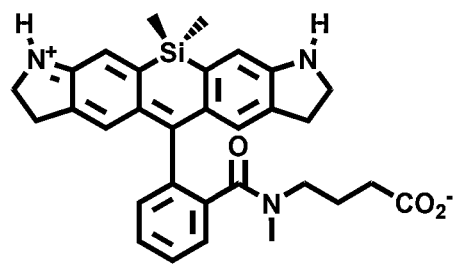
Figure 1B:
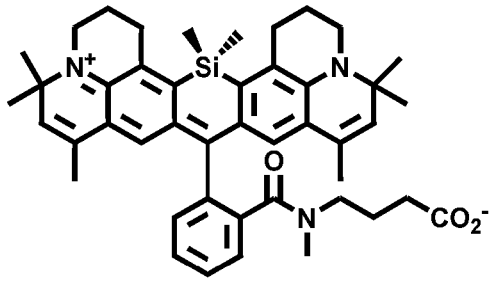
Figure 1B:
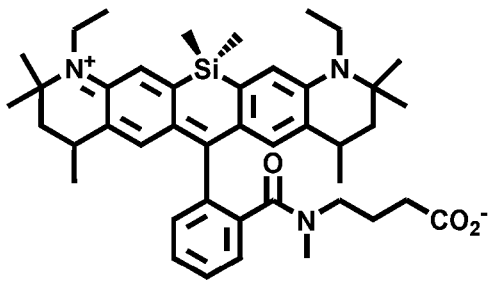
Figure 1B:
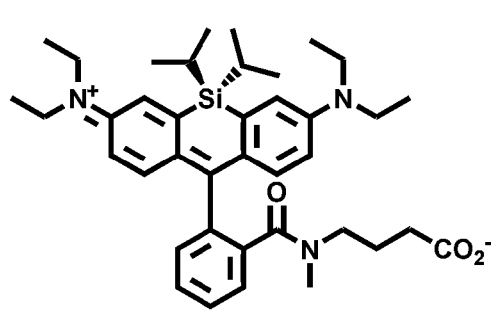
Figure 1B:
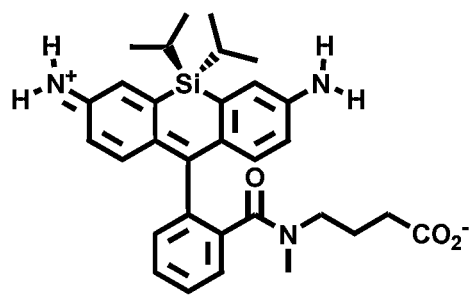
Figure 1C:
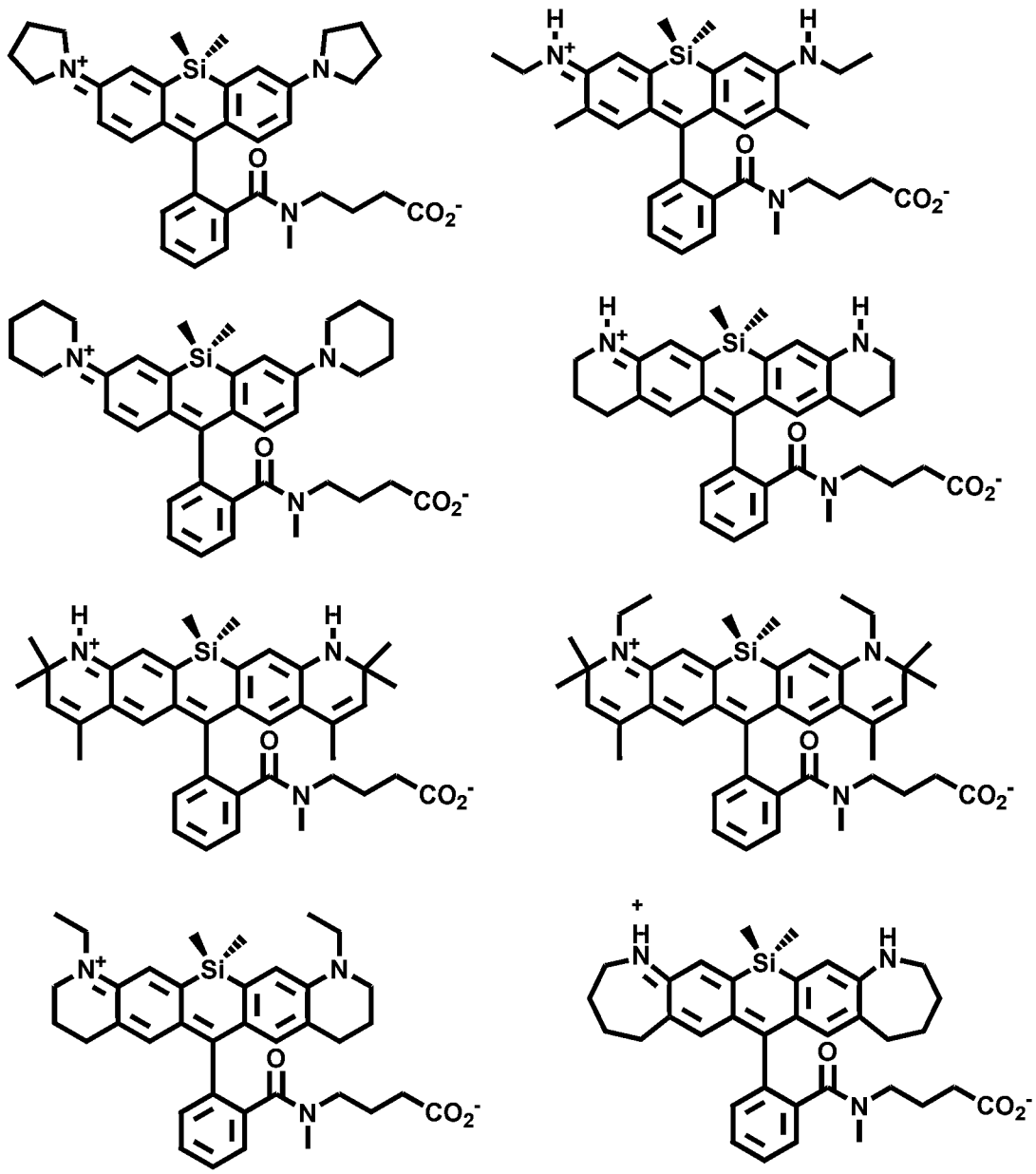
Figure 1D:
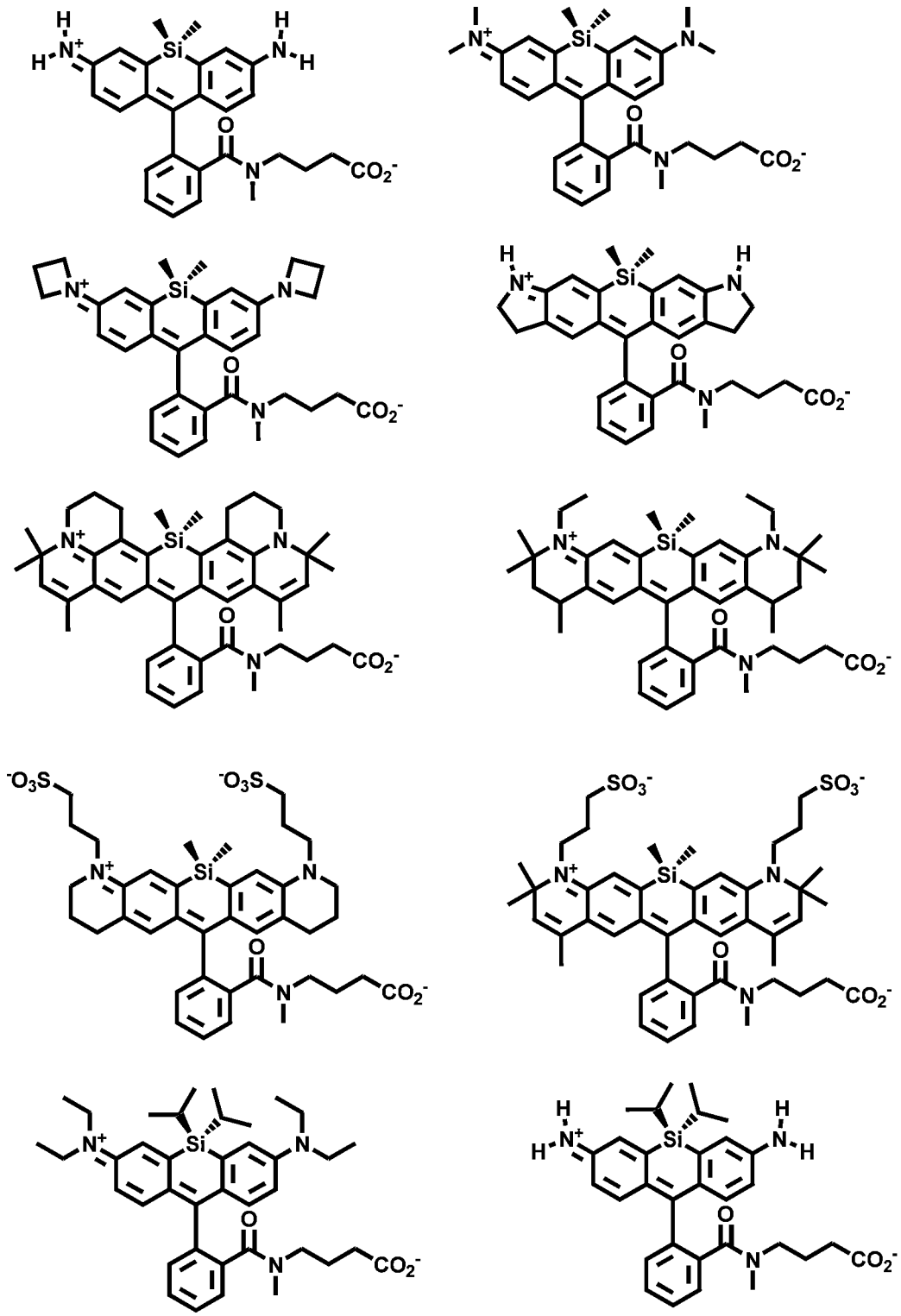
Figure 1E:
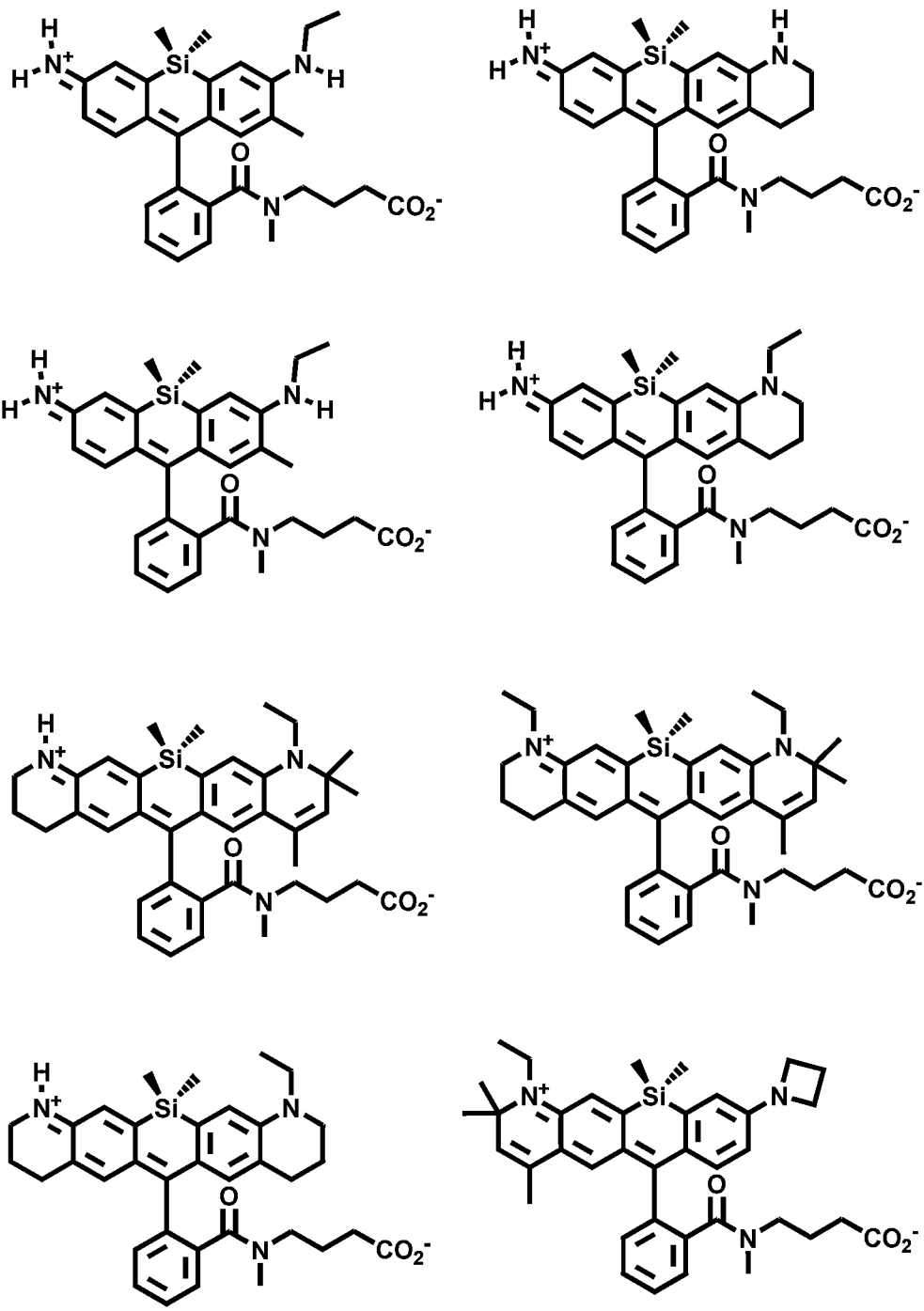
Figure 2:
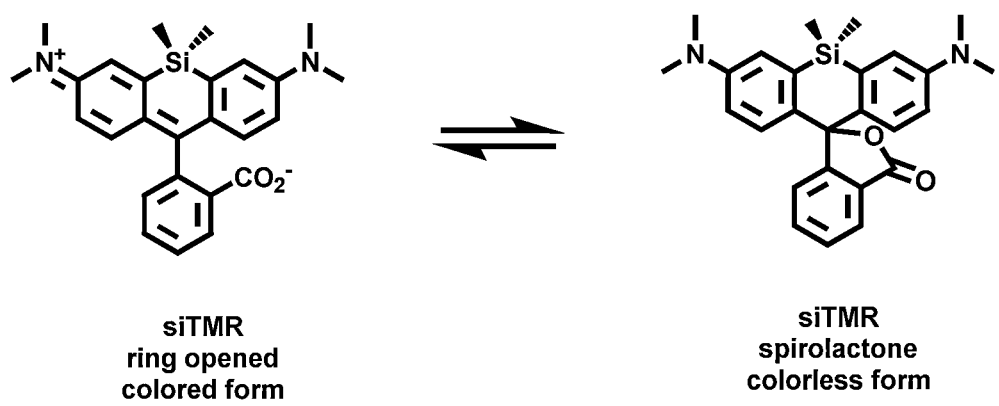
FIG. 2. Equilibrium between the fluorescent, ring-opened form and non-fluorescent, spirolactone form of siTMR.

Many variations of this approach to ortho amide silicon rhodamines can be envisioned. Non-limiting examples are shown in FIGS. 1A-1E.

Improving the hydrophilicity of the compounds described herein. Many commercial fluorescent dyes have a polycyclic aromatic nature and are hydrophobic. Those molecules are also prone to minimize exposure to any hydrophilic environment through interactions with nearby hydrophobic surfaces and residues. These interactions include dye-dye interaction and dye-biomolecule (e.g., proteins, lipids, oligonucleotides) interactions. Hydrophobic interactions can cause substantial quenching effect for fluorescent dyes (see, for example, Randolph, J. B.; Waggoner, A. S. *Nucleic Acids Res.* 1997, 25(14), 2923-2929). One method to overcome this problem is to improve the hydrophilic character of the dye by, for example, introducing a sulfonate substituent into the dye molecule (sulfonated carbocyanine dyes are disclosed in U.S. Pat. No. 5,268,486 and sulfonated xanthene dyes are disclosed in U.S. Pat. No. 6,130,101. Utilizing methods known in the art, and described below in greater detail, the compounds described herein may have improved hydrophilic character through the addition of polar or solubilizing residues (e.g., sulfonate or phosphonate moieties).

For example, sulfonation of the compound (e.g., a compound described herein) is carried out by stirring the dye in fuming sulfuric acid (20-30% $SO_3$ content) or concentrated sulfuric acid at an appropriate temperature. Compounds with electron-donating groups on the xanthylium ring are typically sulfonated at room temperature, while compounds having electron-withdrawing groups such as fluorine and chlorine on the xanthylium ring are typically sulfonated at an elevated temperature, for example at 100-110° C. Monosulfonation of rhodol dyes is carried out by stirring the appropriate rhodol dye in fuming sulfuric acid at 0° C. for several hours. Bis-sulfonation of rhodols is achieved by stirring the dye in fuming sulfuric acid at room temperature for several hours. Where the compound possesses a vinylic methyl group, sulfonation at the vinylic methyl is accomplished by treatment with concentrated sulfuric acid at room temperature. Post-condensation modifications of xanthylium dyes are well known. For example, the xanthenone portion of the dye can be halogenated by treatment with the appropriate halogenating agent, such as liquid bromine. Similarly to nonsulfonated xanthenes, the amino and hydroxyl groups of sulfonated xanthenes can be acylated or alkylated to yield amides, esters, and ethers.

Scheme 7. Synthetic scheme depicting the attachment of a Si-Rhodamine compound to a nucleic acid base via a covalent linker.
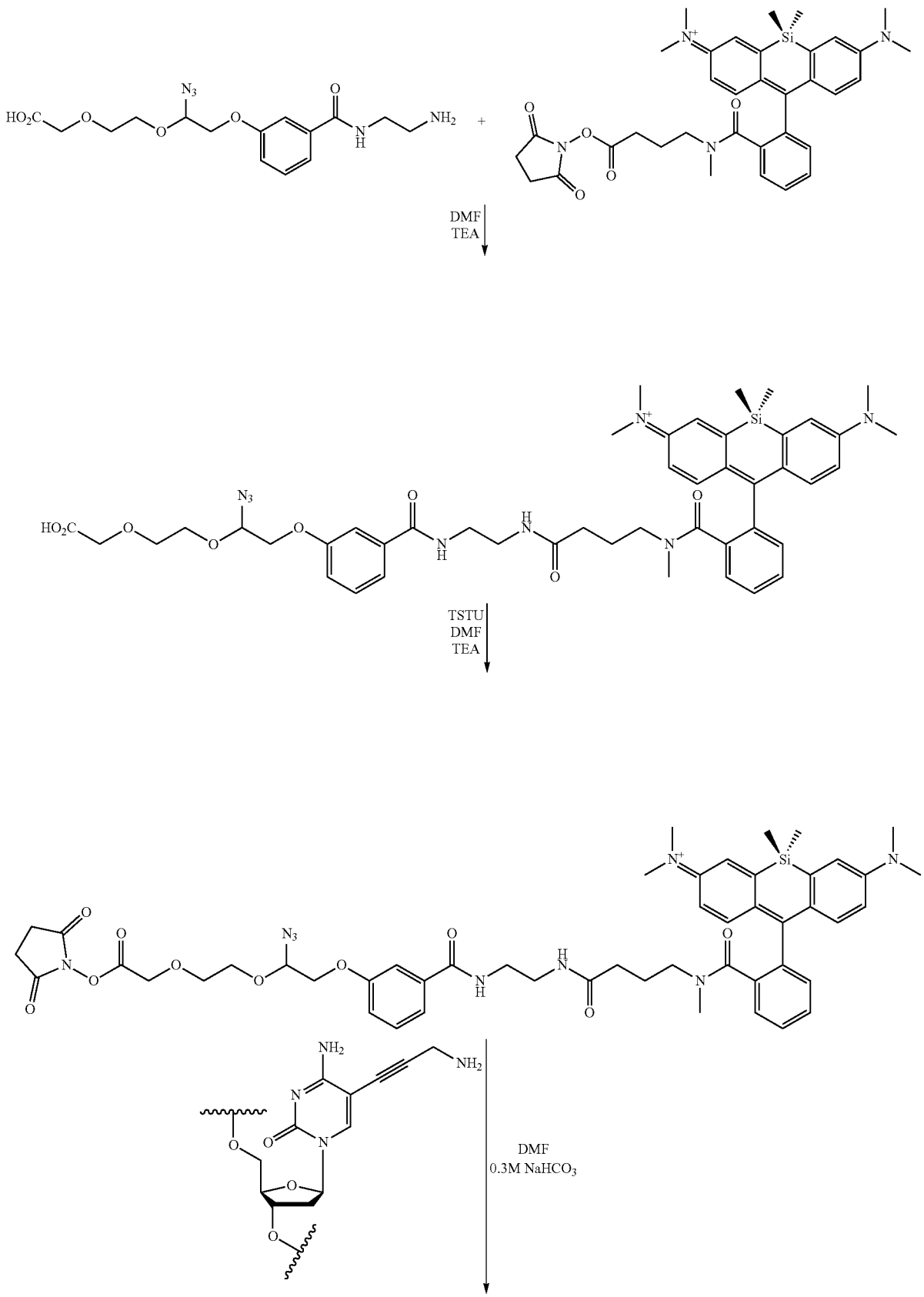

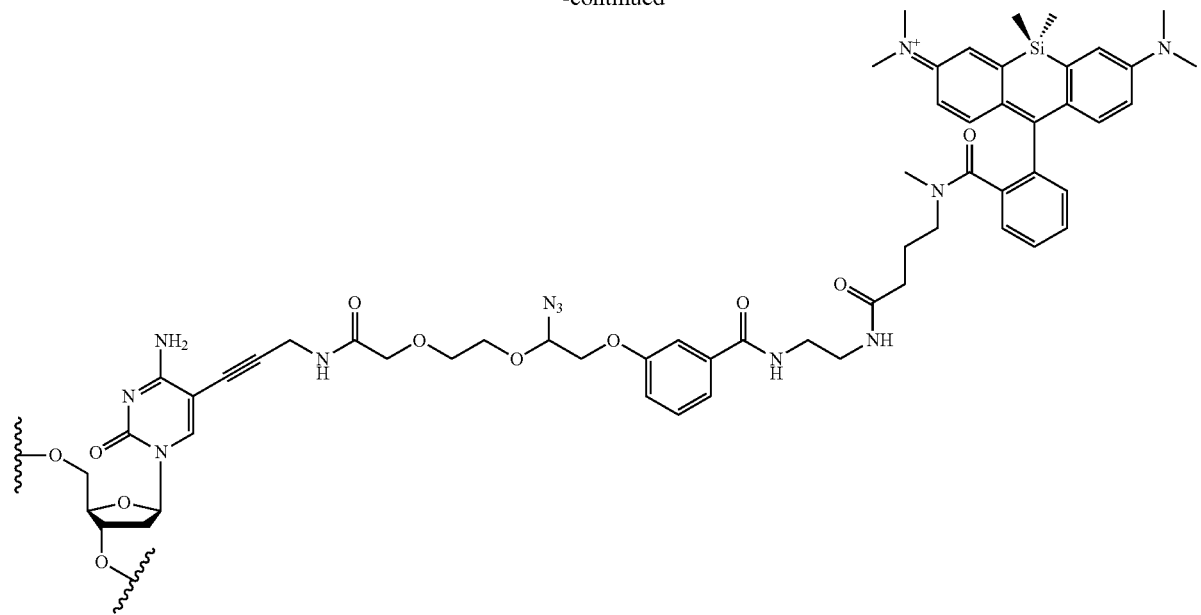
Scheme 8. Synthetic scheme depicting the attachment of a Si-Rhodamine compound to a nucleic acid base via a covalent linker.
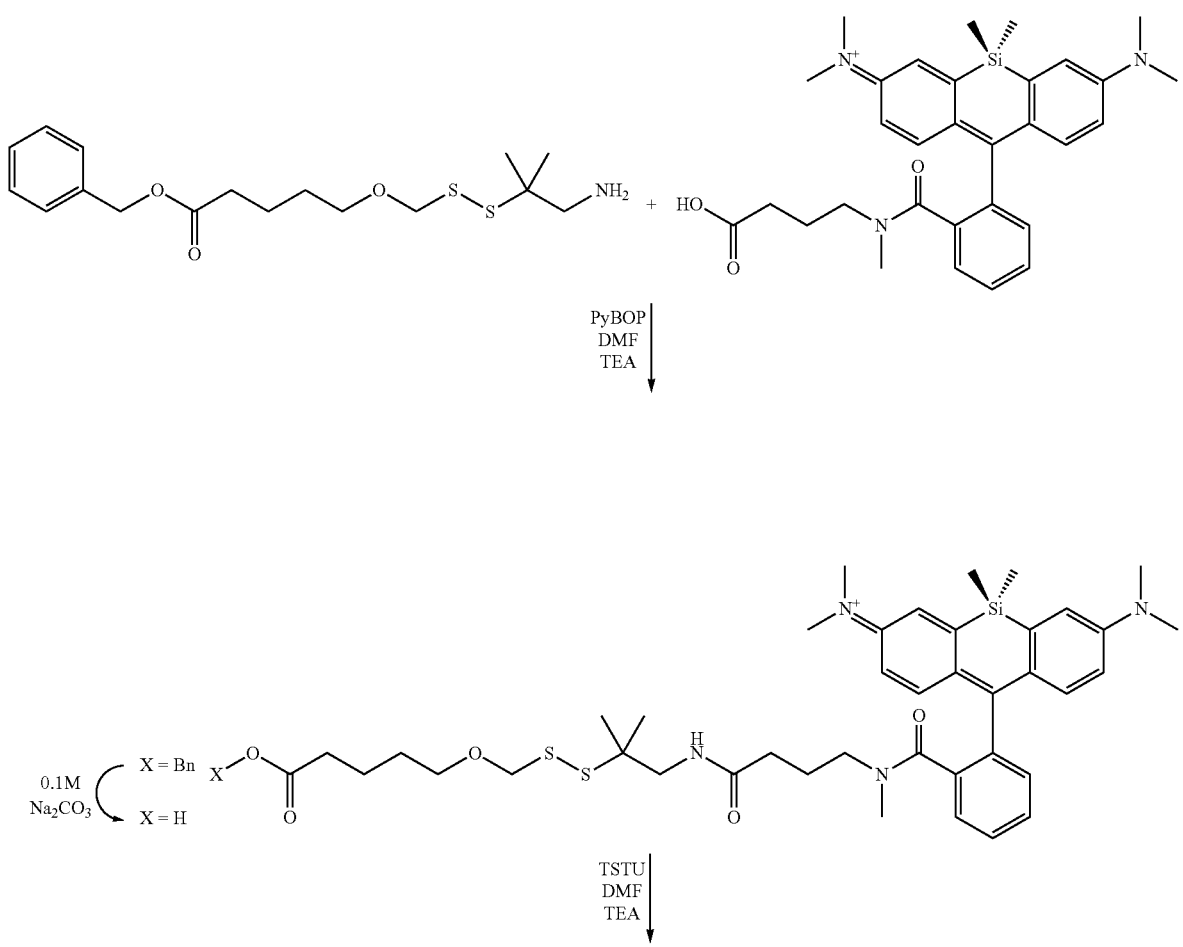

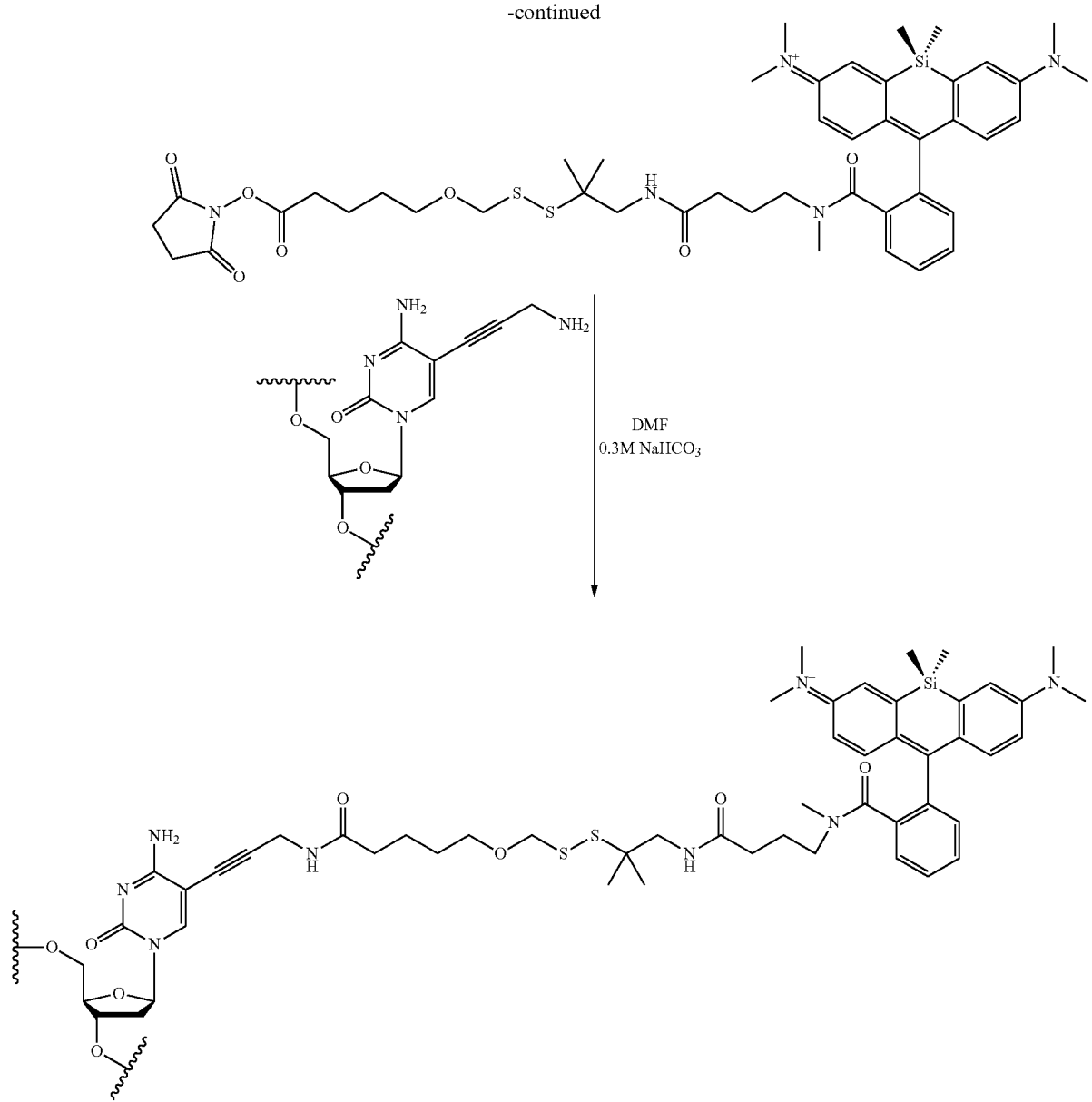
Scheme 9. Synthetic scheme depicting the synthesis of a Si-Rhodamine compound.
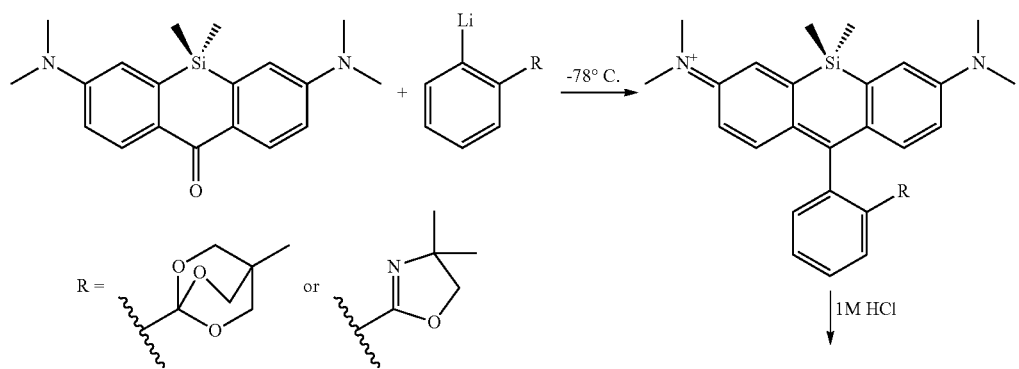

299   300
-continued
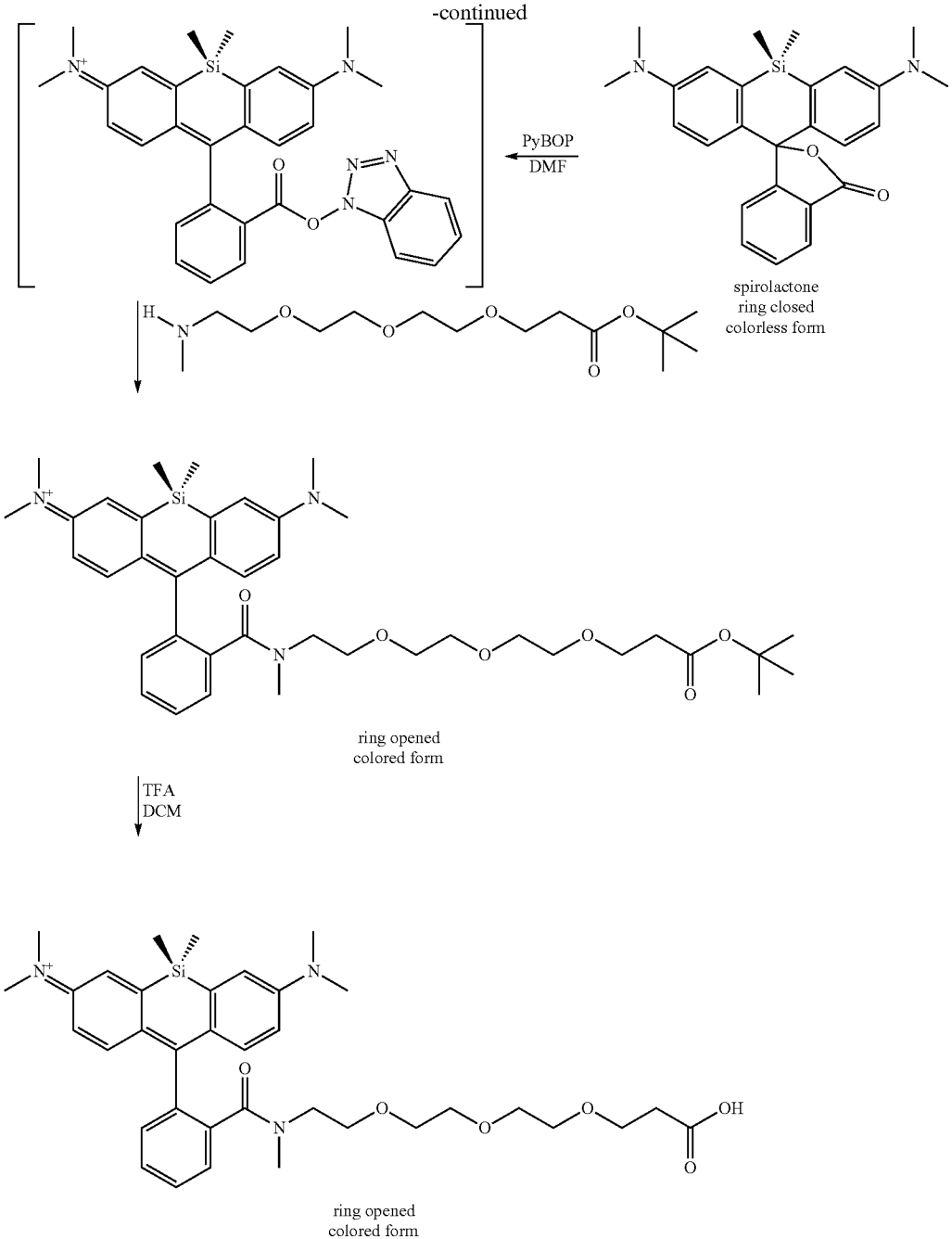
Scheme 10. Generalized synthetic scheme depicting the synthesis of a Si-Rhodamine compound. The symbol R in the scheme below may be any substituent as defined by $R^4$, $R^5$, $R^6$, or $R^7$ as described herein. The symbol R' in Scheme 10 corresponds to —$L^4$—$R^{14}$ and may be any substituent as defined by —$L^4$—$R^{14}$ as described herein.
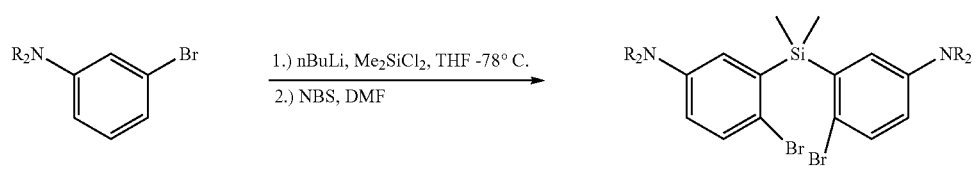

301
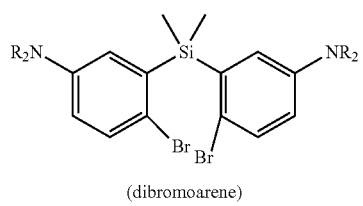
(dibromoarene)
302
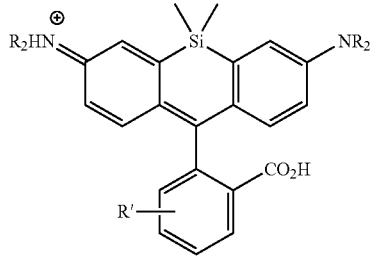
i. t-BuLi
ii. MgBr$_2$—OEt$_2$
iii. anhydride
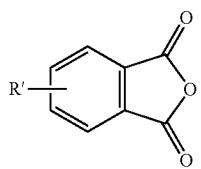
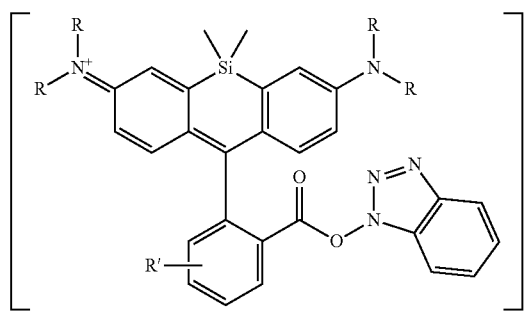
PyBOP
DMF
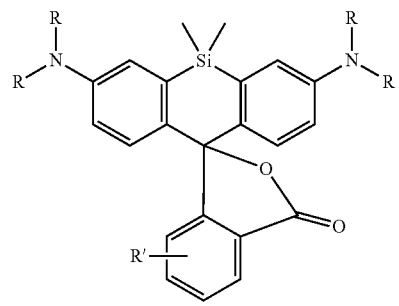
spirolactone
ring closed
colorless form
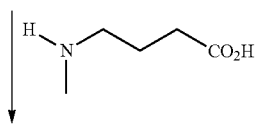
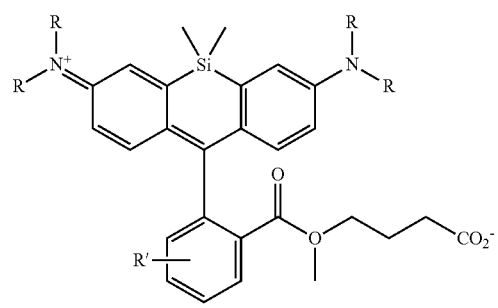
ring opened
colored form

303

Scheme 10A. Variants of the dibromoarene moiety, as depicted in Scheme 10. The symbol n in Scheme 10A is an integer from 1 to 4. The symbol R in Scheme 10A may be any substituent as defined by $R^4$, $R^5$, $R^6$, or $R^7$ as described herein.

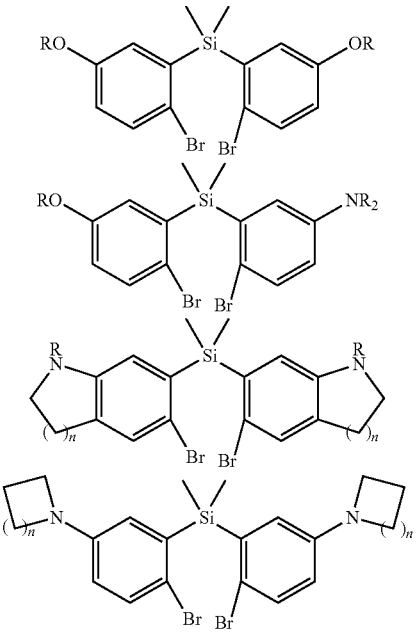

Example 2: Quantifying Photobleaching

The photostability of fluorescent dyes is of crucial importance for the statistical accuracy of nucleic acid sequencing. A fluorophore's structural instability during the excited lifetime makes it susceptible to degradation. High-intensity illumination, such as the illumination sources in nucleic acid sequencing devices can cause the fluorophore to change its structure so that it can no longer fluoresce, referred to as photobleaching. Photobleaching can be controlled by reducing the intensity or time-span of light exposure or modifying the compound to be more resilient to photobleaching. In embodiments, the compounds described herein are less prone to photobleaching (i.e., the compounds are more photostable), relative to a reference fluorophore (e.g., a fluorophore having a similar emission profile, such as fluorophores described in Berlier, Judith E., et al. *Journal of Histochemistry & Cytochemistry*, vol. 51, no. 12, December 2003, pp. 1699-1712, such as Alexa Fluor 680, Alexa Fluor 700, or Cy7 fluorophores).

Measuring photobleaching of the compounds described herein is accomplished according to the following procedure: In separate glass capillary tubes, compounds described herein and reference fluorophores (e.g., Cy7 or Alexa Fluor 700) are filled with solutions of a buffer (e.g., PBS), at pH 7.5. The glass tubes are then excited with light emitted from a fluorescence microscope. Integrated fluorescence emission intensity under continuous illumination can be measured initially and then every 5 sec for about 100 sec. This will provide information on the a rate of photobleaching.

Quantum Yield Determination. Absolute quantum yields ((D) are measured using known techniques in the art, for example utilizing a spectrometer. This instrument uses an integrating sphere to determine photons absorbed and emitted by a sample. Measurements are carried out using dilute samples and self-absorption corrections are performed using the instrument software.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound, or salt thereof, having the formula:

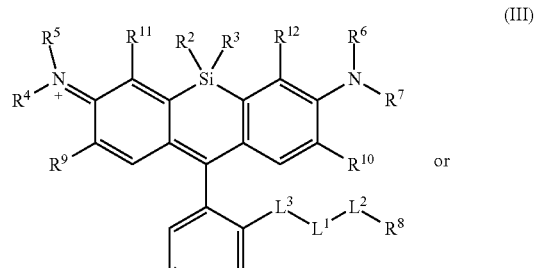

(III)

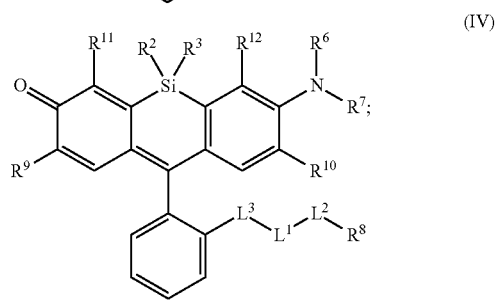

(IV)

wherein,
$L^3$ is

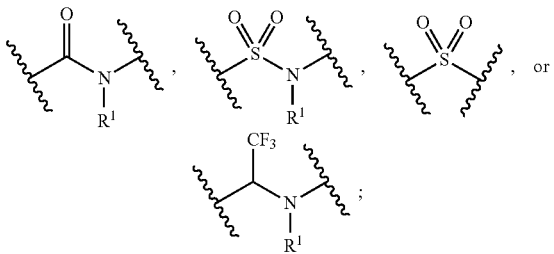

$L^1$-$L^2$-comprises

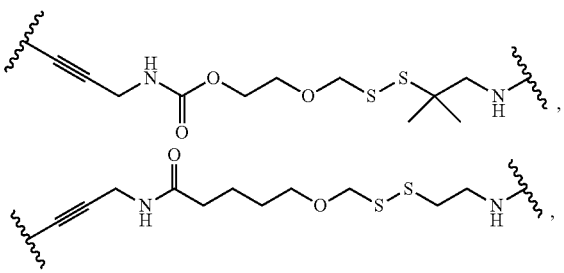

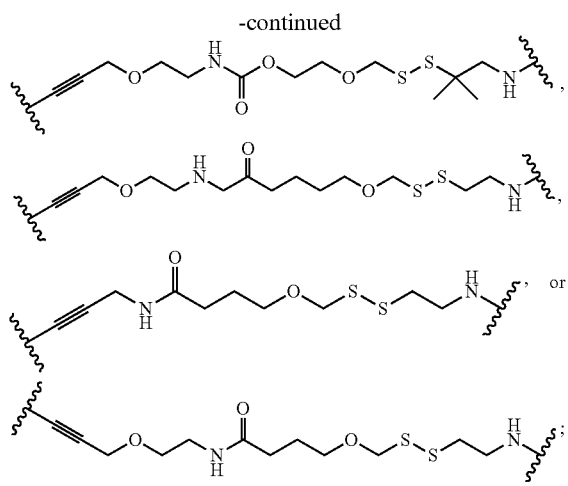

R[1] is substituted or unsubstituted alkyl, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OH, —NH$_2$, —COOH, —CONH$_2$, —SH, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R[2] and R[3] are independently substituted or unsubstituted alkyl, or substituted or unsubstituted heteroalkyl;

R[4] is hydrogen, R[34]-substituted or unsubstituted alkyl, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OH, —NH$_2$, —COOH, —CONH$_2$, —SH, R[34]-substituted or unsubstituted heteroalkyl, R[34]-substituted or unsubstituted cycloalkyl, or R[34]-substituted or unsubstituted heterocycloalkyl;

R[5] is hydrogen, R[35]-substituted or unsubstituted alkyl, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OH, —NH$_2$, —COOH, —CONH$_2$, —SH, R[35]-substituted or unsubstituted heteroalkyl, R[35]-substituted or unsubstituted cycloalkyl, or R[35]-substituted or unsubstituted heterocycloalkyl;

R[6] is hydrogen, R[36]-substituted or unsubstituted alkyl, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OH, —NH$_2$, —COOH, —CONH$_2$, —SH, R[36]-substituted or unsubstituted heteroalkyl, R[36]-substituted or unsubstituted cycloalkyl, or R[36]-substituted or unsubstituted heterocycloalkyl;

R[7] is hydrogen, R[37]-substituted or unsubstituted alkyl, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OH, —NH$_2$, —COOH, —CONH$_2$, —SH, R[37]-substituted or unsubstituted heteroalkyl, R[37]-substituted or unsubstituted cycloalkyl, or R[37]-substituted or unsubstituted heterocycloalkyl;

R[8] is a nucleotide;

R[9] is hydrogen, R[39]-substituted or unsubstituted alkyl, or R[39]-substituted or unsubstituted heteroalkyl;

R[10] is hydrogen, R[40]-substituted or unsubstituted alkyl, or R[40]-substituted or unsubstituted heteroalkyl;

R[11] is hydrogen, R[41]-substituted or unsubstituted alkyl, or R[41]-substituted or unsubstituted heteroalkyl;

R[12] is hydrogen, R[42]-substituted or unsubstituted alkyl, or R[42]-substituted or unsubstituted heteroalkyl;

R[4] and R[5] substituents bonded to the same nitrogen atom may optionally be joined to form a R[34]-substituted or unsubstituted heterocycloalkyl;

R[6] and R[7] substituents bonded to the same nitrogen atom may optionally be joined to form a R[36]-substituted or unsubstituted heterocycloalkyl;

R[4] and R[9] substituents may optionally be joined to form a R[34]-substituted or unsubstituted heterocycloalkyl, or R[39]-substituted or unsubstituted heteroaryl;

R[7] and R[10] substituents may optionally be joined to form a R[37]-substituted or unsubstituted heterocycloalkyl, or R[37]-substituted or unsubstituted heteroaryl;

R[5] and R[11] substituents may optionally be joined to form a R[35]-substituted or unsubstituted heterocycloalkyl, or R[35]-substituted or unsubstituted heteroaryl;

R[6] and R[12] substituents may optionally be joined to form a R[36]-substituted or unsubstituted heterocycloalkyl, or R[36]-substituted or unsubstituted heteroaryl;

R[34] is independently oxo, halogen, —CF$_3$, —CCl$_3$, —CI$_3$, —CBr$_3$, —CHF$_2$, —CHCl$_2$, —CHI$_2$, —CHBr$_2$, —CH$_2$F, —CH$_2$Cl, —CH$_2$I, —CH$_2$Br, —OCH$_2$F, —OCH$_2$Cl, —OCH$_2$I, —OCH$_2$Br, —OCHF$_2$, —OCHCl$_2$, —OCHI$_2$, —OCHBr$_2$, —OCF$_3$, —OCCl$_3$, —OCI$_3$, —OCBr$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —PO$_4$H, —PO$_3$H, —N$_3$, unsubstituted alkyl, unsubstituted heteroalkyl, unsubstituted cycloalkyl, or unsubstituted heterocycloalkyl;

R[35] is independently oxo, halogen, —CF$_3$, —CCl$_3$, —CI$_3$, —CBr$_3$, —CHF$_2$, —CHCl$_2$, —CHI$_2$, —CHBr$_2$, —CH$_2$F, —CH$_2$Cl, —CH$_2$I, —CH$_2$Br, —OCH$_2$F, —OCH$_2$Cl, —OCH$_2$I, —OCH$_2$Br, —OCHF$_2$, —OCHCl$_2$, —OCHI$_2$, —OCHBr$_2$, —OCF$_3$, —OCCl$_3$, —OCI$_3$, —OCBr$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —PO$_4$H, —PO$_3$H, —N$_3$, unsubstituted alkyl, unsubstituted heteroalkyl, unsubstituted cycloalkyl, or unsubstituted heterocycloalkyl;

R[36] is independently oxo, halogen, —CF$_3$, —CCl$_3$, —CI$_3$, —CBr$_3$, —CHF$_2$, —CHCl$_2$, —CHI$_2$, —CHBr$_2$, —CH$_2$F, —CH$_2$Cl, —CH$_2$I, —CH$_2$Br, —OCH$_2$F, —OCH$_2$Cl, —OCH$_2$I, —OCH$_2$Br, —OCHF$_2$, —OCHCl$_2$, —OCHI$_2$, —OCHBr$_2$, —OCF$_3$, —OCCl$_3$, —OCI$_3$, —OCBr$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —PO$_4$H, —PO$_3$H, —N$_3$, unsubstituted alkyl, unsubstituted heteroalkyl, unsubstituted cycloalkyl, or unsubstituted heterocycloalkyl;

R[37] is independently oxo, halogen, —CF$_3$, —CCl$_3$, —CI$_3$, —CBr$_3$, —CHF$_2$, —CHCl$_2$, —CHI$_2$, —CHBr$_2$, —CH$_2$F, —CH$_2$Cl, —CH$_2$I, —CH$_2$Br, —OCH$_2$F, —OCH$_2$Cl, —OCH$_2$I, —OCH$_2$Br, —OCHF$_2$, —OCHCl$_2$, —OCHI$_2$, —OCHBr$_2$, —OCF$_3$, —OCCl$_3$, —OCI$_3$, —OCBr$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —PO$_4$H, —PO$_3$H, —N₃, unsubstituted alkyl, unsubstituted heteroalkyl, unsubstituted cycloalkyl, or unsubstituted heterocycloalkyl;

$R^{39}$ is independently —PO₃H, —PO₄H, —SO₂NH₂, —SO₃H, or —SO₄H;

$R^{40}$ is independently —PO₃H, —PO₄H, —SO₂NH₂, —SO₃H, or —SO₄H;

$R^{41}$ is independently —PO₃H, —PO₄H, —SO₂NH₂, —SO₃H, or —SO₄H; and $R^{42}$ is independently —PO₃H, —PO₄H, —SO₂NH₂, —SO₃H, or —SO₄H.

2. The compound of claim 1, wherein $R^1$ is substituted or unsubstituted $C_1$-$C_6$ alkyl.

3. The compound of claim 1, wherein $R^2$ and $R^3$ are independently substituted or unsubstituted $C_1$-$C_6$ alkyl, or substituted or unsubstituted 2 to 6 membered heteroalkyl.

4. The compound of claim 1, wherein $R^4$ is hydrogen, $R^{34}$-substituted or unsubstituted $C_1$-$C_6$ alkyl, or $R^{34}$-substituted or unsubstituted 2 to 6 membered heteroalkyl;

$R^5$ is hydrogen, $R^{35}$-substituted or unsubstituted $C_1$-$C_6$ alkyl, or $R^{35}$-substituted or unsubstituted 2 to 6 membered heteroalkyl;

$R^6$ is hydrogen, $R^{36}$-substituted or unsubstituted $C_1$-$C_6$ alkyl, or $R^{36}$-substituted or unsubstituted 2 to 6 membered heteroalkyl; and $R^7$ is hydrogen, $R^{37}$-substituted or unsubstituted $C_1$-$C_6$ alkyl, or $R^{37}$-substituted or unsubstituted 2 to 6 membered heteroalkyl.

5. The compound of claim 1, wherein $R^4$ and $R^5$ substituents bonded to the same nitrogen atom are joined to form a $R^{34}$-substituted or unsubstituted 5 membered heterocycloalkyl or $R^{34}$-substituted or unsubstituted 6 membered heterocycloalkyl.

6. The compound of claim 1, wherein $R^6$ and $R^7$ substituents bonded to the same nitrogen atom are joined to form a $R^{36}$-substituted or unsubstituted 5 membered heterocycloalkyl or $R^{36}$-substituted or unsubstituted 6 membered heterocycloalkyl.

7. The compound of claim 1, wherein $R^8$ is

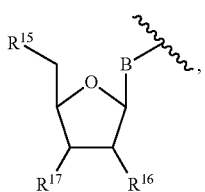

wherein

B is a divalent base;

$R^{15}$ is a 5'-nucleoside protecting group, monophosphate moiety, polyphosphate moiety, or nucleic acid moiety;

$R^{16}$ is hydrogen or —OH; and $R^{17}$ is an —O-polymerase-compatible cleavable moiety, wherein said polymerase-compatible cleavable moiety has the formula:

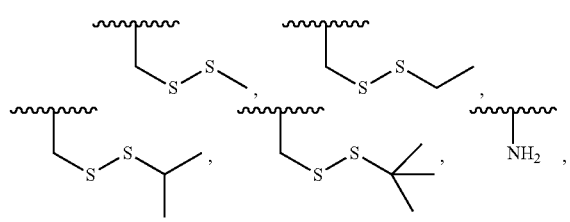

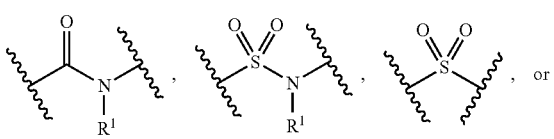

8. The compound of claim 7, wherein $R^{15}$ is a triphosphate moiety.

9. The compound of claim 7, wherein

B is a divalent cytosine, divalent guanine, divalent adenine, divalent thymine, divalent uracil, divalent hypoxanthine, divalent xanthine, divalent 7-methylguanine, divalent 5,6-dihydrouracil, divalent 5-methylcytosine, or divalent 5-hydroxymethylcytosine.

10. A method of detecting the presence of an agent, said method comprising exposing a compound covalently bound to said agent to absorption light and detecting an emission wavelength, wherein said agent is an oligonucleotide, protein, or compound, and wherein said compound covalently bound to said agent has the formula:

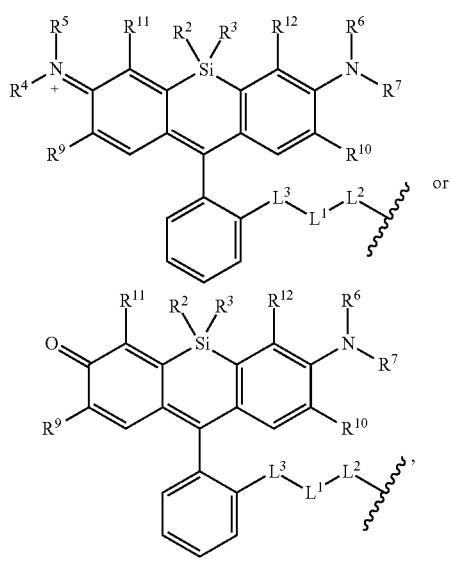

wherein, $L^3$ is

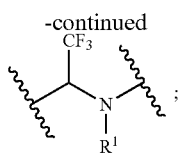

$L^1$-$L^2$-comprises

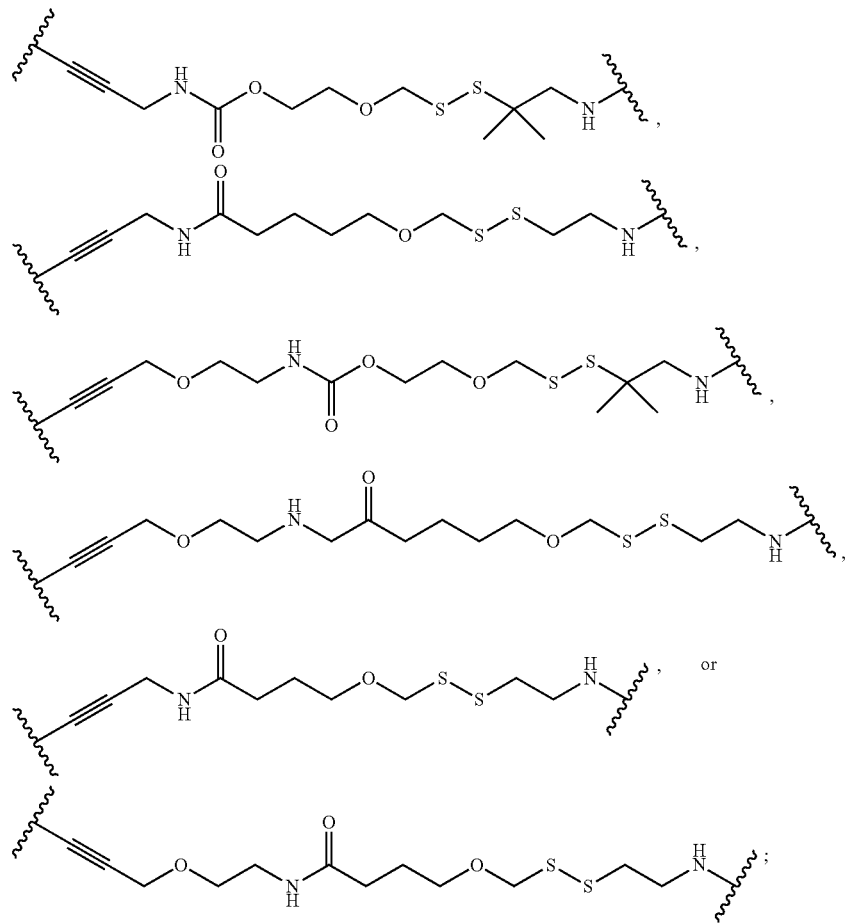

$R^1$ is substituted or unsubstituted alkyl, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OH, —NH$_2$, —COOH, —CONH$_2$, —SH, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ and $R^3$ are independently substituted or unsubstituted alkyl, or substituted or unsubstituted heteroalkyl;

$R^4$ is hydrogen, $R^{34}$-substituted or unsubstituted alkyl, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OH, —NH$_2$, —COOH, —CONH$_2$, —SH, $R^{34}$-substituted or unsubstituted heteroalkyl, $R^{34}$-substituted or unsubstituted cycloalkyl, $R^{34}$-substituted or unsubstituted heterocycloalkyl, $R^{34}$-substituted or unsubstituted aryl, or $R^{34}$-substituted or unsubstituted heteroaryl;

$R^5$ is hydrogen, $R^{35}$-substituted or unsubstituted alkyl, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OH, —NH$_2$, —COOH, —CONH$_2$, —SH, $R^{35}$-substituted or unsubstituted heteroalkyl, $R^{35}$-substituted or unsubstituted cycloalkyl, $R^{35}$-substituted or unsubstituted heterocycloalkyl, $R^{35}$-substituted or unsubstituted aryl, or $R^{35}$-substituted or unsubstituted heteroaryl;

$R^6$ is hydrogen, $R^{36}$-substituted or unsubstituted alkyl, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OH, —NH$_2$, —COOH, —CONH$_2$, —SH, $R^{36}$-substituted or unsubstituted heteroalkyl, $R^{36}$-substituted or unsubstituted cycloalkyl, $R^{36}$-substituted or unsubstituted heterocycloalkyl, $R^{36}$-substituted or unsubstituted aryl, or $R^{36}$-substituted or unsubstituted heteroaryl;

$R^7$ is hydrogen, $R^{37}$-substituted or unsubstituted alkyl, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OH, —NH$_2$, —COOH, —CONH$_2$, —SH, $R^{37}$-substituted or unsubstituted heteroalkyl, $R^{37}$-substituted or unsubstituted cycloalkyl, $R^{37}$-substituted or unsubstituted heterocycloalkyl, $R^{37}$-substituted or unsubstituted aryl, or $R^{37}$-substituted or unsubstituted heteroaryl;

$R^9$ is hydrogen, $R^{39}$-substituted or unsubstituted alkyl, or $R^{39}$-substituted or unsubstituted heteroalkyl;

$R^{10}$ is hydrogen, $R^{40}$-substituted or unsubstituted alkyl, or $R^{40}$-substituted or unsubstituted heteroalkyl;

$R^{11}$ is hydrogen, $R^{41}$-substituted or unsubstituted alkyl, or $R^{41}$-substituted or unsubstituted heteroalkyl;

$R^{12}$ is hydrogen, $R^{42}$-substituted or unsubstituted alkyl, or $R^{42}$-substituted or unsubstituted heteroalkyl;

$R^4$ and $R^5$ substituents bonded to the same nitrogen atom may optionally be joined to form a $R^{34}$-substituted or unsubstituted heterocycloalkyl;

$R^6$ and $R^7$ substituents bonded to the same nitrogen atom may optionally be joined to form a $R^{36}$-substituted or unsubstituted heterocycloalkyl;

$R^4$ and $R^9$ substituents may optionally be joined to form a $R^{34}$-substituted or unsubstituted heterocycloalkyl, or $R^{39}$-substituted or unsubstituted heteroaryl;

$R^7$ and $R^{10}$ substituents may optionally be joined to form a $R^{37}$-substituted or unsubstituted heterocycloalkyl, or $R^{37}$-substituted or unsubstituted heteroaryl;

$R^5$ and $R^{11}$ substituents may optionally be joined to form a $R^{35}$-substituted or unsubstituted heterocycloalkyl, or $R^{35}$-substituted or unsubstituted heteroaryl;

$R^6$ and $R^{12}$ substituents may optionally be joined to form a $R^{36}$-substituted or unsubstituted heterocycloalkyl, or $R^{36}$-substituted or unsubstituted heteroaryl;

$R^{34}$ is independently oxo, halogen, —$CF_3$, —$CCl_3$, —$CI_3$, —$CBr_3$, —$CHF_2$, —$CHCl_2$, —$CHI_2$, —$CHBr_2$, —$CH_2F$, —$CH_2Cl$, —$CH_2I$, —$CH_2Br$, —$OCH_2F$, —$OCH_2Cl$, —$OCH_2I$, —$OCH_2Br$, —$OCHF_2$, —$OCHCl_2$, —$OCHI_2$, —$OCHBr_2$, —$OCF_3$, —$OCCl_3$, —$OCI_3$, —$OCBr_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$PO_4H$, —$PO_3H$, —$N_3$, unsubstituted alkyl, unsubstituted heteroalkyl, unsubstituted cycloalkyl, or unsubstituted heterocycloalkyl;

$R^{35}$ is independently oxo, halogen, —$CF_3$, —$CCl_3$, —$CI_3$, —$CBr_3$, —$CHF_2$, —$CHCl_2$, —$CHI_2$, —$CHBr_2$, —$CH_2F$, —$CH_2Cl$, —$CH_2I$, —$CH_2Br$, —$OCH_2F$, —$OCH_2Cl$, —$OCH_2I$, —$OCH_2Br$, —$OCHF_2$, —$OCHCl_2$, —$OCHI_2$, —$OCHBr_2$, —$OCF_3$, —$OCCl_3$, —$OCI_3$, —$OCBr_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$PO_4H$, —$PO_3H$, —$N_3$, unsubstituted alkyl, unsubstituted heteroalkyl, unsubstituted cycloalkyl, or unsubstituted heterocycloalkyl;

$R^{36}$ is independently oxo, halogen, —$CF_3$, —$CCl_3$, —$CI_3$, —$CBr_3$, —$CHF_2$, —$CHCl_2$, —$CHI_2$, —$CHBr_2$, —$CH_2F$, —$CH_2Cl$, —$CH_2I$, —$CH_2Br$, —$OCH_2F$, —$OCH_2Cl$, —$OCH_2I$, —$OCH_2Br$, —$OCHF_2$, —$OCHCl_2$, —$OCHI_2$, —$OCHBr_2$, —$OCF_3$, —$OCCl_3$, —$OCI_3$, —$OCBr_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$PO_4H$, —$PO_3H$, —$N_3$, unsubstituted alkyl, unsubstituted heteroalkyl, unsubstituted cycloalkyl, or unsubstituted heterocycloalkyl;

$R^{37}$ is independently oxo, halogen, —$CF_3$, —$CCl_3$, —$CI_3$, —$CBr_3$, —$CHF_2$, —$CHCl_2$, —$CHI_2$, —$CHBr_2$, —$CH_2F$, —$CH_2Cl$, —$CH_2I$, —$CH_2Br$, —$OCH_2F$, —$OCH_2Cl$, —$OCH_2I$, —$OCH_2Br$, —$OCHF_2$, —$OCHCl_2$, —$OCHI_2$, —$OCHBr_2$, —$OCF_3$, —$OCCl_3$, —$OCI_3$, —$OCBr_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$PO_4H$, —$PO_3H$, —$N_3$, unsubstituted alkyl, unsubstituted heteroalkyl, unsubstituted cycloalkyl, or unsubstituted heterocycloalkyl;

$R^{39}$ is independently —$PO_3H$, —$PO_4H$, —$SO_2NH_2$, —$SO_3H$, or —$SO_4H$;

$R^{40}$ is independently —$PO_3H$, —$PO_4H$, —$SO_2NH_2$, —$SO_3H$, or —$SO_4H$;

$R^{41}$ is independently —$PO_3H$, —$PO_4H$, —$SO_2NH_2$, —$SO_3H$, or —$SO_4H$; and $R^{42}$ is independently —$PO_3H$, —$PO_4H$, —$SO_2NH_2$, —$SO_3H$, or —$SO_4H$.

11. The compound of claim 1 having formula:

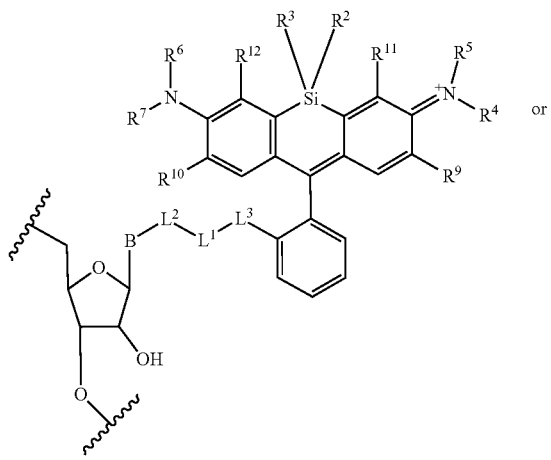

(XI)

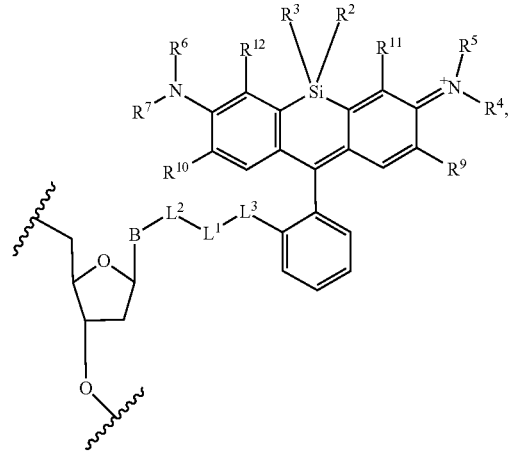

(XII)

wherein, the symbol B is a divalent base; and the symbol ⌇ in formula (XI) or (XII) refers to an attachment point to hydrogen, a phosphate moiety, or a reversible terminator moiety.

12. The compound of claim 1, wherein $R^4$ and $R^9$ substituents are joined to form a $R^{34}$-substituted or unsubstituted 7 membered heterocycloalkyl, or $R^{39}$-substituted or unsubstituted 7 membered heteroaryl.

13. The compound of claim 1, wherein $R^7$ and $R^{10}$ substituents are joined to form a $R^{37}$-substituted or unsubstituted 7 membered heterocycloalkyl, or $R^{37}$-substituted or unsubstituted 7 membered heteroaryl.

14. The compound of claim 1, wherein $R^5$ and $R^{11}$ substituents are joined to form a $R^{35}$-substituted or unsubstituted 6 membered heterocycloalkyl, or $R^{35}$-substituted or unsubstituted 6 membered heteroaryl.

15. The compound of claim 1, wherein $R^6$ and $R^{12}$ substituents are joined to form a $R^{36}$-substituted or unsubstituted 6 membered heterocycloalkyl, or $R^{36}$-substituted or unsubstituted 6 membered heteroaryl.

16. The compound of claim 1, wherein $R^4$ and $R^9$ substituents are joined to form a $R^{34}$-substituted or unsubstituted 6 membered heterocycloalkyl, or $R^{39}$-substituted or unsubstituted 6 membered heteroaryl;

$R^7$ and $R^{10}$ substituents are joined to form a $R^{37}$-substituted or unsubstituted 6 membered heterocycloalkyl, or $R^{37}$-substituted or unsubstituted 6 membered heteroaryl;

$R^5$ and $R^{11}$ substituents are joined to form a $R^{35}$-substituted or unsubstituted 6 membered heterocycloalkyl, or $R^{35}$-substituted or unsubstituted 6 membered heteroaryl; and $R^6$ and $R^{12}$ substituents are joined to form a $R^{36}$-substituted or unsubstituted 6 membered heterocycloalkyl, or $R^{36}$-substituted or unsubstituted 6 membered heteroaryl.

17. The compound of claim 1, having formula

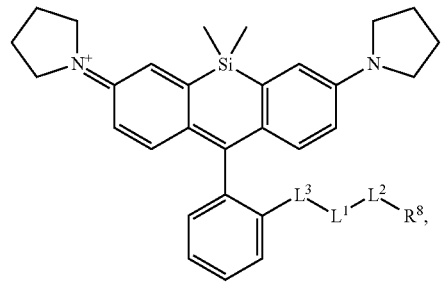

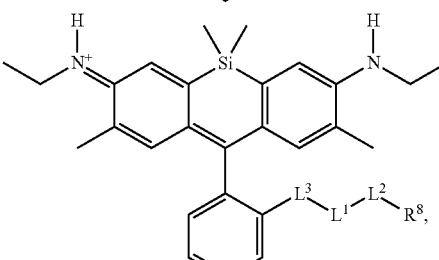

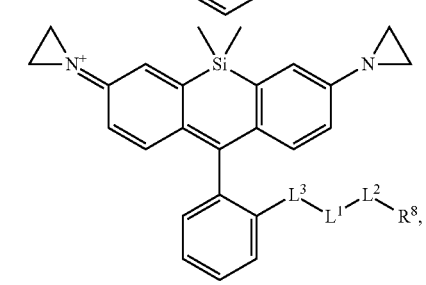

-continued

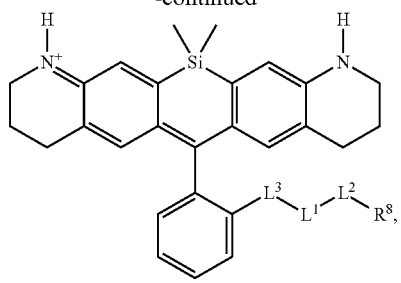

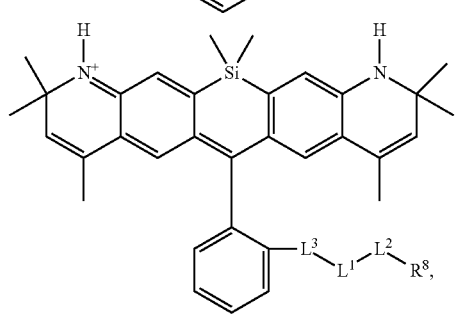

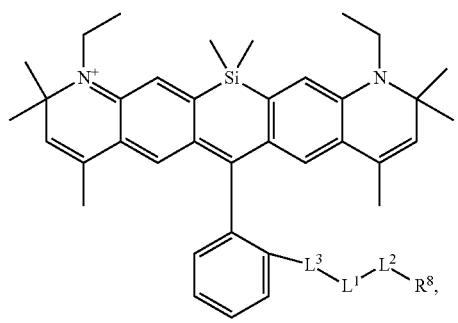

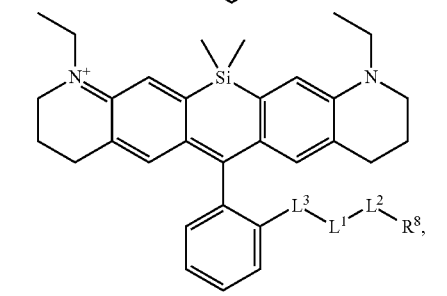

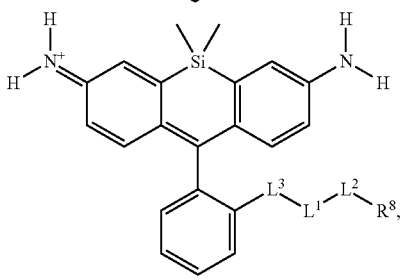

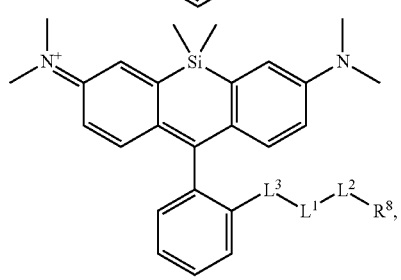

315
-continued
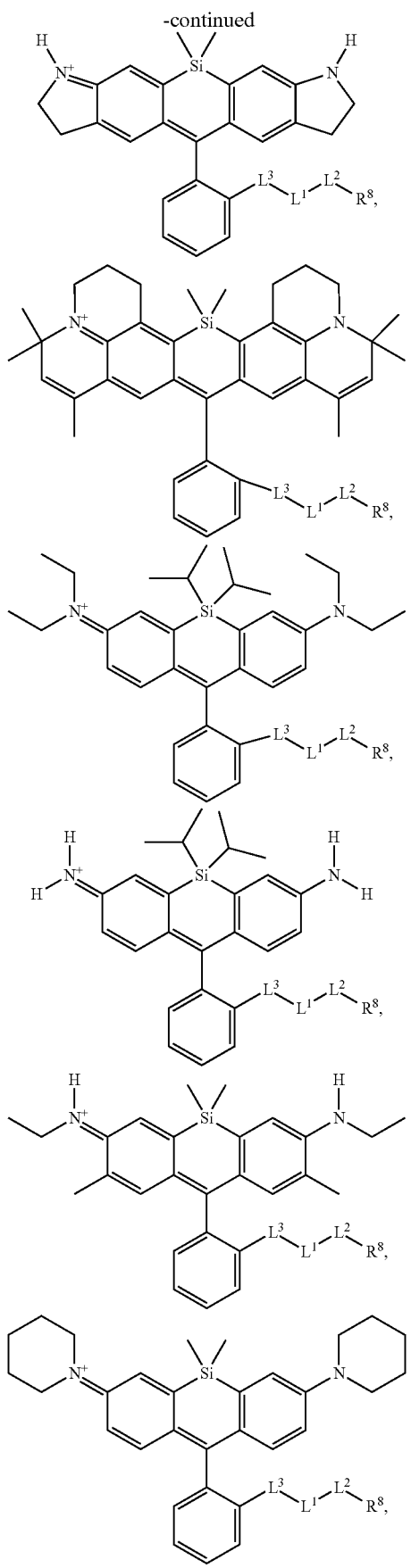
316
-continued
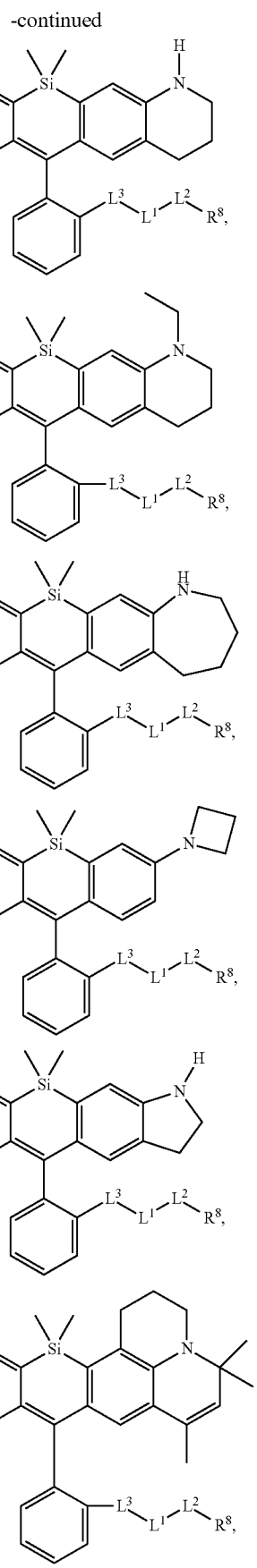

317
-continued
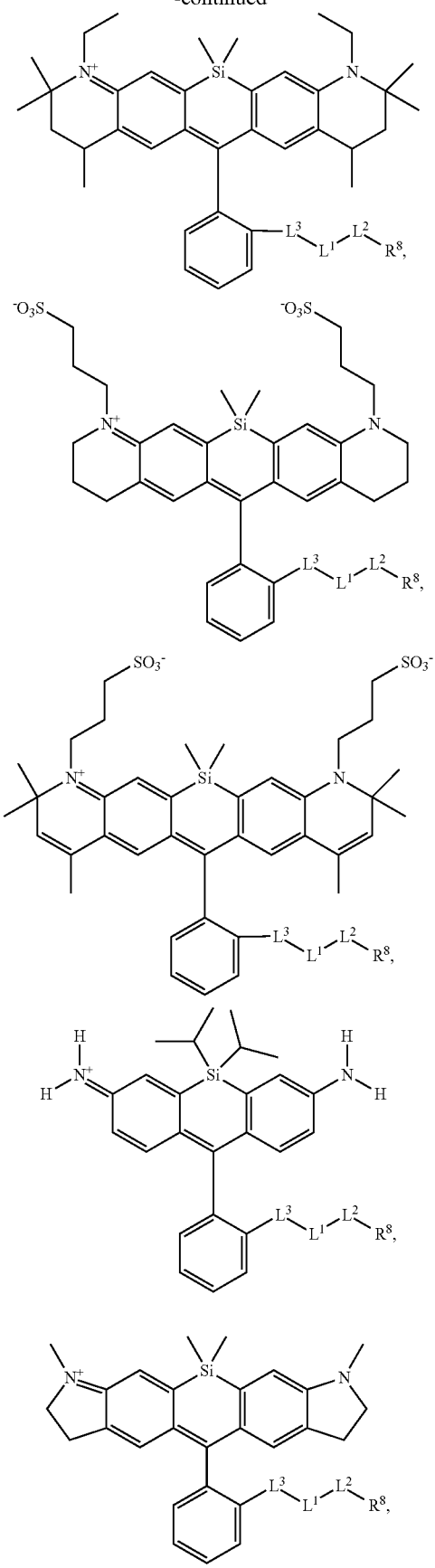
318
-continued
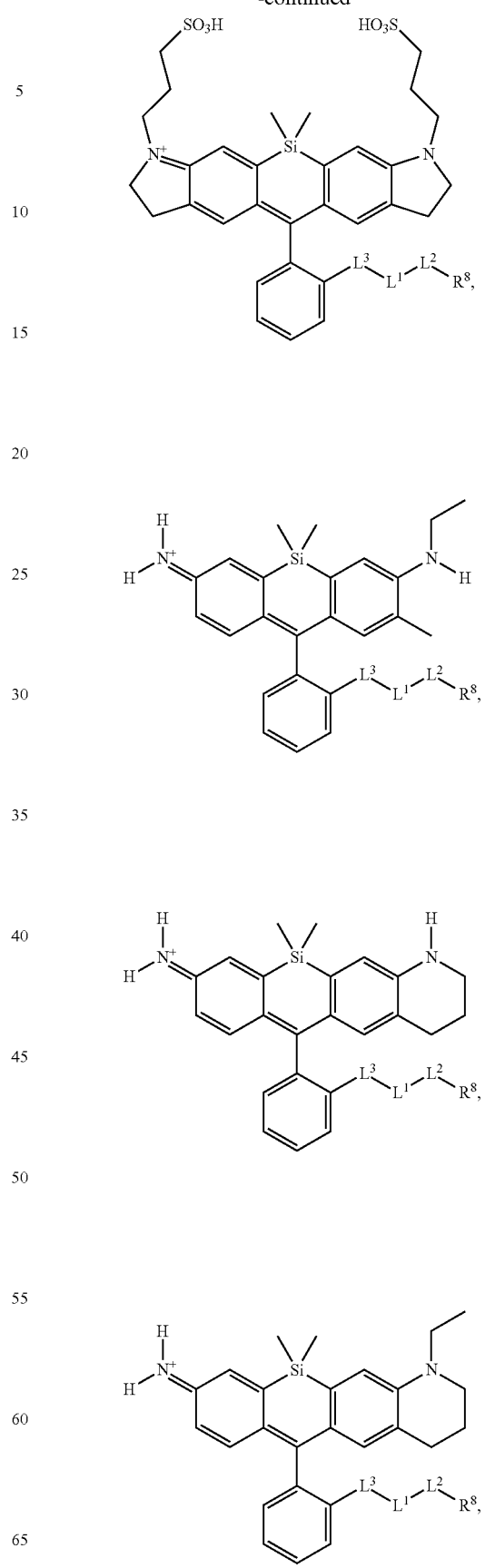

319
-continued
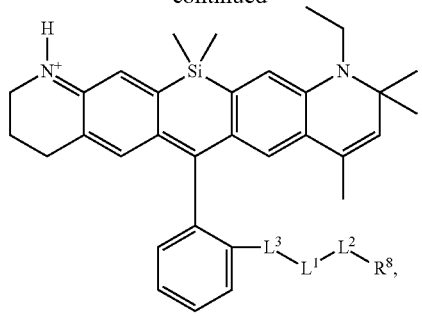
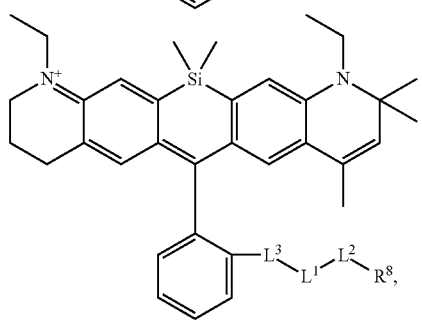
320
-continued
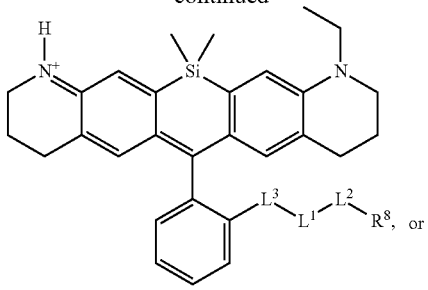
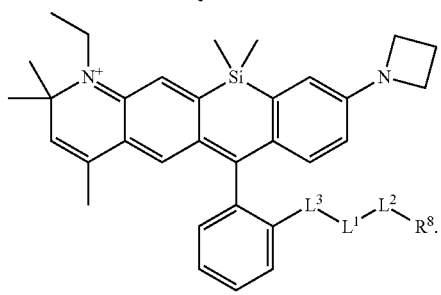
* * * * *